United States Patent
Ma et al.

(10) Patent No.: US 11,434,205 B2
(45) Date of Patent: Sep. 6, 2022

(54) SUBSTITUTED IMIDAZOLE CARBOXYLATE DERIVATIVES AND THE USE THEREOF

(71) Applicant: CHENGDU MFS PHARMA. CO., LTD., Sichuan (CN)

(72) Inventors: Haijun Ma, Sichuan (CN); Changhua Wang, Sichuan (CN); Zhenbiao Xie, Sichuan (CN)

(73) Assignee: Chengdu MFS Pharma. Co., Ltd., Sichuan (CN)

( * ) Notice: Subject to any disclaimer, the term of this patent is extended or adjusted under 35 U.S.C. 154(b) by 0 days.

(21) Appl. No.: 16/966,380

(22) PCT Filed: Jan. 30, 2019

(86) PCT No.: PCT/CN2019/074002
§ 371 (c)(1),
(2) Date: Jul. 30, 2020

(87) PCT Pub. No.: WO2019/149228
PCT Pub. Date: Aug. 8, 2019

(65) Prior Publication Data
US 2020/0369621 A1    Nov. 26, 2020

(30) Foreign Application Priority Data

Jan. 30, 2018   (CN) .......................... 201810093229.2
Jan. 30, 2018   (CN) .......................... 201810093523.3
(Continued)

(51) Int. Cl.
A61K 31/415       (2006.01)
C07D 233/90       (2006.01)
(Continued)

(52) U.S. Cl.
CPC .......... *C07D 233/90* (2013.01); *A61K 31/415* (2013.01); *A61P 23/00* (2018.01);
(Continued)

(58) Field of Classification Search
CPC .. C07D 407/12; C07D 233/90; C07D 405/12; C07D 405/14; C07D 409/12; A61P 23/00; A61P 25/08; A61P 25/20; A61K 31/415
(Continued)

(56) References Cited

FOREIGN PATENT DOCUMENTS

CN        103588757 A   *   2/2014
CN        104168899 A       11/2014
(Continued)

OTHER PUBLICATIONS

Ettmayer et al. "Lessons Learned from Marketed and Investigational Prodrugs." J. Med. Chem., (2004), 47(10): 2393-2404.*
(Continued)

*Primary Examiner* — Taylor V Oh
(74) *Attorney, Agent, or Firm* — Novick, Kim & Lee, PLLC; Allen Xue

(57) ABSTRACT

A compound is shown in formula (I). The derivatives of the compound include a stereoisomer, a pharmaceutically acceptable salt, a solvate, a prodrug, a metabolite, a deuterated derivative. The compound is a structurally novel substituted imidazole formate derivative. Substituted imidazole formate derivatives are used in preparing a drug with sedative, hypnotic and/or anesthetic effects, as well as a drug that can control the state of epilepsy. The compound has a good inhibitory effect on the central nervous system, and provides a new option for clinical screening of and/or preparation of a drug with sedative, hypnotic and/or anesthetic effects and controlling the state of epilepsy.

(Continued)

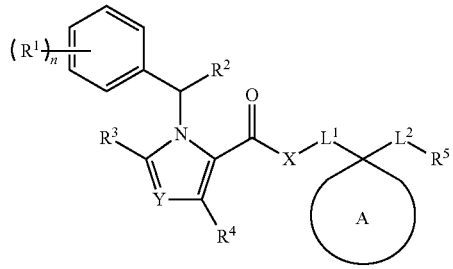

Formula I

14 Claims, 20 Drawing Sheets

(30) Foreign Application Priority Data

Jan. 30, 2018 (CN) .......................... 201810093551.5
Jan. 30, 2018 (CN) .......................... 201810093739.X

(51) Int. Cl.
*A61P 23/00* (2006.01)
*C07D 405/12* (2006.01)
*C07D 405/14* (2006.01)
*C07D 409/12* (2006.01)

(52) U.S. Cl.
CPC ......... *C07D 405/12* (2013.01); *C07D 405/14* (2013.01); *C07D 409/12* (2013.01)

(58) Field of Classification Search
USPC ........................................................ 514/397
See application file for complete search history.

(56) References Cited

FOREIGN PATENT DOCUMENTS

| CN | 105663042 A | 6/2016 |
| CN | 107382812 A | 11/2017 |
| CN | 107382870 A | 11/2017 |
| CN | 107445898 A | 12/2017 |
| WO | 2009146024 A1 | 12/2009 |
| WO | 2011005969 A2 | 1/2011 |

OTHER PUBLICATIONS

Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Balant ed in Wolff et al. Burger's Medicinal Chemistry and Drug Discovery. 5th ed. vol. 1: Principles and Practice, pp. 949-982, 1995.*
Bundgaard, Design of Prodrugs, Chapter 1, p. 1, 1985.*
Silverman, Prodrugs and Drug Delivery Systems, The Organic Chemistry of Drug Design and Drug action, Chapter 8, pp. 352-400, 1992.*
Hulikal, Deuterium Labeled Compounds in Drug Discovery Process, Abstract, 2010.*
Pimlott, PubMed Abstract (Nucl Med Commun. 26(3):183-8), 2005.*
Banker et al., Prodrugs, Modern Pharmaceutics, 3rd edition, Revised and Expanded, pp. 451 and 596.*
Jordan "Tamoxifen . . . " Nature Rev. v.2, p. 205-213 (2003).*
English translation of CN107445898A (Year: 2017).*
English translation of CN 103588757A (Year: 2013).*
Godefroi et al., DL-I-(I-Arylalkyl)imidazole-5-carboxylate Esters. A Novel Type of Hypnotic Agents, Journal of Medicinal Chemistry (1965), 8(2), pp. 220-223 (Year: 1965).*
Chiara et al., General Anesthetic Binding Sites in Human alpha 4Beta3dr-Aminobutyric Acid Type A Receptors (GABAARs), Journal of Biological Chemistry (2016), 291(51), pp. 26529-26539 (Year: 2016).*
Kay, B. et al.; A Dose-Response Relationship for Etomidate, with Some Observations on Cumulation; British Journal of Anaesthesia. 1976; 48(3): 213-6. PubMed: 1259887.
Etomidate, a potent non-barbiturate hypnotic. Intravenous etomidate in mice, rats, guinea-pigs, rabbits and dogs. Arch Int Pharmacodyn Ther. 1975; 214(1): 92-132. PubMed: 1156027, Abstract Only.
Zed, Peter J. et al.; Intubating Conditions and Hemodynamic Effects of Etomidate for Rapid Sequence Intubation in the Emergency Department: An Observational Cohort Study; Acad Emerg Med. 2006; 13(4): 378-83. PubMed: 16531603.
Godefroi, Erik R. et al.; DL-1-(1-Arylalkyl)imidazole-5-carboxylate Esters. A Novel Type of Hypnotic Agents; J Med Chem. 1965; vol. 8: 220-3. PubMed: 14332665.
Tomlin, Sarah L. et al.; Stereoselectiove Effects of Etomidate Optical Isomers on Gamma-aminobutyric Acid Type A Receptors and Animals; Anesthesiology. 1998; 88(3): 708-17. PubMed: 9523815.
Ledingham, I. MCA et al.; Letters to the Editor: Etomidate and Adrenocortical Function; The Lancet. 1983; 1(8339): 1434. PubMed: 6134189.
Kamp, Ryan et al.; Etomidate, sepsis, and adrenal function: not as bad as we thought? Critical Care. 2007; 11(3): 145. PubMed: 17610749.
Forman, Stuart A. et al.; Clinical and Molecular Pharmacology of Etomidate; Anesthesiology. 2011; 114(3): 695-707. PubMed: 21263301.
Chan, Chee Man et al.; Etomidate is associated with mortality and adrenal insufficiency in sepsis: A meta-analysis; Crit Care Med. 2012; 40(11): 2945-53. PubMed: 22971586.
Komatsu, Ryu et al.; Anesthetic Induction with Etomidate, Rather then Propofol, Is Associated with Increased 30-Day Mortality and Cardiovascular Morbidity After Noncardiac Surgery; Anesthesia & Analgesia. 2013; 117(6): 1329-37. PubMed: 24257383.
Bruder, E. A. et al.; Single induction dose of etomidate versus other incudtion agents for endotracheal intubation in critically ill patients; Cochrane Database Syst Rev. 2015; 1: CD010225. PubMed: 25568981.
Schlapfer, Martin et al.; Propofol increases morbidity and mortality in a rat model of sepsis; Critical Care. 2015; 19:45. PubMed: 25887642.
Wagner, R. Lee et al.; Inhibition of Adrenal Steroidogenesis by the Anesthetic Etomidate; The new England Journal of Medicine; May 31, 1984, 310(22): 1415-21. PubMed: 6325910.
Atucha, Erika et al.; Structure-activity relationship of etomidate derivatives at the GABAA receptor: Comparison with binding to 11b-hydroxylase; Bioorganic & Medicinal Chemistry Letters, 2009; 19 (15): 4284-7. PubMed: 19497738.
Pejo, Ervin et al.; Sedative-Hypnotic Binding to 11β-Hydroxylase; Anesthesiology. 2016; 125 (5): 943-951. PubMed: 27541316.

* cited by examiner

SUBSTITUTED IMIDAZOLE CARBOXYLATE DERIVATIVES AND THE USE THEREOF

TECHNICAL FIELD

The present invention belongs to the field of medicinal chemistry, and in particular relates to a novel substituted imidazole carboxylate derivative, as well as the use of the compound in the preparation of drugs with sedative, hypnotic and/or anesthetic effects, as well as drugs capable of controlling the status epilepticus.

BACKGROUND ART

Etomidate, an imidazole derivative, with the chemical name of ethyl R-(+)-1-(1-phenylethyl)-1H-imidazol-5-carboxylate, is a hypnotic and intravenous general anesthesia drug with a wide range of safety window, that used to be one of the commonly used drugs for anesthesia induction. The imidazole derivatives have been used in clinic for 30 years (Br J Anaesth. 1976; 48(3): 213-6. PubMed: 1259887; Arch Int Pharmacodyn Ther. 1975; 214(1): 92-132. PubMed: 1156027; Acad Emerg Med. 2006; 13(4): 378-83. PubMed: 16531603). Etomidate is a kind of non-barbital intravenous sedative. Its action intensity is 4 times that of barbital sodium and 12 times that of thiopental sodium, and it is fast in induction of general anesthesia. After administration, the recovery is also quick. After recovery, the patients no longer show drowsiness, vertigo and other adverse reactions, and has certain anti-vomit effect, so it has been widely used. Its structural formula is shown in the following figure, with a molecular formula of $C_{14}H_{16}N_2O_2$, and the molecular weight is 244.29. The imidazole derivatives are insoluble in water and unstable in neutral solution.

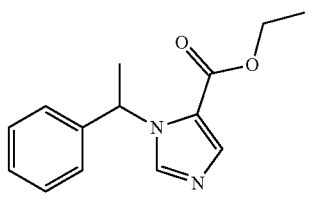 [SMILES: CCOC(=O)c1cncn1C(C)c1ccccc1]

Janssen Pharmaceuticals started to introduce etomidate into clinical practice in the 1970s. As the main R & D members, Janssen P A, et al. recorded the key procedures in etomidate synthesis in a research report published in 1965, and described how to screen etomidate from 42 similar compounds. Among the 11 compounds with definite anesthetic effect, etomidate showed the best safety (i.e. the highest therapeutic index TI) in rats. In addition, the researchers also found that the sedative and hypnotic effect of etomidate was stereoselective, and the efficacy of R-configuration drug is ten times higher than that of S-configuration drug (J Med Chem. 1965; 8: 220-3. PubMed: 14332665; Anesthesiology. 1998; 88(3): 708-17. PubMed: 9523815). The advantages of the imidazole derivatives are very prominent. For example, in the existing general anesthetics, the treatment window is relatively large, and the inhibition on the circulatory system is relatively small. This feature is especially suitable for the elderly, patients with coronary heart disease and hypertension, and critical patients. It used to be a standard drug for anesthesia induction and also used as a drug for total intravenous anesthesia. However, since 1980s, as the long-term use in clinical, some shortcomings of etomidate (such as the quality of recovery is slightly worse than that of propofol), especially the adverse effect of inhibition of adrenocortical function, have been gradually found. It has been reported that etomidate can inhibit the synthesis of adrenocortical hormone, thus reducing the survival rate of critically ill patients (Lancet. 1983; 1(8339): 1434. PubMed: 6134189; Crit Care. 2007; 11(3): 145. PubMed: 17610749; Anesthesiology. 2011; 114(3): 695-707. PubMed: 21263301). Even some studies have shown that the use of etomidate in a single fast sequential induction can increase in-patient mortality (Crit Care Med. 2012; 40(11): 2945-53. PubMed: 22971586; Anesth Analg. 2013; 117(6): 1329-37. PubMed: 24257383); Many researchers deduce that the high mortality rate is related to the inhibition on the synthesis of adrenocortical hormone by etomidate (Cochrane Database Syst Rev. 2015; 1: CD010225. PubMed: 25568981). Meanwhile, propofol, another intravenous general anesthesia drug commonly used in clinic, has relatively small treatment window and has obvious adverse effects of lowering blood pressure in the process of anesthesia induction (Crit Care. 2015; 19:45. PubMed: 25887642), which often increases the occurrence of cardiovascular adverse events. Therefore, it is of great clinical significance and wide application prospect to design a new compound which can not only keep the excellent characteristics of circulatory stability of etomidate, but also not inhibit the synthesis of adrenocortical hormone.

The literature indicates that etomidate can inhibit the synthesis of adrenocortical hormone mainly by 11β hydroxylase and cholesterol side chain lyase, which are the key enzymes in the synthesis of corticosterone, cortisol, etc (N Engl J Med. 1984; 310(22): 1415-21. PubMed: 6325910). Atucha et al. (Bioorg Med Chem Lett. 2009; 19 (15): 4284-7. PubMed: 19497738) found that the ester side chain of etomidate can not only affect the GABA receptor (the main site for the anesthetic effect of etomidate), but also affect the synthesis of adrenocortical hormone. In addition, compared with etomidate, etomidate acid, the main metabolite of etomidate, has little inhibitory effect on 11-β-hydroxylase (Anesthesiology. 2016; 125 (5): 943-951. PubMed: 27541316). If the structure of etomidate is modified to reduce or eliminate the inhibition of the compound itself on the adrenocortical function and also make the metabolites of the compound to have no effect on the adrenocortical function, then the inhibition of the drug on the adrenocortical function can be reduced or eliminated. The follow-up studies based on the structure of etomidate mainly focus on how to reduce or not inhibit the function of adrenal cortex while retaining the advantages of etomidate in clinical application. WO 2009/146024A1 disclosed etomidate analogues with improved pharmacokinetic and pharmacodynamic properties, as well as theirs use as an anesthetic, and disclosed that the compound can be MOC-(R)-etomidate.

WO 2011/005969A2 disclosed etomidate analogues with improved pharmacokinetic and pharmacodynamic properties and their use as an anesthetic, and disclosed that the compound can be MOC-carbon etomidate.

CN 201380014062 disclosed a metomidate and etomidate analogue with improved pharmacokinetics and pharmacodynamic properties, and disclosed that the compound can be cyclopropyl MOC metomidate.

Although follow-up researches of scientists based on the structure of etomidate mainly focused on how to reduce or not inhibit the adrenal cortex function while retaining the advantages of etomidate in clinical application, and have successively found some analogues of etomidate, such as dimethylmethoxycarbonyl methylate (DMMM) and cyclopropyl methoxycarbonyl methylate (CPMM), but scientists still haven't found any compounds that not only retain the unique advantages of etomidate (such as high efficiency, safety), but also eliminate its inhibitory effect on adrenal cortex function.

Therefore, it is of great clinical significance and wide application prospect to design a new compound which can not only keep the excellent characteristics of etomidate circulatory stability, but also not inhibit the synthesis of adrenocortical hormone.

Meanwhile, more safe imidazole derivatives are urgently needed to prepare drugs with sedative, hypnotic and/or anesthetic effects and drugs for controlling the status epilepticusstatus epilepticus.

Content of the Present Invention

In order to solve above problems, the present invention provides a novel series of substituted imidazole carboxylate derivatives.

The present invention further provides that the substituted imidazole carboxylate derivatives have inhibitory effect on central nervous system, as well as the use of the substituted imidazole carboxylate derivatives in the preparation of drugs with sedative, hypnotic and/or anesthetic effects, together with drugs capable of controlling the status epilepticus.

The present invention provides Compounds of formula I, or stereoisomers thereof, or pharmaceutically acceptable salts thereof, or solvates thereof, or prodrugs thereof, or metabolites thereof, or deuterated derivatives thereof:

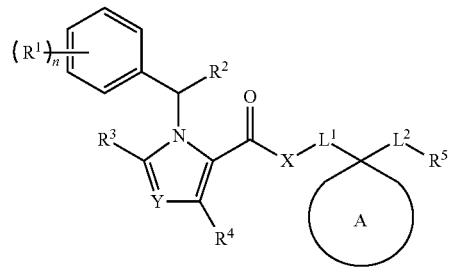

Formula I

X is selected from O, S, or $NR^{30}$, in which $R^{30}$ is selected from hydrogen, deuterium or $C_{1-8}$ alkyl; Y is N;

$R^1$ is independently selected from the group consisting of deuterium, halogen, —CN, —$NO_2$, —$OR^{32}$, —$C(O)R^{32}$, —$CO_2R^{32}$, —$CON(R^{32})_2$, —$N(R^{32})_2$, —$OC(O)R^{32}$, —$SO_2R^{32}$, substituted or unsubstituted 3~8-membered heterocyclic groups, substituted or unsubstituted $C_{1-8}$ alkyls, substituted or unsubstituted $C_{2-8}$ alkenyls, and substituted or unsubstituted $C_{2-8}$ alkynyls;

Wherein, $R^{32}$ is independently of each other selected from the group consisting of hydrogen, deuterium, substituted or unsubstituted $C_{1-8}$ alkyls, substituted or unsubstituted $C_{2-8}$ alkenyls, substituted or unsubstituted $C_{2-8}$ alkynyls, substituted or unsubstituted $C_{3-8}$ cycloalkyls, substituted or unsubstituted 3~8-membered heterocyclic groups, substituted or unsubstituted aryls, and substituted or unsubstituted heteroaryls; said substituents are deuterium, cyano, hydroxyl, carboxyl, halogen, $C_{3-8}$ cycloalkyls or their halogenated or deuterated derivatives, 3~8-membered heterocyclic groups or their halogenated or deuterated derivatives, aryls or their halogenated or deuterated derivatives, and heteroaryls or their halogenated or deuterated derivatives;

n is an integer of 0~5;

$R^2$ is selected from the group consisting of hydrogen, deuterium, halogen, $C_{1-8}$ alkyls or their halogenated or deuterated derivatives, $C_{1-8}$ alkoxyl or their halogenated or deuterated derivatives, $C_{2-8}$ alkenyls or their halogenated or deuterated derivatives, $C_{2-8}$ alkynyls or their halogenated or deuterated derivatives, and 3~8-membered heterocyclic groups or their halogenated or deuterated derivatives;

$R^3$ and $R^4$ are independently of each other selected from the group consisting of hydrogen, deuterium, halogen, substituted or unsubstituted $C_{1-8}$ alkyls; said substituents are deuterium, halogen, $C_{1-8}$ alkyls or their halogenated or deuterated derivatives, $C_{1-8}$ alkoxyls or their halogenated or deuterated derivatives, $C_{3-8}$ cycloalkyls or their halogenated or deuterated derivatives, 3~8-membered heterocyclic groups or their halogenated or deuterated derivatives, aryls or their halogenated or deuterated derivatives, and heteroaryls or their halogenated or deuterated derivatives;

$L^1$ and $L^2$ are independently of each other selected from the group consisting of none, substituted or unsubstituted $C_{1-8}$ alkylenyls; said substituents are deuterium, cyano, hydroxyl, carboxyl, halogen, $C_{1-8}$ alkyls or their halogenated or deuterated derivatives, $C_{1-8}$ alkoxyl or their halogenated or deuterated derivatives, $C_{3-8}$ cycloalkyls or their halogenated or deuterated derivatives, 3~8-membered heterocyclic groups or their halogenated or deuterated derivatives, aryls or their halogenated or deuterated derivatives, and heteroaryls or their halogenated or deuterated derivatives;

$R^5$ is selected from the group consisting of hydrogen, deuterium, halogen, cyano, propadienyl, isocyano, isothiocyano,

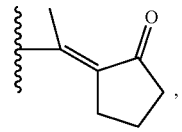 [SMILES: */C(C)=C1\CCCC1=O]

substituted or unsubstituted $C_{1-8}$ alkyls, —$OR^{33}$, —$SR^{33}$, —$OC(O)R^{33}$, $C_{3-8}$-membered cycloalkyls, 3~8-membered heterocyclic groups, aryls, heteroaryls, —$N(R^{33})_2$; or, $R^5$ is selected from the group consisting of —$C(O)R^{33}$, —$C(S)R^{33}$, —$S(O)R^{33}$, —$CON(R^{33})_2$, —$SO_2R^{33}$; or $R^5$ is selected from substituted or unsubstituted $C_{2-8}$ alkenyls, and substituted or unsubstituted $C_{2-8}$ alkynyls;

Wherein, $R^{33}$ are independently of each other selected from the group consisting of hydrogen, deuterium, methylsulfonyl, substituted or unsubstituted $C_{1-8}$ alkyls, substituted or unsubstituted $C_{2-8}$ alkenyls, substituted or unsubstituted $C_{2-8}$ alkynyls, -$L^{31}$-COO-$L^{32}$, substituted or unsubstituted $C_{3-8}$-membered cycloalkyls, substituted or unsubstituted 3~8-membered heterocyclic groups, substituted or unsubstituted aryls, substituted or unsubstituted heteroaryls, —S—$C_{1-8}$ alkyls; $L^{31}$ is selected from substituted or unsubstituted $C_{1-8}$ alkylenyls; $L^{32}$ is selected from substituted or unsubstituted $C_{1-8}$ alkyls;

For above $R^5$ and $R^{33}$, said substituents are deuterium, cyano, hydroxyl, carboxyl, halogen, $C_{1-4}$ alkyls or their halogenated or deuterated derivatives, $C_{1-4}$ alkoxyl or their halogenated or deuterated derivatives, $C_{3-8}$-membered cycloalkyls or their halogenated or deuterated derivatives, 3~8-membered heterocyclic groups or their halogenated or deuterated derivatives, aryls or their halogenated or deuterated derivatives, heteroaryls or their halogenated or deuterated derivatives, —S—$C_{1-4}$ alkyls, =$R^{39}$, substituted or unsubstituted $C_{2-8}$ alkenyls or $C_{2-8}$ alkynyls; in which $R^{39}$ is selected from O, S, $NR^{40}$, or $C(R^{40})_2$, $R^{40}$ is selected from hydrogen, deuterium, halogen, and $C_{1-4}$ alkyls or their halogenated or deuterated derivatives, substituents in said $C_{2-8}$ alkenyls or $C_{2-8}$ alkynyls are selected from deuterium, cyano, hydroxyl, carboxyl, halogen, and $C_{1-4}$ alkyls; Ring A is none, or, ring A is selected from 3~6-membered saturated carbocycles, 3~6-membered unsaturated carbocycles, 3~6-membered saturated heterocycles or 3~6-membered unsaturated heterocycles, all of which are substituted by 0~4 $R^{34}$;

Wherein, $R^{34}$ is independently of each other selected from the group consisting of deuterium, halogen, cyano, isocyano, isothiocyano, nitro, $C_{1-8}$ alkyls or their halogenated or deuterated derivatives, $C_{2-8}$ alkenyls or their halogenated or deuterated derivatives, $C_{2-8}$ alkynyls or their halogenated or deuterated derivatives, —OC(O)$R^{35}$, —C(O)$R^{35}$, —S(O)$R^{35}$, —C(O)N($R^{35}$)$_2$, -$L^{33}$-$R^{36}$, or =$R^{37}$;

$L^{33}$ is selected from $C_{1-4}$ alkylenyls;

$R^{36}$ is selected from cyano, nitro, —OC(O)$R^{35}$, —C(O)$R^{35}$, —S(O)$R^{35}$, and —C(O)N($R^{35}$)$_2$;

$R^{35}$ is independently of each other selected from $C_{1-4}$ alkyls or their halogenated or deuterated derivatives;

$R^{37}$ is selected from O, S, N($R^{38}$), and C($R^{38}$)$_2$; $R^{38}$ is selected from H or $C_{1-4}$ alkyls;

Wherein, when $R^5$ is H and $L^2$ is none, then ring A is not 3~6-membered saturated heterocycles;

When ring A is none, then $L^1$ and $L^2$ are independently of each other selected from none, substituted or unsubstituted $C_{1-8}$ alkylenyls, said substituents are $C_{1-8}$ alkyls or halogen; $R^5$ is C(O)$R^{41}$ or S(O)R; $R^{41}$ is $C_{1-3}$ alkyls or their halogenated or deuterated derivatives;

When ring A is a 3-membered saturated carbocycles not substituted by $R^{34}$, if $L^1$ and $L^2$ are none, then $R^5$ is not hydrogen, ethoxy; if $L^1$ is none, $L^2$ is methylene, then $R^5$ is not methoxy; if $L^1$ is methylene, $L^2$ is none or methylene, then $R^5$ is not methoxy;

When ring A is a 4~6-membered saturated heterocycle not substituted by $R^{34}$, if $L^2$ is none, then $R^5$ is not H; if $R^5$ is H, then $L^2$ is not none;

When n is 0, $R^2$ is methyl, Y is N, $R^3$ and $R^4$ are H, X is O, $L_1$ is methylene, ring A is none, $L_2$ is none, then $R^5$ is not vinyl, ethynyl or propynyl.

Further,

Y is N;

$R^3$ and $R^4$ are independently of each other selected from the group consisting of hydrogen, deuterium, halogen, substituted or unsubstituted $C_{1-8}$ alkyls; said substituents are deuterium, halogen, $C_{1-8}$ alkyls or their halogenated or deuterated derivatives, $C_{1-8}$ alkoxyls or their halogenated or deuterated derivatives, $C_{3-8}$ cycloalkyls or their halogenated or deuterated derivatives, 3~8-membered heterocyclic groups or their halogenated or deuterated derivatives, aryls or their halogenated or deuterated derivatives, and heteroaryls or their halogenated or deuterated derivatives;

Or, X is selected from O or S;

Or, $R^1$ is independently of each other selected from the group consisting of deuterium, halogen, —CN, —NO$_2$, —OR$^{32}$, —C(O)$R^{32}$, —CO$_2$$R^{32}$, —CON($R^{32}$)$_2$, —N($R^{32}$)$_2$, —OC(O)$R^{32}$, $C_{1-3}$ alkyls, $C_{2-3}$ alkenyls, and $C_{2-3}$ alkynyls;

Wherein, $R^{32}$ are independently of each other selected from the group consisting of hydrogen, deuterium, $C_{1-3}$ alkyls, $C_{2-3}$ alkenyls, and $C_{2-3}$ alkynyls;

Or, n is an integer of 0~2;

Or, $R^2$ is selected from hydrogen, deuterium, halogen, and $C_{1-3}$ alkyls or their halogenated or deuterated derivatives.

Further,

The compound is represented by formula II:

Formula II

Y is N;
X is selected from O or S;

$R^5$ is selected from hydrogen, deuterium, halogen, cyano, propadienyl, isocyano, isothiocyano, substituted or unsubstituted $C_{1-8}$ alkyls, —OR$^{33}$, —SR$^{33}$, —OC(O)$R^{33}$, $C_{3-8}$-membered cycloalkyls, 3~8-membered heterocyclic groups, aryls, heteroaryls, and —N($R^{33}$)$_2$; or, $R^5$ is selected from —C(O)$R^{33}$, —C(S)$R^{33}$, —S(O)$R^{33}$, —CON($R^{33}$)$_2$, and —SO$_2$$R^{33}$; or, $R^5$ is selected from substituted or unsubstituted $C_{2-8}$ alkenyls, substituted or unsubstituted $C_{2-8}$ alkynyls; in which, $R^{33}$ are independently of each other selected from the group consisting of hydrogen, deuterium, methylsulfonyl, substituted or unsubstituted $C_{1-8}$ alkyls, substituted or unsubstituted $C_{2-8}$ alkenyls, substituted or unsubstituted $C_{2-8}$ alkynyls, substituted or unsubstituted $C_{3-8}$-membered cycloalkyls, substituted or unsubstituted 3~8-membered heterocyclic groups, substituted or unsubstituted aryls, and substituted or unsubstituted heteroaryls;

For above $R^5$ and $R^{33}$, said substituents are deuterium, cyano, hydroxyl, carboxyl, halogen, $C_{1-4}$ alkyls or their halogenated or deuterated derivatives, $C_{1-4}$ alkoxyl or their halogenated or deuterated derivatives, $C_{3-8}$-membered cycloalkyls or their halogenated or deuterated derivatives, 3~8-membered heterocyclic groups or their halogenated or deuterated derivatives, aryls or their halogenated or deuterated derivatives, heteroaryls or their halogenated or deuterated derivatives, —S—$C_{1-4}$ alkyls, =$R^{39}$, and substituted or unsubstituted $C_{2-6}$ alkenyls or $C_{2-6}$ alkynyls; in which, $R^{39}$ is selected from O, S, N$R^{40}$ or C($R^{40}$)$_2$, $R^{40}$ is selected from hydrogen, deuterium, halogen, $C_{1-4}$ alkyls or their halogenated or deuterated derivatives; For above $C_{2-6}$ alkenyls or $C_{2-6}$ alkynyls, their substituents are selected from deuterium, cyano, hydroxyl, carboxyl, halogen, and $C_{1-4}$ alkyls;

Ring A is none, or, ring A is selected from 3~6-membered saturated carbocycles, 3~6-membered unsaturated carbocycles, 3~6-membered saturated heterocycles or 3~6-membered unsaturated heterocycles, all of which are substituted by 0~4 $R^{34}$;

Wherein, $R^{34}$ is independently of each other selected from the group consisting of deuterium, halogen, cyano, isocyano, isothiocyano, nitro, $C_{1-8}$ alkyls or their halogenated or deuterated derivatives, $C_{2-8}$ alkenyls or their halogenated or deuterated derivatives, $C_{2-8}$ alkynyls or their halogenated or deuterated derivatives, —OC(O)$R^{35}$, —C(O)$R^{35}$, —S(O)$R^{35}$, —C(O)N($R^{35}$)$_2$, -$L^{33}$-$R^{36}$ or =$R^{37}$;

$L^{33}$ is selected from $C_{1-4}$ alkylenyls;

$R^{36}$ is selected from cyano, nitro, —OC(O)$R^{35}$, —C(O)$R^{35}$, —S(O)$R^{35}$, and —C(O)N($R^{35}$)$_2$;

$R^{35}$ is independently of each other selected from $C_{1-4}$ alkyls or their halogenated or deuterated derivatives;

$R^{37}$ is selected from O, S, N($R^{38}$); $R^{38}$ is selected from H or $C_{1-4}$ alkyls.

Further,

Y is N;

X is selected from O or S;

$R^3$ and $R^4$ are independently of each other selected from the group consisting of hydrogen, deuterium, halogen, substituted or unsubstituted $C_{1-4}$ alkyls; said substituents are deuterium, halogen, $C_{1-4}$ alkyls or their halogenated or deuterated derivatives, $C_{1-4}$ alkoxyls or their halogenated or deuterated derivatives, $C_{3-6}$ cycloalkyls or their halogenated or deuterated derivatives, 3~6-membered heterocyclic groups or their halogenated or deuterated derivatives; Or, $R^5$ is selected from hydrogen, deuterium, halogen, propadienyl, cyano, isocyano, isothiocyano,

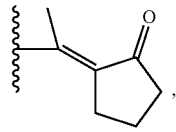 [SMILES: */C(C)=C1\CCCC1=O]

substituted or unsubstituted $C_{1-8}$ alkyls, —$OR^{33}$, —$SR^{33}$, —$OC(O)R^{33}$, $C_{3-8}$-membered cycloalkyls, 3~8-membered heterocyclic groups, aryls, heteroaryls, —$N(R^{33})_2$; or, $R^5$ is selected from —$C(O)R^{33}$, —$C(S)R^{33}$, —$S(O)R^{33}$, —$CON(R^{33})_2$, —$SO_2R^{33}$; or, $R^5$ is selected from substituted or unsubstituted $C_{2-8}$ alkenyls, substituted or unsubstituted $C_{2-8}$ alkynyls;

Wherein, $R^{33}$ are independently of each other selected from the group consisting of hydrogen, deuterium, methylsulfonyl, substituted or unsubstituted $C_{1-4}$ alkyls, substituted or unsubstituted $C_{2-4}$ alkenyls, substituted or unsubstituted $C_{2-4}$ alkynyls, $C_{3-8}$-membered cycloalkyls, 3~8-membered heterocyclic groups, aryls, heteroaryls;

Substituents in above-mentioned $R^5$ and $R^{33}$ are deuterium, cyano, hydroxyl, carboxyl, halogen, $C_{1-4}$ alkyls or their halogenated or deuterated derivatives, $C_{1-4}$ alkoxyls or their halogenated or deuterated derivatives, $C_{3-8}$-membered cycloalkyls, 3~8-membered heterocyclic groups, aryls, heteroaryls, —S—$C_{1-4}$ alkyls, =$R^{39}$, substituted or unsubstituted $C_{2-4}$ alkenyls or $C_{2-4}$ alkynyls; in which, $R^{39}$ is selected from O, S, $NR^{40}$ or $C(R^{40})_2$, $R^{40}$ is selected from hydrogen, deuterium, halogen, $C_{1-4}$ alkyls or their halogenated or deuterated derivatives; substituents in said $C_{2-4}$ alkenyls or $C_{2-4}$ alkynyls are selected from deuterium, cyano, hydroxyl, carboxyl, halogen, and $C_{1-4}$ alkyls;

Or, $L^1$ and $L^2$ are independently of each other selected from none, substituted or unsubstituted $C_{1-4}$ alkylenyls; said substituents are deuterium, cyano, hydroxyl, carboxyl, halogen, $C_{1-4}$ alkyls or their halogenated or deuterated derivatives, $C_{1-4}$ alkoxyl or their halogenated or deuterated derivatives, $C_{3-5}$ cycloalkyls or their halogenated or deuterated derivatives, 3~5-membered heterocyclic groups or their halogenated or deuterated derivatives, aryls or their halogenated or deuterated derivatives, and heteroaryls or their halogenated or deuterated derivatives;

Or, ring A is none, or ring A is selected from 3~6-membered saturated carbocycles, 3~6-membered unsaturated carbocycles, 3~6-membered saturated heterocycles or 3~6-membered unsaturated heterocycles, all of which are substituted by 0~4 $R^{34}$;

Wherein, $R^{34}$ is independently of each other selected from deuterium, halogen, cyano, isocyano, isothiocyano, $C_{1-4}$ alkyls or their halogenated or deuterated derivatives, $C_{2-4}$ alkenyls or their halogenated or deuterated derivatives, $C_{2-4}$ alkynyls or their halogenated or deuterated derivatives, and =$R^{37}$;

$R^{37}$ is selected from O or S.

Further,

Y is N;

X is selected from O or S;

$R^3$ and $R^4$ are independently of each other selected from the group consisting of hydrogen, deuterium, halogen, substituted or unsubstituted $C_{1-2}$ alkyls; said substituents are deuterium, halogen, $C_{1-2}$ alkyls or their halogenated or deuterated derivatives, and $C_{1-2}$ alkoxyl or their halogenated or deuterated derivatives;

Or, $R^5$ is selected from hydrogen, deuterium, halogen, propadienyl, cyano, isocyano, isothiocyano,

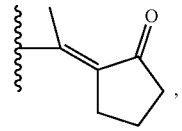 [SMILES: */C(C)=C1\CCCC1=O]

substituted or unsubstituted $C_{1-8}$ alkyls, —$OR^{33}$, —$SR^{33}$, —$OC(O)R^{33}$, $C_{3-8}$-membered cycloalkyls, 3~8-membered heterocyclic groups, aryls, heteroaryls, —$N(R^{33})_2$; or $R^5$ is selected from —$C(O)R^{33}$, —$C(S)R^{33}$, —$S(O)R^{33}$, —$CON(R^{33})_2$, —$SO_2R^{33}$; or, $R^5$ is selected from substituted or unsubstituted $C_{2-8}$ alkenyls, substituted or unsubstituted $C_{2-8}$ alkynyls;

Wherein, $R^{33}$ are independently of each other selected from the group consisting of hydrogen, deuterium, methylsulfonyl, substituted or unsubstituted $C_{1-2}$ alkyls, $C_{3-6}$-membered cycloalkyls, 3~6-membered heterocyclic groups, aryls, and heteroaryls;

Substituents in above-mentioned $R^5$ and $R^{33}$ are deuterium, halogen, cyano, hydroxyl, $C_{1-3}$ alkyls or their halogenated or deuterated derivatives, $C_{1-3}$ alkoxyl or their halogenated or deuterated derivatives, $C_{3-6}$-membered cycloalkyls, 3~6-membered heterocyclic groups, aryls, heteroaryls, —S—$C_{1-2}$ alkyls, =$R^{39}$, substituted or unsubstituted $C_{2-4}$ alkenyls or $C_{2-4}$ alkynyls; in which $R^{39}$ is selected from O, S, $NR^{40}$ or $C(R^{40})_2$, $R^{40}$ is selected from hydrogen, deuterium, halogen, $C_{1-3}$ alkyls or their halogenated or deuterated derivatives; substituents in said $C_{2-4}$ alkenyls or $C_{2-4}$ alkynyls are selected from deuterium, cyano, hydroxyl, carboxyl, halogen, and $C_{1-3}$ alkyls; Or, $L^1$ and $L^2$ are independently of each other selected from none, substituted or unsubstituted $C_{1-3}$ alkylenyls; said substituents are deuterium, halogen, $C_{1-3}$ alkyls or their halogenated or deuterated derivatives, and $C_{1-3}$ alkoxyl or their halogenated or deuterated derivatives; Or, ring A is none, or ring A is selected from 3~6-membered saturated carbocycles, 3~6-membered unsaturated heterocycles, and 3~6-membered saturated heterocycles, all of which are substituted by 0~3 $R^{34}$;

Wherein, $R^{34}$ is independently of each other selected from deuterium, halogen, cyano, isocyano, isothiocyano, $C_{1-3}$ alkyls, $C_{2-3}$ alkenyls, $C_{2-3}$ alkynyls, and =$R^{37}$; $R^{37}$ is selected from O or S.

Further,

Y is N;

X is selected from O or S;

$R^3$ and $R^4$ are independently of each other selected from the group consisting of hydrogen, deuterium, halogen, and halogenated or un-halogenated methyl; Or, $R^5$ is selected from hydrogen, deuterium, halogen, propadienyl, cyano, isocyano, isothiocyano,

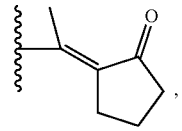 [SMILES: */C(C)=C1\CCCC1=O]

substituted or unsubstituted $C_{1-8}$ alkyls, —$OR^{33}$, —$SR^{33}$, —$OC(O)R^{33}$, $C_{3-8}$-membered cycloalkyls, 3~8-membered heterocyclic groups, aryls, heteroaryls, —N(R$^{33}$)$_2$; or R$^5$ is selected from —C(O)R$^{33}$, —C(S)R$^{33}$, —S(O)R$^{33}$, —CON(R$^{33}$)$_2$, and —SO$_2$R$^{33}$; or R$^5$ is selected from substituted or unsubstituted C$_{2-6}$ alkenyls, and substituted or unsubstituted C$_{2-6}$ alkynyls;

Wherein, R$^{33}$ is selected from hydrogen, deuterium, methylsulfonyl, acetyl, and C$_{1-2}$ alkyls; Said substituents in above-mentioned R$^5$ and R$^{33}$ are deuterium, halogen, hydroxyl, cyano, C$_{1-2}$ alkyls, 3~5-membered heterocyclic groups, —S—CH$_3$, =R$^{39}$, substituted or unsubstituted C$_{2-4}$ alkenyls or C$_{2-4}$ alkynyls; wherein, R$^{39}$ is selected from O, S, NR$^{40}$ or C(R$^{40}$)$_2$, R$^{40}$ is selected from hydrogen, deuterium, halogen, C$_{1-3}$ alkyls; substituents in said C$_{2-4}$ alkenyls or C$_{2-4}$ alkynyls are selected from deuterium, cyano, hydroxyl, carboxyl, halogen, and C$_{1-2}$ alkyls;

Or, L$^1$ and L$^2$ are independently of each other selected from none, substituted or unsubstituted C$_{1-2}$ alkylenyls; said substituents are deuterium, halogen, and C$_{1-2}$ alkyls;

Or, ring A is none, or ring A is selected from 3~6-membered saturated carbocycles, 3~6-membered unsaturated heterocycles, or 3~6-membered saturated heterocycles, all of which are substituted by 0~2 R$^{34}$;

Wherein, R$^{34}$ is independently of each other selected from deuterium, halogen, cyano, isocyano, isothiocyano, C$_{2-3}$ alkenyls, C$_{2-3}$ alkynyls, C$_{1-2}$ alkyls, and =R$^{37}$;

R$^{37}$ is selected from O or S.

Further,

The compound is represented by formula IIAA:

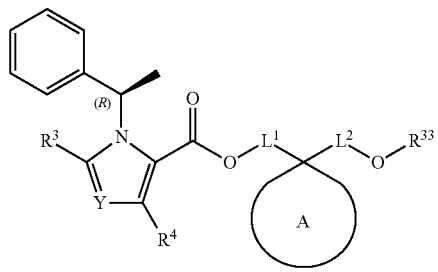

Formula IIAA

Wherein, Y is selected from N;

R$^3$ and R$^4$ are independently of each other selected from the group consisting of hydrogen or deuterium;

L$^1$ and L$^2$ are independently of each other selected from none or methylene;

R$^{33}$ is selected from hydrogen, deuterium, C$_{1-2}$ alkyls, -L$^{31}$-COO-L$^{32}$, 6-membered heterocyclic groups; L$^{31}$ is selected from methylene; L$^{32}$ is selected from methyl;

Ring A is selected from 3~4-membered saturated carbocycles;

Or,

Said compound has a structure of formula IIAB:

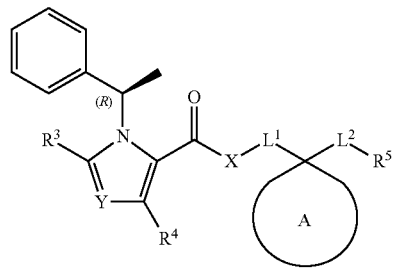

Formula IIAB

Wherein, Y is selected from N;

X is selected from O or S;

R$^3$ and R$^4$ are independently of each other selected from the group consisting of hydrogen or deuterium;

L$^1$ and L$^2$ are independently of each other selected from none, substituted or unsubstituted C$_{1-2}$ alkylenyls; said substituents are deuterium, F, methyl;

R$^5$ is selected from hydrogen, deuterium, halogen, substituted or unsubstituted methyl, —OC(O)R$^{33}$, and 3-membered heterocyclic groups;

Wherein, R$^{33}$ is selected from methyl; said substituents are deuterium, F, C$_{1-2}$ alkyls, and 3-membered heterocyclic groups;

Ring A is selected from 3~6-membered saturated carbocycles substituted by 0~2 R$^{34}$; wherein, R$^{34}$ is independently of each other selected from deuterium, F or =R$^{37}$; R$^{37}$ is selected from 0;

Or,

Said compound has a structure of formula IIAC:

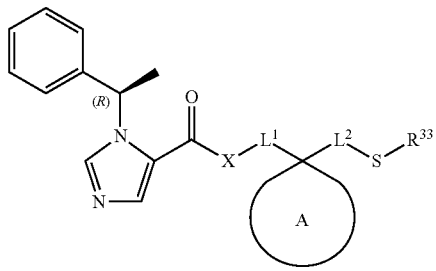

Formula IIAC

Wherein, X is selected from O or S;

L$^1$ and L$^2$ are independently of each other selected from none or methylene;

R$^{33}$ is selected from C$_{1-2}$ alkyls, —S—CH$_3$;

Ring A is selected from 3~4-membered saturated carbocycles;

Or,

Said compound has a structure of formula IIAD:

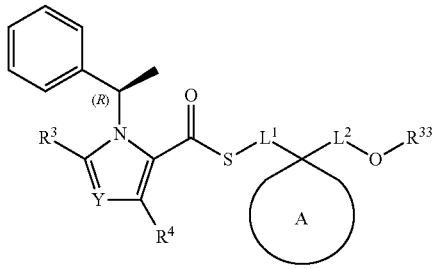

Formula IIAD

Wherein, Y is selected from N; R$^3$ and R$^4$ are independently of each other selected from the group consisting of hydrogen or deuterium;

L$^1$ and L$^2$ are independently of each other selected from none or methylene; R$^{33}$ is selected from hydrogen, deuterium, C$_{1-2}$ alkyls, -L$^{31}$-COO-L$^{32}$, 6-membered heterocyclic groups; L$^{31}$ is selected from methylene; L$^{32}$ is selected from methyl;

Ring A is selected from 3~4-membered saturated carbocycles;

Or,

Said compound has a structure of formula IIBA:

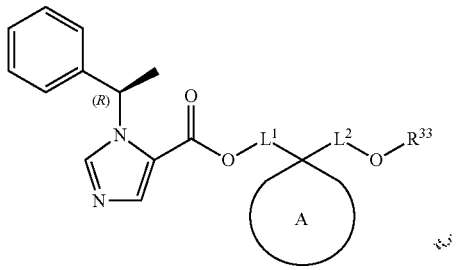

Formula IIBA $L^1$ and $L^2$ are independently of each other selected from none, substituted or unsubstituted methylene; said substituents are deuterium, methyl;

$R^{33}$ is selected from hydrogen, deuterium, methylsulfonyl, acetyl, methyl;

Ring A is selected from 4-membered saturated heterocycles;

Or,

Said compound has a structure of formula IIBB:

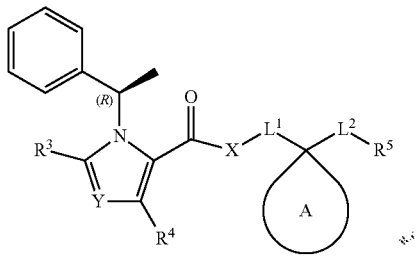

Formula IIBB

Y is selected from N;

X is selected from O or S;

$R^3$ and $R^4$ are independently of each other selected from the group consisting of hydrogen or deuterium;

$L^1$ and $L^2$ are independently of each other selected from none, substituted or unsubstituted $C_{1-2}$ alkylenyls; said substituents are deuterium, F, Cl, and $C_{1-2}$ alkyls;

$R^5$ is selected from hydrogen, deuterium, F, Cl, substituted or unsubstituted $C_{1-2}$ alkyls, 3-membered heterocyclic groups;

said substituents are deuterium, F, Cl, $C_{1-2}$ alkyls, 3-membered heterocyclic groups, and —S—CH$_3$;

Ring A is selected from 3~4-membered saturated heterocycles substituted by 0~2 $R^{34}$; Wherein, $R^{34}$ is independently of each other selected from deuterium or methyl;

Or,

Said compound has a structure of formula IIBC:

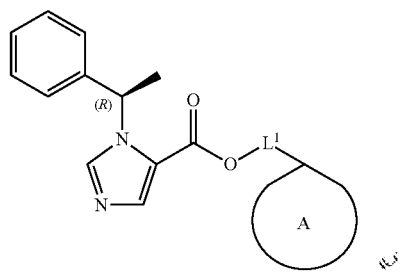

Formula IIBC $L^1$ is selected from none or methylene;

Ring A is selected from 4~5-membered saturated heterocycles or 5-membered unsaturated heterocycles, all of which are substituted by one $R^{34}$; wherein, $R^{34}$ is selected from =$R^{37}$; $R^{37}$ is selected from O;

Or,

Said compound has a structure of formula IICA:

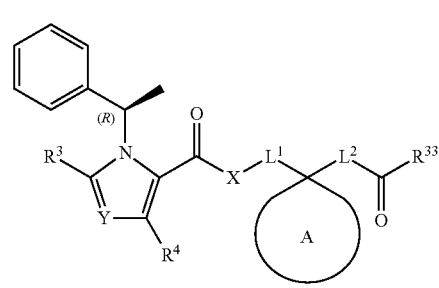

Formula IICA

In the formula,

X is selected from O or S;

Y is N;

$R^3$ and $R^4$ are independently of each other selected from the group consisting of hydrogen, deuterium;

$L^1$ and $L^2$ are independently of each other selected from none, substituted or unsubstituted $C_{1-2}$ alkylenyls; said substituted substituent is deuterium, and methyl;

$R^{33}$ is selected from hydrogen, deuterium, $C_{1-2}$ alkyls;

Ring A is none, or ring A is selected from 3~6-membered saturated carbocycles or 4-membered saturated heterocycles;

Or,

Said compound has a structure of formula IICB:

Formula IICB

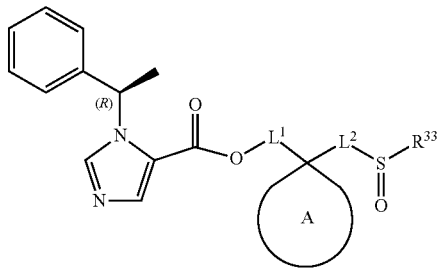

In the formula,
$L^1$ and $L^2$ are independently of each other selected from none, and $C_{1-2}$ alkylenyls;
$R^{33}$ is selected from methyl;
Ring A is none;

Or,

Said compound has a structure of formula IICC:

Formula IICC

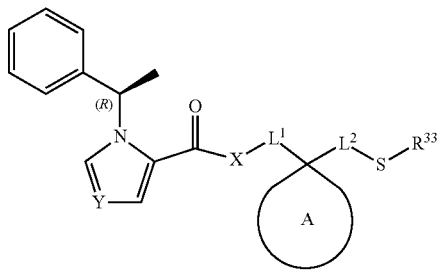

In the formula,
X is selected from O or S;
Y is N;
$L^1$ and $L^2$ are independently of each other selected from none, and $C_{1-2}$ alkylenyls;
$R^{33}$ is selected from methyl;
Ring A is none;

Or,

Said compound has a structure of formula IICD:

Formula IICD

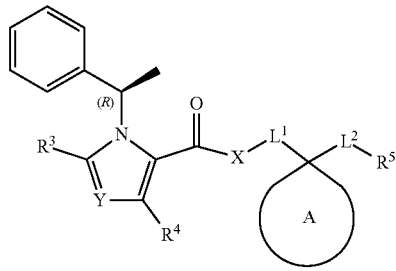

In the formula,
X is O or S;
$L^1$ and $L^2$ are independently of each other selected from none, substituted or unsubstituted $C_{1-4}$ alkylenyls; said substituents are $C_{1-4}$ alkyls or $C_{1-4}$ alkoxyl;

Ring A is none;
$R^5$ is H;

Or,

Said compound has a structure of formula IIDA:

Formula IIDA

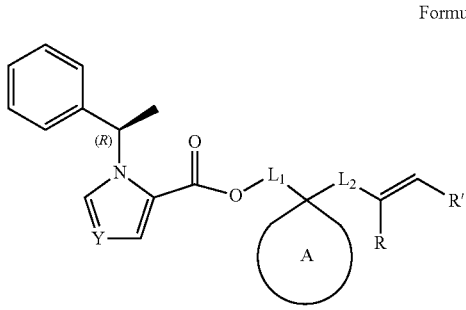

Y is selected from N;
$L^1$ and $L^2$ are independently of each other selected from none, substituted or unsubstituted $C_{1-2}$ alkylenyls; said substituted substituents are deuterium, $C_{1-2}$ alkyls;

R, R' are independently of each other selected from the group consisting of hydrogen, deuterium, $C_{1-2}$ alkyls, $C_{1-2}$ alkoxyl, substituted or unsubstituted $C_{2-4}$ alkenyls or $C_{2-4}$ alkynyls, and said substituents are selected from hydroxyl, $C_{1-2}$ alkyls;

Ring A is none, or ring A is selected from 3~6-membered saturated carbocycles or 4-membered saturated heterocycles;

Or,

Said compound has a structure of formula IIDB:

Formula IIDB

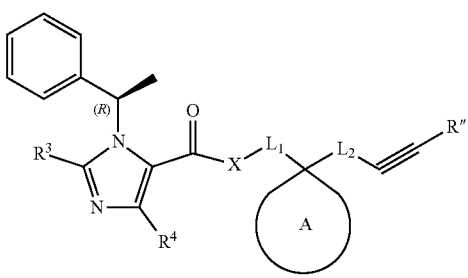

X is selected from O or S;

$R^3$ and $R^4$ are independently of each other selected from the group consisting of hydrogen, deuterium;

$L^1$ and $L^2$ are independently of each other selected from none, substituted or unsubstituted methylene; said substituted substituent is deuterium, $C_{1-2}$ alkyls;

R" is selected from hydrogen, deuterium, $C_{1-2}$ alkyls, $C_{1-2}$ alkoxyl, substituted or unsubstituted $C_{2-4}$ alkenyls or $C_{2-4}$ alkynyls, and said substituent is selected from hydroxyl, $C_{1-2}$ alkyls;

Ring A is none, or ring A is selected from 3~6-membered saturated carbocycles or 4~6-membered saturated heterocycles;

Or,

Said compound has a structure of formula IIDC:

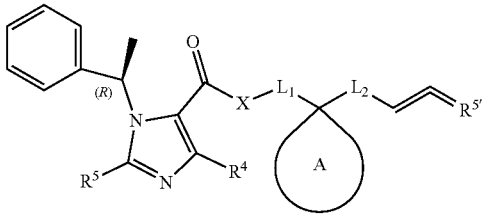

Formula IIDC

X is selected from O or S;

$R^3$ and $R^4$ are independently of each other selected from the group consisting of hydrogen, deuterium;

$L^1$ and $L^2$ are independently of each other selected from none, substituted or unsubstituted methylene; said substituted substituent is deuterium, $C_{1-2}$ alkyls;

$R^{5'}$ is selected from S or $CH_2$;

Ring A is none, or ring A is selected from 3~6-membered saturated carbocycles or 4~6-membered saturated heterocycles;

Or,

Said compound has a structure of formula IIEA:

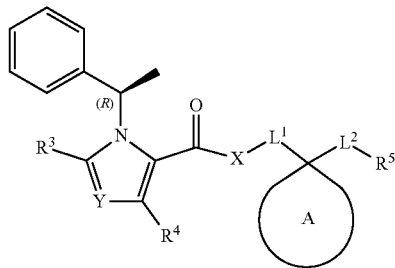

Formula IIEA

Y is selected from N;

X is selected from O or S;

Ring A is selected from 3~6-membered saturated carbocycles substituted by 0~2 $R^{34}$;

Wherein, $R^{34}$ is independently of each other selected from deuterium, halogen, cyano, isothiocyano;

$R^3$ and $R^4$ are independently of each other selected from the group consisting of hydrogen, deuterium, halogen, halogenated or un-halogenated methyl, as well as both of $R^3$ and $R^4$ are not simultaneously hydrogen or deuterium;

$L^1$ and $L^2$ are independently of each other selected from none, substituted or unsubstituted methylene; said substituents are deuterium, $C_{1-4}$ alkyls;

$R^5$ is selected from hydrogen, deuterium, cyano, isocyano, isothiocyano,

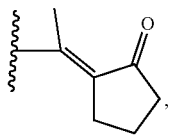 [SMILES: */C(C)=C1\CCCC1=O]

$C_{1-2}$ alkyls, substituted or unsubstituted $C_{2-4}$ alkenyls, substituted or unsubstituted $C_{2-4}$ alkynyls, $-OR^{33}$, $-C(O)R^{33}$;

Wherein, $R^{33}$ is independently of each other selected from $C_{1-2}$ alkyls; said substituent in $R^5$ is selected from $=R^{39}$, $C_{2-4}$ alkenyls or $C_{2-4}$ alkynyls; $R^{39}$ is selected from S, $CH_2$;

Or,

Said compound has a structure of formula IIEA, Y is selected from N;

X is selected from O or S;

Ring A is selected from 3~6-membered saturated heterocycles substituted by 0~2 $R^{34}$;

Wherein, $R^{34}$ is independently of each other selected from deuterium, halogen, cyano, isothiocyano;

$R^3$ and $R^4$ are independently of each other selected from the group consisting of hydrogen, deuterium, halogen, halogenated or un-halogenated methyl, as well as both of $R^3$ and $R^4$ are not simultaneously hydrogen or deuterium;

$L^1$ and $L^2$ are independently of each other selected from none, substituted or unsubstituted methylene; said substituents are deuterium, $C_{1-4}$ alkyls;

$R^5$ is selected from hydrogen, deuterium, cyano, isocyano, isothiocyano,

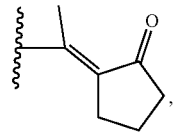 [SMILES: */C(C)=C1\CCCC1=O]

$C_{1-2}$ alkyls, substituted or unsubstituted $C_{2-4}$ alkenyls, substituted or unsubstituted $C_{2-4}$ alkynyls, $-OR^{33}$, $-C(O)R^{33}$;

Wherein, $R^{33}$ is independently of each other selected from $C_{1-2}$ alkyls; the substituent in $R^5$ is selected from $=R^{39}$, $C_{2-4}$ alkenyls or $C_{2-4}$ alkynyls; $R^{39}$ is selected from S, $CH_2$;

Or,

Said compound has a structure of formula IIEA, Y is selected from N;

X is selected from O or S;

Ring A is none;

$R^3$ and $R^4$ are independently of each other selected from the group consisting of hydrogen, deuterium, halogen, halogenated or un-halogenated methyl, as well as both of $R^3$ and $R^4$ are not simultaneously hydrogen or deuterium;

$L^1$ and $L^2$ are independently of each other selected from none, substituted or unsubstituted methylene; said substituents are deuterium, $C_{1-4}$ alkyls;

$R^5$ is selected from hydrogen, deuterium, cyano, isocyano, isothiocyano,

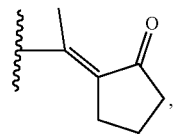 [SMILES: */C(C)=C1\CCCC1=O]

$C_{1-2}$ alkyls, substituted or unsubstituted $C_{2-4}$ alkenyls, substituted or unsubstituted $C_{2-4}$ alkynyls, $-OR^{33}$, $-C(O)R^{33}$;

Wherein, $R^{33}$ is independently of each other selected from $C_{1-2}$ alkyls; said substituent in $R^5$ is selected from $=R^{39}$, $C_{2-4}$ alkenyls or $C_{2-4}$ alkynyls; $R^{39}$ is selected from S, $CH_2$.

Further,
The compound is:
Compound A1
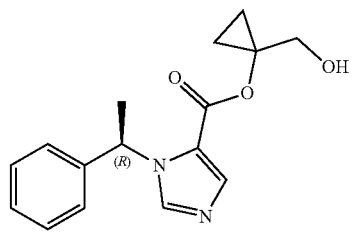
Compound A2
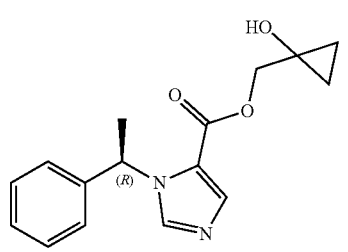
Compound A3
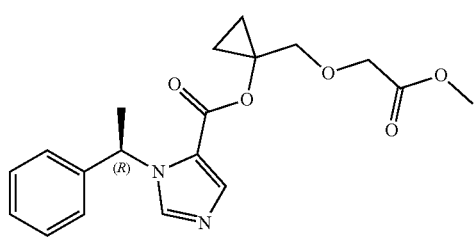
Compound A4
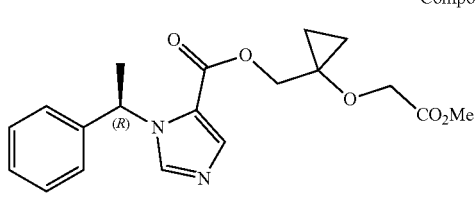
Compound A5
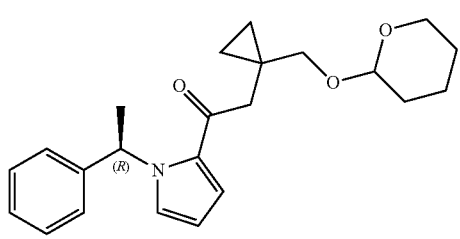
Compound A6
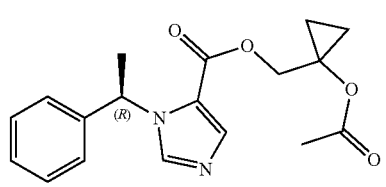
Compound A7
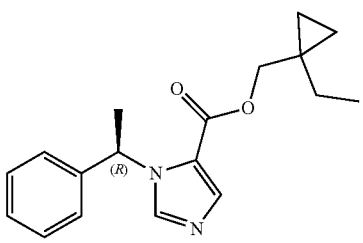
Compound A8
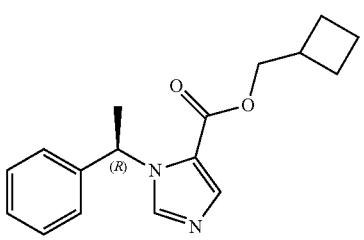
Compound A9
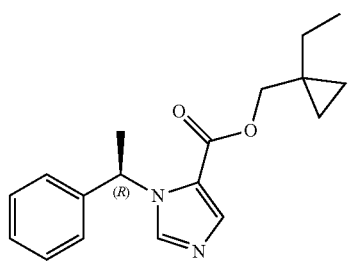
Compound A10
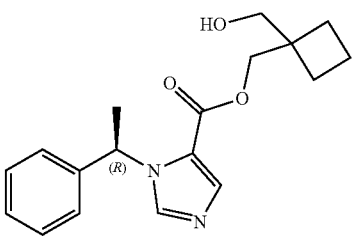
Compound A11
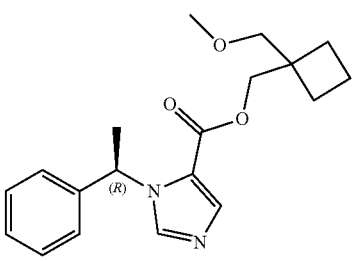
Compound A12
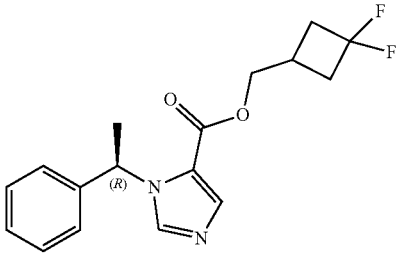

Compound A13

Compound A14

Compound A15

Compound A16

Compound A17

Compound A18

Compound A19

Compound A20

Compound A21

Compound A22

Compound A23

Compound A24

Compound A25
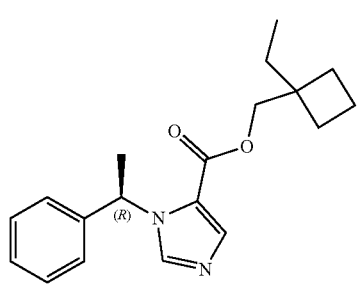
Compound A31
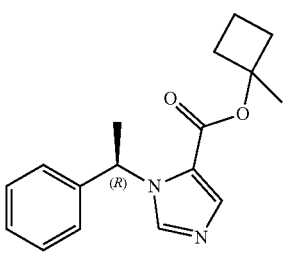
Compound A26
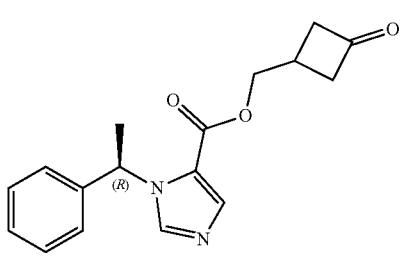
Compound A32
Compound A27
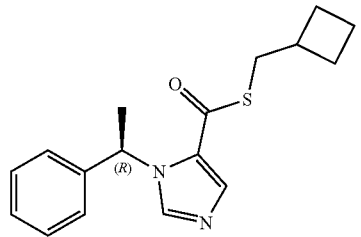
Compound A33
Compound A28
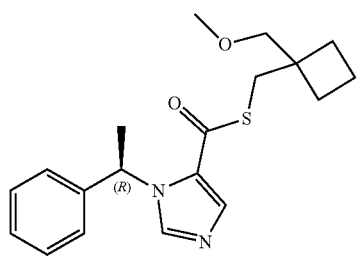
Compound A34
Compound A29
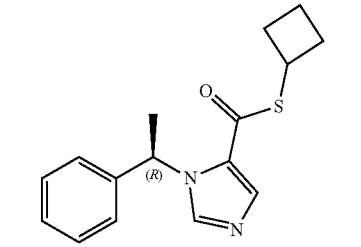
Compound A35
Compound A30
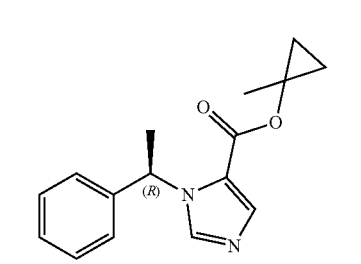
Compound A36

Compound A37
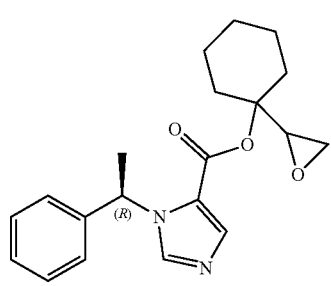
Compound A38
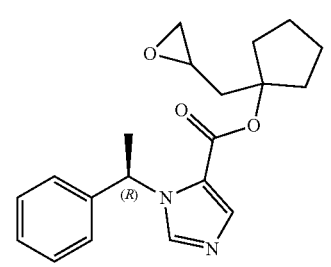
Compound A39
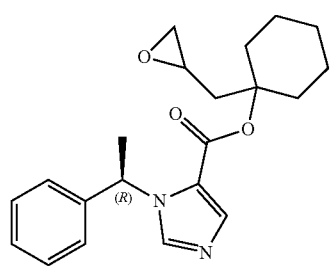
Compound A40
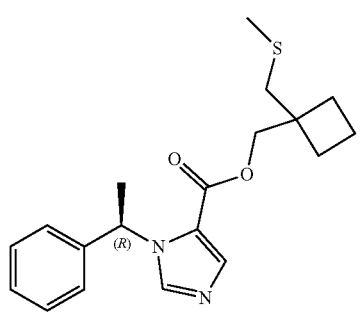
Compound A41
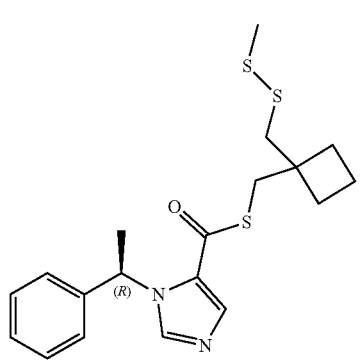
Compound A42
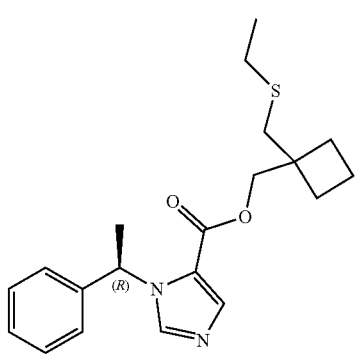
Compound A43
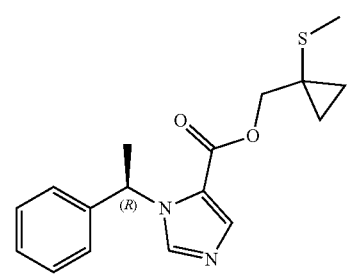
Compound A44
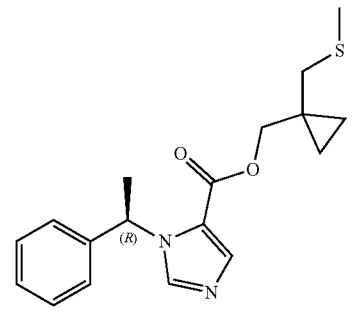
Compound A45
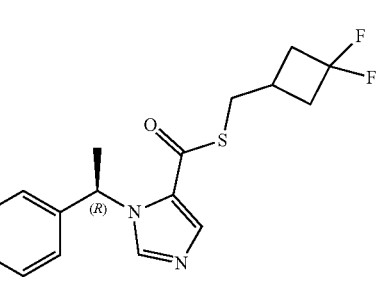
Compound A46
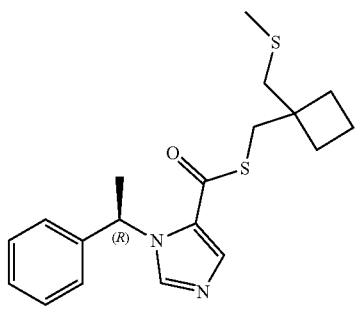

Compound B1
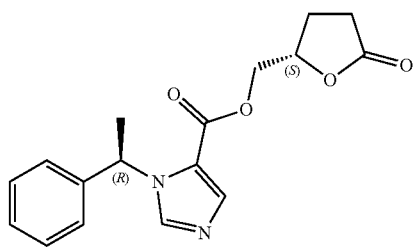
Compound B2
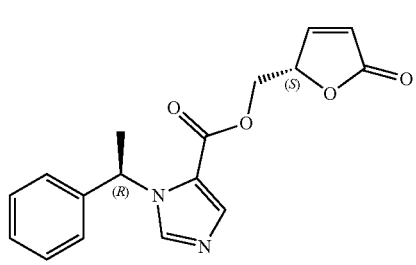
Compound B3
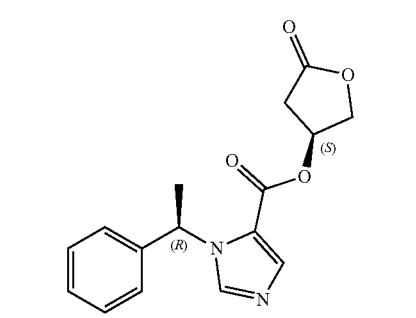
Compound B4
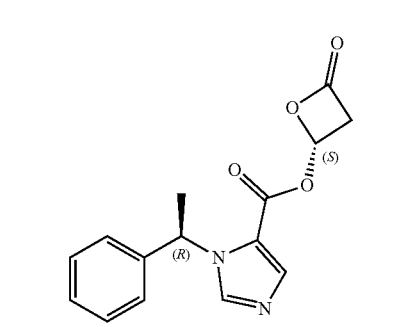
Compound B5
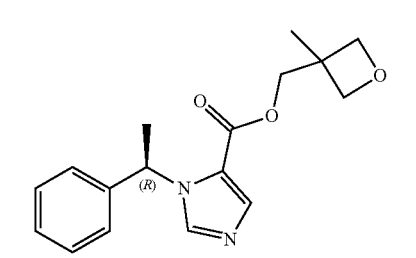
Compound B6
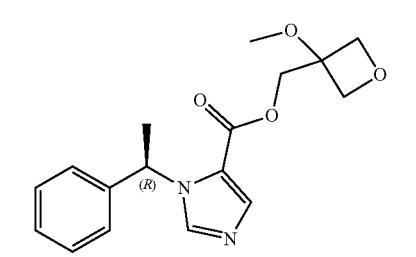
Compound B7
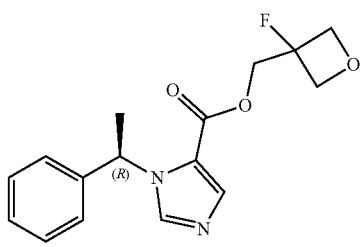
Compound B8
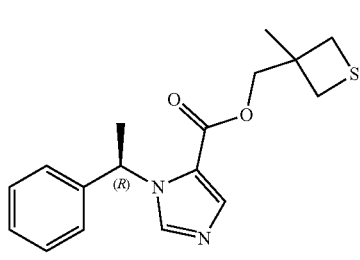
Compound B9
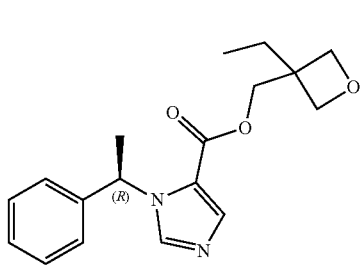
Compound B10
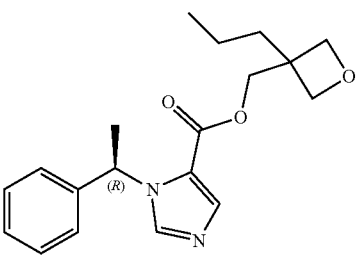
Compound B11
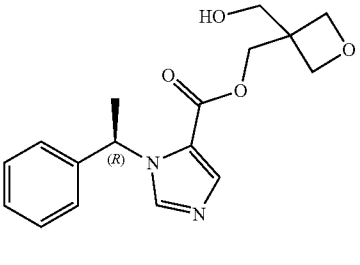
Compound B12
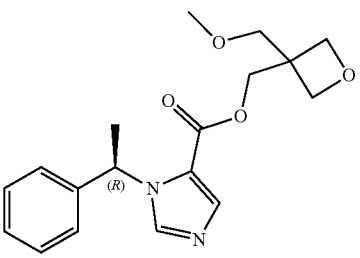

Compound B13
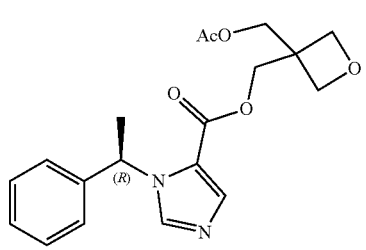
Compound B14
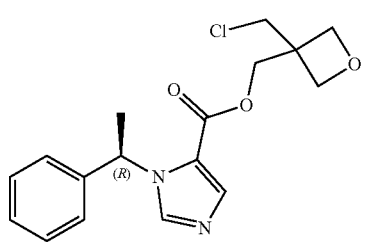
Compound B15
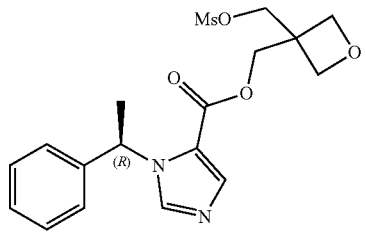
Compound B16
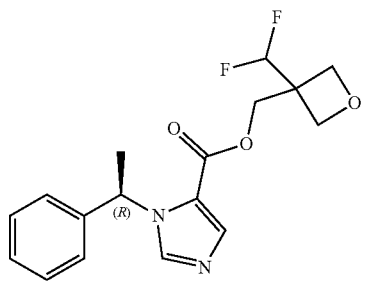
Compound B17
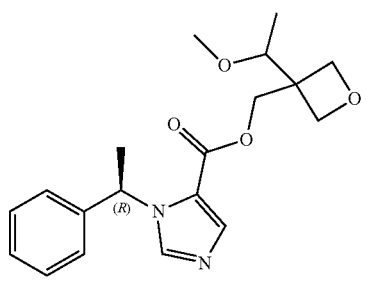
Compound B18
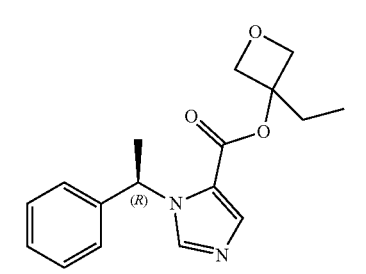
Compound B19
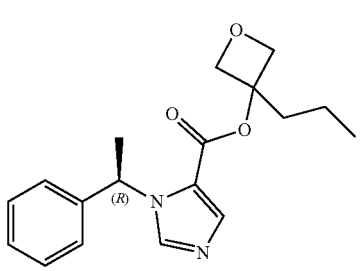
Compound B20
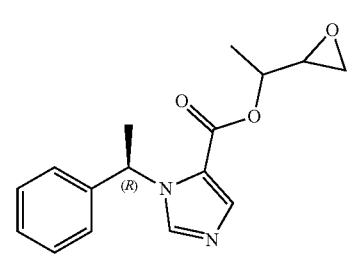
Compound B21
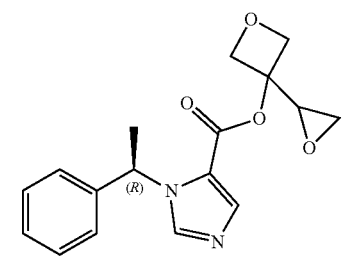
Compound B22
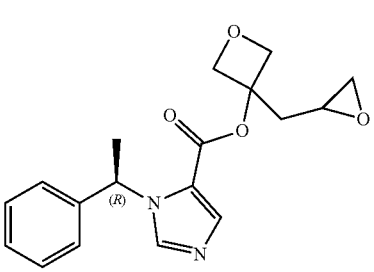
Compound B23
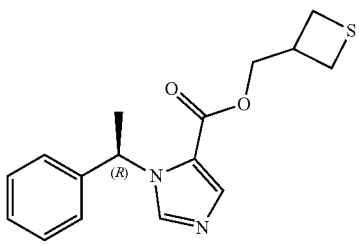
Compound B24
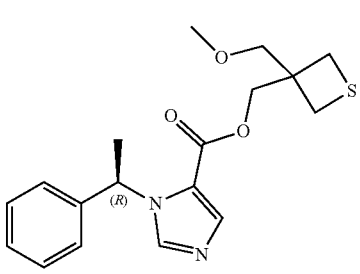

Compound B25
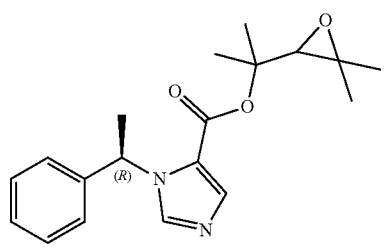
Compound B26
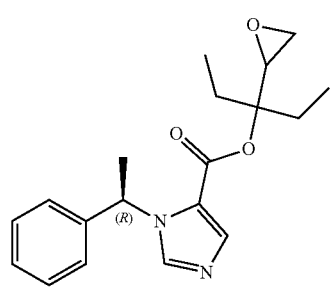
Compound B27
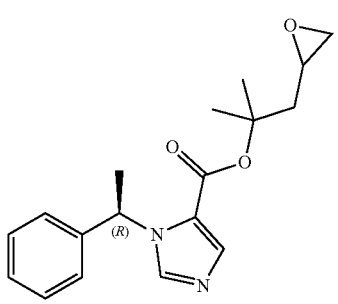
Compound B28
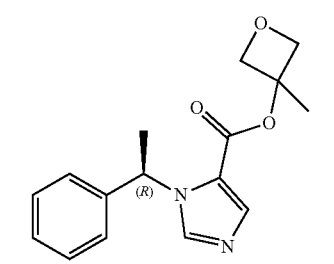
Compound B29
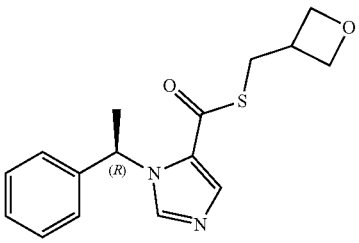
Compound B30
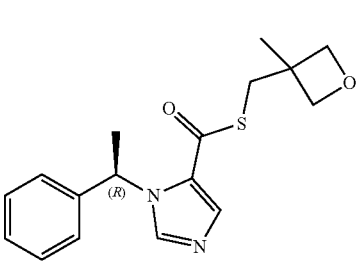
Compound B31
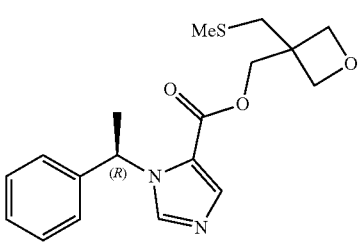
Compound C1
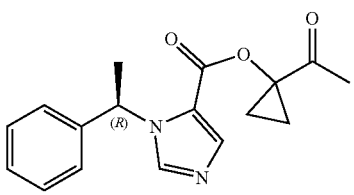
Compound C2
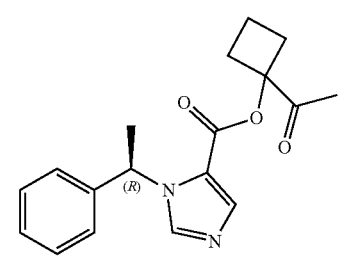
Compound C3
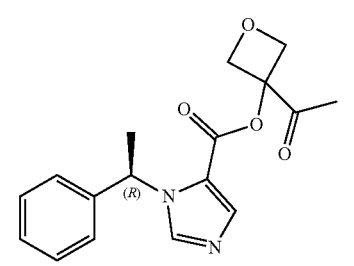
Compound C4
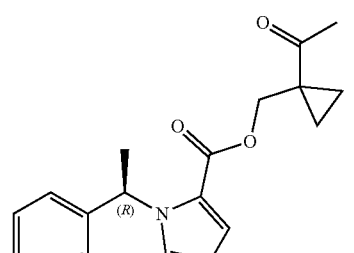
Compound C5
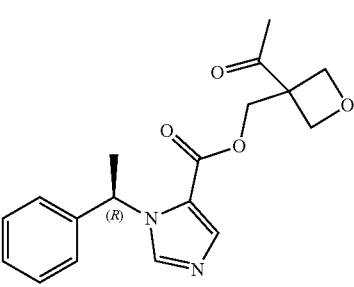

-continued
Compound C6
Compound C7
Compound C8
Compound C9
Compound C10
Compound C11
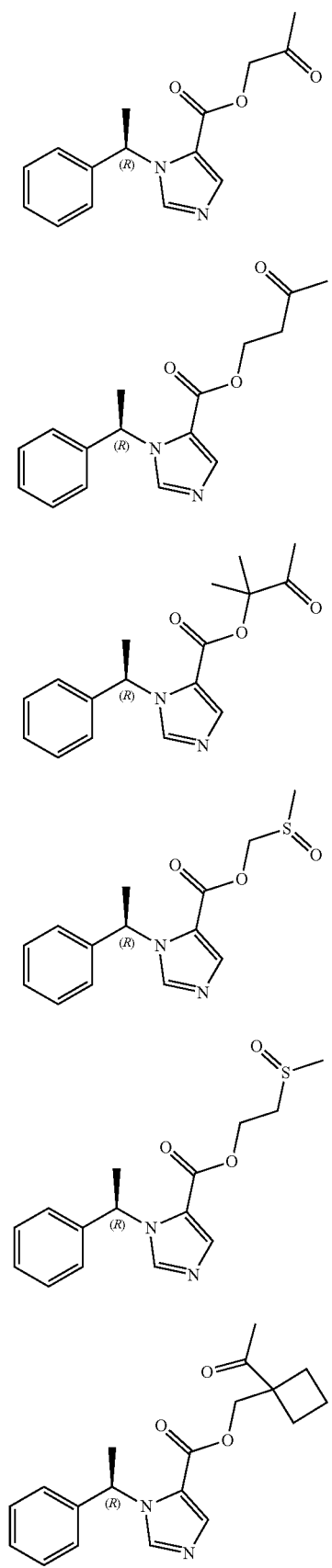
-continued
Compound C12
Compound C13
Compound C14
Compound C15
Compound C16
Compound C17
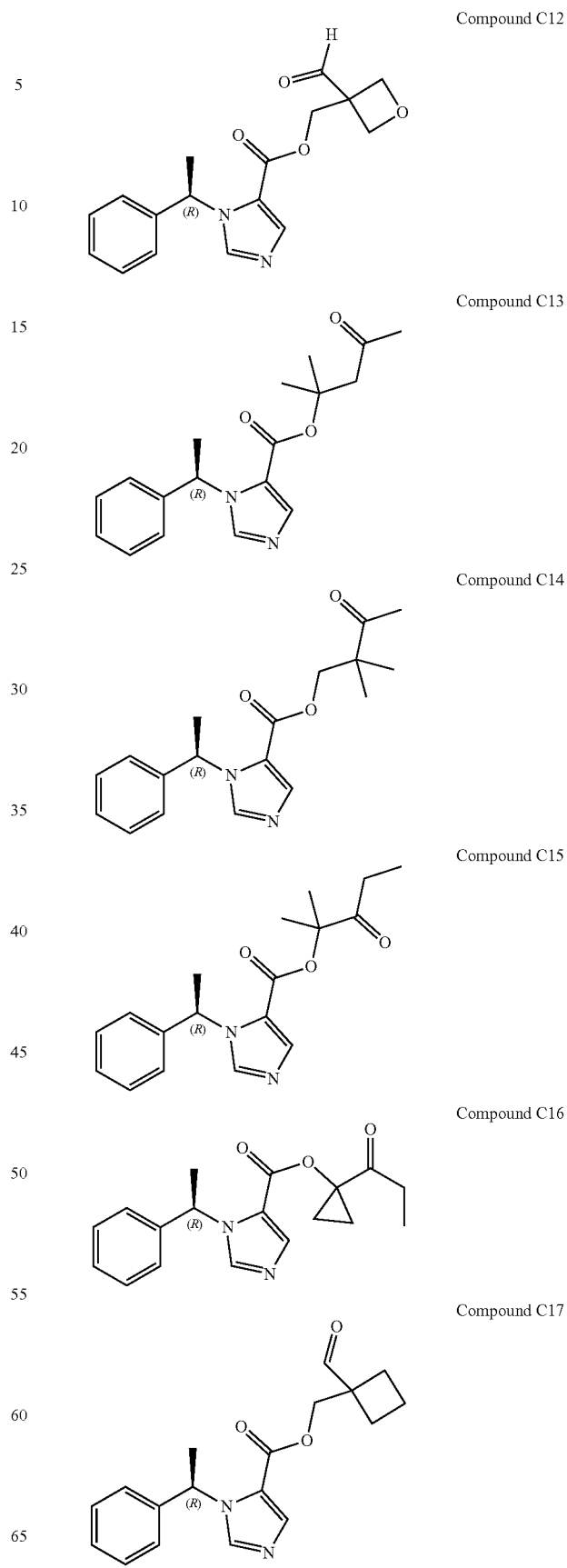

Compound C18
Compound C19
Compound C20
Compound C21
Compound C22
Compound C23
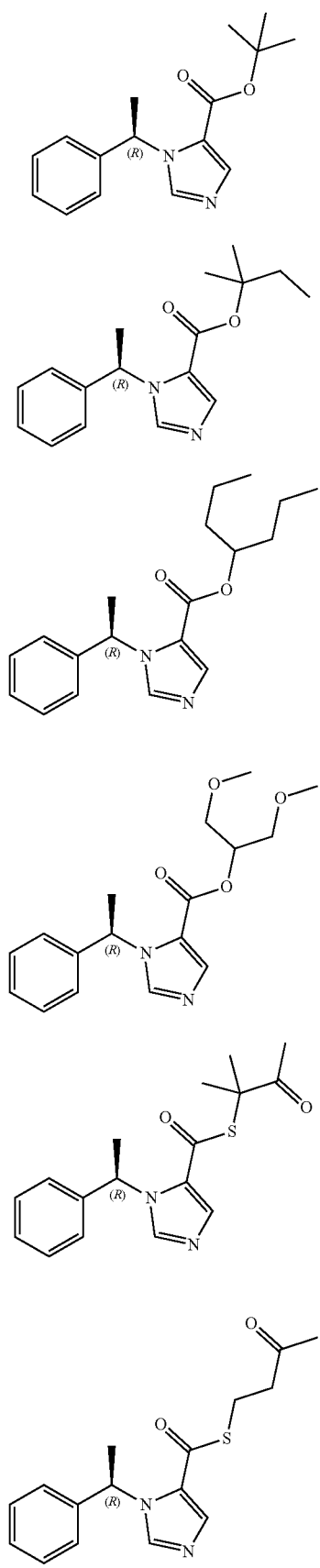
Compound C24
Compound C25
Compound C26
Compound C27
Compound C28
Compound C29
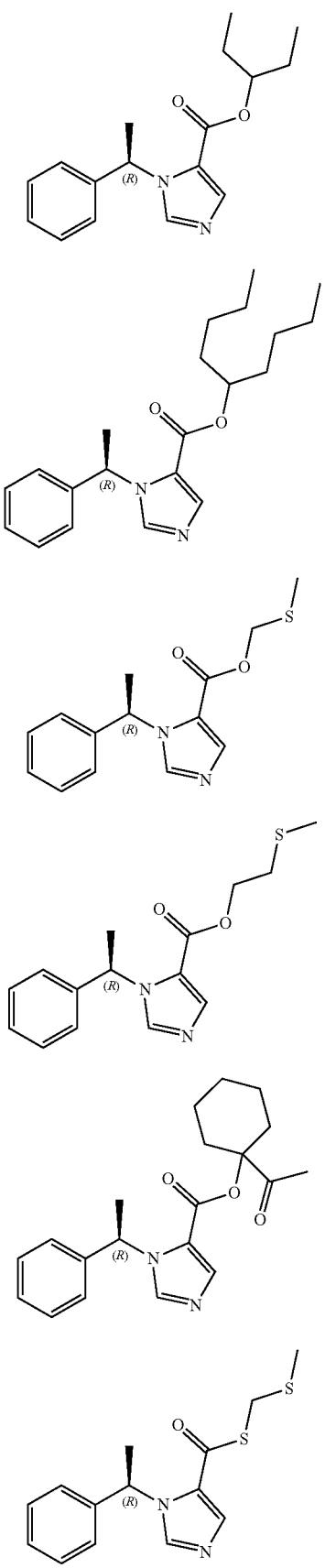

Compound C30
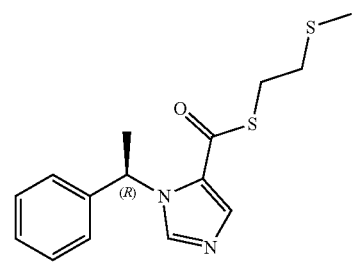
Compound D1
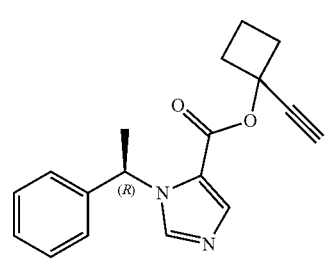
Compound D2
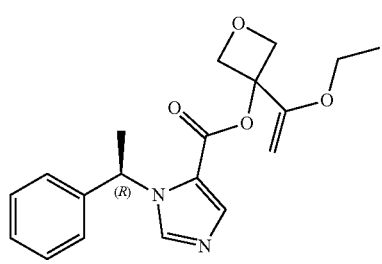
Compound D3
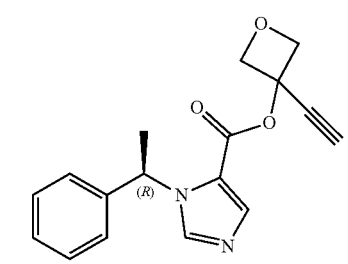
Compound D4
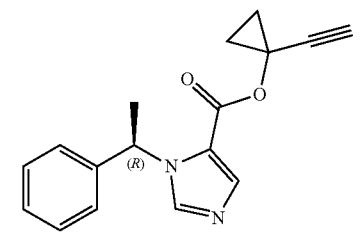
Compound D5
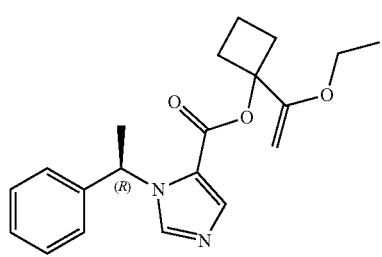
Compound D6
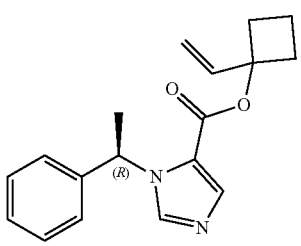
Compound D7
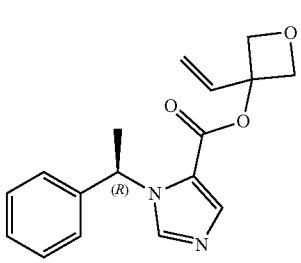
Compound D8
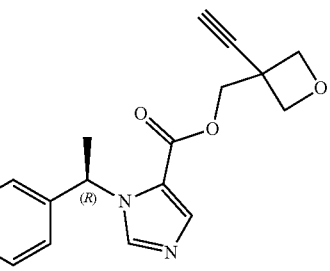
Compound D9
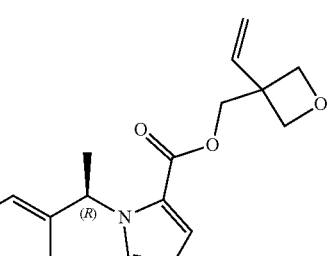
Compound D10
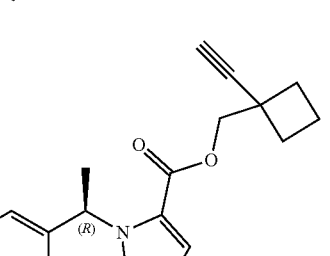
Compound D11
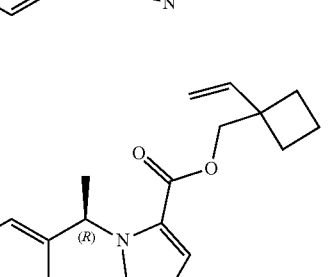

Compound D12
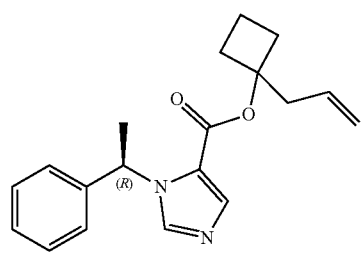
Compound D13
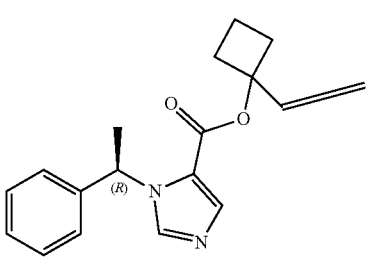
Compound D14
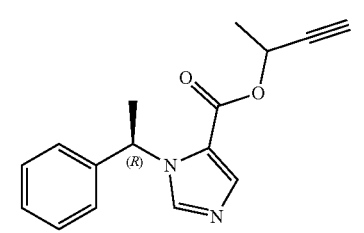
Compound D15
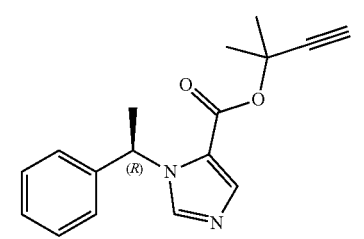
Compound D16
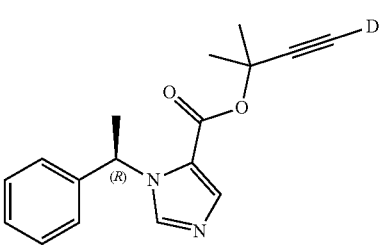
Compound D17
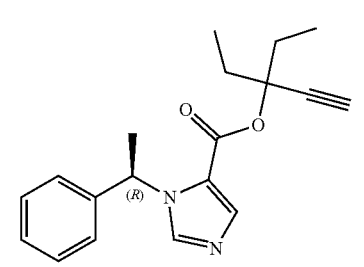
Compound D18
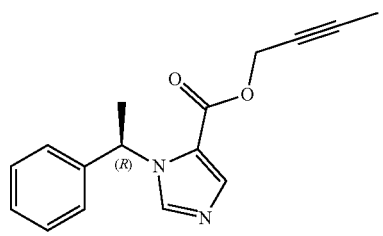
Compound D19
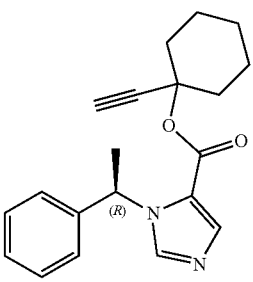
Compound D20
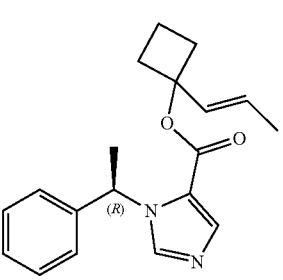
Compound D21
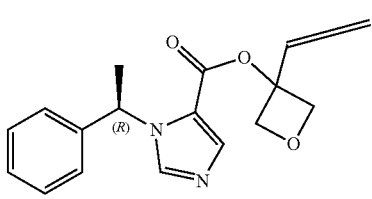
Compound D22
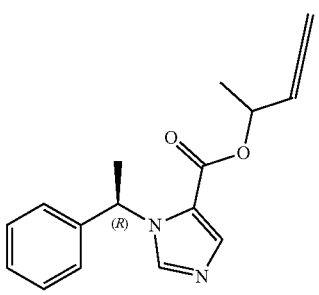
Compound D23
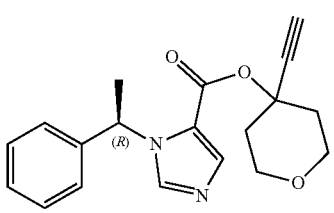

Compound D24
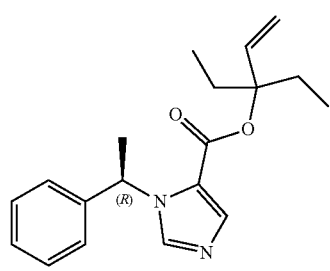
Compound D25
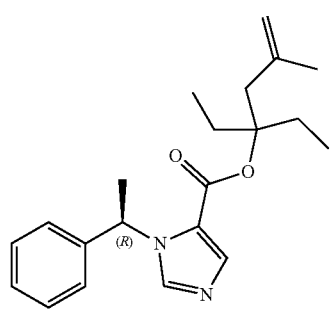
Compound D26
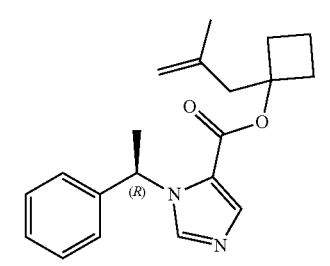
Compound D27
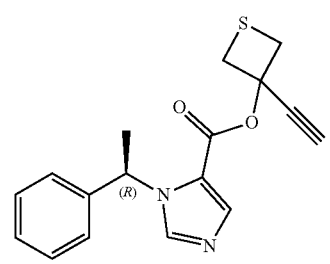
Compound D28
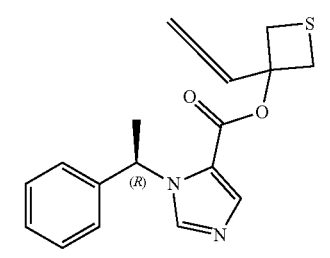
Compound D29
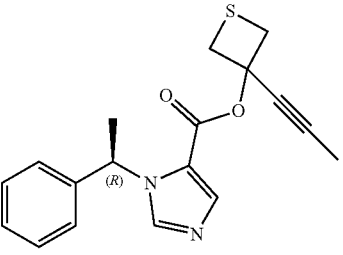
Compound D30
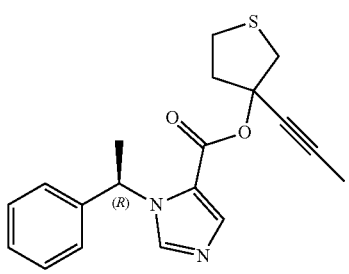
Compound D31

Compound D32
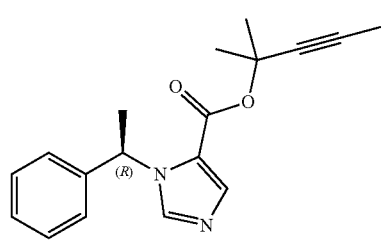
Compound D33
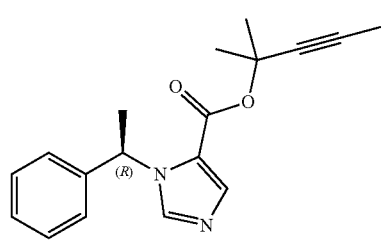
Compound D34
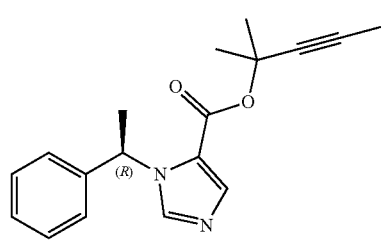
Compound D35
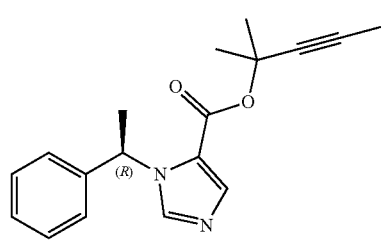

Compound D36
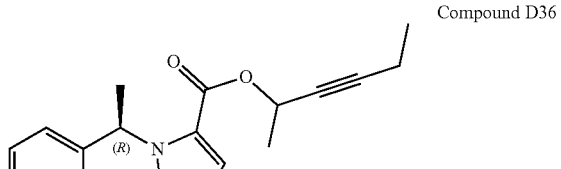
Compound D37
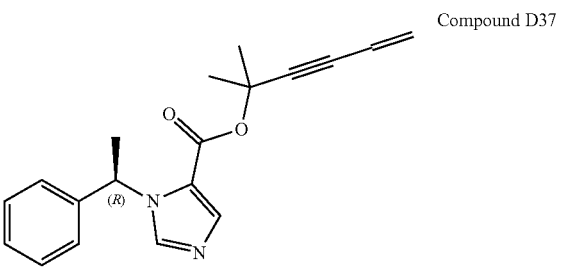
Compound D38
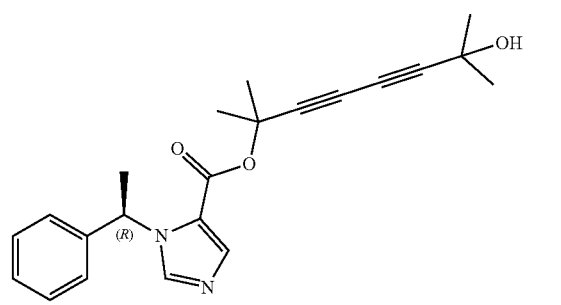
Compound D39
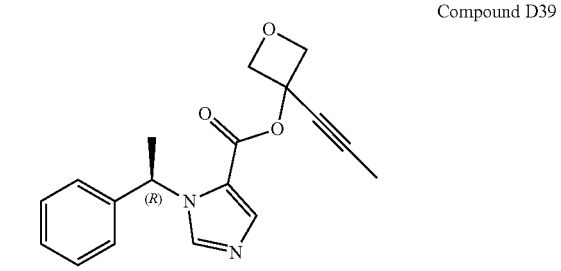
Compound D40
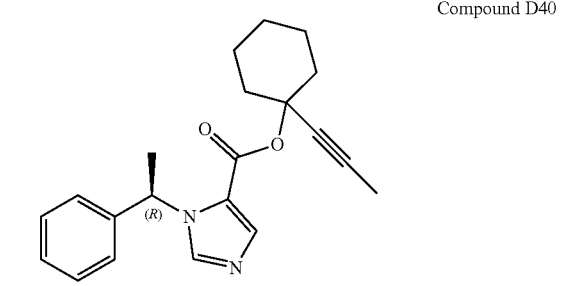
Compound D41
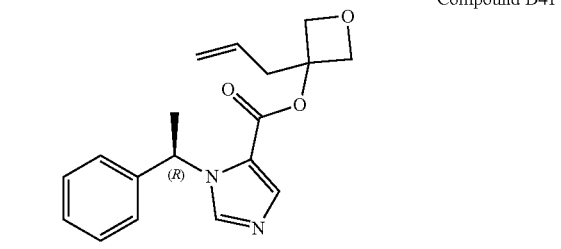
Compound D42
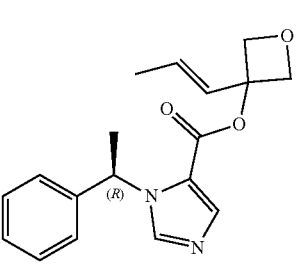
Compound D43
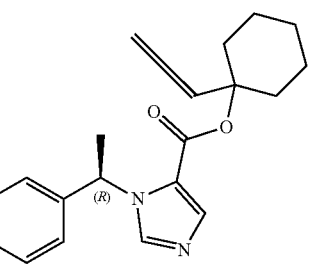
Compound D44
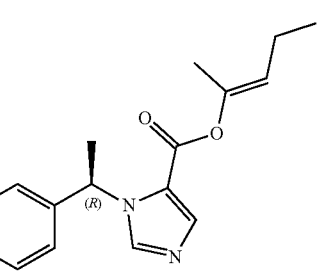
Compound D45
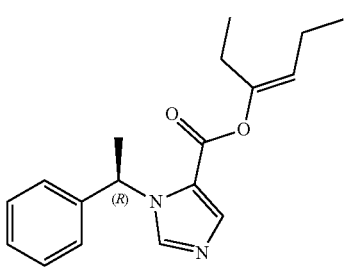
Compound D46
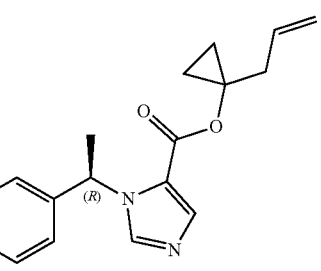
Compound D47
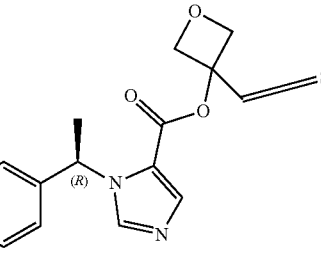

Compound D48
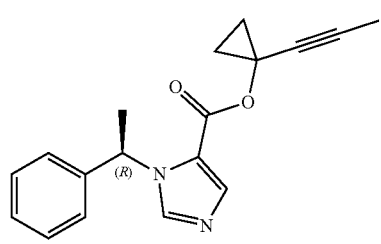
Compound D49
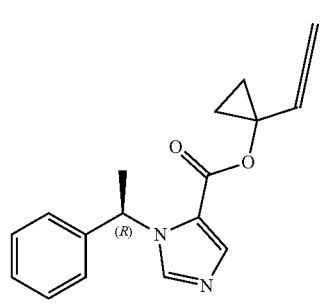
Compound D50
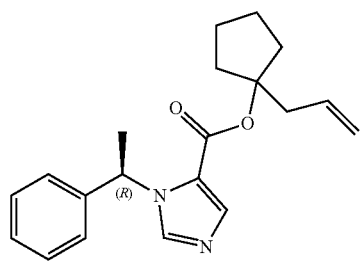
Compound D51
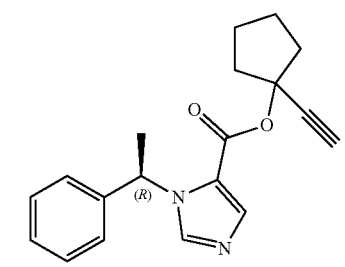
Compound D52
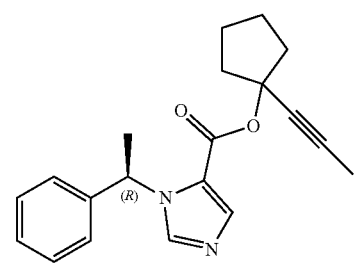
Compound D53
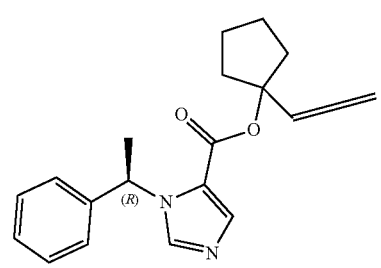
Compound D54
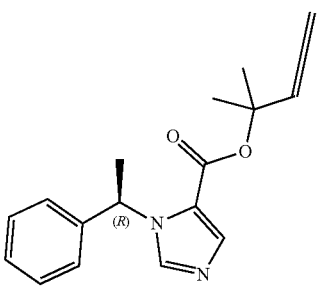
Compound D55
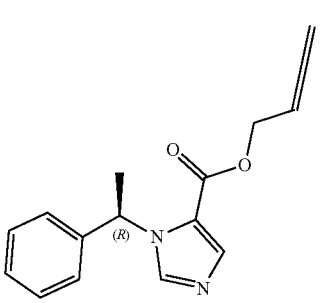
Compound D56
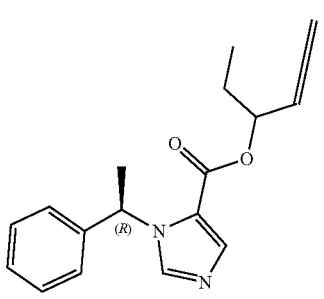
Compound D57
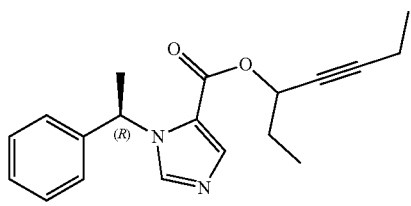
Compound D58
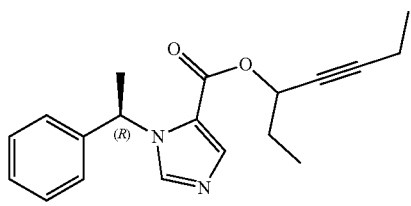
Compound D59
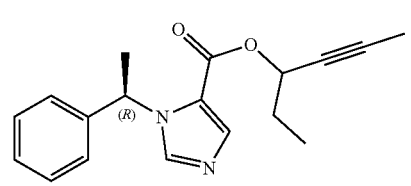

Compound D60
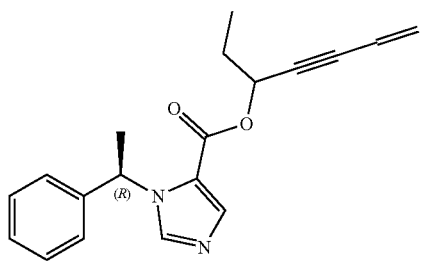
Compound E1
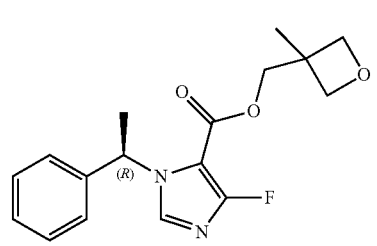
Compound E2
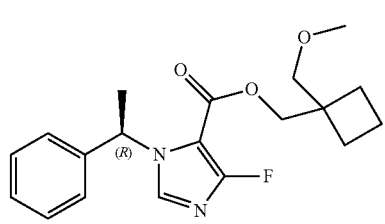
Compound E3
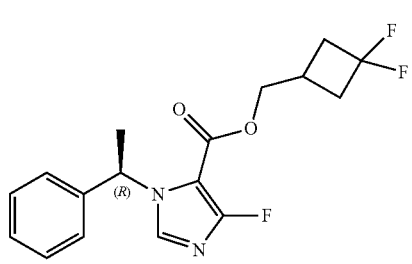
Compound E4
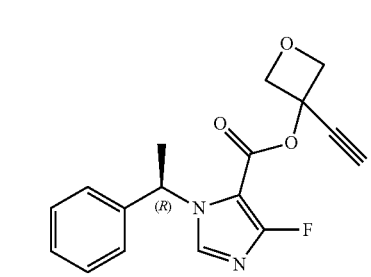
Compound E5
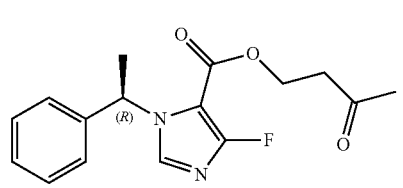
Compound E6
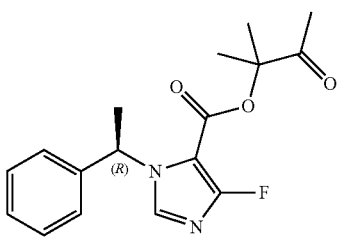
Compound E7
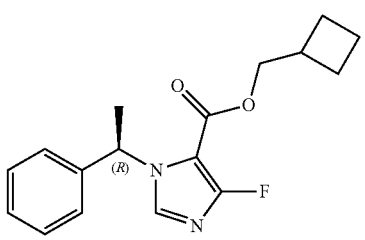
Compound E8
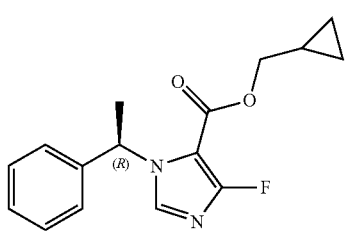
Compound E9
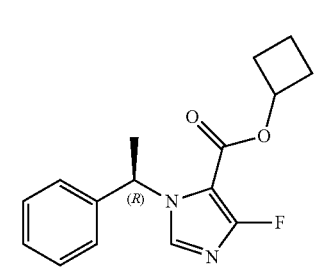
Compound E10
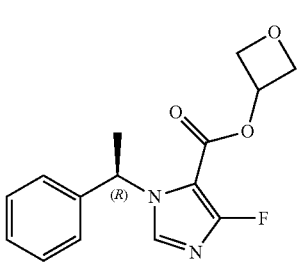
Compound E11
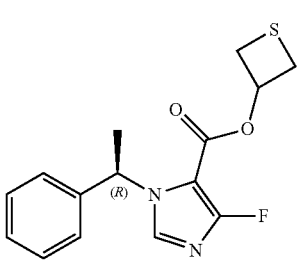

Compound E12
Compound E13
Compound E14
Compound E15
Compound E16
Compound E17
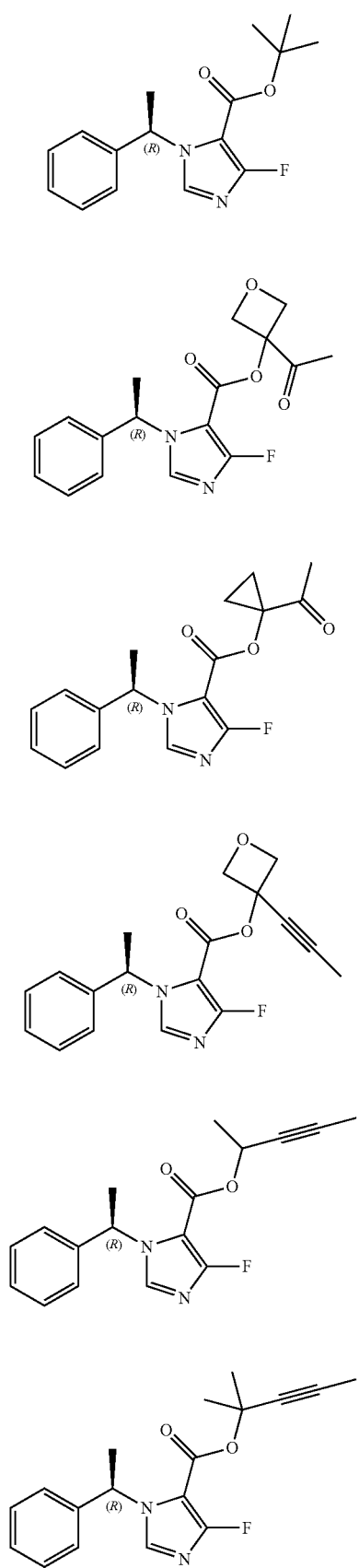
Compound E18
Compound E19
Compound E20
Compound E21
Compound E22
Compound E23
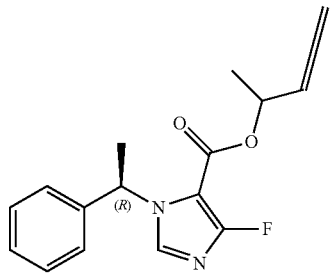
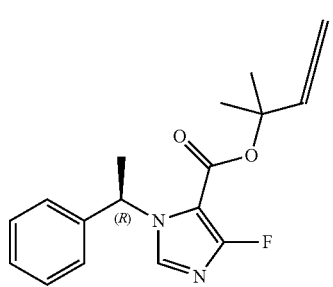
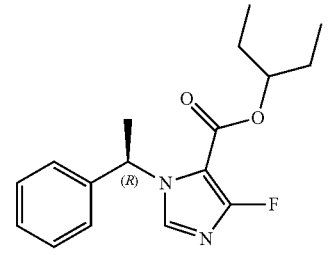

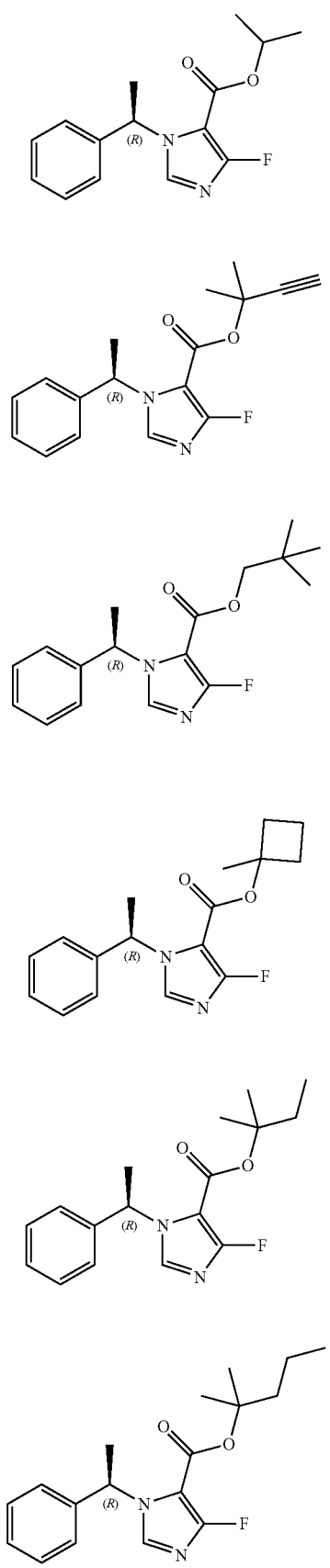

Compound E36
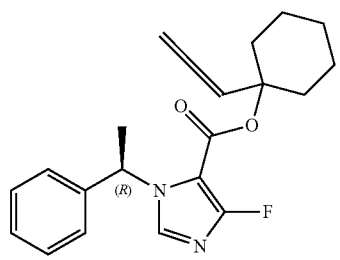
Compound E37
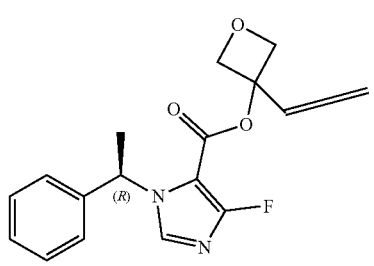
Compound E38
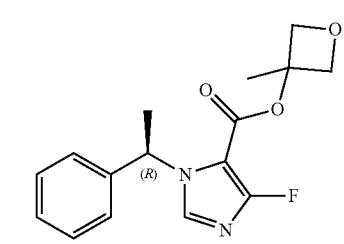
Compound E39
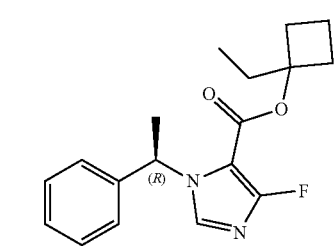
Compound E40
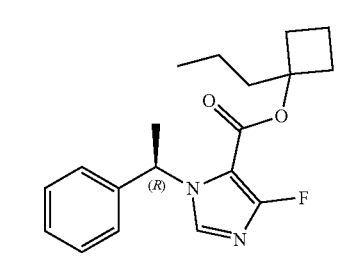
Compound E41
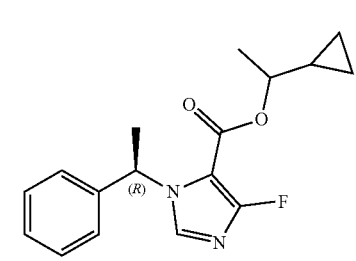
Compound E42
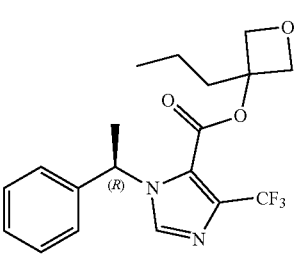
Compound E43
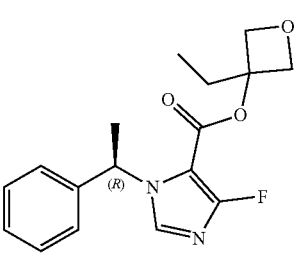
Compound E44
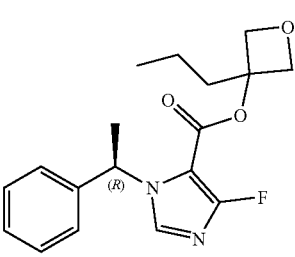
Compound E45
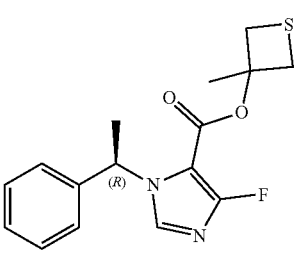
Compound E46
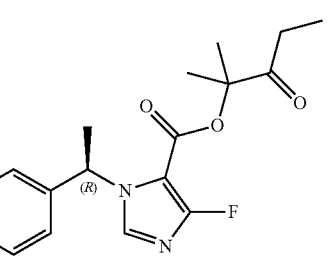
Compound E47
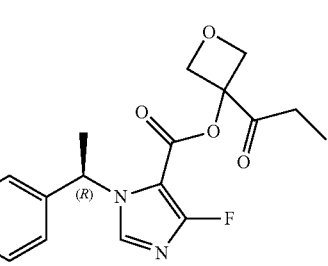

Compound E48
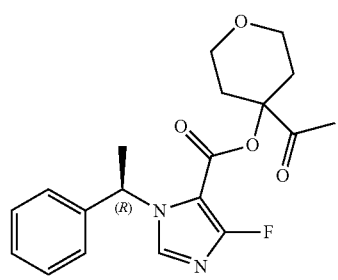
Compound E49
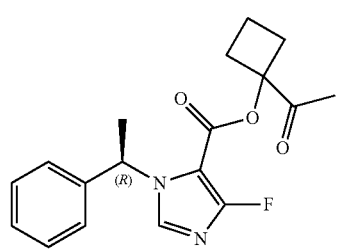
Compound E50
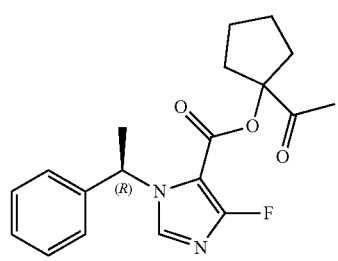
Compound E51
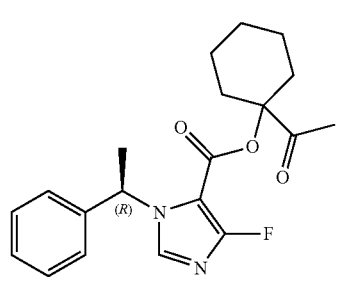
Compound E52
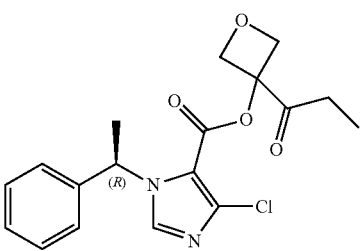
Compound E53
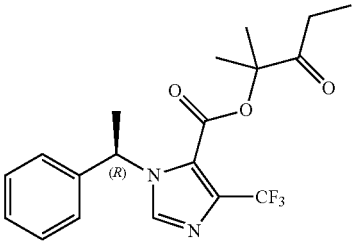
Compound E54
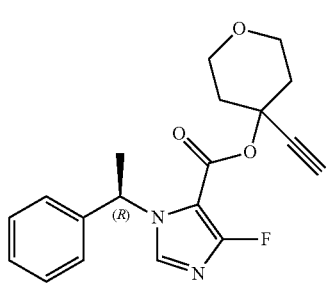
Compound E55
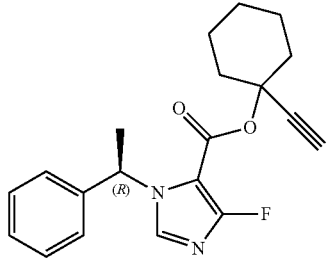
Compound E56
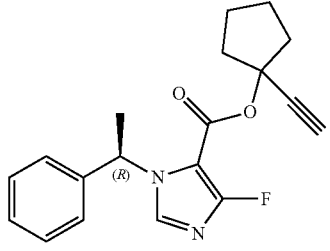
Compound E57
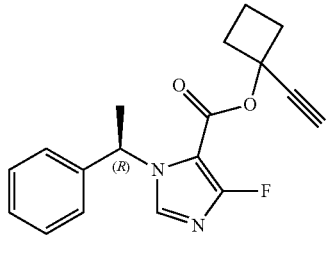
Compound E58
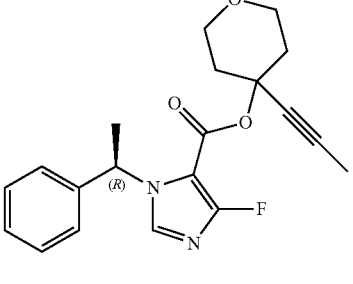
Compound E59
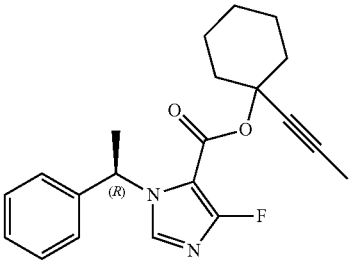

Compound E60
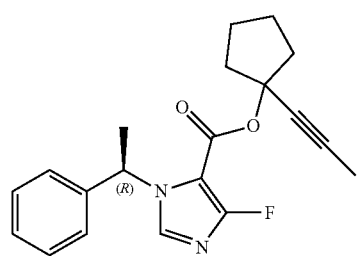
Compound E61
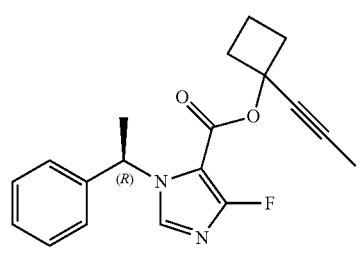
Compound E62
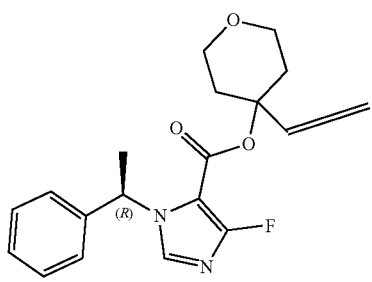
Compound E63
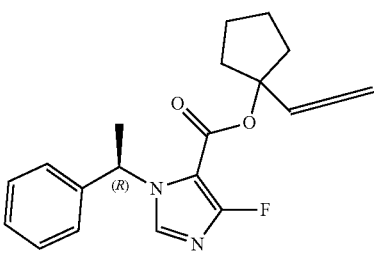
Compound E64
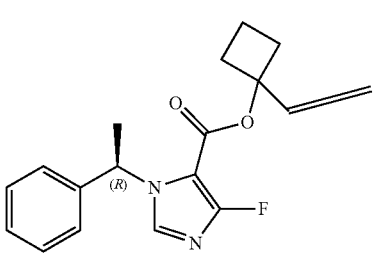
Compound E65
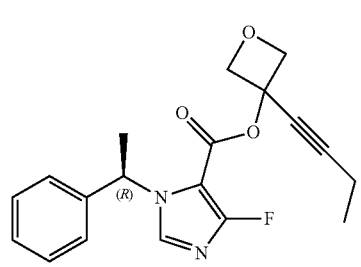
Compound E66
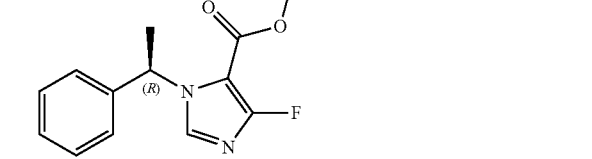
Compound E67
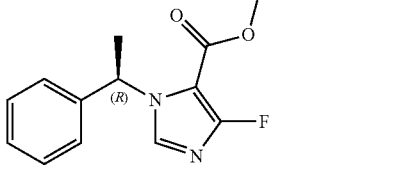
Compound E68
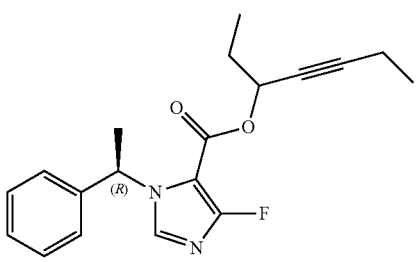
Compound E69
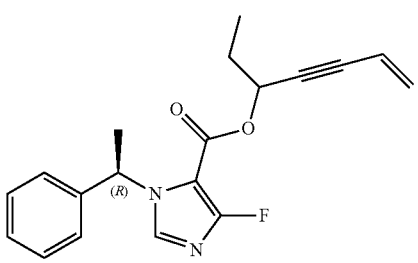
Compound E70
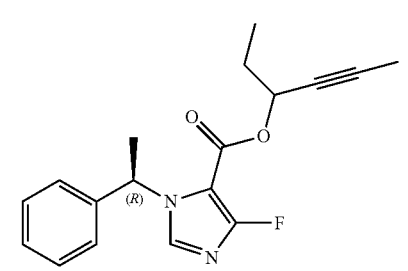
Compound E71
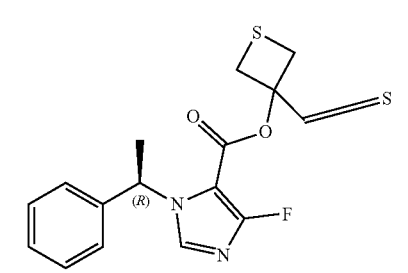

Compound E72
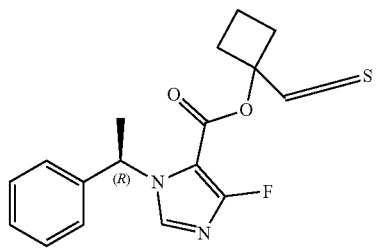
Compound E73
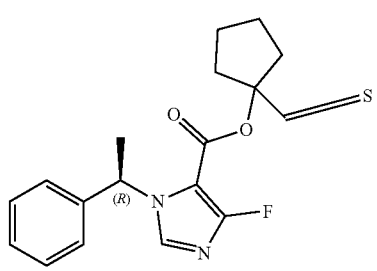
Compound E74
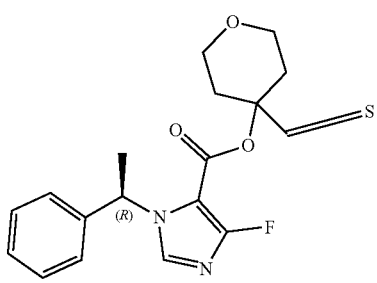
Compound E75
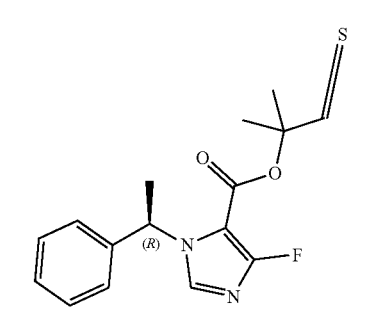
Compound E76
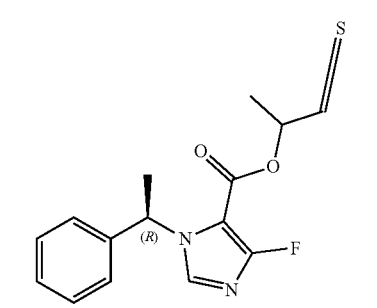
Compound E77
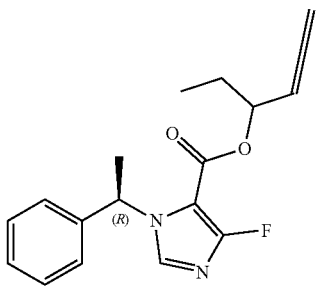
Compound E78
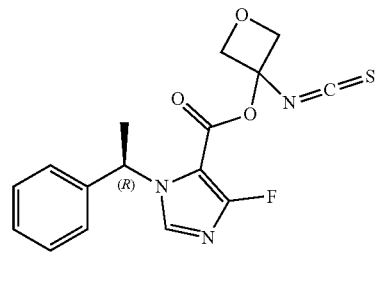
Compound E79
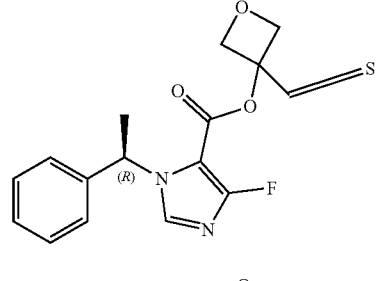
Compound E80
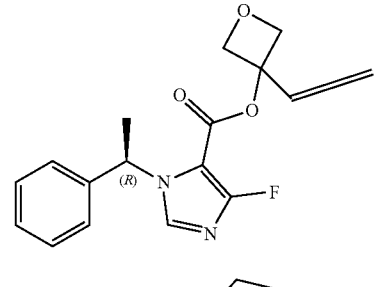
Compound E81
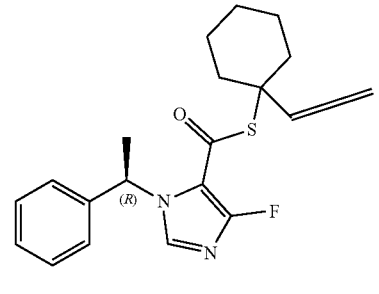
Compound E82
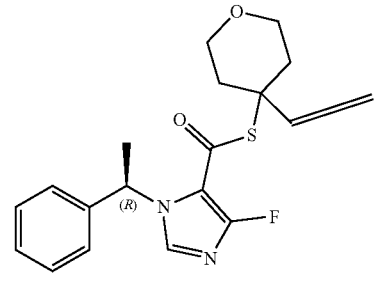

Compound E83
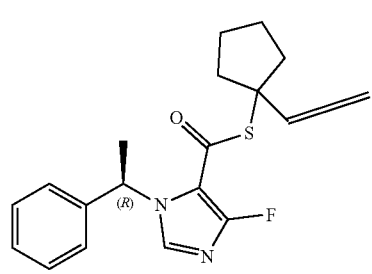
Compound E84
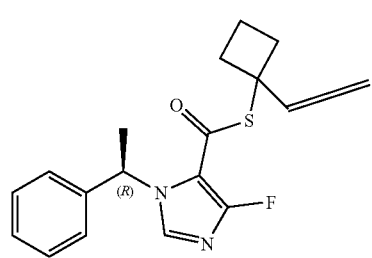
Compound E85
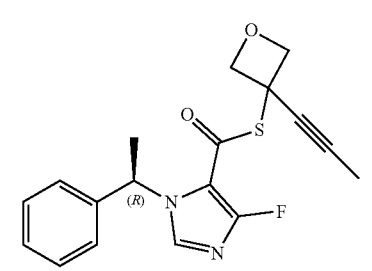
Compound E86
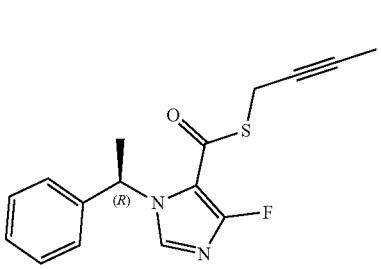
Compound E87
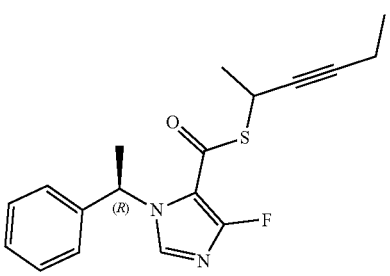
Compound E88
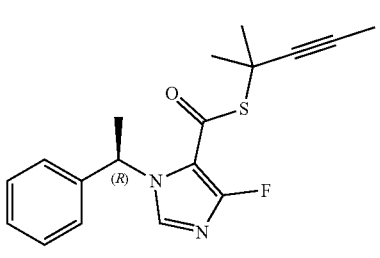
Compound E89
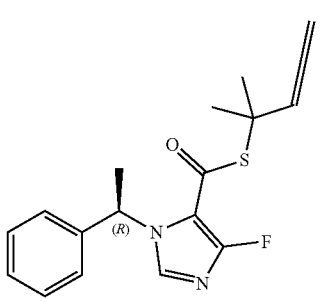
Compound E90
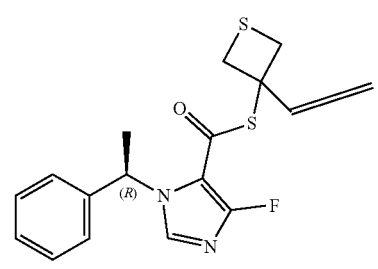
Compound E91
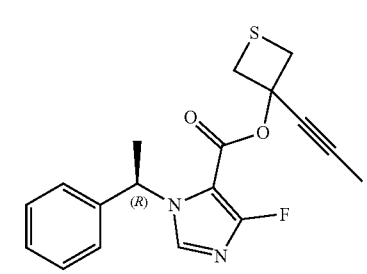
Compound E92
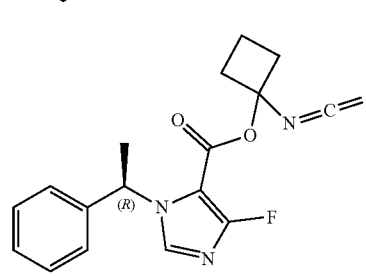
Compound E93
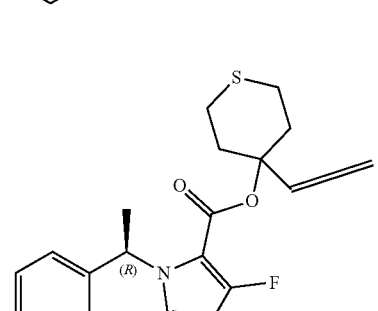
Compound E94
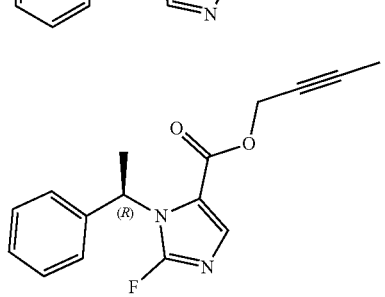

Compound E95
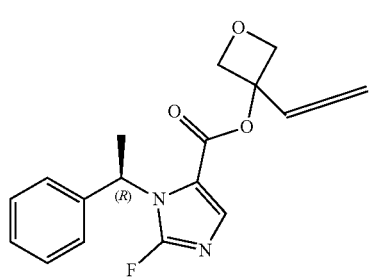
Compound E96
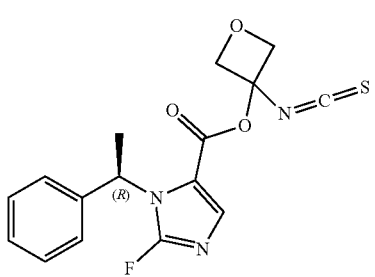
Compound E97
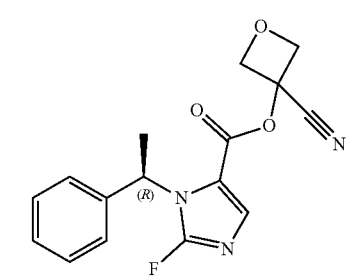
Compound E98
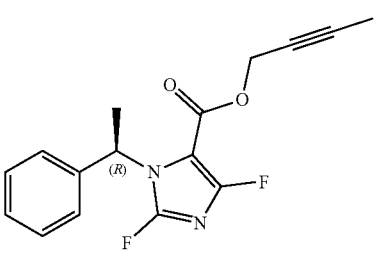
Compound E99
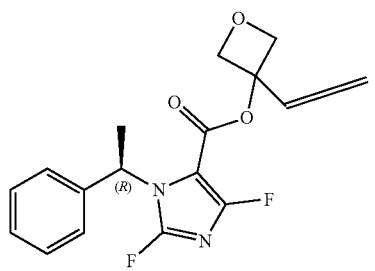
Compound E100
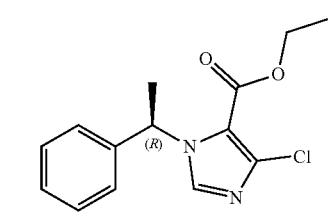
Compound E101
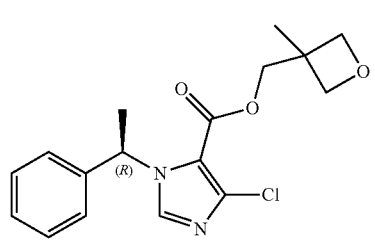
Compound E102
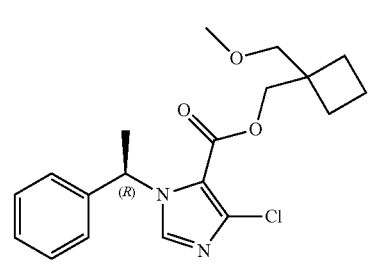
Compound E103
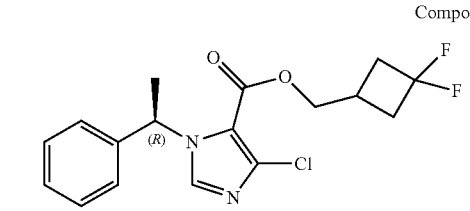
Compound E104
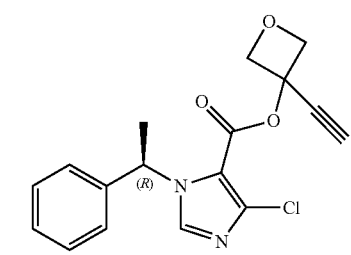
Compound E105
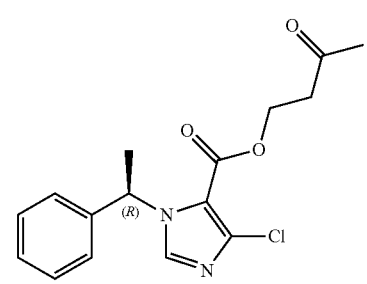
Compound E106
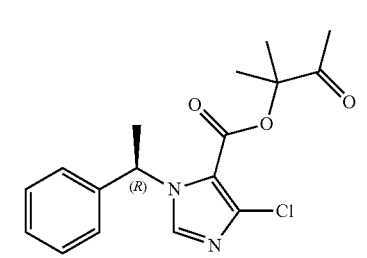

Compound E107
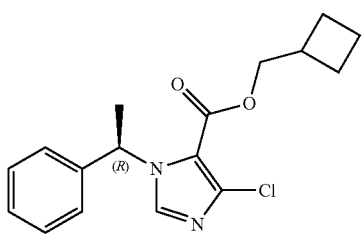
Compound E108
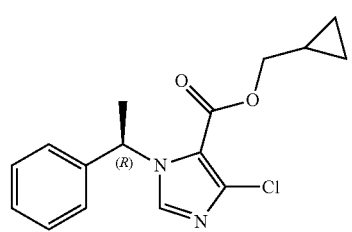
Compound E109
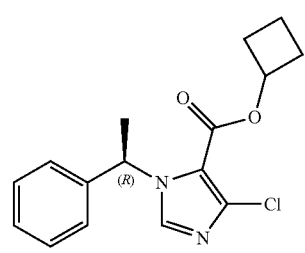
Compound E110
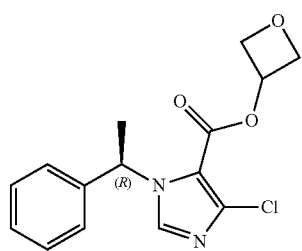
Compound E111
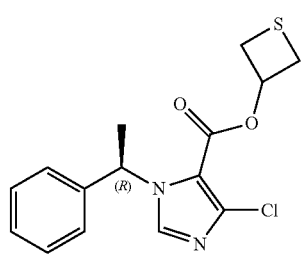
Compound E112
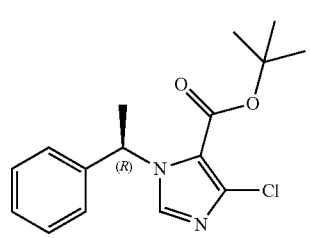
Compound E113
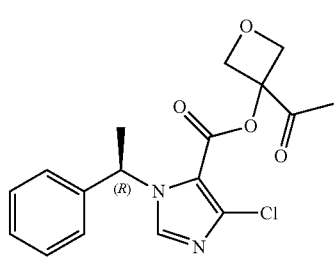
Compound E114
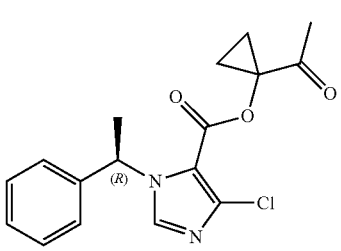
Compound E115
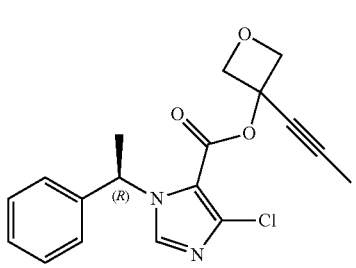
Compound E116
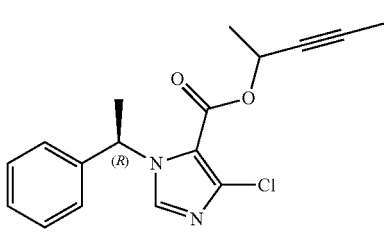
Compound E117
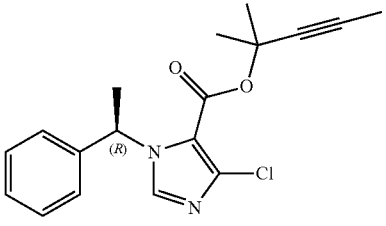
Compound E118
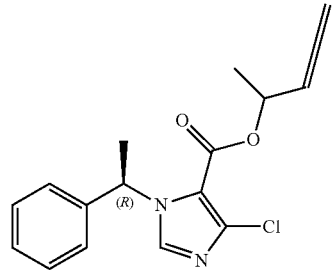

Compound E119
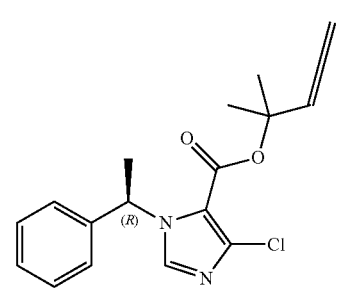
Compound E120
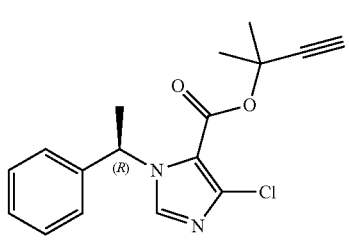
Compound E121
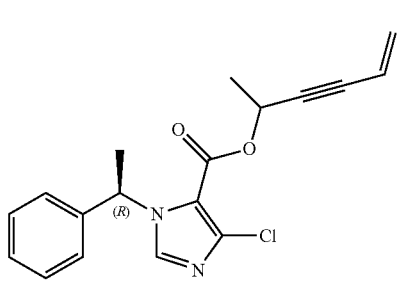
Compound E122
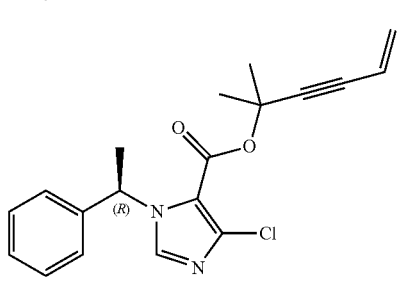
Compound E123
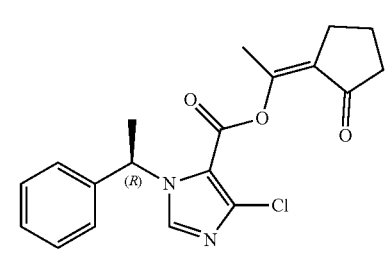
Compound E124
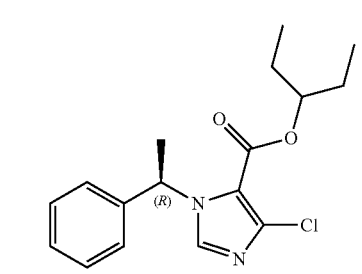
Compound E125
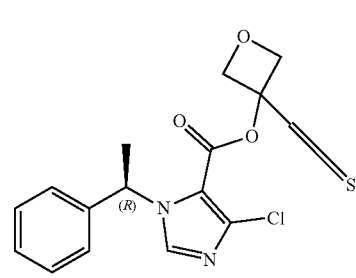
Compound E126
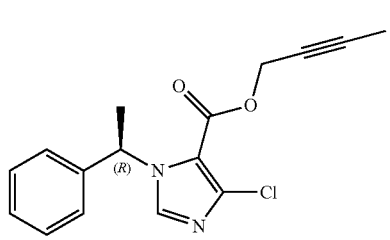
Compound E127
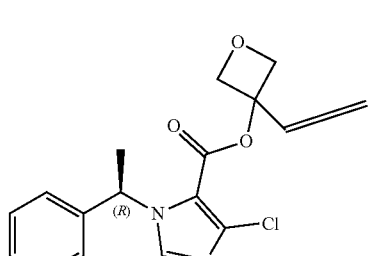
Compound E128
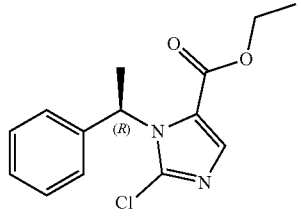
Compound E129
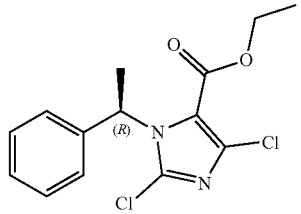
Compound E130
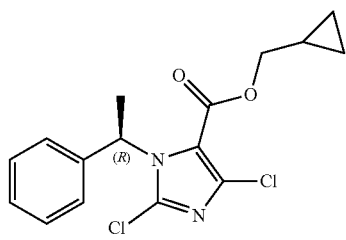

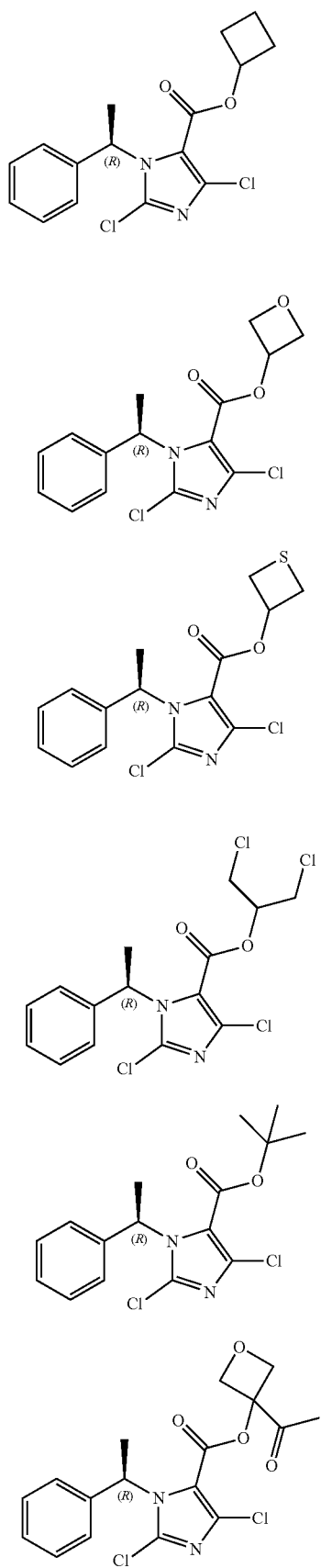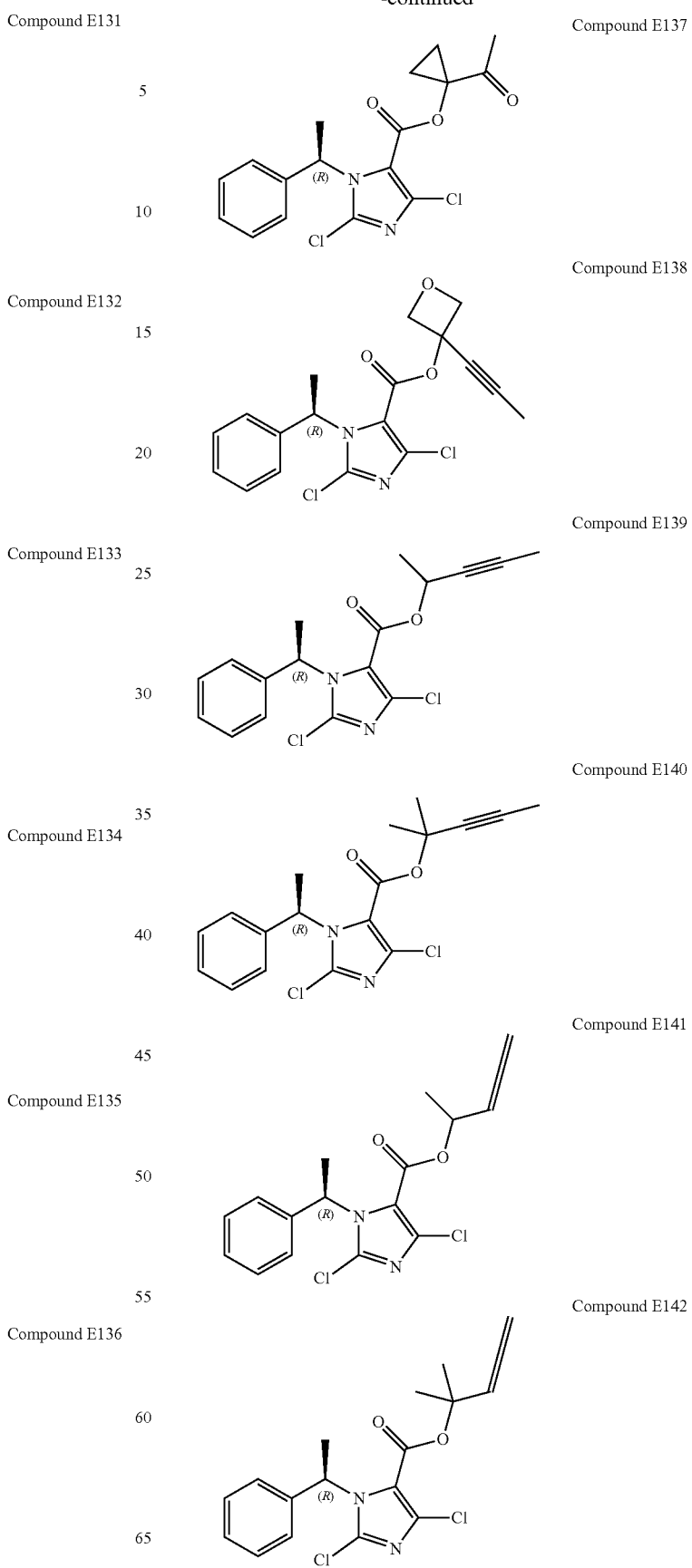
Compound E131
Compound E132
Compound E133
Compound E134
Compound E135
Compound E136
Compound E137
Compound E138
Compound E139
Compound E140
Compound E141
Compound E142

Compound E143
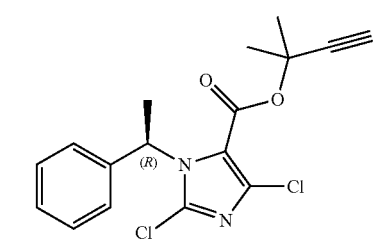
Compound E144
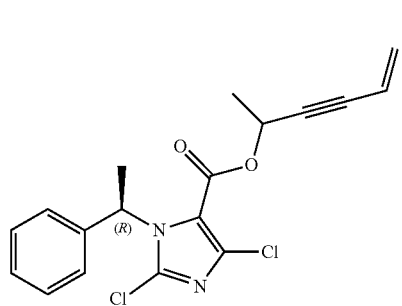
Compound E145
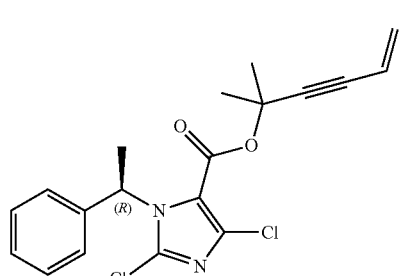
Compound E146
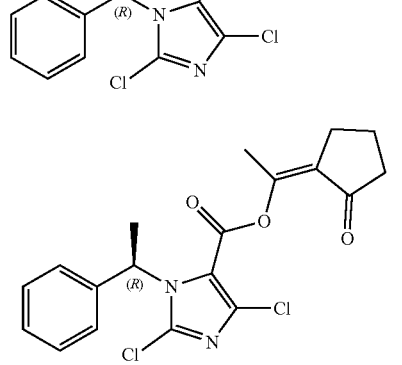
Compound E147
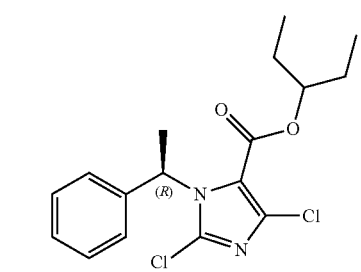
Compound E148
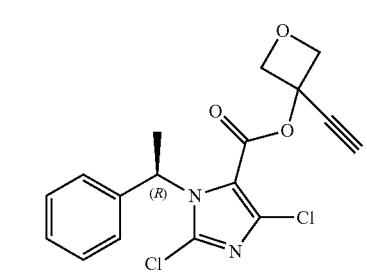
Compound E149
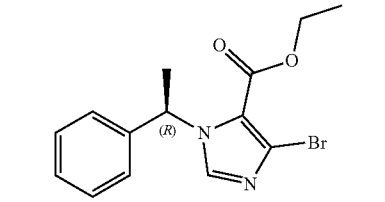
Compound E150
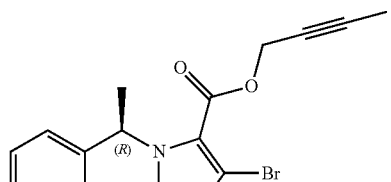
Compound E151
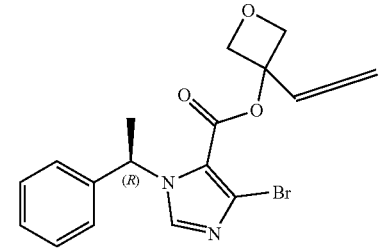
Compound E152
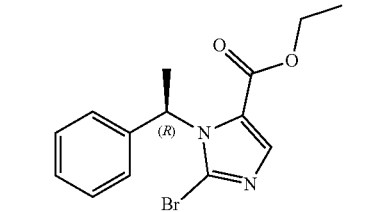
Compound E153
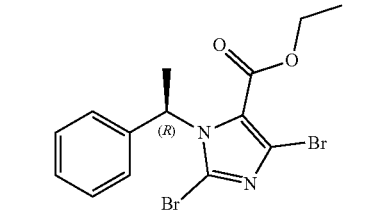
Compound E154
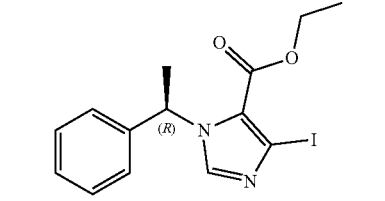
Compound E155

Compound E156

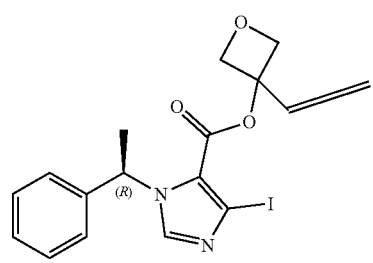

Compound E157

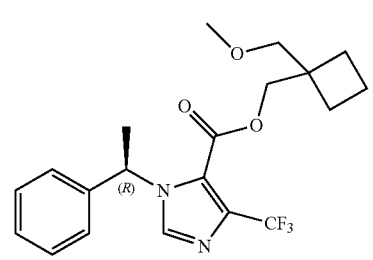

Compound E158

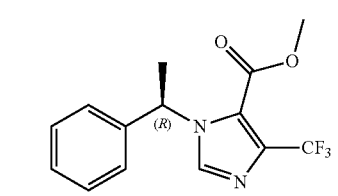

Compound E159

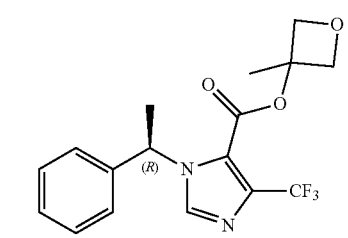

Compound E160

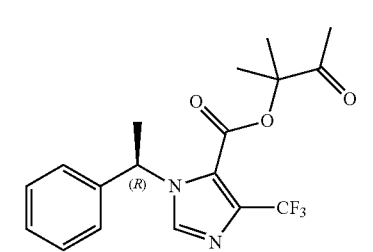

Compound E161

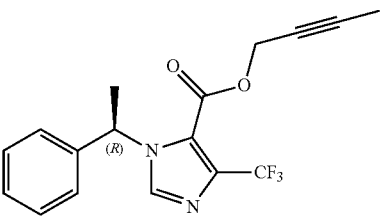

Compound E162

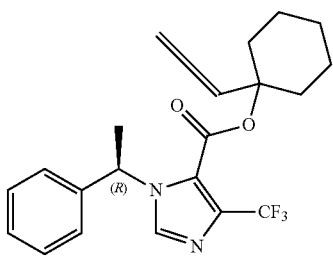

Compound E163

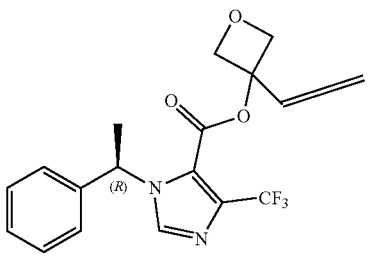

Compound E164

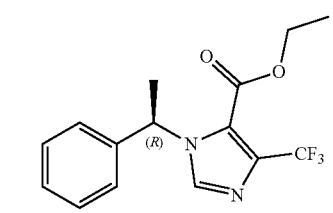

Compound E165

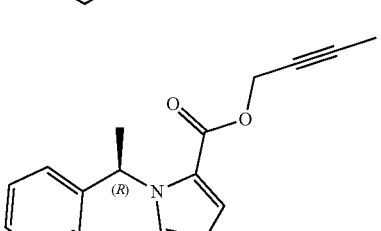

Compound E166

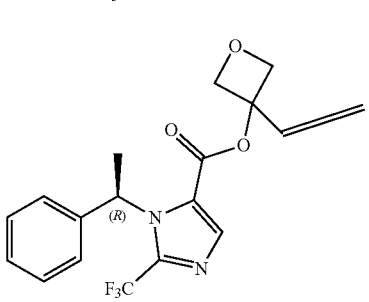

Compound E167

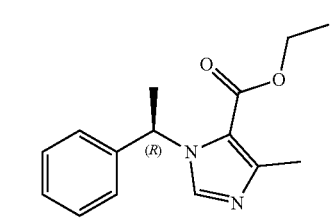

The present invention also provides a drug, it is prepared by using compounds according to any one of the above, or stereoisomers thereof, or pharmaceutically acceptable salts thereof, or solvates thereof, or prodrugs thereof, or metabolites thereof, or deuterated derivatives thereof, or their combinations as active ingredients, with addition of pharmaceutically acceptable excipients.

The present invention also provides the use of compounds according to anyone of the above, or stereoisomers thereof, or pharmaceutically acceptable salts thereof, or solvates thereof, or prodrugs thereof, or metabolites thereof, or deuterated derivatives thereof, or their combinations in preparation of drugs having sedative, hypnotic, and/or anesthetic effects and/or drugs that can be used to control epileptic status.

The "sedative drug" according to the present invention denotes a drug which can effectively help sleep and improve sleep. That is to say, it can avoid the serious harm of insomnia to human body, and it can treat insomnia, and improve sleep quality.

The "hypnotic drug" according to the present invention denotes a drug which can induce sleepiness and promote sleep. That is to say, it can inhibit the central nervous system, and cause sedation in small dose and general anesthesia in excess dose.

The "anesthetic drug" according to the present invention denotes to a reversible functional inhibition of central nerve and/or peripheral nervous system produced by the drug, which is characterized by loss of sensation, especially pain.

Preferably, the anesthesia is general anesthesia.

The "general anesthesia" mentioned in the present invention denotes the temporary inhibition of central nervous system caused by anesthetics after entering the body. The clinical manifestations are loss of mind, disappearance of body pain, forgetting, inhibition of reflex and relaxation of skeletal muscle.

The use of compounds mentioned above, or stereoisomers thereof, or pharmaceutically acceptable salts thereof, or solvates thereof, or prodrugs thereof, or metabolites thereof in preparation of drugs that can be used to control status epilepticus.

The "status epilepticus." mentioned in the present invention denotes that the consciousness is not fully recovered between successive seizures and the seizure frequently recurred, or the seizure lasts for more than 30 minutes and does not stop automatically. Long term epilepsy, if not treated in time, can lead to irreversible brain injury due to high fever, circulatory failure or neuronal excitotoxic injury, with high disability rate and mortality, so epilepsy is a common emergency in internal medicine. The present invention provides a drug, that is prepared by using compounds mentioned above, or stereoisomers thereof, or pharmaceutically acceptable salts thereof, or solvates thereof, or prodrugs thereof, or metabolites thereof, or deuterated derivatives thereof as active ingredients, with addition of pharmaceutically acceptable excipients.

The compounds and derivatives provided in the present invention can be named according to IUPAC (International Union of Pure and Applied Chemistry) or CAS (Chemical Abstracting Service, Columbus, Ohio) naming system.

For the definition of term used in the present the invention: unless otherwise specified, the initial definition provided for the group or the term herein is applicable to those in the whole specification; for terms not specifically defined herein, according to the disclosure content and the context, the term should have the meaning commonly given by those skilled in the field.

"Substitution" means that the hydrogen in a molecule is substituted by other different atoms or molecules.

The structure of the compound mentioned in the present invention denotes the one that can exist stably. "Deuterium" denotes the isotope of hydrogen (H), also known as heavy hydrogen, and the elemental symbol is generally D or 2H.

In the present invention, the structure of substituent "—C(O)$R^{32}$" is:

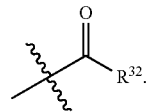

In the present invention, the structure of substituent "—CO$_2$$R^{32}$" is:

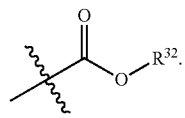

In the present invention, the structure of substituent "—CON($R^{32}$)$_2$" is:

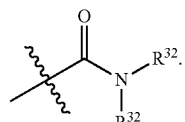

In the present invention, the structure of substituent "—N($R^{32}$)$_2$" is:

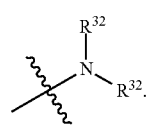

In the present invention, the structure of substituent "—OC(O)$R^{32}$" is:

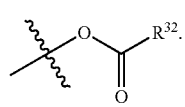

In the present invention, the structure of substituent "—SO$_2$$R^{32}$" is:

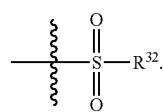

In the present invention, the structure of substituent "—C(S)$R^{33}$" is:

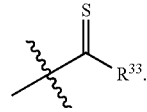

In the present invention, the structure of substituent "—S(O)R^{33}" is:

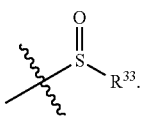

The minimum and the maximum number of carbon atoms in hydrocarbon groups are represented by prefixes, for example, the prefix $(C_a\sim C_b)$ alkyls indicate any alkyls containing "a"~"b" carbon atoms. Therefore, for example, $C_1\sim C_8$ alkyls denote alkyls containing 1~8 carbon atoms. $C_1\sim C_8$ alkyls are straight or branched hydrocarbon chains containing 1~8 carbon atoms.

"Alkyls" is a hydrocarbon group formed by losing one hydrogen in an alkane molecule, such as methyl —CH$_3$, ethyl —CH$_3$CH$_2$, etc.

"Alkylenyls" denotes the hydrocarbon group formed by losing two hydrogens in the alkane molecule, such as methylene —CH$_2$—, ethylidene —CH$_2$CH$_2$—, etc. "C$_{1-8}$ alkylenyls" denotes a straight or branched hydrocarbon chain containing 1~8 carbon atoms.

"Substituted or unsubstituted C$_{1-8}$ alkyls" denotes C$_{1-8}$ alkyls that can be substituted or not be substituted.

"3~6-membered saturated carbocycles" in "ring A is 3~6-membered saturated carbocycles" mentioned in the present invention denotes a carbocycle consisting of 3~6 carbons, in which no double bond exists. For example:

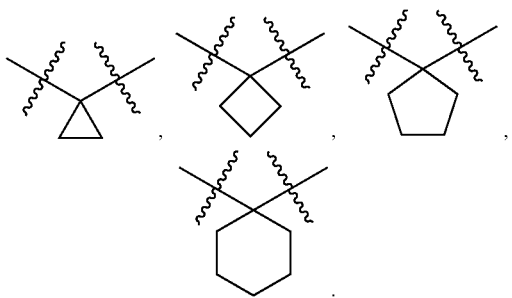

"3~6-membered unsaturated carbocycles" in "ring A is 3~6-membered unsaturated carbocycles" mentioned in the present invention denotes a carbocycle consisting of 3~6 carbons, in which double bond exists. For example:

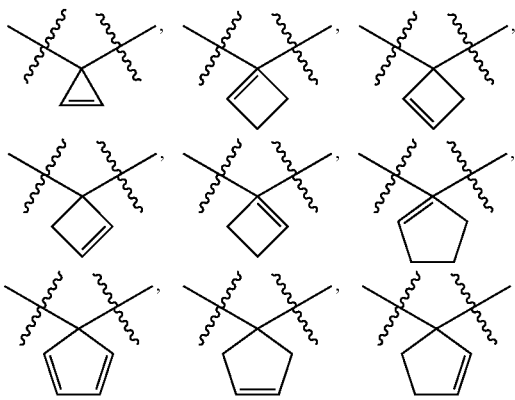

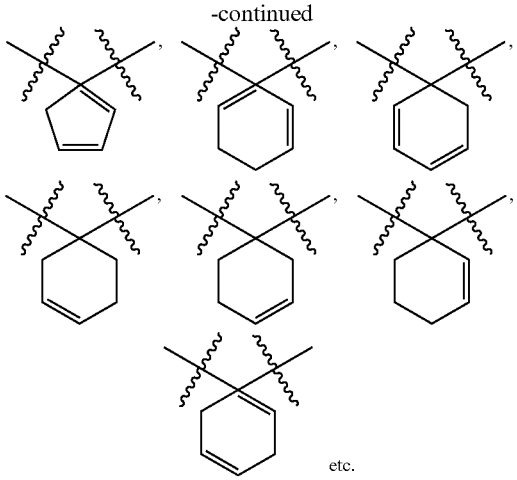

"3~6-membered saturated heterocycles" in "ring A is 3~6-membered saturated heterocycles" mentioned in the present invention denotes a saturated heterocycle without double bonds, in which there is at least one atom selected from O, S, or substituted N, and the remaining ring atoms are carbons. For example:

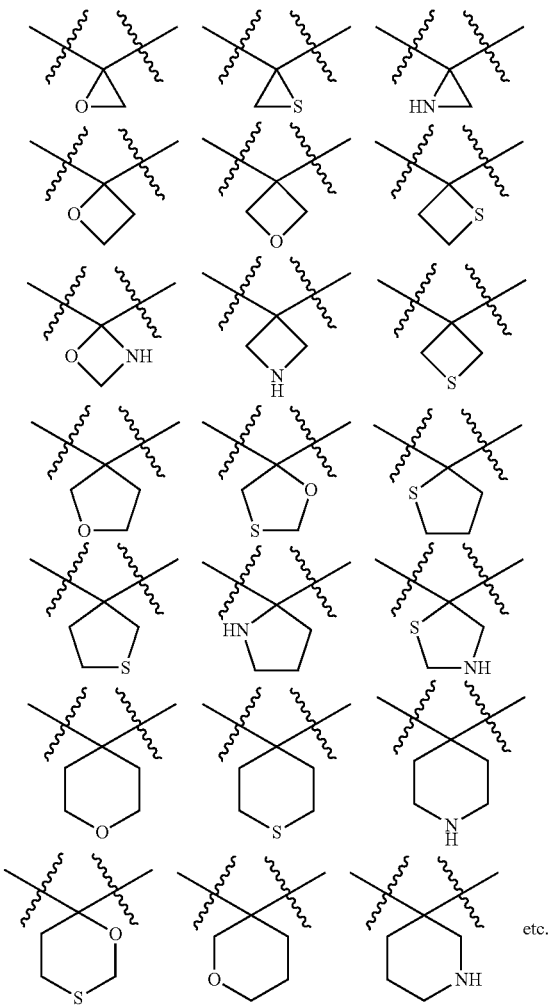

"3~6-membered unsaturated heterocycles" in "ring A is 3~6-membered unsaturated heterocycles" mentioned in the present invention denotes an unsaturated heterocycle containing double bonds, in which there is at least one atom selected from O, S, or substituted N, and the remaining ring atoms are carbons. For example:

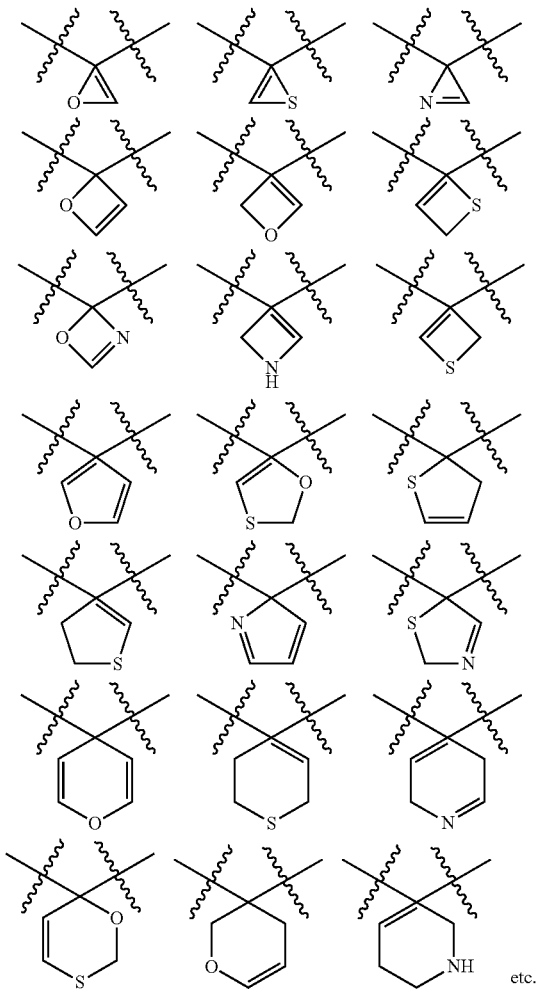

etc.

"Alkynyls" denotes aliphatic hydrocarbon groups with at least one CC triple bond. Said alkynyls can be straight or branched chain. When alkynyls have a limit on carbon numbers before them (such as $C_{2-8}$ alkynyls), for example, the term "$C_{2-8}$ alkynyls" denotes a straight or branched alkynyls with 2-8 carbons.

"Alkenyls" denotes aliphatic hydrocarbon groups with at least one C=C double bond. Said alkenyls can be straight or branched chain. When alkenyls have a limit on carbon numbers before them (such as $C_{2-8}$ alkenyls), for example, the term "$C_{2-8}$ alkenyls" denotes a straight or branched alkenyls with 2-8 carbons.

halogen is fluorine, chlorine, bromine, or iodine.

"Aryls" denote all-carbon monocyclic or fused polycyclic (i.e. ring sharing adjacent carbon atom pairs) groups with conjugated π electron system, such as phenyl and naphthyl. Said aryl ring can be fused to other cyclic groups (including saturated and unsaturated rings), but can not contain hetero atoms such as nitrogen, oxygen, or sulfur. At the same time, the point connecting with the parent must be on the carbon in the ring having the conjugated π electron system. Aryls can be substituted or unsubstituted.

"Heteroaryls" denote the heteroaromatic group containing one or more heteroatoms. The heteroatoms mentioned herein include oxygen, sulfur, and nitrogen. For example, furanyl, thienyl, pyridinyl, pyrazolyl, pyrrolyl, n-alkylpyrrolyl, pyrimidinyl, pyrazinyl, imidazolyl, tetrazolyl, etc. The heteroaromatic ring can be fused to aryls, heterocyclic group or cycloalkyl ring, in which the ring connected with the parent structure is heteroaromatic ring. Heteroaryls can be substituted or unsubstituted.

"Cycloalkyls" denote saturated or unsaturated cyclic hydrocarbon substituents; cyclic hydrocarbon can have one or more rings. For example, "$C_{3-8}$ cycloalkyls" denote cycloalkyls having 3~8 carbons.

"3~8-membered heterocyclic groups" denote saturated or unsaturated cyclic hydrocarbon substituents; cyclic hydrocarbon can have one or more rings, and at least one atom selected from O, S or substituted N, while the remaining ring atoms are carbons.

A carbon atom in the "ring A" of the compound of the present invention is directly connected with $L^1$ and $L^2$. For example:

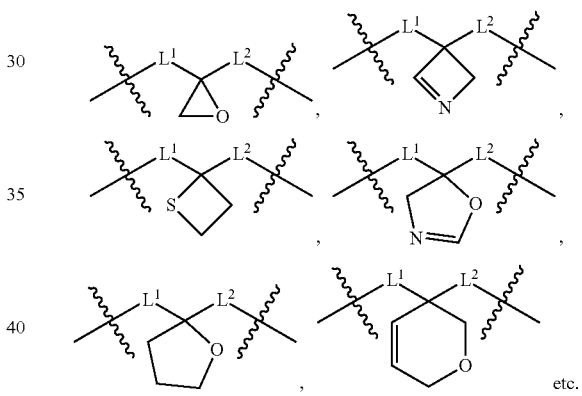

etc.

Ring A is none or 3~6-membered saturated carbocycles, 3~6-membered unsaturated carbocycles, 3~6-membered saturated heterocycles or 3~6-membered unsaturated heterocycles, all of which are substituted by "0~4 $R^{34}$ substituents"; wherein, $R^{34}$ is selected from deuterium, halogen, cyano, nitro, $C_{1-8}$ alkyls or their halogenated or deuterated derivatives, $C_{2-8}$ alkenyls or their halogenated or deuterated derivatives, $C_{2-8}$ alkynyls or their halogenated or deuterated derivatives, —OC(O)$R^{35}$, —C(O)$R^{35}$, —S(O)$R^{35}$, —C(O)N($R^{35}$)$_2$, -$L^{33}$-$R^{36}$, or =$R^{37}$.

Herein, the carbon atom connected to "the substituent $R^{34}$" is not the one directly connected to $L^1$ or $L^2$. For example:

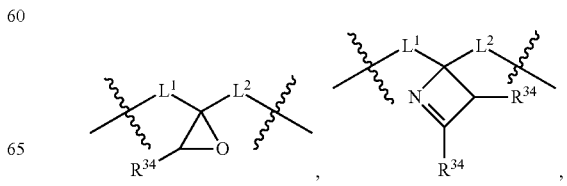

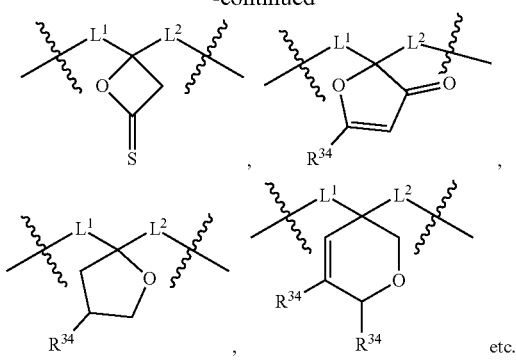

"$C_{1-4}$ alkyls or their halogenated or deuterated derivatives" denote $C_{1-4}$ alkyls or halogen- or deuterium-substituted $C_{1-4}$ alkyls. Other "or their halogenated or deuterated derivatives" have the same definition.

For all the compounds of the present invention, each chiral carbon atom (chiral center) can be optionally R-configurated or S-configurated, or a mixture of R-configuration and S-configuration. "Pharmaceutically acceptable carriers" denote one or more compatible solid or liquid filling materials or gel substances, which are suitable for human use and must be of sufficient purity and low toxicity. "Compatibility" herein means that each component in the composition can be mixed with the compound of the present invention, and the blending of them can not obviously reduce the efficacy of the compound. Some examples of pharmaceutically acceptable carriers are cellulose and its derivatives (such as carboxymethylcellulose sodium, ethylcellulose sodium, cellulose acetate, etc.), gelatin, talcum, solid lubricants (such as stearic acid, magnesium stearate), calcium sulfate, vegetable oil (such as soybean oil, sesame oil, peanut oil, olive oil, etc.), polyols (such as propylene glycol, glycerin, mannitol, sorbitol, etc.), emulsifier (such as Tween®), wetting agent (such as sodium dodecyl sulfate), colorant, seasoning agent, stabilizer, antioxidant, preservative, pyrogen free water, etc.

The term "pharmaceutically acceptable salt" denotes the salt formed by the compound of the present invention and pharmaceutically acceptable inorganic and organic acids, which is suitable for contacting the tissue of the object (e.g. human) without undue side effects. Among them, the preferred inorganic acids include (but not limited to) hydrochloric acid, hydrobromic acid, phosphoric acid, nitric acid, sulfuric acid; the preferred organic acids include (but not limited to) formic acid, acetic acid, propionic acid, succinic acid, naphthalene disulfonic acid (1,5), asiatic acid, oxalic acid, tartaric acid, lactic acid, salicylic acid, benzoic acid, valeric acid, diethylacetic acid, malonic acid, succinic acid, fumaric acid, pimelic acid, adipic acid, maleic acid, malic acid, sulfamic acid, phenylpropionic acid, gluconic acid, ascorbic acid, niacin, isoniacin, methanesulfonic acid, p-toluenesulfonic acid, citric acid, and amino acids.

The term "pharmaceutically acceptable solvate" denotes the solvate formed by the compound of the present invention and pharmaceutically acceptable solvents, in which the pharmaceutically acceptable solvent includes (but not limited to) water, ethanol, methanol, isopropanol, propylene glycol, tetrahydrofuran, and dichloromethane.

As used herein, the term "pharmaceutically acceptable stereoisomer" means that the chiral carbon atom involved in the compound of the present invention may be R-configuration, 5-configuration, or a combination thereof.

The compound of the present invention or composition thereof, as well as the use method thereof: The compounds of the present invention, and various crystal forms, pharmaceutically acceptable inorganic or organic salts, hydrates or solvates thereof, as well as the pharmaceutical composition containing the compound of the present invention as the main active ingredients can be used for sedation, hypnosis and/or general anesthesia. The compound of the present invention can also be used for controlling epileptic persistent state and the like.

The pharmaceutical composition of the present invention includes a compound of the present invention or a pharmaceutically acceptable salt thereof within a safe and effective amount, as well as a pharmaceutically acceptable excipient or carrier thereof.

The administration ways for the compound or pharmaceutical composition of the present invention include (but not limited to) intragastric, intraintestinal, extragastrointestinal (intravenous, intramuscular or subcutaneous), oral and various local administration.

The composition for extragastrointestinal injection (intravenous, intramuscular, subcutaneous) may contain physiologically acceptable sterile aqueous or anhydrous solutions, dispersions, suspensions or emulsions, and sterile powder used for reconstitution into sterile injectable solutions or dispersions. Suitable aqueous and non-aqueous carriers, diluents, solvents or excipients include water, ethanol, polyols and their suitable mixtures.

Solid dosage forms for oral administration include capsules, tablets, pills, powders and granules. In these solid dosage forms, the active compound is mixed with at least one conventional inert excipient (or carrier), such as sodium citrate or dicalcium phosphate, or mixed with following ingredients: (a) bulking agent or compatibilizer, such as starch, lactose, sucrose, glucose, mannitol and silicic acid; (b) binding agent, such as hydroxymethylcellulose, alginate, gelatin, polyvinylpyrrolidone, sucrose and gum arabic; (c) moisturing agent, such as glycerin; (d) disintegrating agent, such as agar, calcium carbonate, potato starch or cassava starch, alginate, some complex silicates, and sodium carbonate; (e) solvents, such as paraffin; (f) absorption accelerators, such as quaternary amine compounds; (g) wetting agents, such as cetyl alcohol and glycerin monostearate; (h) adsorbents, such as kaolin; and (i) lubricants, such as talc, calcium stearate, magnesium stearate, solid polyethylene glycol, sodium dodecyl sulfate, or mixtures thereof. In capsules, tablets and pills, the dosage form may also include buffers.

The liquid dosage forms used for oral administration include pharmaceutically acceptable emulsion, solution, suspension, syrup or tincture. In addition to the active compounds, the liquid dosage form may comprise inert diluents commonly used in the art, such as water or other solvents, solubilizers and emulsifiers, for example, ethanol, isopropanol, ethyl carbonate, ethyl acetate, propylene glycol, 1,3-butanediol, dimethylformamide and oil, especially cottonseed oil, peanut oil, corn germ oil, olive oil, castor oil and sesame oil or the mixture thereof, etc.

Solid dosage forms such as tablets, sugar pills, capsules, pills and granules can be prepared by coating and shell materials, such as casing and other materials known in the art. They may comprise an opaque agent, and the release of the active compound or compound in the composition may be delayed in a certain part of the digestive tract. Examples of embedding components that can be used are polymers and waxes. If necessary, the active compound may also form a microcapsule form with one or more of above excipients.

The dosage form of the compound of the present invention for local administration includes ointment, powder, patch, spray and inhalant. The active ingredient is mixed in sterile conditions with a biologically acceptable carrier and any preservatives, buffers, or propellants that may be required if necessary.

Except for these inert diluents, the composition may also include auxiliaries such as wetting agents, emulsifiers and suspensions, sweeteners, flavouring agents and perfumes.

Except for the active compounds, the suspension may contain a suspending agent, such as ethoxylated isooctadecanol, polyoxyethylene sorbitol and dehydrated sorbitol ester, microcrystalline cellulose, aluminum methoxide and agar or the mixture thereof, etc.

The compound of the present invention can be administered alone or in combination with other pharmaceutically acceptable compounds.

When the pharmaceutical composition is used, the safe and effective amount of the compound of the present invention is administrated to the mammal (such as human) in need thereof, in which the dosage is the pharmaceutically acceptable safe and effective dosage.

When the pharmaceutical composition is used, the safe and effective amount of the compound of the present invention is administrated to the mammal (such as human) that need to be treated, in which the pharmaceutically effective dosage is given. For the person with 60 kg body weight, the daily dosage is usually 1-2000 mg, preferably 5-500 mg. Of course, the specific dose should be adjusted dependent on the route of administration, the health status of patients and other factors, that are all within the scope of technical skill of practical physicians.

Said "room temperature" of the present invention is 25±5° C.

Said "overnight" of the present invention is 12±1 hours.
Said "1N HCl" of the invention is 1 mol/L HCl.

The present invention provides a compound of formula I, which is a structurally novel series of substituted imidazole carboxylate derivatives. The compound has a good inhibitory effect on the central nervous system, and can be used for preparation of drugs with sedation, hypnotic and/or anesthetic properties, as well as of drugs for status epilepticus control, that provide a new choice for the clinical screening and/or preparation of drugs with sedative, hypnotic and/or anesthetic effects and the control of status epilepticus, etc.

Obviously, based on above content of the present invention, according to the common technical knowledge and the conventional means in the field, without department from above basic technical spirits, other various modifications, alternations or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

Figure 1:
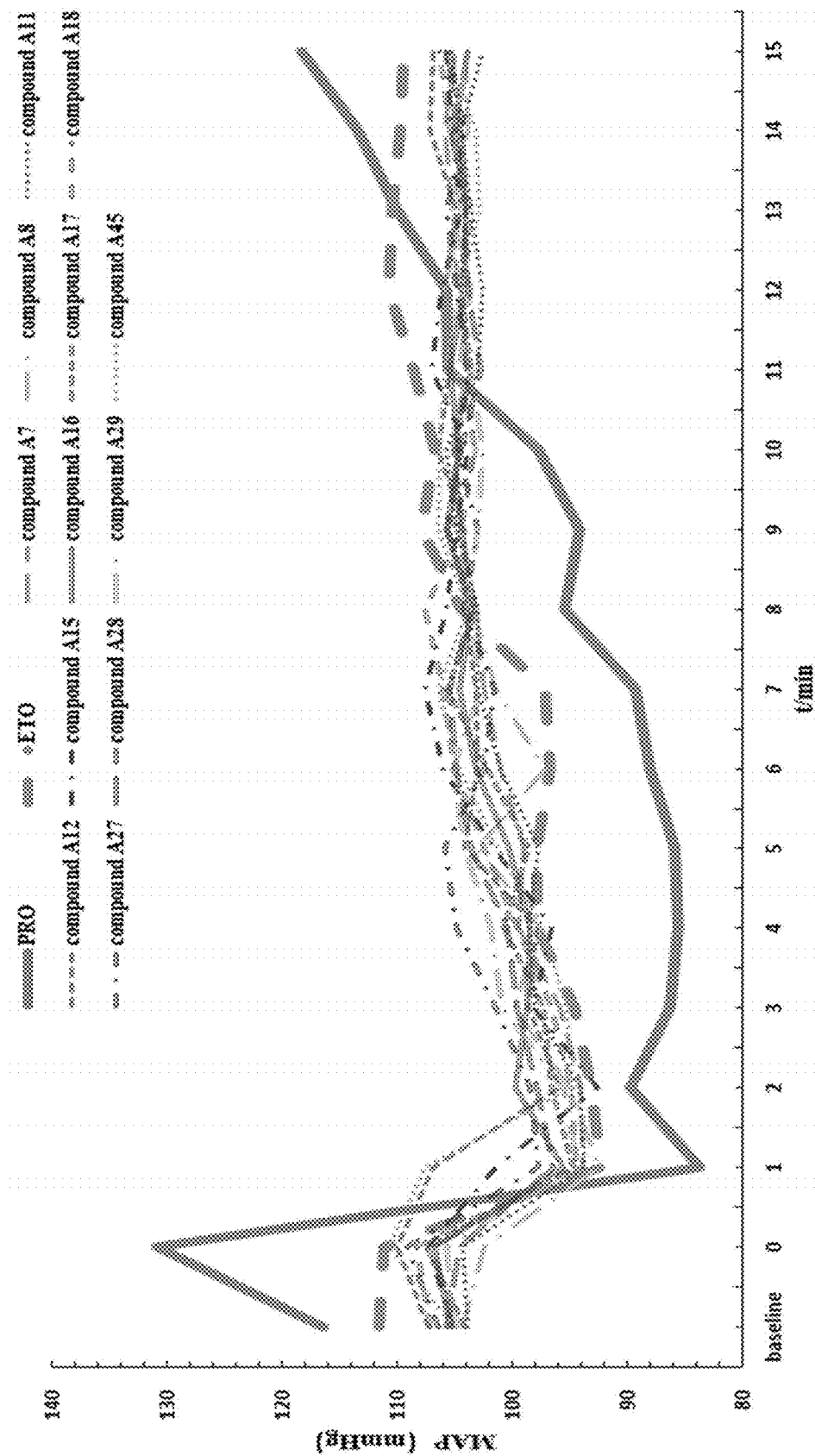
FIGS. 1, 5, 9, 13, and 17 were the effects of the compounds of the present invention on the mean arterial pressure (MAP) (actually measured values).

Notes:
1. All the test animals' righting reflex disappeared within 1 min after the administration;
2. The 0 min on the abscissa in the figure represents the end of administration;
3. The recovery time of the test animals' righting reflex for compounds or drugs were PRO: 645 s (10.75 min); ETO: 440 s (7.33 min); Compound A7: 110 s (1.83 min); Compound A8: 129 s (2.15 min); Compound A11: 225 s (3.75 min); Compound A12: 254 s (4.23 min); Compound A15: 193 s (3.22 min); Compound A16: 167 s (2.78 min); Compound A17: 327 s (5.45 min); Compound A18: 273 s (4.55 min); Compound A27: 126 s (2.10 min); Compound A28: 435 s (7.25 min); Compound A29: 255 s (4.25 min); Compound A45: 200 s (3.33 min); B5: 255 s (4.25 min); Compound B9: 109 s (1.82 min); Compound B10: 81 s (1.35 min); Compound B18: 279 s (4.65 min); Compound B19: 125 s (2.08 min); Compound B20: 161 s (2.68 min); Compound B29: 112 s (1.87 min); Compound C1: 130 s (2.17 min); Compound C2: 182 s (3.03 min); Compound C3: 75 s (1.25 min); Compound C6: 120 s (2.0 min); Compound C7: 112 s (1.87 min); Compound C8: 170 s (2.83 min); Compound C18: 115 s (1.92 min); Compound C20: 243 s (4.05 min); Compound C22: 93 s (1.55 min); Compound C23: 206 s (3.43 min); Compound C24: 135 s (2.25 min); Compound C25: 125 s (2.08 min); Compound C26: 137 s (2.28 min); Compound C27: 186 s (3.1 min); Compound D1: 785 s (13.08 min); Compound D2: 355 s (5.92 min); Compound D3: 76 s (1.27 min); Compound D7: 410 s (6.83 min); Compound D10: 605 s (10.08 min); Compound D13: 109 s (1.82 min); Compound D14: 210 s (3.5 min); Compound D15: 225 s (3.75 min); Compound D18: 317 s (5.28 min); Compound D21: 360 s (6.0 min); Compound D22: 50 s (0.83 min); Compound D34: 170 s (2.83 min); Compound D35: 200 s (3.33 min); Compound D36: 143 s (2.38 min); Compound D37: 165 s (2.75 min); Compound D38: 193 s (3.22 min); Compound D39: 375 s (6.25 min); Compound D40: 441 s (7.35 min); Compound D41: 355 s (5.92 min); Compound D42: 323 s (5.38 min); Compound D43: 117 s (1.95 min); Compound E2: 129 s (2.15 min); Compound E6: 174 s (2.90 min); Compound E8: 120 s (2.00 min); Compound E9: 77 s (1.28 min); Compound E10: 162 s (2.70 min); Compound E11: 93 s (1.55 min); Compound E12: 214 s (3.57 min); Compound E15: 72 s (1.20 min); Compound E16: 200 s (3.33 min); Compound E17: 196 s (3.27 min); Compound E18: 158 s (2.63 min); Compound E19: 56 s (0.93 min); Compound E20: 51 s (0.85 min); Compound E21: 155 s (2.58 min); Compound E22: 66 s (1.10 min); Compound E23: 92 s (1.53 min); Compound E24: 75 s (1.25 min); Compound E25: 134 s (2.23 min); Compound E26: 94 s (1.57 min); Compound E27: 246 s (4.10 min); Compound E28: 150 s (2.5 min); Compound E29: 165 s (2.75 min); Compound E30: 80 s (1.33 min); Compound E31: 105 s (1.75 min); Compound E32: 219 s (3.65 min); Compound E33: 247 s (4.12 min); Compound E35: 151 s (2.52 min); Compound E37: 100 s (1.67 min); Compound E38: 122 s (2.03 min); Compound E64: 149 s (2.48 min); Compound E90: 85 s (1.42 min); Compound E100: 110 s (1.83 min); Compound E102: 288 s (4.80 min); Compound E116: 92 s (1.53 min); Compound E121: 184 s (3.07 min); Compound E129: 52 s (0.87 min); Compound E133: 138 s (2.30 min); Compound E146: 201 s (3.35 min); Compound E148: 58 s (0.97 min); Compound E157: 182 s (3.03 min); Compound E160: 65 s (1.08 min); Compound E161: 140 s (2.33 min); Compound E163: 95 s (1.58 min); Compound E164: 77 s (1.28 min).

Figure 2:
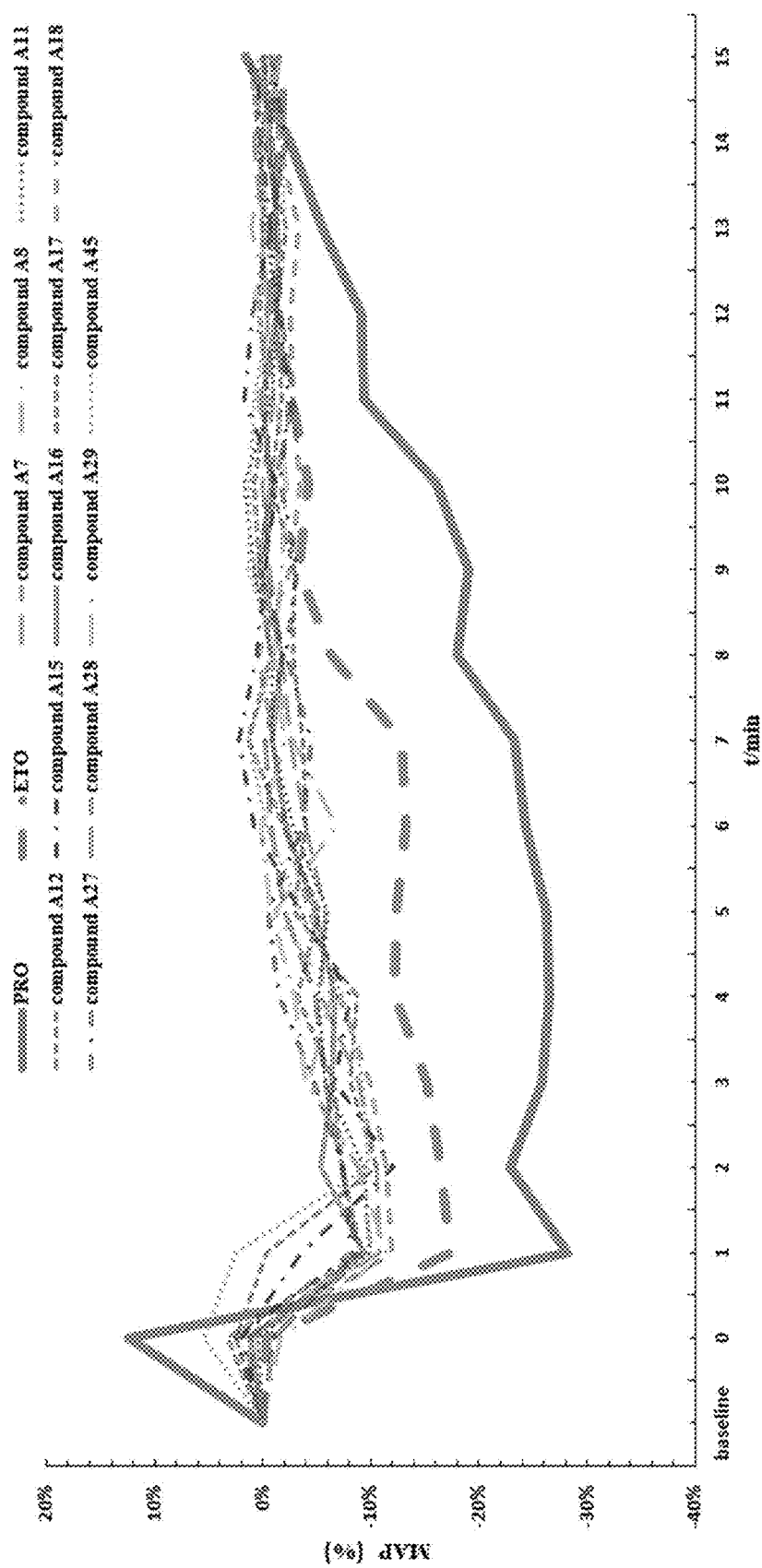
Figure 6:
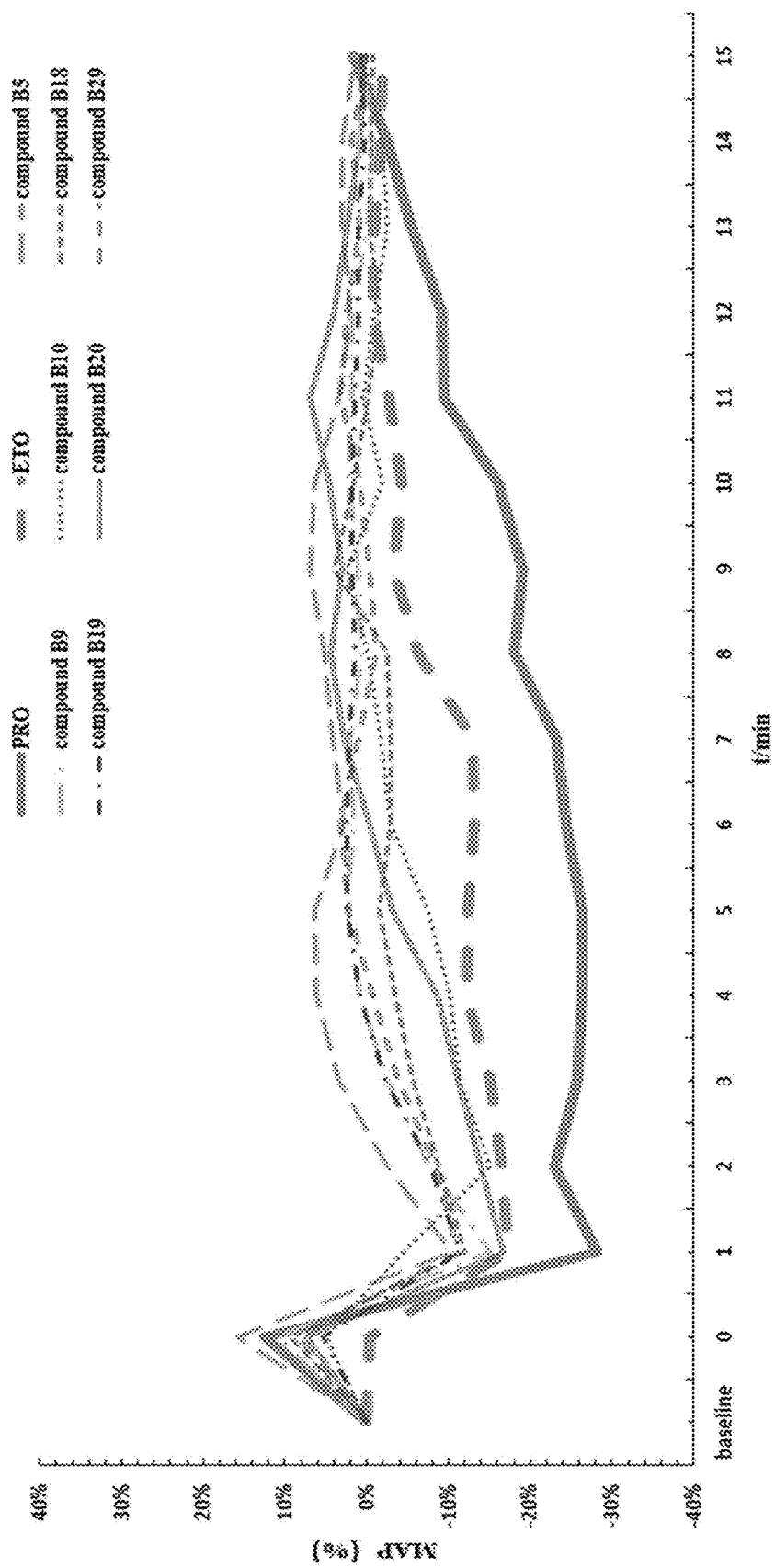
Figure 10:
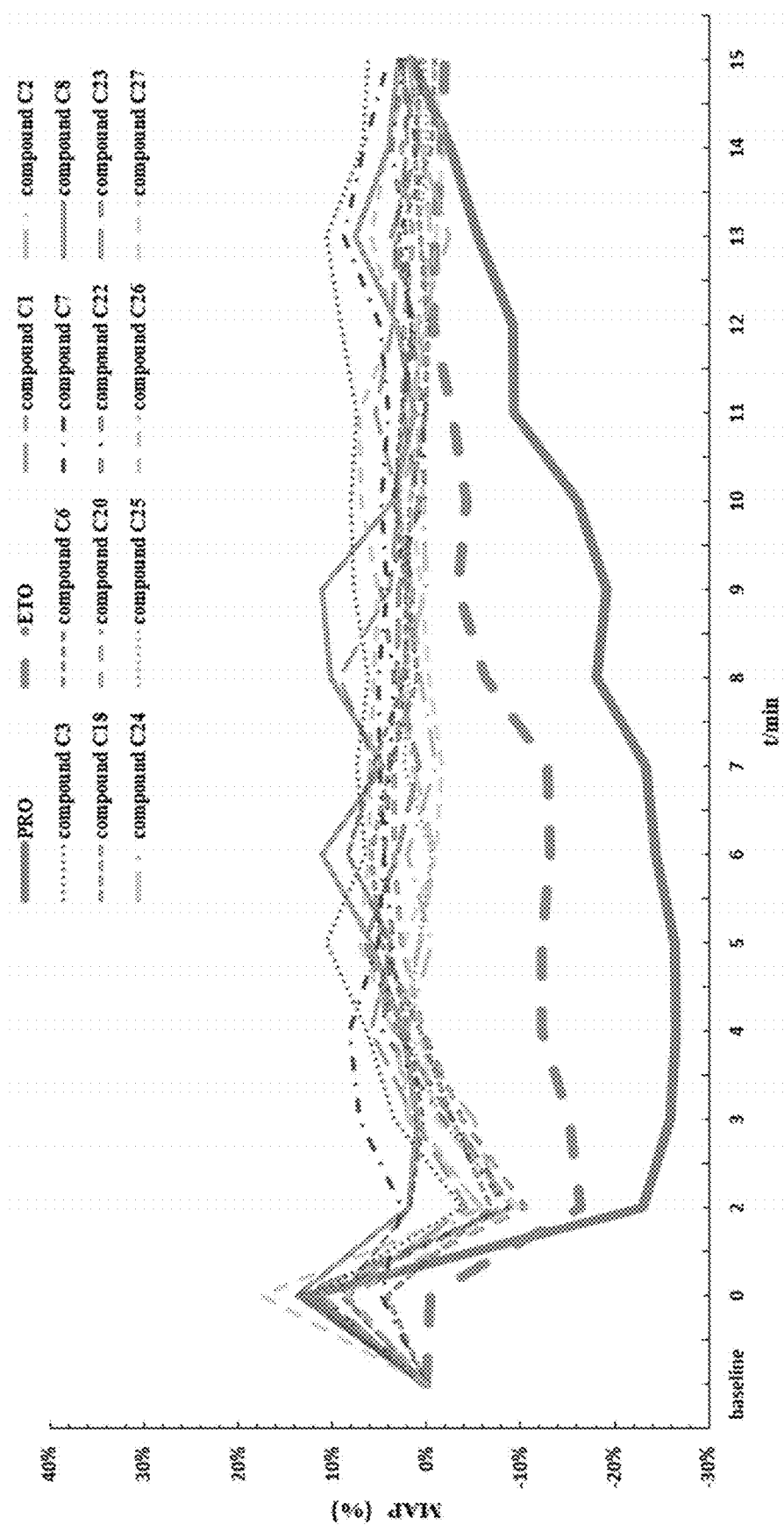
Figure 14:
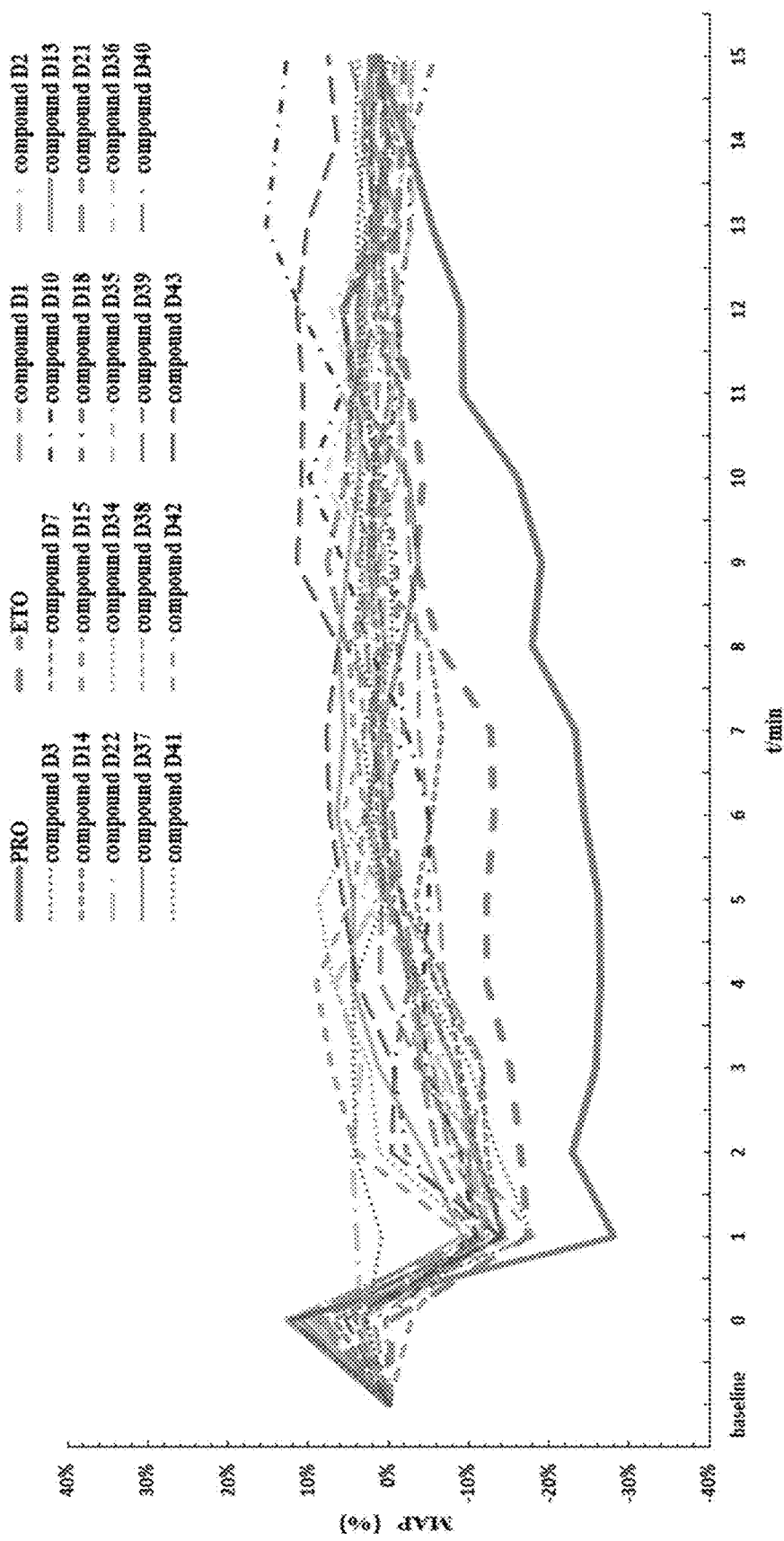
Figure 18:
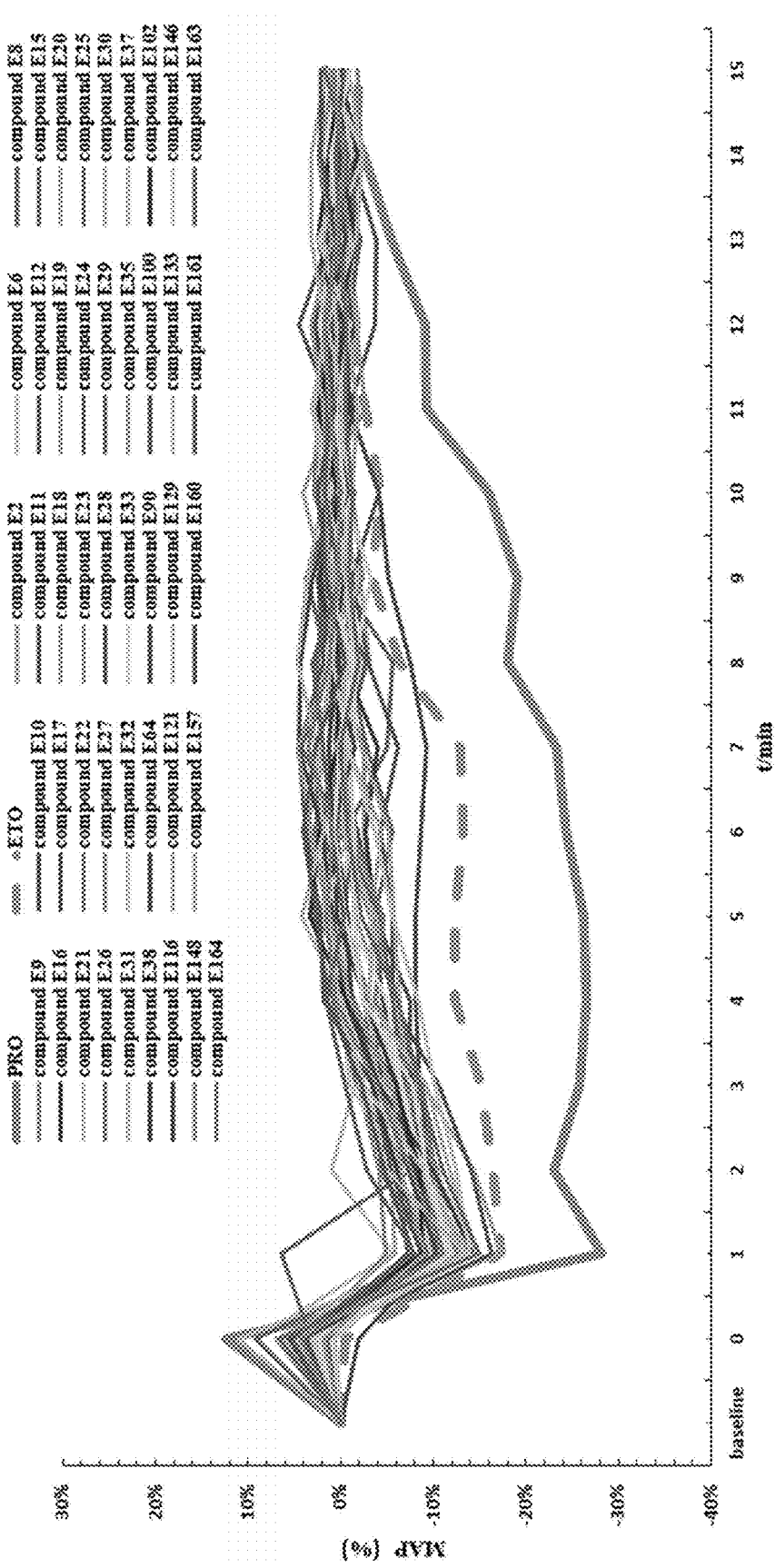

FIGS. 2, 6, 10, 14, and 18 were the effects (rate of change) of the compounds of the present invention on the mean arterial pressure (MAP).

Notes:
1. All the test animals' righting reflex disappeared within 1 min after the administration;
2. The 0 min on the abscissa in the figure represents the end of administration;

3. The recovery time of the test animals' righting reflex for compounds or drugs were PRO: 645 s (10.75 min); ETO: 440 s (7.33 min); Compound A7: 110 s (1.83 min); Compound A8: 129 s (2.15 min); Compound A11: 225 s (3.75 min); Compound A12: 254 s (4.23 min); Compound A15: 193 s (3.22 min); Compound A16: 167 s (2.78 min); Compound A17: 327 s (5.45 min); Compound A18: 273 s (4.55 min); Compound A27: 126 s (2.10 min); Compound A28: 435 s (7.25 min); Compound A29: 255 s (4.25 min); Compound A45: 200 s (3.33 min); Compound B5: 255 s (4.25 min); Compound B9: 109 s (1.82 min); Compound B10: 81 s (1.35 min); Compound B18: 279 s (4.65 min); Compound B19: 125 s (2.08 min); Compound B20: 161 s (2.68 min); Compound B29: 112 s (1.87 min); Compound C1: 130 s (2.17 min); Compound C2: 182 s (3.03 min); Compound C3: 75 s (1.25 min); Compound C6: 120 s (2.0 min); Compound C7: 112 s (1.87 min); Compound C8: 170 s (2.83 min); Compound C18: 115 s (1.92 min); Compound C20: 243 s (4.05 min); Compound C22: 93 s (1.55 min); Compound C23: 206 s (3.43 min); Compound C24: 135 s (2.25 min); Compound C25: 125 s (2.08 min); Compound C26: 137 s (2.28 min); Compound C27: 186 s (3.1 min); Compound D1: 785 s (13.08 min); Compound D2: 355 s (5.92 min); Compound D3: 76 s (1.27 min); Compound D7: 410 s (6.83 min); Compound D10: 605 s (10.08 min); Compound D13: 109 s (1.82 min); Compound D14: 210 s (3.5 min); Compound D15: 225 s (3.75 min); Compound D18: 317 s (5.28 min); Compound D21: 360 s (6.0 min); Compound D22: 50 s (0.83 min); Compound D34: 170 s (2.83 min); Compound D35: 200 s (3.33 min); Compound D36: 143 s (2.38 min); Compound D37: 165 s (2.75 min); Compound D38: 193 s (3.22 min); Compound D39: 375 s (6.25 min); Compound D40: 441 s (7.35 min); Compound D41: 355 s (5.92 min); Compound D42: 323 s (5.38 min); Compound D43: 117 s (1.95 min); Compound E2: 129 s (2.15 min); Compound E6: 174 s (2.90 min); Compound E8: 120 s (2.00 min); Compound E9: 77 s (1.28 min); Compound E10: 162 s (2.70 min); Compound E11: 93 s (1.55 min); Compound E12: 214 s (3.57 min); Compound E15: 72 s (1.20 min); Compound E16: 200 s (3.33 min); Compound E17: 196 s (3.27 min); Compound E18: 158 s (2.63 min); Compound E19: 56 s (0.93 min); Compound E20: 51 s (0.85 min); Compound E21: 155 s (2.58 min); Compound E22: 66 s (1.10 min); Compound E23: 92 s (1.53 min); Compound E24: 75 s (1.25 min); Compound E25: 134 s (2.23 min); Compound E26: 94 s (1.57 min); Compound E27: 246 s (4.10 min); Compound E28: 150 s (2.5 min); Compound E29: 165 s (2.75 min); Compound E30: 80 s (1.33 min); Compound E31: 105 s (1.75 min); Compound E32: 219 s (3.65 min); Compound E33: 247 s (4.12 min); Compound E35: 151 s (2.52 min); Compound E37: 100 s (1.67 min); Compound E38: 122 s (2.03 min); Compound E64: 149 s (2.48 min); Compound E90: 85 s (1.42 min); Compound E100: 110 s (1.83 min); Compound E102: 288 s (4.80 min); Compound E116: 92 s (1.53 min); Compound E121: 184 s (3.07 min); Compound E129: 52 s (0.87 min); Compound E133: 138 s (2.30 min); Compound E146: 201 s (3.35 min); Compound E148: 58 s (0.97 min); Compound E157: 182 s (3.03 min); Compound E160: 65 s (1.08 min); Compound E161: 140 s (2.33 min); Compound E163: 95 s (1.58 min); Compound E164: 77 s (1.28 min).

Figure 3:
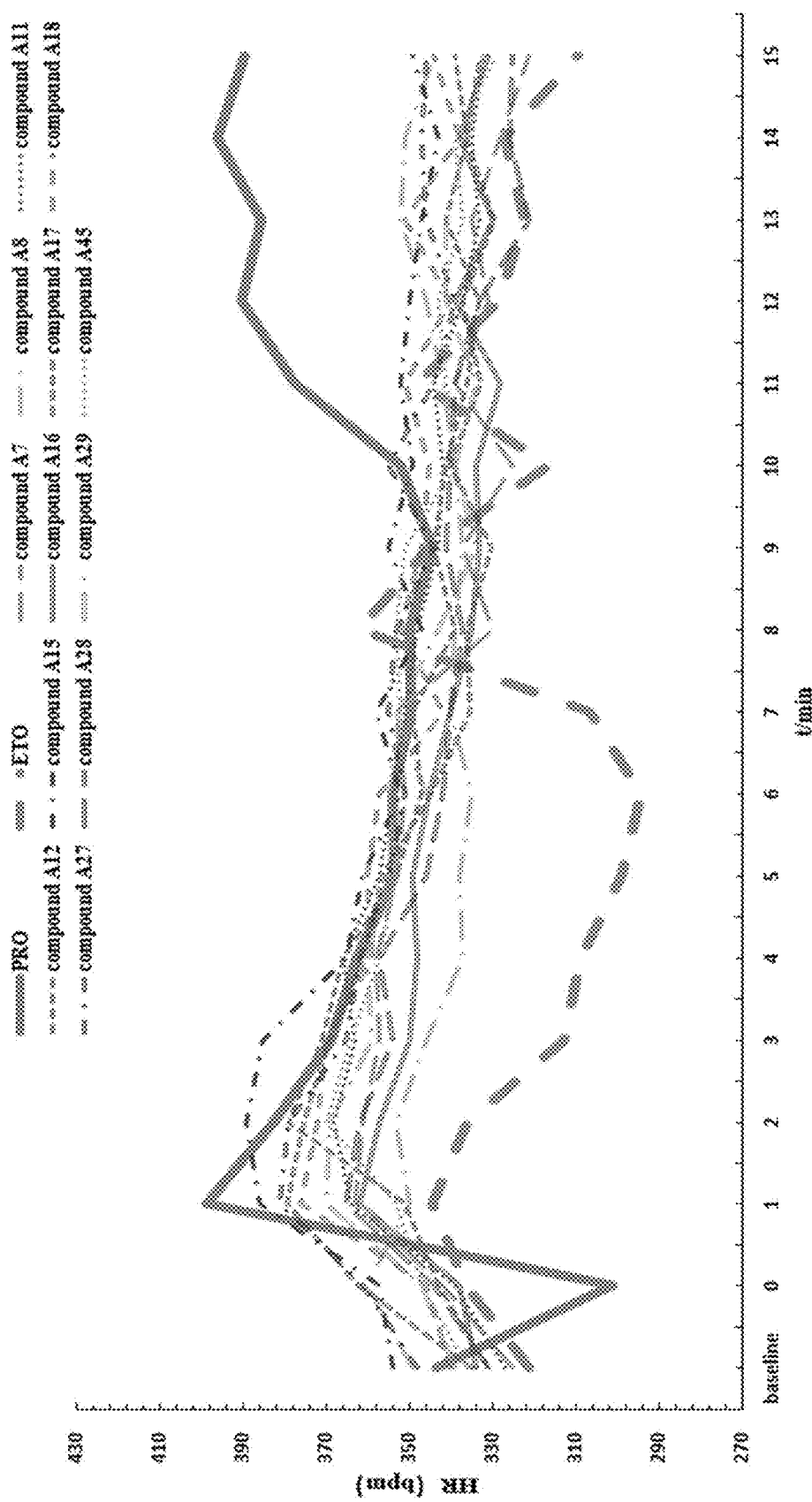
Figure 7:
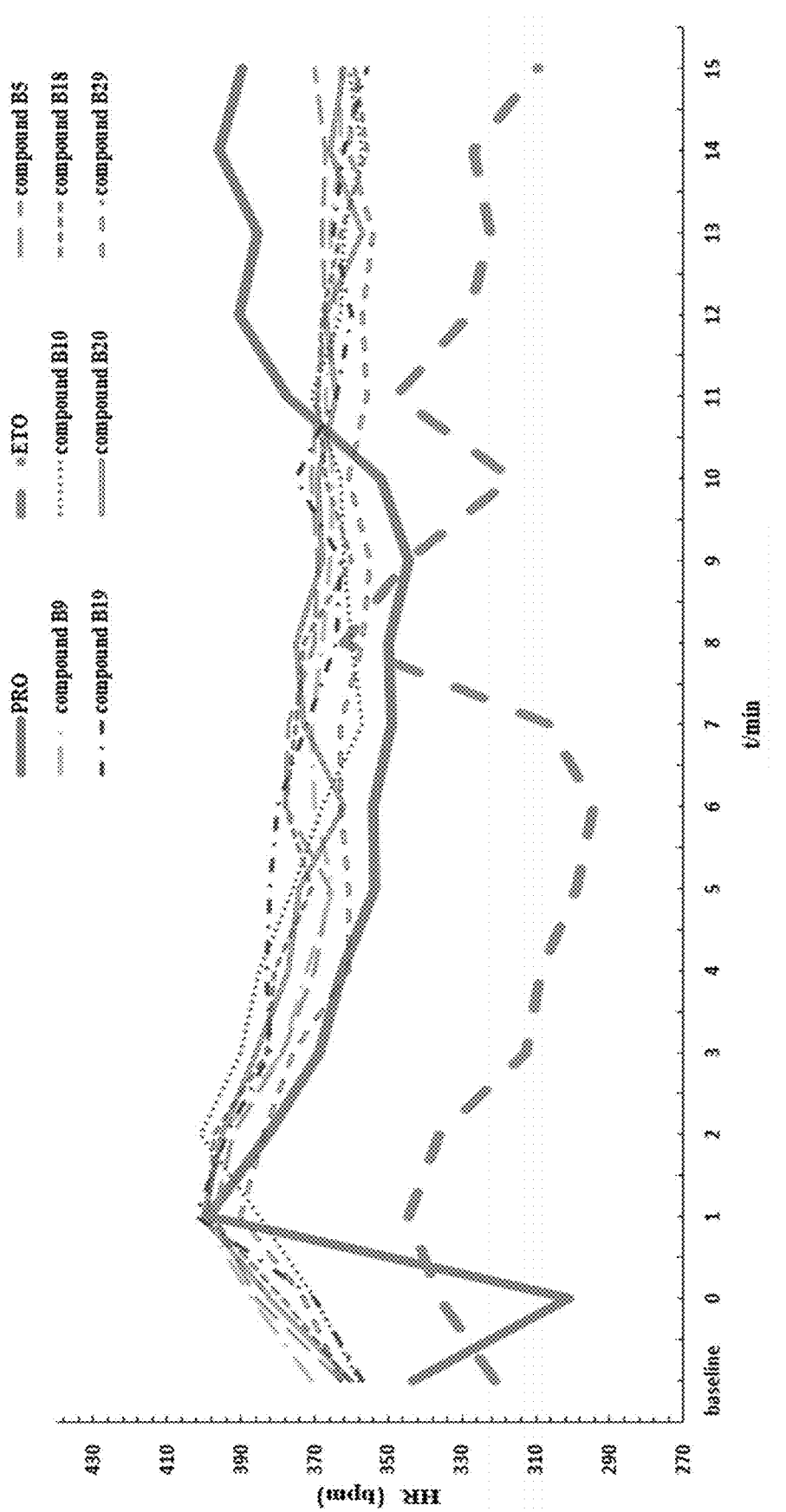
Figure 11:
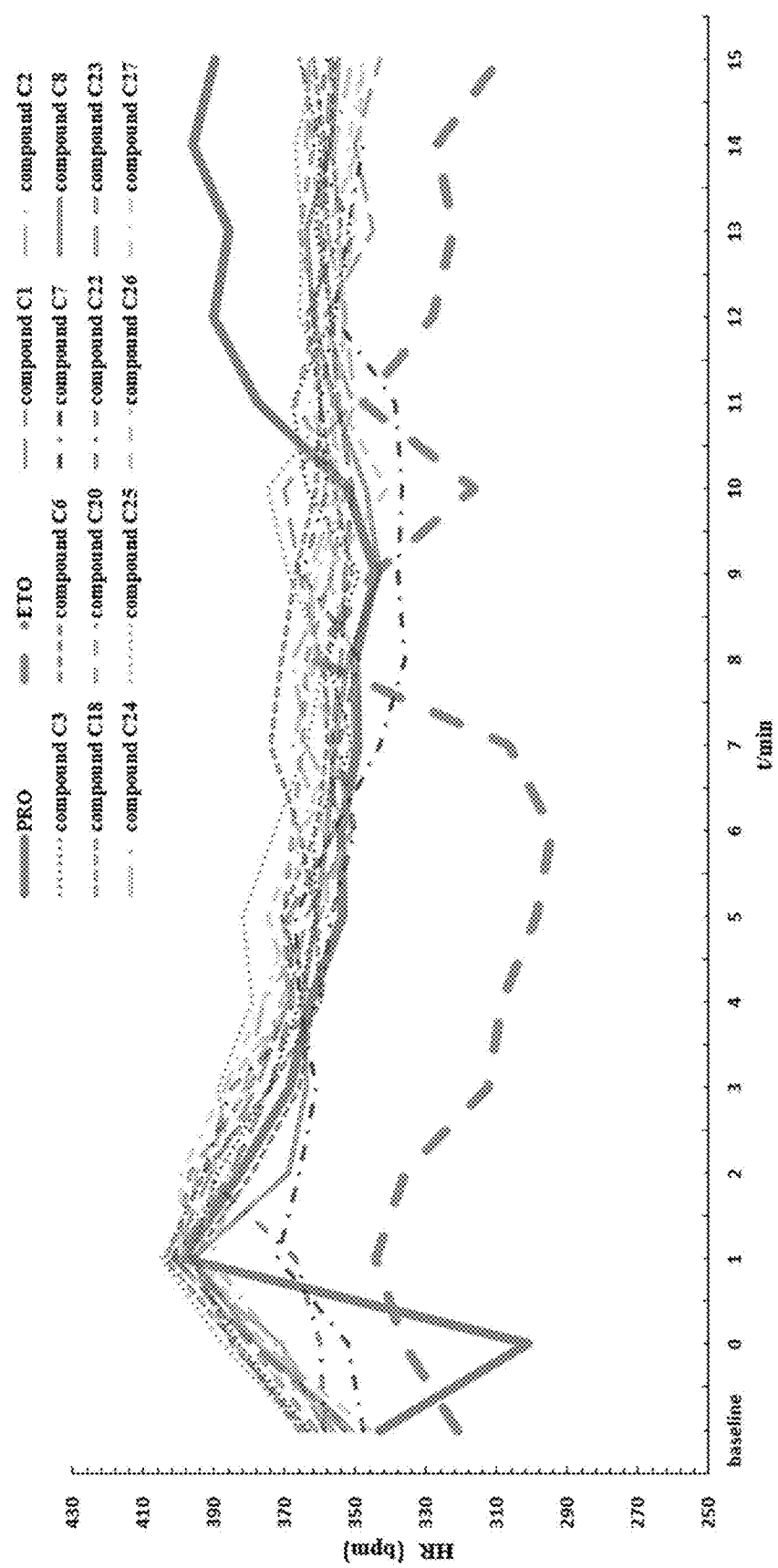
Figure 15:
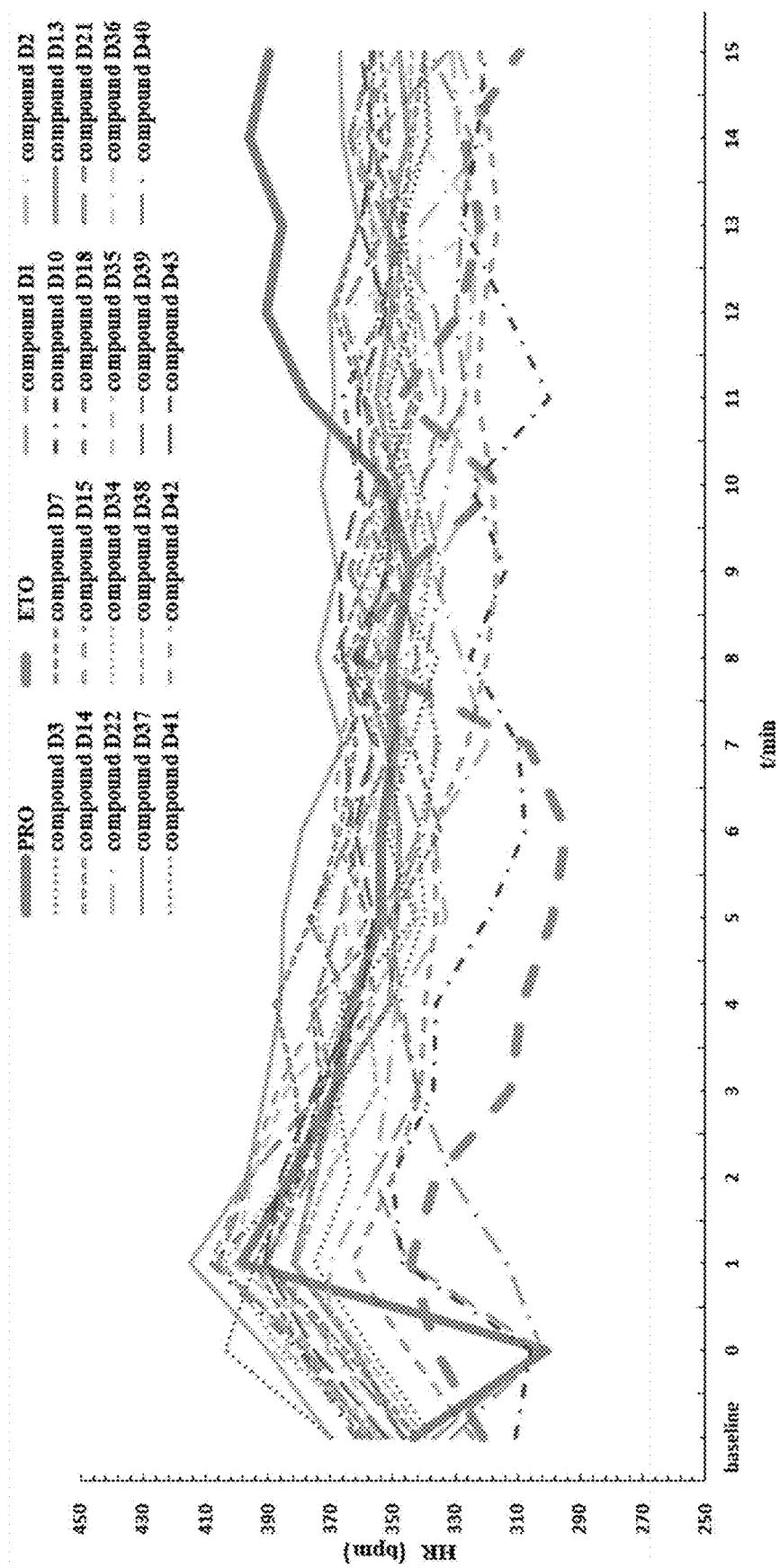
Figure 19:
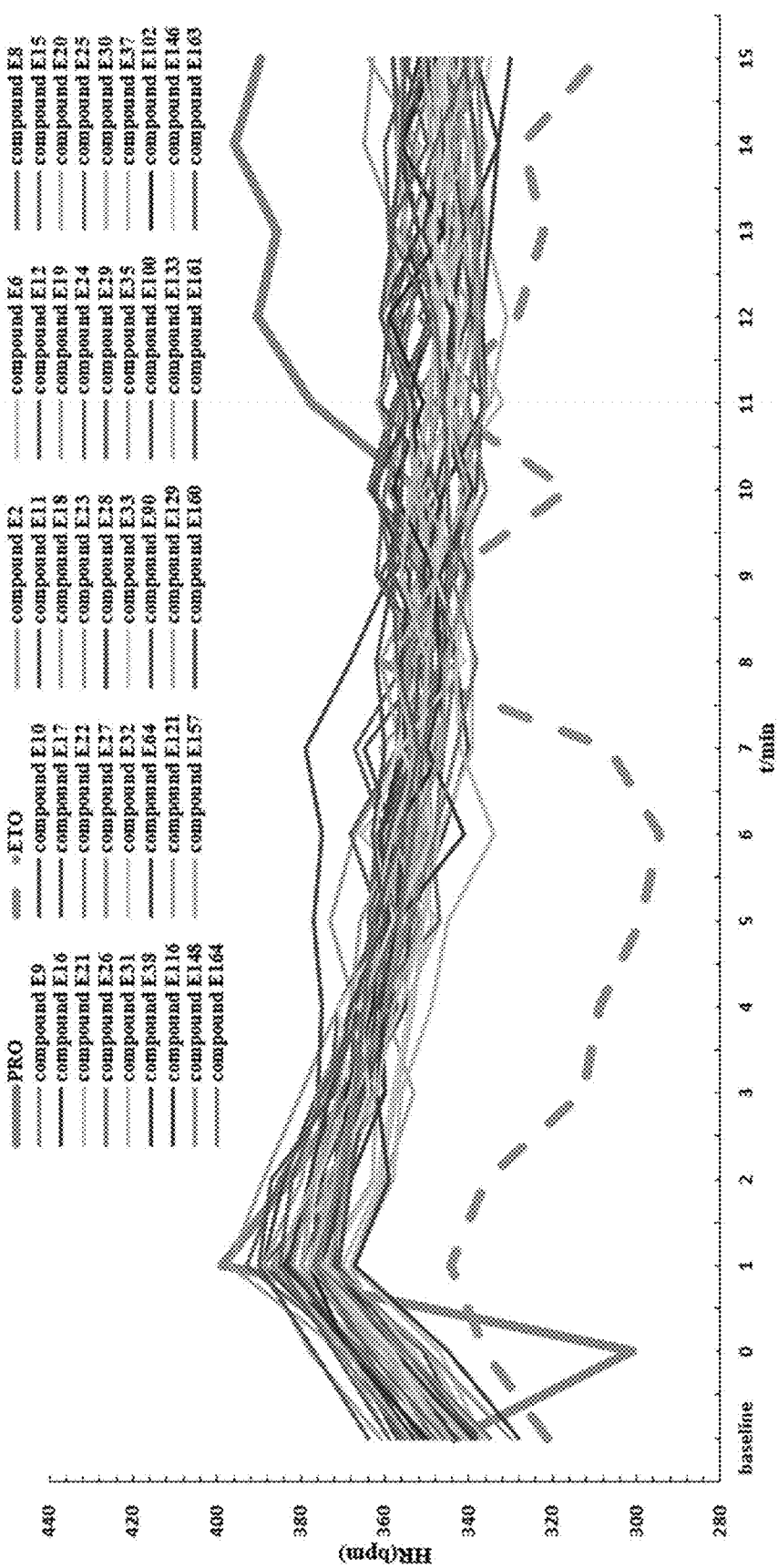

FIGS. 3, 7, 11, 15, 19 were the effects of the compounds of the present invention on heart rate (HR) (actually measured values).

Figure 4:
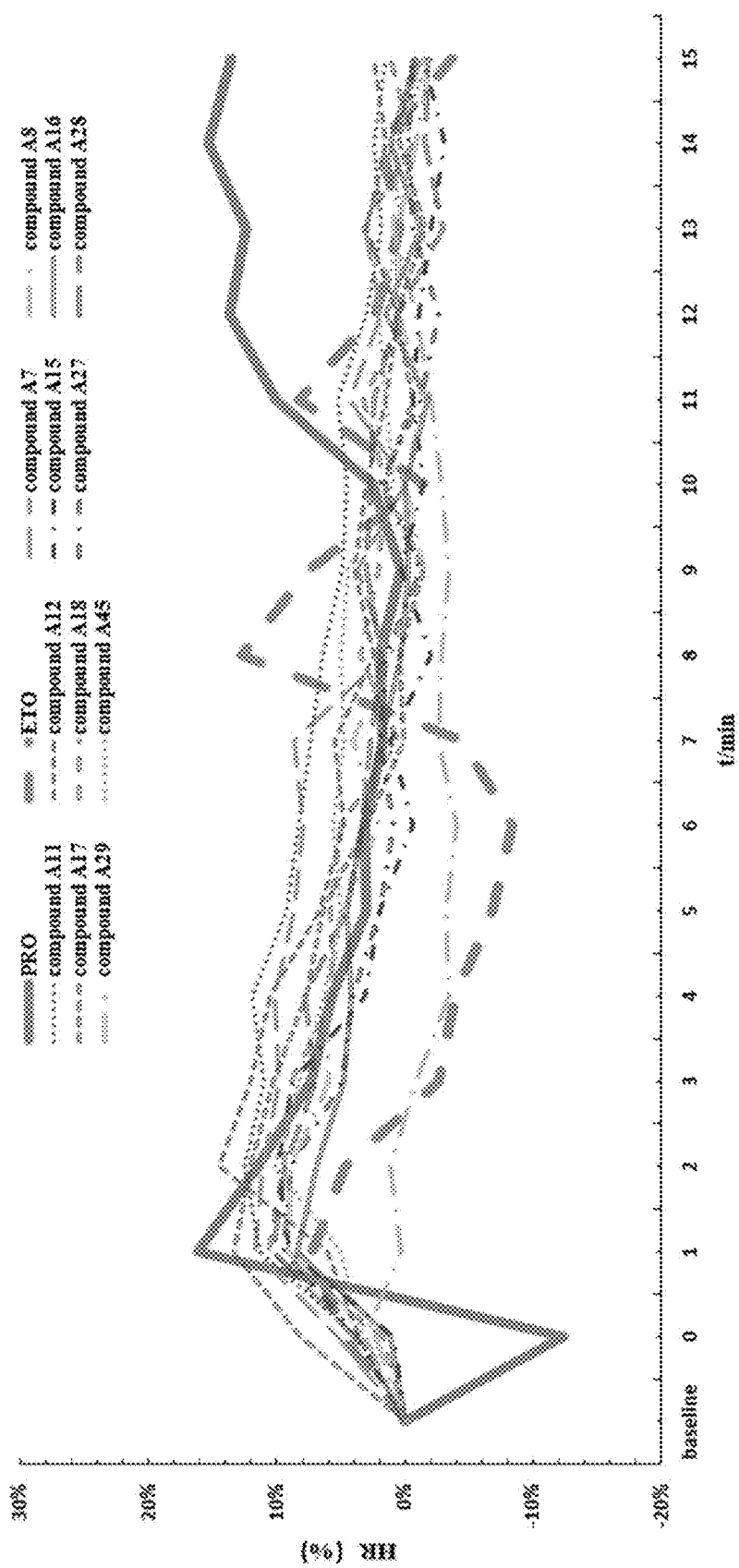
Figure 8:
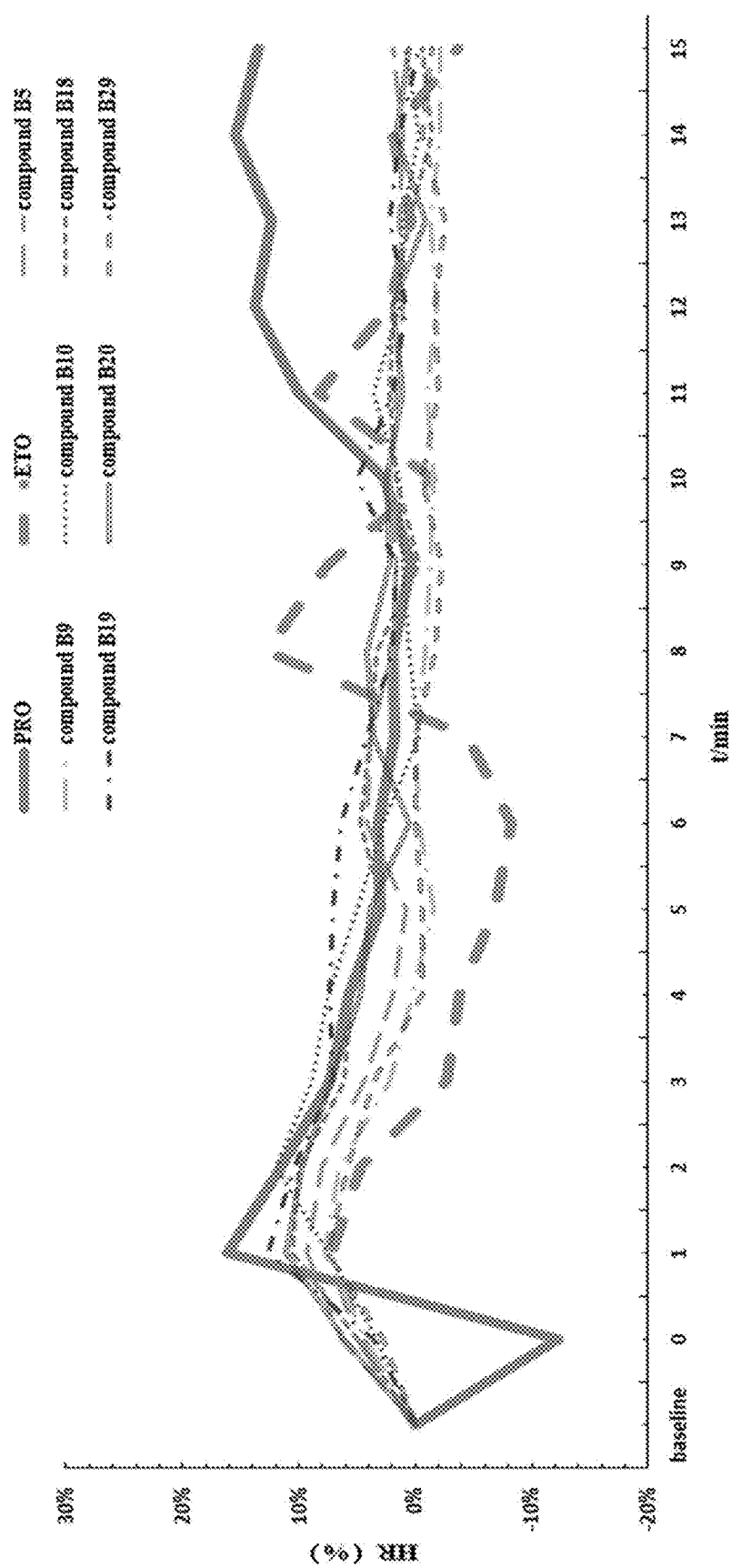
Figure 12:
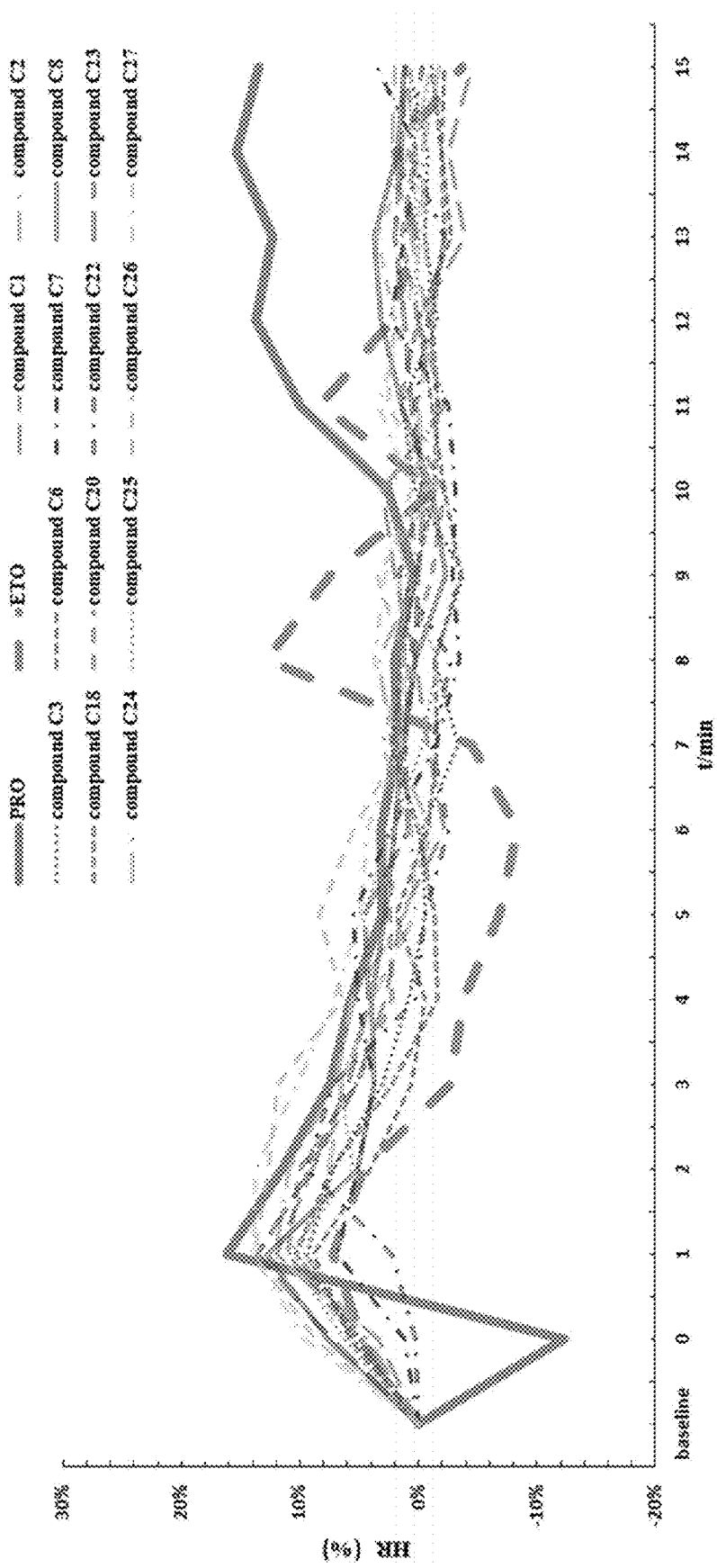
Figure 16:
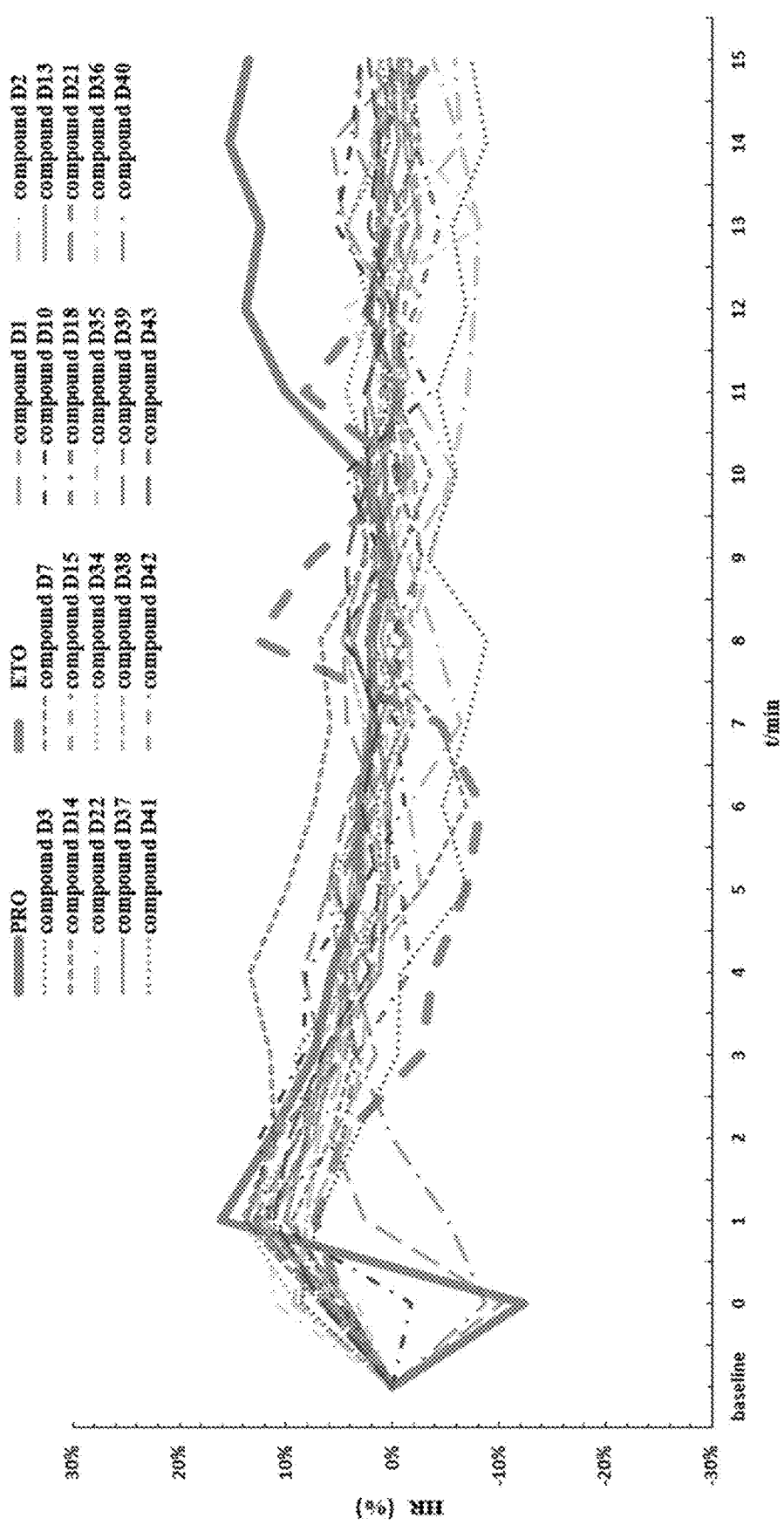
Figure 20:
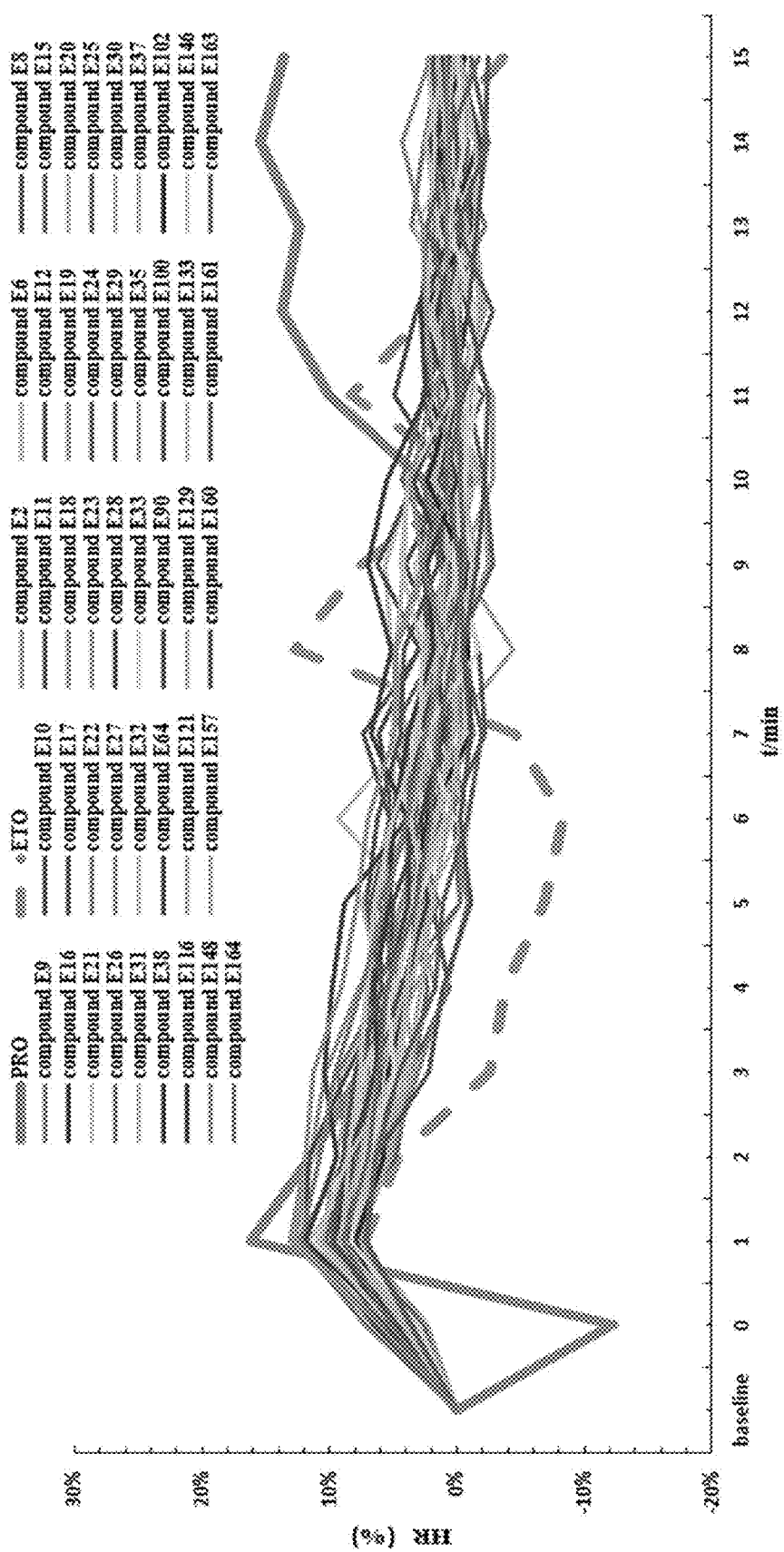

Notes:

1. All the test animals' righting reflex disappeared within 1 min after the administration;

2. The 0 min on the abscissa in the figure represents the end of administration;

FIGS. 4, 8, 12, 16, and 20 were the effects (rate of change) of the compounds of the present invention on heart rate (HR).

Notes:

1. All the test animals' righting reflex disappeared within 1 min after the administration;

2. The 0 min on the abscissa in the figure represents the end of administration;

3. The recovery time of the test animals' righting reflex for compounds or drugs were PRO: 645 s (10.75 min); ETO: 440 s (7.33 min); Compound A7: 110 s (1.83 min); Compound A8: 129 s (2.15 min); Compound A11: 225 s (3.75 min); Compound A12: 254 s (4.23 min); Compound A15: 193 s (3.22 min); Compound A16: 167 s (2.78 min); Compound A17: 327 s (5.45 min); Compound A18: 273 s (4.55 min); Compound A27: 126 s (2.10 min); Compound A28: 435 s (7.25 min); Compound A29: 255 s (4.25 min); Compound A45: 200 s (3.33 min); Compound B5: 255 s (4.25 min); Compound B9: 109 s (1.82 min); Compound B10: 81 s (1.35 min); Compound B18: 279 s (4.65 min); Compound B19: 125 s (2.08 min); Compound B20: 161 s (2.68 min); Compound B29: 112 s (1.87 min); Compound C1: 130 s (2.17 min); Compound C2: 182 s (3.03 min); Compound C3: 75 s (1.25 min); Compound C6: 120 s (2.0 min); Compound C7: 112 s (1.87 min); Compound C8: 170 s (2.83 min); Compound C18: 115 s (1.92 min); Compound C20: 243 s (4.05 min); Compound C22: 93 s (1.55 min); Compound C23: 206 s (3.43 min); Compound C24: 135 s (2.25 min); Compound C25: 125 s (2.08 min); Compound C26: 137 s (2.28 min); Compound C27: 186 s (3.1 min); Compound D1: 785 s (13.08 min); Compound D2: 355 s (5.92 min); Compound D3: 76 s (1.27 min); Compound D7: 410 s (6.83 min); Compound D10: 605 s (10.08 min); Compound D13: 109 s (1.82 min); Compound D14: 210 s (3.5 min); Compound D15: 225 s (3.75 min); Compound D18: 317 s (5.28 min); Compound D21: 360 s (6.0 min); Compound D22: 50 s (0.83 min); Compound D34: 170 s (2.83 min); Compound D35: 200 s (3.33 min); Compound D36: 143 s (2.38 min); Compound D37: 165 s (2.75 min); Compound D38: 193 s (3.22 min); Compound D39: 375 s (6.25 min); Compound D40: 441 s (7.35 min); Compound D41: 355 s (5.92 min); Compound D42: 323 s (5.38 min); Compound D43: 117 s (1.95 min); Compound E2: 129 s (2.15 min); Compound E6: 174 s (2.90 min); Compound E8: 120 s (2.00 min); Compound E9: 77 s (1.28 min); Compound E10: 162 s (2.70 min); Compound E11: 93 s (1.55 min); Compound E12: 214 s (3.57 min); Compound E15: 72 s (1.20 min); Compound E16: 200 s (3.33 min); Compound E17: 196 s (3.27 min); Compound E18: 158 s (2.63 min); Compound E19: 56 s (0.93 min); Compound E20: 51 s (0.85 min); Compound E21: 155 s (2.58 min); Compound E22: 66 s (1.10 min); Compound E23: 92 s (1.53 min); Compound E24: 75 s (1.25 min); Compound E25: 134 s (2.23 min); Compound E26: 94 s (1.57 min); Compound E27: 246 s (4.10 min); Compound E28: 150 s (2.5 min); Compound E29: 165 s (2.75 min); Compound E30: 80 s (1.33 min); Compound E31: 105 s (1.75 min); Compound E32: 219 s (3.65 min); Compound E33: 247 s (4.12 min); Compound E35: 151 s (2.52 min); Compound E37: 100 s (1.67 min); Compound E38: 122 s (2.03 min); Compound E64: 149 s (2.48 min); Compound E90: 85 s (1.42 min); Compound E100: 110 s (1.83 min); Compound E102: 288 s (4.80 min); Compound E116: 92 s (1.53 min); Compound E121: 184 s (3.07 min); Compound E129: 52 s (0.87 min); Compound E133: 138 s (2.30 min); Compound E146: 201 s (3.35 min); Compound E148: 58 s (0.97 min); Compound E157: 182 s (3.03 min); Compound E160: 65 s (1.08 min); Compound E161: 140 s (2.33 min); Compound E163: 95 s (1.58 min); Compound E164: 77 s (1.28 min).

EXAMPLES

All starting materials and equipments used in the present invention were known products, acquired by purchasing commercially available products The structures of the compounds were confirmed by 1H NMR and/or MS spectra. NMR spectra were recorded on a Bruker NMR 400 Avance III spectrometer, using $d_6$-DMSO or $CDCl_3$ as deuterated solvent. NMR Chemical shift (δ) was given in part per million (ppm) relative to the internal standard of tetramethylsilane (TMS)

Agilent LCMS 1260-6110 (ESI) was used in the present invention. Column: Waters X-Bridge C18 (50 mm×4.6 mm×3.5 μm). Column temperature: 40° C.; Flow rate: 2.0 mL/min; Chromatographic analysis was performed in gradient mode. The mobile phases were composed of 0.05% TFA in water (A) and 0.05% TFA in Acetonitrile (B). A gradient elution was applied from 95% A and 5% B to 0% A and 100% B within 3 mins, then extended for another 1 min, and at end changed back to 95% A and 5% B within 0.05 mins and kept eluting for another 0.7 mins.

1) Materials and Reagents

The silica gel plate (HSGF254) for thin layer chromatography was bought from Yantai Xinnuo Chemical Co., Ltd, with the thickness of 1 mm.

Thin layer chromatography (TLC) was bought from Yantai Jiangyou silicone Development Co., Ltd., with the thickness of 0.2±0.03 mm.

Silica gel used for column chromatography was mostly made by Rushan Sun Desiccant Co., Ltd. (Weihai, Shandong) with 100-200 meshes or 200-300 meshes.

2) The Main Instruments

Electronic Balance JA2003N (manufactured by Shanghai Yoke Instrument Co., Ltd);

Magnetic Stirrer (model: 98-2, manufactured by Shanghai Sile Instrument Co., Ltd);

Contact Voltage Regulator (manufacturer: Zhejiang Tianzheng Electric Co., Ltd);

Temperature Controller (made by Shanghai Lulin Electric Co., Ltd);

Three-function Ultraviolet Analysis (model: ZF-2, manufactured by Shanghai Anting Electronic Instrument Factory);

Rotary Evaporator R-201 (manufactured by Shanghai Shenshun Biological Technology Co., Ltd)

Constant Temperature Water Bath (model: W201D, manufactured by Shanghai Shenshun Biological Technology Co., Ltd)

Circulating Water Vacuum Pump SHB-III (manufactured by Zhengzhou Huicheng Technology Industry and Trade Co., Ltd)

Mobile Water Pump SHB-B95 (manufactured by Zhengzhou Huicheng Technology Industry and Trade Co., Ltd)

Low-temperature Cooling Liquid Circulating Pump (manufactured by Gongyi Yuhua Instrument Co., Ltd)

Rotary Vane Vacuum Pump (manufactured by Linhai Yonghao Vacuum Equipment Co., Ltd)

Ultraviolet High-pressure Mercury Lamp (manufactured by Beijing Tianmai Henghui Lamp-house Electric Appliances Co., Ltd)

General Procedure A:

At room temperature, R-1-(1-phenethyl)-1H-imidazole-5-carboxylic acid or its derivatized acids (1 eq), DCC (1.5 eq) and DMAP (1.5 eq) were dissolved in dichloromethane. After stirring 5 min, Alcohol or Thiol was added dropwise into above mixture using a syringe and the mixture was stirred at room temperature overnight. The reaction was monitored by TLC until completion, then it was concentrated under reduced pressure. Methyl tert-butyl ether was added to the residue and stirred, filtered, the filter cake was washed with methyl tert-butyl ether, the filtrate was concentrated under reduced pressure. The residue was purified by silica gel column chromatography or Prep-TLC to give the desired product.

General Procedure B:

In an ice bath, NaH (60% in mineral oil, 1.2 eq) was added in portions into the mixture of etomidate derivatized alcohol in THF at 0° C., then it was stirred at 0° C. for 30 min. Iodomethane, iodoethane or methyl bromoacetate in THF was added into the mixture with a syringe slowly. The mixture was reacted at 0° C. until completion, which was monitored by TLC. The mixture was quenched with the saturated ammonium chloride solution and extracted with dichloromethane. The combined organic layers were washed with saturated brine, dried over anhydrous sodium sulfate, filtered and concentrated under reduced pressure. The residue was purified by silica gel column chromatography or Prep-TLC to give the target product.

General Procedure C:

In an ice bath, alchol (1 eq) and $Et_3N$ (1.5 eq) were dissolved in dichloromethane at 0° C., then methanesulfonyl chloride (1.5 eq) was added into the mixture slowly using a syring at 0° C., then the mixture was allowed to react at 0° C. for 1 hour. The reaction was monitored by TLC until completion. The mixture was quenched with 1N HCl, the combined organic layers were washed with saturated sodium bicarbonate solution and saturated brine, dried over anhydrous sodium sulfate, filtered and concentrated under reduced pressure to give crude product, which was used for next step directly without further purification.

In an ice bath, the above crude product (1 eq) was dissolved in DMF, NaHS (1.5 eq) was added in portions into the mixture (0.5 mmol/min), the mixture was allowed to react at 0° C. for 1 hour. The reaction was monitored by TLC until completion. The mixture was quenched with saturated brine, extracted with ethyl acetate (3×10 mL). The combined organic layers were washed with saturated brine (30 mL), dried over anhydrous sodium sulfate, filtered and concentrated under reduced pressure to give crude product, which was used for next step directly without further purification.

Example A1 Preparation of Compounds A1 and A3

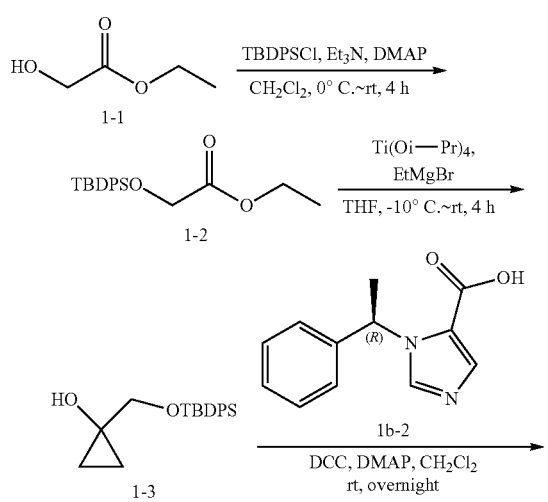

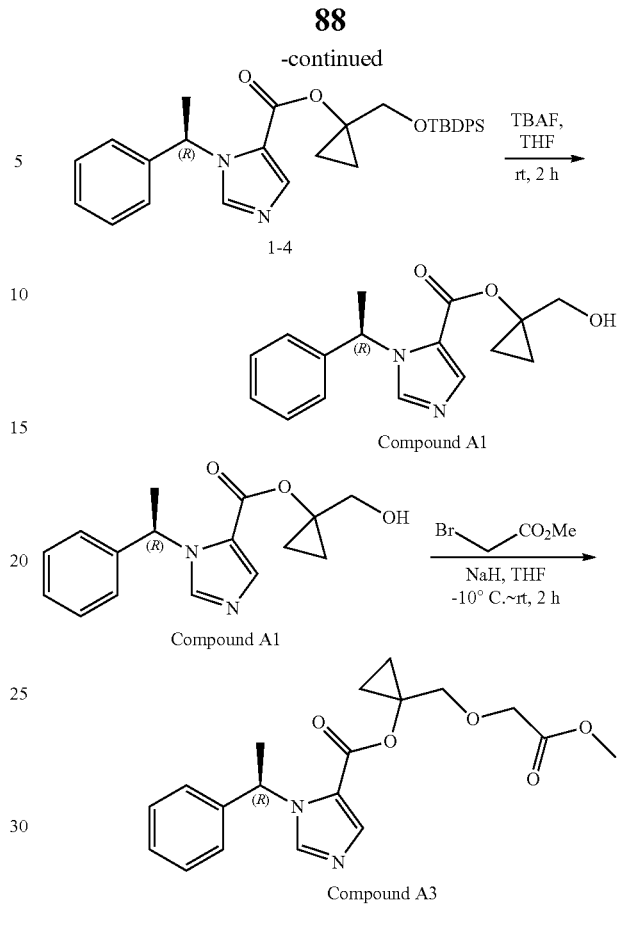

1. Preparation of ethyl 2-((tert-butyldiphenylsilyl)oxy)acetate (1-2)

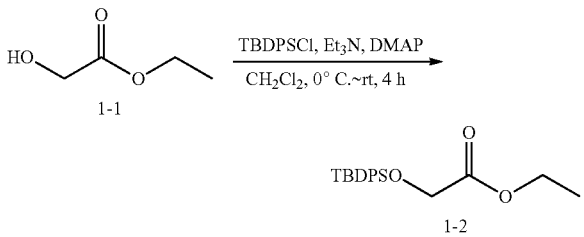

In an ice bath, to the mixture of ethyl 2-hydroxyacetate (1-1) (10.0 g, 96.1 mmol), $Et_3N$ (29.1 g, 0.288 mol) and DMAP (1.17 g, 9.61 mmol) in dichloromethane (100 mL) was added tert-butylchlorodiphenylsilane (29.1 g, 0.106 mol) dropwise over a 30-min period at 0° C. After addition, the ice bath was removed and the mixture was allowed to react at room temperature for 4 hrs. When the reaction was completed, it was quenched with water. The combined organic layers were washed with 1N HCl and saturated brine, dried over anhydrous sodium sulfate, filtered and concentrated under reduced pressure. The residue was purified by silica gel column chromatography (ethyl acetate/petroleum ether (v/v) at any ratio within the range of 1/100 to 1/50), with TLC (ethyl acetate/petroleum ether (v/v)=1/10) monitoring, and collecting the fraction with Rf=0.6~0.7, to give compound 1-2 (34.0 g, yield 100%) as colorless oil. ESI[M+H]$^+$=365.2

2. Preparation of 1-(((Tert-butyldiphenylsilyl)oxy)methyl)cyclopropan-1-ol (1-3)

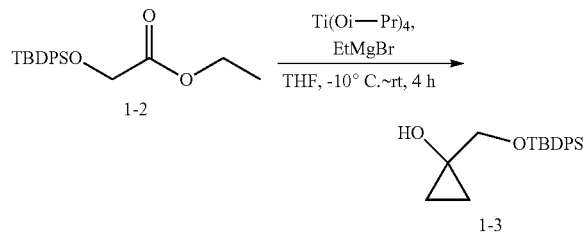

To the mixture of 1-2 (6.50 g, 19.0 mmol) in THF (100 mL) was added Ti(Oi-Pr)$_4$ (1.17 g, 4.12 mmol) over a 5-min period using a syringe at −10° C., then ethylmagnesium bromide (45 mL, 1 mol/L in THF, 45 mmol) was added dropwise into the mixture at the rate of 1 mL/min and the temperature was controlled below 5° C. The mixture was allowed to react at room temperature for 4 hrs. The reaction was monitored by TLC until completion. The mixture was quenched with water and extracted with hexane (3×50 mL). The combined organic layers were washed with saturated brine (50 mL), dried over anhydrous sodium sulfate, filtered and concentrated under reduced pressure. The residue was purified by silica gel column chromatography (ethyl acetate/petroleum ether (v/v) at any ratio within the range of 1/3 to 1/1.5), with TLC (ethyl acetate/petroleum ether (v/v)=1/2) monitoring, and collecting the fraction with Rf=0.4~0.5, to give compound 1-3 (1.34 g, yield 22%) as colorless oil. ESI[M+Na]$^+$=349.3

3. Preparation of 1-(((Tert-butyldiphenylsilyl)oxy)methyl)cyclopropyl(R)-1-(1-phenylethyl)-1H-imidazole-5-carboxylate (1-4)

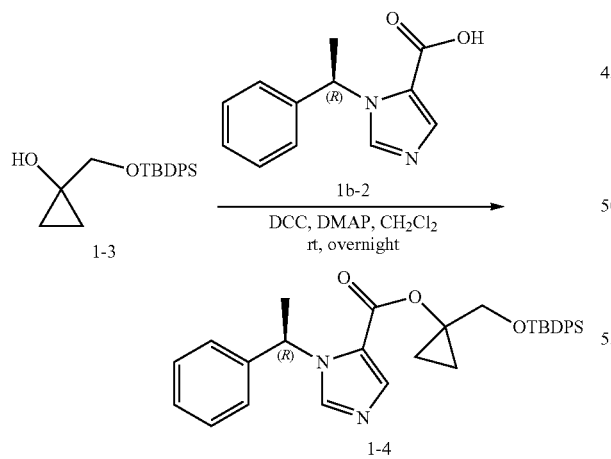

The title compound was prepared according to the general procedure A, using 1b-2 (910 mg, 4.21 mmol) and 1-3 (1.30 g, 3.98 mmol) as the raw materials. The crude product was purified by silica gel column chromatography (ethyl acetate/petroleum ether (v/v) at any ratio within the range of 1/10 to 1/1), with TLC (ethyl acetate/petroleum ether (v/v)=1/2) monitoring, and collecting the fraction with Rf=0.5~0.6, to give compound 1-4 (1.50 g, yield 72%) as colorless oil. ESI[M+H]$^+$=525.3

4. Preparation of Compound A1

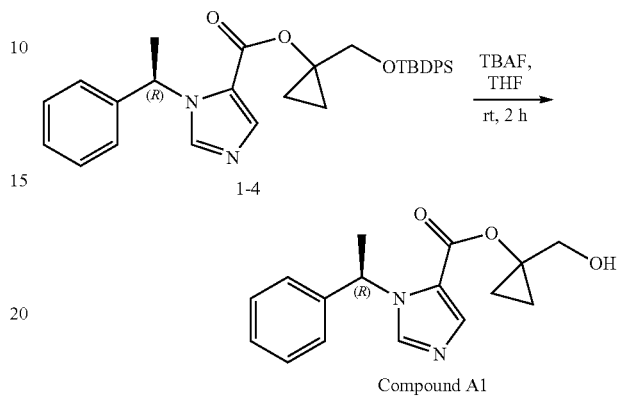

Compound A1

At room temperature, TBAF (2.86 mL, 1 mol/L in THF, 2.86 mmol) was added into the solution of 1-4 (1.5 g, 2.86 mmol) in THF and the mixture was allowed to react at room temperature for 2 hrs. The reaction was monitored by TLC until completion, and then it was concentrated under reduced pressure. The residue was purified by silica gel column chromatography (ethyl acetate/petroleum ether (v/v) at any ratio within the range of 1/3 to 1/1), with TLC (ethyl acetate/petroleum ether (v/v)=1/1) monitoring, and collecting the fraction with Rf=0.3~0.4, to give the product A1 (778 mg, yield 95%) as colorless oil. ESI[M+H]$^+$=287.2

5. Preparation of Compound A3

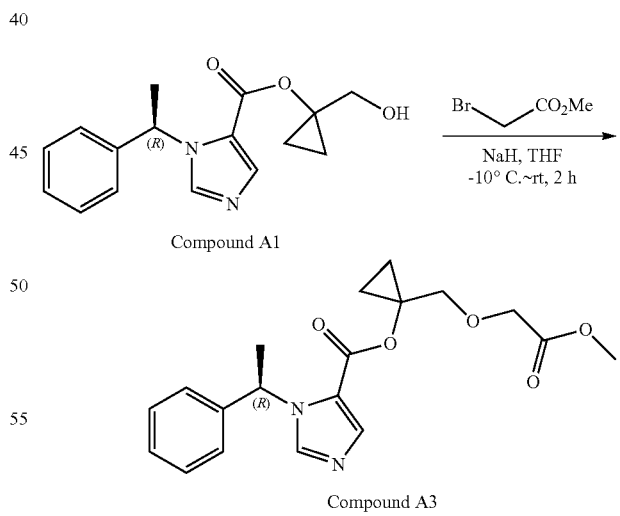

Compound A3

The title compound was prepared according to the general procedure B, using A1 (181 mg, 0.63 mmol) and methyl 2-bromoacetate (115 mg, 0.75 mmol) as the raw materials. The crude product was purified by Prep-TLC (ethyl acetate/petroleum ether (v/v)=1/1) and the fraction with Rf=0.4~0.5 was collected and dried to give the title compound A3 (80 mg, yield 35%) as colorless oil. ESI[M+H]$^+$=359.2

Example A2 Preparation of Compounds A2, A4 and A6

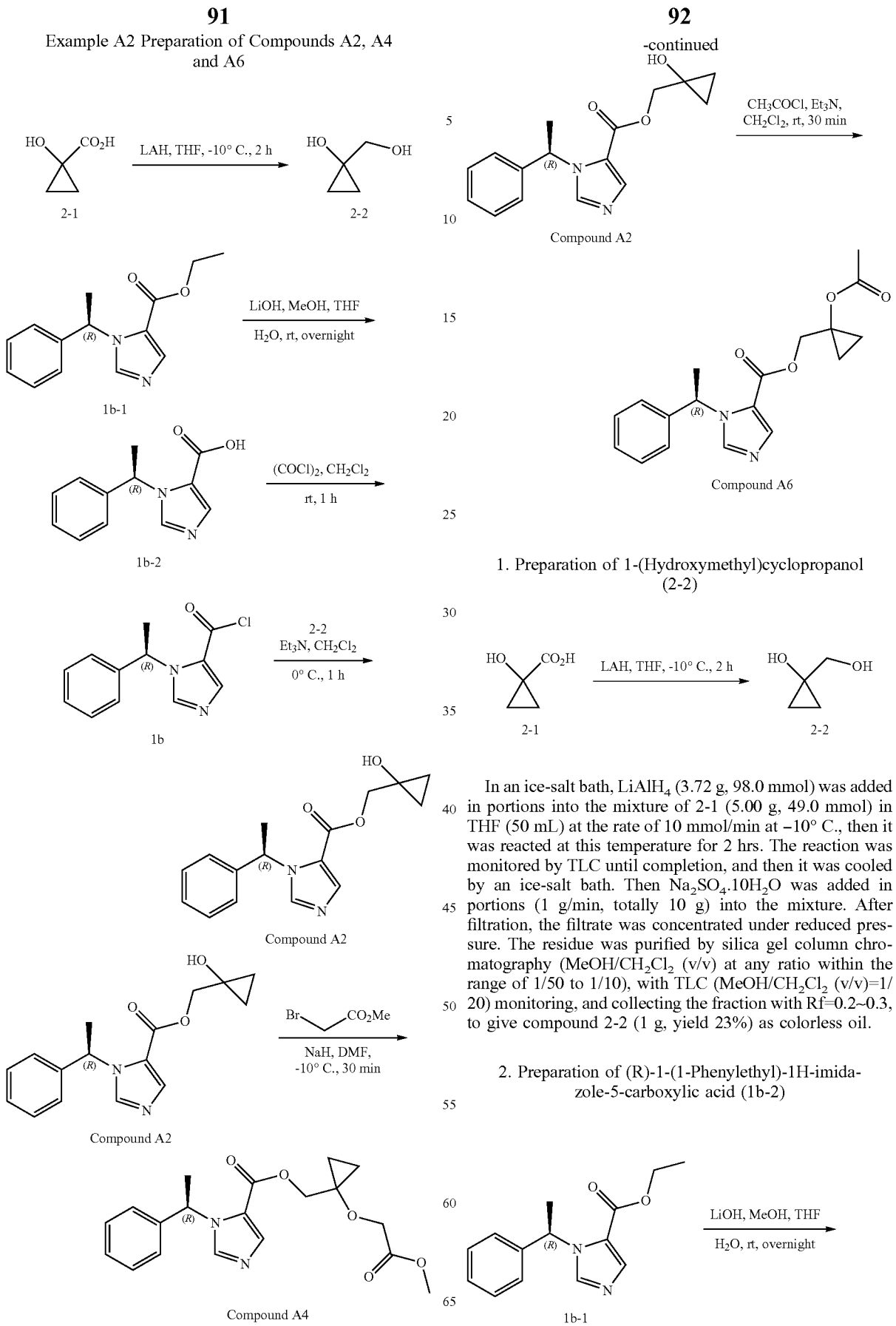

1. Preparation of 1-(Hydroxymethyl)cyclopropanol (2-2)

In an ice-salt bath, LiAlH$_4$ (3.72 g, 98.0 mmol) was added in portions into the mixture of 2-1 (5.00 g, 49.0 mmol) in THF (50 mL) at the rate of 10 mmol/min at −10° C., then it was reacted at this temperature for 2 hrs. The reaction was monitored by TLC until completion, and then it was cooled by an ice-salt bath. Then Na$_2$SO$_4$·10H$_2$O was added in portions (1 g/min, totally 10 g) into the mixture. After filtration, the filtrate was concentrated under reduced pressure. The residue was purified by silica gel column chromatography (MeOH/CH$_2$Cl$_2$ (v/v) at any ratio within the range of 1/50 to 1/10), with TLC (MeOH/CH$_2$Cl$_2$ (v/v)=1/20) monitoring, and collecting the fraction with Rf=0.2~0.3, to give compound 2-2 (1 g, yield 23%) as colorless oil.

2. Preparation of (R)-1-(1-Phenylethyl)-1H-imidazole-5-carboxylic acid (1b-2)

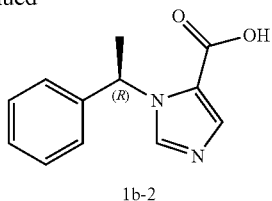

1b-2

At room temperature, LiOH (980 mg, 41.0 mmol) was added to the mixture of 1b-1 (5.00 g, 20.5 mmol) in MeOH/THF/H$_2$O (60 mL, 1/1/1), then the mixture was stirred at room temperature overnight. The reaction was concentrated under reduced pressure, the residue was poured into water (50 mL), and then it was adjusted pH to 4-5 using 1N HCl. The solution was extracted with CH$_2$Cl$_2$ (3×15 ml). The combined organic layers were washed with saturated brine, dried over anhydrous sodium sulfate, filtered and concentrated to give the compound 1b-2 (4.10 g, yield 93%) as a white solid.

3. Preparation of (R)-1-(1-Phenylethyl)-1H-imidazole-5-carbonyl chloride (1b)

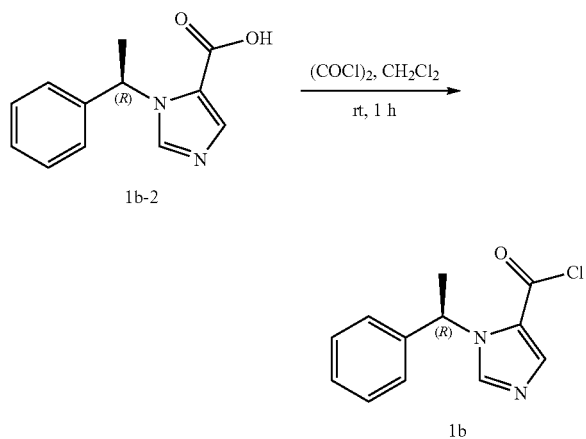

In an ice bath, to a solution of 1b-2 (3.00 g, 13.9 mmol) in dichloromethane (30 mL) was added oxalyl dichloride (2 mL) slowly at the rate of 1 mL/min using a syringe at 0° C., then it was stirred at room temperature for 1 hour. The reaction mixture was concentrated under reduced pressure to give 1b (3.10 g, crude) as a white solid.

4. Preparation of Compound A2

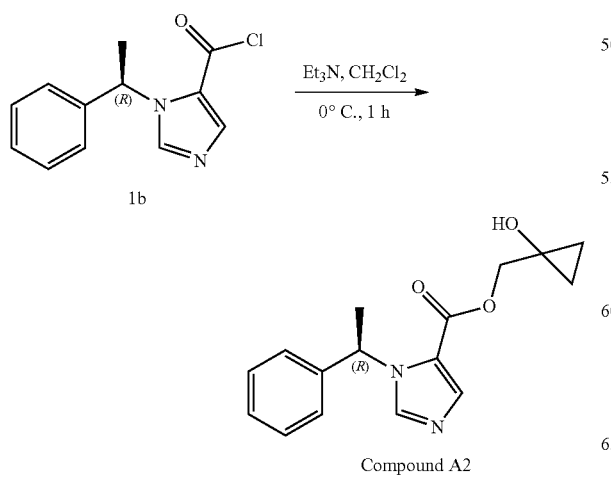

In an ice-water bath, 1b (3.10 g, crude) was added into the mixture of 2-2 (1.22 g, 13.9 mmol) and Et$_3$N (2.81 g, 27.8 mmol) in dichloromethane (30 mL) at 0° C., the mixture was allowed to react at this temperature for 1 hour. The mixture was concentrated under reduced pressure. The residue was purified by silica gel column chromatography (ethyl acetate/petroleum ether (v/v) at any ratio within the range of 1/8 to 1/1), with TLC (ethyl acetate/petroleum ether (v/v)=1/1) monitoring, and collecting the fraction with Rf=0.3~0.4, to give the title compound A2 (1.80 g, yield 45% for 2 steps) as colorless oil. ESI[M+H]$^+$=287.2

$^1$H NMR (400 MHz, d$_6$-DMSO) δ 8.31 (d, J=0.7 Hz, 1H), 7.76 (d, J=1.0 Hz, 1H), 7.37-7.29 (m, 2H), 7.27-7.25 (m, 1H), 7.22-7.10 (m, 2H), 6.26 (t, J=7.2 Hz, 1H), 5.60 (s, 1H), 4.15 (s, 2H), 1.85 (d, J=7.2 Hz, 3H), 0.72-0.58 (m, 2H), 0.60-0.50 (m, 2H).

5. Preparation of Compound A4

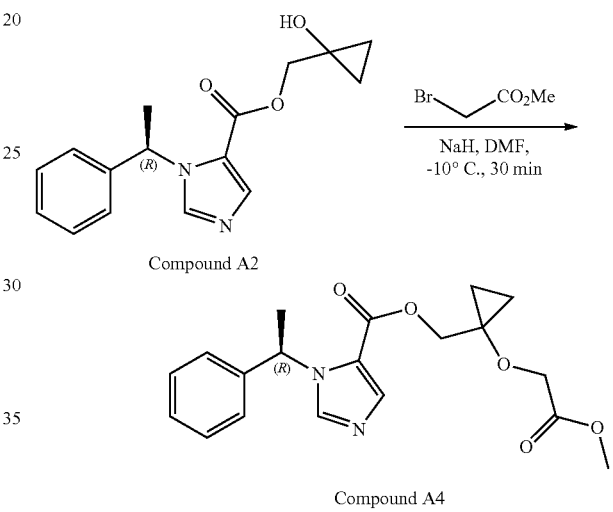

The title compound A4 was prepared according to the the general procedure B, using compound 2 (1.10 g, 3.84 mmol) and methyl 2-bromoacetate (609 mg, 3.98 mmol) as the raw materials. The crude product was purified by Prep-TLC (ethyl acetate/petroleum ether (v/v)=1/1) and the fraction with Rf=0.4~0.5 was collected to give the title compound A4 (190 mg, yield 14%) as colorless oil. ESI[M+H]$^+$=359.3

$^1$H NMR (400 MHz, d$_6$-DMSO) δ 8.33 (s, 1H), 7.69 (d, J=0.4 Hz, 1H), 7.34-7.31 (m, 2H), 7.28-7.26 (m, 1H), 7.20-7.18 (m, 2H), 6.25-6.24 (m, 1H), 4.30-4.29 (m, 2H), 4.19 (s, 2H), 3.52 (s, 3H), 1.85 (d, J=7.2 Hz, 3H), 0.88-0.87 (m, 2H), 0.69-0.64 (m, 2H).

6. Preparation of Compound A6

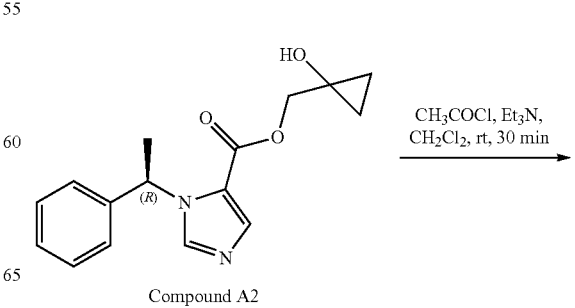

-continued

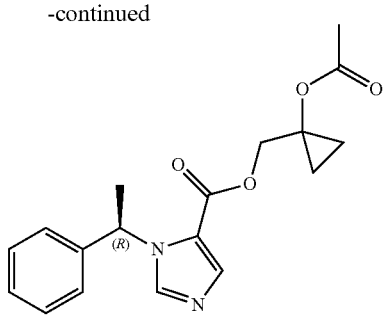

Compound A6

At room temperature, acetyl chloride (151 mg, 1.92 mmol) was added into the mixture of A2 (550 mg, 1.92 mmol) and Et$_3$N (388 mg, 3.84 mmol) in dichloromethane (20 mL) at the rate of 1 mmol/min with a syringe, then the mixture was reacted at this temperature for 30 min. The mixture was concentrated under reduced pressure, the residue was purified by silica gel column chromatography (ethyl acetate/petroleum ether (v/v) at any ratio within the range of 1/8 to 1/1), with TLC (ethyl acetate/petroleum ether (v/v)=1/1) monitoring, and collecting the fraction with Rf=0.4~0.5, to give the title compound A6 (250 mg, yield 40%) as colorless oil. ESI[M+H]$^+$=329.2 $^1$H NMR (400 MHz, d$_6$-DMSO) δ 8.91 (s, 1H), 8.06 (s, 1H), 7.37~7.34 (m, 2H), 7.31-7.27 (m, 1H), 7.24-7.22 (m, 2H), 6.30-6.26 (m, 1H), 4.52 (d, J=12.4 Hz, 1H), 4.39 (d, J=12.4 Hz, 1H), 1.96-1.87 (m, 3H), 1.86 (s, 3H), 0.92~0.86 (m, 4H).

Example A3 Preparation of Compound A5

1. Preparation of 1-(((Tetrahydro-2H-pyran-2-yl)oxy)methyl)cyclopropanol (5-1)

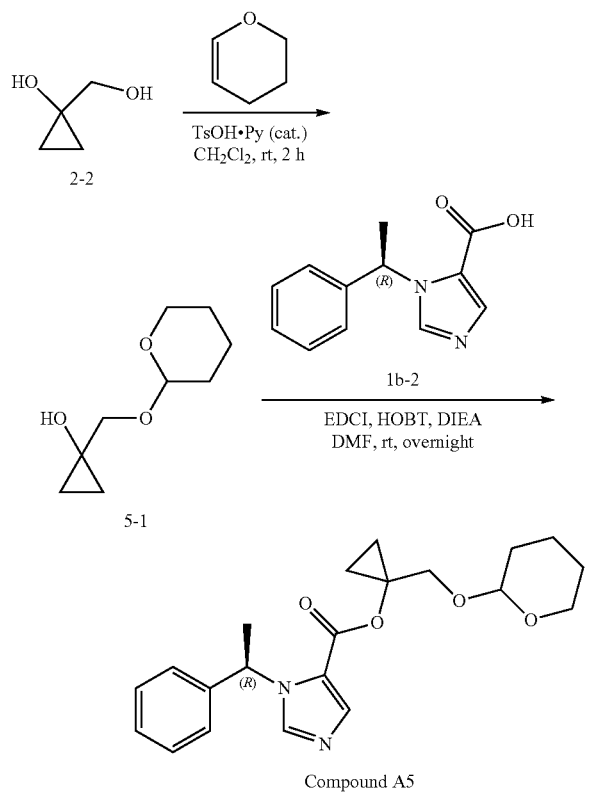

At room temperature, 3,4-dihydro-2H-pyran (478 mg, 5.68 mmol), 2-2 (500 mg, 5.68 mmol) and pyridinium p-toluenesulfonate (70.4 mg, 0.28 mmol) were dissolved in dichloromethane (10 mL), the mixture was stirred at room temperature for 2 hrs. The reaction was monitored by TLC until completion, then it was concentrated under reduced pressure. The residue was purified by silica gel column chromatography (ethyl acetate/petroleum ether (v/v) at any ratio within the range of 1/10 to 1/1), with TLC (ethyl acetate/petroleum ether (v/v)=1/1) monitoring, and collecting the fraction with Rf=0.3~0.4, to give the compound 5-1 (510 mg, yield 52%) as colorless oil.

2. Preparation of Compound A5

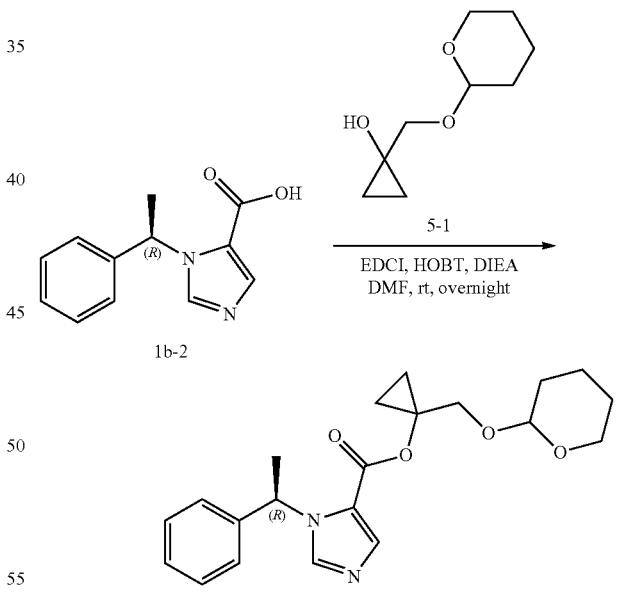

At room temperature, 5-1 (510 mg, 2.96 mmol), 1b-2 (640 mg, 2.96 mmol), EDCI (567 mg, 2.96 mmol), HOBT (400 mg, 2.96 mmol) and DIEA (765 mg, 5.92 mmol) were dissolved in DMF (5 mL), then the mixture was stirred at room temperature overnight. The reaction was monitored by TLC until completion. The mixture was quenched with water and extracted with EtOAc (3×15 mL). The combined organic layers were washed with saturated brine (20 mL), dried over anhydrous sodium sulfate, filtered and concentrated under reduced pressure to give the title compound A5 (50 mg, yield 5%) as colorless oil. ESI[M+H]⁺=371.2

¹H NMR (400 MHz, d₆-DMSO) δ 8.33-8.30 (m, 1H), 7.69-7.64 (m, 1H), 7.34-7.31 (m, 2H), 7.28-7.26 (m, 1H), 7.19-7.17 (m, 2H), 6.27-6.25 (m, 1H), 4.80-4.13 (m, 2H), 3.78-3.51 (m, 2H), 2.52-2.51 (m, 1H), 1.86-1.82 (m, 3H), 1.70-1.32 (m, 6H), 0.85-0.66 (m, 4H).

Example A4 Preparation of Compound A7

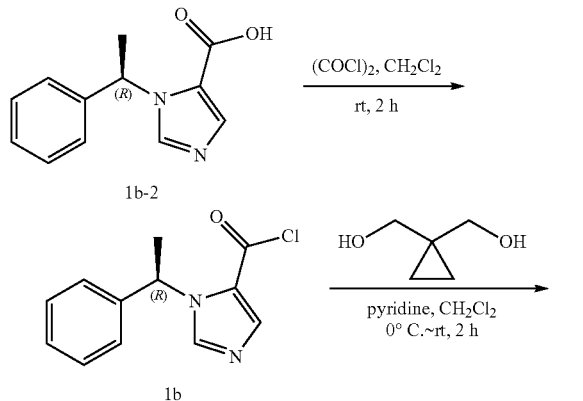

The title compound A7 was prepared according to the operation method of preparing compound 2, using 1b-2 (200 mg, 0.92 mmol) and cyclopropane-1,1-diyldimethanol (94 mg, 0.92 mmol) as the raw materials. The crude product was purified by Prep-TLC (ethyl acetate/petroleum ether (v/v)=1/1) and the fraction with Rf=0.2~0.3 was collected to give the title compound A7 (223 mg, yield 81% for 2 steps) as colorless oil. ESI[M+H]⁺=301.3

¹H NMR (400 MHz, CDCl₃) δ 7.82 (s, 1H), 7.79 (s, 1H), 7.36-7.29 (m, 3H), 7.18-7.17 (m, 2H), 6.35 (q, J=7.1 Hz, 1H), 4.20 (s, 2H), 3.45-3.33 (m, 2H), 1.87 (d, J=7.1 Hz, 3H), 0.64-0.51 (m, 4H).

Example A5 Preparation of Compound A8

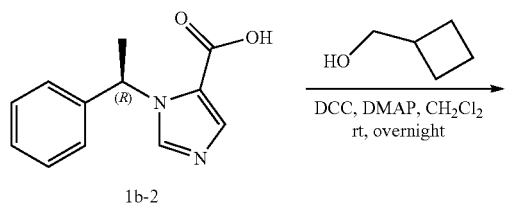

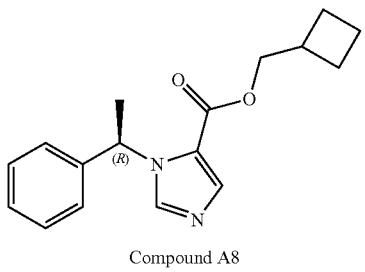

Compound A8

The title compound A8 was prepared according to the general procedure A, using 1b-2 (324 mg, 1.50 mmol) and cyclobutylmethanol (80.0 mg, 0.93 mmol) as the raw materials. The crude product was purified by Prep-TLC (ethyl acetate/petroleum ether (v/v)=1/1) and the fraction with Rf=0.5~0.6 was collected to give the title compound A8 (136 mg, yield 52%) as colorless oil. ESI[M+H]⁺=285.3

¹H NMR (400 MHz, d₆-DMSO) δ 8.31 (s, 1H), 7.68 (d, J=0.8 Hz, 1H), 7.33 (t, J=7.3 Hz, 2H), 7.26 (t, J=7.3 Hz, 1H), 7.16 (d, J=7.2 Hz, 2H), 6.23 (q, J=7.2 Hz, 1H), 4.23-3.99 (m, 2H), 2.58-2.51 (m, 1H), 2.03-1.89 (m, 2H), 1.89-1.76 (m, 5H), 1.76-1.69 (m, 2H).

Example A6 Preparation of Compound A9

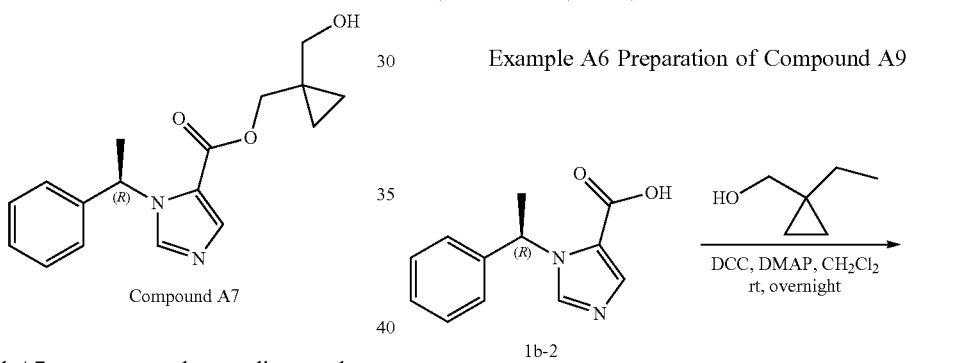

The title compound A9 was prepared according to the general procedure A, using 1b-2 (216 mg, 1.0 mmol) and (1-ethylcyclopropyl)methanol (100.0 mg, 1.0 mmol) as the raw materials. The crude product was purified by Prep-TLC (ethyl acetate/petroleum ether (v/v)=1/1) and the fraction with Rf=0.4~0.5 was collected to give the title compound A9 (56 mg, yield 19%) as colorless oil. ESI[M+H]⁺=299.3

¹H NMR (400 MHz, CDCl₃) δ 7.84 (s, 1H), 7.79 (s, 1H), 7.40-7.25 (m, 3H), 7.21-7.14 (m, 2H), 6.30 (q, J=7.1 Hz, 1H), 4.20 (s, 2H), 1.87 (d, J=7.1 Hz, 3H), 1.56-1.50 (m, 2H), 1.10-0.96 (m, 3H), 0.64-0.51 (m, 4H).

Example A7 Preparation of Compounds A10 and A11

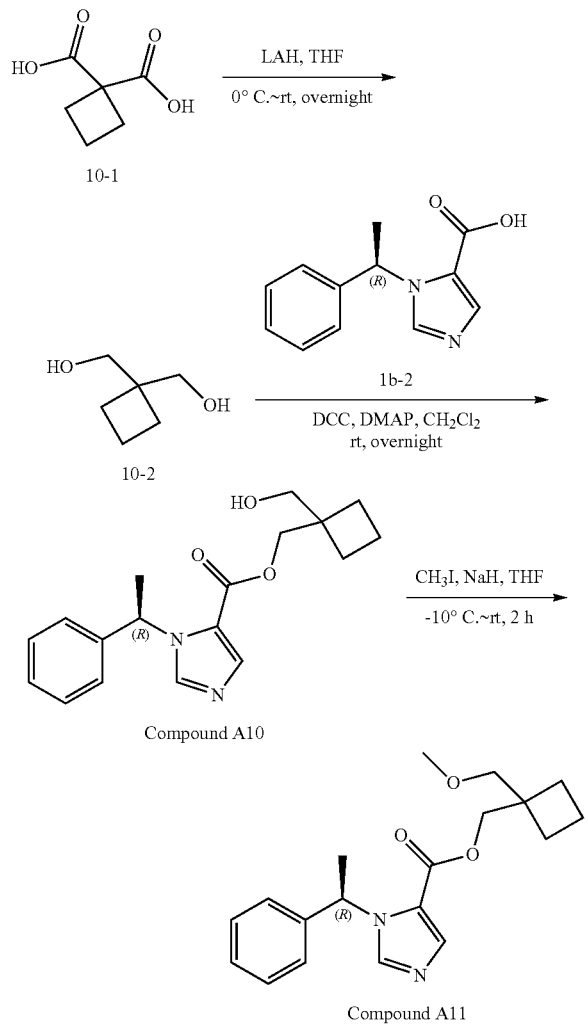

Compound A11

1. Preparation of Cyclobutane-1,1-diyldimethanol (10-2)

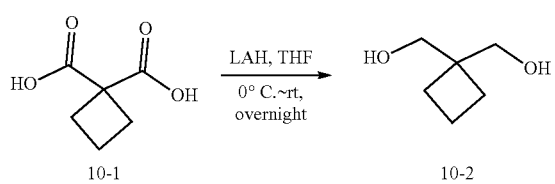 [SMILES: O=C(O)C1(C(=O)O)CCC1 ; OCC1(CO)CCC1]

In an ice-water bath, LAH (2.28 g, 0.06 mol) was added in portions into the mixture of 10-1 (4.32 g, 0.03 mol) in THF (80 mL) at the rate of 10 mmol/min at 0° C., and the mixture was allowed to react at room temperature overnight. Na$_2$SO$_4$·10H$_2$O was added in portions (5 g/min, totally 20 g) into the mixture at 0° C., then it was filtered and the filter cake was washed with THF (150 mL). The filtrate was concentrated under reduced pressure and the residue was purified by silica gel column chromatography with ethyl acetate/petroleum ether (v/v=1/1) and the eluate was monitored by TLC (ethyl acetate/petroleum ether (v/v=1/1). The fraction with Rf=0.2~0.3 was collected and dried to give 10-2 (3.02 g, yield 87%) as colorless oil. ESI[M+H]$^+$=116.1

2. Preparation of Compound A10

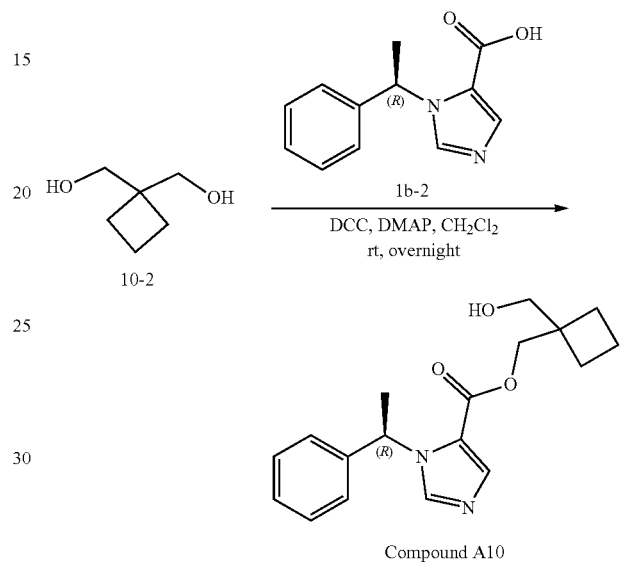

The title compound A10 was prepared according to the general procedure A, using 1b-2 (432 mg, 2.00 mmol) and 10-2 (648 mg, 5.58 mmol) as the raw materials. The crude product was purified by silica gel column chromatography (MeOH/CH$_2$Cl$_2$ (v/v) at any ratio within the range of 1/100 to 1/10), with TLC (MeOH/CH$_2$Cl$_2$ (v/v)=1/50) monitoring, and collecting the fraction with Rf=0.5~0.6, to give the title compound A10 (340 mg, yield 54%) as colorless oil. ESI [M+H]$^+$=315.3

$^1$H NMR (400 MHz, CDCl$_3$) δ 7.86 (s, 1H), 7.82 (s, 1H), 7.39-7.28 (m, 3H), 7.21-7.16 (m, 2H), 6.36 (q, J=7.0 Hz, 1H), 4.37-4.27 (m, 2H), 3.52 (q, J=11.4 Hz, 2H), 2.02-1.91 (m, 2H), 1.88 (d, J=7.1 Hz, 3H), 1.87-1.79 (m, 4H).

3. Preparation of Compound A11

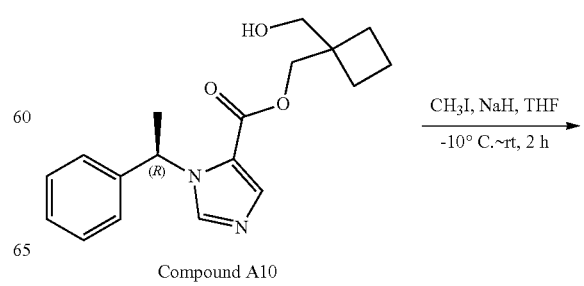

Example A9 Preparation of Compound A13

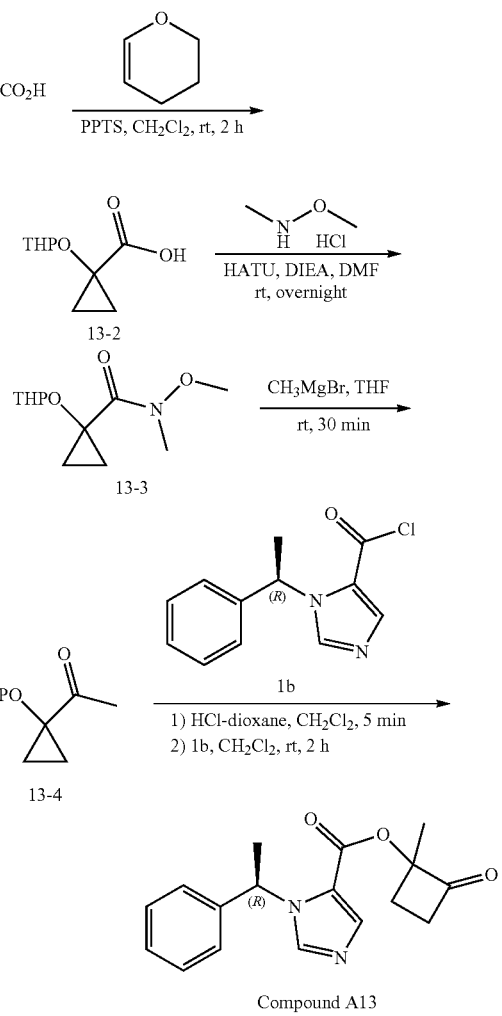

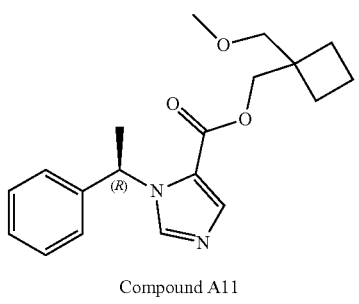

Compound A11

The title compound A11 was prepared according to the general procedure B, using compound A10 (157 mg, 0.50 mmol) and iodomethane (85 mg, 0.60 mmol) as the raw materials. The crude product was purified by Prep-TLC (ethyl acetate/petroleum ether (v/v)=1/1) and the fraction with Rf=0.4~0.5 was collected to give the title compound A11 (15 mg, yield 9%) as colorless oil. ESI[M+H]$^+$=329.2

$^1$H NMR (400 MHz, CDCl$_3$) δ 7.84 (s, 1H), 7.79 (s, 1H), 7.41-7.27 (m, 3H), 7.24-7.18 (m, 2H), 6.41 (q, J=7.1 Hz, 1H), 4.27 (q, J=10.9 Hz, 2H), 3.37 (s, 2H), 3.33 (s, 3H), 1.97-1.80 (m, 6H), 1.90 (d, J=7.1 Hz, 3H).

Example A8 Preparation of Compound A12

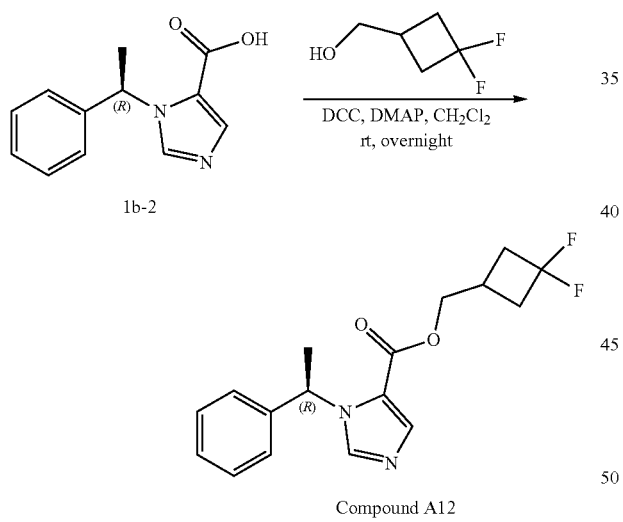

Compound A12

The title compound A12 was prepared according to the general procedure A, using 1b-2 (177 mg, 0.82 mmol) and (3,3-difluorocyclobutyl)methanol (100 mg, 0.82 mmol) as the raw materials. The crude product was purified by Prep-TLC (ethyl acetate/petroleum ether (v/v)=1/1) and the fraction with Rf=0.4~0.5 was collected to give the title compound A12 (142 mg, yield 54%) as colorless oil. ESI[M+H]$^+$=321.2

$^1$H NMR (400 MHz, d$_6$-DMSO) δ 8.32 (s, 1H), 7.71 (s, 1H), 7.33 (t, J=7.3 Hz, 2H), 7.26 (t, J=7.3 Hz, 1H), 7.16 (d, J=7.2 Hz, 2H), 6.21 (q, J=7.1 Hz, 1H), 4.30-3.93 (m, 2H), 2.66-2.60 (m, 2H), 2.42-2.24 (m, 3H), 1.84 (d, J=7.2 Hz, 3H).

1. Preparation of 1-((Tetrahydro-2H-pyran-2-yl)oxy) cyclopropanecarboxylic acid (13-2)

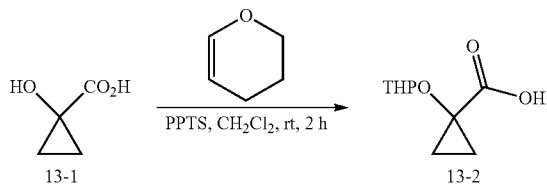

At room temperature, 3,4-dihydro-2H-pyran (823 mg, 9.79 mmol), 13-1 (1.00 g, 9.79 mmol) and pyridinium p-toluenesulfonate (123 mg, 0.49 mmol) were dissolved in dichloromethane (10 mL), The mixture was stirred at room temperature for 2 hrs. The mixture was concentrated under reduced pressure. The residue was purified by by silica gel column chromatography ethyl acetate/petroleum ether (v/v=1/10) and eluate was monitored by TLC (ethyl acetate/ petroleum ether (v/v)=1/5). The fraction with Rf=0.3~0.4 was collected and dried to give compound 13-2 (1.20 g, yield 66%) as a white solid.

2. Preparation of N-Methoxy-N-methyl-1-((tetrahydro-2H-pyran-2-yl)oxy)cyclopropanecarboxamide (13-3)

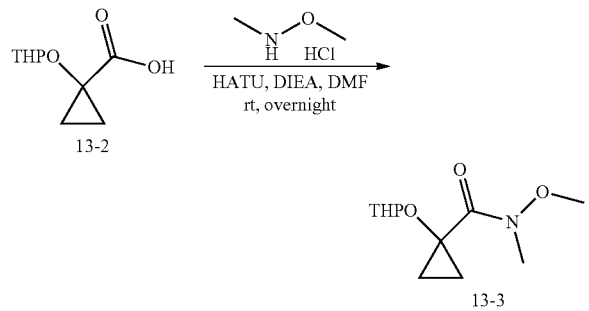

At room temperature, N, O-dimethylhydroxylamine hydrochloride (628 mg, 6.44 mmol), 13-2 (1.20 g, 6.44 mmol), HATU (2.45 g, 6.44 mmol) and DIEA (1.67 g, 12.9 mmol) were dissolved in DMF (10 mL), then the mixture was stirred at room temperature overnight. The reaction was monitored by TLC until completion. The mixture was quenched with water and extracted with EtOAc (3×10 mL). The combined organic layers were washed with saturated brine (20 mL), dried over anhydrous sodium sulfate, filtered and concentrated under reduced pressure. The residue was purified by silica gel column chromatography (ethyl acetate/petroleum ether (v/v)=1/10) and the eluate was monitored by TLC (ethyl acetate/petroleum ether (v/v)=1/1). The fraction with Rf=0.5~0.6 was collected and dried to give compound 13-3 (1.20 g, yield 81%) as a white solid.

3. Preparation of 2-Hydroxy-2-methylcyclobutan-1-one (13-4)

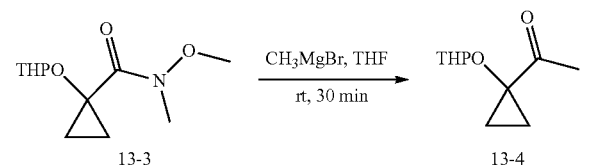

At room temperature, methylmagnesium bromide (6.54 mL, 1 mol/L in THF, 6.54 mmol) was added dropwise into the mixture of 5-1 (500 mg, 1.41 mmol) in anhydrous THF (20 mL) at the rate of 1 mL/min using a syringe, then the mixture was reacted at room temperature for 30 min. The reaction was monitored by TLC until completion. The mixture was quenched with water and extracted with EtOAc (3×15 mL). The combined organic layers were washed with saturated brine (20 mL), dried over anhydrous sodium sulfate, filtered and concentrated under reduced pressure. The residue was purified by silica gel column chromatography (ethyl acetate/petroleum ether (v/v)=1/10) and the eluate was monitored by TLC (ethyl acetate/petroleum ether (v/v)=1/7). The fraction with Rf=0.5~0.6 was collected and dried to give compound 13-4 (80 mg, yield 24%) as colorless oil.

4. Preparation of Compound A13

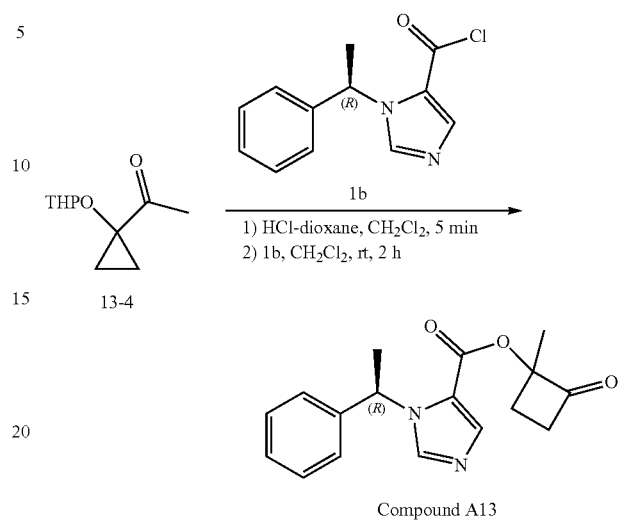

At room temperature, HCl/Dioxane (0.15 mL, 4 M) was added into the mixture of 13-4 (150 mg, 0.81 mmol) in dichloromethane (10 mL), then the mixture was reacted at this temperature for 5 min. 1b (190 mg, 0.81 mmol) was added to the mixture, then the mixture was reacted at room temperature for 2 hrs. The mixture was concentrated under reduced pressure and the residue was purified by Prep-TLC (MeOH/CH$_2$Cl$_2$ (v/v)=1/10), the fraction with Rf=0.3~0.4 was collected and dried to give the title compound A13 (35 mg, yield 14%) as colorless oil. ESI[M+H]$^+$=299.1 $^1$H NMR (400 MHz, d$_6$-DMSO) δ 8.35 (d, J=6.3 Hz, 1H), 7.74 (s, 1H), 7.38-7.30 (m, 2H), 7.29-7.27 (m, 1H), 7.20-7.10 (m, 2H), 6.15-6.11 (m, 1H), 3.05-2.97 (m, 2H), 2.31-2.28 (m, 1H), 2.05-1.94 (m, 1H), 1.84 (dd, J=7.2, 2.3 Hz, 3H), 1.45 (d, J=5.8 Hz, 3H).

Example A10 Preparation of Compound A14

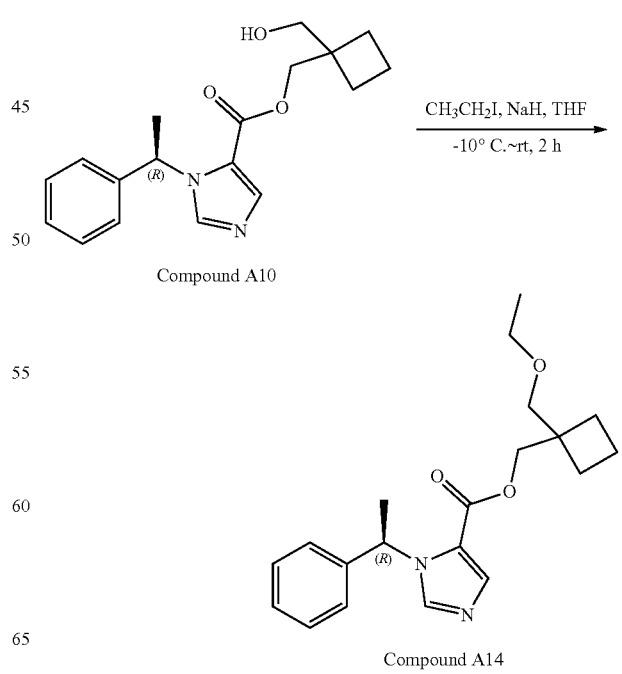

The title compound A14 was prepared according to the general procedure B, using compound A10 (157 mg, 0.50 mmol) and iodoethane (94 mg, 0.60 mmol) as the raw materials. The crude product was purified by Prep-TLC (ethyl acetate/petroleum ether (v/v)=1/1) and the fraction with Rf=0.4~0.5 was collected and dried to give the title compound A14 (35 mg, yield 20%) as colorless oil. ESI[M+H]$^+$=343.3

$^1$H NMR (400 MHz, CDCl$_3$) δ 7.87 (s, 1H), 7.81 (s, 1H), 7.39-7.25 (m, 3H), 7.25-7.19 (m, 2H), 6.39 (q, J=7.1 Hz, 1H), 4.29-4.25 (m, 2H), 3.39 (s, 2H), 3.47-3.45 (m, 2H), 1.96-1.79 (m, 6H), 1.90 (d, J=7.1 Hz, 3H), 1.01-1.10 (m, 3H)

Example A11 Preparation of Compound A15

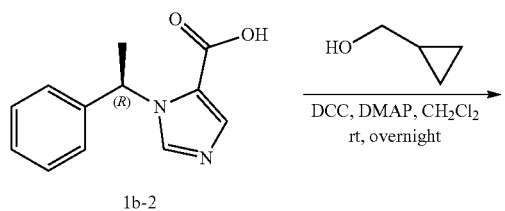

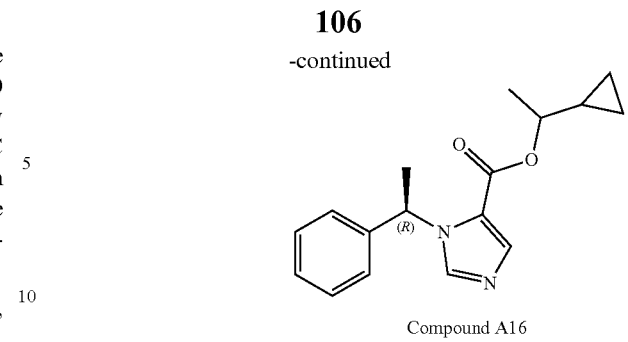

Compound A15

The title compound A15 was prepared according to the general procedure A, using 1b-2 (100 mg, 0.46 mmol) and cyclopropylmethanol (33 mg, 0.46 mmol) as the raw materials. The crude product was purified by Prep-TLC (ethyl acetate/petroleum ether (v/v)=1/2) and the fraction with Rf=0.5~0.6 was collected and dried to give the title compound A15 (383 mg, yield 66%) as colorless oil. ESI[M+H]$^+$=271.3

$^1$H NMR (400 MHz, CDCl$_3$) δ 7.83 (s, 1H), 7.77 (s, 1H), 7.40-7.27 (m, 3H), 7.23-7.15 (m, 2H), 6.38 (q, J=7.2 Hz, 1H), 4.05 (qd, J=11.4, 7.3 Hz, 2H), 1.87 (d, J=7.1 Hz, 3H), 1.17-1.14 (m, 1H), 0.66-0.43 (m, 2H), 0.42-0.18 (m, 2H).

Example A12 Preparation of Compound A16

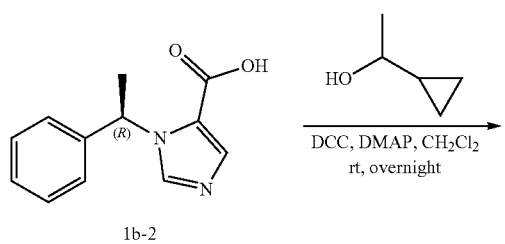

Compound A16

The title compound A16 was prepared according to the general procedure A, using 1b-2 (100 mg, 0.46 mmol) and 1-cyclopropylethanol (39.6 mg, 0.46 mmol) as the raw materials. The crude product was purified by Prep-TLC (ethyl acetate/petroleum ether (v/v)=1/2) and the fraction with Rf=0.4~0.5 was collected and dried to give the title compound A16 (96 mg, yield 73%) as colorless oil. ESI[M+H]$^+$=285.3

$^1$H NMR (400 MHz, CDCl$_3$) δ 7.79 (s, 1H), 7.74 (s, 1H), 7.38-7.28 (m, 3H), 7.22-7.14 (m, 2H), 6.43-6.29 (m, 1H), 4.57-4.41 (m, 1H), 1.87 (d, J=7.1 Hz, 3H), 1.34 (t, J=6.2 Hz, 3H), 1.12-0.95 (m, 1H), 0.64-0.18 (m, 4H).

Example A13 Preparation of Compound A17

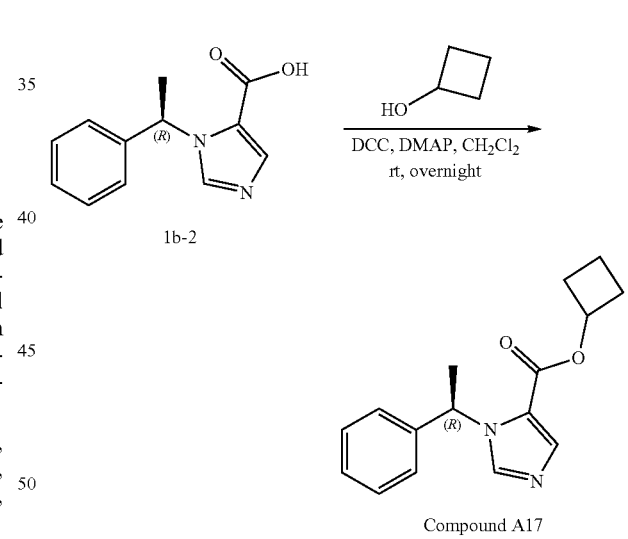

Compound A17

The title compound A17 was prepared according to the general procedure A, using 1b-2 (100 mg, 0.46 mmol) and cyclobutanol (33.2 mg, 0.46 mmol) as the raw materials. The crude product was purified by Prep-TLC (ethyl acetate/petroleum ether (v/v)=1/2) and the fraction with Rf=0.4~0.5 was collected and dried to give the title compound A17 (66 mg, yield 53%) as a white solid. ESI[M+H]$^+$=271.3 $^1$H NMR (400 MHz, CDCl$_3$) δ 7.80 (s, 1H), 7.79 (s, 1H), 7.39-7.27 (m, 3H), 7.22-7.16 (m, 2H), 6.36 (q, J=7.1 Hz, 1H), 5.19-5.02 (m, 1H), 2.50-2.28 (m, 2H), 2.21-2.07 (m, 2H), 1.86 (d, J=7.1 Hz, 3H), 1.85-1.77 (m, 1H), 1.73-1.56 (m, 1H).

Example A14 Preparation of Compound A18

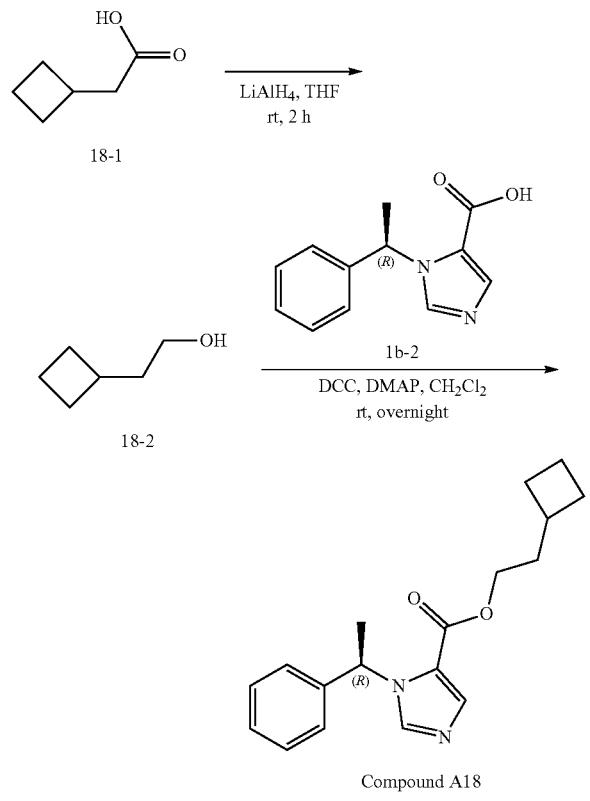

1. Preparation of 2-Cyclobutylethanol (18-2)

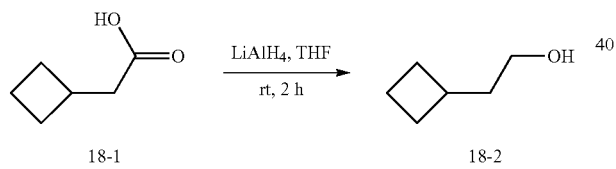

At room temperature, LiAlH$_4$ (133 mg, 3.50 mmol) was added in portions into the mixture of 18-1 (200 mg, 1.75 mmol) in THF (10 mL) at the rate of 1 mmol/min, then the mixture was reacted at this temperature for 2 hrs. The reaction was quenched with Na$_2$SO$_4$·10H$_2$O and filtered, the filtrate was concentrated under reduced pressure to give compound 18-2 (120 mg, yield 68%) as colorless oil. ESI[M+H]$^+$=100.1.

2. Preparation of Compound A18

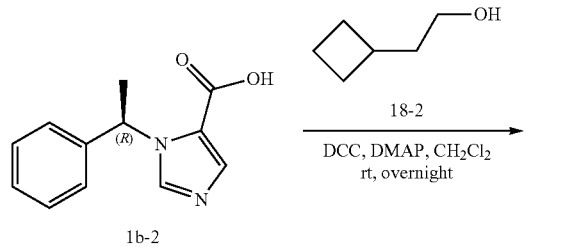

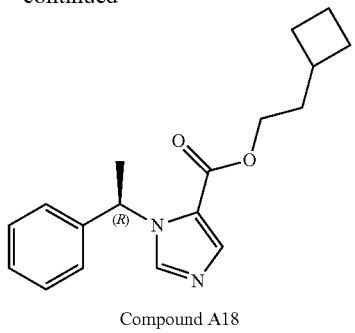

The title compound A18 was prepared according to the general procedure A, using 1b-2 (100 mg, 0.46 mmol) and 2-cyclobutylethanol (46.1 mg, 0.46 mmol) as the raw materials. The crude product was purified by Prep-TLC (ethyl acetate/petroleum ether (v/v)=1/1) and the fraction with Rf=0.4~0.5 was collected and dried to give the title compound A18 (84 mg, yield 61%) as colorless oil. ESI[M+H]$^+$=299.3.

$^1$H NMR (400 MHz, CDCl$_3$) δ 7.76 (s, 2H), 7.36~7.32 (m, 3H), 7.21-7.18 (m, 2H), 6.37 (q, J=7.1 Hz, 1H), 4.26~3.88 (m, 2H), 2.37-2.31 (m, 1H), 2.06-2.00 (m, 2H), 1.90-1.71 (m, 7H), 1.68-1.64 (m, 2H).

Example A15 Preparation of Compound A19

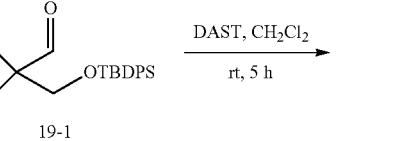

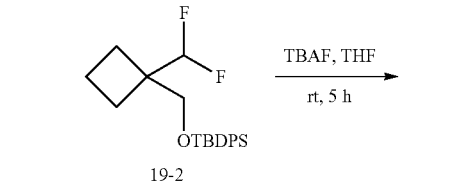

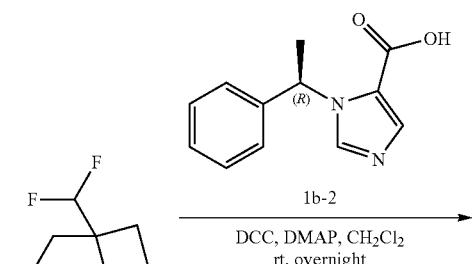

1. Preparation of (1-(Difluoromethyl)cyclobutyl)methanol (19-3)

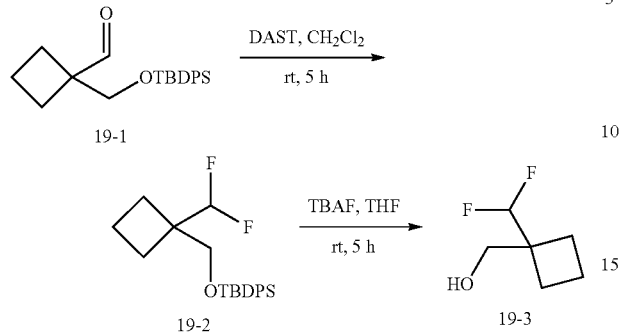

At room temperature, DAST (484 mg, 3.0 mmol) was added into the mixture of 19-1 (705 mg, 2.0 mmol) in dichloromethane (10 mL) at the rate of 1 mmol/min using a syringe, then the mixture was allowed to react at room temperature for 5 hrs. The reaction was monitored by TLC until completion. The mixture was quenched with water and extracted with EtOAc (3×15 mL). The combined organic layers were washed with saturated brine (20 mL), dried over anhydrous sodium sulfate, filtered and concentrated under reduced pressure to give crude compound 19-2.

At room temperature, TBAF (6.0 mL, 1 mol/L in THF, 6 mmol) was added into the solution of 19-2 (crude) in THF (10 mL) and the mixture was allowed to react at this temperature for 5 hrs. The reaction was monitored by TLC until completion, and then it was concentrated under reduced pressure. The residue was purified by silica gel column chromatography (ethyl acetate/petroleum ether (v/v) at any ratio within the range of 1/3 to 1/1), with TLC (ethyl acetate/petroleum ether (v/v)=1/1) monitoring, and collecting the fraction with Rf=0.3~0.4, to give compound 19-3 (83 mg, yield 30%) as colorless oil. ESI[M+H]$^+$=137.2

2. Preparation of Compound A19

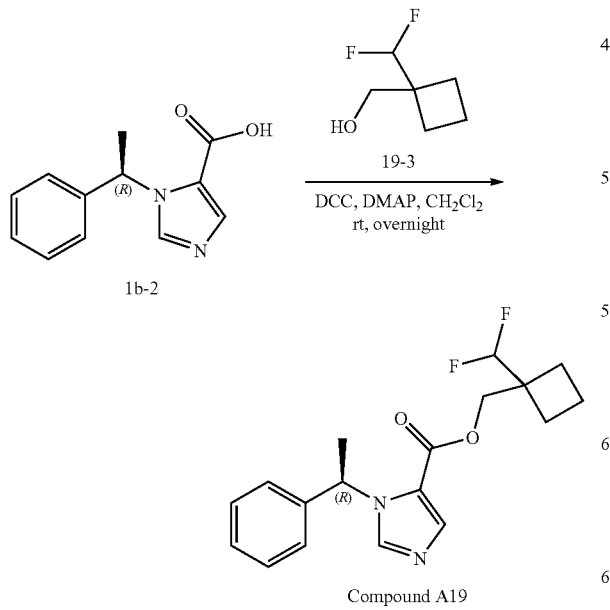

The title compound A19 was prepared according to the general procedure A, using 1b-2 (127 mg, 0.59 mmol) and 19-3 (80 mg, 0.59 mmol) as the raw materials. The crude product was purified by Prep-TLC (ethyl acetate/petroleum ether (v/v)=1/1) and the fraction with Rf=0.4~0.5 was collected and dried to give the title compound A19 (35 mg, yield 18%) as colorless oil. ESI[M+H]$^+$=335.3 $^1$H NMR (400 MHz, CDCl$_3$) δ 7.79 (s, 1H), 7.71 (s, 1H), 7.40-7.27 (m, 3H), 7.21-7.15 (m, 2H), 6.40 (q, J=7.2 Hz, 1H), 4.91 (q, J=57.6 Hz, 1H), 4.25 (m, 2H), 2.00-1.81 (m, 6H), 1.86 (d, J=7.1 Hz, 3H).

Example A16 Preparation of Compound A20

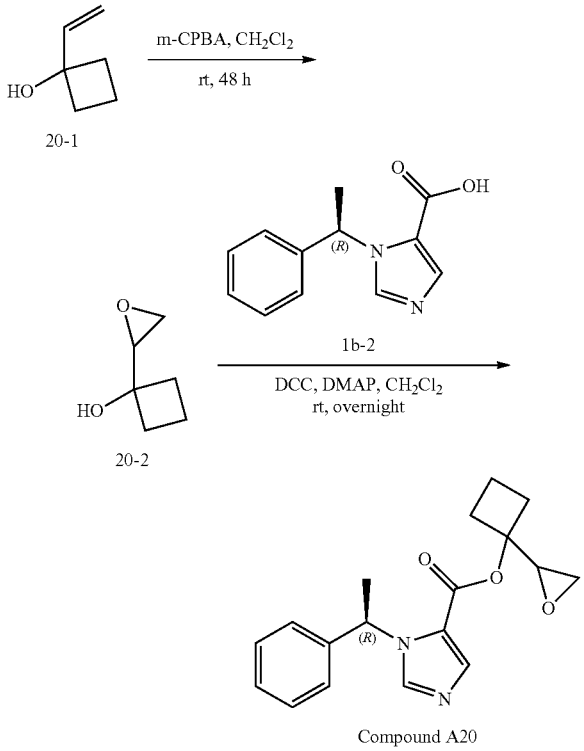

Compound A20

1. Preparation of 1-(Oxiran-2-yl)cyclobutan-1-ol (20-2)

At room temperature, m-CPBA (777 mg, 4.5 mmol) was added in portions into the mixture of 20-1 (294 mg, 3.0 mmol) in dichloromethane (10 mL) at the rate of 1 mmol/min over a 3-min period, then the mixture was reacted at this temperature for 48 hrs. The reaction was monitored by TLC until completion, the mixture was quenched with water and extracted with CH$_2$Cl$_2$ (3×15 mL). The combined organic layers were washed with saturated brine (20 mL), dried over anhydrous sodium sulfate, filtered and concentrated under reduced pressure to give crude compound 20-2, which was used for next step directly without further purification.

2. Preparation of Compound A20

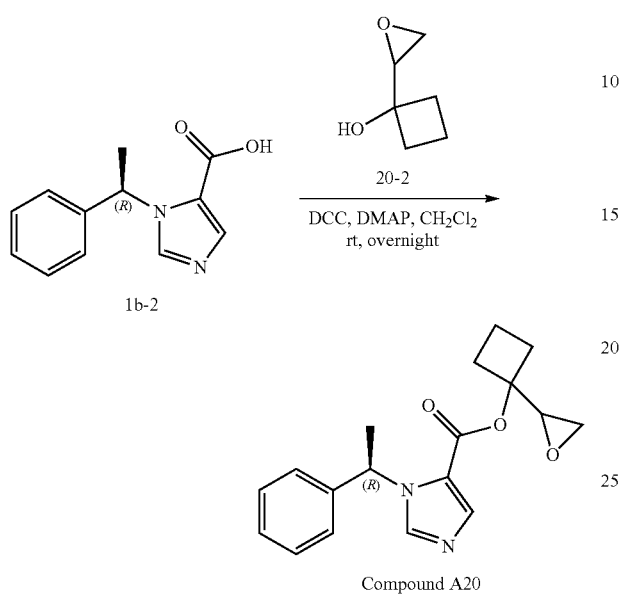

Compound A20

The title compound A20 was prepared according to the general procedure A, using 1b-2 (216 mg, 1.0 mmol) and crude 20-2 (from last step) as the raw materials. The crude product was purified by Prep-TLC (ethyl acetate/petroleum ether (v/v)=1/1) and the fraction with Rf=0.4~0.5 was collected and dried to give the title compound A20 (78 mg, yield 25%) as colorless oil. ESI[M+H]$^+$=313.3

Example A17 Preparation of Compound A21

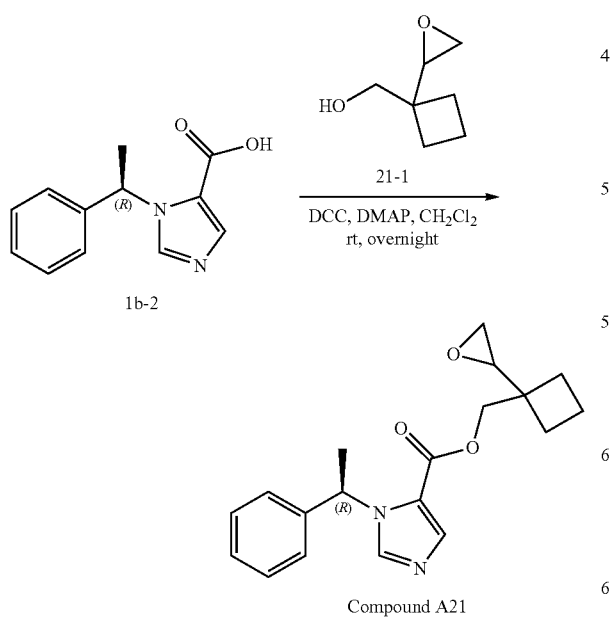

Compound A21

Compound 21-1 was prepared according to the operation method of compound 20-2.

The target compound A21 was prepared according to the general procedure A, using 1b-2 (216 mg, 1.0 mmol) and 21-1 (crude) as the raw materials. The crude product was purified by Prep-TLC (ethyl acetate/petroleum ether (v/v)=1/1) and the fraction with Rf=0.4~0.5 was collected and dried to give the title compound A21 (56 mg, yield 17%) as colorless oil. ESI[M+H]$^+$=327.3

Example A18 Preparation of Compound A22

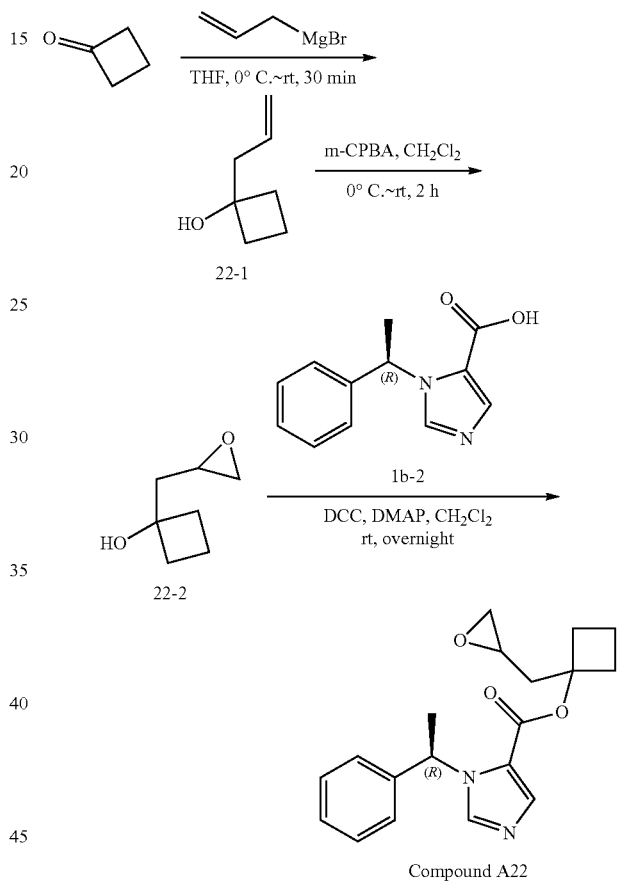

Compound A22

1. Preparation of 1-(Oxiran-2-ylmethyl)cyclobutan-1-ol (22-2)

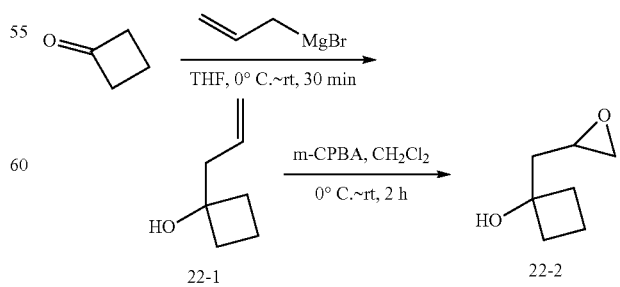

In an ice bath, cyclobutanone (500 mg, 7.13 mmol) was dissolved in THF (5 mL). allylmagnesium bromide (28.5 mL, 14.27 mmol, 0.5 mol/L) was added dropwise into the mixture at the rate of 2 mL/min at 0° C., then the mixture was reacted at this temperature for 30 min. The reaction was monitored by TLC until completion. The mixture was quenched with saturated ammonium chloride solution and extracted with EtOAc (3×10 mL). The combined organic layers were washed with saturated brine (30 mL), dried over anhydrous sodium sulfate, filtered and concentrated under reduced pressure to give crude compound 22-1 (486 mg, yield 61%) as colorless oil, which was used for next step directly without further purification. ESI[M+H]$^+$=113.1

In an ice bath, m-CPBA (1.12 g, 6.49 mmol) was added in portions into the mixture of 22-1 (486 mg, 4.33 mmol) in dichloromethane (10 mL) over a 5-min period, then the mixture was reacted at room temperature for 4 hrs. The reaction was monitored by TLC until completion. The mixture was quenched with saturated sodium bicarbonate and extracted with CH$_2$Cl$_2$ (3×10 mL). The combined organic layers were washed with saturated brine (30 mL), dried over anhydrous sodium sulfate, filtered and concentrated under reduced pressure to give crude compound 22-2 (80 mg, yield 14%), which was used for next step directly without further purification. ESI[M+H]$^+$=129.1

2. Preparation of Compound A22

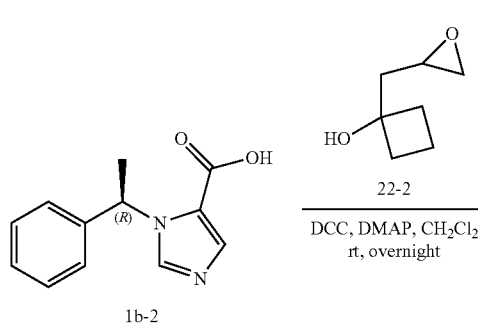

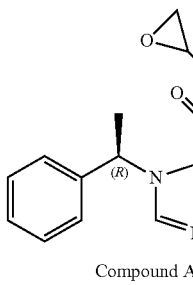

Compound A22

The title compound A22 was prepared according to the general procedure A, using 1b-2 (43 mg, 0.20 mmol) and 22-2 (80 mg, 0.62 mmol) as the raw materials. The crude product was purified by Prep-TLC (ethyl acetate/petroleum ether (v/v)=1/1) and the fraction with Rf=0.4~0.5 was collected and dried to give the title compound A22 (10 mg, yield 15%) as colorless oil. ESI[M+H]$^+$=327.1 $^1$H NMR (400 MHz, CDCl$_3$) δ 7.87-7.60 (m, 2H), 7.38-7.28 (m, 3H), 7.22-7.12 (m, 2H), 6.31 (q, J=7.0 Hz, 1H), 2.97-2.87 (m, 1H), 2.65-2.57 (m, 1H), 2.49-2.09 (m, 7H), 2.05-1.92 (m, 2H), 1.86 (d, J=7.1 Hz, 3H), 1.80-1.66 (m, 1H).

Example A19 Preparation of Compound A23

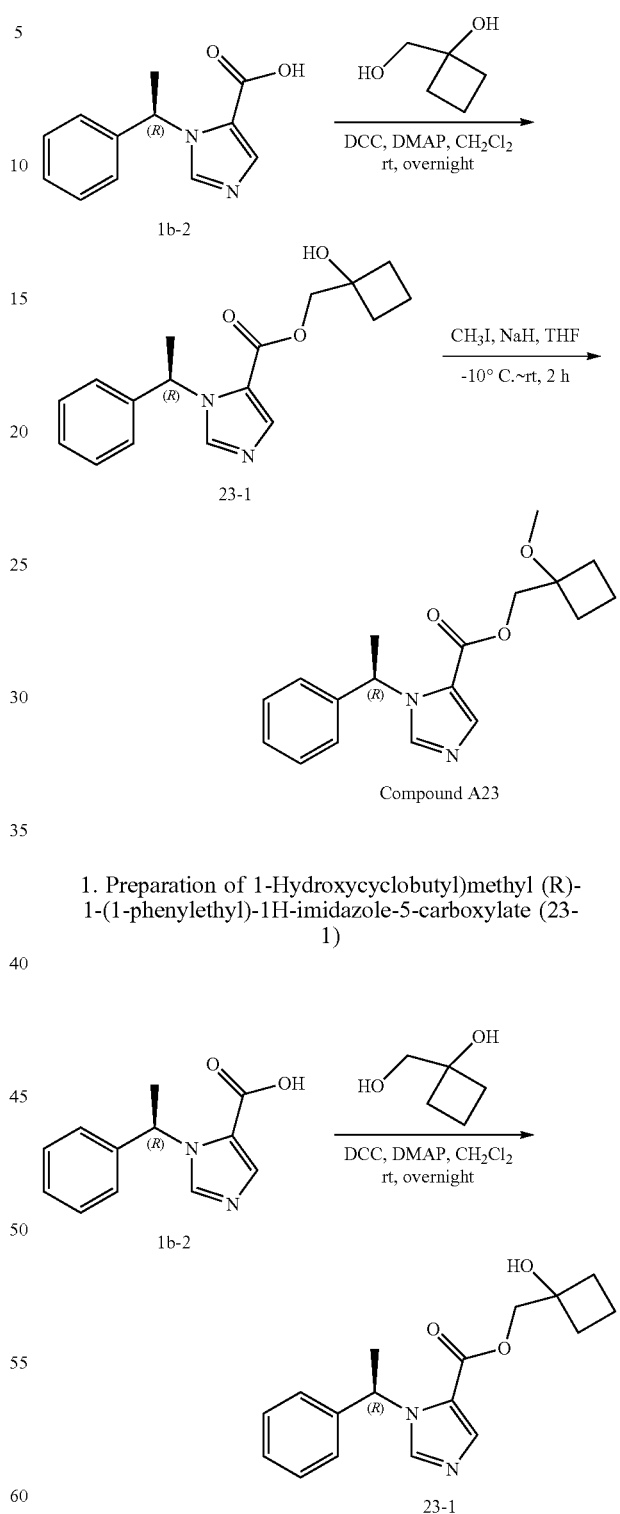

1. Preparation of 1-Hydroxycyclobutyl)methyl (R)-1-(1-phenylethyl)-1H-imidazole-5-carboxylate (23-1)

The compound A23 was prepared according to the general procedure A, using 1b-2 (432 mg, 2.0 mmol) and 1-(hydroxymethyl)cyclobutanol (204 mg, 2.0 mmol) as the raw materials. The crude product was purified by silica gel column chromatography (MeOH/CH$_2$Cl$_2$ (v/v) at any ratio within the range of 1/100 to 1/10), with TLC (MeOH/CH$_2$Cl$_2$ (v/v)=1/50) monitoring, and collecting the fraction with Rf=0.4~0.5, to give the compound 23-1 (281 mg, yield 47%) as colorless oil. ESI[M+H]$^+$=301.3

2. Preparation of Compound A23

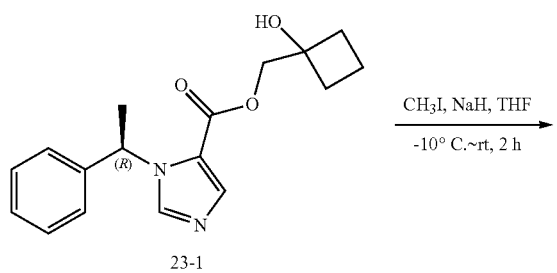

The title compound A23 was prepared according to the general procedure B, using 23-1 (150 mg, 0.50 mmol) and iodomethane (85 mg, 0.60 mmol) as the raw materials. The crude product was purified by Prep-TLC (ethyl acetate/petroleum ether (v/v)=1/1) and the fraction with Rf=0.4~0.5 was collected and dried to give the title compound A23 (35 mg, yield 22%) as colorless oil. ESI[M+H]$^+$=315.2

Example A20 Preparation of Compound A24

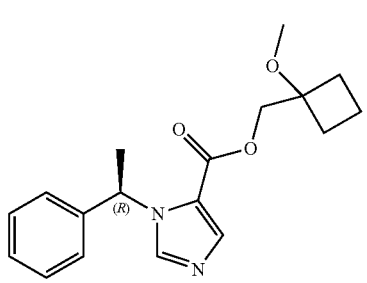

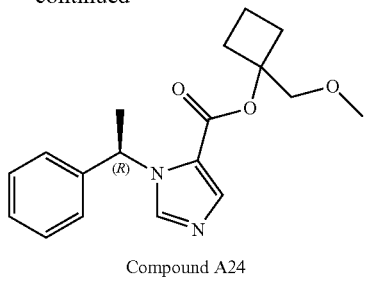

Compound A24

1. Preparation of 1-(Hydroxymethyl)cyclobutyl (R)-1-(1-phenylethyl)-1H-imidazole-5-carboxylate (24-1)

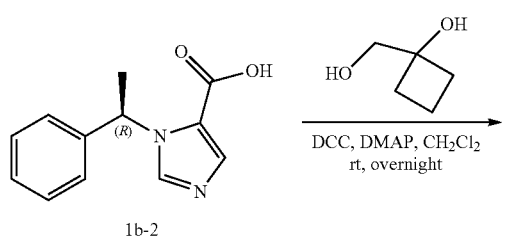

The compound 24-1 was prepared according to the general procedure A, using 1b-2 (632 mg, 3.0 mmol) and 1-(hydroxymethyl)cyclobutanol (306 mg, 3.0 mmol) as the raw materials. The crude product was purified by silica gel column chromatography (MeOH/CH$_2$Cl$_2$ (v/v) at any ratio within the range of 1/100 to 1/10), with TLC (MeOH/CH$_2$Cl$_2$ (v/v)=1/50) monitoring, and collecting the fraction with Rf=0.4~0.5, to give the title compound 24-1 (147 mg, yield 16%) as colorless oil. ESI[M+H]$^+$=301.3

2. Preparation of Compound A24

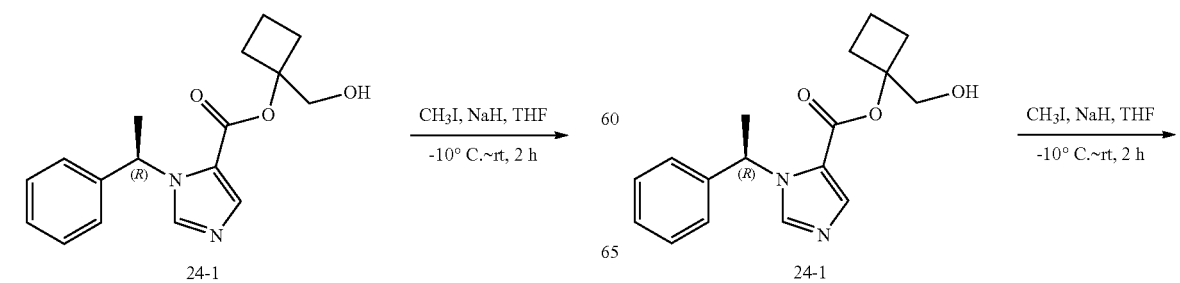

Example A22 Preparation of Compound A26

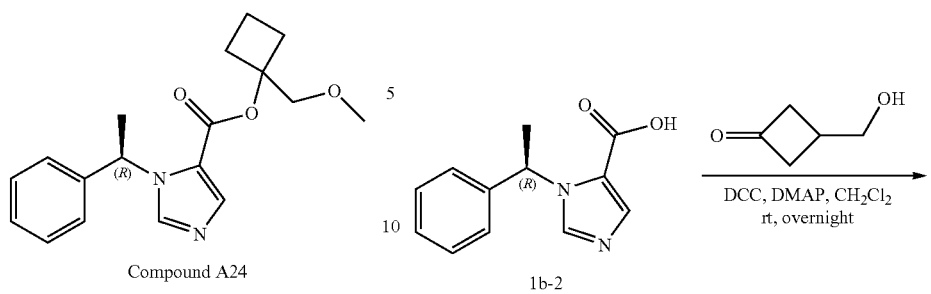

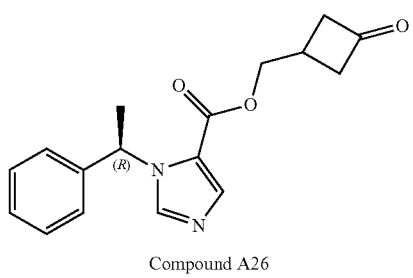

The title compound A26 was prepared according to the general procedure A, using 1b-2 (216 mg, 1.0 mmol) and 3-(hydroxymethyl)cyclobutanone (100 mg, 1.0 mmol) as the raw materials. The crude product was purified by Prep-TLC (ethyl acetate/petroleum ether (v/v)=1/1) and the fraction with Rf=0.4~0.5 was collected and dried to give the title compound A26 (102 mg, yield 34%) as colorless oil. ESI [M+H]$^+$=299.3.

The title compound A24 was prepared according to the general procedure B, using 24-1 (102 mg, 0.34 mmol) and iodomethane (48 mg, 0.34 mmol) as the raw materials. The crude product was purified by Prep-TLC (ethyl acetate/petroleum ether (v/v)=1/1) and the fraction with Rf=0.4~0.5 was collected and dried to give the title compound A24 (15 mg, yield 14%) as colorless oil. ESI[M+H]$^+$=315.2

$^1$H NMR (400 MHz, CDCl$_3$) δ 7.82 (s, 1H), 7.79 (s, 1H), 7.43-7.27 (m, 3H), 7.26-7.18 (m, 2H), 6.41 (q, J=7.1 Hz, 1H), 3.37 (s, 2H), 3.25 (s, 3H), 2.10-1.85 (m, 6H), 1.90 (d, J=7.1 Hz, 3H).

Example A21 Preparation of Compound A25

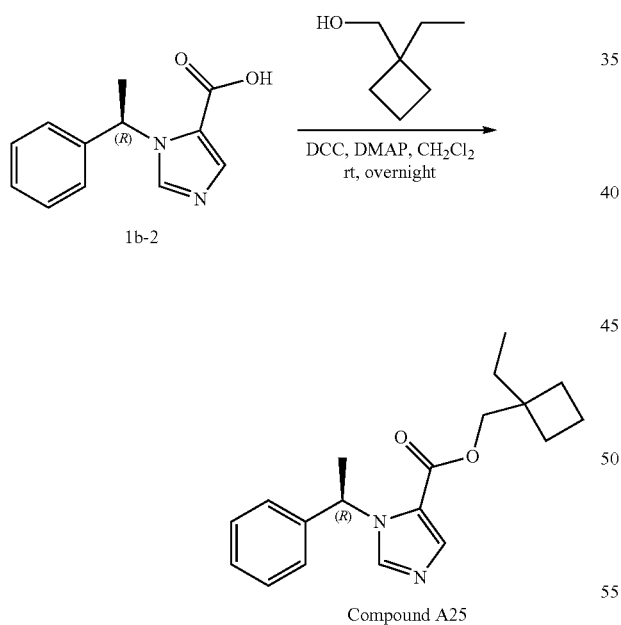

The title compound A25 was prepared according to the general procedure A, using 1b-2 (216 mg, 1.0 mmol) and (1-ethylcyclobutyl)methanol (114 mg, 1.0 mmol) as the raw materials. The crude product was purified by Prep-TLC (ethyl acetate/petroleum ether (v/v)=1/1) and the fraction with Rf=0.4~0.5 was collected and dried to give the title compound A25 (189 mg, yield 60%) as colorless oil. ESI [M+H]$^+$=313.3

Example A23 Preparation of Compound A27

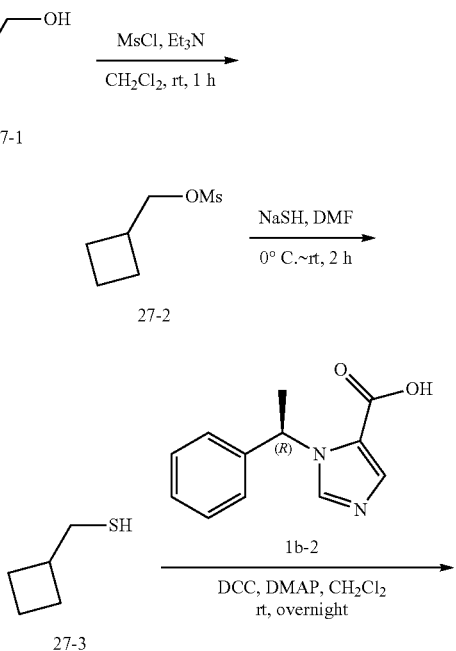

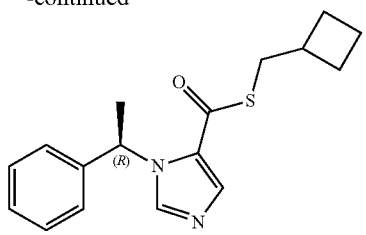

Compound A27

1, Preparation of Cyclobutylmethanethiol (27-3)

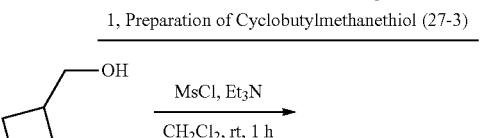

The compound 27-3 was prepared according to the general procedure C, using 27-1 (200 mg, 2.32 mmol) as the raw material. 130 mg of crude 27-3 as colorless oil was obtained. ESI[M+H]$^+$=103.1

2. Preparation of Compound A27

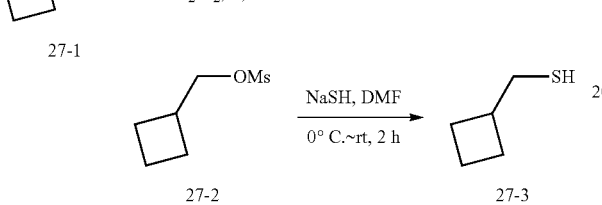

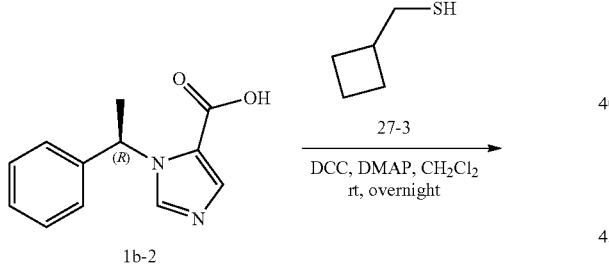

Compound A27

The title compound A27 was prepared according to the general procedure A, using 1b-2 (100 mg, 0.46 mmol) and 27-3 (130 mg, 1.27 mmol) as the raw materials. The crude product was purified by Prep-TLC (ethyl acetate/petroleum ether (v/v)=1/1) and the fraction with Rf=0.5~0.6 was collected and dried to give the title compound A27 (22 mg, yield 16%) as colorless oil. ESI[M+H]$^+$=301.1 $^1$H NMR (400 MHz, CDCl$_3$) δ 7.91 (s, 1H), 7.78 (s, 1H), 7.38-7.28 (m, 3H), 7.18 (d, J=7.0 Hz, 2H), 6.28 (q, J=7.1 Hz, 1H), 3.27-2.97 (m, 2H), 2.51 (dt, J=15.6, 7.8 Hz, 1H), 2.08 (ddd, J=19.7, 9.8, 5.7 Hz, 2H), 1.91-1.78 (m, 5H), 1.70 (dd, J=20.2, 8.8 Hz, 2H).

Example A24 Preparation of Compound A28

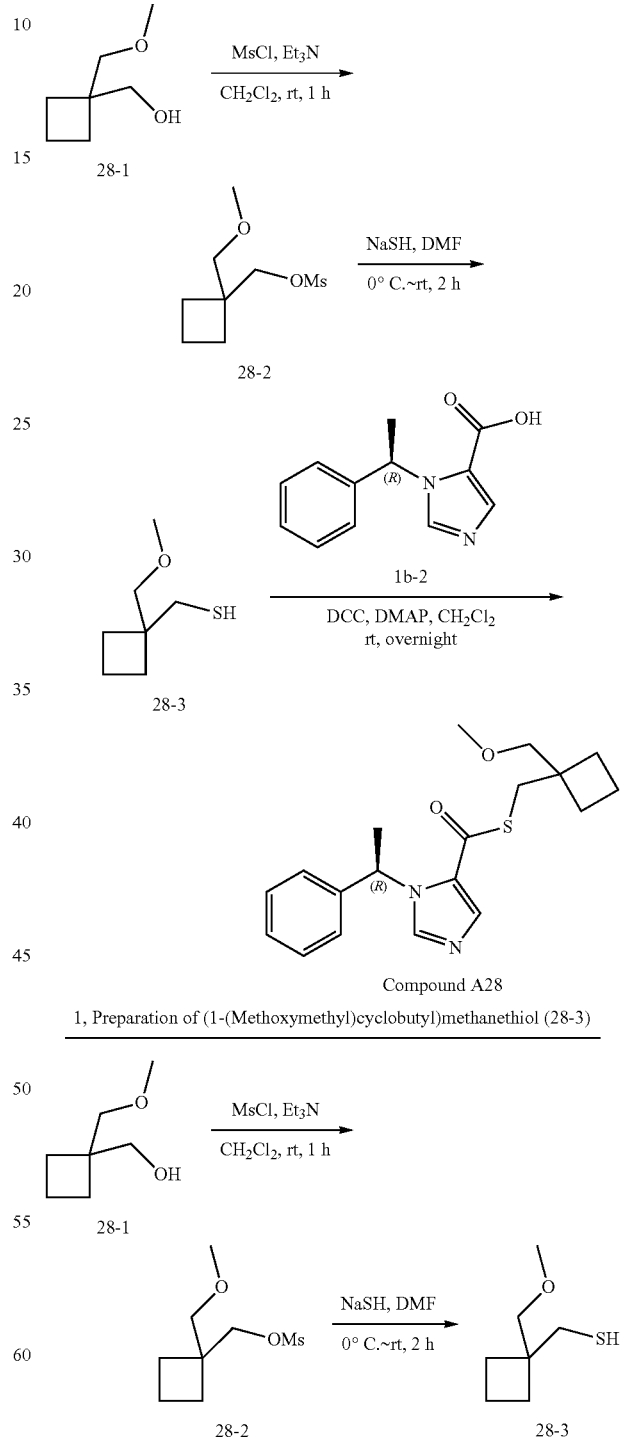

Compound A28

1, Preparation of (1-(Methoxymethyl)cyclobutyl)methanethiol (28-3)

The compound 28-3 was prepared according to the general procedure C, using 28-1 (200 mg, 1.54 mmol) as the raw material. 156 mg of crude compound 28-3 as colorless oil was obtained. ESI[M+H]⁺=147.1

2. Preparation of Compound A28

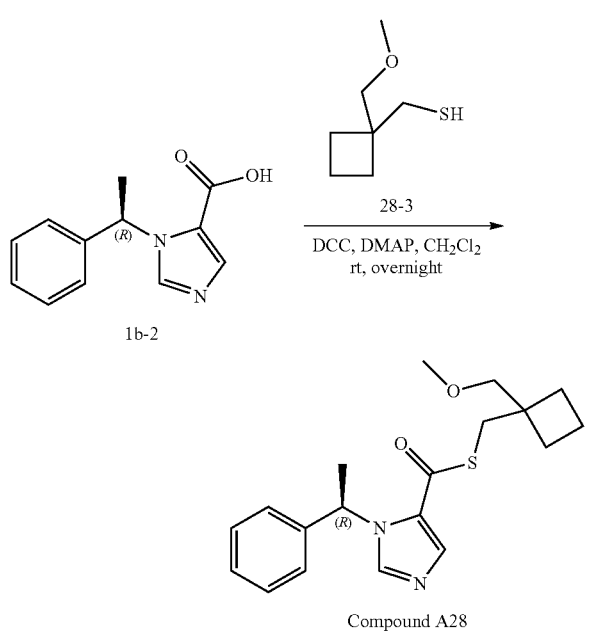

The title compound A28 was prepared according to the general procedure A, using 1b-2 (100 mg, 0.46 mmol) and 28-3 (156 mg, 1.07 mmol) as the raw materials. The crude product was purified by Prep-TLC (ethyl acetate/petroleum ether (v/v)=1/1) and the fraction with Rf=0.5~0.6 was collected and dried to give the title compound A28 (44 mg, yield 13%) as colorless oil. ESI[M+H]⁺=345.2 $^1$H NMR (400 MHz, CDCl$_3$) δ 7.95 (s, 1H), 7.81 (s, 1H), 7.39-7.28 (m, 3H), 7.18 (d, J=7.0 Hz, 2H), 6.30 (d, J=7.0 Hz, 1H), 3.33 (s, 3H), 3.30 (s, 2H), 3.27 (s, 2H), 1.94-1.73 (m, 9H).

Example A25 Preparation of Compound A29

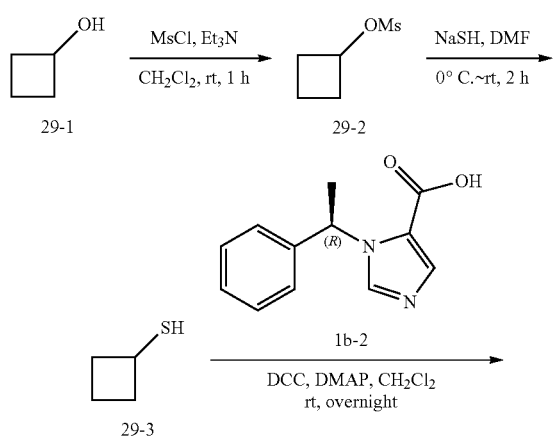

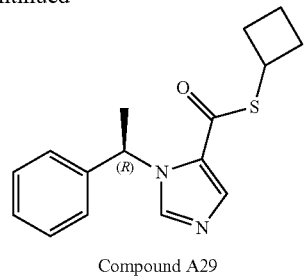

Compound A29

1. Preparation of (1-(Methoxymethyl)cyclobutyl)methanethiol (29-3)

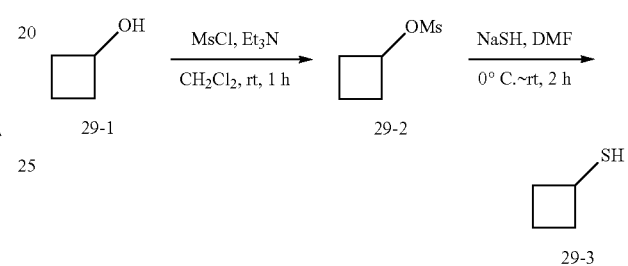

The compound 29-3 was prepared according to the general procedure C, using 29-1 (200 mg, 2.77 mmol) as the raw material. 94 mg of crude compound 29-3 as colorless oil was obtained. ESI[M+H]⁺=89.1

2. Preparation of Compound A29

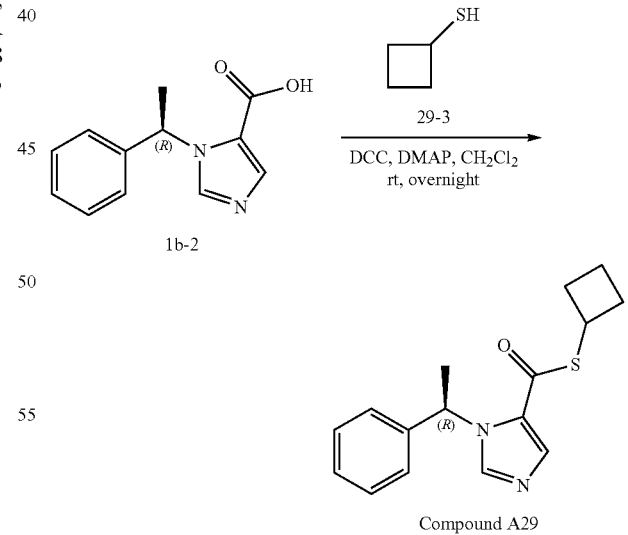

The title compound A29 was prepared according to the general procedure A, using 1b-2 (100 mg, 0.46 mmol) and 29-3 (94 mg, 1.07 mmol) as the raw materials. The crude product was purified by Prep-TLC (ethyl acetate/petroleum ether (v/v)=1/1) and the fraction with Rf=0.5~0.6 was collected and dried to give the title compound A29 (24 mg, yield 18%) as colorless oil. ESI[M+H]⁺=287.0 ¹H NMR (400 MHz, CDCl₃) δ 7.91 (s, 1H), 7.76 (s, 1H), 7.39-7.27 (m, 3H), 7.22-7.15 (m, 2H), 6.28 (q, J=6.9 Hz, 1H), 5.87-5.71 (m, 1H), 5.16-5.00 (m, 2H), 3.16-2.89 (m, 2H), 2.37 (q, J=7.1 Hz, 2H), 1.85 (d, J=7.1 Hz, 3H).

Example A26 Preparation of Compound A30

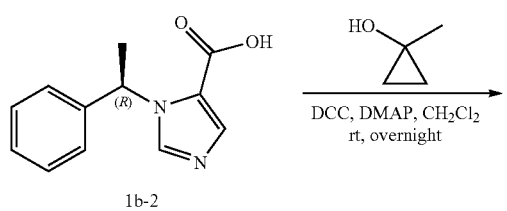

The title compound A30 was prepared according to the general procedure A, using 1b-2 (100 mg, 0.46 mmol) and 1-methylcyclopropanol (50 mg, 0.69 mmol) as the raw materials. The crude product was purified by Prep-TLC (ethyl acetate/petroleum ether (v/v)=1/1) and the fraction with Rf=0.5~0.6 was collected and dried to give the title compound A30 (93 mg, yield 75%) as colorless oil. ESI[M+H]⁺=271.1

¹H NMR (400 MHz, CDCl₃) δ 7.93 (s, 1H), 7.79 (s, 1H), 7.39-7.25 (m, 3H), 7.21-7.14 (m, 2H), 6.27 (q, J=7.0 Hz, 1H), 1.83 (d, J=7.1 Hz, 3H), 1.55 (s, 3H), 1.00-0.82 (m, 2H), 0.76-0.60 (m, 2H).

Example A27 Preparation of Compound A31

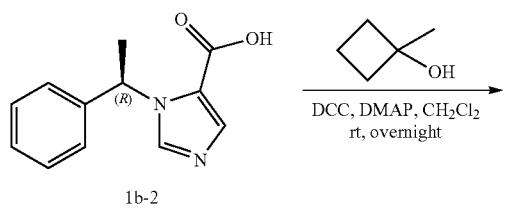

The title compound A31 was prepared according to the general procedure A, using 1b-2 (100 mg, 0.46 mmol) and 1-methylcyclobutanol (59 mg, 0.69 mmol) as the raw materials. The crude product was purified by Prep-TLC (ethyl acetate/petroleum ether (v/v)=1/1) and the fraction with Rf=0.5~0.6 was collected and dried to give the title compound A31 (101 mg, yield 77%) as colorless oil. ESI[M+H]⁺=285.1

¹H NMR (400 MHz, CDCl₃) δ 7.81 (s, 1H), 7.78 (s, 1H), 7.34-7.26 (m, 3H), 7.25-7.10 (m, 2H), 6.38 (q, J=7.1 Hz, 1H), 2.45-2.00 (m, 4H), 1.86 (d, J=7.1 Hz, 3H), 1.80-1.45 (m, 2H), 1.49 (s, 3H).

Example A28 Preparation of Compound A32

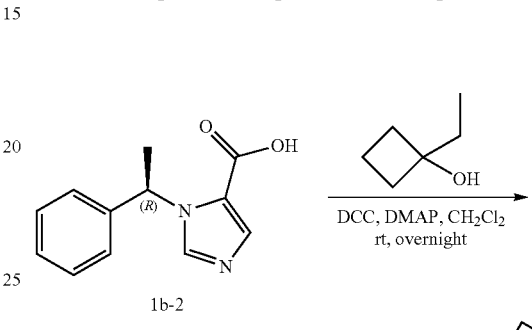

The title compound A32 was prepared according to the general procedure A, using 1b-2 (100 mg, 0.46 mmol) and 1-ethylcyclobutanol (69 mg, 0.69 mmol) as the raw materials. The crude product was purified by Prep-TLC (ethyl acetate/petroleum ether (v/v)=1/1) and the fraction with Rf=0.5~0.6 was collected and dried to give the title compound A32 (113 mg, yield 82%) as colorless oil. ESI[M+H]⁺=299.1

¹H NMR (400 MHz, CDCl₃) δ 7.80 (s, 1H), 7.79 (s, 1H), 7.35-7.28 (m, 3H), 7.26-7.13 (m, 2H), 6.39 (q, J=7.1 Hz, 1H), 2.50-2.28 (m, 2H), 2.21-2.07 (m, 2H), 1.87 (d, J=7.1 Hz, 3H), 1.80-1.45 (m, 4H), 0.96 (t, J=7.2 Hz, 3H).

Example A29 Preparation of Compound A33

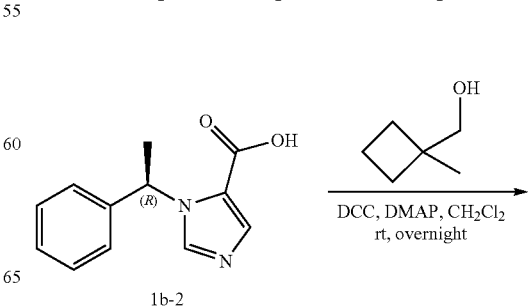

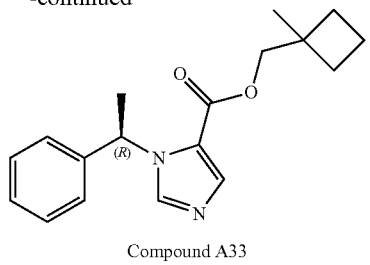

Compound A33

The title compound A33 was prepared according to the general procedure A, using 1b-2 (100 mg, 0.46 mmol) and (1-methylcyclobutyl)methanol (69 mg, 0.69 mmol) as the raw materials. The crude product was purified by Prep-TLC (ethyl acetate/petroleum ether (v/v)=1/1) and the fraction with Rf=0.5~0.6 was collected and dried to give the title compound A33 (108 mg, yield 79%) as colorless oil. ESI [M+H]$^+$=299.1

$^1$H NMR (400 MHz, d$_6$-DMSO) δ 8.29 (s, 1H), 7.67 (s, 1H), 7.37-7.30 (m, 2H), 7.29-7.25 (m, 1H), 7.17-7.15 (m, 2H), 6.27 (q, J=7.2 Hz, 1H), 4.20-3.85 (m, 2H), 1.90-1.75 (m, 2H), 1.80-1.54 (m, 5H), 1.65-1.40 (m, 2H).

Example A30 Preparation of Compound A34

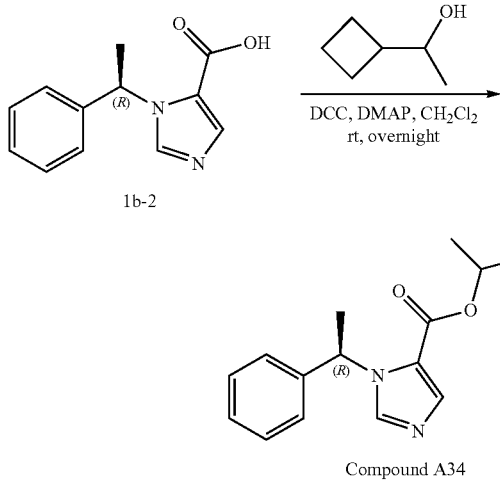

Compound A34

The title compound A34 was prepared according to the general procedure A, using 1b-2 (100 mg, 0.46 mmol) and 1-cyclobutylethanol (69 mg, 0.69 mmol) as the raw materials. The crude product was purified by Prep-TLC (ethyl acetate/petroleum ether (v/v)=1/1) and the fraction with Rf=0.5~0.6 was collected and dried to give the title compound A34 (99 mg, yield 72%) as colorless oil. ESI[M+H]$^+$=299.1

$^1$H NMR (400 MHz, CDCl$_3$) δ 7.81 (s, 1H), 7.78 (s, 1H), 7.42-7.26 (m, 3H), 7.25-7.14 (m, 2H), 6.39 (q, J=7.2 Hz, 1H), 4.58-4.40 (m, 1H), 2.59-2.50 (m, 1H), 1.86 (d, J=7.1 Hz, 3H), 1.86-1.54 (m, 6H), 1.34 (t, J=6.2 Hz, 3H).

Example A31 Preparation of Compound A35

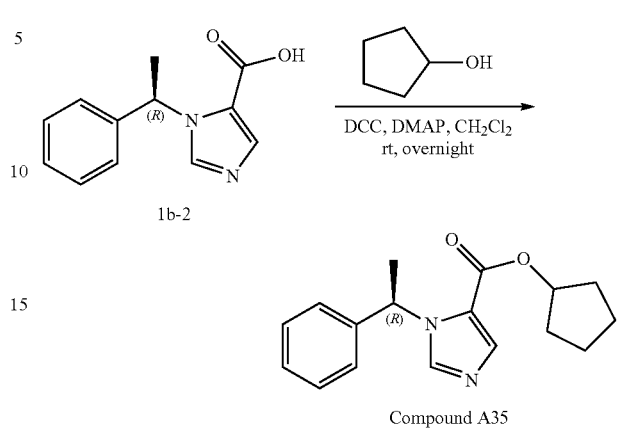

Compound A35

The title compound A35 was prepared according to the general procedure A, using 1b-2 (100 mg, 0.46 mmol) and cyclopentanol (59 mg, 0.69 mmol) as the raw materials. The crude product was purified by Prep-TLC (ethyl acetate/petroleum ether (v/v)=1/1) and the fraction with Rf=0.5~0.6 was collected and dried to give the title compound A35 (113 mg, yield 86%) as colorless oil. ESI[M+H]$^+$=285.1

$^1$H NMR (400 MHz, CDCl$_3$) δ 7.92 (s, 1H), 7.78 (s, 1H), 7.40-7.24 (m, 3H), 7.20-7.12 (m, 2H), 6.26 (q, J=7.0 Hz, 1H), 5.25-5.01 (m, 1H), 1.98-2.02 (m, 2H), 1.84 (d, J=7.1 Hz, 3H), 1.95-1.61 (m, 6H).

Example A32 Preparation of Compound A36

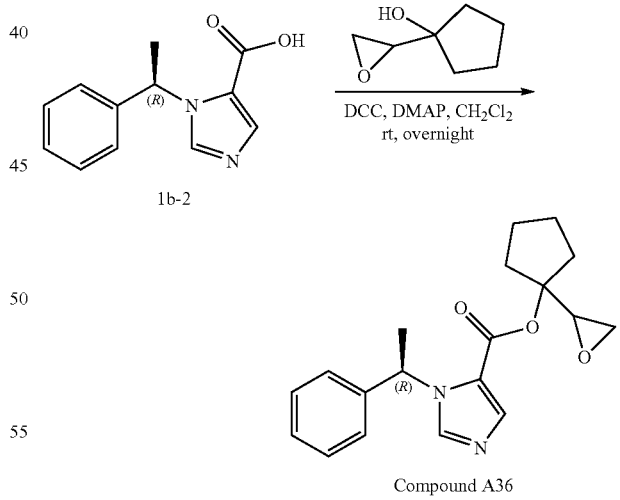

Compound A36

The title compound A36 was prepared according to the general procedure A, using 1b-2 (108 mg, 0.5 mmol) and 1-(oxiran-2-yl)cyclopentanol (64 mg, 0.5 mmol) as the raw materials. The crude product was purified by Prep-TLC (ethyl acetate/petroleum ether (v/v)=1/1) and the fraction with Rf=0.4~0.5 was collected and dried to give the title compound A36 (75 mg, yield 46%) as colorless oil. ESI[M+H]$^+$=327.3

Example A33 Preparation of Compound A37

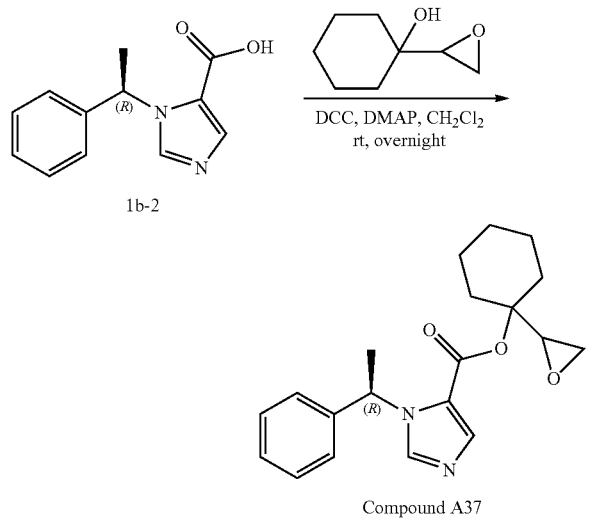

Compound A37

The title compound A37 was prepared according to the general procedure A, using 1b-2 (108 mg, 0.5 mmol) and 1-(oxiran-2-yl)cyclohexanol (71 mg, 0.5 mmol) as the raw materials. The crude product was purified by Prep-TLC (ethyl acetate/petroleum ether (v/v)=1/1) and the fraction with Rf=0.5~0.6 was collected and dried to give the title compound A37 (78 mg, yield 46%) as colorless oil. ESI[M+H]$^+$=341.2

$^1$H NMR (400 MHz, CDCl$_3$) δ 8.11 (s, 1H), 7.87 (s, 1H), 7.45-7.33 (m, 4H), 7.29-7.26 (m, 1H), 6.50-6.39 (m, 1H), 3.37-3.31 (m, 1H), 2.83-2.71 (m, 2H), 2.29-2.11 (m, 2H), 1.87 (d, J=7.1 Hz, 3H), 1.64-1.32 (m, 8H).

Example A34 Preparation of Compound A38

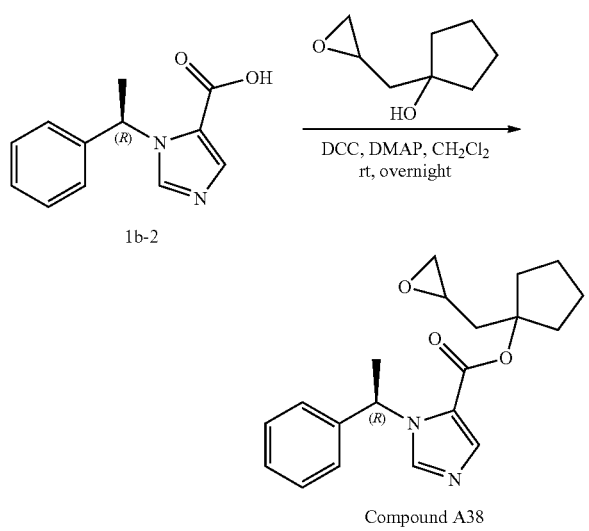

Compound A38

The title compound A38 was prepared according to the general procedure A, using 1b-2 (108 mg, 0.5 mmol) and 1-(oxiran-2-ylmethyl)cyclopentanol (71 mg, 0.5 mmol) as the raw materials. The crude product was purified by Prep-TLC (ethyl acetate/petroleum ether (v/v)=1/1) and the fraction with Rf=0.4~0.5 was collected and dried to give the title compound A38 (89 mg, yield 52%) as colorless oil. ESI[M+H]$^+$=341.2

Example A35 Preparation of Compound A39

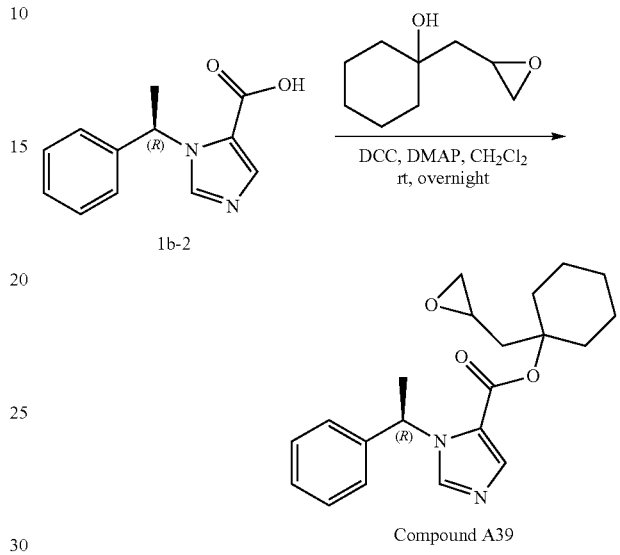

Compound A39

The title compound A39 was prepared according to the general procedure A, using 1b-2 (108 mg, 0.5 mmol) and 1-(oxiran-2-ylmethyl)cyclohexanol (78 mg, 0.5 mmol) as the raw materials. The crude product was purified by Prep-TLC (ethyl acetate/petroleum ether (v/v)=1/1) and the fraction with Rf=0.4~0.5 was collected and dried to give the title compound A39 (76 mg, yield 43%) as colorless oil. ESI[M+H]$^+$=355.2

Example A36 Preparation of Compound A40

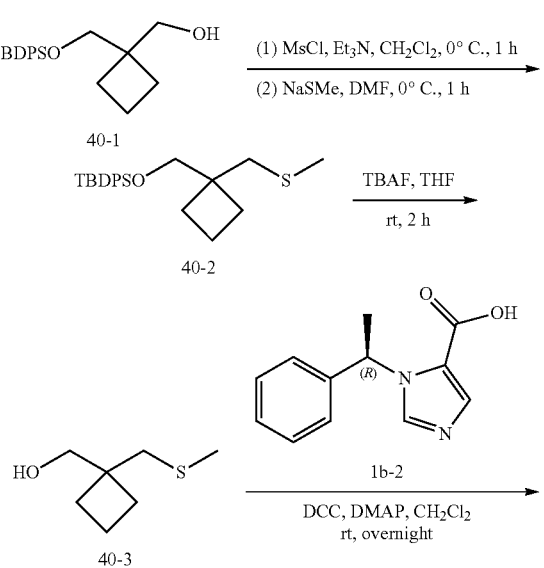

129
-continued

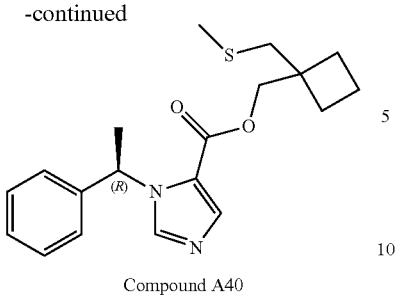

Compound A40

1. Preparation of (1-((Methylthio)methyl)cyclobutyl)methanol (40-3)

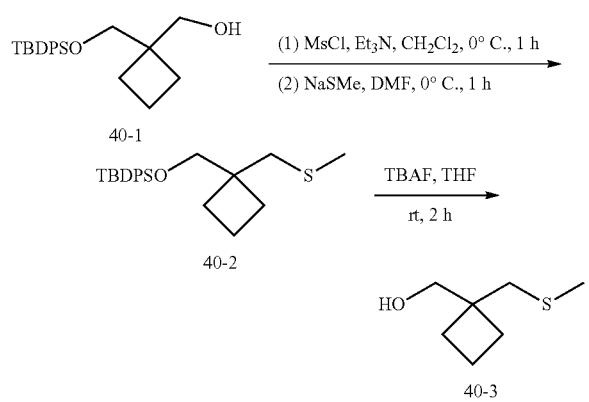

The compound 40-2 was prepared according to the general procedure C, using 40-1 (1.0 g, 3.0 mmol) as the raw material. 631 mg of crude compound 40-2 as colorless oil was obtained. ESI[M+H]$^+$=385.3

At room temperature, TBAF (6.0 mL, 1 mol/L in THF, 6.0 mmol) was added into the solution of 40-2 (631 mg, 1.5 mmol) in THF (10 mL) and the mixture was allowed to react at room temperature for 2 hrs. The reaction was monitored by TLC until completion. The mixture was quenched with saturated brine and extracted with EtOAc (3×10 mL). The combined organic layers were washed with saturated brine (30 mL), dried over anhydrous sodium sulfate, filtered and concentrated under reduced pressure to give compound 40-3 (221 mg, yield 50% for 3 steps) as colorless oil, which was used for next step directly without further purification. ESI[M+H]$^+$=147.1

2. Preparation of Compound A40

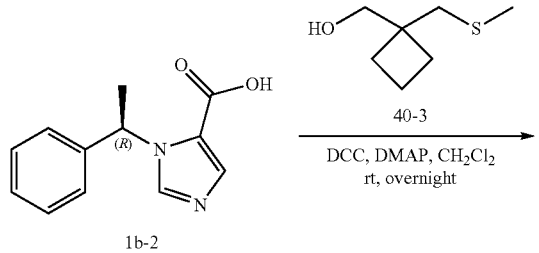

130
-continued

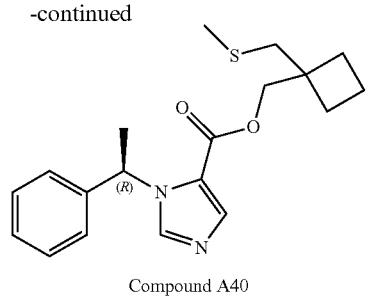

Compound A40

The title compound A40 was prepared according to the general procedure A, using 1b-2 (216 mg, 1.0 mmol) and 40-3 (146 mg, 1.0 mmol) as the raw materials. The crude product was purified by Prep-TLC (ethyl acetate/petroleum ether (v/v)=1/1) and the fraction with Rf=0.5~0.6 was collected and dried to give the title compound A40 (75 mg, yield 22%) as colorless oil. ESI[M+H]$^+$=345.3 $^1$H NMR (400 MHz, CDCl$_3$) δ 7.84 (s, 1H), 7.80 (s, 1H), 7.42-7.28 (m, 3H), 7.25-7.16 (m, 2H), 6.40 (q, J=7.2 Hz, 1H), 4.43-4.14 (m, 2H), 2.75 (s, 2H), 2.10 (s, 3H), 1.97~1.90 (m, 6H), 1.88 (d, J=7.1 Hz, 3H).

Example A37 Preparation of Compound A41

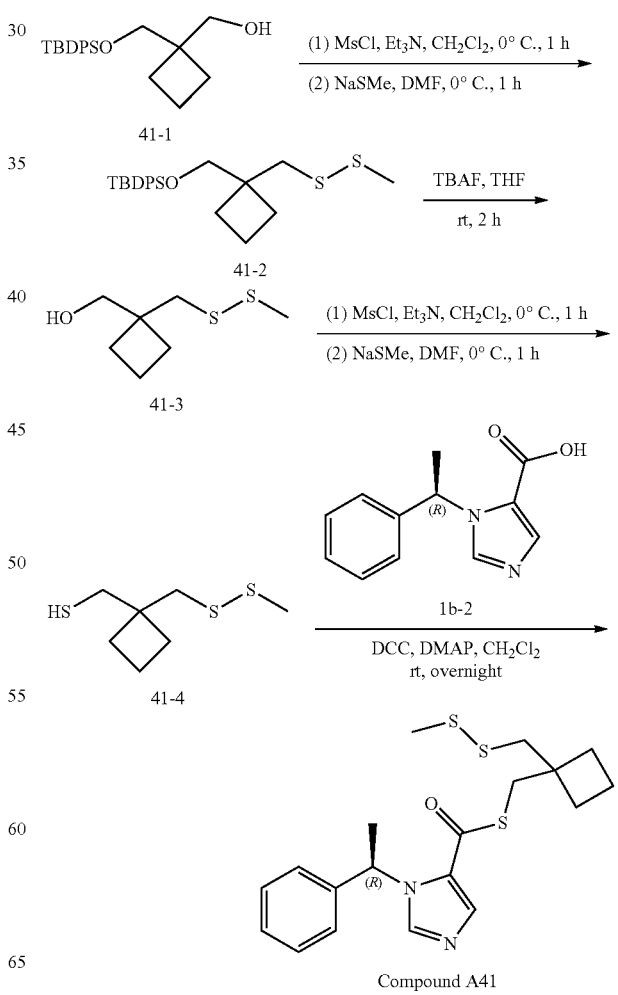

Compound A41

1. Preparation of (1-((Methyldisulfanyl)methyl)cyclobutyl)methanol (41-3)

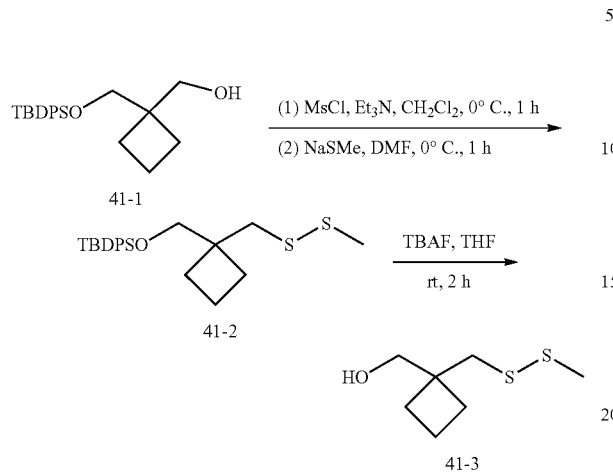

The compound 41-2 was prepared according to the general procedure C, using 41-1 (1.0 g, 3.0 mmol) as the raw material. 631 mg of compound 41-2 as colorless oil was obtained. ESI[M+H]$^+$=417.3

At room temperature, TBAF (6.0 mL, 1 mol/L in THF, 6.0 mmol) was added into the solution of 41-2 (631 mg, 1.5 mmol) in THF (10 mL) and the mixture was allowed to react at room temperature for 2 hrs. The reaction was monitored by TLC until completion. The mixture was quenched with saturated brine and extracted with EtOAc (3×10 mL). The combined organic layers were washed with saturated brine (30 mL), dried over anhydrous sodium sulfate, filtered and concentrated under reduced pressure to give compound 41-3 (221 mg, yield 41% for 3 steps) as colorless oil, which was used for next step directly without further purification. ESI[M+H]$^+$=179.1

2. Preparation of (1-((Methyldisulfanyl)methyl)cyclobutyl)methanethiol (41-4)

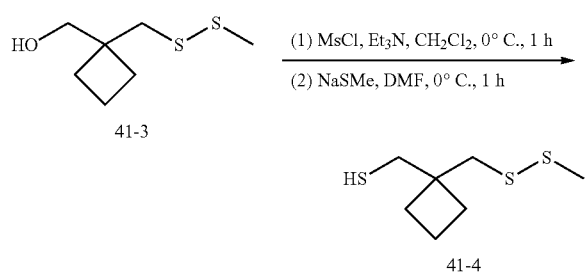

The compound 41-4 was prepared according to the general procedure C, using 41-3 (221 mg, 1.2 mmol) as the raw material. 95 mg of compound 41-4 (yield 40%) as colorless oil was obtained. ESI[M+H]$^+$=195.0

3. Preparation of Compound A41

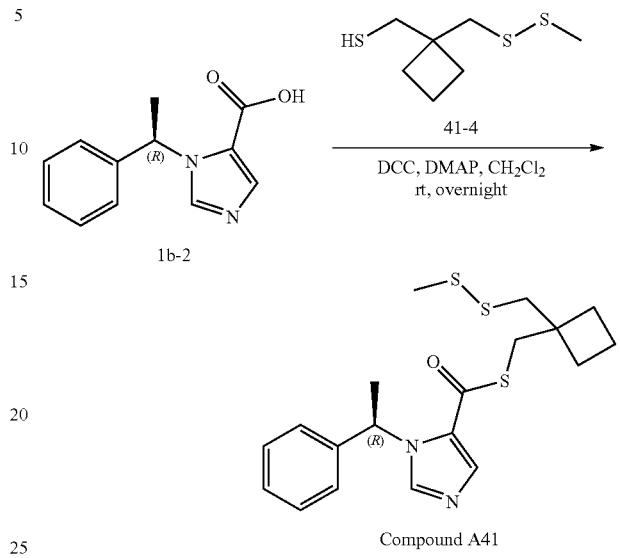

The compound A41 was prepared according to the general procedure A, using 1b-2 (100 mg, 0.46 mmol) and 41-4 (95 mg, 0.49 mmol) as the raw materials. The crude product was purified by Prep-TLC (ethyl acetate/petroleum ether (v/v)=1/2) and the fraction with Rf=0.4~0.5 was collected to give the title compound A41 (104 mg, yield 58%) as colorless oil. ESI[M+H]$^+$=393.2 $^1$H NMR (400 MHz, CDCl$_3$) δ 7.84 (s, 1H), 7.79 (s, 1H), 7.42-7.28 (m, 3H), 7.23-7.12 (m, 2H), 6.36 (q, J=7.1 Hz, 1H), 4.45-3.98 (m, 4H), 2.95 (s, 3H), 2.09-1.90 (m, 6H), 1.88 (d, J=7.1 Hz, 3H).

Example A38 Preparation of Compound A42

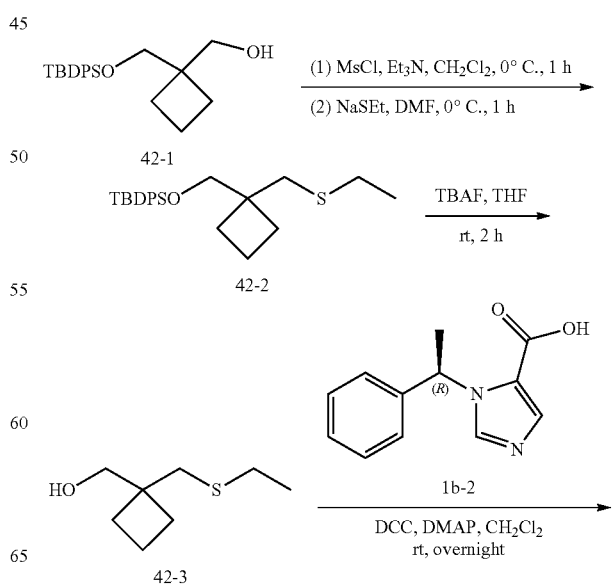

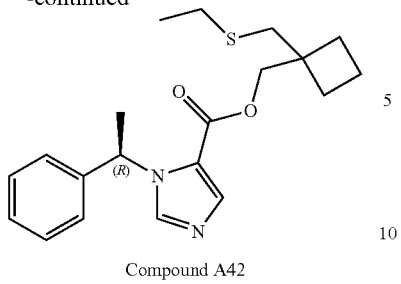

Compound A42

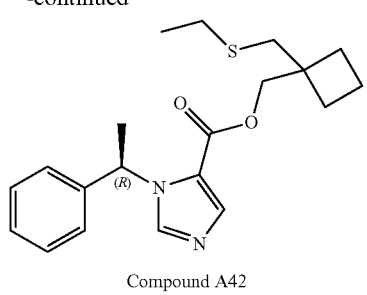

Compound A42

1. Preparation of
(1-((ethylthio)methyl)cyclobutyl)methanol (42-3)

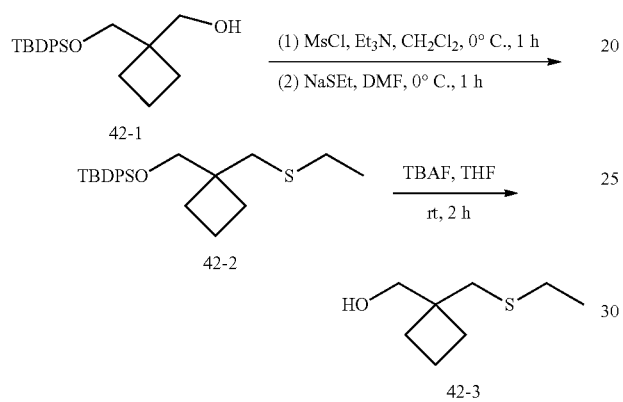

The compound 42-2 was prepared according to the general procedure C, using 42-1 (1.4 g, 4.0 mmol) as the raw material. 758 mg of crude compound 42-2 as colorless oil was obtained. ESI[M+H]$^+$=399.3

At room temperature, TBAF (7.6 mL, 1 mol/L in THF, 7.6 mmol) was added into the solution of 42-2 (758 mg, 1.9 mmol) in THF (10 mL) and the mixture was allowed to react at room temperature for 2 hrs. The reaction was monitored by TLC until completion. The mixture was quenched with saturated brine and extracted with EtOAc (3×10 mL). The combined organic layers were washed with saturated brine (30 mL), dried over anhydrous sodium sulfate, filtered and concentrated under reduced pressure to give crude compound 42-3 (214 mg, yield 33% for 3 steps) as colorless oil, which was used for next step directly without further purification. ESI[M+H]$^+$=161.2

2. Preparation of Compound A42

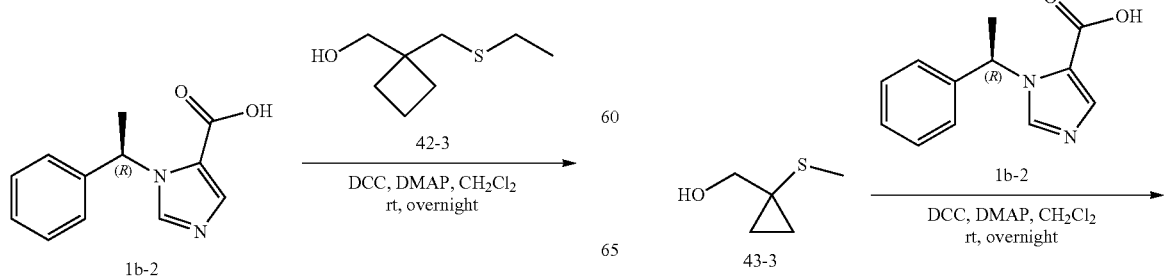

The title compound A42 was prepared according to the general procedure A, using 1b-2 (216 mg, 1.0 mmol) and 42-3 (192 mg, 1.2 mmol) as the raw materials. The crude product was purified by Prep-TLC (ethyl acetate/petroleum ether (v/v)=1/1) and the fraction with Rf=0.5~0.6 was collected and dried to give the title compound A42 (88 mg, yield 25%) as colorless oil. ESI[M+H]$^+$=359.3 $^1$H NMR (400 MHz, CDCl$_3$) δ 7.83 (s, 1H), 7.81 (s, 1H), 7.41-7.25 (m, 3H), 7.22-7.15 (m, 2H), 6.37 (q, J=7.2 Hz, 1H), 4.41-4.12 (m, 2H), 2.77-2.68 (m, 4H), 1.95-1.88 (m, 6H), 1.85 (d, J=7.1 Hz, 3H), 1.30 (t, J=7.1 Hz, 3H).

Example A39 Preparation of Compound A43

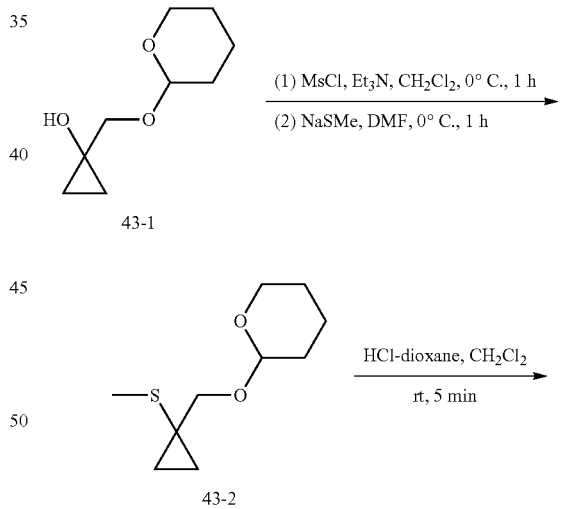

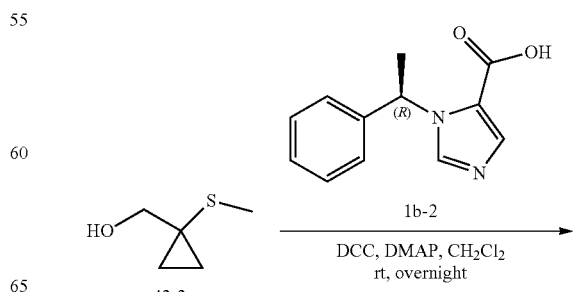

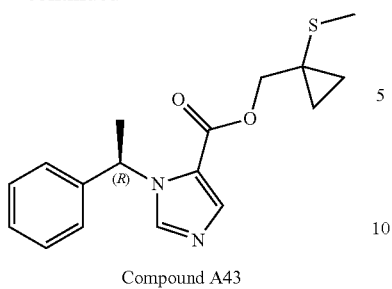

Compound A43

1. Preparation of (1-(Methylthio)cyclopropyl)methanol (43-3)

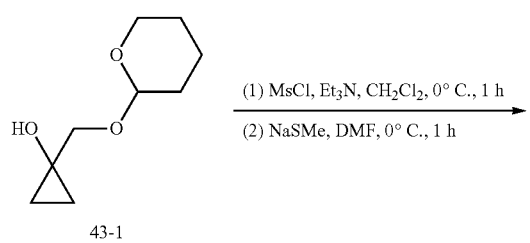

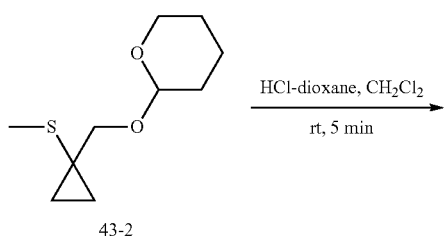

The compound 43-2 was prepared according to the general procedure C, using 43-1 (689 mg, 4.0 mmol) as the raw material. 402 mg of compound 43-2 as colorless oil was obtained. ESI[M+H]$^+$=203.3

At room temperature, HCl/Dioxane (0.5 mL, 4 mol/L, 2 mmol) was added into the mixture of 43-2 (402 mg, 1.99 mmol) in dichloromethane (5 mL), then the mixture was reacted at this temperature for 5 min. The reaction was monitored by TLC until completion. The reaction system was used for next step directly without any treatment. ESI[M+H]$^+$=119.1

2. Preparation of Compound A43

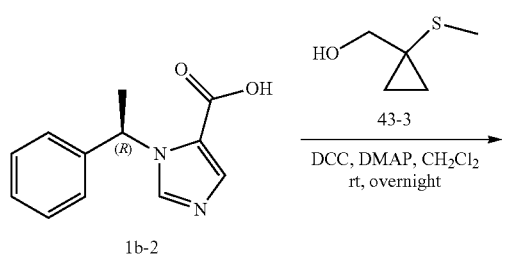

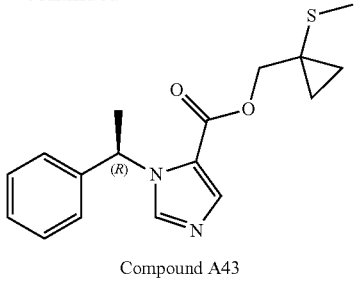

Compound A43

The title compound A43 was prepared according to the general procedure A, using 1b-2 (216 mg, 1.0 mmol) and the reaction system of 43-3 (from last step) as the raw materials. The crude product was purified by Prep-TLC (ethyl acetate/petroleum ether (v/v)=1/2) and the fraction with Rf=0.4~0.5 was collected and dried to give the title compound A43 (47 mg, yield 15%) as colorless oil. ESI[M+H]$^+$=317.3

$^1$H NMR (400 MHz, CDCl$_3$) δ 7.83 (s, 1H), 7.80 (s, 1H), 7.43~7.28 (m, 3H), 7.25-7.18 (m, 2H), 6.39 (q, J=7.1 Hz, 1H), 4.35~4.24 (m, 2H), 2.15 (s, 3H), 1.88 (d, J=7.1 Hz, 3H), 0.68~0.52 (m, 4H).

Example A40 Preparation of Compound A44

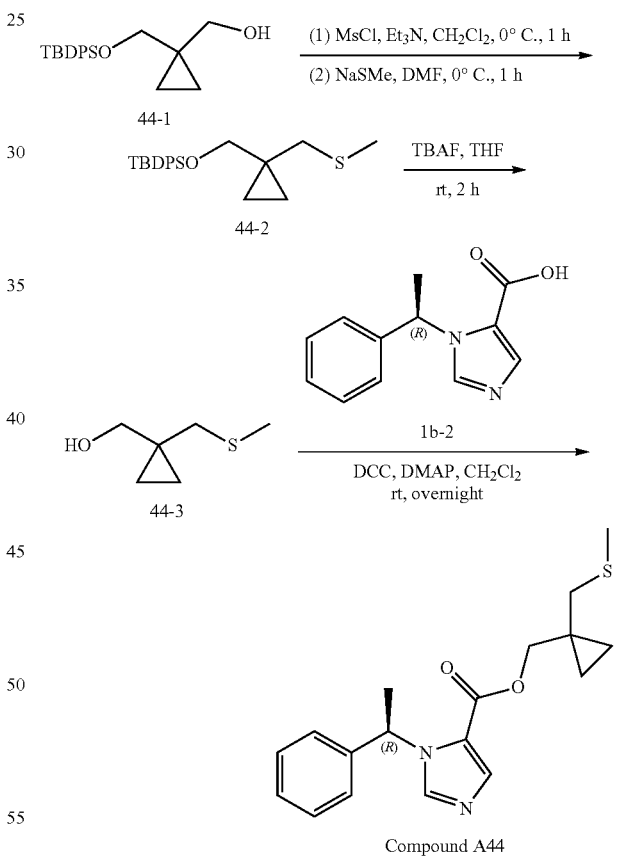

Compound A44

1. Preparation of (1-((Methylthio)methyl)cyclopropyl)methanol (44-3)

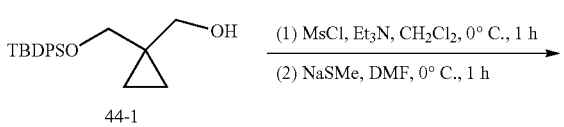

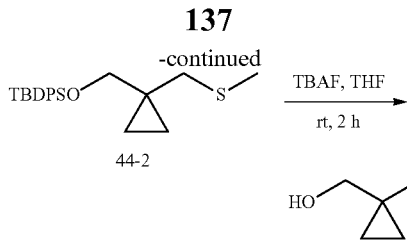

The compound 44-2 was prepared according to the general procedure C, using 44-1 (1.70 g, 5.0 mmol) as the raw material. 871 mg of compound 44-2 as colorless oil was obtained. ESI[M+H]$^+$=371.3

At room temperature, TBAF (9.4 mL, 1 mol/L in THF, 9.4 mmol) was added into the solution of 44-2 (871 mg, 2.35 mmol) in THF (10 mL) and the mixture was allowed to react at room temperature for 2 hrs. The reaction was monitored by TLC until completion. The mixture was quenched with saturated brine and extracted with EtOAc (3×10 mL). The combined organic layers were washed with saturated brine (30 mL), dried over anhydrous sodium sulfate, filtered and concentrated under reduced pressure to give crude compound 44-3 (165 mg, yield 25% for 3 steps) as colorless oil, which was used for next step directly without further purification. ESI[M+H]$^+$=133.2

2. Preparation of Compound A44

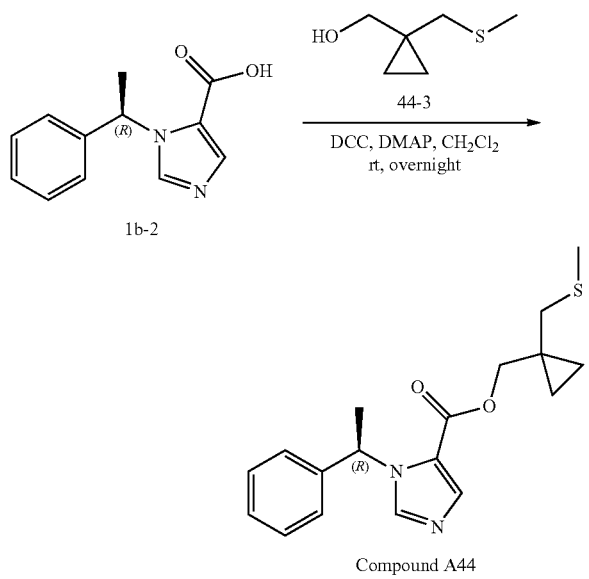

Compound A44

The title compound A44 was prepared according to the general procedure A, using 1b-2 (216 mg, 1.0 mmol) and 44-3 (160 mg, 1.2 mmol) as the raw materials. The crude product was purified by Prep-TLC (ethyl acetate/petroleum ether (v/v)=1/2) and the fraction with Rf=0.4~0.5 was collected and dried to give the title compound A44 (247 mg, yield 82%) as colorless oil. ESI[M+H]$^+$=331.3

$^1$H NMR (400 MHz, CDCl$_3$) δ 7.83 (s, 1H), 7.82 (s, 1H), 7.41-7.28 (m, 3H), 7.23-7.16 (m, 2H), 6.37 (q, J=7.1 Hz, 1H), 4.31-4.21 (m, 2H), 2.60 (d, J=1.5 Hz, 2H), 2.11 (s, 3H), 1.87 (d, J=7.1 Hz, 3H), 0.66-0.52 (m, 4H).

Example A41 Preparation of Compound A45

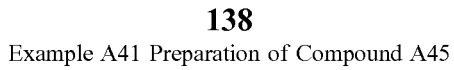

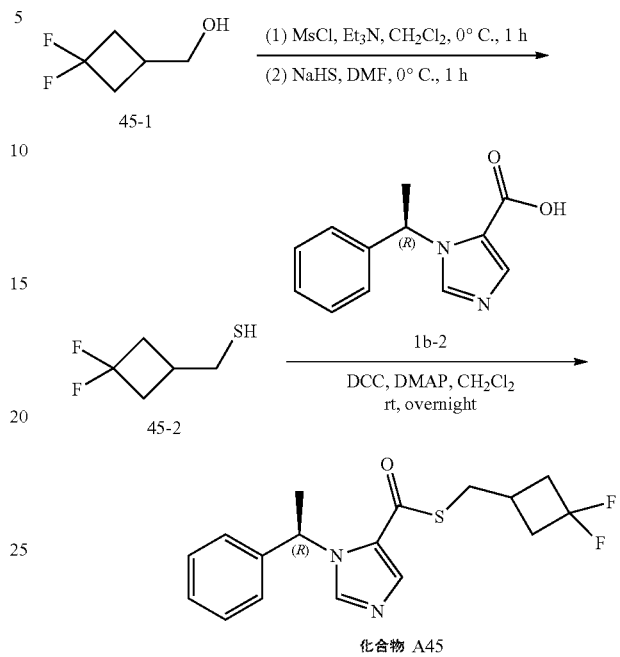

化合物 A45

The compound 45-2 was prepared according to the general procedure C, using 45-1 (244 mg, 2.0 mmol) as the raw material. 171 mg of compound 45-2 (yield 62% for 2 steps) as colorless oil was obtained. ESI[M+H]$^+$=139.1

The title compound A45 was prepared according to the general procedure A, using 1b-2 (216 mg, 1.0 mmol) and 45-2 (166 mg, 1.2 mmol) as the raw materials. The crude product was purified by Prep-TLC (ethyl acetate/petroleum ether (v/v)=1/2) and the fraction with Rf=0.4~0.5 was collected and dried to give the title compound A45 (45 mg, yield 14%) as colorless oil. ESI[M+H]$^+$=313.2

$^1$H NMR (400 MHz, CDCl$_3$) δ 7.91 (d, J=0.6 Hz, 1H), 7.76 (s, 1H), 7.39-7.27 (m, 3H), 7.21-7.07 (m, 2H), 6.22 (q, J=7.1 Hz, 1H), 3.12 (d, J=7.3 Hz, 2H), 2.75-2.55 (m, 2H), 2.44-2.31 (m, 1H), 2.30-2.13 (m, 2H), 1.85 (d, J=7.1 Hz, 3H).

Example A42 Preparation of Compound A46

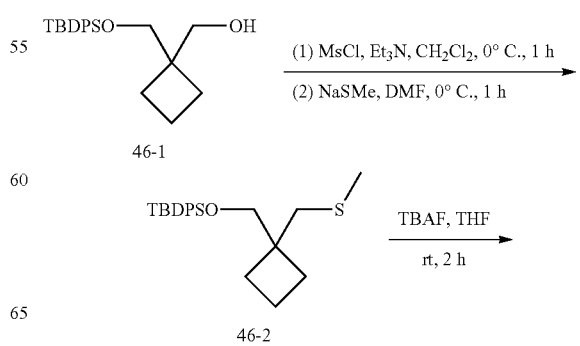

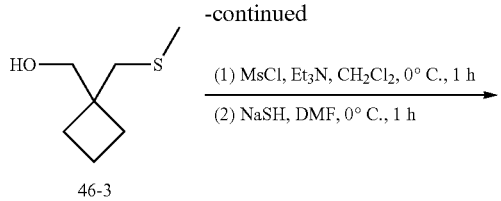

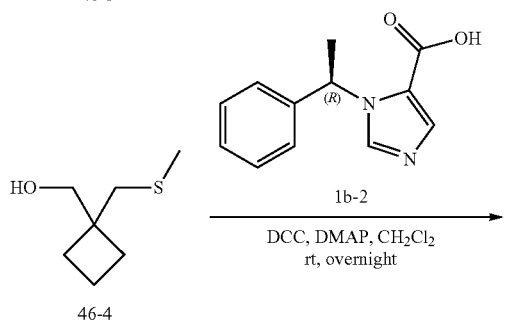

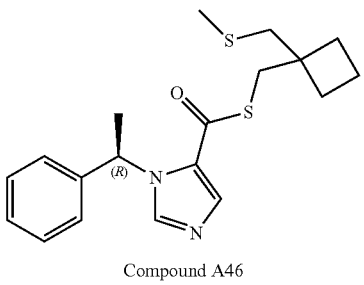

Compound A46

1. Preparation of (1-((Methylthio)methyl)cyclobutyl)methanol (46-3)

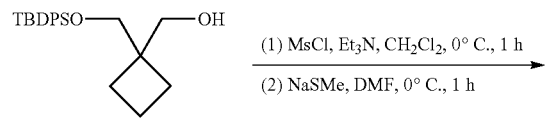

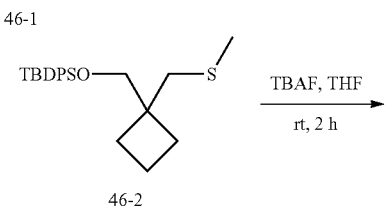

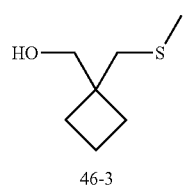

The compound 46-2 was prepared according to the general procedure C, using 46-1 (1.77 g, 5.0 mmol) as the raw material. 1.3 g of crude compound 46-2 as colorless oil was obtained. ESI[M+H]$^+$=385.3

At room temperature, TBAF (13.6 mL, 1 mol/L in THF, 13.6 mmol) was added into the solution of 46-2 (1.3 g, 3.4 mmol) in THF (10 mL) and the mixture was allowed to react at room temperature for 2 hrs. The reaction was monitored by TLC until completion, then it was quenched with saturated brine and extracted with EtOAc (3×10 mL). The combined organic layers were washed with saturated brine (30 mL), dried over anhydrous sodium sulfate, filtered and concentrated under reduced pressure to give crude compound 46-3 (438 mg, yield 60% for 3 steps) as colorless oil, which was used for next step directly without further purification. ESI[M+H]$^+$=147.2

2. Preparation of Compound A46

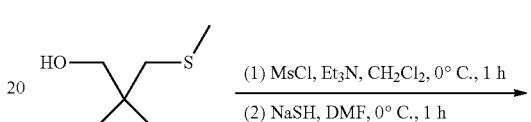

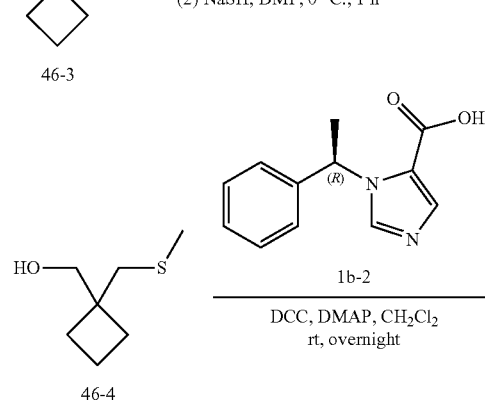

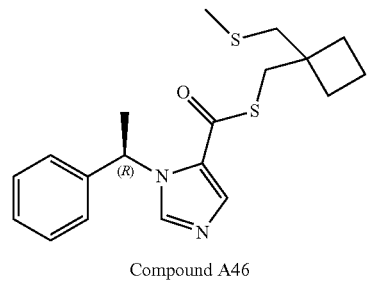

Compound A46

The compound 46-4 was prepared according to the general procedure C, using 46-3 (438 mg, 3.0 mmol) as the raw material. 197 mg of compound 46-4 (yield 35% for 2 steps) as colorless oil was obtained. ESI[M+H]$^+$=163.1

The title compound A46 was prepared according to the general procedure A, using 1b-2 (216 mg, 1.0 mmol) and 46-2 (194 mg, 1.2 mmol) as the raw materials. The crude product was purified by Prep-TLC (ethyl acetate/petroleum ether (v/v)=1/1) and the fraction with Rf=0.5~0.6 was collected and dried to give the title compound A46 (120 mg, yield 33%) as colorless oil. ESI[M+H]$^+$=361.1 $^1$H NMR (400 MHz, CDCl$_3$) δ 7.80 (s, 1H), 7.75 (s, 1H), 7.40-7.28 (m, 3H), 7.21-7.15 (m, 2H), 6.18 (q, J=7.2 Hz, 1H), 2.77~2.66 (m, 4H), 2.11 (s, 3H), 1.90~1.85 (m, 6H), 1.89 (d, J=7.1 Hz, 3H).

Example B1 Preparation of Compound B1

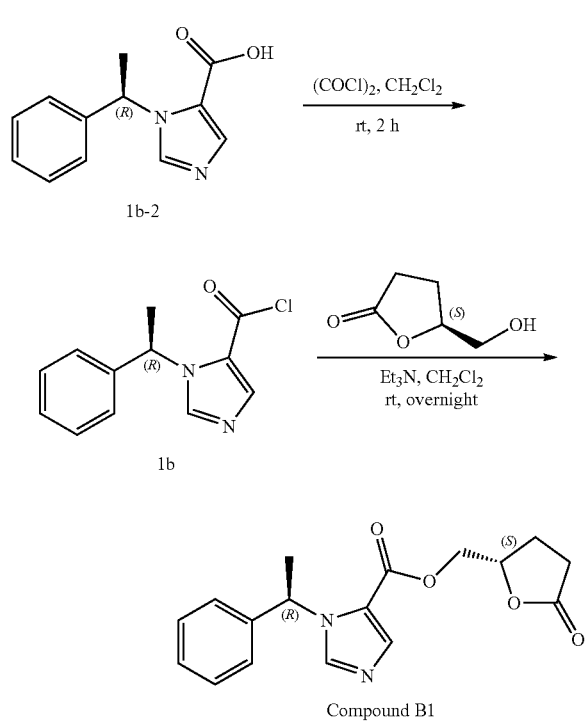

1. Preparation of (R)-1-(1-Phenylethyl)-1H-imidazole-5-carbonyl chloride (1b)

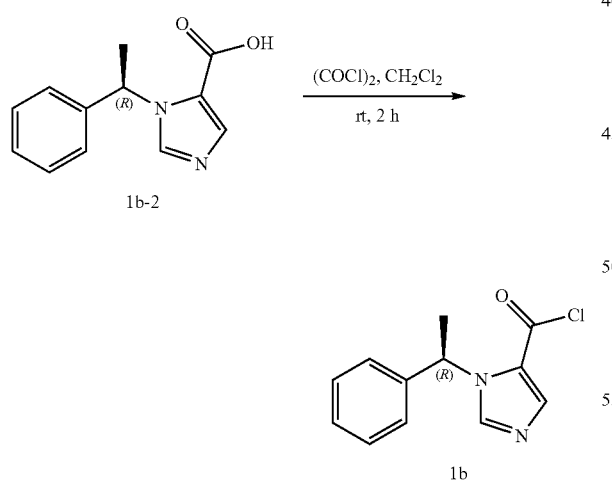

In an ice bath, oxalyl dichloride (2 mL) was slowly added into a solution of 1b-2 (200 mg, 0.92 mmol) in dichloromethane (20 mL) at the rate of 1 mL/min using a syringe at 0° C., then it was stirred at room temperature for 2 hrs. The reaction mixture was concentrated under reduced pressure to give compound 1b (220 mg, crude) as a white solid.

2. Preparation of Compound B1

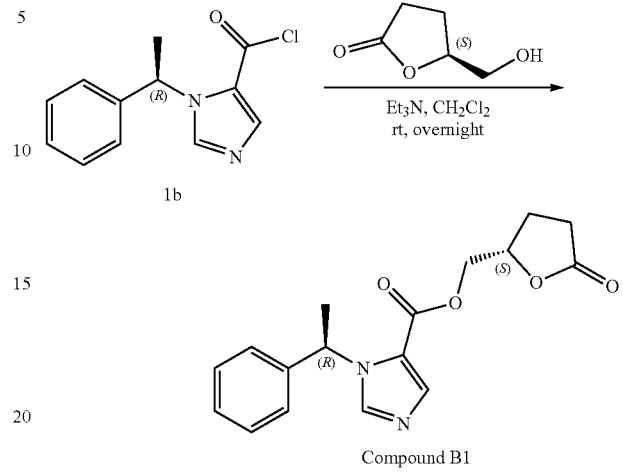

In an ice-water bath, 1b from last step was added into the mixture of (S)-5-(hydroxymethyl)dihydrofuran-2(3H)-one (107 mg, 0.92 mmol) and Et₃N (2.81 g, 27.8 mmol) in dry dichloromethane (30 mL) at 0° C., then the mixture was allowed to react at this temperature for 1 hour. The mixture was concentrated under reduced pressure. The residue was purified by silica gel column chromatography (ethyl acetate/petroleum ether (v/v) at any ratio within the range of 1/10 to 1/1), with TLC (ethyl acetate/petroleum ether (v/v)=1/1) monitoring, and collecting the fraction with Rf=0.3~0.4, to give the title compound B1 (75 mg, yield 26% for 2 steps) as colorless oil. ESI[M+H]⁺=315.3

¹H NMR (400 MHz, d₆-DMSO) δ 8.35 (s, 1H), 7.71 (d, J=0.8 Hz, 1H), 7.35-7.32 (m, 2H), 7.28-7.26 (m, 1H), 7.19-7.17 (m, 2H), 6.23-6.21 (m, 1H), 4.80-4.78 (m, 1H), 4.40 (dd, J=12.0, 2.8 Hz, 1H), 4.27-4.22 (m, 1H), 2.49-2.47 (m, 2H), 2.26-2.25 (m, 1H), 1.96-1.91 (m, 1H), 1.85 (d, J=7.2 Hz, 3H).

Example B2 Preparation of Compound B2

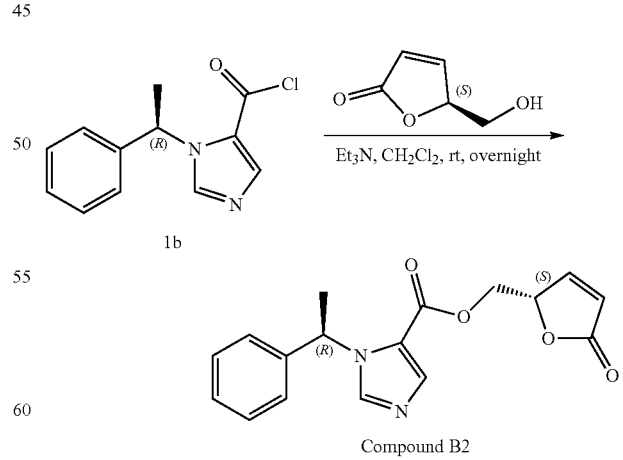

In an ice-water bath, 1b was added into the mixture of (S)-5-(hydroxymethyl)furan-2(5H)-one (65 mg, 0.56 mmol) and Et₃N (113 mg, 1.12 mmol) in dry dichloromethane (5 mL) at 0° C., then the mixture was allowed to react at this temperature overnight. The mixture was concentrated under reduced pressure. The residue was purified by silica gel column chromatography (ethyl acetate/petroleum ether (v/v) at any ratio within the range of 1/10 to 1/1), with TLC (ethyl acetate/petroleum ether (v/v)=1/1) monitoring, and collecting the fraction with Rf=0.4~0.5, to give the title compound B2 (20 mg, yield 12% for 2 steps) as colorless oil. ESI[M+H]$^+$=313.2

$^1$H NMR (400 MHz, d$_6$-DMSO) δ 8.34 (s, 1H), 7.73-7.71 (d, J=0.8 Hz, 1H), 7.59 (s, 1H), 7.36-7.32 (m, 2H), 7.29-7.27 (m, 1H), 7.17-7.15 (m, 2H), 6.24-6.22 (m, 1H), 6.18-6.16 (m, 1H), 5.47 (d, J=1.6 Hz, 1H), 4.57 (dd, J=12.0, 3.2 Hz, 1H), 4.37 (dd, J=12.0, 4.4 Hz, 1H), 1.83 (d, J=7.6 Hz, 3H).

Example B3 Preparation of Compound B3

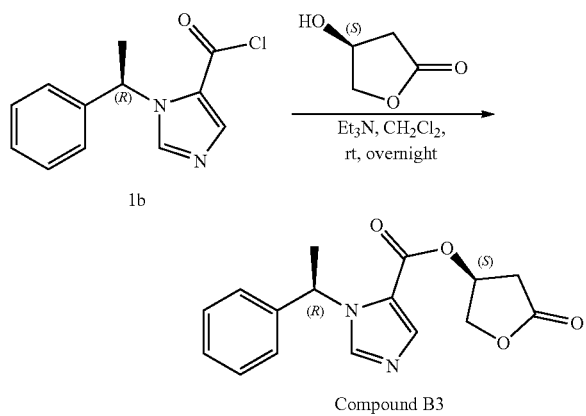

Compound B3

The title compound B3 was prepared according to the preparation method of Example B1, using 1b (234 mg, 1.0 mmol) and (S)-4-hydroxydihydrofuran-2(3H)-one (102 mg, 1.0 mmol) as the raw materials. ESI[M+H]$^+$=301.2

Example B4 Preparation of Compound B4

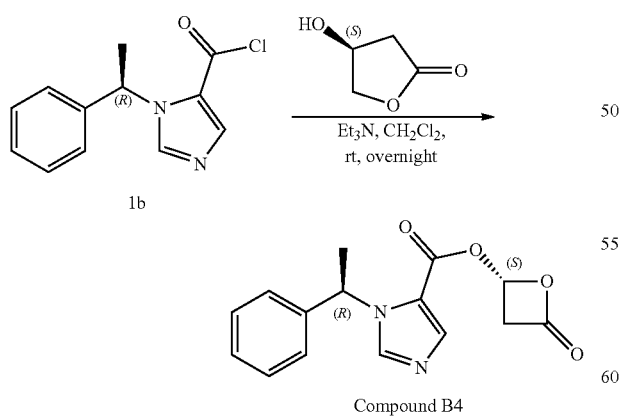

Compound B4

The title compound B4 was prepared according to the preparation method of Example B1, using 1b (234 mg, 1.0 mmol) and (S)-4-hydroxydihydrofuran-2(3H)-one (88 mg, 1.0 mmol) as the raw materials. ESI[M+H]$^+$=287.2

Example B5 Preparation of Compound B5

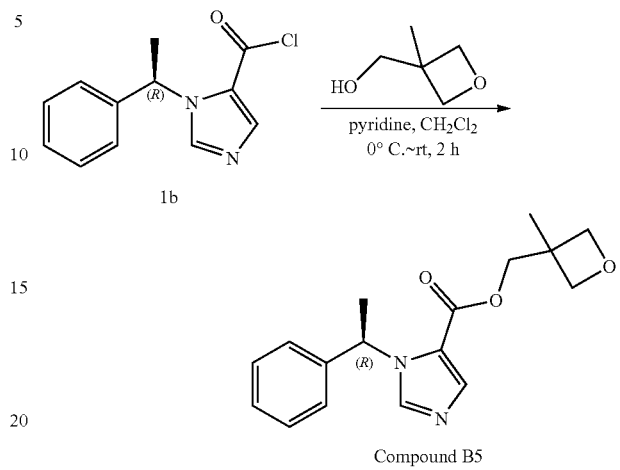

Compound B5

In an ice-water bath, 1b was added into the mixture of (3-methyloxetan-3-yl)methanol (102 mg, 1.00 mmol) and pyridine (79.1 mg, 1.00 mmol) in dry dichloromethane (10 mL) at 0° C., then the mixture was allowed to react at this temperature for 2 hrs. The mixture was concentrated under reduced pressure. The residue was purified by silica gel column chromatography (ethyl acetate/petroleum ether (v/v) at any ratio within the range 1/10 to 1/1), with TLC (ethyl acetate/petroleum ether (v/v)=1/1) monitoring, and collecting the fraction with Rf=0.3~0.4, to give the title compound B5 (170 mg, yield 57% for 2 steps) as colorless oil. ESI[M+H]$^+$=301.3

$^1$H NMR (400 MHz, CDCl$_3$) δ 7.97 (s, 1H), 7.85 (s, 1H), 7.44-7.29 (m, 3H), 7.24-7.16 (m, 2H), 6.39 (q, J=7.0 Hz, 1H), 4.51 (dd, J=6.1, 2.0 Hz, 2H), 4.42 (dd, J=6.1, 1.5 Hz, 2H), 4.39-4.30 (m, 2H), 1.90 (d, J=7.1 Hz, 3H), 1.35 (s, 3H).

Example B6 Preparation of Compound B6

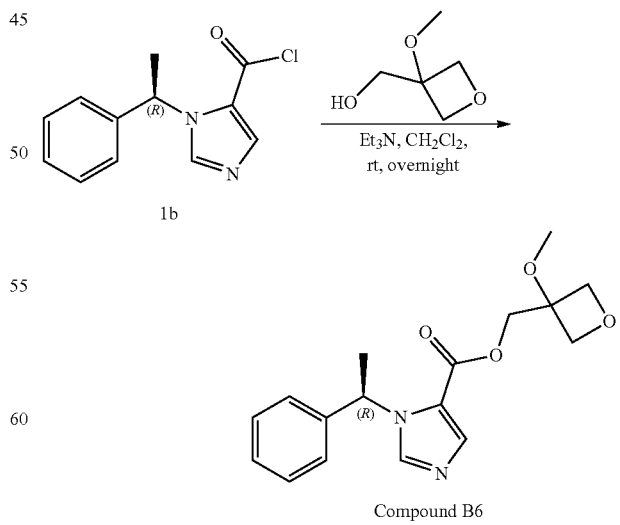

Compound B6

The title compound B6 was prepared according to the preparation method of Example B1, using 1b (234 mg, 1.0 mmol) and (3-methoxyoxetan-3-yl)methanol (118 mg, 1.0 mmol) as the raw materials. ESI[M+H]⁺=317.2

¹H NMR (400 MHz, d₆-DMSO) δ 8.29 (s, 1H), 7.65 (s, 1H), 7.32 (t, J=7.3 Hz, 2H), 7.25 (t, J=7.3 Hz, 1H), 7.17 (d, J=7.2 Hz, 2H), 6.24-6.22 (m, 1H), 4.39-4.22 (m, 6H), 3.75 (s, 3H), 1.88 (d, J=7.2 Hz, 3H).

Example B7 Preparation of Compound B7

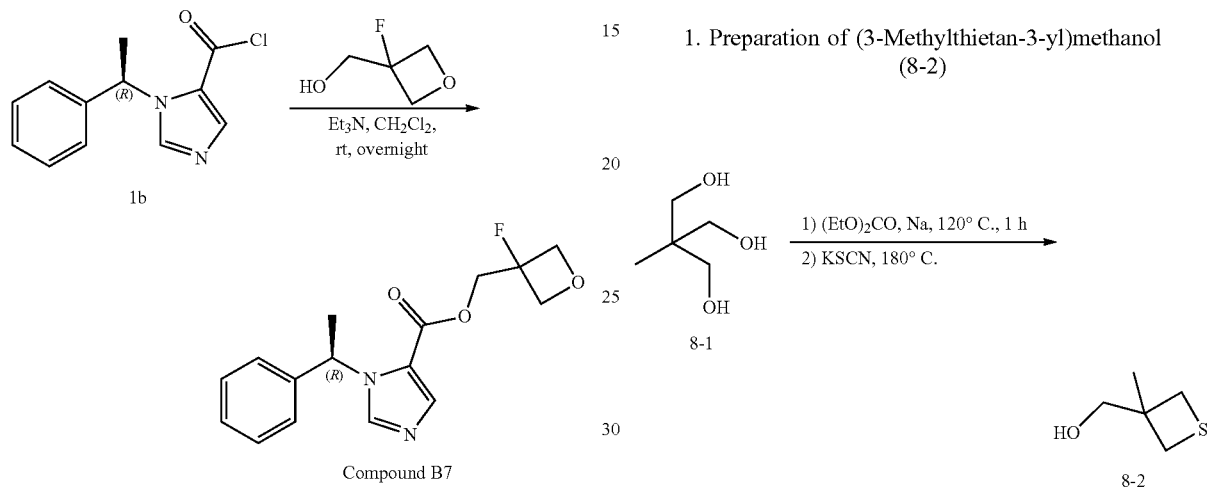

Compound B7

The title compound B7 was prepared according to the preparation method of Example B1, using 1b (234 mg, 1.0 mmol) and (3-fluorooxetan-3-yl)methanol (106 mg, 1.0 mmol) as the raw materials. ESI[M+H]⁺=305.2

¹H NMR (400 MHz, d₆-DMSO) δ 8.33 (s, 1H), 7.74 (s, 1H), 7.35 (t, J=7.3 Hz, 2H), 7.25-7.17 (m, 3H), 6.24-6.22 (m, 1H), 4.70-4.51 (m, 6H), 1.91 (d, J=7.2 Hz, 3H).

Example B8 Preparation of Compound B8

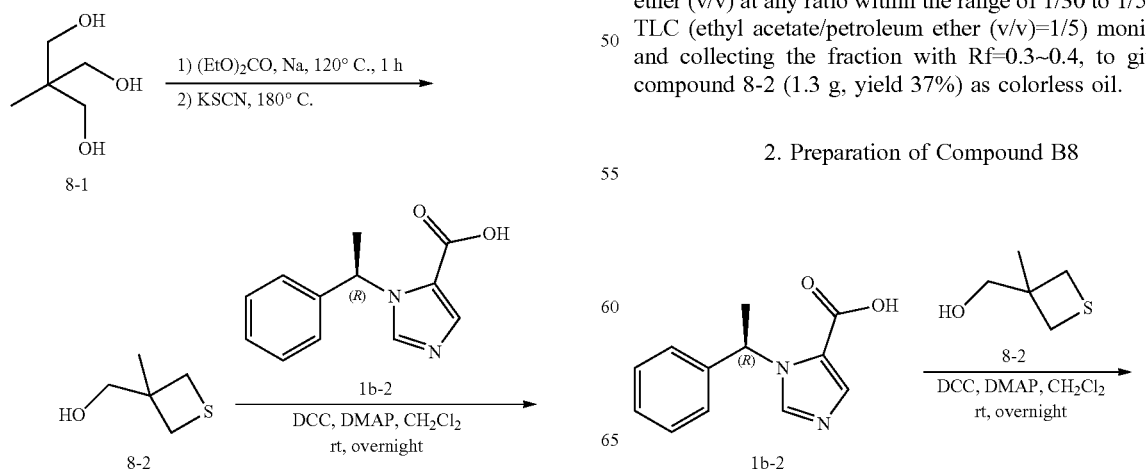

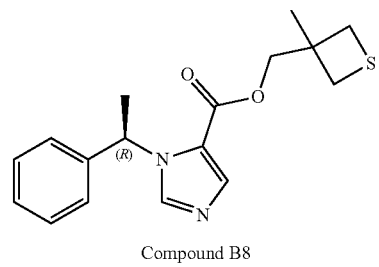

Compound B8

1. Preparation of (3-Methylthietan-3-yl)methanol (8-2)

Na (2.4 mg, 0.104 mmol) was added into the mixture of 2-(hydroxymethyl)-2-methylpropane-1,3-diol (8-1) (3.6 g, 0.03 mol) and diethyl carbonate (3.54 g, 0.03 mol), then the mixture was reacted at 120° C. for 1 hour. The solvent was concentrated under reduced pressure, then the dried KSCN (3.54 g, 0.03 mol) was added into the residue. The mixture was reacted at 180° C. for 1 hour. The mixture was quenched with saturated ammonium chloride solution (10 mL) and extracted with dichloromethane (3×10 mL). The combined organic layers were washed with saturated brine (50 mL), dried over anhydrous sodium sulfate, filtered and concentrated under reduced pressure. The residue was purified by silica gel column chromatography (ethyl acetate/petroleum ether (v/v) at any ratio within the range of 1/30 to 1/5), with TLC (ethyl acetate/petroleum ether (v/v)=1/5) monitoring, and collecting the fraction with Rf=0.3~0.4, to give the compound 8-2 (1.3 g, yield 37%) as colorless oil.

2. Preparation of Compound B8

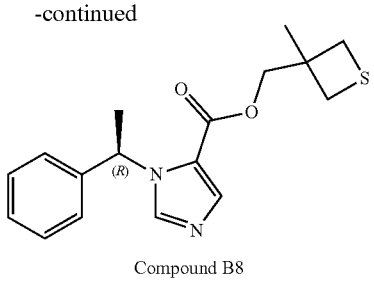

Compound B8

The title compound B8 was prepared according to the general procedure A, using 1b-2 (324 mg, 1.50 mmol) and 8-2 (306 mg, 2.59 mmol) as the raw materials. The crude product was purified by Prep-TLC (ethyl acetate/petroleum ether (v/v)=1/1) and the fraction with Rf=0.5~0.6 was collected and dried to give the title compound B8 (300 mg, yield 63%) as colorless oil. ESI[M+H]$^+$=317.2

$^1$H NMR (400 MHz, CDCl$_3$) δ 7.85 (s, 2H), 7.41-7.28 (m, 3H), 7.23-7.17 (m, 2H), 6.38 (q, J=7.0 Hz, 1H), 4.24 (q, J=10.9 Hz, 2H), 3.08 (d, J=9.4 Hz, 2H), 2.92 (dd, J=9.4, 1.1 Hz, 2H), 1.89 (d, J=7.1 Hz, 3H), 1.33 (s, 3H).

Example B9 Preparation of Compound B9

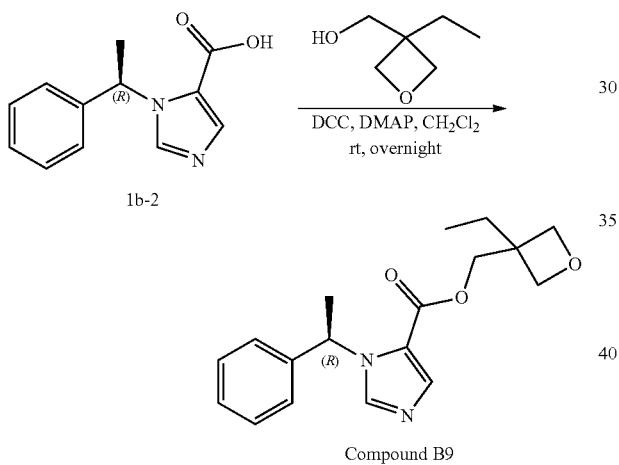

Compound B9

The title compound B9 was prepared according to the general procedure A, using 1b-2 (200 mg, 0.93 mmol) and (3-ethyloxetan-3-yl)methanol (107 mg, 0.93 mmol) as the raw materials. The crude product was purified by Prep-TLC (ethyl acetate/petroleum ether (v/v)=1/1) and the fraction with Rf=0.3~0.4 was collected and dried to give the title compound B9 (210 mg, yield 72%) as colorless oil. ESI[M+H]$^+$=315.3

$^1$H NMR (400 MHz, d$_6$-DMSO) δ 8.33 (s, 1H), 7.71 (d, J=0.8 Hz, 1H), 7.33 (t, J=7.3 Hz, 2H), 7.26 (dd, J=8.5, 6.0 Hz, 1H), 7.16 (d, J=7.2 Hz, 2H), 6.23 (q, J=7.2 Hz, 1H), 4.34-4.18 (m, 6H), 1.85 (d, J=7.2 Hz, 3H), 1.63 (q, J=7.5 Hz, 2H), 0.85-0.81 (m, 3H).

Example B10 Preparation of Compound B10

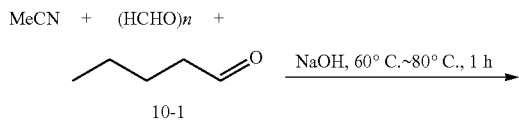

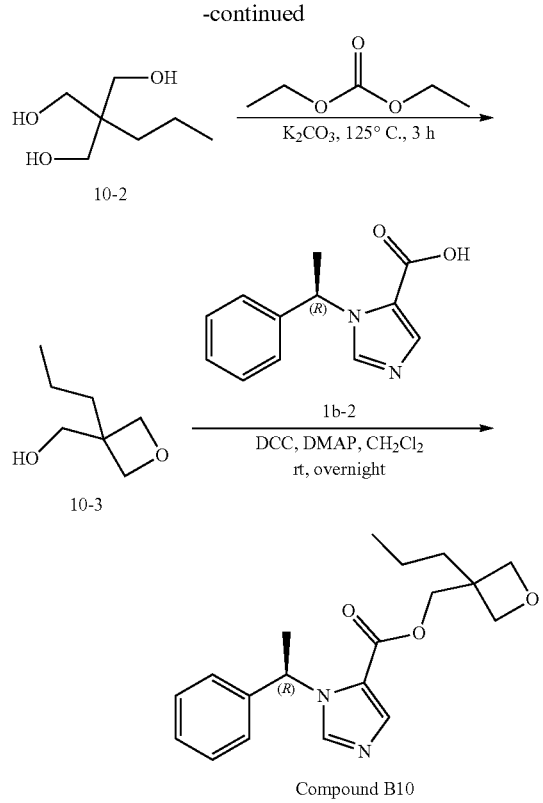

Compound B10

1. Preparation of 2-(Hydroxymethyl)-2-propylpropane-1,3-diol (10-2)

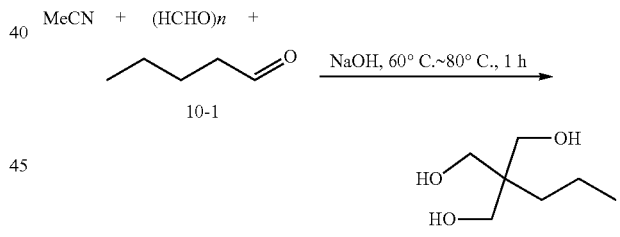

At room temperature, pentanal (10-1) (8.0 g, 0.093 mol) was added dropwise into the mixture of acetonitrile (470 mg, 2.57 mmol), paraformaldehyde (470 mg, 2.57 mmol) and NaOH (470 mg, 2.57 mmol) at the rate of 1 mL/min, then the mixture was reacted at 80° C. for 1 hour. The reaction was monitored by TLC until completion. The mixture was quenched with saturated ammonium chloride solution (20 mL) and extracted with dichloromethane (3×10 mL). The combined organic layers were washed with saturated brine (50 mL), dried over anhydrous sodium sulfate, filtered and concentrated under reduced pressure. The residue was purified by silica gel column chromatography (ethyl acetate/petroleum ether (v/v) at any ratio within the range of 1/1 to 10/1), with TLC (ethyl acetate) monitoring, and collecting the fraction with Rf=0.2~0.3, to give the compound 10-2 (7.2 g, yield 52%) as colorless oil.

2. Preparation of (3-Propyloxetan-3-yl)methanol (10-3)

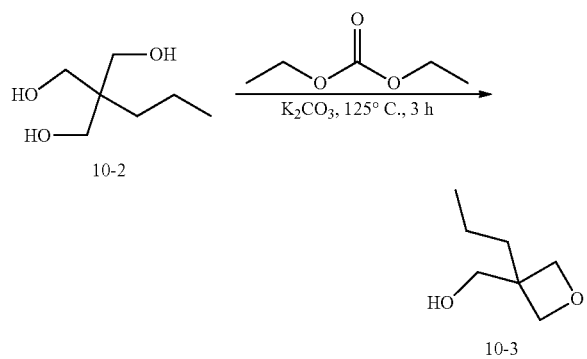

The mixture of 10-2 (1.0 g, 6.75 mmol), diethyl carbonate (797 mg, 6.75 mmol) and K₂CO₃ (7.7 mg, 0.056 mmol) was reacted at 125° C. for 3 hrs. The reaction was monitored by TLC until completion. The mixture was quenched with saturated ammonium chloride solution (20 mL) and extracted with dichloromethane (3×10 mL). The combined organic layers were washed with saturated brine (50 mL), dried over anhydrous sodium sulfate, filtered and concentrated under reduced pressure. The residue was purified by silica gel column chromatography (ethyl acetate/petroleum ether (v/v) at any ratio within the range of 1/10 to 1/1), with TLC (ethyl acetate/petroleum ether (v/v)=1/1) monitoring, and collecting the fraction with Rf=0.3~0.4, to give compound 10-3 (338 mg, yield 38%) as colorless oil.

3. Preparation of Compound B10

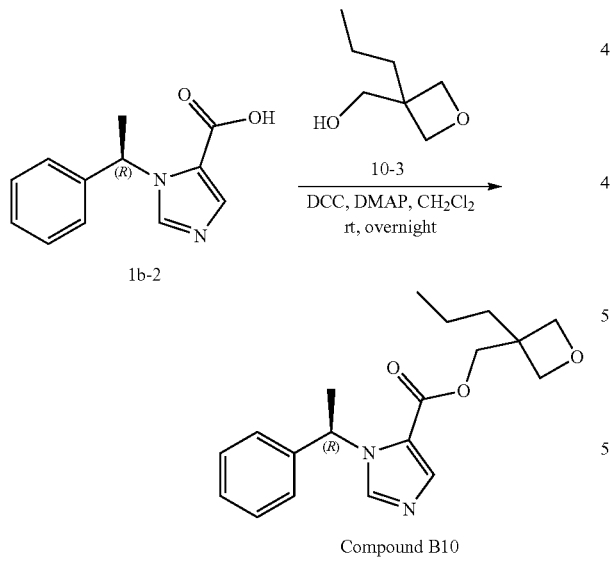

The title compound B10 was prepared according to the general procedure A, using 1b-2 (324 mg, 1.50 mmol) and 10-3 (338 mg, 2.60 mmol) as the raw materials. The crude product was purified by Prep-TLC (ethyl acetate/petroleum ether (v/v)=1/1) and the fraction with Rf=0.5~0.6 was collected and dried to give the title compound B10 (130 mg, yield 26%) as colorless oil. ESI[M+H]⁺=329.4

$^1$H NMR (400 MHz, CDCl₃) δ 7.87 (s, 1H), 7.81 (s, 1H), 7.42-7.29 (m, 3H), 7.23-7.16 (m, 2H), 6.38 (q, J=7.0 Hz, 1H), 4.51~4.34 (m, 6H), 1.89 (d, J=7.1 Hz, 3H), 1.75~1.67 (m, 2H), 1.39-1.22 (m, 3H), 0.94 (t, J=7.3 Hz, 3H).

Example B11 Preparation of Compounds B11~B15

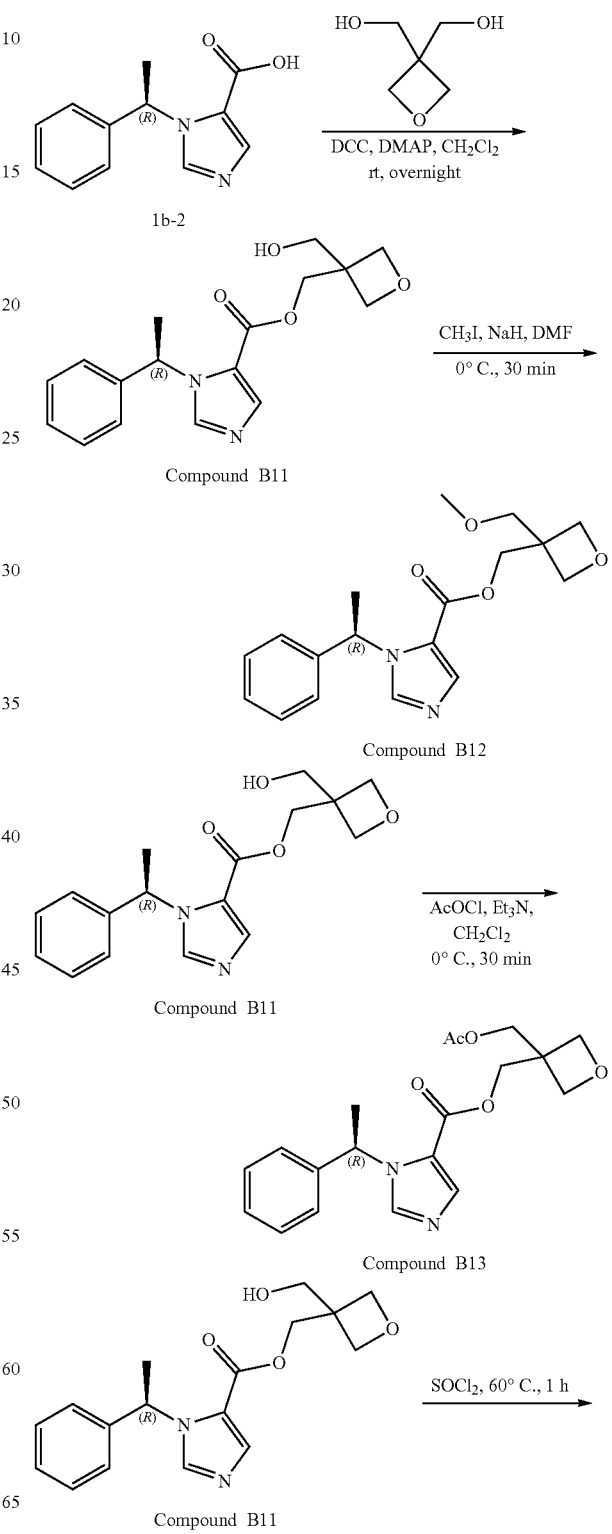

-continued

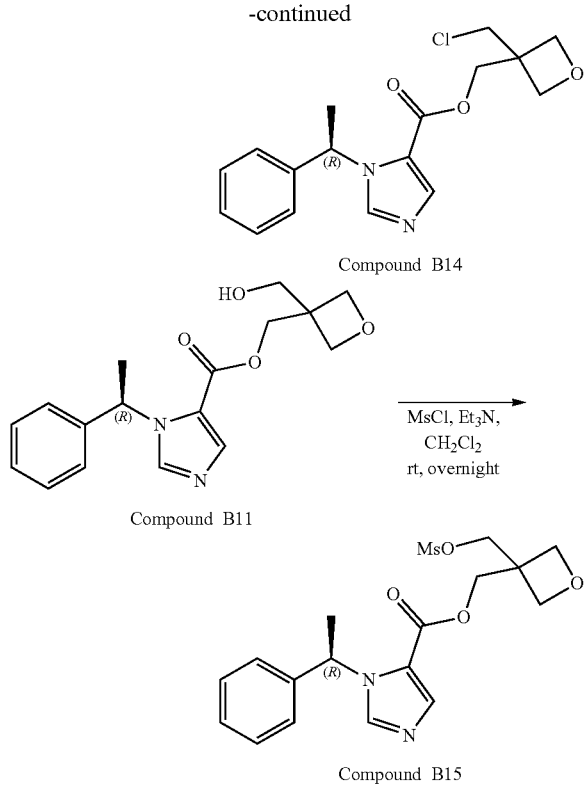

1. Preparation of Compound B11

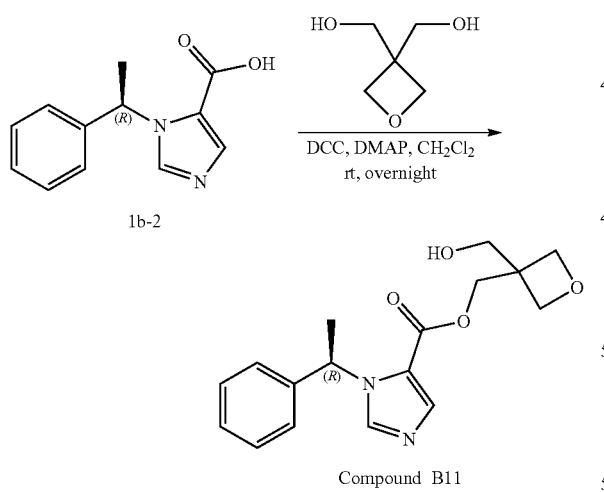

The title compound B11 was prepared according to the general procedure A, using 1b-2 (200 mg, 0.93 mmol) and oxetane-3,3-diyldimethanol (161 mg, 1.36 mmol) as the raw materials. The crude product was purified by Prep-TLC (ethyl acetate/petroleum ether (v/v)=1/1) and the fraction with Rf=0.3~0.4 was collected and dried to give the title compound B11 (170 mg, yield 41%) as colorless oil. ESI[M+H]$^+$=317.2

$^1$H NMR (400 MHz, d$_6$-DMSO) δ 8.31 (s, 1H), 7.71 (s, 1H), 7.34 (t, J=7.3 Hz, 2H), 7.26 (t, J=7.3 Hz, 1H), 7.18 (d, J=7.2 Hz, 2H), 6.25~6.23 (m, 1H), 4.98 (t, J=5.4 Hz, 1H), 4.39~4.22 (m, 6H), 3.60 (d, J=5.4 Hz, 2H), 1.85 (d, J=7.2 Hz, 3H).

2. Preparation of Compound B12

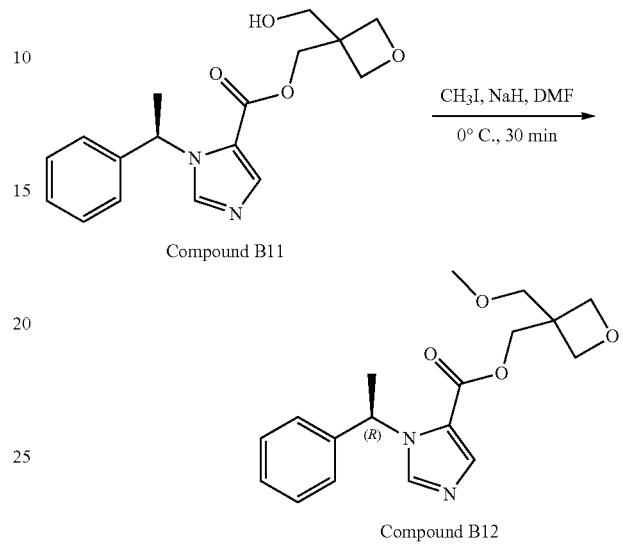

The title compound B12 was prepared according to the general procedure B, using B11 (70.0 mg, 0.22 mmol) and iodomethane (565 mg, 3.98 mmol) as the raw materials. The crude product was purified by Prep-TLC (ethyl acetate/petroleum ether (v/v)=1/1) and the fraction with Rf=0.4~0.5 was collected and dried to give the title compound B12 (8.0 mg, yield 11%) as colorless oil. ESI[M+H]$^+$=331.3

$^1$H NMR (400 MHz, d$_6$-DMSO) δ 8.20 (d, J=2.0 Hz, 1H), 7.90 (s, 1H), 7.40-7.40 (m, 3H), 7.26-7.25 (m, 2H), 6.47 (brs, 1H), 6.54-6.47 (m, 6H), 3.63 (s, 2H), 3.36 (s, 3H), 1.94-1.93 (m, 3H).

3. Preparation of Compound B13

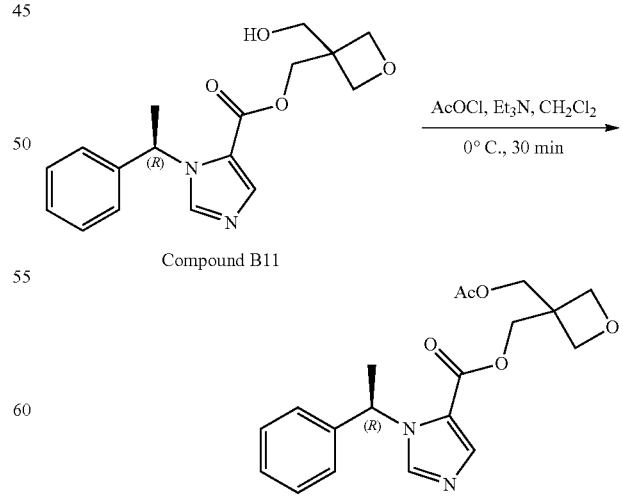

At room temperature, acetyl chloride (17.3 mg, 0.22 mmol) was added into the mixture of B11 (70.0 mg, 0.22 mmol) and triethylamine (45 mg, 0.44 mmol) in dichloromethane (5 mL) at the rate of 1 mL/min using a syringe, then the mixture was reacted at this temperature for 30 min, then it was concentrated under reduced pressure. The residue was purified by Prep-TLC (ethyl acetate/petroleum ether (v/v)=1/3) and the fraction with Rf=0.4~0.6 was collected and dried to give the title compound B13 (39.0 mg, yield 49%) as colorless oil. ESI[M+H]⁺=359.2

¹H NMR (400 MHz, CDCl₃) δ 7.84 (s, 1H), 7.80 (s, 1H), 7.38-7.31 (m, 3H), 7.20-7.18 (m, 2H), 6.34-6.32 (m, 1H), 4.53-4.43 (m, 6H), 4.33 (s, 2H), 2.07 (s, 3H), 1.88 (d, J=7.2 Hz, 3H).

4. Preparation of Compound B14

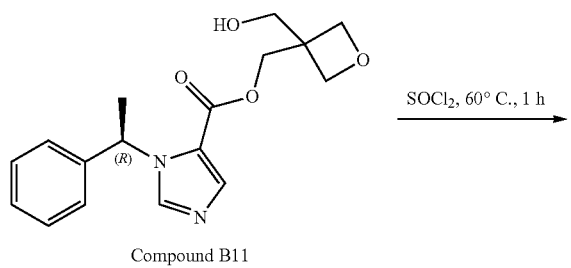

B11 (316 mg, 1.0 mmol) and thionyl chloride (0.5 ml) were reacted at 60° C. for 1 hour, then the reaction was concentrated under reduced pressure. The residue was purified by Prep-TLC (ethyl acetate/petroleum ether (v/v)=1/1) and the fraction with Rf=0.4~0.6 was collected and dried to give the title compound B14 (39.0 mg, yield 12%) as colorless oil. ESI[M+H]⁺=335.2 ¹H NMR (400 MHz, CDCl₃) δ 7.85 (s, 1H), 7.81 (s, 1H), 7.37-7.30 (m, 3H), 7.21-7.19 (m, 2H), 6.34-6.32 (m, 1H), 4.53-4.43 (m, 6H), 3.95 (s, 2H), 1.89 (d, J=7.2 Hz, 3H).

5. Preparation of Compound B15

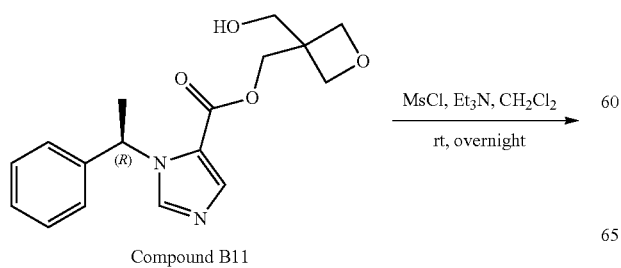

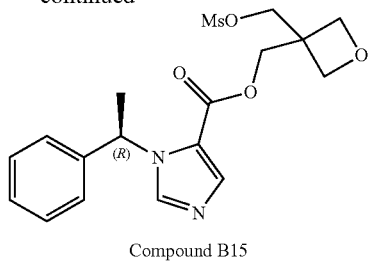

In an ice bath, methanesulfonyl chloride (25.2 mg, 0.22 mmol) was added into the mixture of B11 (70.0 mg, 0.22 mmol) and triethylamine (44.4 mg, 0.44 mmol) in dichloromethane (20 mL) at 0° C., then the mixture was allowed to react at room temperature overnight. The mixture was concentrated under reduced pressure. The residue was purified by silica gel column chromatography (ethyl acetate/petroleum ether (v/v) at any ratio within the range of 1/10 to 1/1), with TLC (ethyl acetate/petroleum ether (v/v)=1/2) monitoring, and collecting the fraction with Rf=0.3~0.4, to give the compound B15 (54.0 mg, yield 62%) as colorless oil. ESI[M+H]⁺=395.2

¹H NMR (400 MHz, d₆-DMSO) δ 8.33 (s, 1H), 7.79 (d, J=0.8 Hz, 1H), 7.34 (t, J=7.3 Hz, 2H), 7.27 (t, J=7.3 Hz, 1H), 7.18 (d, J=7.2 Hz, 2H), 6.26-6.17 (m, 1H), 4.52-4.33 (m, 8H), 3.22 (s, 3H), 1.85 (d, J=7.2 Hz, 3H).

Example B12 Preparation of Compound B16

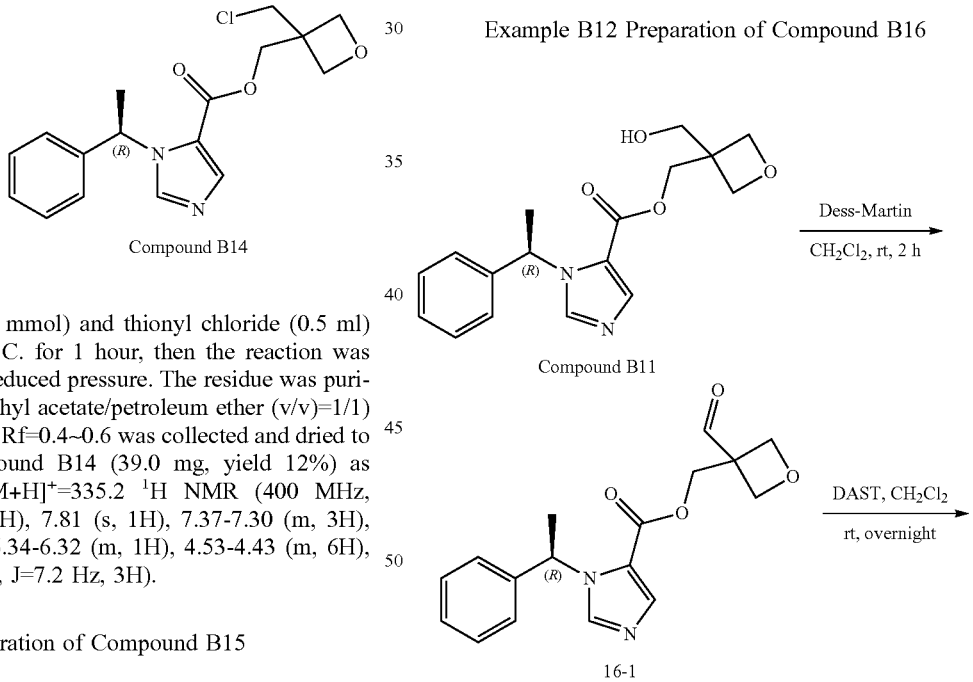

1. Preparation of (R)-(3-Formyloxetan-3-yl)methyl 1-(1-phenylethyl)-1H-imidazole-5-carboxylate (16-1)

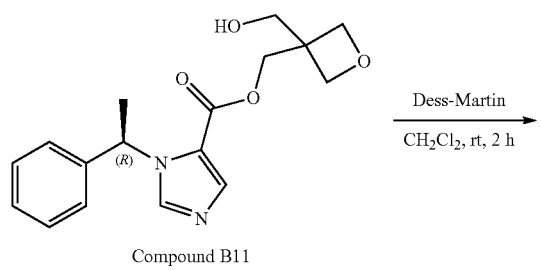

Compound B11

In an ice-water bath, Dess-Martin (848 mg, 2.0 mmol) was added in portions into the mixture of B11 (316 mg, 1.0 mmol) in dichloromethane (30 mL) at the rate of 0.2 mmol/min at 0° C., then the mixture was allowed to react at room temperature for 2 hrs. The mixture was concentrated under reduced pressure. The crude product was purified by silica gel column chromatography (ethyl acetate/petroleum ether (v/v) at any ratio within the range of 1/10 to 1/1), with TLC (ethyl acetate/petroleum ether (v/v)=1/2) monitoring, and collecting the fraction with Rf=0.3~0.4, to give compound 16-1 (151 mg, yield 48%) as colorless oil. ESI[M+H]$^+$=315.2

2. Preparation of Compound B16

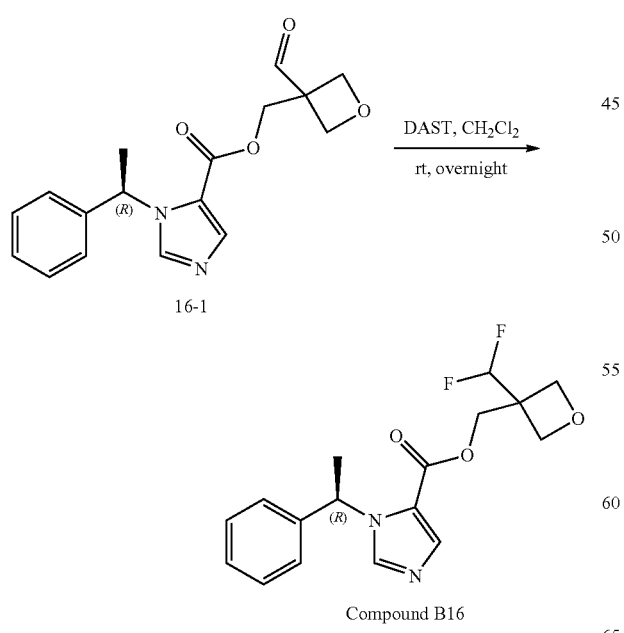

At room temperature, DAST (77 mg, 0.48 mmol) was added into the mixture of 16-1 (151 mg, 0.48 mmol) in dichloromethane (20 mL), then the mixture was allowed to react at room temperature overnight. The reaction was monitored by TLC until completion and the mixture was concentrated under reduced pressure. The residue was purified by silica gel column chromatography (ethyl acetate/petroleum ether (v/v) at any ratio within the range of 1/10 to 1/1), with TLC (ethyl acetate/petroleum ether (v/v)=1/1) monitoring, and collecting the fraction with Rf=0.3~0.4, to give the title compound B16 (32 mg, yield 20%) as colorless oil. ESI[M+H]$^+$=337.2

$^1$H NMR (400 MHz, CDCl$_3$) δ 7.98 (s, 1H), 7.85 (s, 1H), 7.40-7.27 (m, 3H), 7.21-7.15 (m, 2H), 6.30 (q, J=7.2 Hz, 1H), 4.90 (q, J=57.6 Hz, 1H), 4.45-4.22 (m, 6H), 1.86 (d, J=7.1 Hz, 3H).

Example B13 Preparation of Compound B17

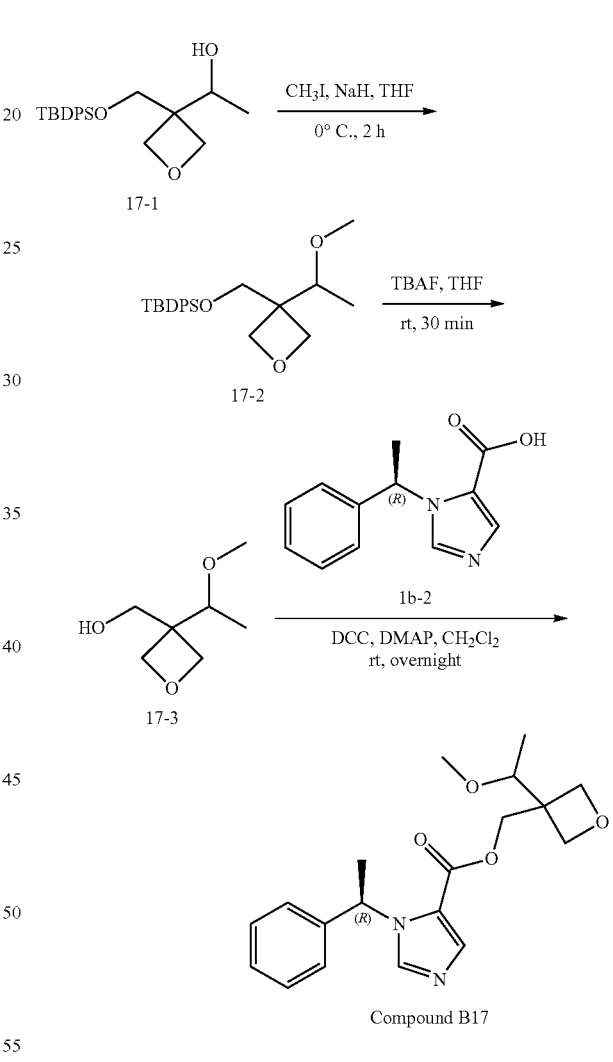

1. Preparation of Tert-butyl((3-(1-methoxyethyl) oxetan-3-yl)methoxy)diphenylsilane (17-2)

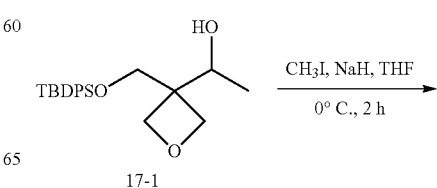

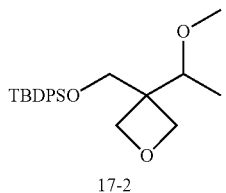

17-2

The compound 17-2 was prepared according to the general procedure B, using 17-1 (200 mg, 0.54 mmol) and iodomethane (77 mg, 0.54 mmol) as the raw materials. The crude product was purified by Prep-TLC (ethyl acetate/petroleum ether (v/v)=1/5) and the fraction with Rf=0.3~0.4 was collected and dried to give the compound 17-2 (180 mg, yield 87%) as colorless oil.

2. Preparation of (3-(1-Methoxyethyl)oxetan-3-yl)methanol (17-3)

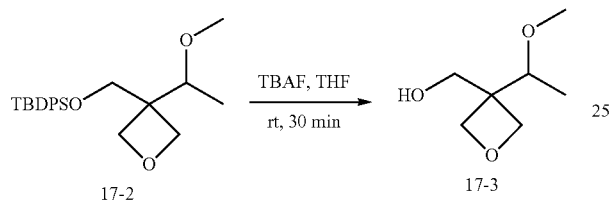

TBAF (2.34 mL, 1 mol/L in THF, 2.34 mmol) was added into the solution of 17-2 (180 mg, 0.47 mmol) in THF and the mixture was allowed to react at room temperature for 30 mins. The reaction was concentrated under reduced pressure. The residue was purified by silica gel column chromatography (ethyl acetate/petroleum ether (v/v) at any ratio within the range of 1/10 to 1/1), with TLC (ethyl acetate/petroleum ether (v/v)=1/2) monitoring, and collecting the fraction with Rf=0.3~0.4, to give compound 17-3 (40 mg, yield 58%) as colorless oil.

3. Preparation of Compound B17

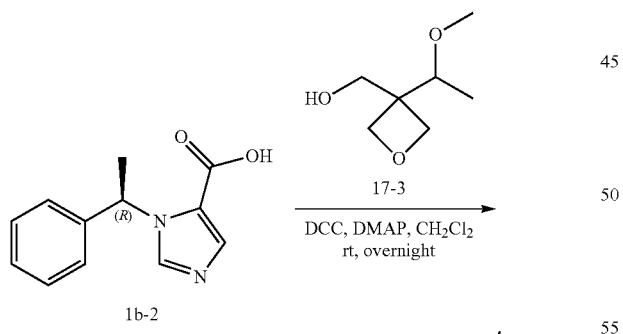

The title compound B17 was prepared according to the general procedure A, using 1b-2 (59 mg, 0.27 mmol) and 17-3 (40 mg, 0.27 mmol) as the raw materials. The crude product was purified by Prep-TLC (ethyl acetate/petroleum ether (v/v)=1/1) and the fraction with Rf=0.5~0.6 was collected and dried to give the title compound B17 (61 mg, yield 65%) as colorless oil. ESI[M+H]$^+$=345.3

$^1$H NMR (400 MHz, CDCl$_3$) δ 7.80 (s, 2H), 7.40-7.28 (m, 3H), 7.19 (d, J=7.1 Hz, 2H), 6.38-6.36 (m, 1H), 4.62-4.34 (m, 6H), 3.67-3.58 (m, 1H), 3.34 (d, J=6.9 Hz, 3H), 1.88 (d, J=7.1 Hz, 3H), 1.19 (t, J=6.2 Hz, 3H).

Example B14 Preparation of Compound B18

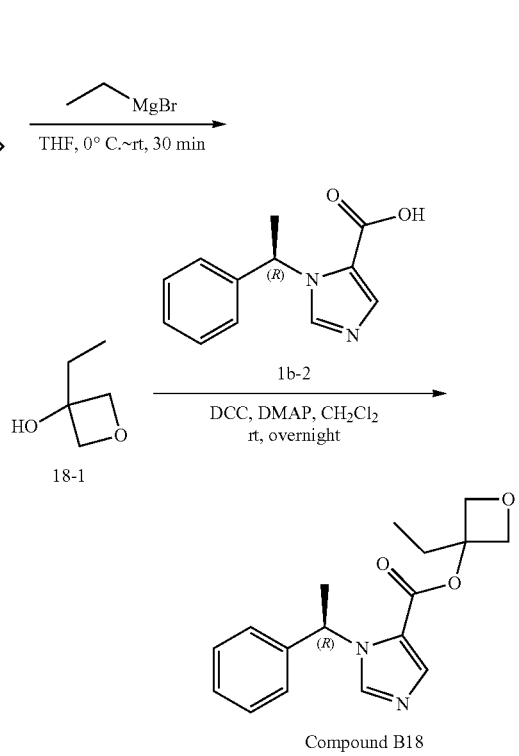

Compound B18

1. Preparation of 3-ethyloxetan-3-ol (18-1)

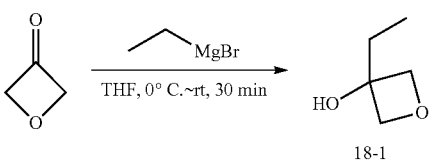

In an ice bath, oxetan-3-one (360 mg, 5 mmol) was dissolved in THF (5 mL). ethylmagnesium bromide (6.0 mL, 6 mmol, 1.0 mol/L) was added dropwise into the mixture at the rate of 1 mL/min using a syring at 0° C., then the mixture was reacted at this temperature for 30 min. The reaction was monitored by TLC until completion. The mixture was quenched with saturated ammonium chloride solution and extracted with EtOAc (3×10 mL). The combined organic layers were washed with saturated brine (30 mL), dried over anhydrous sodium sulfate, filtered and concentrated under reduced pressure to give crude compound 18-1 (455 mg, yield 89%) as colorless oil, which was used for next step directly without further purification. ESI[M+H]⁺=103.1

2. Preparation of Compound B18

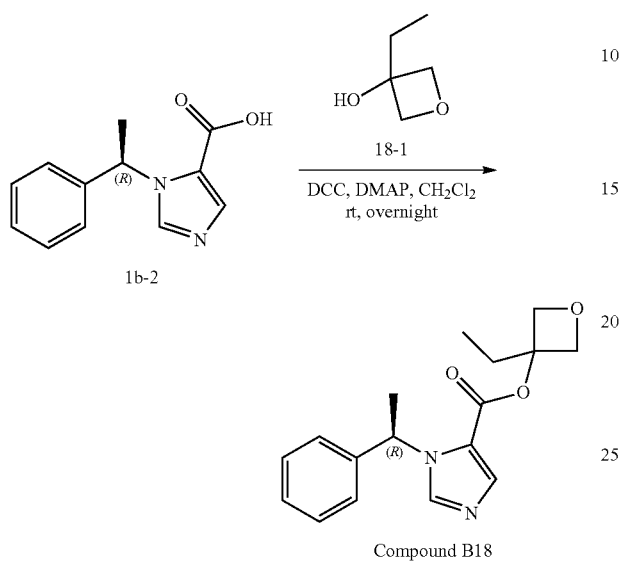

The title compound B18 was prepared according to the general procedure A, using 1b-2 (200 mg, 0.92 mmol) and 18-1 (153 mg, 1.5 mmol) as the raw materials. The crude product was purified by Prep-TLC (ethyl acetate/petroleum ether (v/v)=1/1) and the fraction with Rf=0.4~0.6 was collected and dried to give the title compound B18 (143 mg, yield 52%) as colorless oil. ESI[M+H]⁺=301.3

$^1$H NMR (400 MHz, CDCl$_3$) δ 7.99 (s, 1H), 7.85 (s, 1H), 7.48~7.29 (m, 3H), 7.26-7.08 (m, 2H), 6.31 (d, J=6.8 Hz, 1H), 4.78 (dd, J=24.8, 7.5 Hz, 2H), 4.64~4.50 (m, 2H), 2.24-2.05 (m, 2H), 1.90 (d, J=7.0 Hz, 3H), 0.91 (t, J=7.5 Hz, 3H).

Example B15 Preparation of Compound B19

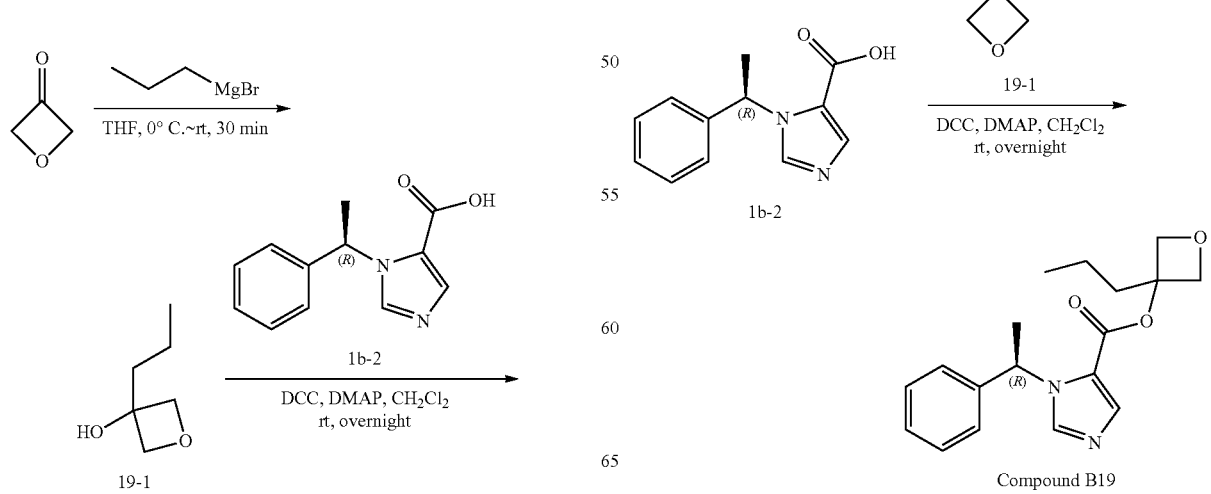

1. Preparation of 3-ethyloxetan-3-ol (19-1)

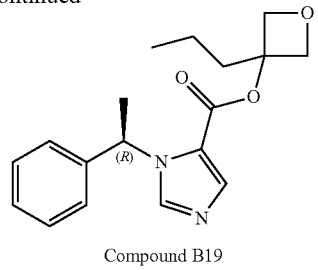

In an ice bath, oxetan-3-one (360 mg, 5 mmol) was dissolved in THF (5 mL). propylmagnesium bromide (6.0 mL, 6 mmol, 1.0 mol/L) was added dropwise into the mixture at the rate of 1 mL/min using a syringe at 0° C., then the mixture was reacted at this temperature for 30 min. The reaction was monitored by TLC until completion. The mixture was quenched with saturated ammonium chloride solution and extracted with EtOAc (3×10 mL). The combined organic layers were washed with saturated brine (30 mL), dried over anhydrous sodium sulfate, filtered and concentrated under reduced pressure to give crude compound 19-1 (486 mg, yield 84%) as colorless oil, which was used for next step directly without further purification. ESI[M+H]⁺=117.1

2. Preparation of Compound B19

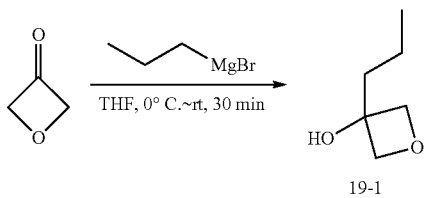

The title compound B19 was prepared according to the general procedure A, using 1b-2 (200 mg, 0.92 mmol) and 19-1 (174 mg, 1.5 mmol) as the raw materials. The crude product was purified by Prep-TLC (ethyl acetate/petroleum ether (v/v)=1/1) and the fraction with Rf=0.4~0.6 was collected and dried to give the title compound B19 (120 mg, yield 41%) as colorless oil. ESI[M+H]$^+$=315.4

$^1$H NMR (400 MHz, CDCl$_3$) δ 7.79 (s, 2H), 7.41-7.27 (m, 3H), 7.19-7.11 (m, 2H), 6.26 (d, J=7.1 Hz, 1H), 4.80 (d, J=7.3 Hz, 1H), 4.74 (d, J=7.3 Hz, 1H), 4.57 (t, J=7.2 Hz, 2H), 2.10 (td, J=7.1, 3.0 Hz, 2H), 1.87 (d, J=7.1 Hz, 3H), 1.35-1.26 (m, 2H), 0.89 (t, J=7.4 Hz, 3H).

Example B16 Preparation of Compound B20

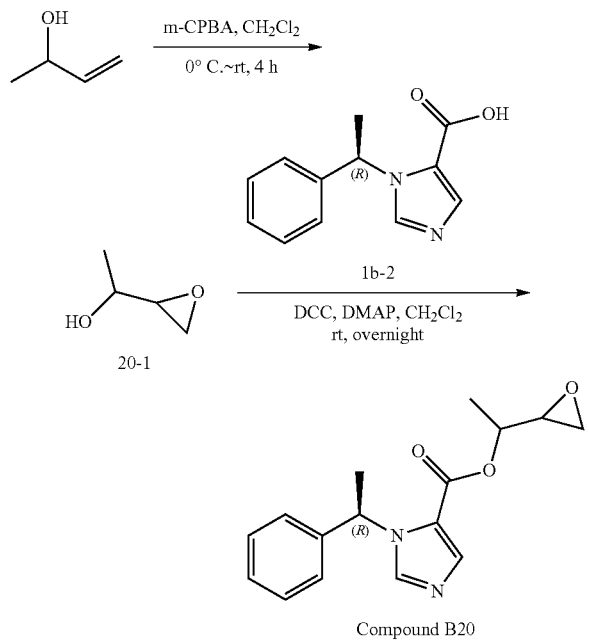

1. Preparation of 1-(Oxiran-2-yl)ethan-1-ol (20-1)

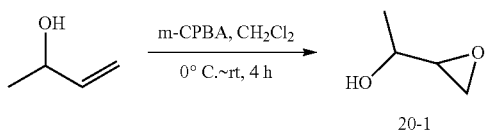

In an ice-water bath, m-CPBA (518 mg, 3 mmol) was added in portions into the mixture of but-3-en-2-ol (144 mg, 2 mmol) in dichloromethane (10 mL) over a 2-min period, then the mixture was reacted at room temperature for 4 hrs. The reaction was monitored by TLC until completion. The mixture was quenched with saturated sodium carbonate and extracted with CH$_2$Cl$_2$ (3×10 mL). The combined organic layers were washed with saturated brine (30 mL), dried over anhydrous sodium sulfate, filtered and concentrated under reduced pressure to give crude compound 20-1 (98 mg, 56%), which was used for next step directly without further purification.

2. Preparation of Compound B20

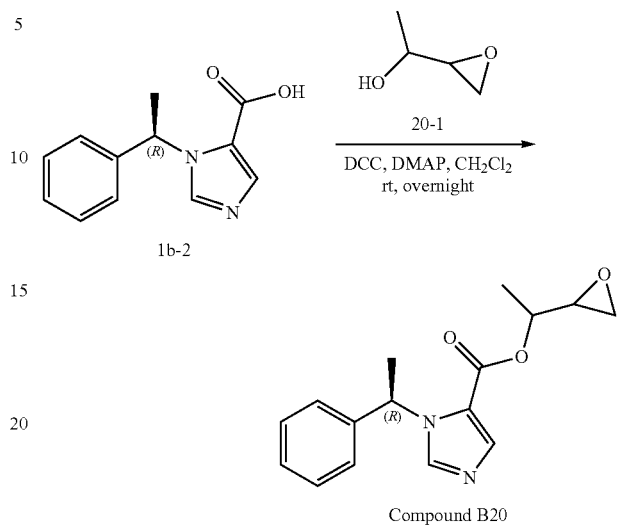

The title compound B20 was prepared according to the general procedure A, using 1b-2 (43 mg, 0.20 mmol) and 20-1 (35 mg, 0.40 mmol) as the raw materials. The crude product was purified by Prep-TLC (ethyl acetate/petroleum ether (v/v)=1/1) and the fraction with Rf=0.4~0.6 was collected and dried to give the title compound B20 (20 mg, yield 35%) as colorless oil. ESI[M+H]$^+$=287.1

$^1$H NMR (400 MHz, CDCl$_3$) δ 8.10 (s, 1H), 7.93 (s, 1H), 7.45-7.31 (m, 3H), 7.25-7.17 (m, 2H), 6.29-6.23 (m, 1H), 5.18-4.96 (m, 1H), 3.21-3.12 (m, 1H), 2.83-2.69 (m, 2H), 1.91 (d, J=7.0 Hz, 3H), 1.42-1.39 (m, 3H)

Example B17 Preparation of Compound B21

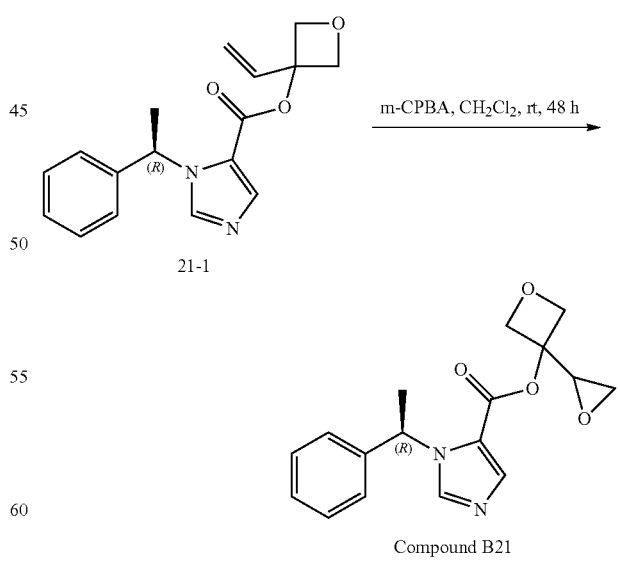

At room temperature, m-CPBA (117 mg, 0.68 mmol) was added in portions into the mixture of 21-1 (100 mg, 0.34 mmol) in dichloromethane (10 mL) at the rate of 0.2 mmol/min over a 4-min period, then the mixture was reacted at this temperature for 48 hrs. The reaction was monitored by TLC until completion, then it was concentrated under reduced pressure. The residue was purified by silica gel column chromatography (ethyl acetate/petroleum ether (v/v) at any ratio within the range of 1/10 to 1/1), with TLC (ethyl acetate/petroleum ether (v/v)=1/1) monitoring, and collecting the fraction with Rf=0.4~0.5, to give the title compound B21 (20 mg, yield 19%) as colorless oil. ESI[M+H]$^+$=315.2

Example B18 Preparation of Compound B22

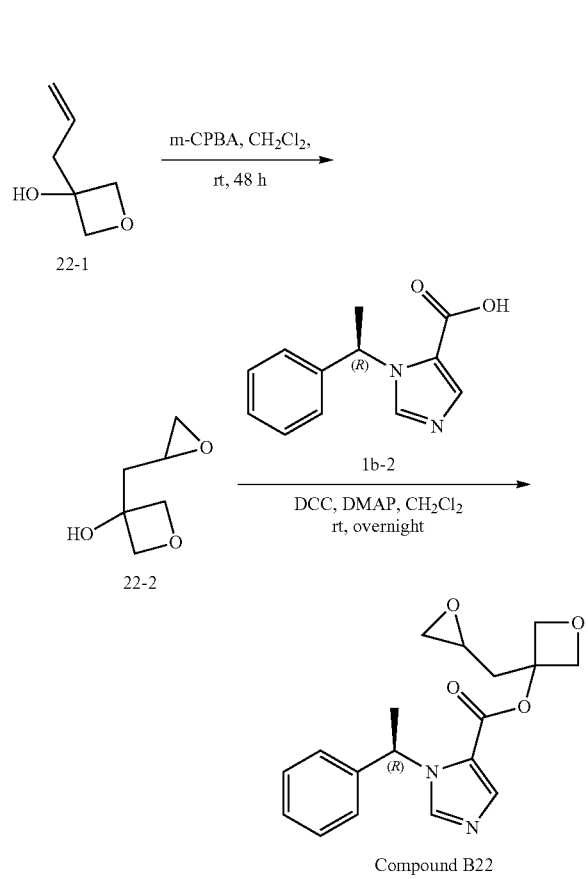

1. Preparation of 3-(Oxiran-2-ylmethyl)oxetan-3-ol (22-2)

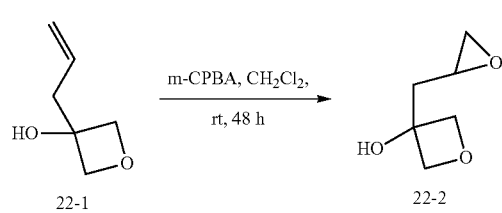

At room temperature, m-CPBA (777 mg, 4.5 mmol) was added in portions into the mixture of 22-1 (342 mg, 3.0 mmol) in dichloromethane (10 mL) at the rate of 1 mmol/min over a 3-min period, then the mixture was reacted at this temperature for 48 hrs. The reaction was monitored by TLC until completion. The mixture was quenched with water and extracted with CH$_2$Cl$_2$ (3×15 mL). The combined organic layers were washed with saturated brine (20 mL), dried over anhydrous sodium sulfate, filtered and concentrated under reduced pressure to give crude compound 22-2, which was used for next step directly without further purification.

2. Preparation of Compound B22

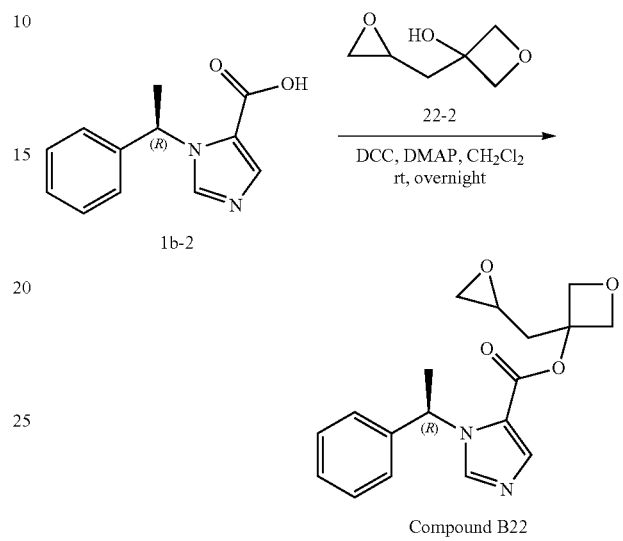

The title compound B22 was prepared according to the general procedure A, using 1b-2 (216 mg, 1.0 mmol) and crude 22-2 (from last step) as the raw materials. The crude product was purified by Prep-TLC (ethyl acetate/petroleum ether (v/v)=1/1) and the fraction with Rf=0.3~0.4 was collected and dried to give the title compound B22 (66 mg, yield 20%) as colorless oil. ESI[M+H]$^+$=329.2

Example B19 Preparation of Compound B23

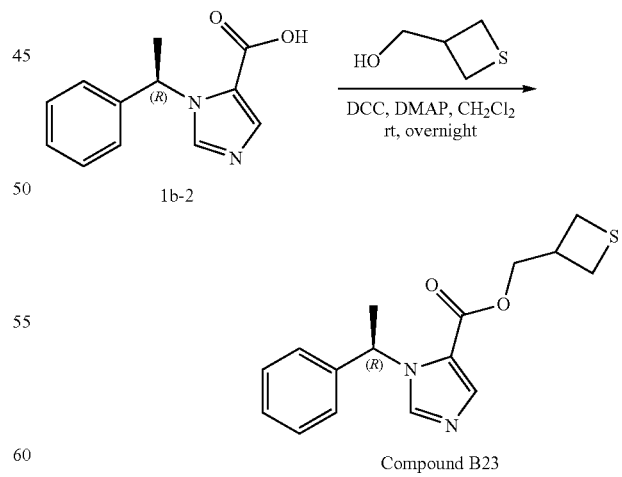

The title compound B23 was prepared according to the general procedure A, using 1b-2 (216 mg, 1.0 mmol) and thietan-3-ylmethanol (104 mg, 1.0 mmol) as the raw materials. The crude product was purified by Prep-TLC (ethyl acetate/petroleum ether (v/v)=1/1) and the fraction with Rf=0.4~0.5 was collected and dried to give the title compound B23 (180 mg, yield 60%) as colorless oil. ESI[M+H]⁺=303.2

Example B20 Preparation of Compound B24

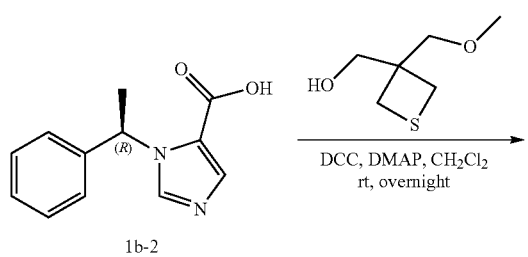

Compound B24

The title compound B24 was prepared according to the general procedure A, using 1b-2 (216 mg, 1.0 mmol) and (3-(methoxymethyl)thietan-3-yl) methanol (148 mg, 1.0 mmol) as the raw materials. The crude product was purified by Prep-TLC (ethyl acetate/petroleum ether (v/v)=1/1) and the fraction with Rf=0.4~0.5 was collected and dried to give the title compound B24 (150 mg, yield 43%) as colorless oil. ESI[M+H]⁺=347.2

$^1$H NMR (400 MHz, CDCl$_3$) δ 7.90 (s, 1H), 7.62 (s, 1H), 7.42-7.27 (m, 3H), 7.21-7.15 (m, 2H), 6.20-6.15 (m, 1H), 4.24-4.08 (m, 4H), 3.69 (s, 3H), 3.08-2.93 (m, 4H), 1.88 (d, J=7.1 Hz, 3H).

Example B21 Preparation of Compound B25

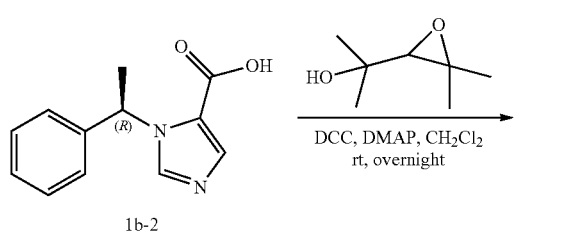

Compound B25

The title compound B25 was prepared according to the general procedure A, using 1b-2 (108 mg, 0.5 mmol) and 2-(3,3-dimethyloxiran-2-yl)propan-2-ol (65 mg, 0.5 mmol) as the raw materials. The crude product was purified by Prep-TLC (ethyl acetate/petroleum ether (v/v)=1/1) and the fraction with Rf=0.5~0.6 was collected and dried to give the title compound B25 (62 mg, yield 38%) as colorless oil. ESI[M+H]⁺=329.2

Example B22 Preparation of Compound B26

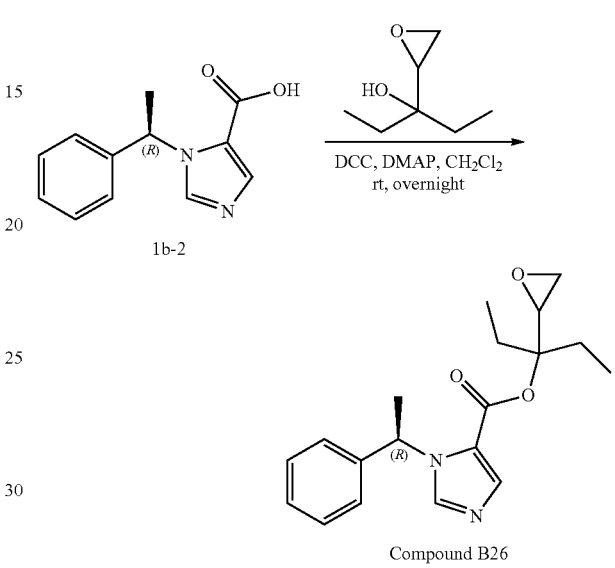

Compound B26

The title compound B26 was prepared according to the general procedure A, using 1b-2 (108 mg, 0.5 mmol) and 3-(oxiran-2-yl)pentan-3-ol (65 mg, 0.5 mmol) as the raw materials. The crude product was purified by Prep-TLC (ethyl acetate/petroleum ether (v/v)=1/1) and the fraction with Rf=0.4~0.5 was collected and dried to give the title compound B26 (63 mg, yield 38%) as colorless oil. ESI[M+H]⁺=329.3

Example B23 Preparation of Compound B27

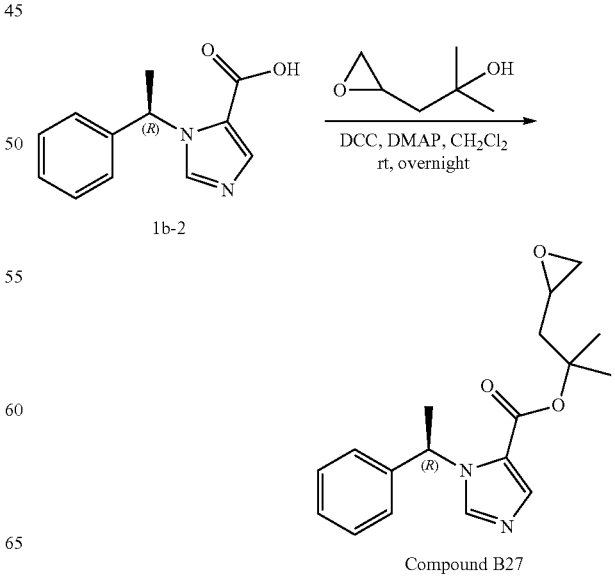

Compound B27

The title compound B27 was prepared according to the general procedure A, using 1b-2 (108 mg, 0.5 mmol) and 2-methyl-1-(oxiran-2-yl)propan-2-ol (58 mg, 0.5 mmol) as the raw materials. The crude product was purified by Prep-TLC (ethyl acetate/petroleum ether (v/v)=1/1) and the fraction with Rf=0.5~0.6 was collected and dried to give the title compound B27 (89 mg, yield 57%) as colorless oil. ESI[M+H]$^+$=315.2

Example B24 Preparation of Compound B28

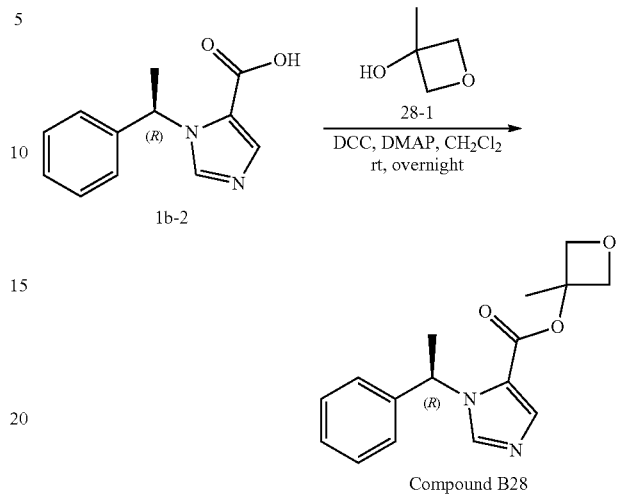

2. Preparation of Compound B28

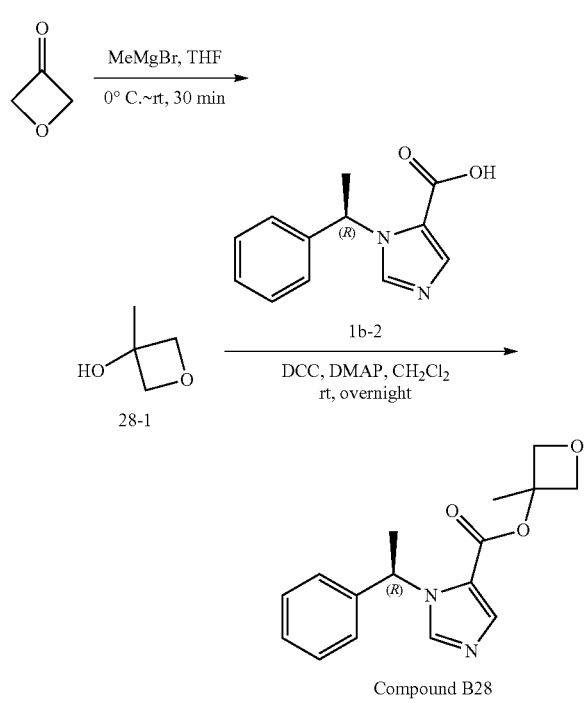

The title compound B28 was prepared according to the general procedure A, using 1b-2 (200 mg, 0.92 mmol) and 28-1 (132 mg, 1.5 mmol) as the raw materials. The crude product was purified by Prep-TLC (ethyl acetate/petroleum ether (v/v)=1/1) and the fraction with Rf=0.4~0.6 was collected and dried to give the title compound B28 (150 mg, yield 57%) as colorless oil. ESI[M+H]$^+$=287.2

$^1$H NMR (400 MHz, CDCl$_3$) δ 7.79 (s, 2H), 7.39-7.28 (m, 3H), 7.20-7.10 (m, 2H), 6.27 (q, J=7.1 Hz, 1H), 4.80 (dd, J=26.3, 7.2 Hz, 2H), 4.60-4.48 (m, 2H), 1.87 (d, J=7.1 Hz, 3H), 1.73 (s, 3H).

Example B25 Preparation of Compound B29

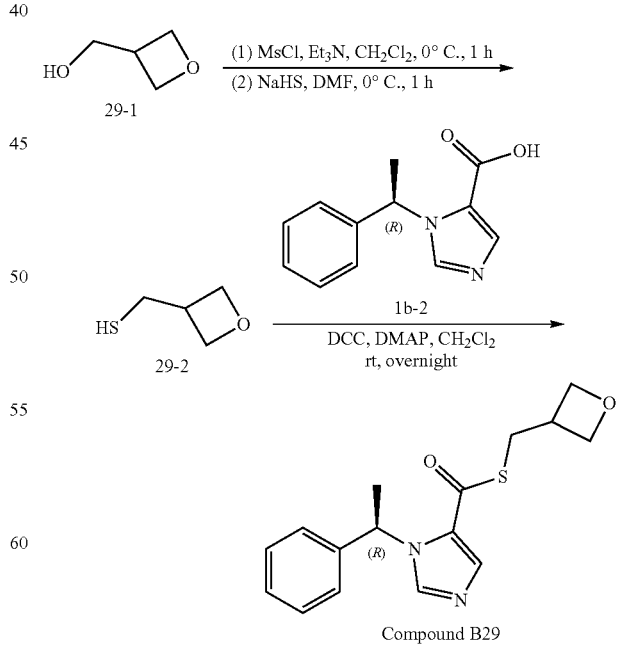

1. Preparation of 3-Methyloxetan-3-ol (28-1)

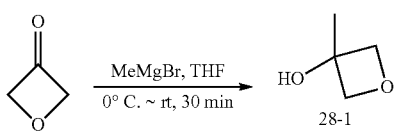

In an ice bath, oxetan-3-one (360 mg, 5 mmol) was dissolved in THF (5 mL). Methylmagnesium bromide (6.0 mL, 1.0 mol/L in THF, 6 mmol) was added dropwise into the mixture at the rate of 1 mL/min using a syringe at 0° C., then the mixture was reacted at this temperature for 30 min. The reaction was monitored by TLC until completion, then the mixture was quenched with saturated ammonium chloride solution and extracted with EtOAc (3×10 mL). The combined organic layers were washed with saturated brine (30 mL), dried over anhydrous sodium sulfate, filtered and concentrated under reduced pressure to give crude compound 28-1 (352 mg, yield 80%) as colorless oil, which was used for next step directly without further purification.

The compound 29-2 was prepared according to the general procedure C, using 29-1 (264 mg, 3.0 mmol) as the raw material. 134 mg of compound 29-2 (yield 43% for 2 steps) as colorless oil was obtained. ESI[M+H]+=105.1

The title compound B29 was prepared according to the general procedure A, using 1b-2 (216 mg, 1.0 mmol) and 29-2 (134 mg, 1.3 mmol) as the raw materials. The crude product was purified by Prep-TLC (ethyl acetate/petroleum ether (v/v)=1/1) and the fraction with Rf=0.4~0.6 was collected and dried to give the title compound B29 (109 mg, yield 36%) as colorless oil. ESI[M+H]⁺=303.3

¹H NMR (400 MHz, CDCl₃) δ 7.93 (s, 1H), 7.90 (s, 1H), 7.52-7.31 (m, 3H), 7.19-7.17 (m, 2H), 6.25 (q, J=6.8 Hz, 1H), 4.82-4.75 (m, 2H), 4.41-4.35 (m, 2H), 3.31 (d, J=7.2 Hz, 2H), 3.24-3.14 (m, 1H), 1.87 (d, J=7.2 Hz, 3H).

Example B26 Preparation of Compound B30

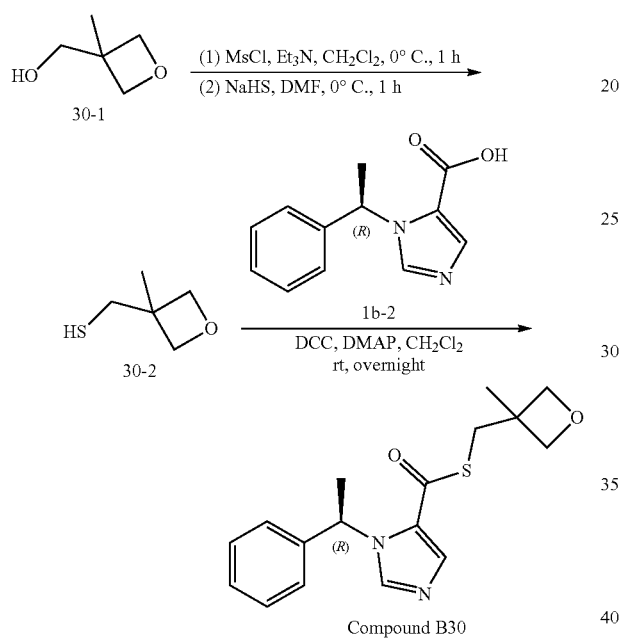

Compound B30

The compound 30-2 was prepared according to the general procedure C, using 30-1 (306 mg, 3.0 mmol) as the raw material. 142 mg of compound 30-2 (yield 40% for 2 steps) as colorless oil was obtained. ESI[M+H]+=119.1

The title compound B30 was prepared according to the general procedure A, using 1b-2 (216 mg, 1.0 mmol) and 30-2 (142 mg, 1.2 mmol) as the raw materials. The crude product was purified by Prep-TLC (ethyl acetate/petroleum ether (v/v)=1/1) and the fraction with Rf=0.5~0.6 was collected and dried to give the title compound B30 (291 mg, yield 92%) as colorless oil. ESI[M+H]⁺=317.2 ¹H NMR (400 MHz, CDCl₃) δ 7.96 (s, 1H), 7.86 (s, 1H), 7.37-7.30 (m, 3H), 7.17-7.16 (m, 2H), 6.25 (q, J=7.2 Hz, 1H), 4.41-4.38 (m, 2H), 4.36-4.33 (m, 2H), 3.33 (s, 2H), 1.86 (d, J=6.8 Hz, 3H), 1.32 (s, 3H).

Example B27 Preparation of Compound B31

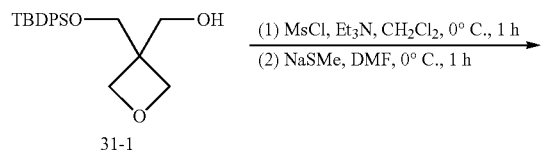

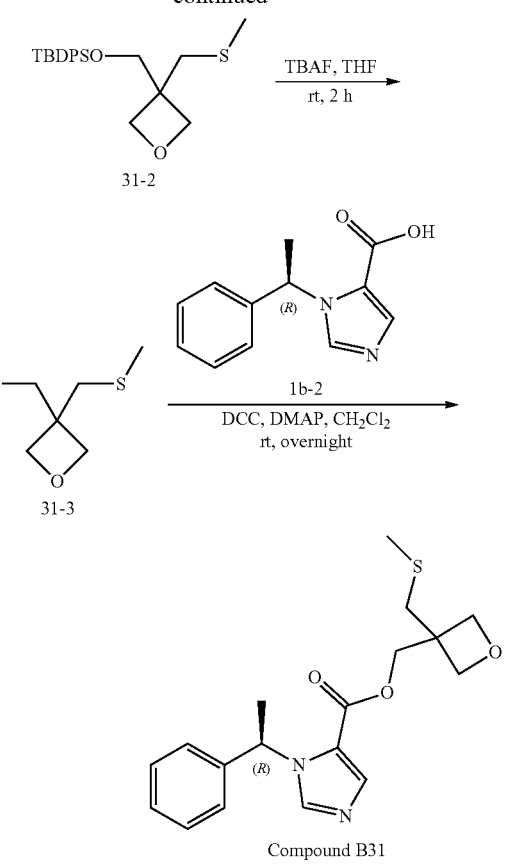

Compound B31

1. Preparation of (3-((Methylthio)methyl)oxetan-3-yl)methanol (31-3)

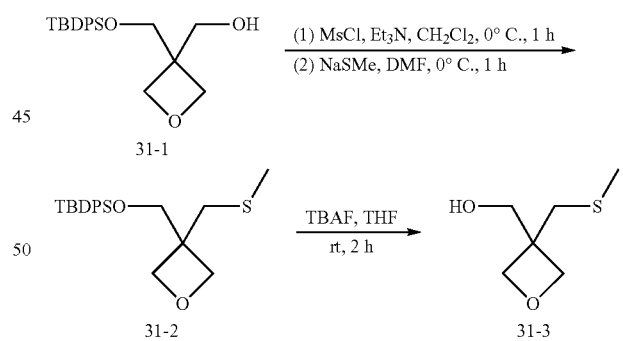

The compound 31-2 was prepared according to the general procedure C, using 31-1 (1.1 g, 3.1 mmol) as the raw material. 540 mg of crude compound 31-2 as colorless was obtained. ESI[M+H]⁺=105.1

At room temperature, TBAF (5.6 mL, 1 mol/L in THF, 5.6 mmol) was added into the solution of 31-2 (540 mg, 1.4 mmol) in THF (10 mL) and the mixture was allowed to react at this temperature for 2 hrs. The reaction was monitored by TLC until completion, then it was concentrated under reduced pressure to give crude product 31-3 (165 mg, yield 36% for 3 steps) as colorless oil, which was used for next step directly without further purification. ESI[M+H]⁺=149.2

2. Preparation of Compound B31

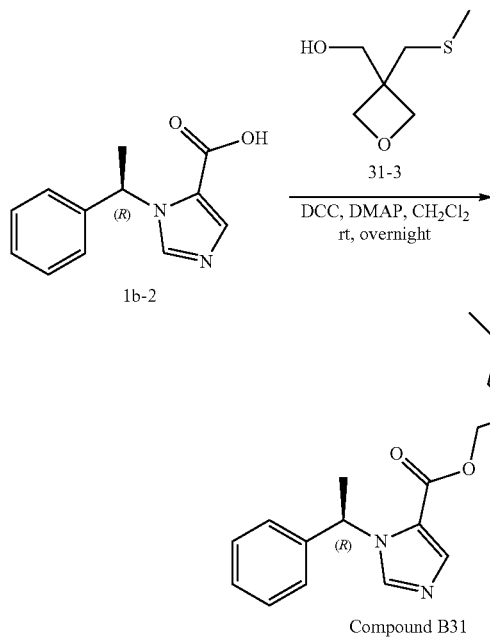

The title compound B31 was prepared according to the general procedure A, using 1b-2 (216 mg, 1.0 mmol) and 31-3 (148 mg, 1.0 mmol) as the raw materials. The crude product was purified by Prep-TLC (ethyl acetate/petroleum ether (v/v)=1/1) and the fraction with Rf=0.4~0.6 was collected and dried to give the title compound B31 (125 mg, yield 36%) as colorless oil. ESI[M+H]$^+$=347.2

$^1$H NMR (400 MHz, CDCl$_3$) δ 7.84 (s, 1H), 7.75 (s, 1H), 7.39-7.29 (m, 3H), 7.15 (d, J=6.9 Hz, 2H), 6.22 (d, J=7.1 Hz, 1H), 4.81 (q, J=6.7 Hz, 2H), 4.68 (q, J=11.5 Hz, 2H), 4.59-4.51 (m, 2H), 2.71-2.68 (m, 2H), 2.10 (s, 3H), 1.88 (d, J=7.1 Hz, 3H).

Example C1 Preparation of Compound C1

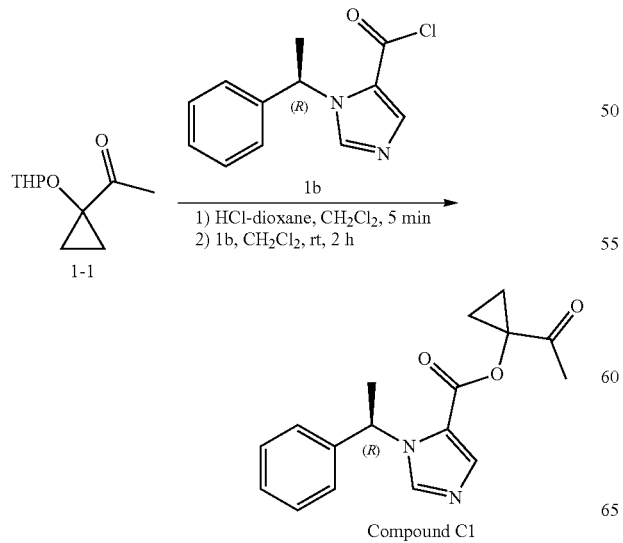

At room temperature, HCl/Dioxane (0.15 mL, 4 mol/L, 0.60 mmol) was added into the mixture of 1-1 (150 mg, 0.81 mmol) in dichloromethane (10 mL) at the rate of 1 mL/min, then the mixture was reacted at this temperature for 5 min. 1b (190 mg, 0.81 mmol) was added to the mixture, then the mixture was reacted for 2 hrs at room temperature. The mixture was concentrated under reduced pressure and the residue was purified by Prep-TLC (MeOH/CH$_2$Cl$_2$ (v/v)=1/10), the fraction with Rf=0.4~0.6 was collected and dried to give the title compound C1 (15 mg, yield 6%) as colorless oil. ESI[M+H]$^+$=299.2

$^1$H NMR (400 MHz, d$_6$-DMSO) δ 8.38 (s, 1H), 7.77 (s, 1H), 7.33 (t, J=7.3 Hz, 2H), 7.28-7.26 (m, 1H), 7.16 (d, J=7.2 Hz, 2H), 6.15 (q, J=7.2 Hz, 1H), 1.89 (s, 3H), 1.85 (d, J=7.2 Hz, 3H), 1.59-1.44 (m, 2H), 1.35-1.10 (m, 2H).

Example C2 Preparation of Compound C2

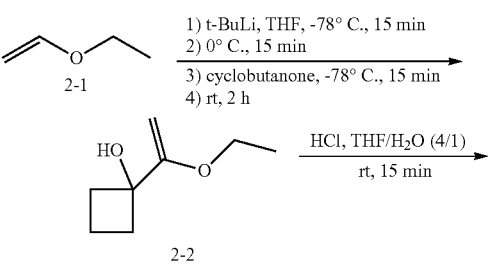

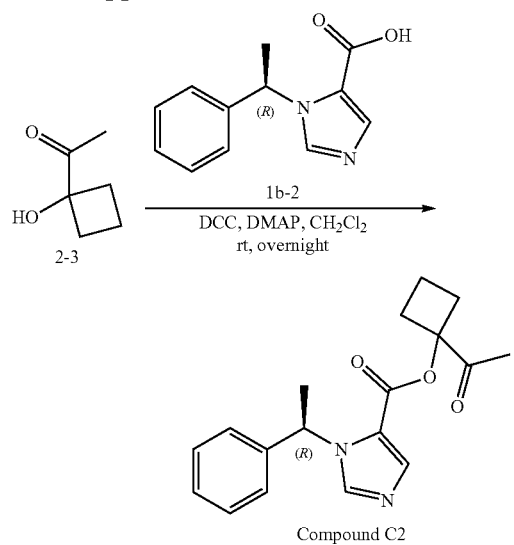

1. Preparation of 1-(1-Ethoxyvinyl)cyclobutan-1-ol (2-2)

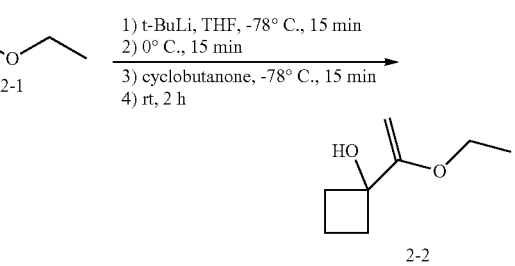

Ethoxyethene (2-1) (3.60 g, 50.0 mmol) was dissolved in the anhydrous THF (20 mL) under nitrogen atmosphere and the mixture was cooled to −78° C. by a dry ice-acetone bath. Then t-BuLi (20 mL, 1.0 mol/L in pentane, 20 mmol) was added slowly into the mixture over a 5-min period using a syringe under −70° C. The mixture was stirred at −78° C. for 15 min, then the dry ice-acetone bath was replaced with an ice-water bath and continued to react for 15 min. The mixture temperature was cooled down to −78° C. by a dry ice-acetone bath, and then Cyclobutanone (700.9 mg, 10.0 mmol) in anhydrous THF (20 mL) was added slowly into the reaction solution at the rate of 1 mL/min. The mixture was warmed to room temperature slowly and allowed to react for 2 hrs. The reaction was monitored by TLC until completion. The mixture was quenched with the saturated ammonium chloride solution (30 mL) and extracted with dichloromethane (3×10 mL). The combined organic layers were washed with saturated brine (50 mL), dried over anhydrous sodium sulfate, filtered and concentrated under reduced pressure. The crude product was purified by silica gel column chromatography (ethyl acetate/petroleum ether (v/v)=1/100) and the eluate was monitored by TLC (ethyl acetate/petroleum ether (v/v)=1/10). The fraction with Rf=0.6~0.7 was collected and dried to give compound 2-2 (1.98 g, contain lots of dichloromethane) as colorless oil.

2. Preparation of 1-(1-Hydroxycyclobutyl)ethan-1-one (2-3)

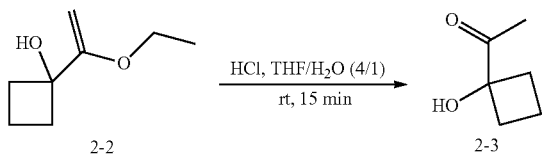

At room temperature, HCl (45 mL, 0.1 mol/L, 4.5 mmol) was added into the mixture of 2-2 (288 mg, 2 mmol) in THF/H₂O (45 mL, 4/1), then the mixture was stirred at this temperature for 15 min. The reaction was monitored by TLC until completion, then it was extracted with dichloromethane (3×10 mL). The combined organic layers were washed with saturated brine (50 mL), dried over anhydrous sodium sulfate, filtered and concentrated under reduced pressure to give crude compound 2-3, which was used for next step directly without further purification.

3. Preparation of Compound C2

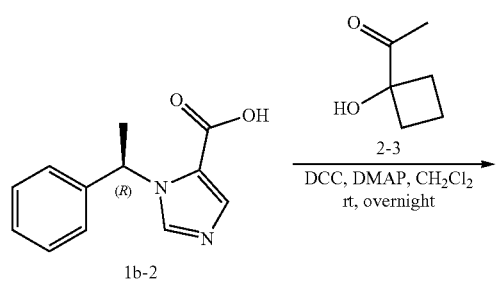

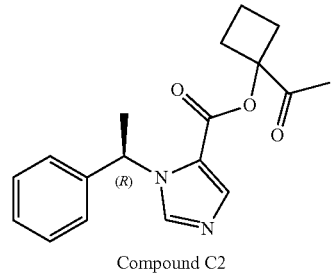

Compound C2

The title compound C2 was prepared according to the general procedure A, using 1b-2 (324 mg, 1.50 mmol) and 2-3 (crude) as the raw materials. The crude product was purified by Prep-TLC (ethyl acetate/petroleum ether (v/v)= 1/1) and the fraction with Rf=0.5~0.6 was collected and dried to give the title compound C2 (115 mg, yield 25%) as colorless oil. ESI[M+H]⁺=313.3

¹H NMR (400 MHz, CDCl₃) δ 7.90 (s, 1H), 7.85 (s, 1H), 7.36-7.27 (m, 3H), 7.15-7.08 (m, 2H), 6.25 (q, J=7.1 Hz, 1H), 2.74-2.64 (m, 1H), 2.58-2.49 (m, 1H), 2.35-2.20 (m, 2H), 2.00-1.90 (m, 1H), 1.88 (s, 3H), 1.86 (d, J=7.2 Hz, 3H), 1.90~1.83 (m, 1H).

Example C3 Preparation of Compound C3

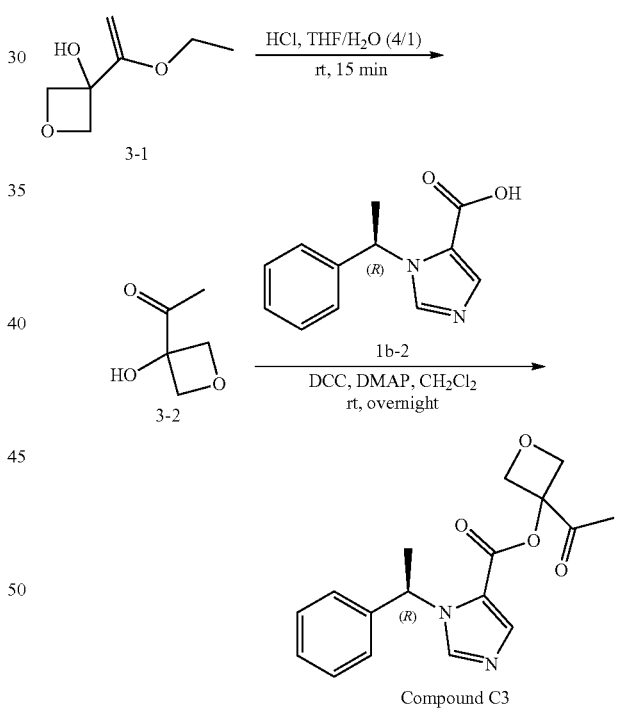

Compound C3

1. Preparation of 1-(3-Hydroxyoxetan-3-yl)ethan-1-one (3-2)

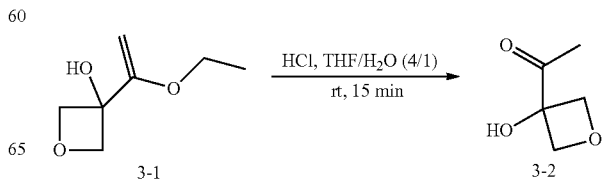

At room temperature, HCl (45 mL, 0.1 mol/L, 4.5 mmol) was added into the mixture of 3-1 (288 mg, 2 mmol) in THF/H₂O (45 mL, 4/1), then it was stirred at this temperature for 15 min. The reaction was monitored by TLC until completion, then it was extracted with dichloromethane (3×10 mL). The combined organic layers were washed with saturated brine (50 mL), dried over anhydrous sodium sulfate, filtered and concentrated under reduced pressure to give crude compound 3-2, which was used for next step directly without further purification.

2. Preparation of Compound C3

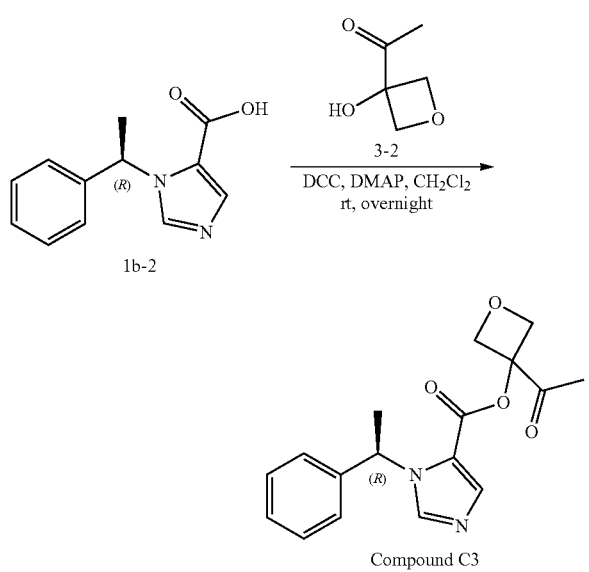

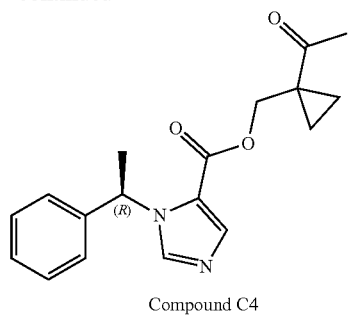

Compound C4

The title compound C4 was prepared according to the general procedure A, using 1b-2 (216 mg, 1.0 mmol) and 1-(1-(hydroxymethyl)cyclopropyl)ethanone (114 mg, 1.0 mmol) as the raw materials. The crude product was purified by Prep-TLC (ethyl acetate/petroleum ether (v/v)=1/1) and the fraction with Rf=0.4~0.6 was collected and dried to give the title compound C4 (98 mg, yield 31%) as colorless oil. ESI[M+H]⁺=313.2

¹H NMR (400 MHz, d₆-DMSO) δ 8.35 (s, 1H), 7.74 (s, 1H), 7.32 (t, J=7.3 Hz, 2H), 7.27-7.25 (m, 1H), 7.17 (d, J=7.2 Hz, 2H), 6.11 (q, J=7.2 Hz, 1H), 4.31-4.21 (m, 2H), 1.88 (s, 3H), 1.82 (d, J=7.2 Hz, 3H), 1.50~1.40 (m, 2H), 1.30-1.11 (m, 2H).

The title compound C3 was prepared according to the general procedure A, using 1b-2 (324 mg, 1.50 mmol) and 3-2 as the raw materials. The crude product was purified by Prep-TLC (ethyl acetate/petroleum ether (v/v)=1/1) and the fraction with Rf=0.4~0.5 was collected and dried to give the title compound C3 (26 mg, yield 5.5%) as a white solid. ESI[M+H]⁺=315.3 41 NMR (400 MHz, CDCl₃) δ 7.97 (s, 1H), 7.91 (s, 1H), 7.39-7.27 (m, 3H), 7.16-7.07 (m, 2H), 6.19 (q, J=7.0 Hz, 1H), 4.98 (d, J=7.6 Hz, 1H), 4.91 (d, J=7.7 Hz, 1H), 4.79 (d, J=7.6 Hz, 1H), 4.74 (d, J=7.6 Hz, 1H), 2.17 (s, 3H), 1.87 (d, J=7.1 Hz, 3H).

Example C4 Preparation of Compound C4

Example C5 Preparation of Compound C5

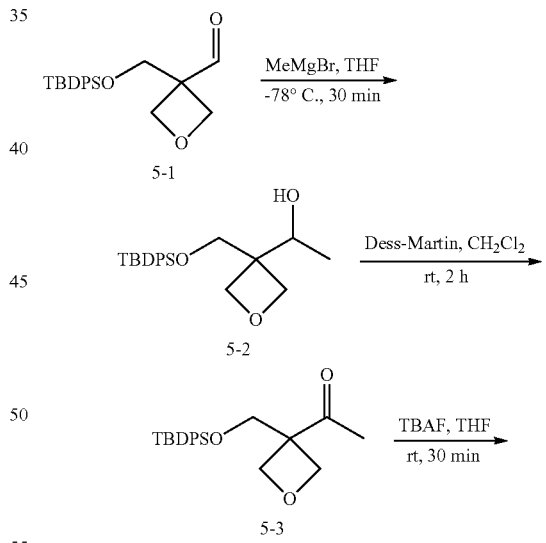

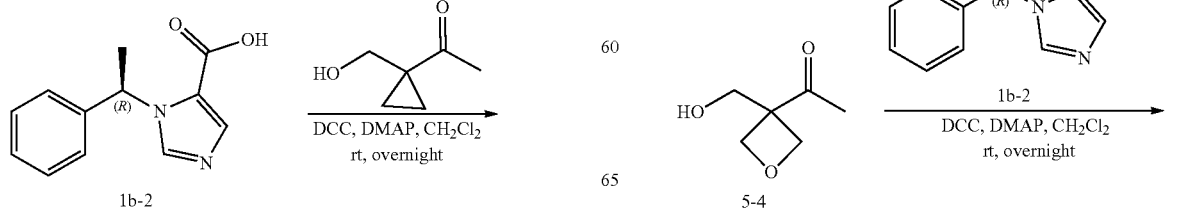

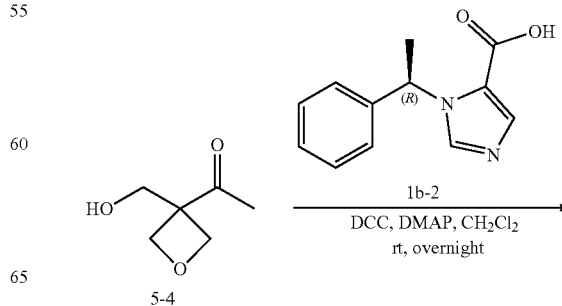

-continued

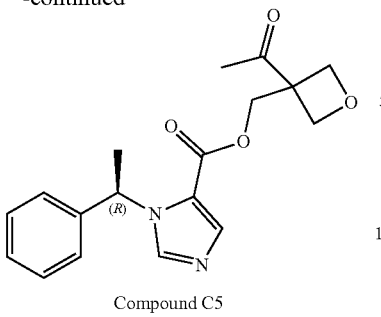

Compound C5

1. Preparation of 1-(3-(((Tert-butyldiphenylsilyl)oxy)methyl)oxetan-3-yl)ethan-1-ol (5-2)

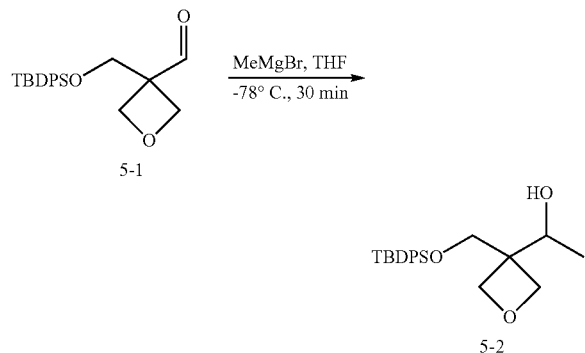

At room temperature, 5-1 (500 mg, 1.41 mmol) was dissolved in anhydrous THF (20 mL) under nitrogen atmosphere and the mixture was cooled to −78° C. by a dry ice-acetone bath. Then methylmagnesium bromide (6.54 mL, 1 mol/L in THF, 6.54 mmol) was added into the mixture at the rate of 1 mL/min using a syringe (1 mL/min), then the mixture was reacted at this temperature for 30 min. The reaction was monitored by TLC until completion. The mixture was quenched with saturated ammonium chloride solution (10 mL) and extracted with EtOAc (3×10 mL). The combined organic layers were washed with saturated brine (30 mL), dried over anhydrous sodium sulfate, filtered and concentrated under reduced pressure. The residue was purified by Prep-TLC (ethyl acetate/petroleum ether (v/v)=1/1) and the fraction with Rf=0.5~0.6 was collected and dried to give the compound 5-2 (345 mg, yield 24%) as colorless oil.

2. Preparation of 1-(3-(((Tert-butyldiphenylsilyl)oxy)methyl)oxetan-3-yl)ethan-1-one (5-3)

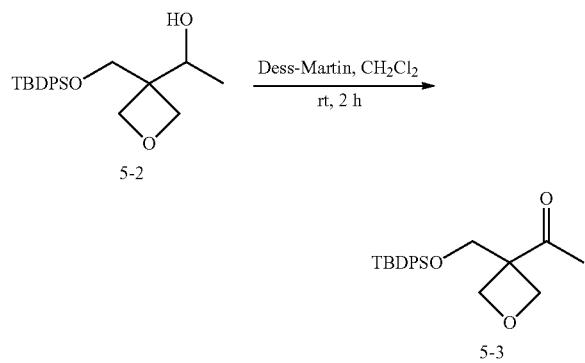

In an ice-water bath, Dess-Martin (339 mg, 0.8 mmol) was added in portions into the mixture of 5-2 (145 mg, 0.4 mmol) in dichloromethane (30 mL) at the rate of 0.1 mmol/min at 0° C., then the mixture was allowed to react at room temperature for 2 hrs. The reaction was monitored by TLC until completion. The mixture was filtered and the filtrate was washed with saturated sodium bicarbonate solution, saturated brine (50 mL), dried over anhydrous sodium sulfate, filtered and concentrated under reduced pressure to give crude compound 5-3 (200 mg) as colorless oil.

3. Preparation of 1-(3-(Hydroxymethyl)oxetan-3-yl)ethan-1-one (5-4)

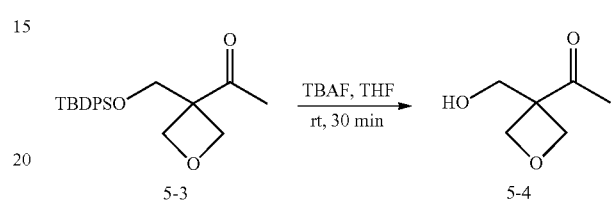

At room temperature, TBAF (1.0 mL, 1 mol/L in THF, 1.0 mmol) was added into the mixture of 5-3 (200 mg, 0.54 mmol) in THF (10 mL), then the mixture was stirred at room temperature for 20 mins. The reaction was monitored by TLC until completion, then it was concentrated under reduced pressure. The residue was purified by silica gel column chromatography ethyl acetate/petroleum ether (v/v=1/10) and eluate was monitored by TLC (ethyl acetate/petroleum ether (v/v)=1/1). The fraction with the product Rf=0.3~0.4 was collected and dried to give crude compound 5-4 (80 mg) as colorless.

4. Preparation of Compound C5

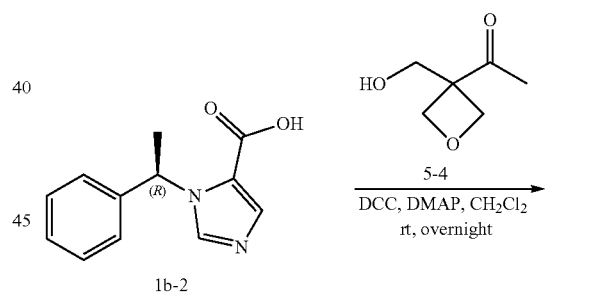

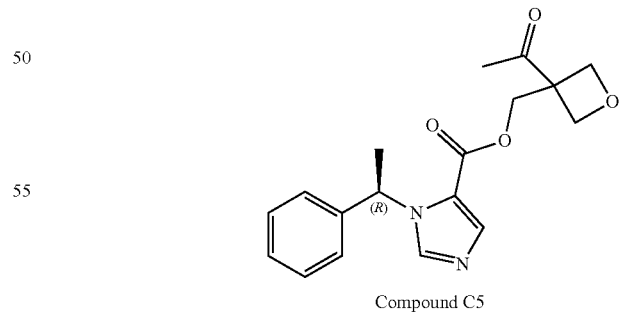

Compound C5

The title compound C5 was prepared according to the general procedure A, using 1b-2 (130 mg, 0.6 mmol) and 5-4 (80 mg) as the raw materials. The crude product was purified by Prep-TLC (ethyl acetate/petroleum ether (v/v)=1/1.5) and the fraction with Rf=0.3~0.4 was collected and dried to give the title compound C5 (40 mg, yield 20%) as colorless oil. ESI[M+H]$^+$=329.2

¹H NMR (400 MHz, CDCl₃) δ 7.85 (s, 1H), 7.76 (s, 1H), 7.40-7.29 (m, 3H), 7.17 (d, J=6.9 Hz, 2H), 6.30 (d, J=7.1 Hz, 1H), 4.86 (d, J=6.7 Hz, 2H), 4.69 (q, J=11.5 Hz, 2H), 4.60-4.50 (m, 2H), 2.30 (s, 4H), 1.88 (d, J=7.1 Hz, 3H).

Example C6 Preparation of Compound C6

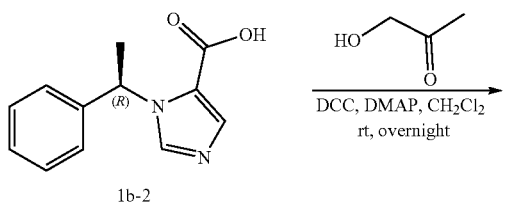

1b-2

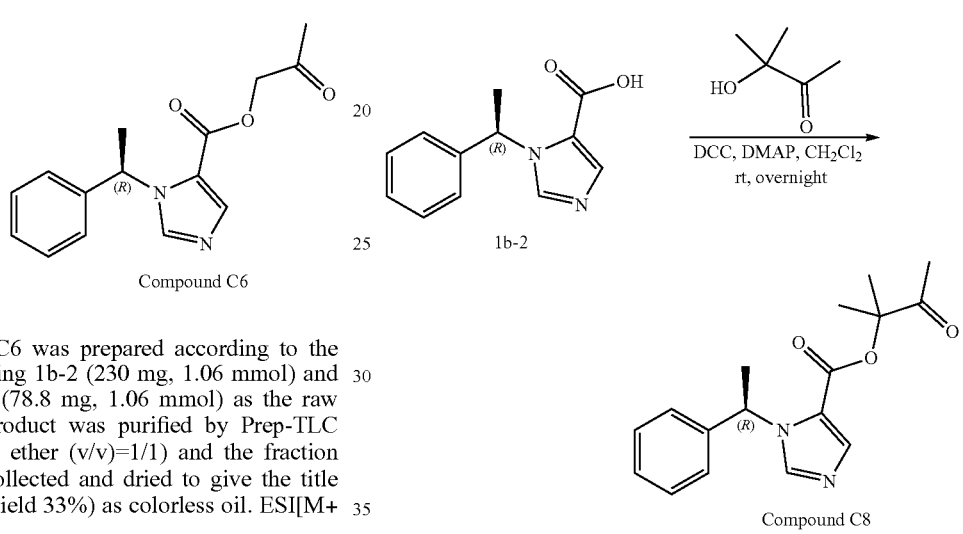

Compound C6

The title compound C6 was prepared according to the general procedure A, using 1b-2 (230 mg, 1.06 mmol) and 1-hydroxypropan-2-one (78.8 mg, 1.06 mmol) as the raw materials. The crude product was purified by Prep-TLC (ethyl acetate/petroleum ether (v/v)=1/1) and the fraction with Rf=0.4~0.5 was collected and dried to give the title compound C6 (95 mg, yield 33%) as colorless oil. ESI[M+H]⁺=273.4

¹H NMR (400 MHz, d₆-DMSO) δ 8.37 (s, 1H), 7.77 (d, J=0.8 Hz, 1H), 7.33 (t, J=7.3 Hz, 2H), 7.29-7.22 (m, 1H), 7.21-7.14 (m, 2H), 6.20 (q, J=7.1 Hz, 1H), 4.94-4.83 (m, 2H), 2.08 (s, 3H), 1.85 (d, J=7.2 Hz, 3H).

Example C7 Preparation of Compound C7

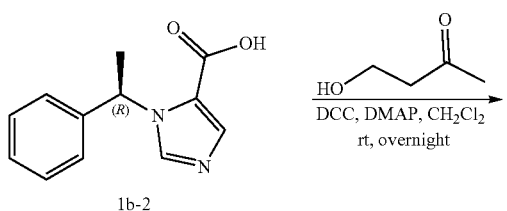

1b-2

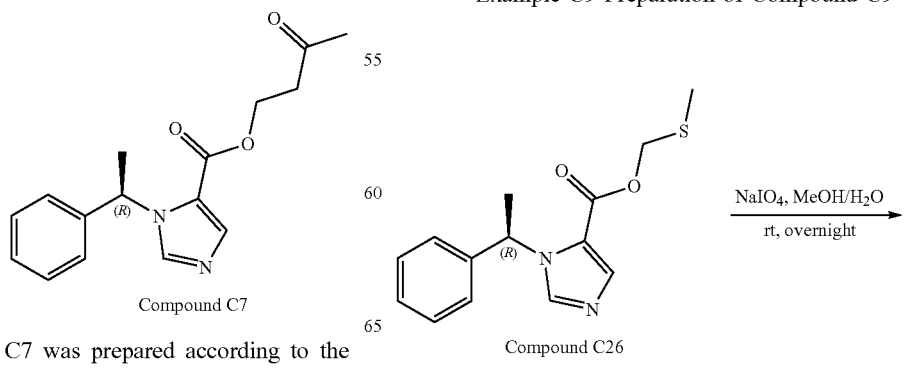

Compound C7

The title compound C7 was prepared according to the general procedure A, using 1b-2 (230 mg, 1.06 mmol) and 4-hydroxybutan-2-one (93.4 mg, 1.06 mmol) as the raw materials. The crude product was purified by Prep-TLC (ethyl acetate/petroleum ether (v/v)=1/1) and the fraction with Rf=0.5~0.6 was collected and dried to give the title compound C7 (28 mg, yield 9%) as colorless oil. ESI[M+H]⁺=287.4

¹H NMR (400 MHz, d₆-DMSO) δ 8.30 (s, 1H), 7.63 (s, 1H), 7.33 (t, J=7.3 Hz, 2H), 7.26 (t, J=7.2 Hz, 1H), 7.17 (d, J=7.3 Hz, 2H), 6.21 (q, J=7.1 Hz, 1H), 4.35-4.27 (m, 2H), 2.82 (t, J=6.2 Hz, 2H), 2.11 (s, 3H), 1.83 (d, J=7.2 Hz, 3H).

Example C8 Preparation of Compound C8

The title compound C8 was prepared according to the general procedure A, using 1b-2 (324 mg, 1.50 mmol) and 3-hydroxy-3-methylbutan-2-one (153 mg, 1.50 mmol) as the raw materials. The crude product was purified by Prep-TLC (ethyl acetate/petroleum ether (v/v)=1/1) and the fraction with Rf=0.5-0.6 was collected and dried to give the title compound C8 (25 mg, yield 8%) as colorless oil. ESI[M+H]⁺=301.3

¹H NMR (400 MHz, CDCl₃) δ 7.94 (s, 1H), 7.87 (s, 1H), 7.40-7.28 (m, 3H), 7.18-7.12 (m, 2H), 6.29 (q, J=7.0 Hz, 1H), 1.95 (s, 3H), 1.88 (d, J=7.1 Hz, 3H), 1.54 (s, 3H), 1.49 (s, 3H).

Example C9 Preparation of Compound C9

Compound C26

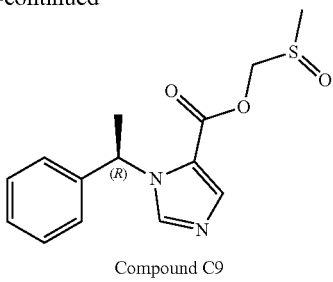

Compound C9

At room temperature, NaIO$_4$ (90 mg, 0.50 mmol) was added to the mixture of C26 (90 mg, 0.33 mmol) in MeOH/H$_2$O (20 mL, v/v=1/1), then the mixture was reacted at room temperature overnight.

The reaction was monitored by TLC until completion. The mixture was quenched with saturated ammonium chloride solution (20 mL) and extracted with dichloromethane (3×10 mL). The combined organic layers were washed with saturated brine (50 mL), dried over anhydrous sodium sulfate, filtered and concentrated under reduced pressure. The residue was purified by Prep-TLC (MeOH/CH$_2$Cl$_2$ (v/v)=1/20) and the fraction with Rf=0.5~0.6 was collected and dried to give the title compound C9 (83 mg, yield 86%) as a white solid. ESI[M+H]$^+$=293.2

$^1$H NMR (400 MHz, CDCl$_3$) δ 8.07 (d, J=14.1 Hz, 1H), 8.00 (d, J=3.1 Hz, 1H), 7.45-7.31 (m, 3H), 7.21 (t, J=6.3 Hz, 2H), 6.32 (q, J=7.1 Hz, 1H), 5.40-5.17 (m, 1H), 5.07 (dd, J=49.9, 10.5 Hz, 1H), 2.62 (d, J=11.8 Hz, 3H), 1.91 (d, J=7.1 Hz, 3H).

Example C10 Preparation of Compound C10

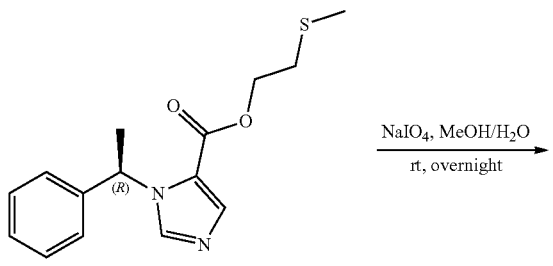

At room temperature, NaIO$_4$ (199 mg, 0.93 mmol) was added to the mixture of C27 (180 mg, 0.62 mmol) in MeOH/H$_2$O (20 mL, v/v=1/1), then the mixture was reacted at room temperature overnight. The reaction was monitored by TLC until completion. The mixture was quenched with saturated ammonium chloride solution (20 mL) and extracted with dichloromethane (3×10 mL). The combined organic layers were washed with saturated brine (50 mL), dried over anhydrous sodium sulfate, filtered and concentrated under reduced pressure. The residue was purified by Prep-TLC (MeOH/CH$_2$Cl$_2$ (v/v)=1/20) and the fraction with Rf=0.5~0.6 was collected and dried to give the title compound C10 (149 mg, yield 78%) as a white solid. ESI[M+H]$^+$=307.3

$^1$H NMR (400 MHz, CDCl$_3$) δ 7.81 (s, 1H), 7.81 (s, 1H), 7.40-7.28 (m, 3H), 7.20-7.16 (m, 2H), 6.32 (d, J=7.1 Hz, 1H), 4.85-4.48 (m, 2H), 3.26-2.84 (m, 2H), 2.64 (d, J=2.5 Hz, 3H), 1.87 (d, J=7.1 Hz, 3H).

Example C11 Preparation of Compound C11

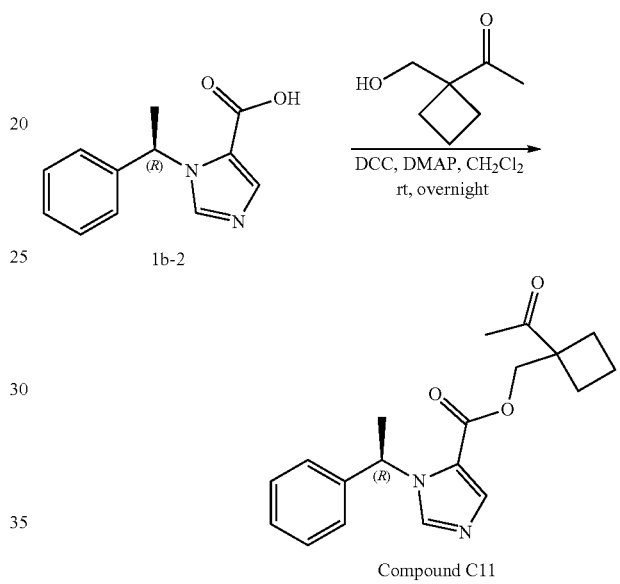

The title compound C11 was prepared according to the general procedure A, using 1b-2 (216 mg, 1.0 mmol) and 1-(1-(hydroxymethyl)cyclobutyl)ethanone (128 mg, 1.0 mmol) as the raw materials. The crude product was purified by Prep-TLC (ethyl acetate/petroleum ether (v/v)=1/1) and the fraction with Rf=0.4-0.6 was collected and dried to give the title compound C11 (108 mg, yield 33%) as colorless oil. ESI[M+H]$^+$=327.1

$^1$H NMR (400 MHz, CDCl$_3$) δ 7.77 (s, 1H), 7.73 (s, 1H), 7.40-7.27 (m, 3H), 7.22-7.10 (m, 2H), 6.30 (q, J=7.1 Hz, 1H), 4.50 (dd, J=27.4, 11.3 Hz, 2H), 2.46-2.35 (m, 2H), 2.16 (s, 3H), 2.05-1.88 (m, 4H), 1.86 (d, J=7.1 Hz, 3H).

Example C12 Preparation of Compound C12

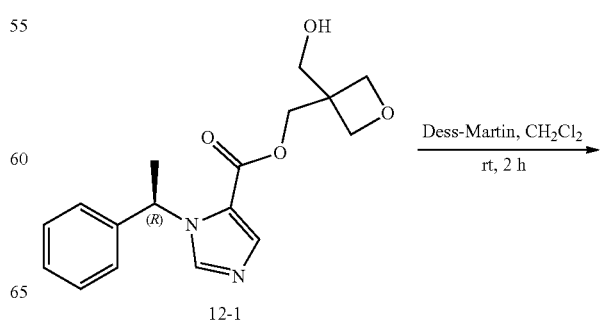

12-1

Example C14 Preparation of Compound C14

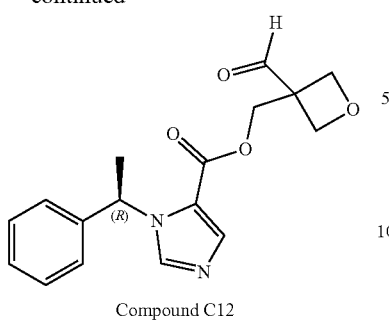

Compound C12

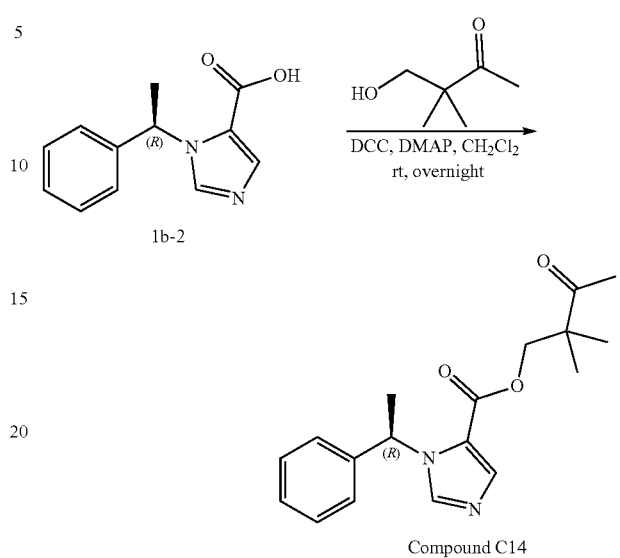

Compound C14

In an ice-water bath, Dess-Martin (848 mg, 2.0 mmol) was added into the mixture of 12-1 (316 mg, 1.0 mmol) in dichloromethane (30 mL) at the rate of 0.5 mmol/min over a 4-min period at 0° C., then the mixture was allowed to react at room temperature for 2 hrs. The reaction was monitored by TLC until completion. The mixture was filtered and the filtrate was washed with saturated sodium bicarbonate solution, saturated brine (50 mL), dried over anhydrous sodium sulfate, filtered and concentrated under reduced pressure. The crude product was purified by Prep-TLC (ethyl acetate/petroleum ether (v/v)=1/1) and the fraction with Rf=0.4~0.5 was collected and dried to give the title compound C12 (75 mg, yield 24%) as colorless oil. ESI[M+H]$^+$=315.2

The title compound C14 was prepared according to the general procedure A, using 1b-2 (216 mg, 1.0 mmol) and 4-hydroxy-3,3-dimethylbutan-2-one (116 mg, 1.0 mmol) as the raw materials. The crude product was purified by Prep-TLC (ethyl acetate/petroleum ether (v/v)=1/1) and the fraction with Rf=0.4~0.5 was collected and dried to give the title compound C14 (180 mg, yield 57%) as colorless oil. ESI[M+H]$^+$=315.3

Example C13 Preparation of Compound C13

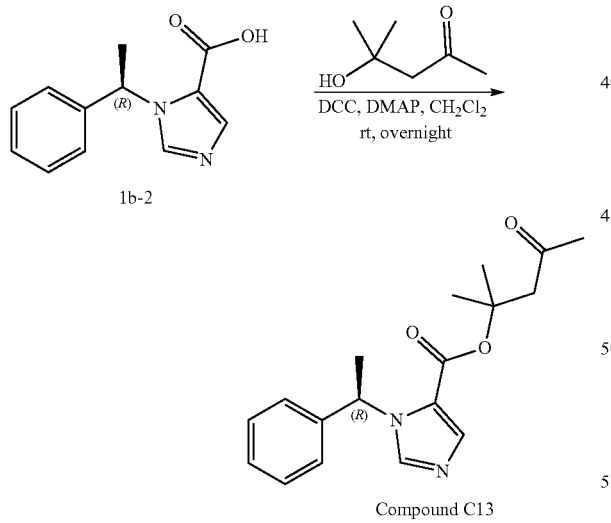

Compound C13

Example C15 Preparation of Compound C15

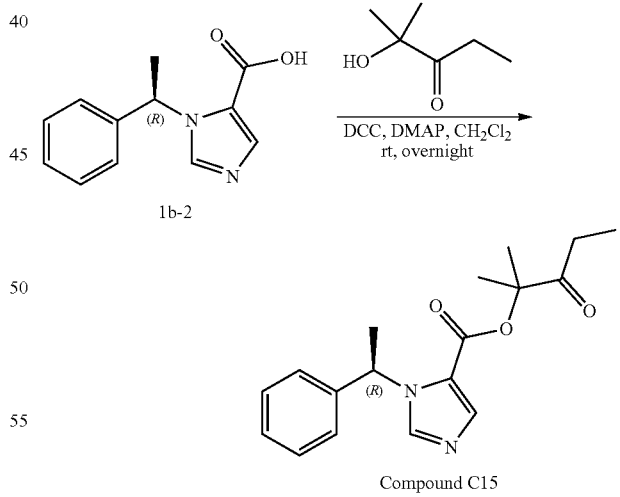

Compound C15

The title compound C13 was prepared according to the general procedure A, using 1b-2 (216 mg, 1.0 mmol) and 4-hydroxy-4-methylpentan-2-one (116 mg, 1.0 mmol) as the raw materials. The crude product was purified by Prep-TLC (ethyl acetate/petroleum ether (v/v)=1/1) and the fraction with Rf=0.4~0.6 was collected and dried to give the title compound C13 (115 mg, yield 37%) as colorless oil. ESI[M+H]$^+$=315.3

The title compound C15 was prepared according to the general procedure A, using 1b-2 (216 mg, 1.0 mmol) and 2-hydroxy-2-methylpentan-3-one (116 mg, 1.0 mmol) as the raw materials. The crude product was purified by Prep-TLC (ethyl acetate/petroleum ether (v/v)=1/1) and the fraction with Rf=0.3~0.4 was collected and dried to give the title compound C15 (110 mg, yield 35%) as colorless oil. ESI[M+H]$^+$=315.3

$^1$H NMR (400 MHz, CDCl$_3$) δ 7.91 (s, 1H), 7.84 (s, 1H), 7.35-7.22 (m, 3H), 7.19-7.10 (m, 2H), 6.11 (q, J=7.0 Hz, 1H), 2.83 (q, J=7.2 Hz, 2H), 1.88 (d, J=7.1 Hz, 3H), 1.51 (s, 3H), 1.45 (s, 3H), 1.40 (t, J=7.2 Hz, 3H).

Example C16 Preparation of Compound C16

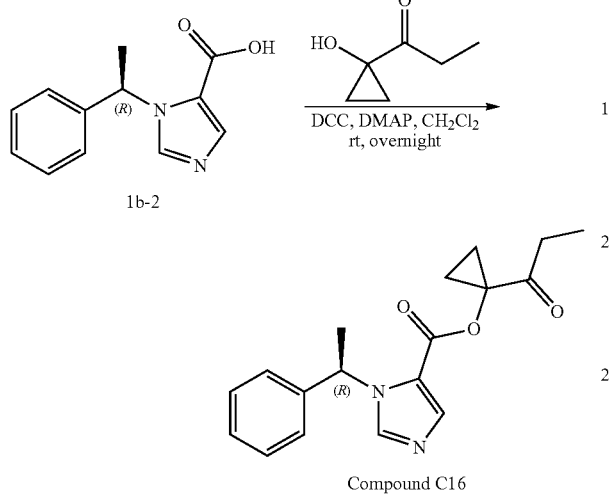

The title compound C16 was prepared according to the general procedure A, using 1b-2 (216 mg, 1.0 mmol) and 1-(1-hydroxycyclopropyl)propan-1-one (114 mg, 1.0 mmol) as the raw materials. The crude product was purified by Prep-TLC (ethyl acetate/petroleum ether (v/v)=1/1) and the fraction with Rf=0.3~0.5 was collected and dried to give the title compound C16 (46 mg, yield 15%) as colorless oil. ESI[M+H]$^+$=313.2

$^1$H NMR (400 MHz, CDCl$_3$) δ 7.92 (s, 1H), 7.85 (s, 1H), 7.41-7.22 (m, 3H), 7.17-7.10 (m, 2H), 6.11 (q, J=7.0 Hz, 1H), 2.82 (q, J=7.2 Hz, 2H), 1.89 (d, J=7.1 Hz, 3H), 1.51-1.41 (m, 5H), 1.30-1.11 (m, 2H).

Example C17 Preparation of Compound C17

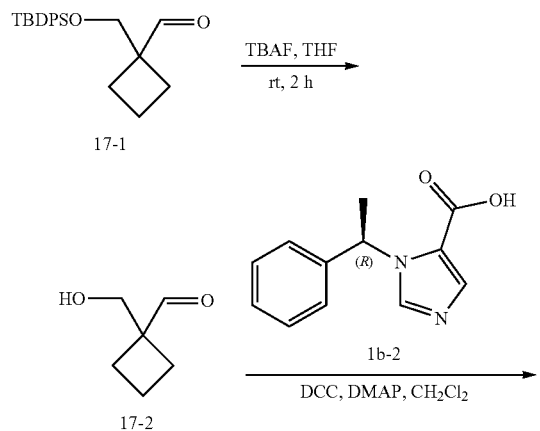

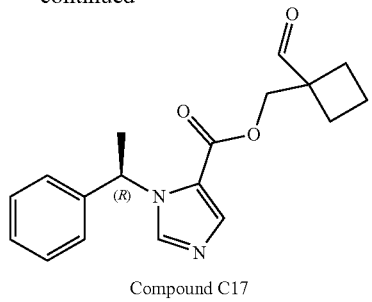

1. Preparation of 1-(Hydroxymethyl)cyclobutane-1-carbaldehyde (17-2)

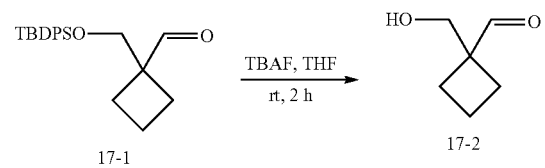

At room temperature, TBAF (3.0 mL, 1 mol/L in THF, 3.0 mmol) was added into the mixture of 17-1 (460 mg, 1.3 mmol) in THF (15 mL) and the mixture was stirred at room temperature for 2 hrs. The reaction was monitored by TLC until completion, then it was concentrated under reduced pressure. The residue was purified by silica gel column chromatography ethyl acetate/petroleum ether (v/v=1/20~1/5) and eluate was monitored by TLC (ethyl acetate/petroleum ether (v/v)=1/10). The fraction with the product Rf=0.5~0.6 was collected and dried to give compound 17-2 (92 mg, yield 62%) as colorless 2. Preparation of Compound C17

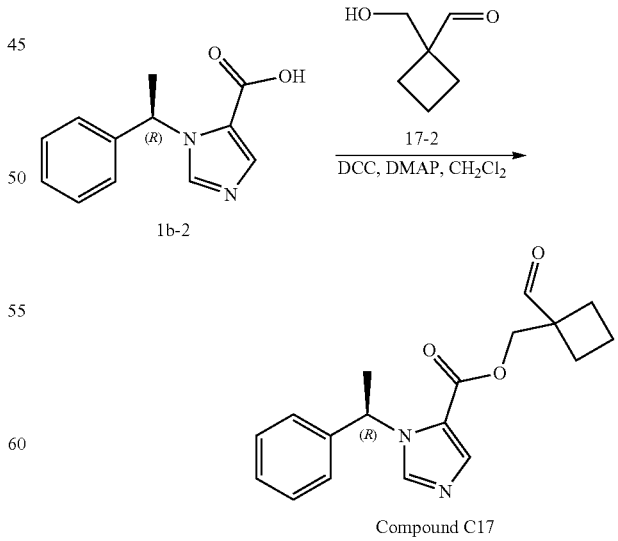

The title compound C17 was prepared according to the general procedure A, using 1b-2 (216 mg, 1.0 mmol) and 17-2 (92 mg, 0.81 mmol) as the raw materials. The crude product was purified by Prep-TLC (ethyl acetate/petroleum ether (v/v)=1/1.5) and the fraction with Rf=0.5~0.6 was collected and dried to give the title compound C17 (97 mg, yield 31%) as a white solid. ESI[M+H]⁺=313.3

¹H NMR (400 MHz, CDCl₃) δ 9.71 (s, 1H), 7.84 (s, 1H), 7.75 (s, 1H), 7.40-7.28 (m, 3H), 7.23-7.15 (m, 2H), 6.32 (q, J=7.1 Hz, 1H), 4.52 (dd, J=29.6, 11.4 Hz, 2H), 2.43-2.31 (m, 2H), 2.13-2.04 (m, 1H), 2.04-1.93 (m, 3H), 1.87 (d, J=7.1 Hz, 3H).

Example C18 Preparation of Compound C18

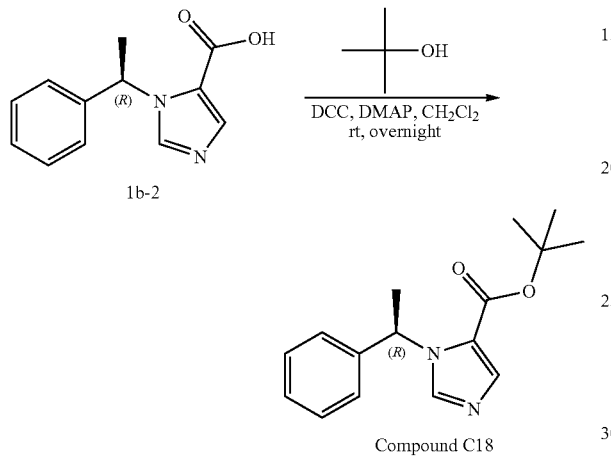

Compound C18

The title compound C18 was prepared according to the general procedure A, using 1b-2 (216 mg, 1.0 mmol) and 2-methylpropan-2-ol (82 mg, 1.1 mmol) as the raw materials. The crude product was purified by Prep-TLC (ethyl acetate/petroleum ether (v/v)=1/1) and the fraction with Rf=0.5-0.6 was collected and dried to give the title compound C18 (220 mg, yield 81%) as colorless oil. ESI[M+H]⁺=273.3

¹H NMR (400 MHz, CDCl₃) δ 7.71 (s, 1H), 7.69 (s, 1H), 7.41-7.27 (m, 3H), 7.23-7.14 (m, 2H), 6.37 (q, J=7.1 Hz, 1H), 1.86 (d, J=7.1 Hz, 3H), 1.51 (s, 9H).

Example C19 Preparation of Compound C19

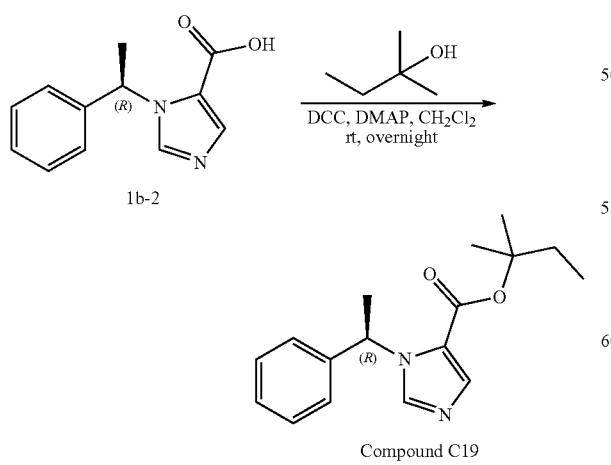

Compound C19

The title compound C19 was prepared according to the general procedure A, using 1b-2 (100 mg, 0.46 mmol) and 2-methylbutan-2-ol (61 mg, 0.69 mmol) as the raw materials. The crude product was purified by Prep-TLC (ethyl acetate/petroleum ether (v/v)=1/1) and the fraction with Rf=0.4~0.6 was collected and dried to give the title compound C19 (143 mg, yield 52%) as colorless oil. ESI[M+H]⁺=287.3

¹H NMR (400 MHz, CDCl₃) δ 7.97 (s, 1H), 7.83 (s, 1H), 7.38-7.25 (m, 3H), 7.24-7.08 (m, 2H), 6.38 (d, J=7.1 Hz, 1H), 2.00-1.75 (m, 5H), 1.48 (s, 3H), 1.46 (s, 3H), 0.89 (t, J=7.4 Hz, 3H).

Example C20 Preparation of Compound C20

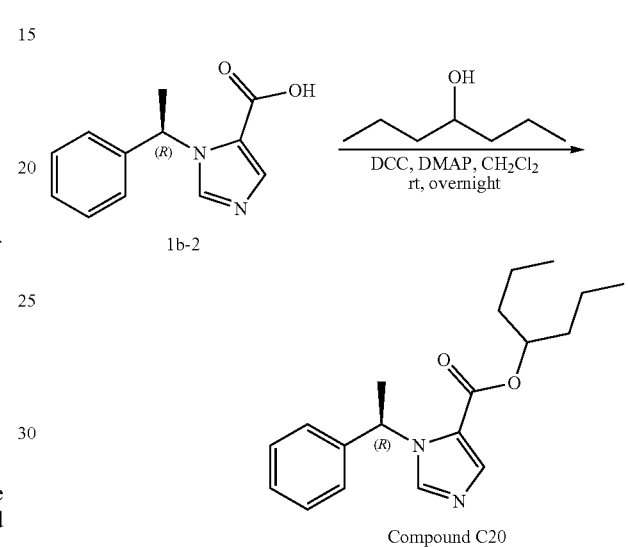

Compound C20

The title compound C20 was prepared according to the general procedure A, using 1b-2 (100 mg, 0.46 mmol) and heptan-4-ol (64 mg, 0.55 mmol) as the raw materials. The crude product was purified by Prep-TLC (ethyl acetate/petroleum ether (v/v)=1/1) and the fraction with Rf=0.5~0.6 was collected and dried to give the title compound C20 (133.1 mg, yield 92%) as colorless oil. ESI[M+H]⁺=315.1

¹H NMR (400 MHz, CDCl₃) δ 7.81 (s, 1H), 7.79 (s, 1H), 7.38-7.28 (m, 3H), 7.22-7.16 (m, 2H), 6.39 (q, J=7.0 Hz, 1H), 5.05-4.91 (m, 1H), 1.88 (d, J=7.1 Hz, 3H), 1.69-1.52 (m, 4H), 1.38-1.17 (m, 4H), 0.94-0.81 (m, 6H).

Example C21 Preparation of Compound C21

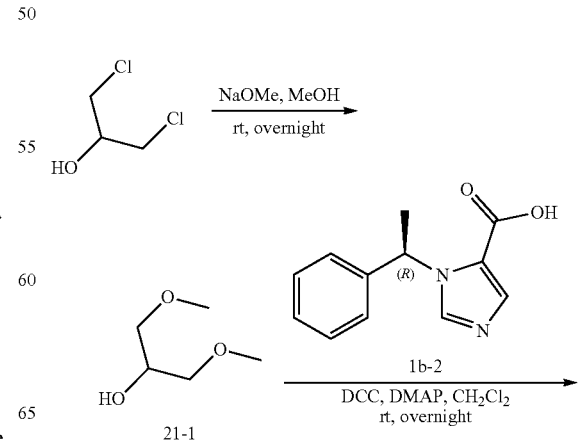

-continued

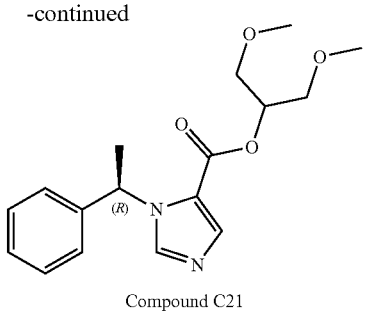

Compound C21

1. Preparation of 1,3-dimethoxypropan-2-ol (21-1)

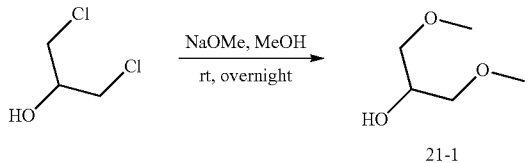

At room temperature, 1,3-dichloropropan-2-ol (645 mg, 5.0 mmol) and NaOMe (810 mg, 15.0 mmol) were dissolved in methanol (20 mL), then it was stirred at room temperature overnight. The reaction was monitored by TLC until completion. The mixture was filtered and the filtrate was concentrated under reduced pressure to give crude compound 21-1 (200.6 mg) as colorless oil, which was used for next step directly without further purification. ESI[M+H]$^+$=121.1

2. Preparation of Compound C21

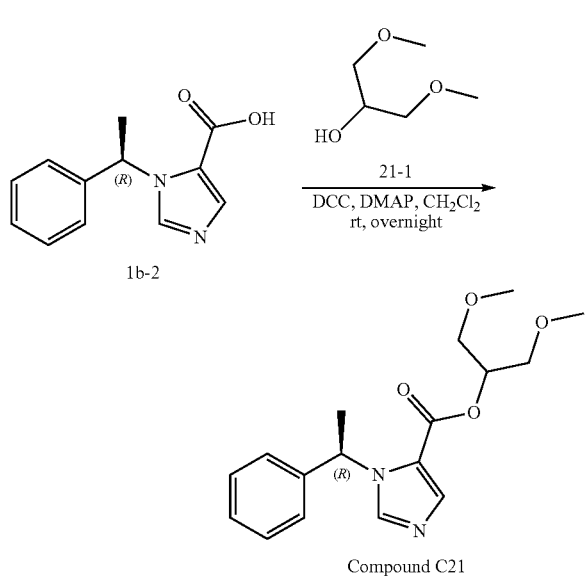

Compound C21

The title compound C21 was prepared according to the general procedure A, using 1b-2 (216 mg, 1.0 mmol) and 21-1 (180 mg, 1.5 mmol) as the raw materials. The crude product was purified by Prep-TLC (ethyl acetate/petroleum ether (v/v)=1/1) and the fraction with Rf=0.4~0.6 was collected and dried to give the title compound C21 (269 mg, yield 84%) as colorless oil. ESI[M+H]$^+$=319.0 $^1$H NMR (400 MHz, CDCl$_3$) δ 7.83 (s, 1H), 7.77 (s, 1H), 7.39-7.28 (m, 3H), 7.24-7.16 (m, 2H), 6.36 (q, J=7.0 Hz, 1H), 5.29 (p, J=5.1 Hz, 1H), 3.63-3.55 (m, 4H), 3.37 (s, 3H), 3.33 (s, 3H), 1.87 (d, J=7.1 Hz, 3H).

Example C22 Preparation of Compound C22

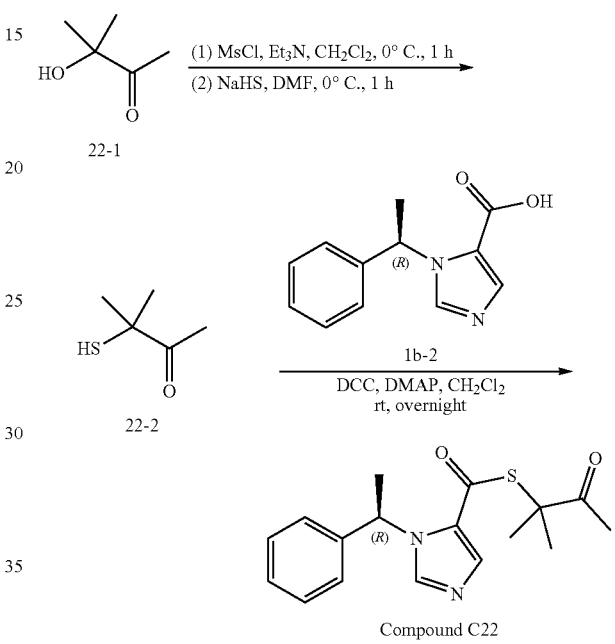

Compound C22

Compound 22-2 was prepared according to the general procedure C, using 22-1 (306 mg, 3.0 mmol) as the raw material. 124 mg of 22-2 (yield 35% for 2 steps) as colorless oil was obtained. ESI[M+H]$^+$=119.1

The title compound C22 was prepared according to the general procedure A, using 1b-2 (216 mg, 1.0 mmol) and 22-2 (124 mg, 1.0 mmol) as the raw materials. The crude product was purified by Prep-TLC (ethyl acetate/petroleum ether (v/v)=1/1) and the fraction with Rf=0.5~0.6 was collected and dried to give the title compound C22 (169 mg, yield 53%) as colorless oil. ESI[M+H]$^+$=317.2

$^1$H NMR (400 MHz, CDCl$_3$) δ 7.88 (s, 1H), 7.80 (s, 1H), 7.37-7.27 (m, 3H), 7.15-7.05 (m, 2H), 6.17 (q, J=7.1 Hz, 1H), 2.12 (s, 3H), 1.82 (d, J=7.1 Hz, 3H), 1.55 (s, 3H), 1.47 (s, 3H).

Example C23 Preparation of Compound C23

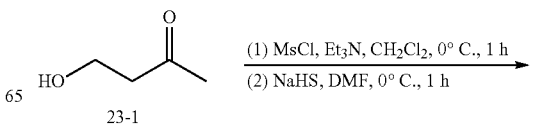

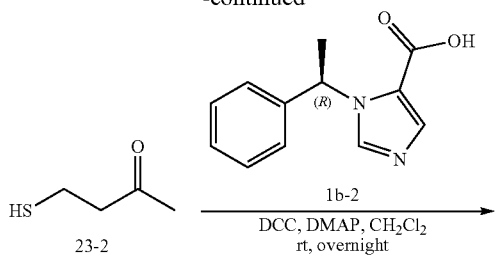

Compound 23-2 was prepared according to the general procedure C, using 23-1 (264 mg, 3.0 mmol) as the raw material. 165 mg of 23-2 (yield 53% for 2 steps) as colorless oil was obtained. ESI[M+H]⁺=105.1

The title compound C23 was prepared according to the general procedure A, using 1b-2 (216 mg, 1.0 mmol) and 23-2 (125 mg, 1.2 mmol) as the raw materials. The crude product was purified by Prep-TLC (ethyl acetate/petroleum ether (v/v)=1/1) and the fraction with Rf=0.4~0.5 was collected and dried to give the title compound C23 (247 mg, yield 82%) as colorless oil. ESI[M+H]⁺=303.2

$^1$H NMR (400 MHz, CDCl$_3$) δ 7.89 (s, 1H), 7.78 (s, 1H), 7.41-7.27 (m, 3H), 7.22-7.13 (m, 2H), 6.25 (q, J=7.1 Hz, 1H), 3.20-3.12 (m, 2H), 2.79 (t, J=6.7 Hz, 2H), 2.15 (s, 3H), 1.85 (d, J=7.1 Hz, 3H).

Example C24 Preparation of Compound C24

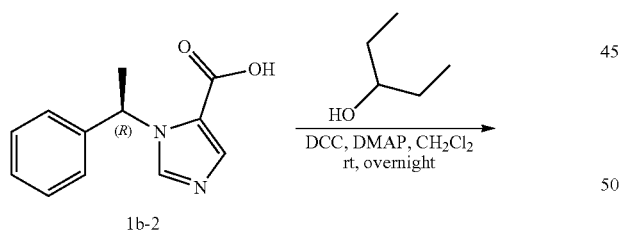

The title compound C24 was prepared according to the general procedure A, using 1b-2 (108 mg, 0.50 mmol) and pentan-3-ol (53 mg, 0.60 mmol) as the raw materials. The crude product was purified by Prep-TLC (ethyl acetate/petroleum ether (v/v)=1/1) and the fraction with Rf=0.5~0.6 was collected and dried to give the title compound C24 (98 mg, yield 68%) as colorless oil. ESI[M+H]⁺=287.1

$^1$H NMR (400 MHz, CDCl$_3$) δ 7.77 (d, J=0.6 Hz, 1H), 7.72 (s, 1H), 7.38-7.27 (m, 3H), 7.22-7.14 (m, 2H), 6.37 (q, J=7.1 Hz, 1H), 4.93-4.84 (m, 1H), 1.87 (d, J=7.1 Hz, 3H), 1.70-1.52 (m, 4H), 0.89 (t, J=7.4 Hz, 3H), 0.84 (t, J=7.5 Hz, 3H).

Example C25 Preparation of Compound C25

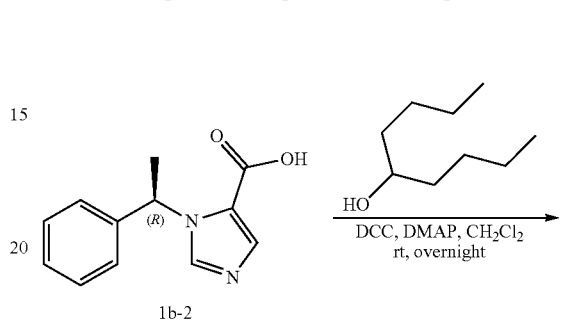

The title compound C25 was prepared according to the general procedure A, using 1b-2 (108 mg, 0.50 mmol) and nonan-5-ol (87 mg, 0.60 mmol) as the raw materials. The crude product was purified by Prep-TLC (ethyl acetate/petroleum ether (v/v)=1/1) and the fraction with Rf=0.5~0.6 was collected and dried to give the title compound C25 (132 mg, yield 77%) as a white solid. ESI[M+H]⁺=343.1

$^1$H NMR (400 MHz, CDCl$_3$) δ 7.77 (s, 2H), 7.38-7.27 (m, 3H), 7.22-7.12 (m, 2H), 6.38 (q, J=7.1 Hz, 1H), 5.07-4.95 (m, 1H), 1.87 (d, J=7.1 Hz, 3H), 1.65-1.49 (m, 4H), 1.38-1.13 (m, 8H), 0.95-0.77 (m, 6H).

Example C26 Preparation of Compound C26

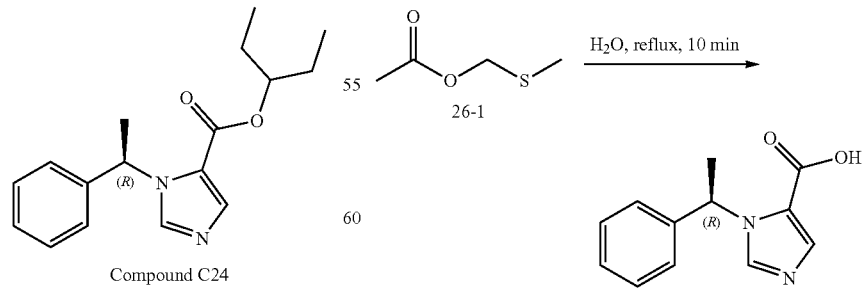

-continued

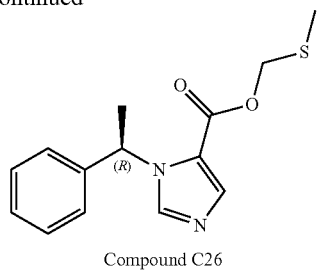

Compound C26

1. Preparation of (Methylthio)methanol (26-2)

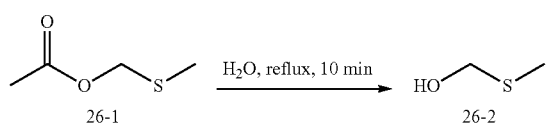

At room temperature, 26-1 (721 mg, 6.0 mmol) was dissolved in $H_2O$ (10 mL), then the mixture was heated to reflux for 10 min. The reaction was monitored by TLC until completion. The mixture was cooled and extracted with EtOAc (3×10 mL). The combined organic layers were washed with saturated brine (30 mL), dried over anhydrous sodium sulfate, filtered and concentrated under reduced pressure to give compound 26-2 (454 mg, crude) as colorless oil, which was used for next step directly without further purification.

2. Preparation of Compound C26

The title compound C26 was prepared according to the general procedure A, using 1b-2 (216 mg, 1.0 mmol) and 26-2 (78.0 mg, 1.0 mmol) as the raw materials. The crude product was purified by Prep-TLC (ethyl acetate/petroleum ether (v/v)=1/1) and the fraction with Rf=0.5~0.6 was collected and dried to give the title compound C26 (152 mg, yield 55%) as colorless oil. ESI[M+H]$^+$=277.3

$^1$H NMR (400 MHz, CDCl$_3$) δ 7.86 (s, 2H), 7.39-7.30 (m, 3H), 7.22-7.20 (m, 2H), 6.37 (q, J=7.2 Hz, 1H), 5.35 (d, J=11.6 Hz, 1H), 5.26 (d, J=11.6 Hz, 1H), 2.25 (s, 3H), 1.89 (d, J=7.2 Hz, 3H).

Example C27 Preparation of Compound C27

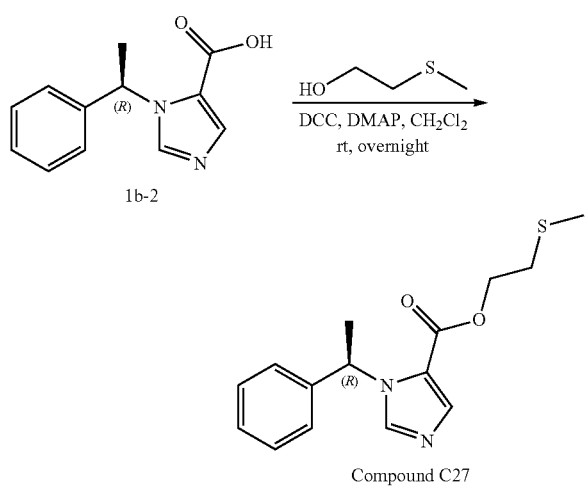

The title compound C27 was prepared according to the general procedure A, using 1b-2 (216 mg, 1.0 mmol) and 2-(methylthio)ethanol (92.0 mg, 1.0 mmol) as the raw materials. The crude product was purified by Prep-TLC (ethyl acetate/petroleum ether (v/v)=1/1) and the fraction with Rf=0.5~0.6 was collected and dried to give the title compound C27 (100 mg, yield 34%) as colorless oil. ESI [M+H]$^+$=291.2

$^1$H NMR (400 MHz, d$_6$-DMSO) δ 8.32 (s, 1H), 7.69 (s, 1H), 7.33 (t, J=7.3 Hz, 2H), 7.26 (t, J=7.3 Hz, 1H), 7.17 (d, J=7.2 Hz, 2H), 6.24 (d, J=7.2 Hz, 1H), 4.30 (qd, J=11.2, 4.6 Hz, 2H), 2.73 (t, J=6.6 Hz, 2H), 2.08 (s, 3H), 1.84 (d, J=7.2 Hz, 3H).

Example C28 Preparation of Compound C28

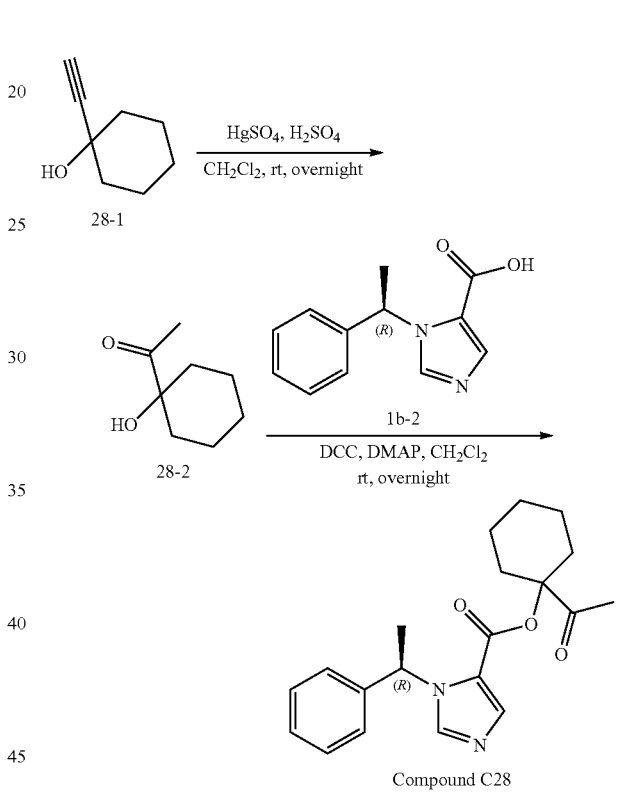

1. Preparation of 1-(1-Hydroxycyclohexyl)ethan-1-one (28-2)

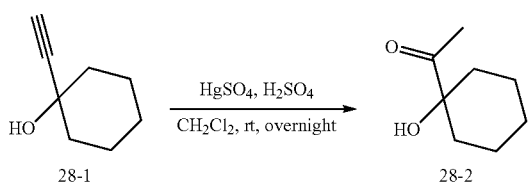

At room temperature, 28-1 (300 mg, 2.42 mmol) and HgSO$_4$/H$_2$SO$_4$/silica gel (1 g) were dissolved in dichloromethane (10 mL), then the mixture was stirred at room temperature overnight. The reaction was monitored by TLC until completion, then it was quenched with saturated sodium bicarbonate solution and extracted with dichloromethane (3×10 mL). The combined organic layers were washed with saturated brine (30 mL), dried over anhydrous sodium sulfate, filtered and concentrated under reduced pressure to give compound 28-2 (123 mg, crude) as colorless oil, which was used for next step directly without further purification. ESI[M+H]$^+$=143.1

2. Preparation of Compound C28

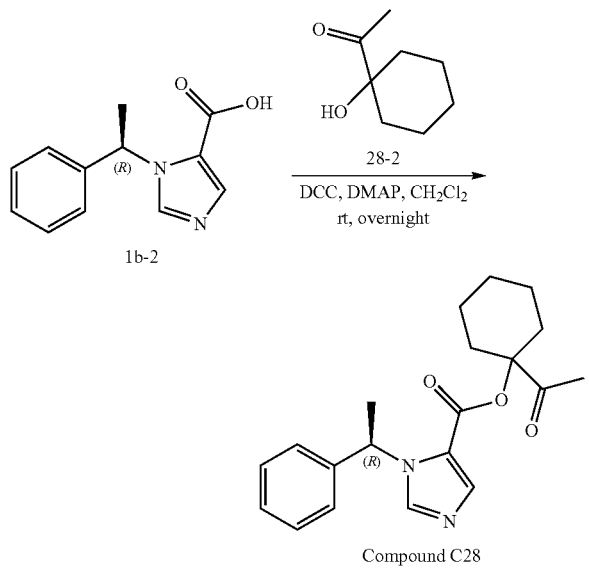

The title compound C28 was prepared according to the general procedure A, using 1b-2 (43 mg, 0.20 mmol) and 28-2 (123 mg, 1.1 mmol) as the raw materials. The crude product was purified by Prep-TLC (ethyl acetate/petroleum ether (v/v)=1/1) and the fraction with Rf=0.4~0.6 was collected and dried to give the title compound C28 (22 mg, yield 32%) as colorless oil. ESI[M+H]$^+$=341.2

$^1$H NMR (400 MHz, CDCl$_3$) δ 7.95 (s, 1H), 7.90 (s, 1H), 7.40-7.26 (m, 3H), 7.18-7.07 (m, 2H), 6.28 (q, J=7.1 Hz, 1H), 2.17-1.95 (m, 2H), 1.89 (s, 3H), 1.87 (d, J=7.2 Hz, 3H), 1.80-1.41 (m, 7H), 1.39-1.18 (m, 1H).

Example C29 Preparation of Compound C29

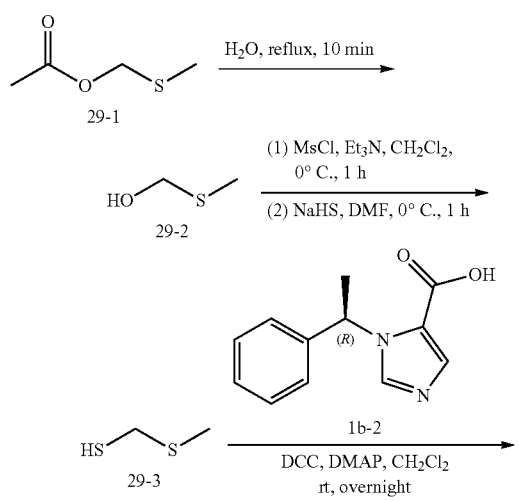

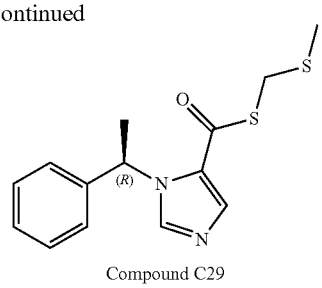

Compound C29

1. Preparation of (Methylthio)methanol (29-2)

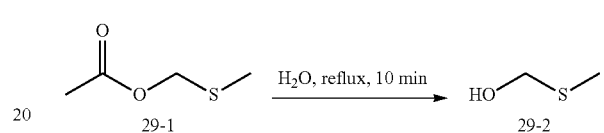

At room temperature, 29-1 (721 mg, 6.0 mmol) was dissolved in H$_2$O (10 mL), then the mixture was heated to reflux for 10 min. The reaction was monitored by TLC until completion. The mixture was cooled and extracted with EtOAc (3×10 mL). The combined organic layers were washed with saturated brine (30 mL), dried over anhydrous sodium sulfate, filtered and concentrated under reduced pressure to give compound 29-2 (454 mg, crude) as colorless oil, which was used for next step directly without further purification.

2. Preparation of (Methylthio)methanethiol (29-3)

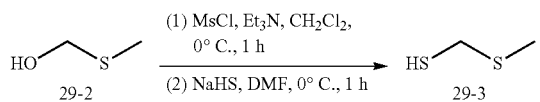

The compound 29-3 was prepared according to the general procedure C, using 29-2 (454 mg, 5.8 mmol) as the raw material. 214 mg of crude compound 29-3 (yield 39% for 3 steps) as colorless oil was obtained, which was used for next step directly without further purification.

3. Preparation of Compound C29

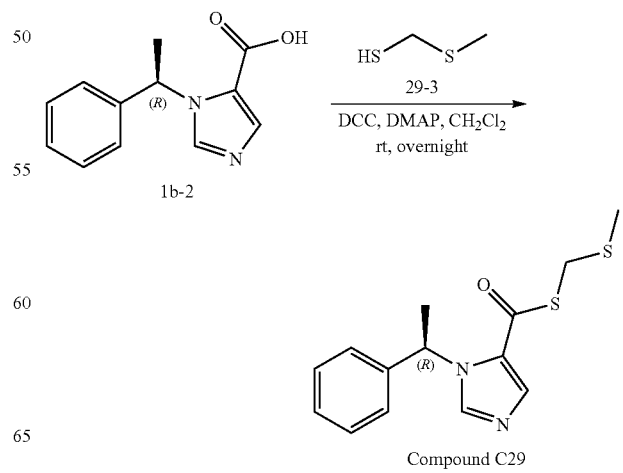

Compound C29

The title compound C29 was prepared according to the general procedure A, using 1b-2 (216 mg, 1.0 mmol) and 29-3 (79 mg, 1.2 mmol) as the raw materials. The crude product was purified by Prep-TLC (ethyl acetate/petroleum ether (v/v)=1/1) and the fraction with Rf=0.5~0.6 was collected and dried to give the title compound C29 (76 mg, yield 26%) as colorless oil. ESI[M+H]$^+$=293.2 $^1$H NMR (400 MHz, CDCl$_3$) δ 7.80 (s, 2H), 7.44-7.32 (m, 3H), 7.33-7.27 (m, 2H), 6.07 (q, J=7.4 Hz, 1H), 4.35-4.16 (m, 1H), 4.06-3.84 (m, 1H), 1.93 (d, J=7.1 Hz, 6H).

Example C30 Preparation of Compound C30

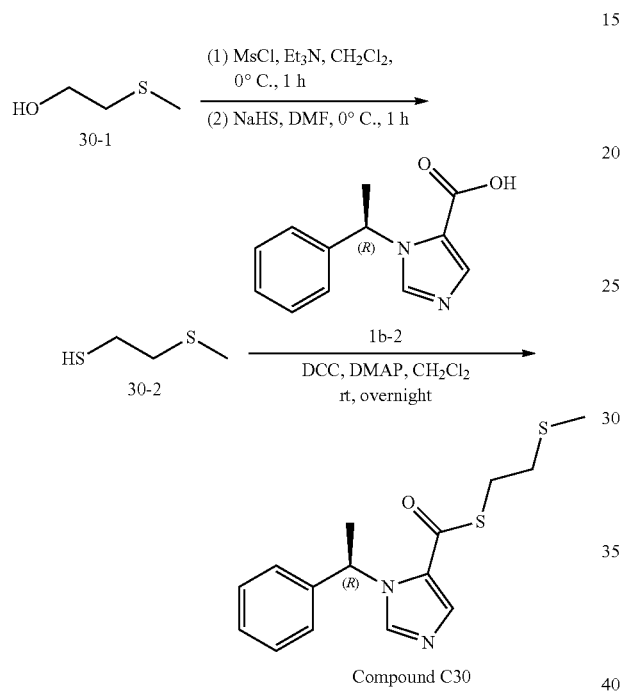

Compound C30

The compound 30-2 was prepared according to the general procedure C, using 30-1 (276 mg, 3.0 mmol) as the raw material. 123 mg of 30-2 (yield 38% for 2 steps) as colorless oil was obtained. ESI[M+H]$^+$=109.1

The title compound C30 was prepared according to the general procedure A, using 1b-2 (216 mg, 1.0 mmol) and 30-2 (123 mg, 1.1 mmol) as the raw materials. The crude product was purified by Prep-TLC (ethyl acetate/petroleum ether (v/v)=1/1) and the fraction with Rf=0.5~0.6 was collected to give the title compound C30 (89 mg, yield 29%) as colorless oil. ESI[M+H]$^+$=307.1

$^1$H NMR (400 MHz, CDCl$_3$) δ 7.91 (s, 1H), 7.74 (s, 1H), 7.40-7.26 (m, 3H), 7.21-7.14 (m, 2H), 6.26 (q, J=7.1 Hz, 1H), 3.37-2.95 (m, 2H), 2.76-2.59 (m, 2H), 2.18 (s, 3H), 1.85 (d, J=7.1 Hz, 3H).

Example D1 Preparation of Compound D1

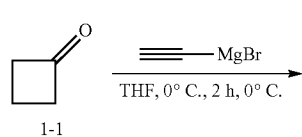

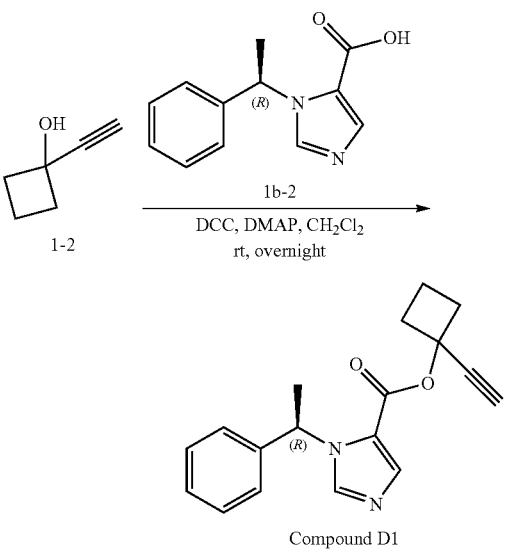

Compound D1

1. Preparation of 1-ethynylcyclobutan-1-ol (1-2)

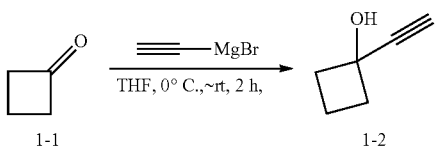

Cyclobutanoe (1-1) (700.6 mg, 10.0 mmol) was dissolved in the anhydrous THF (10 mL) under nitrogen atmosphere and the mixture was cooled to 0° C. by an ice-water bath. Ethynylmagnesium bromide (26 mL, 1.3 mol/L in THF, 13 mmol) was added slowly into the reaction solution over a 25-min period using a syringe at 0° C., then it was allowed to react for 2 hrs at room temperature. The reaction was monitored by TLC until completion. The mixture was quenched with saturated ammonium chloride solution (30 mL) and extracted with dichloromethane (3×10 mL). The combined organic layers were washed with saturated brine (50 mL), dried over anhydrous sodium sulfate, filtered and concentrated under reduced pressure to give crude product 1-2, which was used for next step directly without further purification.

2. Preparation of Compound D1

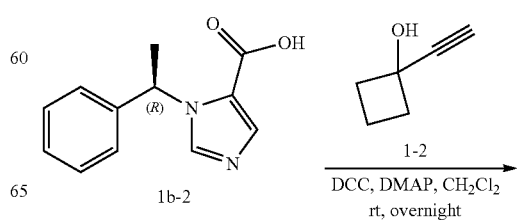

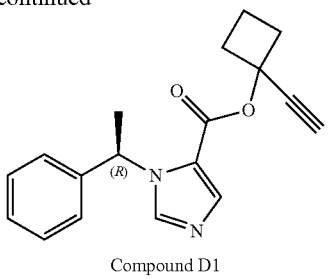

Compound D1

The title compound D1 was prepared according to the general procedure A, using 1b-2 (432 mg, 2.0 mmol) and 1-2 as raw materials. The crude product was purified by Prep-TLC (ethyl acetate/petroleum ether (v/v)=1/1) and the fraction with Rf=0.4~0.5 was collected and dried to give the title compound D1 (519 mg, yield 88%) as a white solid. ESI[M+H]$^+$=295.3

Example D2 Preparation of Compound D2

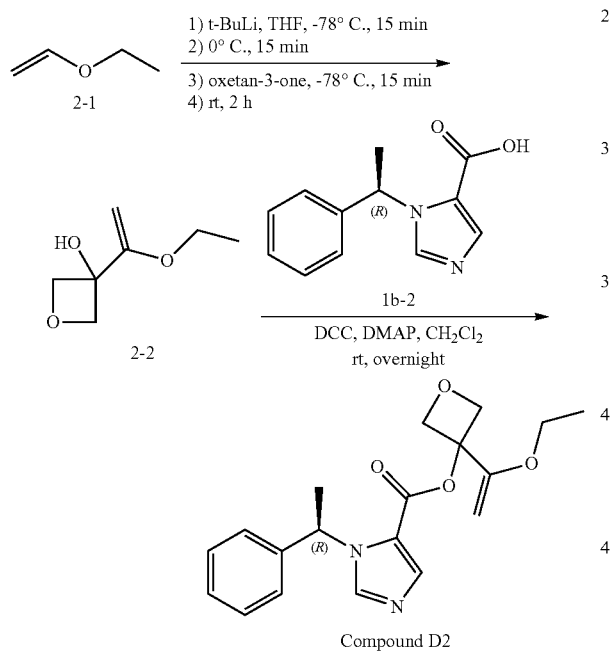

Compound D2

1. Preparation of 3-(1-Ethoxyvinyl)oxetan-3-ol (2-2)

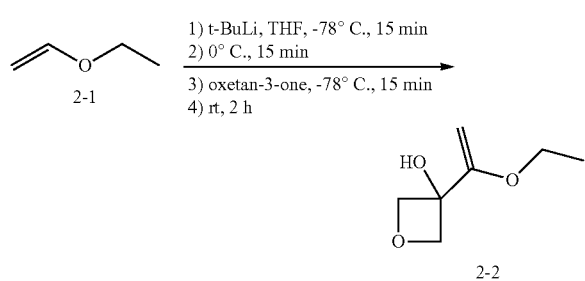

Ethoxyethene (2-1) (3.60 g, 50.0 mmol) was dissolved in the anhydrous THF (20 mL) under nitrogen atmosphere and the mixture was cooled to −78° C. by a dry ice-acetone bath. Then t-BuLi (20 mL, 1.0 mol/L in pentane, 20 mmol) was added slowly into the mixture over a 5-min period using a syringe under −70° C. The mixture was stirred at −78° C. for 15 min, then the dry ice-acetone bath was replaced with an ice-water bath and continued to react for 15 min. The mixture temperature was cooled down to −78° C. by a dry ice-acetone bath, and then oxetan-3-one (720.6 mg, 10.0 mmol) in anhydrous THF (20 mL) was added slowly into the reaction solution over a 10-min period. The mixture was warmed to room temperature slowly and allowed to react for 2 hrs. The reaction was monitored by TLC until completion. The mixture was quenched with the saturated ammonium chloride solution (30 mL) and extracted with dichloromethane (3×10 mL). The combined organic layers were washed with saturated brine (50 mL), dried over anhydrous sodium sulfate, filtered and concentrated under reduced pressure. The crude product was purified by silica gel column chromatography (ethyl acetate/petroleum ether (v/v) at any ratio within the range of 1/5 to 1/3), with TLC (ethyl acetate/petroleum ether (v/v)=1/3) monitoring, and collecting the fraction with Rf=0.4~0.5, to give product 2-2 (545 mg, yield 8%) as colorless oil.

2. Preparation of Compound D2

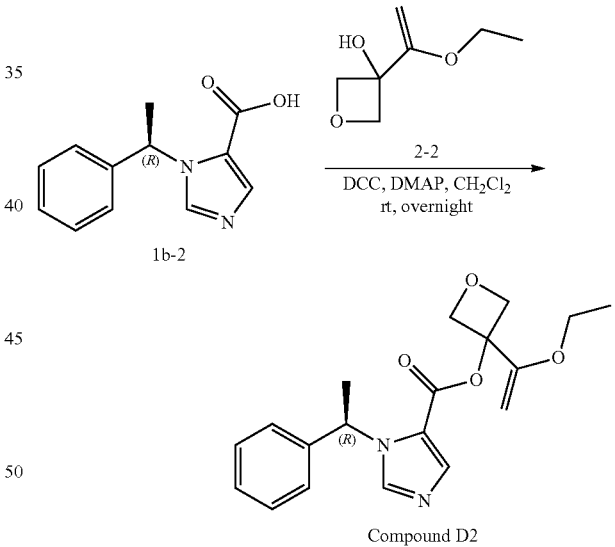

Compound D2

The title compound was prepared according to the general procedure A, using 1b-2 (324 mg, 1.50 mmol) and 2-2 (545 mg) as raw materials. The crude product was purified by Prep-TLC (ethyl acetate/petroleum ether (v/v)=1/1) and the fraction with Rf=0.3~0.4 was collected and dried to give the compound D2 (98 mg, yield 19%) as a white solid. ESI[M+H]$^+$=343.3

$^1$H NMR (400 MHz, CDCl$_3$) δ 7.90 (d, J=0.7 Hz, 1H), 7.79 (s, 1H), 7.38-7.27 (m, 3H), 7.20-7.11 (m, 2H), 6.27 (q, J=7.1 Hz, 1H), 4.96 (dd, J=12.1, 7.5 Hz, 2H), 4.83 (d, J=7.2 Hz, 1H), 4.74 (d, J=7.4 Hz, 1H), 4.14 (d, J=3.2 Hz, 1H), 4.08 (d, J=3.2 Hz, 1H), 3.81 (q, J=7.0 Hz, 2H), 1.86 (d, J=7.1 Hz, 3H), 1.32 (t, J=7.0 Hz, 3H).

Example D3 Preparation of Compound D3

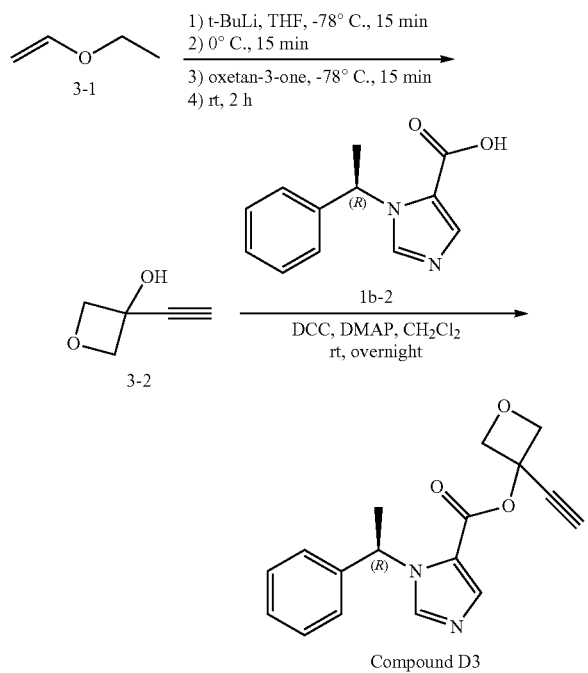

1. Preparation of 3-Ethynyloxetan-3-ol (3-2)

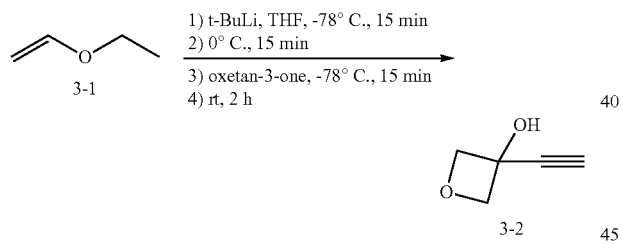

Ethoxyethene (3-1) (3.60 g, 50.0 mmol) was dissolved in the anhydrous THF (20 mL) under nitrogen atmosphere and the mixture was cooled to −78° C. by a dry ice-acetone bath. Then t-BuLi (20 mL, 1.0 mol/L in pentane, 20 mmol) was added slowly into the mixture over a 5-min period using a syringe under −70° C. The mixture was stirred at −78° C. for 15 min, then the dry ice-acetone bath was replaced with an ice-water bath and continued to react for 15 min. The mixture temperature was cooled down to −78° C. by a dry ice-acetone bath, and then oxetan-3-one (720.6 mg, 10.0 mmol) in anhydrous THF (20 mL) was added slowly into the reaction solution over a 10-min period. The mixture was warmed to room temperature slowly and allowed to react for 2 hrs. The reaction was monitored by TLC until completion. The mixture was quenched with the saturated ammonium chloride solution (30 mL) and extracted with dichloromethane (3×10 mL). The combined organic layers were washed with saturated brine (50 mL), dried over anhydrous sodium sulfate, filtered and concentrated under reduced pressure. The crude product was purified by silica gel column chromatography (ethyl acetate/petroleum ether (v/v) at any ratio within the range of 1/5 to 1/3), with TLC (ethyl acetate/petroleum ether (v/v)=1/3) monitoring, and collecting the fraction with Rf=0.5~0.6, to give product 3-2 (365 mg, yield 8%) as colorless oil.

2. Preparation of Compound D3

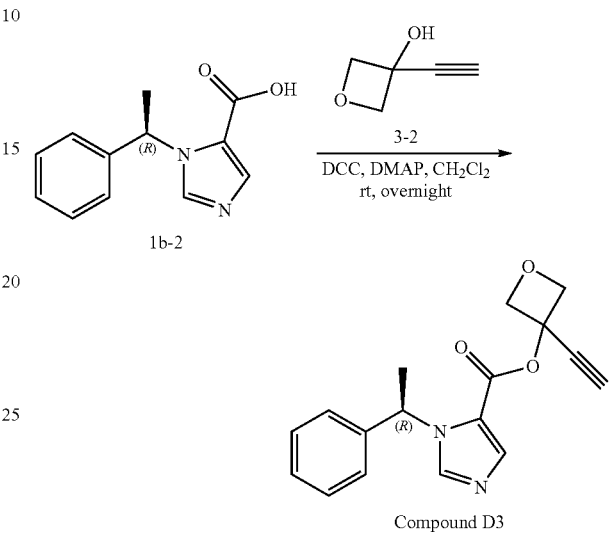

The title compound was prepared according to the general procedure A, using 1b-2 (324 mg, 1.50 mmol) and 3-2 as raw materials. The crude product was purified by Prep-TLC (ethyl acetate/petroleum ether (v/v)=1/1) and the fraction with Rf=0.3~0.4 was collected and dried to give the compound D3 (27 mg, yield 8.3%) as a white solid. ESI[M+H]$^+$=297.3

$^1$H NMR (400 MHz, CDCl$_3$) δ 8.09 (s, 1H), 7.93 (s, 1H), 7.42-7.35 (m, 3H), 7.25-7.21 (m, 2H), 6.35 (q, J=7.0 Hz, 1H), 4.96 (dd, J=7.5, 3.9 Hz, 2H), 4.88 (d, J=7.5 Hz, 1H), 4.77 (d, J=7.6 Hz, 1H), 2.82 (s, 1H), 1.91 (d, J=7.1 Hz, 3H).

Example D4 Preparation of Compound D4

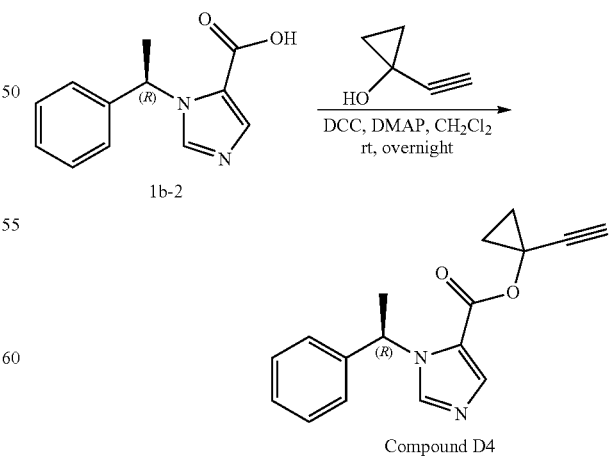

The title compound was prepared according to the general procedure A, using 1b-2 (216 mg, 1.0 mmol) and 1-ethynylcyclopropan-1-ol (82 mg, 1.0 mmol) as raw materials. The crude product was purified by Prep-TLC (ethyl acetate/petroleum ether (v/v)=1/1) and the fraction with Rf=0.4~0.5 was collected and dried to give the compound D4 (87 mg, yield 31%) as a white solid. ESI[M+H]$^+$=281.2

Example D5 Preparation of Compound D5

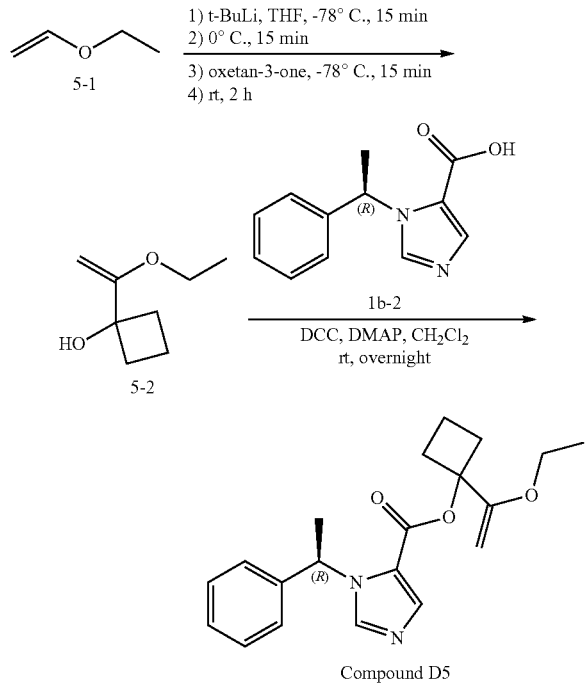

1. Preparation of 1-(1-Ethoxyvinyl)cyclobutan-1-ol (5-2)

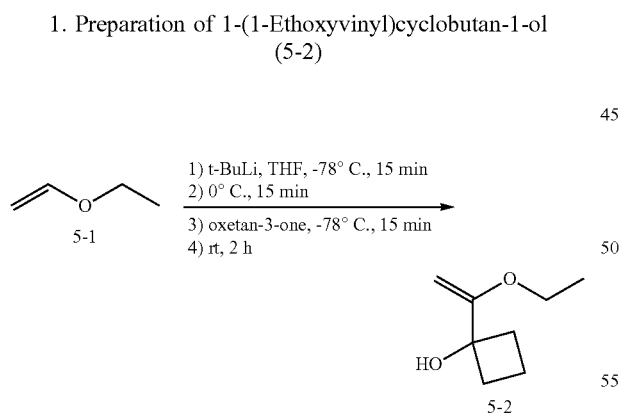

The preparation method of compound 5-2 was the same as compound 2-2 using cyclobutanoe (700.9 mg, 10.0 mmol) as raw materials. The residue was purified by silica gel column chromatography (ethyl acetate/petroleum ether (v/v) at any ratio within the range of 1/5 to 1/3), with TLC (ethyl acetate/petroleum ether (v/v)=1/3) monitoring, and collecting the fraction with Rf=0.5~0.6, to give compound 3-2 (415 mg, yield 29%) as colorless oil.

2. Preparation of Compound D5

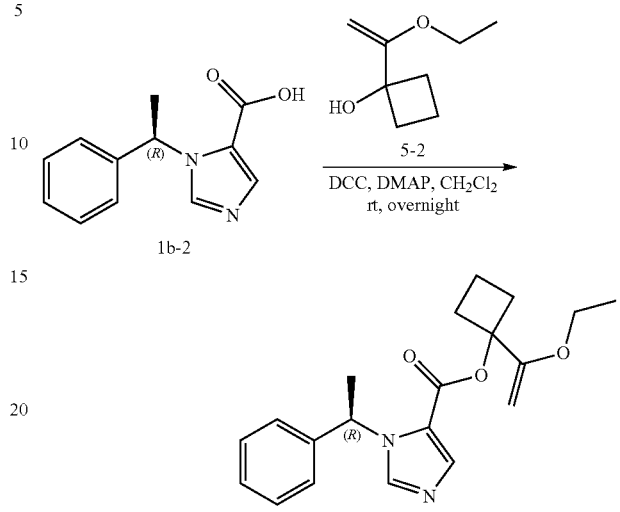

The title compound was prepared according to the general procedure A, using 1b-2 (216 mg, 1.0 mmol) and 5-2 (142 mg, 1.0 mmol) as raw materials. The crude product was purified by Prep-TLC (ethyl acetate/petroleum ether (v/v)=1/1) and the fraction with Rf=0.3~0.4 was collected and dried to give the title compound D5 (18 mg, yield 5%) as a white solid. ESI[M+H]$^+$=341.3

Example D6 Preparation of Compound D6

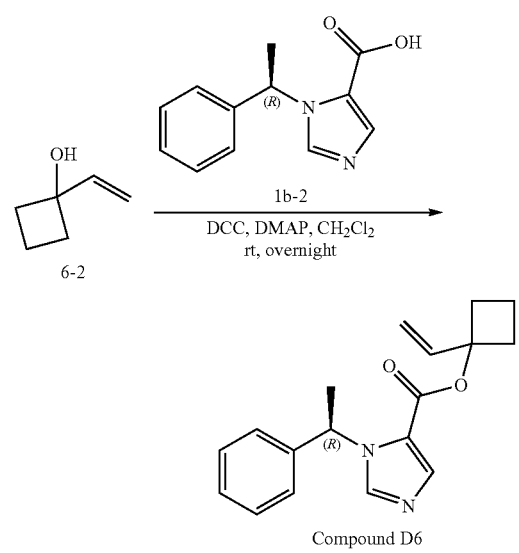

1. Preparation of 1-vinylcyclobutan-1-ol (6-2)

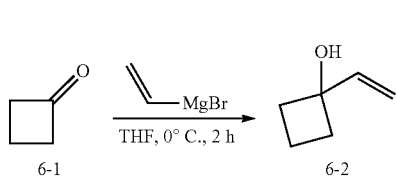

Cyclobutanoe (6-1) (140 mg, 2.0 mmol) was dissolved in the anhydrous THF (10 mL) under nitrogen atmosphere and the mixture was cooled to 0° C. by an ice-water bath. Vinylmagnesium bromide (2.0 mL, 1.3 mol/L in THF, 2.6 mmol) was added slowly into the reaction mixture over a 5-min period using a syringe at 0° C. and the mixture was allowed to react at 0° C. for 2 hrs. The reaction was monitored by TLC until completion. The mixture was quenched with the saturated ammonium chloride solution (10 mL) and extracted with dichloromethane (3×10 mL). The combined organic layers were washed with saturated brine (50 mL), dried over anhydrous sodium sulfate, filtered and concentrated under reduced pressure to give crude compound 6-2 as colorless oil, which was used for next step directly without further purification.

2. Preparation of Compound D6

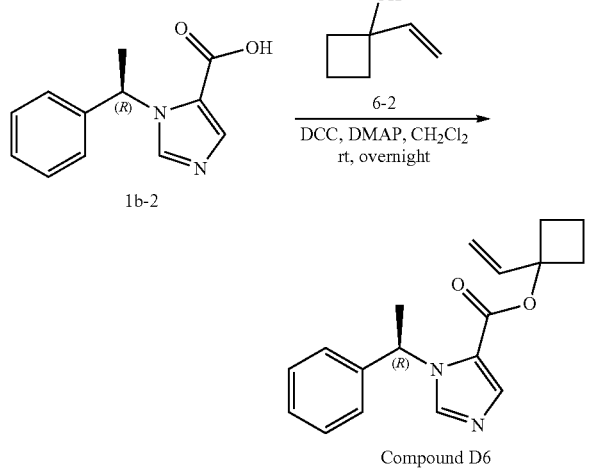

The title compound was prepared according to the general procedure A, using 1b-2 (216 mg, 1.0 mmol) and 6-2 as raw materials The crude product was purified by Prep-TLC (ethyl acetate/petroleum ether (v/v)=1/1) and the fraction with Rf=0.3~0.4 was collected and dried to give the title compound D6 (54 mg, yield 18%) as a white solid. ESI[M+H]$^+$=297.1

$^1$H NMR (400 MHz, CDCl$_3$) δ 7.78 (s, 1H), 7.73 (s, 1H), 7.38-7.27 (m, 3H), 7.22-7.16 (m, 2H), 6.34 (q, J=7.1 Hz, 1H), 6.16 (dd, J=17.4, 10.8 Hz, 1H), 5.27~5.13 (m, 2H), 2.49-2.35 (m, 4H), 1.94-1.86 (m, 1H), 1.85 (d, J=7.1 Hz, 3H), 1.79~1.68 (m, 1H).

Example D7 Preparation of Compound D7

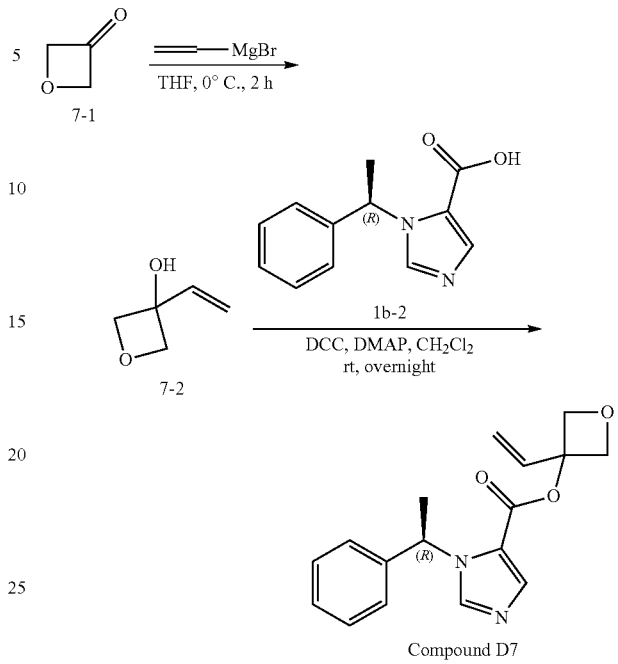

1. Preparation of 3-vinyloxetan-3-ol (7-2)

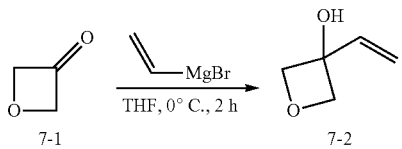

Oxetan-3-one (7-1) (144 mg, 2.0 mmol) was dissolved in the anhydrous THF (10 mL) under nitrogen atmosphere and the mixture was cooled to 0° C. by an ice-water bath. Vinylmagnesium bromide (2.0 mL, 1.3 mol/L in THF, 2.6 mmol) was added slowly into the reaction mixture over a 15-min period using a syringe at 0° C. and the mixture was allowed to react at 0° C. for 2 hrs. The reaction was monitored by TLC until completion. The mixture was quenched with the saturated ammonium chloride solution (30 mL) and extracted with dichloromethane (3×10 mL). The combined organic layers were washed with saturated brine (50 mL), dried over anhydrous sodium sulfate, filtered and concentrated under reduced pressure to give crude compound 7-2 as colorless oil, which was used for next step directly without further purification.

2. Preparation of Compound D7

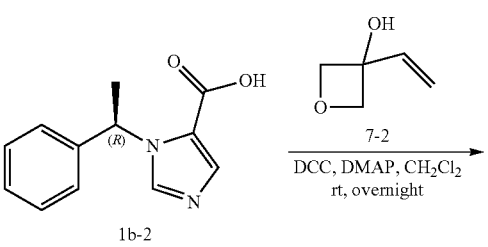

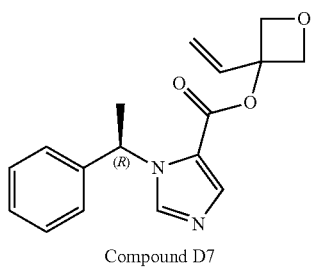

Compound D7

The title compound was prepared according to the general procedure A, using 1b-2 (216 mg, 1.0 mmol) and 7-2 as raw materials. The crude product was purified by Prep-TLC (ethyl acetate/petroleum ether (v/v)=1/1) and the fraction with Rf=0.4~0.5 was collected and dried to give the title compound D7 (61 mg, two steps yield 20%) as a white solid. ESI[M+H]$^+$=299.2

$^1$H NMR (400 MHz, d$_6$-DMSO) δ 8.36-8.32 (m, 1H), 7.81 (d, J=0.7 Hz, 1H), 7.35~7.31 (m, 2H), 7.28-7.25 (m, 1H), 7.14-7.13 (m, 2H), 6.28-5.98 (m, 2H), 5.18 (t, J=14.5 Hz, 2H), 4.78 (d, J=7.5 Hz, 1H), 4.66~4.63 (m, 3H), 1.84 (d, J=7.2 Hz, 3H).

Example D8 Preparation of Compound D8

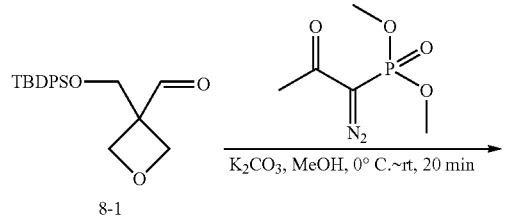

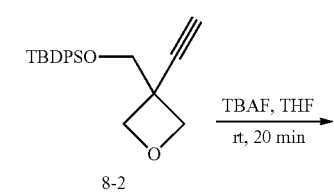

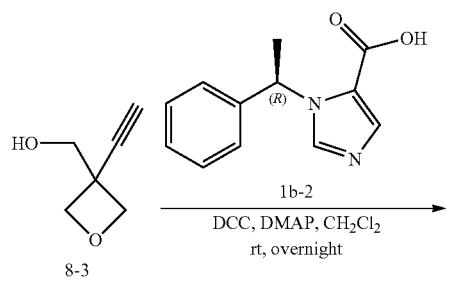

Compound D8

1. Preparation of Tert-butyl((3-ethynyloxetan-3-yl)methoxy) diphenylsilane (8-2)

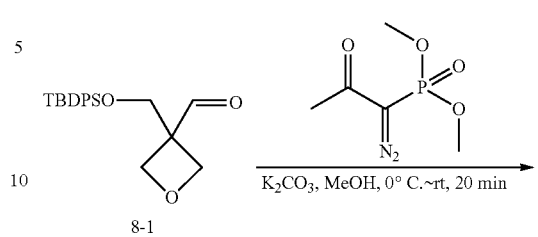

8-1 (300 mg, 0.85 mmol), dimethyl (1-diazo-2-oxopropyl)phosphonate (211 mg, 1.1 mmol) and K$_2$CO$_3$ (470 mg, 3.4 mmol) were dissolved in MeOH (30 mL) at 0° C., then it was warmed to room temperature slowly and allowed to react for 20 min. The reaction was monitored by TLC until completion. The mixture was filtered and the filter cake was washed with ethyl acetate (20 mL). The filtrate was concentrated under reduced pressure and the residue was purified by silica gel column chromatography (ethyl acetate/petroleum ether (v/v) at any ratio within the range of 1/20 to 1/10), with TLC (ethyl acetate/petroleum ether (v/v)=1/10) monitoring, and collecting the fraction with Rf=0.5~0.6, to give the product 8-2 (280 mg, yield 94.0%) as colorless oil.

2. Preparation of (3-Ethynyloxetan-3-yl)methanol (8-3)

At room temperature, TBAF (1.60 mL, 1 mol/L in THF, 1.60 mmool) was added into the solution of 8-2 (280 mg, 0.80 mmol) in THF (10 mL) and the mixture was allowed to react at room temperature for 20 min. The reaction was monitored by TLC until completion. The mixture was concentrated under reduced pressure to give crude compound 8-3 (350 mg) as colorless oil, which was used for next step directly without further purification.

3. Preparation of Compound D8

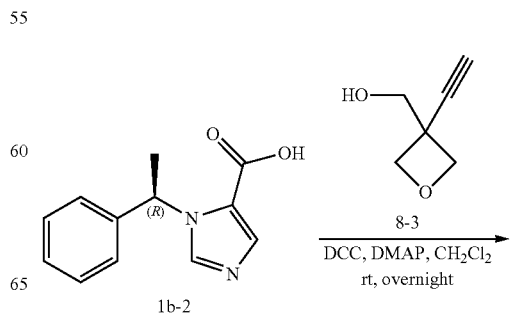

209

-continued

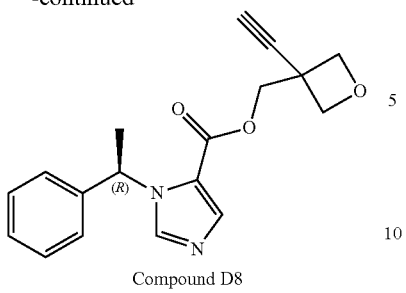

Compound D8

The title compound was prepared according to the general procedure A, using 1b-2 (324 mg, 1.5 mmol) and 8-3 as raw materials. The crude product was purified by Prep-TLC (ethyl acetate/petroleum ether (v/v)=1/1) and the fraction with Rf=0.5~0.6 was collected and dried to give the product D8 (153 mg, yield 33%) as colorless oil. ESI[M+H]$^+$=311.2

$^1$H NMR (400 MHz, CDCl$_3$) δ 7.85 (s, 1H), 7.79 (s, 1H), 7.42-7.28 (m, 3H), 7.18 (d, J=7.1 Hz, 2H), 6.34 (q, J=7.1 Hz, 1H), 4.81 (dd, J=5.9, 3.5 Hz, 2H), 4.54-4.51 (m, 4H), 2.39 (s, 1H), 1.88 (d, J=7.1 Hz, 3H).

Example D9 Preparation of Compound D9

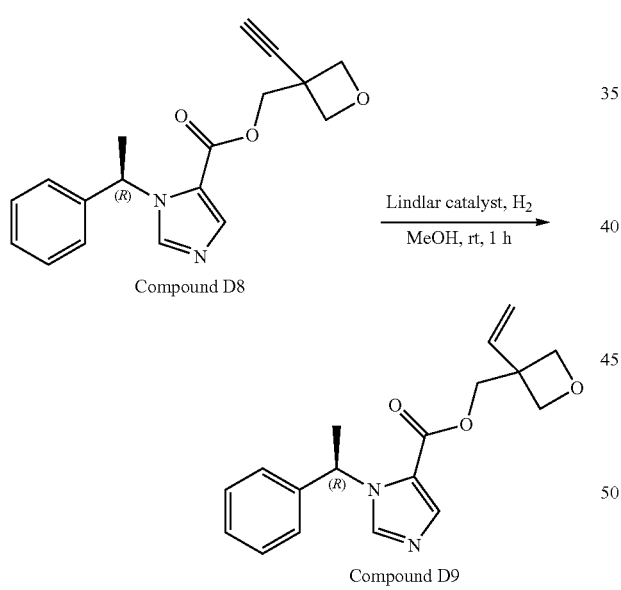

Compound D8 (93 mg, 0.3 mmol) and Lindlar catalyst (9 mg) were dissolved in methanol (10 mL). The mixture was replaced three times with hydrogen, then it was allowed to react at room temperature for 1 hour under hydrogen. The reaction was monitored by TLC until completion. The mixture was concentrated under reduced pressure and the residue was purified by Prep-TLC (ethyl acetate/petroleum ether (v/v)=1/1) and the fraction with Rf=0.4~0.5 was collected and dried to give the product D9 (63 mg, yield 67%) as colorless oil. ESI[M+H]$^+$=313.2

210

Example D10 Preparation of Compound D10

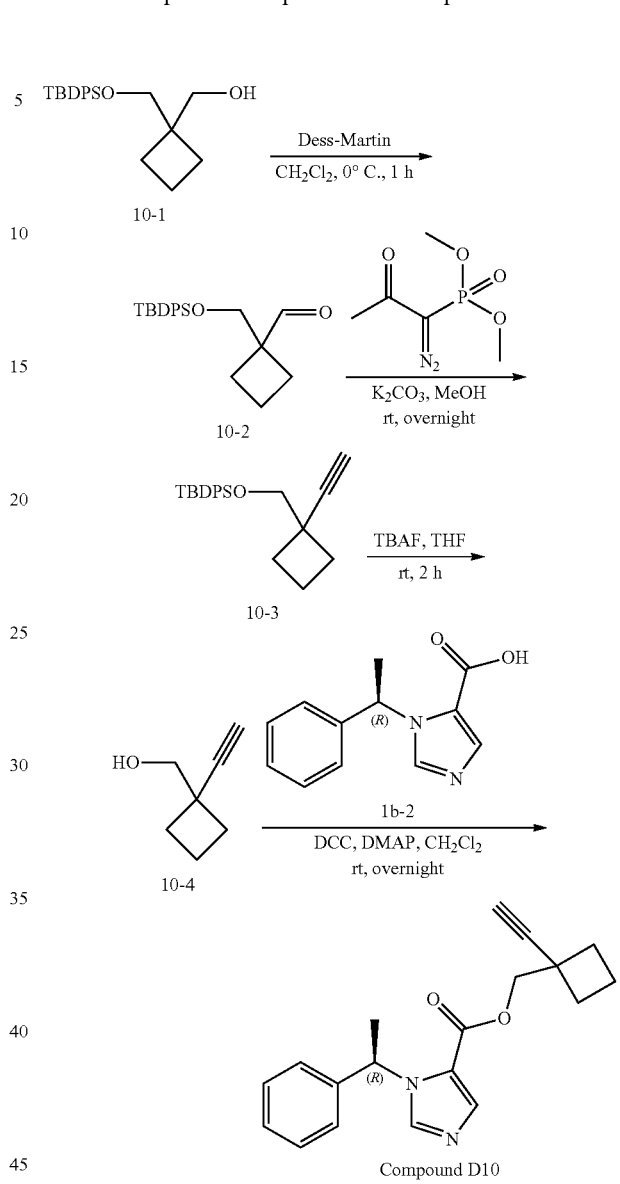

1. Preparation of 1-(((Tert-butyldiphenylsilyl)oxy)methyl)cyclobutane-1-carbaldehyde (10-2)

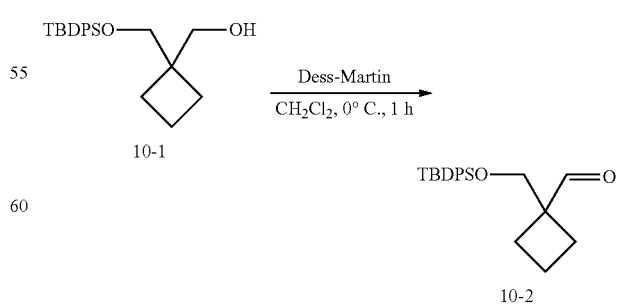

Dess-Martin (12.72 g, 30.0 mmol) was added in portions into the solution of compound 10-1 (5.31 g, 15.0 mmol) in dichloromethane (50 mL) at the rate of 5 mmol/1 min at 0° C., then the mixture was allowed to react for 1 hour. The reaction was monitored by TLC until completion. The mixture was filtered and the filter cake was washed with dichloromethane (50 mL). The filtrate was alkalinized with saturated NaHCO₃ solution and washed saturated brine (50 mL), dried over anhydrous sodium sulfate, filtered and concentrated under reduced pressure. The residue was purified by silica gel column chromatography (ethyl acetate/petroleum ether (v/v) at any ratio within the range of 1/20 to 1/10), with TLC (ethyl acetate/petroleum ether (v/v)=1/10) monitoring, and collecting the fraction with Rf=0.4~0.5, to give product 10-2 (4.58 g, yield 87%) as colorless oil.

2. Preparation of Tert-butyl((1-ethynylcyclobutyl)methoxy)diphenylsilane(10-3)

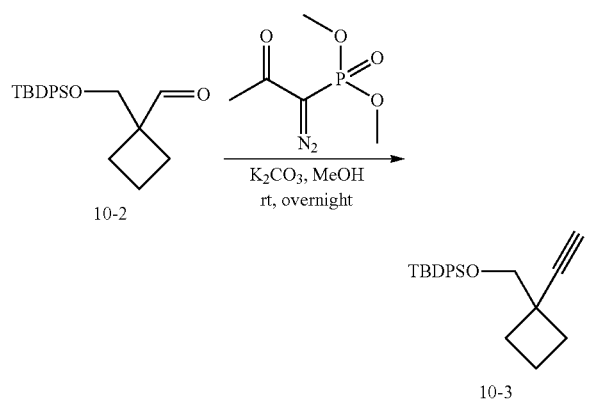

Compound 10-2 (528 mg, 1.5 mmol), dimethyl (1-diazo-2-oxopropyl)phosphonate (384 mg, 2.0 mmol) and K₂CO₃ (829 mg, 6.0 mmol) were dissolved in MeOH (50 mL) at 0° C. The mixture was warmed to room temperature slowly, then it was allowed to react at this temperature for 20 min. The reaction was monitored by TLC until completion. The mixture was filtered and the filter cake was washed with ethyl acetate (30 mL). The filtrate was concentrated under reduced pressure to give crude compound 10-3, which was used for next step directly without further purification.

3. Preparation of (1-Ethynylcyclobutyl)methanol (10-4)

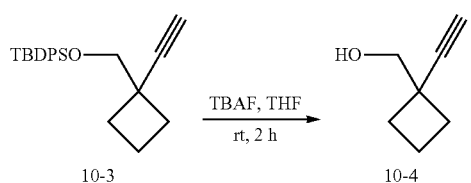

At room temperature, TBAF (3.0 mL, 1 mol/L in THF, 3.0 mmol) was added into the solution of 10-3 in THF (15 mL) and the mixture was allowed to react at room temperature for 2 hrs. The reaction was monitored by TLC until completion, then it was concentrated under reduced pressure. The residue was purified by silica gel column chromatography (ethyl acetate/petroleum ether (v/v) at any ratio within the range of 1/5 to 1/1), with TLC (ethyl acetate/petroleum ether (v/v)= 1/1) monitoring, and collecting the fraction with Rf=0.5~0.6, to give compound 10-4 (85 mg, two steps yield 51%) as colorless oil.

4. Preparation of Compound D10

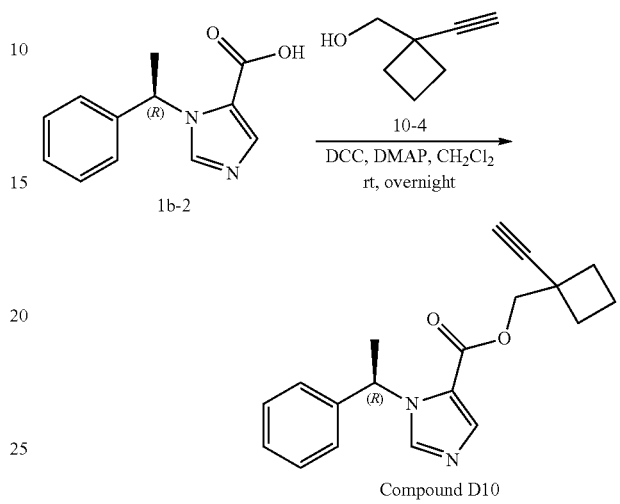

The title compound was prepared according to the general procedure A, using 1b-2 (216 mg, 1.0 mmol) and 10-4 (85 mg, 0.77 mmol) as raw materials. The crude product was purified by Prep-TLC (ethyl acetate/petroleum ether (v/v)= 1/1) and the fraction with Rf=0.5~0.6 was collected and dried to give the product D10 (183 mg, yield 59%) as colorless oil. ESI[M+H]⁺=309.3

¹H NMR (400 MHz, CDCl₃) δ 7.85 (s, 1H), 7.77 (s, 1H), 7.40-7.27 (m, 3H), 7.23-7.15 (m, 2H), 6.37 (q, J=7.1 Hz, 1H), 4.43-4.14 (m, 2H), 2.37-2.26 (m, 2H), 2.25 (s, 1H), 2.20-2.02 (m, 3H), 2.02-1.90 (m, 1H), 1.87 (d, J=7.1 Hz, 3H).

Example D11 Preparation of Compound D11

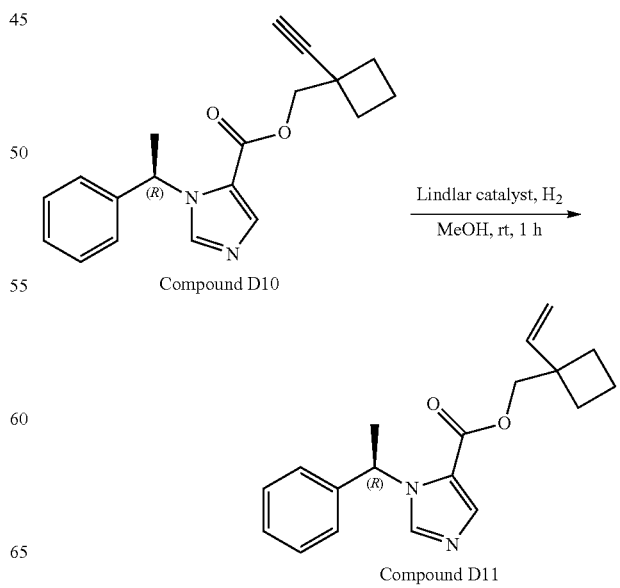

The compound D10 (93 mg, 0.3 mmol) and Lindlar catalyst (9 mg) were dissolved in methanol (10 mL). The mixture was replaced three times with hydrogen, then it was allowed to react at room temperature for 1 hour under hydrogen. The reaction was monitored by TLC until completion. The mixture was concentrated under reduced pressure and the residue was purified by Prep-TLC (ethyl acetate/petroleum ether (v/v)=1/1) and the fraction with Rf=0.4~0.5 was collected and dried to give the product D11 (48 mg, yield 52%) as colorless oil. ESI[M+H]$^+$=311.2

$^1$H NMR (400 MHz, CDCl$_3$) δ 7.85 (s, 1H), 7.79 (s, 1H), 7.42-7.28 (m, 3H), 7.18 (d, J=7.1 Hz, 2H), 6.34 (q, J=7.1 Hz, 1H), 5.86 (dd, J=10.5 Hz, 1H), 5.18 (dd, J=1.5 Hz, J=1.3 Hz, 1H), 5.11 (dd, J=1.3 Hz, 1H), 4.17 (s, 2H), 2.05-1.82 (m, 6H), 1.87 (d, J=7.1 Hz, 3H).

Example D12 Preparation of Compound D12

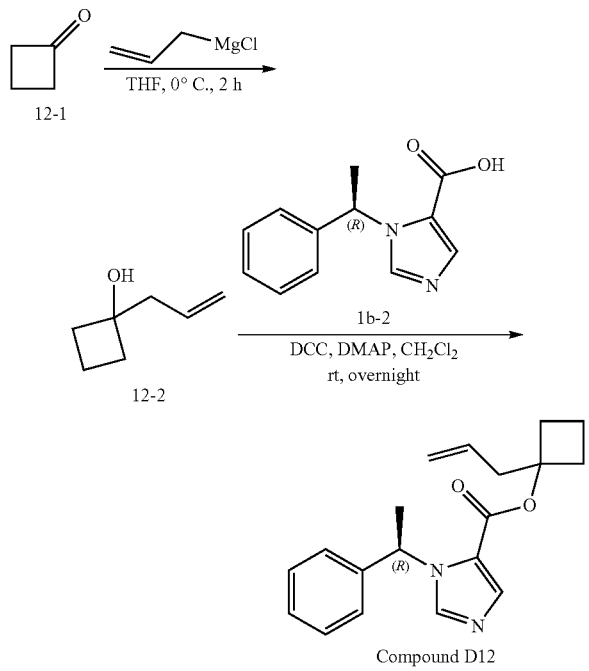

Compound D12

The compound 12-2 was synthesized using cyclobutanoe (12-1) (210.3 mg, 3.0 mmol) and allylmagnesium chloride as raw materials according to the preparation method of compound 6-2.

The target compound D12 was prepared according to the general procedure A, using 1b-2 (216 mg, 1.0 mmol) and 12-2 (112 mg, 0.77 mmol) as raw materials. The crude product was purified by Prep-TLC (ethyl acetate/petroleum ether (v/v)=1/1) and the fraction with Rf=0.5~0.6 was collected and dried to give the product D12 (183 mg, yield 59%) as colorless oil. ESI[M+H]$^+$=311.2

$^1$H NMR (400 MHz, CDCl$_3$) δ 7.82 (s, 1H), 7.76 (s, 1H), 7.43-7.28 (m, 3H), 7.24-7.16 (m, 2H), 6.39 (q, J=7.1 Hz, 1H), 5.95-5.84 (m, 1H), 5.23-5.21 (m, 1H), 5.21-5.15 (m, 1H), 2.40-2.38 (m, 2H), 2.13-2.02 (m, 4H), 1.87 (d, J=7.1 Hz, 3H), 1.83-1.69 (m, 1H), 1.65-1.46 (m, 1H).

Example D13 Preparation of Compound D13

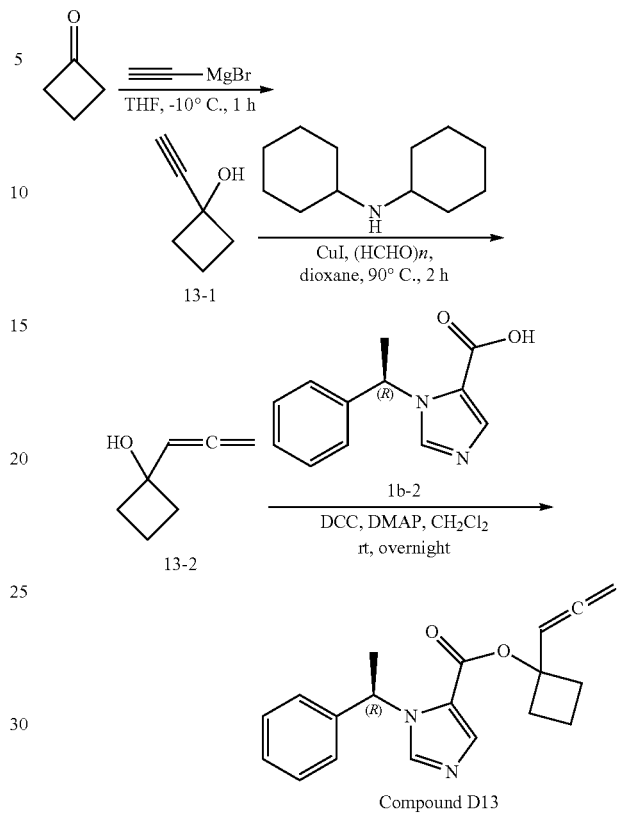

Compound D13

The preparation method of compound 13-2 was the same as compound 21-2 using cyclobutanoe as raw material.

The target compound D13 was prepared according to the general procedure A, using 1b-2 (50 mg, 0.23 mmol) and 13-2 (39 mg, 0.35 mmol) as raw materials. The crude product was purified by Prep-TLC (ethyl acetate/petroleum ether (v/v)=1/1) and the fraction with Rf=0.3~0.4 was collected and dried to give the product D13 (18 mg, yield 25%) as colorless oil. ESI[M+H]$^+$=309.3

$^1$H NMR (400 MHz, CDCl$_3$) δ 7.78 (s, 1H), 7.73 (s, 1H), 7.40-7.27 (m, 3H), 7.23-7.13 (m, 2H), 6.35 (q, J=7.0 Hz, 1H), 5.61 (t, J=6.6 Hz, 1H), 4.99-4.82 (m, 2H), 2.53-2.34 (m, 4H), 1.89-1.78 (m, 1H), 1.85 (d, J=7.1 Hz, 3H), 1.77-1.60 (m, 1H).

Example D14 Preparation of Compound D14

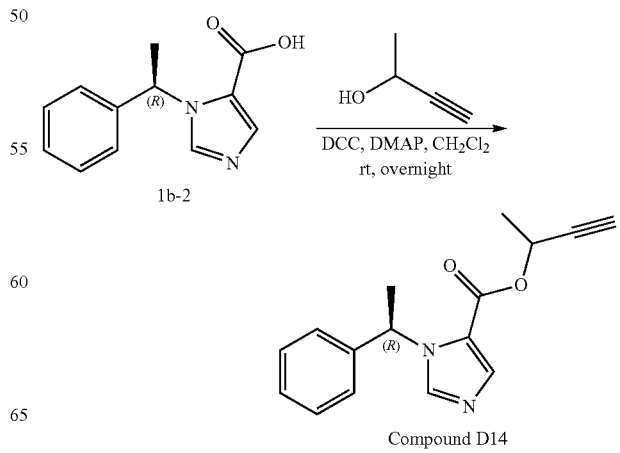

Compound D14

215

The title compound was prepared according to the general procedure A, using b-2 (108 mg, 0.5 mmol) and but-3-yn-2-ol (35 mg, 0.50 mmol) as raw materials. The crude product was purified by Prep-TLC (ethyl acetate/petroleum ether (v/v)=1/1) and the fraction with Rf=0.3~0.4 was collected and dried to give the product D14 (71 mg, yield 53%) as a white solid. ESI[M+H]$^+$=269.2

$^1$H NMR (400 MHz, CDCl$_3$) δ 7.89-7.78 (m, 2H), 7.43-7.28 (m, 3H), 7.26-7.11 (m, 2H), 6.43-6.31 (m, 1H), 5.64-5.47 (m, 1H), 2.49 (dd, J=8.8, 2.1 Hz, 1H), 1.88 (d, J=7.1 Hz, 3H), 1.57 (dd, J=6.7, 3.8 Hz, 3H).

Example D15 Preparation of Compound D15

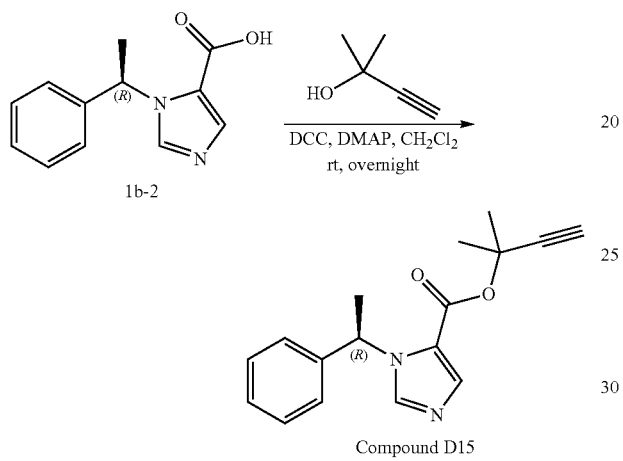

Compound D15

The title compound was prepared according to the general procedure A, using 1b-2 (100 mg, 0.46 mmol) and 2-methylbut-3-yn-2-ol (39 mg, 0.46 mmol) as raw materials. The crude product was purified by Prep-TLC (ethyl acetate/petroleum ether (v/v)=1/1) and the fraction with Rf=0.5~0.6 was collected and dried to give the product D15 (95 mg, yield 73%) as a white solid. ESI[M+H]$^+$=283.3

$^1$H NMR (400 MHz, CDCl$_3$) δ 7.73 (s, 1H), 7.70 (s, 1H), 7.38-7.27 (m, 3H), 7.25-7.17 (m, 2H), 6.38 (q, J=7.1 Hz, 1H), 2.58 (s, 1H), 1.86 (d, J=7.1 Hz, 3H), 1.74 (s, 3H), 1.72 (s, 3H).

Example D16 Preparation of Compound D16

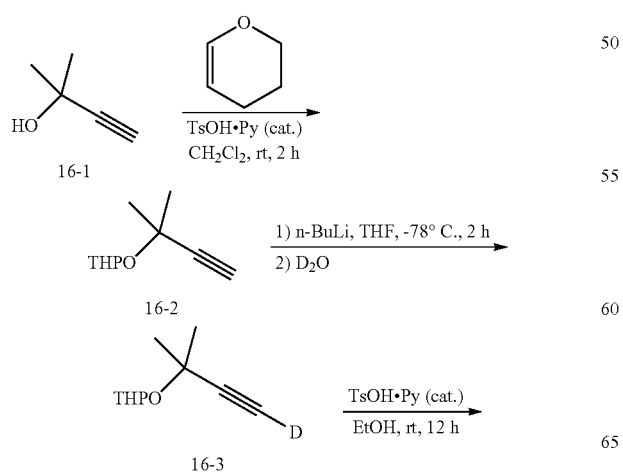

216

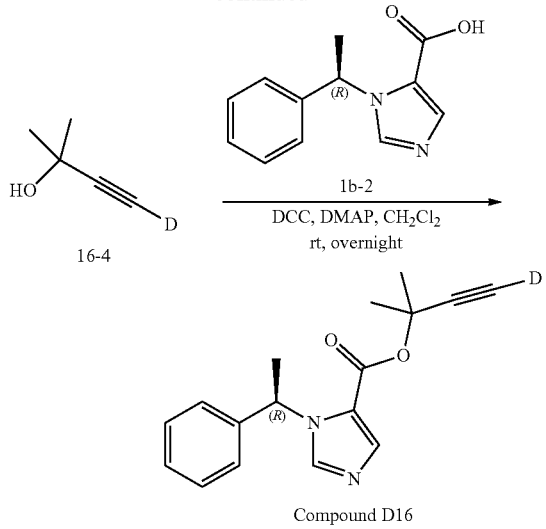

Compound D16

1. Preparation of 2-((2-Methylbut-3-yn-2-yl)oxy) tetrahydro-2H-pyran (16-2)

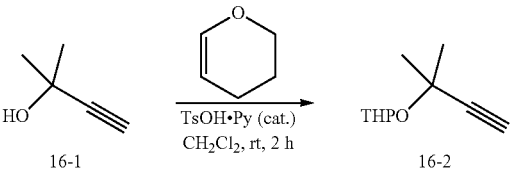

At room temperature, 3,4-dihydro-2H-pyran (420.6 mg, 5.0 mmol), 16-1 (420.6 mg, 5.0 mmol) and pyridinium 4-toluenesulfonate (63 mg, 0.25 mmol) were dissolved in dichloromethane (20 mL) and then the mixture was allowed to react at room temperature for 2 hrs. The reaction was monitored by TLC until completion. The mixture was concentrated under reduced pressure and the residue was purified by silica gel column chromatography (ethyl acetate/ petroleum ether (v/v) at any ratio within the range of 1/15 to 1/1), with TLC (ethyl acetate/petroleum ether (v/v)=1/2) monitoring, and collecting the fraction with Rf=0.3~0.4, to give product 16-2 (546 mg, yield 65%) as colorless oil.

2. Preparation of 2-((2-Methylbut-3-yn-2-yl)oxy) tetrahydro-2H-pyran (16-3)

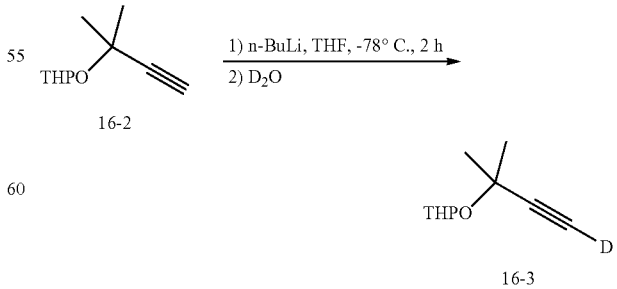

Compound 16-2 (532 mg, 3.2 mmol) was dissolved in the anhydrous THF (10 mL) under nitrogen atmosphere and the mixture was cooled to −78° C. by a dry ice-acetone bath. t-BuLi (5.8 mL, 1.0 mol/L in pentane, 5.8 mmol) was added slowly into the reaction solution over a 5-min period using a syringe under −70° C. After the t-BuLi was added completely, then it was allowed to react for 2 hrs at −78° C., then the mixture was quenched with the D2O (2 mL) and extracted with diethyl ether (3×10 mL). The combined organic layers were washed with saturated brine (20 mL), dried over anhydrous sodium sulfate, filtered and concentrated under reduced pressure to give crude product 16-3, which was used for next step directly without further purification.

3. Preparation of 2-Methylbut-3-yn-4-d-2-ol (16-4)

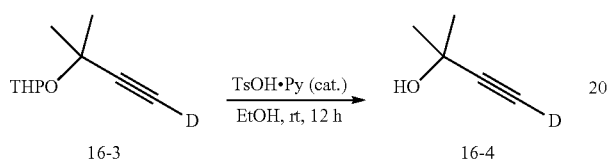

At room temperature, compound 16-3 (3.2 mmol) and pyridinium 4-toluenesulfonate (402 mg, 1.6 mmol) were dissolved in ethanol (20 mL), and then it was allowed to react at room temperature for 12 hrs. The reaction was monitored by TLC until completion, and then it was concentrated under reduced pressure. The residue was purified by silica gel column chromatography (ethyl acetate/petroleum ether (v/v) at any ratio within the range of 1/10 to 1/1), with TLC (ethyl acetate/petroleum ether (v/v)=1/1) monitoring, and collecting the fraction with Rf=0.3~0.4, to give product 16-4 (143 g, yield 52%) as colorless oil.

4. Preparation of Compound D16

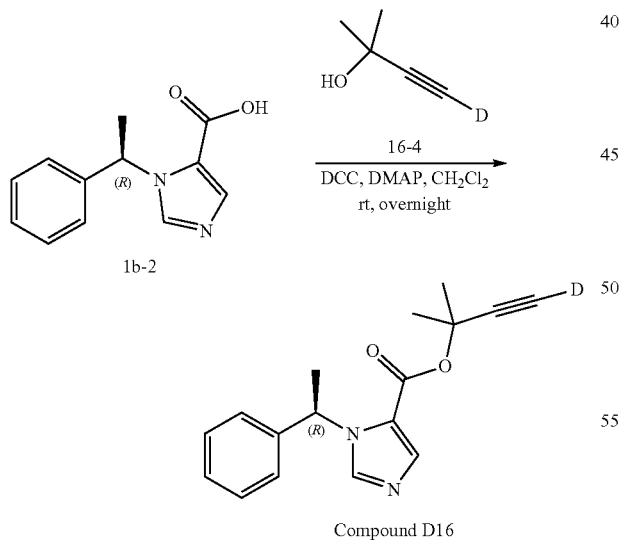

The title compound was prepared according to the general procedure A, using 1b-2 (216 mg, 1.0 mmol) and 16-4 (126 mg, 1.5 mmol) as raw materials. The crude product was purified by Prep-TLC (ethyl acetate/petroleum ether (v/v)= 1/1) and the fraction with Rf=0.5~0.6 was collected and dried to give the product D16 (53 mg, yield 19%) as colorless oil. ESI[M+H]$^+$=284.3

$^1$H NMR (400 MHz, CDCl$_3$) δ 7.72 (s, 1H), 7.69 (s, 1H), 7.40-7.28 (m, 3H), 7.26-7.16 (m, 2H), 6.39 (q, J=7.1 Hz, 1H), 1.85 (d, J=7.1 Hz, 3H), 1.75 (s, 3H), 1.71 (s, 3H).

Example D17 Preparation of Compound D17

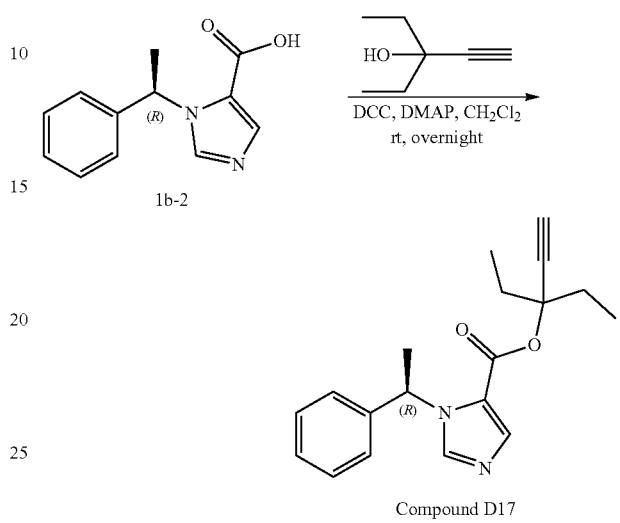

The title compound was prepared according to the general procedure A, using 1b-2 (100 mg, 0.46 mmol) and 3-ethyl-pent-1-yn-3-ol (52 mg, 0.46 mmol) as raw materials. The crude product was purified by Prep-TLC (ethyl acetate/petroleum ether (v/v)=1/1) and the fraction with Rf=0.5~0.6 was collected and dried to give the product D17 (53 mg, yield 37%) as colorless oil. ESI[M+H]$^+$=311.3

$^1$H NMR (400 MHz, CDCl$_3$) δ 7.80 (s, 1H), 7.76 (s, 1H), 7.43-7.28 (m, 3H), 7.25-7.14 (m, 2H), 6.40 (q, J=6.9 Hz, 1H), 2.63 (s, 1H), 2.21-2.03 (m, 2H), 2.03-1.92 (m, 2H), 1.87 (d, J=7.1 Hz, 3H), 1.02 (t, J=7.4 Hz, 3H), 0.96 (t, J=7.4 Hz, 3H).

Example D18 Preparation of Compound D18

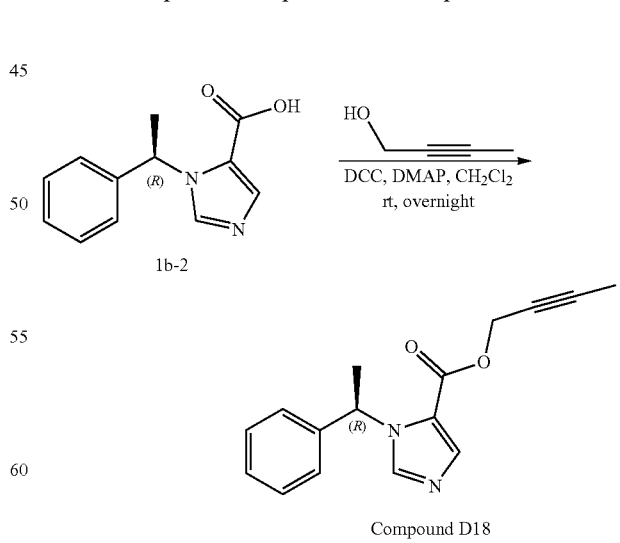

The title compound was prepared according to the general procedure A, using 1b-2 (100 mg, 0.46 mmol) and but-2-yn-1-ol (32 mg, 0.46 mmol) as raw materials. The crude product was purified by Prep-TLC (ethyl acetate/petroleum ether (v/v)=1/1) and the fraction with Rf=0.5~0.6 was collected and dried to give the product D18 (95 mg, yield 73%) as colorless oil. ESI[M+H]⁺=269.2

¹H NMR (400 MHz, CDCl₃) δ 7.84 (s, 1H), 7.75 (s, 1H), 7.40-7.27 (m, 3H), 7.23-7.14 (m, 2H), 6.34 (q, J=7.1 Hz, 1H), 4.78 (qq, J=15.2, 2.3 Hz, 2H), 1.87 (d, J=1.3 Hz, 3H), 1.86 (d, J=3.2 Hz, 3H).

Example D19 Preparation of Compound D19

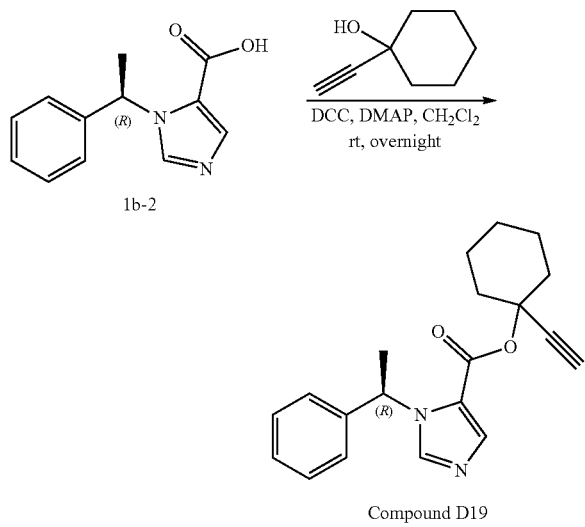

Compound D19

The title compound was prepared according to the general procedure A, using 1b-2 (100 mg, 0.46 mmol) and 1-ethynylcyclohexan-1-ol (57 mg, 0.46 mmol) as raw materials. The crude product was purified by Prep-TLC (ethyl acetate/petroleum ether (v/v)=1/1) and the fraction with Rf=0.4~0.5 was collected and dried to give the product D19 (86 mg, yield 58%) as colorless oil. ESI[M+H]⁺=323.2

¹H NMR (400 MHz, CDCl₃) δ 7.75 (s, 1H), 7.74 (s, 1H), 7.39-7.28 (m, 3H), 7.25-7.20 (m, 2H), 6.40 (q, J=7.1 Hz, 1H), 2.65 (s, 1H), 2.23-2.09 (m, 2H), 2.04-1.90 (m, 2H), 1.87 (d, J=7.1 Hz, 3H), 1.72-1.57 (m, 4H), 1.57-1.47 (m, 1H), 1.43-1.32 (m, 1H).

Example D20 Preparation of Compound D20

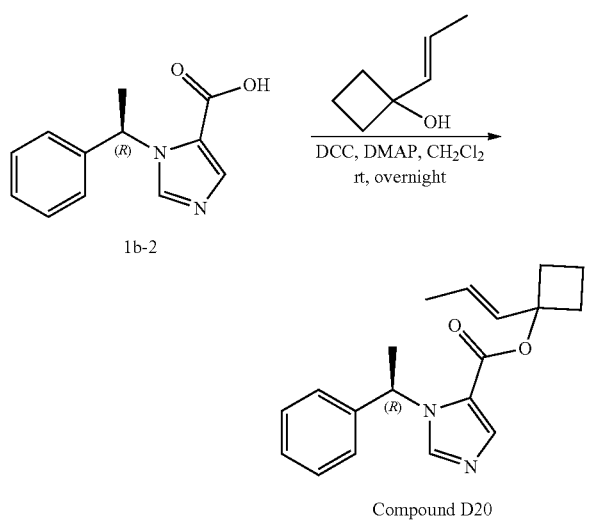

Compound D20

The title compound was prepared according to the general procedure A, using 1b-2 (216 mg, 1.0 mmol) and (E)-1-(prop-1-en-1-yl)cyclobutan-1-ol (112.2 mg, 1.0 mmol) as raw materials. The crude product was purified by Prep-TLC (ethyl acetate/petroleum ether (v/v)=1/1) and the fraction with Rf=0.4~0.5 was collected and dried to give the product D20 (105 mg, yield 34%) as a white solid. ESI[M+H]⁺=311.3

Example D21 Preparation of Compound D21

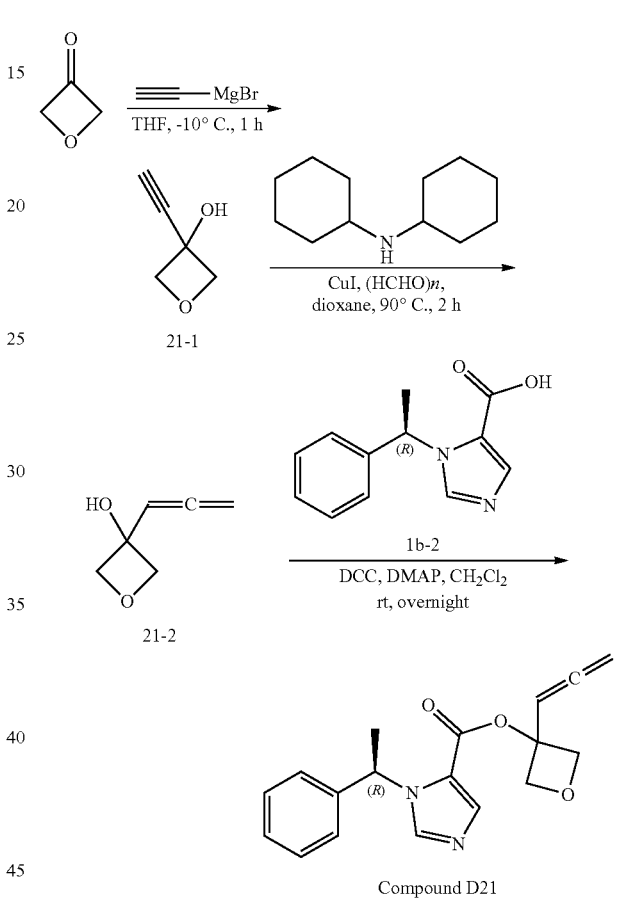

Compound D21

1. Preparation of 3-Ethynyloxetan-3-ol (21-1)

Oxetan-3-one (300 mg, 4.16 mmol) was dissolved into anhydrous THF (10 mL) under nitrogen atmosphere and the mixture was cooled to −10° C. by an ice-water bath. Ethynylmagnesium bromide (8.32 mL, 0.5 mol/L in THF, 4.16 mmol) was added dropwise into the reaction mixture over a 15-min period using a syringe at −10° C., and then it was allowed to react at room temperature for 2 hrs. The reaction was monitored by TLC until completion. The mixture was quenched with the saturated ammonium chloride solution (10 mL) and extracted with dichloromethane (3×10 mL). The combined organic layers were washed with saturated brine (50 mL), dried over anhydrous sodium sulfate, filtered and concentrated under reduced pressure. The residue was purified by silica gel column chromatography (ethyl acetate/petroleum ether (v/v) at any ratio within the range of 1/10 to 1/5), with TLC (ethyl acetate/petroleum ether (v/v)=1/2) monitoring, and collecting the fraction with Rf=0.3~0.4, to give compound 21-1 (498 mg, yield 73.2%) as colorless oil.

2. Preparation of 3-(Propa-1,2-dien-1-yl)oxetan-3-ol (21-2)

Compound 21-1 (498 mg, 5.08 mmol), dicyclohexylamine (1.66 g, 9.14 mmol), CuI (483 mg, 2.54 mmol) and (HCHO)$_n$ (381 mg, 12.7 mmol) were dissolved in dioxane (10 mL). The mixture was stirred for 2 hrs at 90° C. The reaction was monitored by TLC until completion. The mixture was cooled, filtered and diluted with water and extracted with ethyl acetate (3×10 mL). The combined organic layers were washed with saturated brine (50 mL), dried over anhydrous sodium sulfate, filtered and concentrated under reduced pressure. The residue was purified by silica gel column chromatography (ethyl acetate/petroleum ether (v/v) at any ratio within the range of 1/10 to 1/5), with TLC (ethyl acetate/petroleum ether (v/v)=1/2) monitoring, and collecting the fraction with Rf=0.3~0.4, to give compound 21-2 (120 mg, yield 21%) as colorless oil.

3. Preparation of Compound D21

The title compound was prepared according to the general procedure A, using 1b-2 (216 mg, 1.0 mmol) and 21-2 as raw materials. The crude product was purified by Prep-TLC (ethyl acetate/petroleum ether (v/v)=1/1) and the fraction with Rf=0.4~0.5 was collected and dried to give the product D21 (30.0 mg, yield 10%) as colorless oil. ESI[M+H]$^+$=311.2

$^1$H NMR (400 MHz, CDCl$_3$) δ 7.81 (s, 1H), 7.76 (s, 1H), 7.39-7.28 (m, 3H), 7.15 (d, J=7.0 Hz, 2H), 6.32-6.20 (m, 1H), 5.63 (t, J=6.6 Hz, 1H), 5.00-4.95 (m, 1H), 4.92-4.88 (m, 2H), 4.82-4.80 (m, 1H), 4.78-4.74 (m, 2H), 1.86 (d, J=7.1 Hz, 3H).

Example D22 Preparation of Compound D22

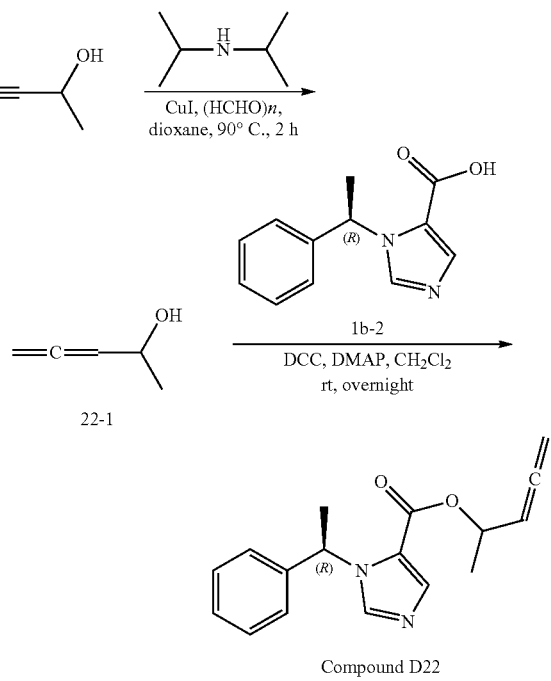

1. Preparation of Penta-3,4-dien-2-ol (22-1)

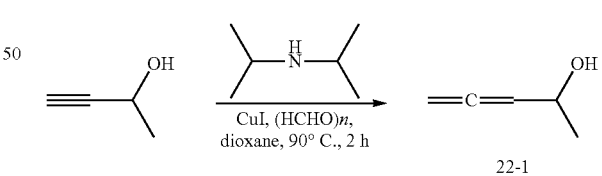

But-3-yn-2-ol (350 mg, 4.99 mmol), diisopropylamine (909 mg, 8.98 mmol), CuI (476 mg, 2.50 mmol) and (HCHO)$_n$ (375 mg, 12.5 mmol) were dissolved in dioxane (10 mL) and the mixture was stirred at 90° C. for 2 hrs. The reaction was monitored by TLC until completion. The mixture was cooled and filtered. The filtrate was diluted with water and extracted with ethyl acetate (3×10 mL). The combined organic layers were washed with hydrochloric acid (50 mL, 6 N), dried over anhydrous sodium sulfate, filtered and concentrated under reduced pressure to give crude compound 22-1 as colorless oil, which was used for next step directly without further purification.

2. Preparation of Compound D22

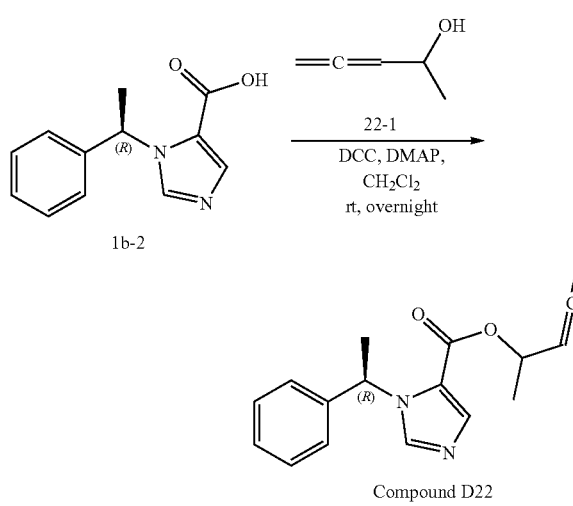

Compound D22

The title compound was prepared according to the general procedure A, using 1b-2 (216 mg, 1.0 mmol) and 22-1 as raw materials. The crude product was purified by Prep-TLC (ethyl acetate/petroleum ether (v/v)=1/1) and the fraction with Rf=0.3~0.4 was collected and dried to give the product D22 (80.0 mg, yield 28%) as colorless oil. ESI[M+H]$^+$=283.2

$^1$H NMR (400 MHz, CDCl$_3$) δ 7.78 (s, 1H), 7.74 (d, J=1.6 Hz, 1H), 7.39-7.28 (m, 3H), 7.23-7.15 (m, 2H), 6.36 (dd, J=7.1, 3.5 Hz, 1H), 5.51-5.48 (m, 1H), 5.34-5.26 (m, 1H), 4.90-4.87 (m, 1H), 4.85-4.79 (m, 1H), 1.86 (d, J=7.1 Hz, 3H), 1.39 (dd, J=6.4, 4.1 Hz, 3H).

Example D23 Preparation of Compound D23

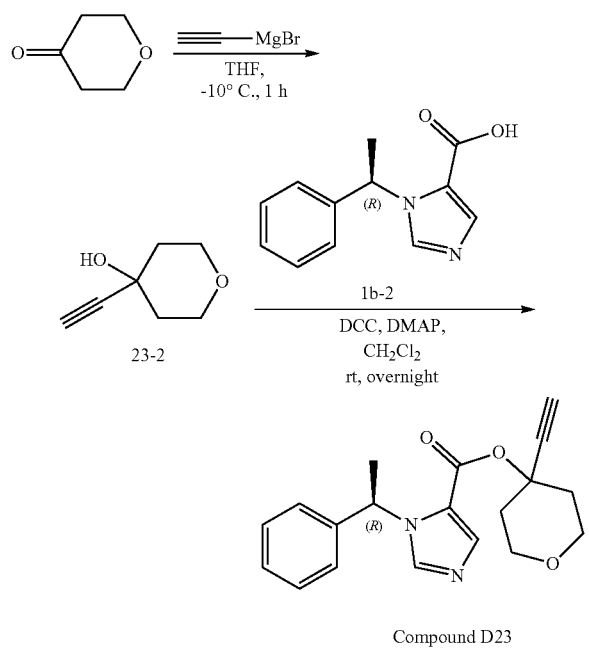

Compound D23

1. Preparation of 4-Ethynyltetrahydro-2H-pyran-4-ol (23-2)

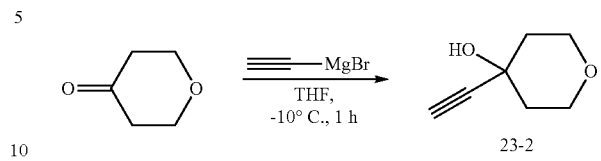

Tetrahydro-4H-pyran-4-one (600 mg, 5.99 mmol) was dissolved in anhydrous THF (10 mL) under nitrogen atmosphere and the mixture was cooled to −10° C. by an ice-water bath. Then ethynylmagnesium bromide (12.0 mL, 0.5 mol/L in THF, 5.99 mmol) was added dropwise into the reaction mixture over a 15-min period using a syringe at −10° C. and the mixture was allowed to react at room temperature for 2 hrs. The reaction was monitored by TLC until completion. The mixture was quenched with the saturated ammonium chloride solution (10 mL) and extracted with dichloromethane (3×10 mL). The combined organic layers were washed with saturated brine (50 mL), dried over anhydrous sodium sulfate, filtered and concentrated under reduced pressure. The residue was purified by silica gel column chromatography (ethyl acetate/petroleum ether (v/v) at any ratio within the range of 1/10 to 1/5), with TLC (ethyl acetate/petroleum ether (v/v)=1/2) monitoring, and collecting the fraction with Rf=0.3~0.4, to give product 23-2 (313 mg, yield 41%) as colorless oil.

2. Preparation of Compound D23

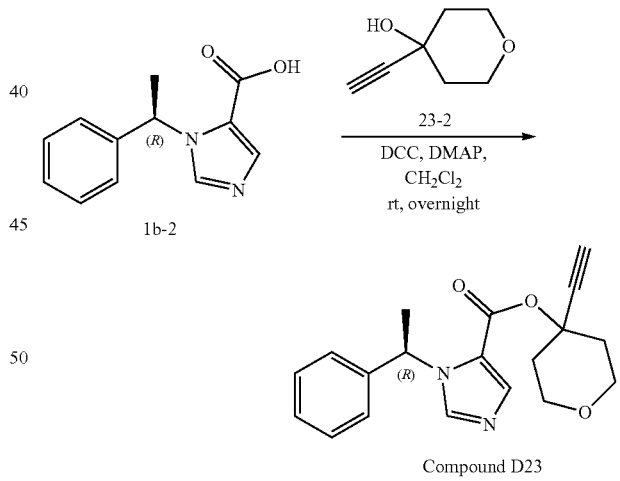

Compound D23

The title compound was prepared according to the general procedure A, using 1b-2 (216 mg, 1.0 mmol) and 23-2 as raw materials. The crude product was purified by Prep-TLC (ethyl acetate/petroleum ether (v/v)=1/1) and the fraction with Rf=0.3~0.4 was collected and dried to give the product D23 (194 mg, yield 60%) as colorless oil. ESI[M+H]$^+$=325.2

$^1$H NMR (400 MHz, CDCl$_3$) δ 7.84 (s, 1H), 7.79 (s, 1H), 7.40-7.28 (m, 3H), 7.24-7.16 (m, 2H), 6.37 (q, J=6.9 Hz, 1H), 3.99-3.65 (m, 4H), 2.34-2.19 (m, 2H), 2.15-2.00 (m, 2H), 1.88 (d, J=7.1 Hz, 3H).

Example D24 Preparation of Compound D24

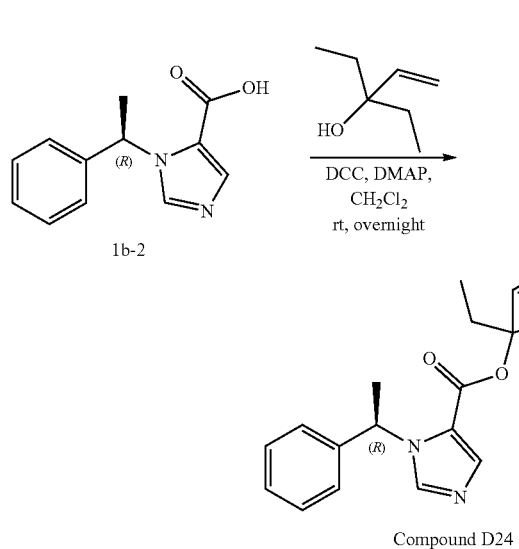

Compound D24

The title compound was prepared according to the general procedure A, using 1b-2 (216 mg, 1.0 mmol) and 3-ethyl-pent-1-en-3-ol (114 mg, 1.0 mmol) as raw materials. The crude product was purified by Prep-TLC (ethyl acetate/petroleum ether (v/v)=1/1) and the fraction with Rf=0.5~0.6 was collected and dried to give the product D24 (110 mg, yield 35%) as colorless oil. ESI[M+H]$^+$=313.3

Example D25 Preparation of Compound D25

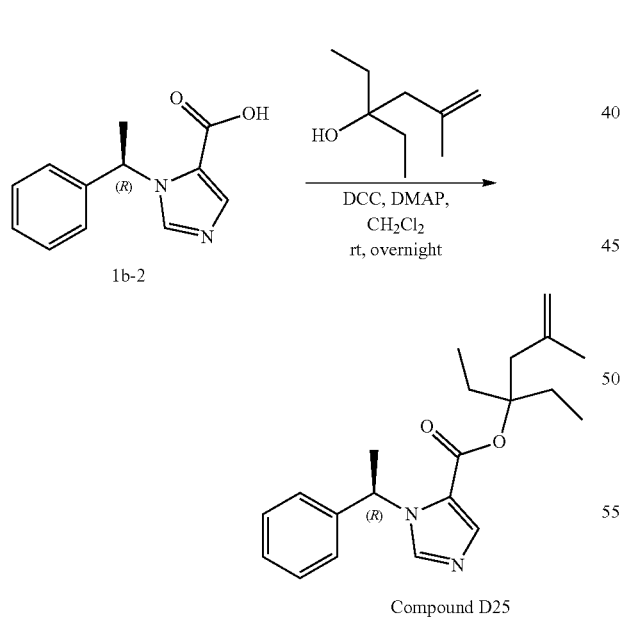

Compound D25

The title compound was prepared according to the general procedure A, using 1b-2 (216 mg, 1.0 mmol) and 3-ethyl-5-methylhex-5-en-3-ol (142 mg, 1.0 mmol) as raw materials. The crude product was purified by Prep-TLC (ethyl acetate/petroleum ether (v/v)=1/1) and the fraction with Rf=0.3~0.5 was collected and dried to give the product D25 (88 mg, yield 26%) as colorless oil. ESI[M+H]$^+$=341.3

Example D26 Preparation of Compound D26

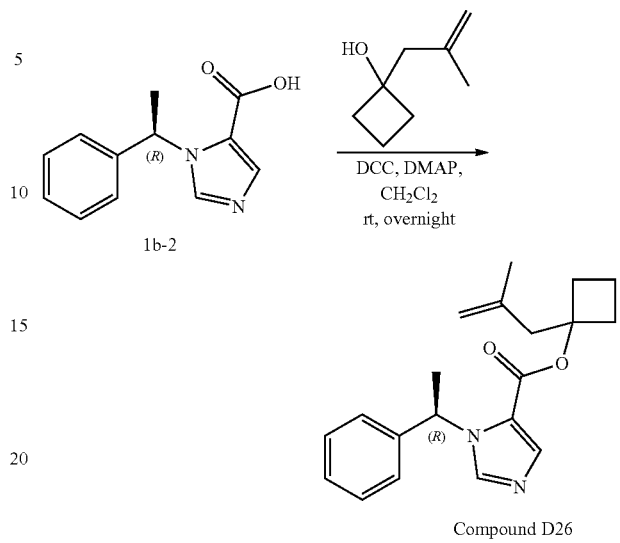

Compound D26

The title compound was prepared according to the general procedure A, using 1b-2 (216 mg, 1.0 mmol) and 1-(2-methylallyl)cyclobutan-1-ol (126 mg, 1.0 mmol) as raw materials. The crude product was purified by Prep-TLC (ethyl acetate/petroleum ether (v/v)=1/1) and the fraction with Rf=0.5~0.6 was collected and dried to give the product D26 (35 mg, yield 11%) as colorless oil. ESI[M+H]$^+$=325.3

Example D27 Preparation of Compound D27

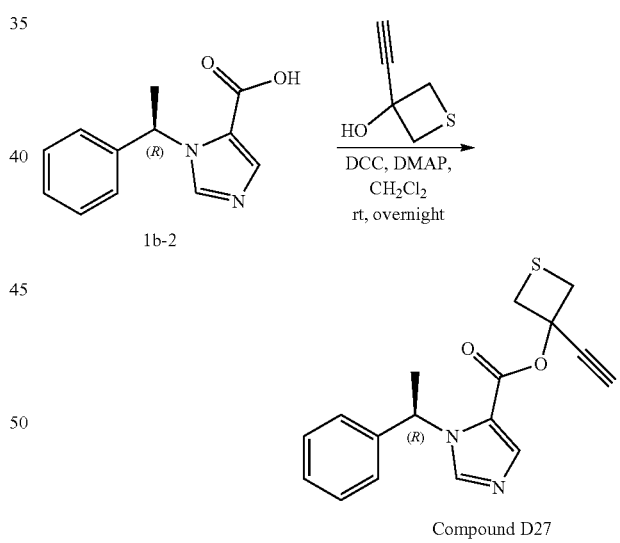

Compound D27

3-Ethynylthietan-3-ol was synthesized using thietan-3-one and ethynylmagnes-ium bromide as raw materials.

The target compound D27 was prepared according to the general procedure A, using 1b-2 (216 mg, 1.0 mmol) and 3-ethynylthietan-3-ol (114 mg, 1.0 mmol) as raw materials. The crude product was purified by Prep-TLC (ethyl acetate/petroleum ether (v/v)=1/1) and the fraction with Rf=0.3~0.4 was collected and dried to give the product D27 (78 mg, yield 25%) as colorless oil. ESI[M+H]$^+$=311.2

$^1$H NMR (400 MHz, CDCl$_3$) δ 8.05 (s, 1H), 7.91 (s, 1H), 7.43-7.35 (m, 3H), 7.27-7.21 (m, 2H), 6.31 (q, J=7.0 Hz, 1H), 4.11-3.87 (m, 4H), 2.81 (s, 1H), 1.90 (d, J=7.1 Hz, 3H).

Example D28 Preparation of Compound D28

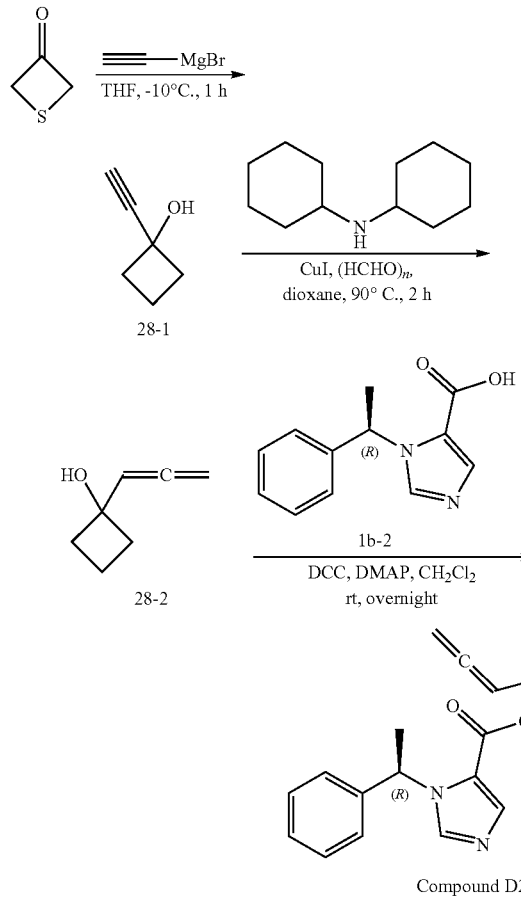

The preparation method of compound 28-2 was the same as the compound 21-2 using thietan-3-one as starting material.

The target compound D28 was prepared according to the general procedure A, using 1b-2 (216 mg, 1.0 mmol) and 3-(propa-1,2-dien-1-yl)thietan-3-ol (1286 mg, 1.0 mmol) as raw materials. The crude product was purified by Prep-TLC (ethyl acetate/petroleum ether (v/v)=1/1) and the fraction with Rf=0.3~0.5 was collected and dried to give the product D28 (42 mg, yield 13%) as colorless oil. ESI[M+H]$^+$=326.1

$^1$H NMR (400 MHz, CDCl$_3$) δ 7.75 (s, 1H), 7.73 (s, 1H), 7.40-7.28 (m, 3H), 7.25-7.14 (m, 2H), 6.39 (q, J=7.0 Hz, 1H), 5.75 (t, J=6.8 Hz, 1H), 5.15-4.91 (m, 2H), 3.887-3.61 (m, 2H), 3.46-3.31 (m, 2H), 1.85 (d, J=7.1 Hz, 3H).

Example D29 Preparation of Compound D29

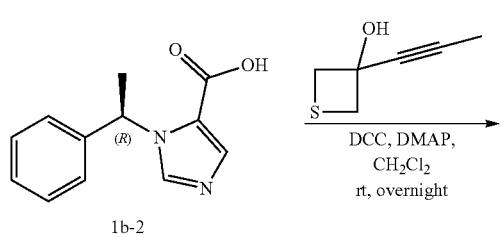

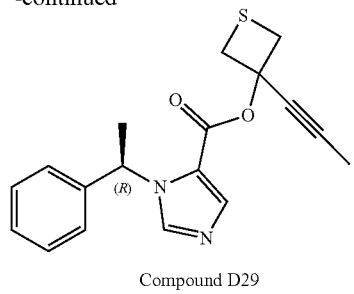

Compound D29

The title compound D29 was prepared according to the general procedure A, using 1b-2 (216 mg, 1.0 mmol) and 3-(prop-1-ynyl)thietan-3-ol (128 mg, 1.0 mmol) as raw materials. The crude product was purified by Prep-TLC (ethyl acetate/petroleum ether (v/v)=1/1) and the fraction with Rf=0.3~0.5 was collected and dried to give the product D29 (21 mg, yield 6.4%) as colorless oil. ESI[M+H]$^+$=327.2

$^1$H NMR (400 MHz, CDCl$_3$) δ 7.89 (s, 1H), 7.77 (s, 1H), 7.40-7.20 (m, 3H), 7.17-7.10 (m, 2H), 6.31 (q, J=7.2 Hz, 1H), 4.82-4.77 (m, 2H), 4.10-3.87 (m, 4H), 2.81 (s, 1H), 1.88 (d, J=7.2 Hz, 3H).

Example D30 Preparation of Compound D30

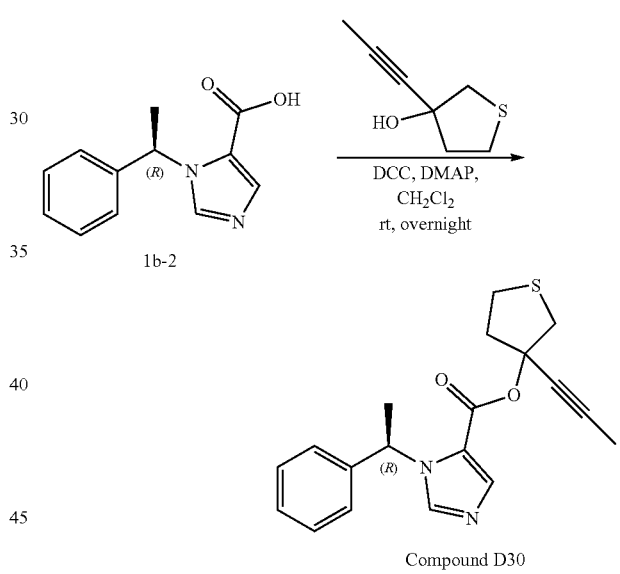

Compound D30

The title compound D30 was prepared according to the general procedure A, using 1b-2 (216 mg, 1.0 mmol) and 3-(prop-1-yn-1-yl)tetrahydrothiophen-3-ol (140 mg, 1.0 mmol) as raw materials. The crude product was purified by Prep-TLC (ethyl acetate/petroleum ether (v/v)=1/1) and the fraction with Rf=0.4~0.6 was collected and dried to give the product D30 (79 mg, yield 24%) as colorless oil. ESI[M+H]$^+$=341.1

Example D31 Preparation of Compound D31

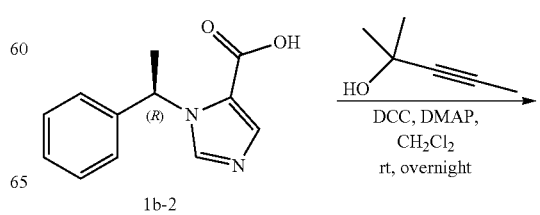

-continued

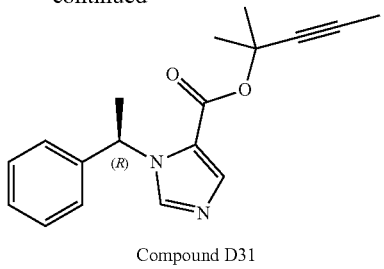

Compound D31

The title compound D31 was prepared according to the general procedure A, using 1b-2 (216 mg, 1.0 mmol) and 2-methylpent-3-yn-2-ol (98 mg, 1.0 mmol) as raw materials. The crude product was purified by Prep-TLC (ethyl acetate/petroleum ether (v/v)=1/1) and the fraction with Rf=0.4~0.5 was collected and dried to give the product D31 (35 mg, yield 12%) as colorless oil. ESI[M+H]$^+$=297.3

$^1$H NMR (400 MHz, CDCl$_3$) δ 7.88 (s, 1H), 7.77 (s, 1H), 7.41-7.28 (m, 3H), 7.24-7.14 (m, 2H), 6.31 (q, J=7.1 Hz, 1H), 1.87 (d, J=7.1 Hz, 3H), 1.84 (s, 3H), 1.70 (s, 3H), 1.70 (s, 3H).

Example D32 Preparation of Compound D32

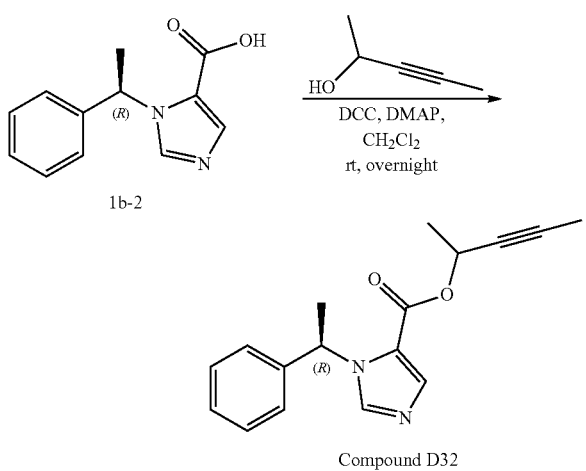

Compound D32

The title compound D32 was prepared according to the general procedure A, using 1b-2 (216 mg, 1.0 mmol) and pent-3-yn-2-ol (84 mg, 1.0 mmol) as raw materials. The crude product was purified by Prep-TLC (ethyl acetate/petroleum ether (v/v)=1/1) and the fraction with Rf=0.3~0.5 was collected and dried to give the product D32 (45 mg, yield 16%) as colorless oil. ESI[M+H]$^+$=283.3

$^1$H NMR (400 MHz, CDCl$_3$) δ 7.81 (d, J=3.2 Hz, 1H), 7.72 (d, J=23.7 Hz, 1H), 7.40-7.26 (m, 3H), 7.23-7.12 (m, 2H), 6.47-6.25 (m, 1H), 5.64-5.32 (m, 1H), 1.94-1.74 (m, 6H), 1.55-1.43 (m, 3H).

Example D33 Preparation of Compound D33

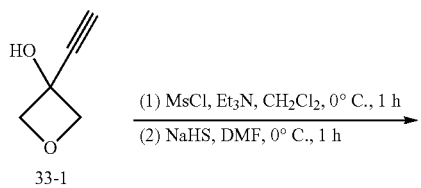

33-1

(1) MsCl, Et$_3$N, CH$_2$Cl$_2$, 0° C., 1 h
(2) NaHS, DMF, 0° C., 1 h

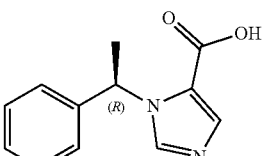

33-2

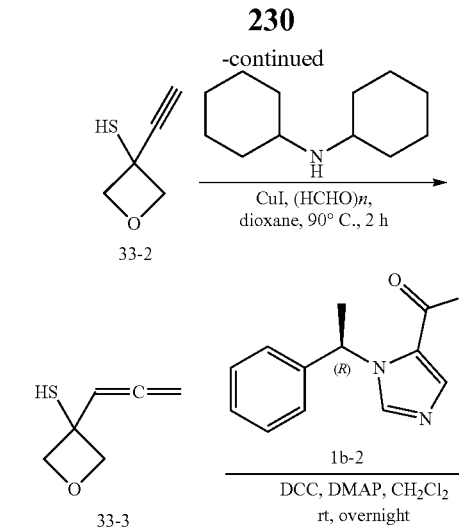

Compound D33

The compound 33-2 was synthesized according to the general procedure C using 33-1 (294 mg, 3.0 mmol) as raw materials. 140 mg of compound 33-2 as colorless oil (yield 41%, two steps) was obtained.

The preparation method of the compound 33-3 was the same as the compound 21-2 using 33-2 as raw material.

The title compound was prepared according to the general procedure A, using 1b-2 (100 mg, 0.46 mmol) and 33-3 (88 mg, 10.69 mmol) as raw materials. The crude product was purified by Prep-TLC (ethyl acetate/petroleum ether (v/v)=1/1) and the fraction with Rf=0.4~0.5 was collected and dried to give the product D33 (45 mg, yield 30%) as colorless oil. ESI[M+H]$^+$=327.2

$^1$H NMR (400 MHz, CDCl$_3$) δ 8.05 (s, 1H), 7.91 (s, 1H), 7.45-7.30 (m, 3H), 7.25-7.19 (m, 2H), 6.38 (q, J=7.0 Hz, 1H), 6.35-6.25 (m, 1H), 5.68 (t, J=6.6 Hz, 1H), 5.50-4.84 (m, 6H), 1.87 (d, J=7.1 Hz, 3H).

Example D34 Preparation of Compound D34

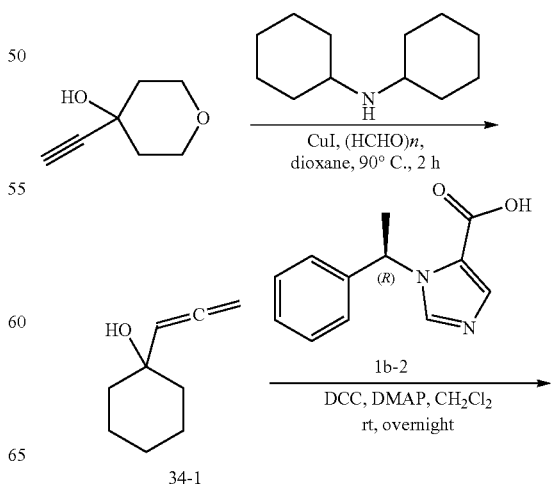

34-1

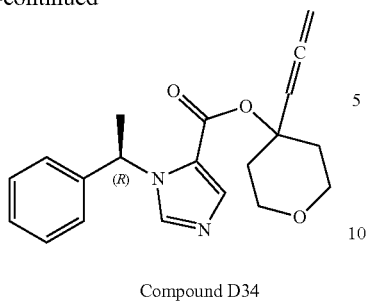

Compound D34

1. Preparation of 4-(Propa-1,2-dien-1-yl)tetrahydro-2H-pyran-4-ol (34-1)

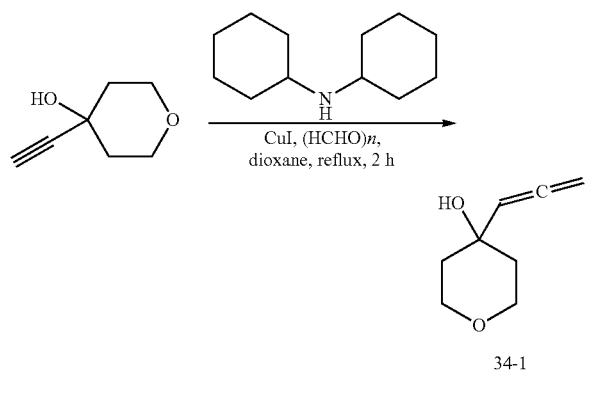

4-Ethynyltetrahydro-2H-pyran-4-ol (213 mg, 1.69 mmol), dicyclohexylamine (551 mg, 3.04 mmol), CuI (162 mg, 0.85 mmol) and (HCHO)$_n$ (127 mg, 4.23 mmol) were dissolved in dioxane (10 mL), then the mixture was stirred at 90° C. for 2 hrs. The reaction was monitored by TLC until completion. The mixture was cooled and filtered. The filtrate was diluted with water and extracted with ethyl acetate (3×10 mL). The combined organic layers were washed with saturated brine (50 mL), dried over anhydrous sodium sulfate, filtered and concentrated under reduced pressure to give crude product 34-1 as colorless oil, which was used for next step directly without further purification.

2. Preparation of Compound D34

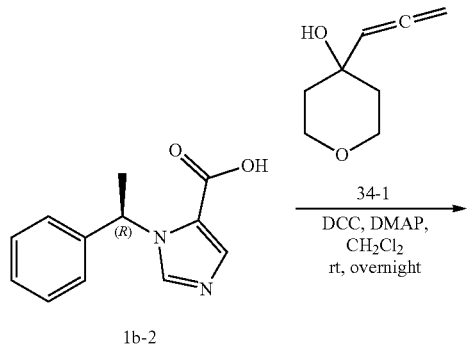

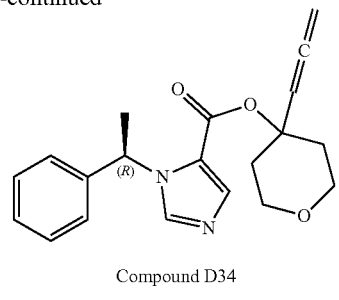

Compound D34

The title compound was prepared according to the general procedure A, using 1b-2 (216 mg, 1.0 mmol) and 34-1 as raw materials. The crude product was purified by Prep-TLC (ethyl acetate/petroleum ether (v/v)=1/1) and the fraction with Rf=0.3~0.4 was collected and dried to give the product D34 (59.0 mg, yield 18%) as colorless oil. ESI[M+H]$^+$=339.3

$^1$H NMR (400 MHz, CDCl$_3$) δ 8.24 (s, 1H), 7.88 (s, 1H), 7.42 (d, J=6.3 Hz, 3H), 6.45 (d, J=6.6 Hz, 1H), 5.65 (t, J=6.7 Hz, 1H), 5.03~4.87 (m, 2H), 3.70 (dd, J=22.4, 4.7 Hz, 4H), 2.18 (d, J=12.3 Hz, 2H), 2.13~2.01 (m, 2H), 1.93 (d, J=6.7 Hz, 3H).

Example D35 Preparation of Compound D35

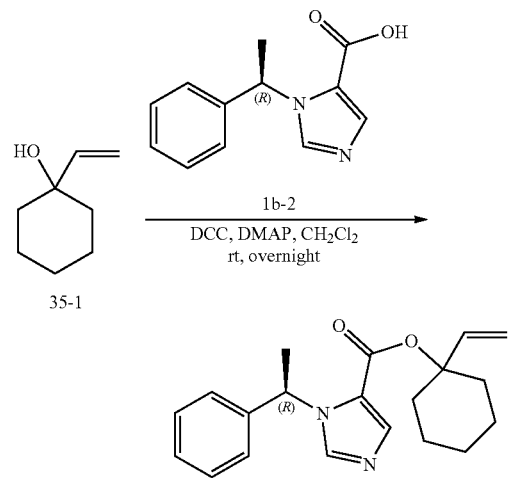

Compound D35

1. Preparation of 1-Vinylcyclohexan-1-ol (35-1)

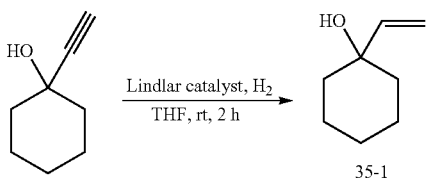

1-Ethynylcyclohexan-1-ol (1.0 g, 8.05 mmol) and Lindlar catalyst (100 mg) were dissolved in THF (20 mL), then it was allowed to react at room temperature for 2 hrs under hydrogen. The reaction was monitored by TLC until completion. The mixture was filtered and concentrated under reduced pressure to give crude compound 35-1 as colorless oil, which was used for next step directly without further purification.

2. Preparation of Compound D35

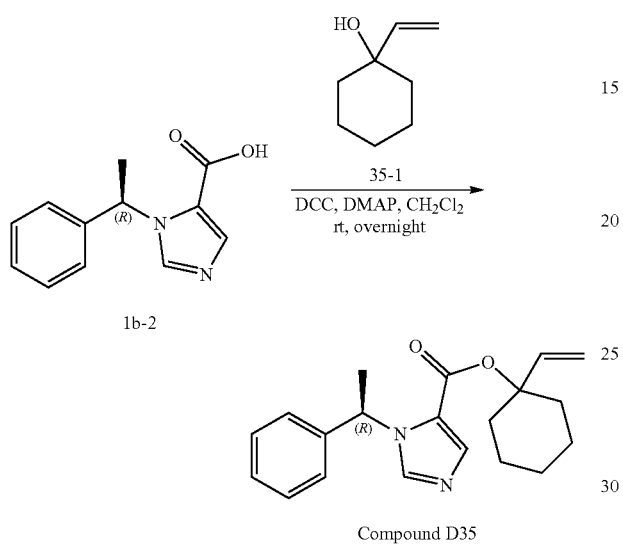

Compound D35

The title compound was prepared according to the general procedure A, using 1b-2 (216 mg, 1.0 mmol) and 35-1 as raw materials. The crude product was purified by Prep-TLC (ethyl acetate/petroleum ether (v/v)=1/1) and the fraction with Rf=0.3~0.4 was collected to give the product D35 (59 mg, yield 18%) as colorless oil. ESI[M+H]$^+$=325.3

$^1$H NMR (400 MHz, CDCl$_3$) δ 7.76 (s, 1H), 7.70 (s, 1H), 7.39-7.28 (m, 3H), 7.18 (d, J=6.7 Hz, 2H), 6.36 (q, J=7.1 Hz, 1H), 6.10 (dd, J=17.6, 11.0 Hz, 1H), 5.14 (d, J=8.3 Hz, 1H), 5.10 (d, J=0.8 Hz, 1H), 2.25~2.22 (m, 2H), 1.84 (d, J=7.1 Hz, 3H), 1.68~1.40 (m, 7H), 1.30-1.25 (m, 1H).

Example D36 Preparation of Compound D36

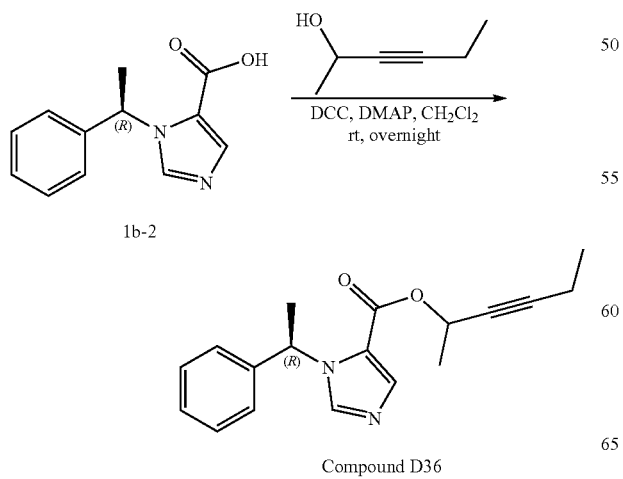

Compound D36

The title compound was prepared according to the general procedure A, using 1b-2 (108 mg, 0.5 mmol) and hex-3-yn-2-ol (49.1 mg, 0.5 mmol) as raw materials. The crude product was purified by Prep-TLC (ethyl acetate/petroleum ether (v/v)=1/1) and the fraction with Rf=0.4~0.5 was collected and dried to give the product D36 (105 mg, yield 53%) as colorless oil. ESI[M+H]$^+$=297.3

$^1$H NMR (400 MHz, CDCl$_3$) δ 7.90~7.79 (m, 2H), 7.40-7.27 (m, 3H), 7.24-7.14 (m, 2H), 6.45-6.32 (m, 1H), 5.62~5.48 (m, 1H), 2.27-2.14 (m, 2H), 1.92-1.81 (m, 3H), 1.55-1.45 (m, 3H), 1.17-1.03 (m, 3H).

Example D37 Preparation of Compounds D37 and D38

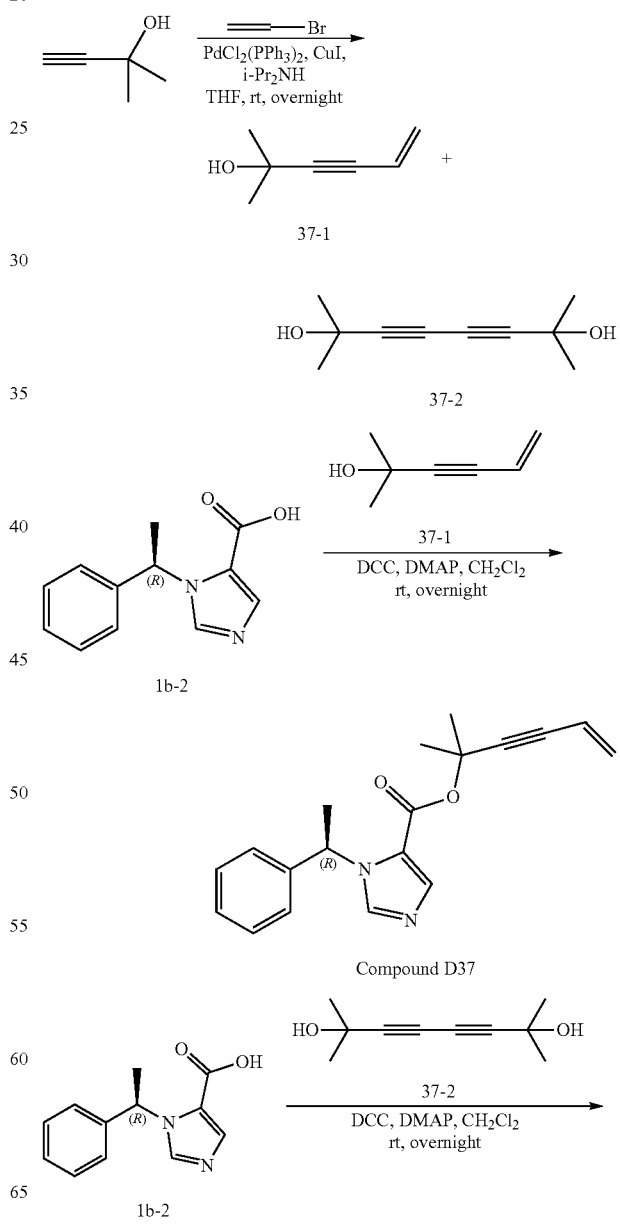

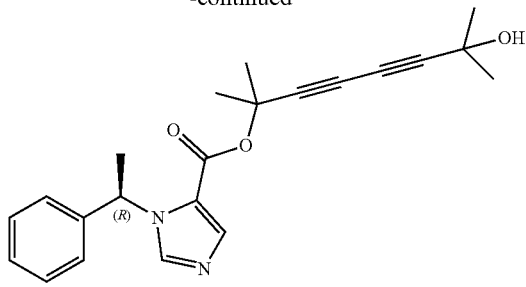

Compound D38

1. Preparation of 2-Methylhex-5-en-3-yn-2-ol (37-1) and 2,7-Dimethylocta-3,5-diyne-2,7-diol (37-2)

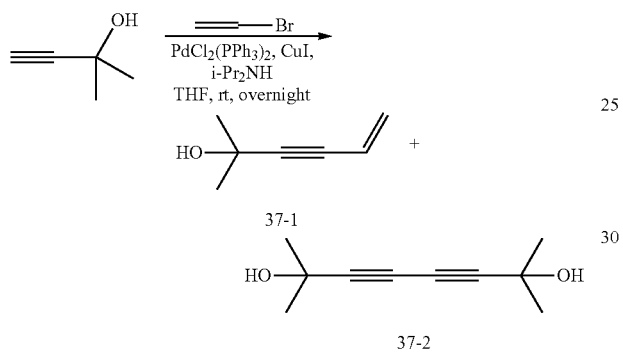

At room temperature, 2-methylbut-3-yn-2-ol (253 mg, 3.0 mmol), CuI (229 mg, 1.2 mmol), PdCl$_2$(PPh$_3$)$_2$ (421 mg, 0.6 mmol) and i-Pr$_2$NH (607 mg, 6 mmol) were dissolved in THF (10 mL). The mixture was replaced with nitrogen and bromoethene (15 mL, 1 M in THF, 15 mmol) was added into mixture using a syringe, then it was stirred at room temperature overnight. The mixture was poured into water (30 mL) and extracted with ethyl acetate (3×10 mL). The combined organic layers were washed with saturated brine (50 mL), dried over anhydrous sodium sulfate, filtered and concentrated under reduced pressure. The residue was purified by Prep-TLC (ethyl acetate/petroleum ether (v/v)=1/8) to give compounds 37-1 (139 mg, yield 42%) and 37-2 (98 mg, yield 20%) as colorless oil.

2. Preparation of Compound D37

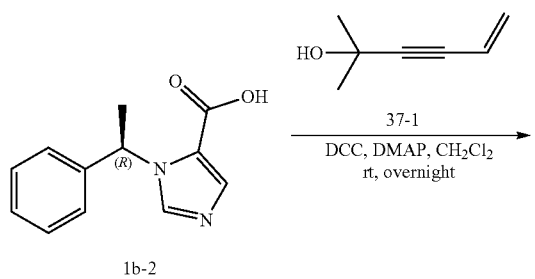

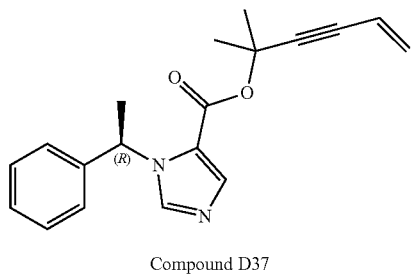

Compound D37

The title compound was prepared according to the general procedure A, using 1b-2 (100 mg, 0.46 mmol) and 37-1 (76 mg, 0.69 mmol) as raw materials. The crude product was purified by Prep-TLC (ethyl acetate/petroleum ether (v/v)=1/1) and the fraction with Rf=0.3~0.4 was collected and dried to give the product D37 (101 mg, yield 71%) as colorless oil. ESI[M+H]$^+$=309.3

$^1$H NMR (400 MHz, CDCl$_3$) δ 7.75 (s, 1H), 7.73 (s, 1H), 7.40-7.28 (m, 3H), 7.25-7.14 (m, 2H), 6.39 (q, J=7.0 Hz, 1H), 5.88-5.73 (m, 1H), 5.61 (dd, J=17.6, 2.2 Hz, 1H), 5.48 (dd, J=11.1, 2.2 Hz, 1H), 1.87 (d, J=7.1 Hz, 3H), 1.75 (s, 3H), 1.73 (s, 3H).

3. Preparation of Compound D38

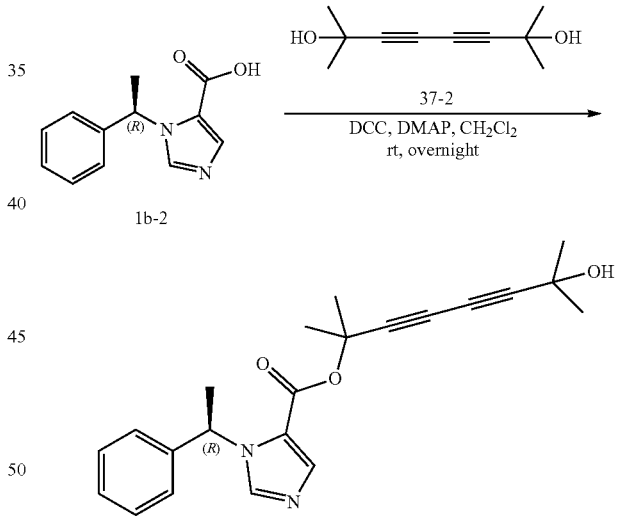

Compound D38

The title compound was prepared according to the general procedure A, using 1b-2 (100 mg, 0.46 mmol) and 37-2 (95 mg, 0.57 mmol) as raw materials. The crude product was purified by Prep-TLC (ethyl acetate/petroleum ether (v/v)=1/1) and the fraction with Rf=0.4~0.5 was collected and dried to give the product D38 (83 mg, yield 50%) as colorless oil. ESI[M+H]$^+$=365.3

$^1$H NMR (400 MHz, CDCl$_3$) δ 7.81 (s, 1H), 7.74 (s, 1H), 7.40-7.30 (m, 3H), 7.25-7.21 (m, 2H), 6.39 (q, J=7.0 Hz, 1H), 1.88 (d, J=7.1 Hz, 3H), 1.74 (s, 3H), 1.70 (s, 3H), 1.53 (s, 6H).

Example D38 Preparation of Compound D39

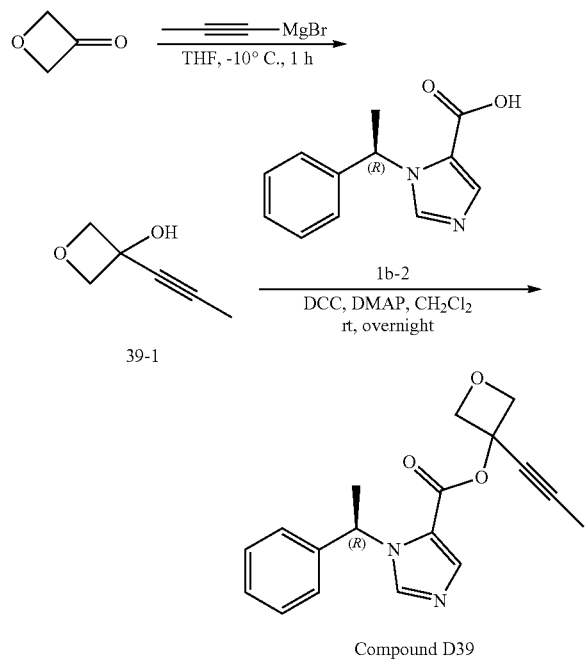

1. Preparation of 3-(Prop-1-yn-1-yl)oxetan-3-ol (39-1)

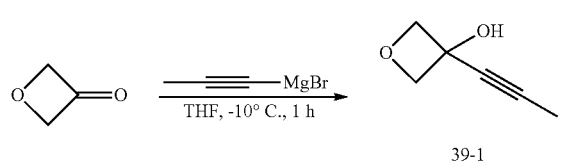

Oxetan-3-one (181 mg, 2.51 mmol) was dissolved in the anhydrous THF (10 mL) under nitrogen atmosphere and the mixture was cooled to −10° C. by an ice-salt bath. Prop-1-yn-1-ylmagnesium bromide (5.0 mL, 0.5 mol/L in THF, 2.5 mmol) was added slowly into the reaction solution over a 15-min period using a syringe at −10° C. and the mixture was allowed to react at −10° C. for 2 hrs. The reaction was monitored by TLC until completion. The mixture was quenched with the saturated ammonium chloride solution (10 mL) and extracted with ethyl acetate (3×10 mL). The combined organic layers were washed with saturated brine (50 mL), dried over anhydrous sodium sulfate, filtered and concentrated under reduced pressure to give crude compound 39-1 as colorless oil, which was used for next step directly without further purification.

2. Preparation of Compound D39

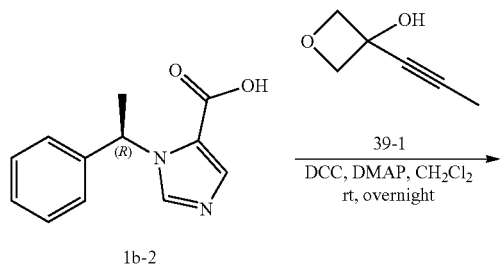

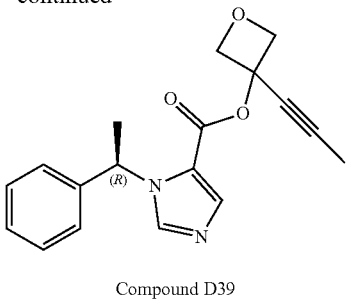

Compound D39

The title compound was prepared according to the general procedure A, using 1b-2 (216 mg, 1.0 mmol) and 39-1 as raw materials. The crude product was purified by Prep-TLC (ethyl acetate/petroleum ether (v/v)=1/1) and the fraction with Rf=0.4~0.5 was collected and dried to give the product D39 (220 mg, yield 68%) as colorless oil. ESI[M+H]$^+$=311.2

$^1$H NMR (400 MHz, CDCl$_3$) δ 7.85 (s, 1H), 7.83 (s, 1H), 7.43~7.27 (m, 3H), 7.23-7.16 (m, 2H), 6.31 (q, J=7.0 Hz, 1H), 4.99-4.82 (m, 3H), 4.74 (d, J=7.3 Hz, 1H), 1.89 (s, 3H), 1.88 (d, J=7.2 Hz, 3H).

Example D39 Preparation of Compound D40

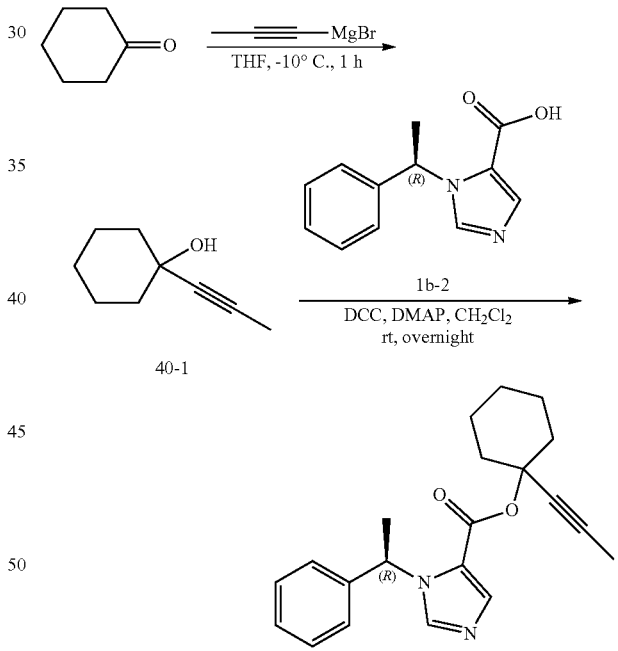

1. Preparation of 1-(Prop-1-yn-1-yl)cyclohexan-1-ol (40-1)

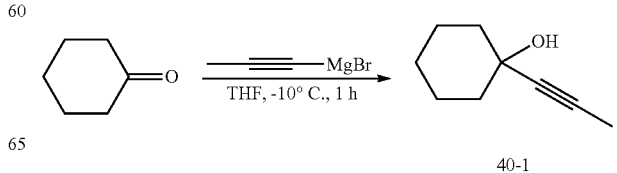

Cyclohexanone (181 mg, 1.85 mmol) was dissolved in the anhydrous THF (10 mL) under nitrogen atmosphere and the mixture was cooled to −10° C. by an ice-salt bath. Prop-1-yn-1-ylmagnesium bromide (3.69 mL, 0.5 mol/L in THF, 1.85 mmol) was added slowly into the reaction solution over a 15-min period using a syringe at −10° C. and the mixture was allowed to react at −10° C. for 2 hrs. The reaction was monitored by TLC until completion. The mixture was quenched with the saturated ammonium chloride solution (10 mL) and extracted with ethyl acetate (3×10 mL). The combined organic layers were washed with saturated brine (50 mL), dried over anhydrous sodium sulfate, filtered and concentrated under reduced pressure to give crude compound 40-1 as colorless oil, which was used for next step directly without further purification.

2. Preparation of Compound D40

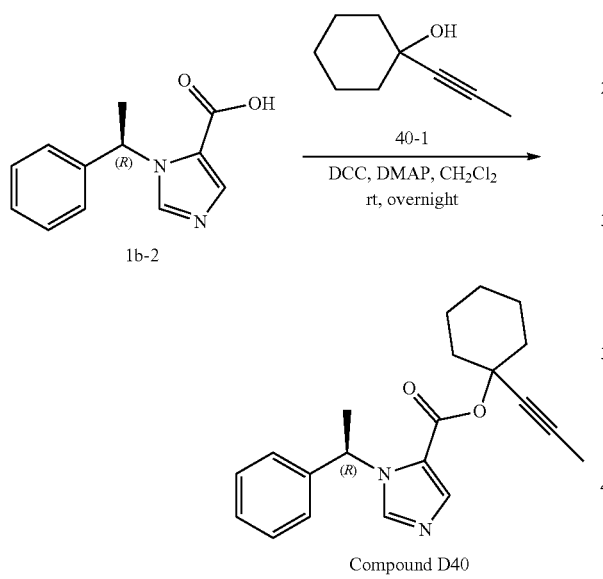

The title compound was prepared according to the general procedure A, using 1b-2 (216 mg, 1.0 mmol) and 40-1 as raw materials. The crude product was purified by Prep-TLC (ethyl acetate/petroleum ether (v/v)=1/1) and the fraction with Rf=0.4~0.5 was collected and dried to give product D40 (225 mg, yield 67%) as colorless oil. ESI[M+H]$^+$=337.3

$^1$H NMR (400 MHz, CDCl$_3$) δ 7.77 (s, 1H), 7.74 (s, 1H), 7.40-7.28 (m, 3H), 7.26-7.20 (m, 2H), 6.42 (q, J=7.1 Hz, 1H), 2.17-2.02 (m, 2H), 2.01-1.90 (m, 2H), 1.87 (d, J=7.0 Hz, 3H), 1.87 (s, 3H), 1.69-1.54 (m, 4H), 1.54-1.29 (m, 2H).

Example D40 Preparation of Compound D41

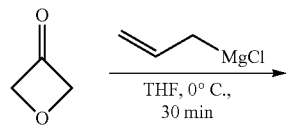

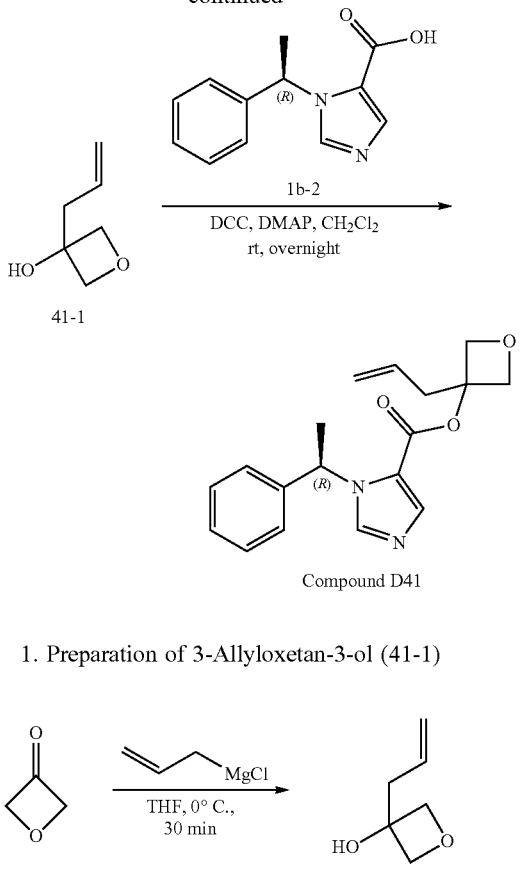

1. Preparation of 3-Allyloxetan-3-ol (41-1)

Oxetan-3-one (360 mg, 4.99 mmol) was dissolved in the anhydrous THF (10 mL) under nitrogen atmosphere and the mixture was cooled to 0° C. by an ice-water bath. Allyl-magnesium chloride (4.99 mL, 1.0 mol/L in THF, 4.99 mmol) was added slowly into the reaction solution over a 15-min period using a syringe at 0° C. and the mixture was allowed to react at this temperature for 30 min. The reaction was monitored by TLC until completion. The mixture was quenched with the saturated ammonium chloride solution (10 mL) and extracted with ethyl acetate (3×10 mL). The combined organic layers were washed with saturated brine (50 mL), dried over anhydrous sodium sulfate, filtered and concentrated under reduced pressure to give crude compound 41-1 as colorless oil, which was used for next step directly without further purification.

2. Preparation of Compound D41

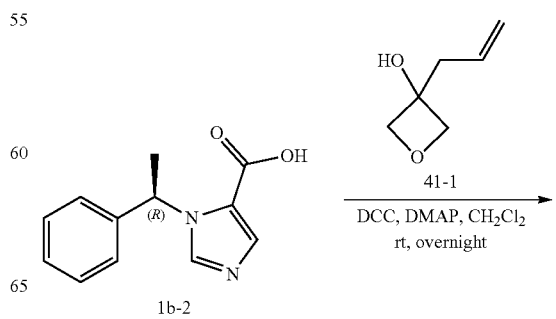

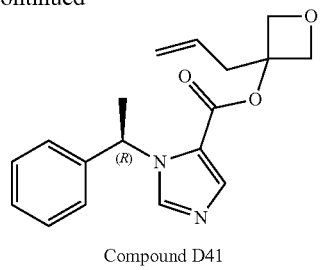

Compound D41

The title compound was prepared according to the general procedure A, using 1b-2 (216 mg, 1.0 mmol) and 41-1 as raw materials. The crude product was purified by Prep-TLC (ethyl acetate/petroleum ether (v/v)=1/1) and the fraction with Rf=0.4~0.5 was collected and dried to give the product D41 (80 mg, yield 26%) as colorless oil. ESI[M+H]$^+$=313.2

$^1$H NMR (400 MHz, CDCl$_3$) δ 7.79 (s, 2H), 7.38-7.28 (m, 3H), 7.18-7.13 (m, 2H), 6.25 (q, J=7.1 Hz, 1H), 5.72 (ddt, J=17.3, 10.3, 7.1 Hz, 1H), 5.15-5.06 (m, 2H), 4.80 (d, J=7.4 Hz, 1H), 4.74 (d, J=7.4 Hz, 1H), 4.64-4.56 (m, 2H), 2.86 (d, J=7.0 Hz, 2H), 1.87 (d, J=7.1 Hz, 3H).

Example D41 Preparation of Compound D42

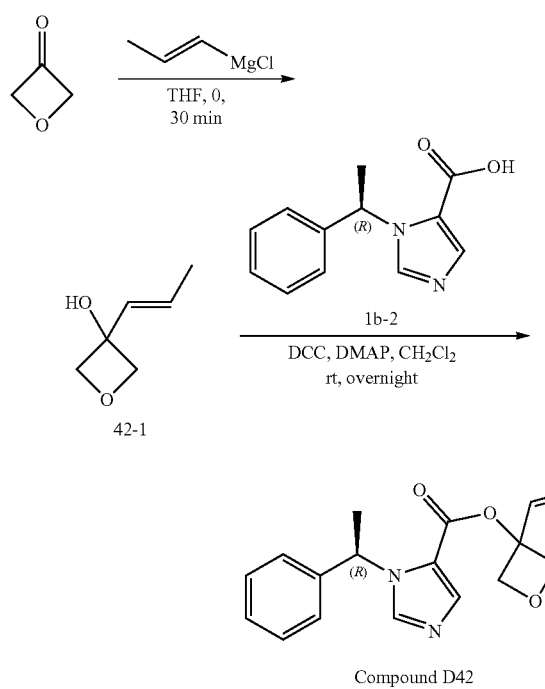

1. Preparation of (E)-3-(Prop-1-en-1-yl)oxetan-3-ol (42-1)

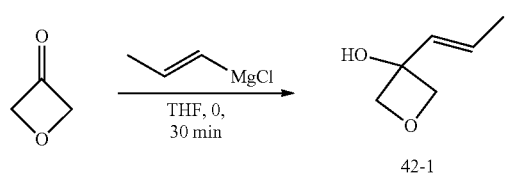

Oxetan-3-one (360 mg, 4.99 mmol) was dissolved in the anhydrous THF (10 mL) under nitrogen atmosphere and the mixture was cooled to 0° C. by an ice-water bath. (E)-Prop-1-en-1-ylmagnesium chloride (4.99 mL, 1.0 mol/L in THF, 4.99 mmol) was added slowly into the reaction solution over a 15-min period using a syringe at 0° C. and the mixture was allowed to react at this temperature for 30 min. The reaction was monitored by TLC. After the reaction was completed, the mixture was quenched with the saturated ammonium chloride solution (10 mL) and extracted with ethyl acetate (3×10 mL). The combined organic layers were washed with saturated brine (50 mL), dried over anhydrous sodium sulfate, filtered and concentrated under reduced pressure to give crude compound 42-1 as colorless oil, which was used for next step directly without further purification.

2. Preparation of Compound D42

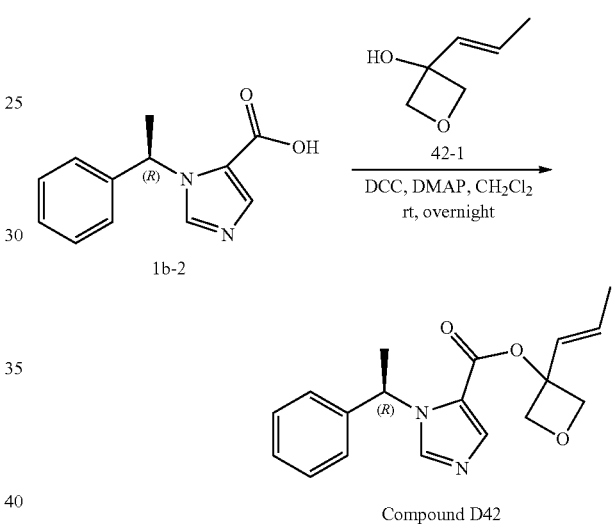

The title compound was prepared according to the general procedure A, using 1b-2 (216 mg, 1.0 mmol) and 42-1 as raw materials. The crude product was purified by Prep-TLC (ethyl acetate/petroleum ether (v/v)=1/1) and the fraction with Rf=0.4~0.5 was collected and dried to give the product D42 (80 mg, yield 26%) as colorless oil. ESI[M+H]$^+$=313.2

$^1$H NMR (400 MHz, CDCl$_3$) δ 7.90-7.80 (m, 2H), 7.43-7.30 (m, 3H), 7.18 (dd, J=9.8, 3.9 Hz, 2H), 6.29 (dd, J=7.1, 3.8 Hz, 1H), 5.95 (ddd, J=17.1, 13.3, 1.5 Hz, 1H), 5.80-5.64 (m, 1H), 5.02-4.77 (m, 3H), 4.72 (d, J=8.0 Hz, 1H), 1.87 (dd, J=7.1, 2.9 Hz, 3H), 1.73 (dd, J=6.3, 1.4 Hz, 1.34H), 1.60 (dd, J=7.2, 1.7 Hz, 1.67H).

Example D42 Preparation of Compound D43

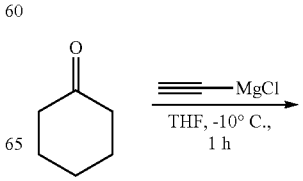

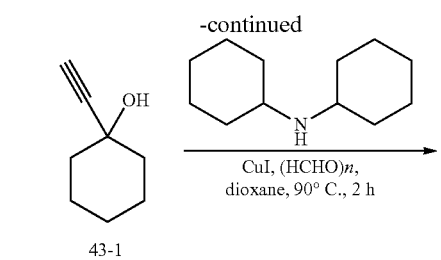

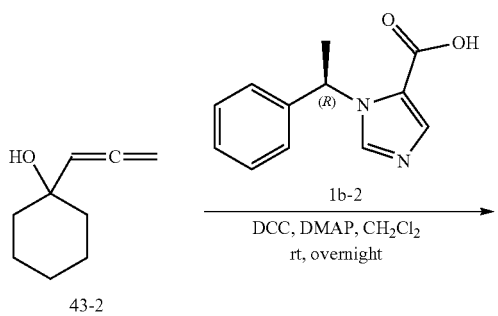

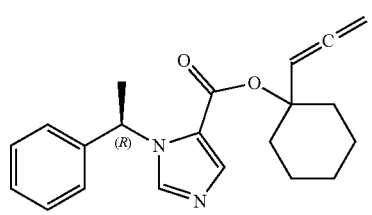

Compound D43

The preparation method of compound 43-2 was the same as compound 21-2 using cyclohexanone as starting material.

The target compound D43 was prepared according to the general procedure A, using 1b-2 (100 mg, 0.46 mmol) and 43-2 (95 mg, 0.69 mmol) as raw materials. The crude product was purified by Prep-TLC (ethyl acetate/petroleum ether (v/v)=1/1) and the fraction with Rf=0.4~0.5 was collected and dried to give the product D43 (124 mg, yield 80%) as colorless oil. ESI[M+H]$^+$=337.3

$^1$H NMR (400 MHz, CDCl$_3$) δ 8.20 (s, 1H), 7.98 (s, 1H), 7.45-7.35 (m, 3H), 7.33-7.26 (m, 2H), 6.50-6.40 (m, 1H), 5.60 (s, 1H), 4.99-4.90 (m, 2H), 2.36-2.25 (m, 2H), 2.13 (t, J=5.8 Hz, 2H), 1.93 (d, J=7.0 Hz, 3H), 1.63-1.50 (m, 6H).

Example D43 Preparation of Compound D44

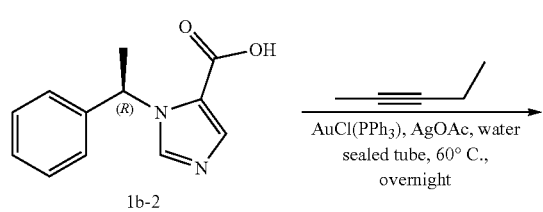

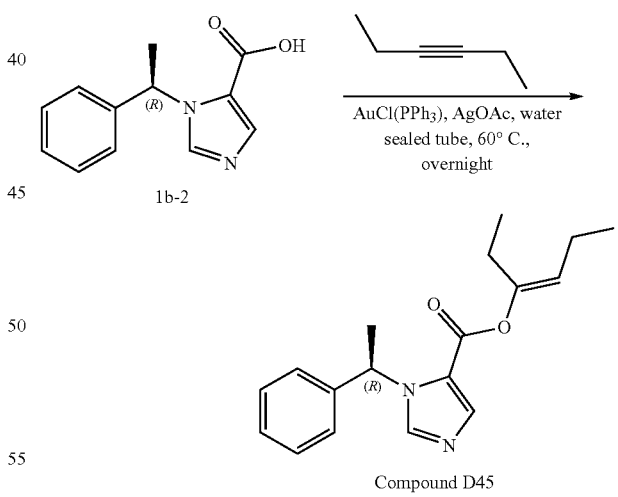

Compound D44

At room temperature, 1b-2 (216 mg, 1.0 mmol), AgOAc (13 mg, 1.0 mmol), AuCl(PPh$_3$) (25 mg, 0.05 mmol) and pent-2-yne (82 mg, 1.2 mmol) were dissolved in the water (3.0 mL) under nitrogen atmosphere. The mixture was stirred in a sealed tube at 60° C. overnight. The reaction was monitored by TLC until completion, then it was quenched with the saturated ammonium chloride solution (10 mL) and extracted with ethyl acetate (3×10 mL). The combined organic layers were washed with saturated brine (50 mL), dried over anhydrous sodium sulfate, filtered and concentrated under reduced pressure to give crude product. The crude product was purified by Prep-TLC (ethyl acetate/petroleum ether (v/v)=1/1). The fraction with Rf=0.4~0.6 was collected and dried to give product D44 (15 mg, yield 5%) as colorless oil. ESI[M+H]$^+$=285.2

$^1$H NMR (400 MHz, CDCl$_3$) δ 7.86 (s, 1H), 7.80 (s, 1H), 7.40-7.26 (m, 3H), 7.24-7.10 (m, 2H), 6.35 (q, J=7.1 Hz, 1H), 5.09 (t, J=7.1 Hz, 1H), 1.86 (d, J=7.1 Hz, 3H), 1.90-1.74 (m, 2H), 0.85 (t, J=7.5 Hz, 3H).

Example D44 Preparation of Compound D45

The preparation method of Compound D45 was the same as the compound D44 using 1b-2 (216 mg, 1.0 mmol) and hex-3-yne (99 mg, 1.2 mmol) as raw materials. The crude product was purified by Prep-TLC (ethyl acetate/petroleum ether (v/v)=1/1) and the fraction with Rf=0.4~0.5 was collected and dried to give the product D45 (7 mg, yield 2%) as colorless oil. ESI[M+H]$^+$=299.0

$^1$H NMR (400 MHz, CDCl$_3$) δ 7.88 (s, 1H), 7.81 (s, 1H), 7.39-7.27 (m, 3H), 7.22-7.11 (m, 2H), 6.31 (q, J=7.0 Hz,

1H), 5.05 (t, J=7.2 Hz, 1H), 2.23-2.14 (m, 2H), 1.88 (d, J=7.1 Hz, 3H), 1.86-1.75 (m, 2H), 1.01 (t, J=7.5 Hz, 3H), 0.87 (t, J=7.5 Hz, 3H).

Example D45 Preparation of Compound D46

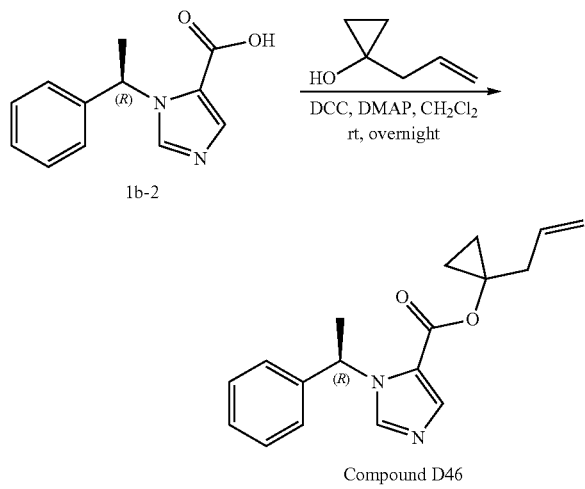

Compound D46

The title compound was prepared according to the general procedure A, using 1b-2 (100 mg, 0.46 mmol) and 1-allyl-cyclopropan-1-ol (68 mg, 0.69 mmol) as raw materials. The crude product was purified by Prep-TLC (ethyl acetate/petroleum ether (v/v)=1/1) and the fraction with Rf=0.4~0.5 was collected and dried to give the product D46 (45 mg, yield 14%) as colorless oil. ESI[M+H]$^+$=297.2

$^1$H NMR (400 MHz, CDCl$_3$) δ 8.04 (s, 1H), 7.96 (s, 1H), 7.41-7.33 (m, 3H), 7.25-7.20 (m, 2H), 6.36 (q, J=7.1 Hz, 1H), 5.75-5.36 (m, 1H), 5.10-4.98 (m, 2H), 2.69-2.54 (m, 2H), 1.86 (d, J=7.1 Hz, 3H), 0.86-0.61 (m, 4H).

Example D46 Preparation of Compound D47

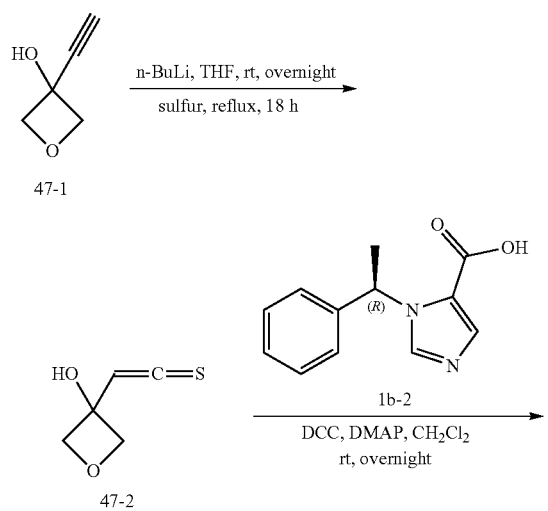

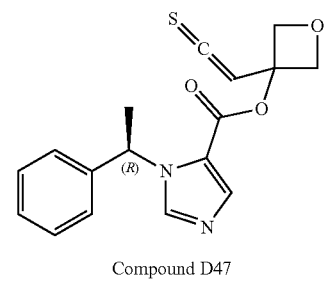

Compound D47

The compound 47-1 was synthesized using oxetan-3-one and ethynylmagnesium bromide as raw materials, then it reacted with n-BuLi and sulfur to afford compound 47-2.

The target compound D47 was prepared according to the general procedure A, using 1b-2 (100 mg, 0.46 mmol) and 47-2 (90 mg, 0.69 mmol) as materials. The crude product was purified by Prep-TLC (ethyl acetate/petroleum ether (v/v)=1/1) and the fraction with Rf=0.4~0.5 was collected and dried to give the product D47 (18 mg, yield 12%) as colorless oil. ESI[M+H]$^+$=329.1

$^1$H NMR (400 MHz, CDCl$_3$) δ 7.82 (s, 1H), 7.78 (s, 1H), 7.40-7.28 (m, 3H), 7.20-7.15 (m, 2H), 6.35-6.27 (m, 1H), 5.63-4.89 (m, 5H), 1.87 (d, J=7.1 Hz, 3H).

Example D47 Preparation of Compound D48

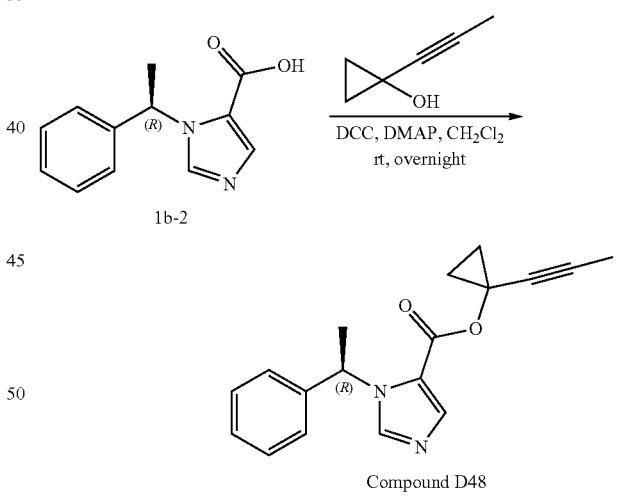

Compound D48

The title compound was prepared according to the general procedure A, using 1b-2 (100 mg, 0.46 mmol) and 1-(prop-1-yn-1-yl)cyclopropan-1-ol (66 mg, 0.69 mmol) as raw materials. The crude product was purified by Prep-TLC (ethyl acetate/petroleum ether (v/v)=1/1) and the fraction with Rf=0.4~0.5 was collected and dried to give the product D48 (56 mg, yield 41%) as colorless oil. ESI[M+H]$^+$=295.2

$^1$H NMR (400 MHz, CDCl$_3$) δ 8.00 (s, 1H), 7.86 (s, 1H), 7.45-7.35 (m, 3H), 7.27-7.22 (m, 2H), 6.35 (q, J=7.1 Hz, 1H), 1.87 (d, J=7.1 Hz, 3H), 1.85 (s, 3H), 0.85-0.61 (m, 4H).

Example D48 Preparation of Compound D49

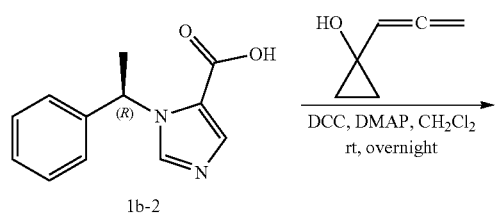

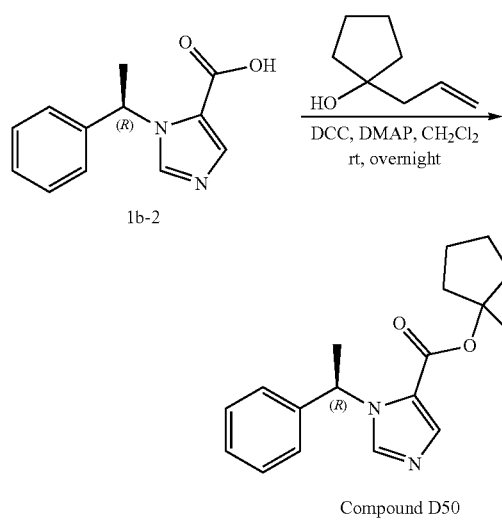

The title compound was prepared according to the general procedure A, using 1b-2 (100 mg, 0.46 mmol) and 1-(propa-1,2-dien-1-yl)cyclopropan-1-ol (66 mg, 0.69 mmol) as raw materials. The crude product was purified by Prep-TLC (ethyl acetate/petroleum ether (v/v)=1/1) and the fraction with Rf=0.4~0.6 was collected and dried to give the product D49 (26 mg, yield 19%) as colorless oil. ESI[M+H]$^+$=295.1

$^1$H NMR (400 MHz, CDCl$_3$) δ 8.00 (s, 1H), 7.88 (s, 1H), 7.44-7.29 (m, 3H), 7.25-7.20 (m, 2H), 6.30 (q, J=7.0 Hz, 1H), 5.65-5.60 (m, 1H), 5.04-4.85 (m, 2H), 1.83 (d, J=7.1 Hz, 3H), 0.86-0.60 (m, 4H).

Example D49 Preparation of Compound D50

The title compound was prepared according to the general procedure A, using 1b-2 (100 mg, 0.46 mmol) and 1-allyl-cyclopentan-1-ol (87 mg, 0.69 mmol) as raw materials. The crude product was purified by Prep-TLC (ethyl acetate/petroleum ether (v/v)=1/1) and the fraction with Rf=0.4~0.6 was collected and dried to give the product D50 (96 mg, yield 64%) as colorless oil. ESI[M+H]$^+$=325.2

$^1$H NMR (400 MHz, CDCl$_3$) δ 8.01 (s, 1H), 7.90 (s, 1H), 7.40-7.30 (m, 3H), 7.25-7.21 (m, 2H), 6.29 (q, J=7.1 Hz, 1H), 5.75-5.67 (m, 1H), 5.15-5.06 (m, 2H), 2.87 (d, J=7.0 Hz, 2H), 2.08-1.91 (m, 2H), 1.85 (d, J=7.1 Hz, 3H), 1.81-1.30 (m, 6H).

Example D50 Preparation of Compound D51

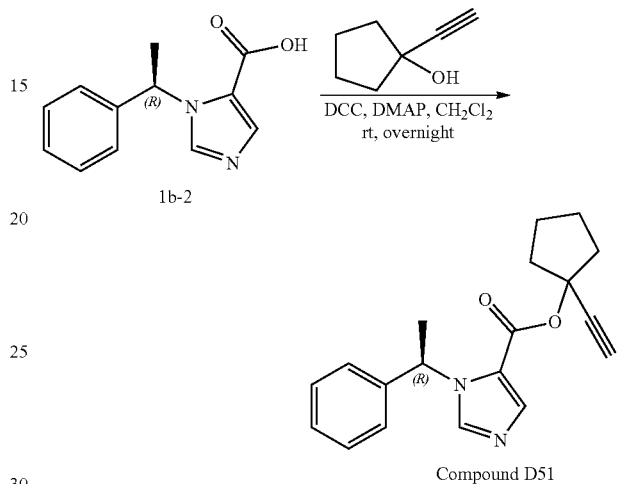

The title compound was prepared according to the general procedure A, using 1b-2 (100 mg, 0.46 mmol) and 1-ethynylcyclopentan-1-ol (76 mg, 0.69 mmol) as raw materials. The crude product was purified by Prep-TLC (ethyl acetate/petroleum ether (v/v)=1/1) and the fraction with Rf=0.4~0.6 was collected and dried to give the product D51 (116 mg, yield 82%) as colorless oil. ESI[M+H]$^+$=309.1

$^1$H NMR (400 MHz, CDCl$_3$) δ 8.02 (s, 1H), 7.91 (s, 1H), 7.45-7.30 (m, 3H), 7.25-7.21 (m, 2H), 6.37 (q, J=7.0 Hz, 1H), 2.63 (s, 1H), 2.04-1.90 (m, 2H), 1.85 (d, J=7.1 Hz, 3H), 1.83-1.34 (m, 6H).

Example D51 Preparation of Compound D52

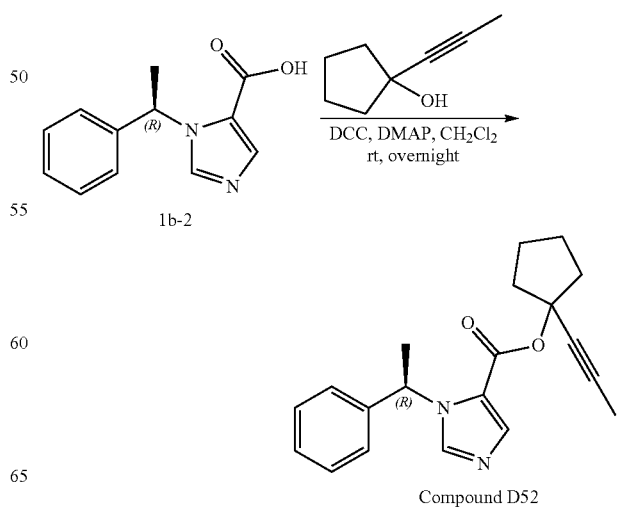

The title compound was prepared according to the general procedure A, using 1b-2 (100 mg, 0.46 mmol) and 1-(prop-1-yn-1-yl)cyclopentan-1-ol (86 mg, 0.69 mmol) as raw materials. The crude product was purified by Prep-TLC (ethyl acetate/petroleum ether (v/v)=1/1) and the fraction with Rf=0.4~0.6 was collected and dried to give the product D52 (80 mg, yield 54%) as colorless oil. ESI[M+H]$^+$=323.2

$^1$H NMR (400 MHz, CDCl$_3$) δ 8.03 (s, 1H), 7.89 (s, 1H), 7.42-7.30 (m, 3H), 7.25-7.21 (m, 2H), 6.38 (q, J=7.0 Hz, 1H), 2.01-1.90 (m, 2H), 1.87 (d, J=7.1 Hz, 3H), 1.86 (s, 3H), 1.83-1.34 (m, 6H).

Example D52 Preparation of Compound D53

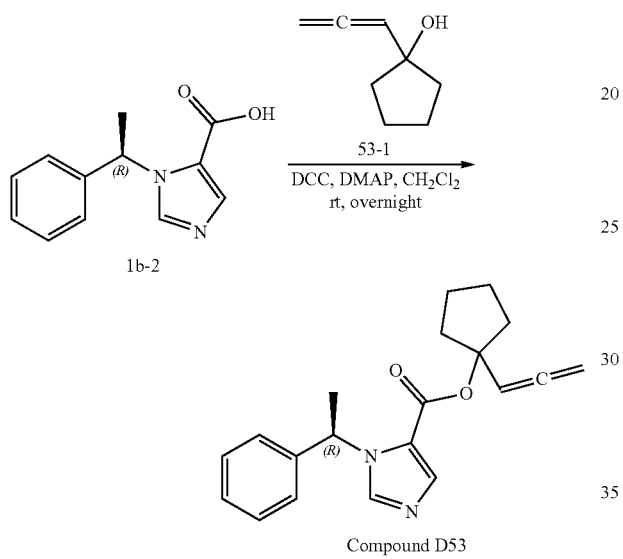

Compound D53

The preparation method of the compound 53-1 was the same as compound 21-2 using 1-ethynylcyclopentan-1-ol as raw materials.

The target compound D53 was prepared according to the general procedure A, using 1b-2 (100 mg, 0.46 mmol) and 53-1 (86 mg, 0.69 mmol) as raw materials. The crude product was purified by Prep-TLC (ethyl acetate/petroleum ether (v/v)=1/1) and the fraction with Rf=0.4~0.6 was collected and dried to give the product D53 (43 mg, yield 29%) as colorless oil. ESI[M+H]$^+$=323.2

$^1$H NMR (400 MHz, CDCl$_3$) δ 7.79 (s, 1H), 7.73 (s, 1H), 7.41-7.29 (m, 3H), 7.25-7.21 (m, 2H), 6.38 (q, J=7.1 Hz, 1H), 5.67-5.61 (m, 1H), 5.05-4.87 (m, 2H), 2.08-1.92 (m, 2H), 1.87 (d, J=7.1 Hz, 3H), 1.85-1.34 (m, 6H).

Example D53 Preparation of Compound D54

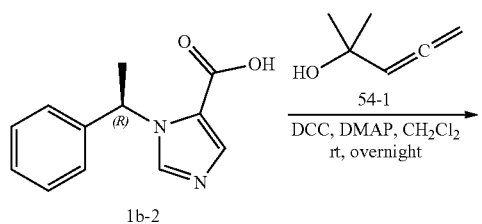

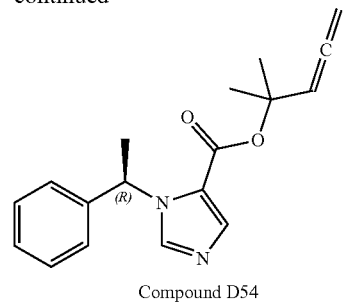

Compound D54

The preparation method of compound 54-1 was the same as compound 21-2 using 2-methylbut-3-yn-2-ol as raw materials.

The target compound D54 was prepared according to the general procedure A, using 1b-2 (100 mg, 0.46 mmol) and 54-1 (68 mg, 0.69 mmol) as raw materials. The crude product was purified by Prep-TLC (ethyl acetate/petroleum ether (v/v)=1/1) and the fraction with Rf=0.4~0.6 was collected and dried to give the product D54 (28 mg, yield 21%) as colorless oil. ESI[M+H]$^+$=297.2

$^1$H NMR (400 MHz, CDCl$_3$) δ 8.03 (s, 1H), 7.89 (s, 1H), 7.44-7.30 (m, 3H), 7.24-7.21 (m, 2H), 6.38 (q, J=7.0 Hz, 1H), 6.17-5.55 (m, 1H), 5.45-4.69 (m, 2H), 2.06-1.85 (m, 6H), 1.82-1.59 (m, 3H).

Example D54 Preparation of Compound D55

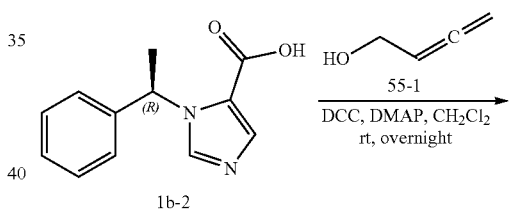

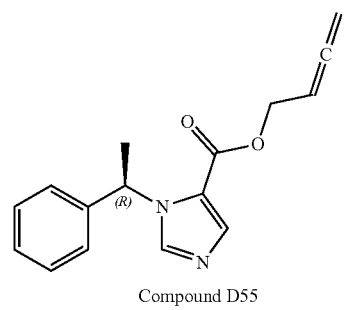

Compound D55

The preparation method of compound 55-1 was the same as compound 21-2 using prop-2-yn-1-ol as raw materials.

The target compound D55 was prepared according to the general procedure A, using 1b-2 (100 mg, 0.46 mmol) and 55-1 (48 mg, 0.69 mmol) as raw materials. The crude product was purified by Prep-TLC (ethyl acetate/petroleum ether (v/v)=1/1) and the fraction with Rf=0.4~0.6 was collected and dried to give the product D55 (79 mg, yield 64%) as colorless oil. ESI[M+H]$^+$=269.1

$^1$H NMR (400 MHz, CDCl$_3$) δ 7.81 (s, 1H), 7.79 (s, 1H), 7.42-7.27 (m, 3H), 7.25-7.19 (m, 2H), 6.39-6.25 (m, 1H), 5.50-5.25 (m, 3H), 4.89-4.73 (m, 2H), 1.83 (d, J=7.1 Hz, 3H).

Example D55 Preparation of Compound D56

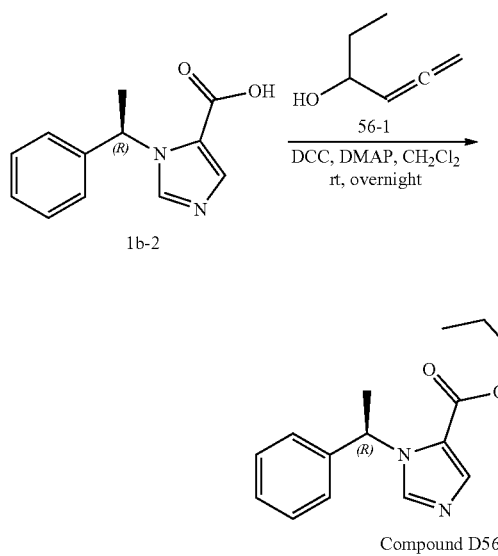

The preparation method of compound 56-1 was the same as compound 21-2 using pent-1-yn-3-ol as raw materials.

The target compound D56 was prepared according to the general procedure A, using 1b-2 (100 mg, 0.46 mmol) and 56-1 (48 mg, 0.69 mmol) as raw materials. The crude product was purified by Prep-TLC (ethyl acetate/petroleum ether (v/v)=1/1) and the fraction with Rf=0.4~0.6 was collected and dried to give the product D56 (98 mg, yield 72%) as colorless oil. ESI[M+H]$^+$=297.2

$^1$H NMR (400 MHz, CDCl$_3$) δ 7.80 (s, 1H), 7.79 (s, 1H), 7.35-7.27 (m, 3H), 7.24-7.21 (m, 2H), 6.35-6.21 (m, 1H), 5.26-5.18 (m, 2H), 4.92-4.74 (m, 2H), 1.82 (d, J=7.1 Hz, 3H), 1.70-1.68 (m, 2H), 0.93 (t, J=7.4 Hz, 3H).

Example D56 Preparation of Compound D57

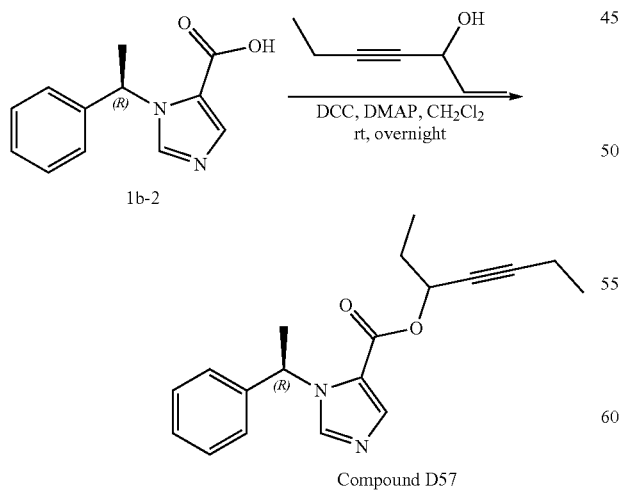

The title compound was prepared according to the general procedure A, using 1b-2 (100 mg, 0.46 mmol) and hept-4-yn-3-ol (78 mg, 0.69 mmol) as raw materials. The crude product was purified by Prep-TLC (ethyl acetate/petroleum ether (v/v)=1/1) and the fraction with Rf=0.4~0.6 was collected and dried to give the product D57 (113 mg, yield 79%) as colorless oil. ESI[M+H]$^+$=311.2

$^1$H NMR (400 MHz, CDCl$_3$) δ 7.92-7.75 (m, 2H), 7.41-7.28 (m, 3H), 7.25-7.11 (m, 2H), 6.44-6.31 (m, 1H), 5.65-5.41 (m, 1H), 2.30-2.11 (m, 4H), 1.95-1.80 (m, 3H), 1.16-1.02 (m, 3H), 0.95-0.79 (m, 3H).

Example D57 Preparation of Compound D58

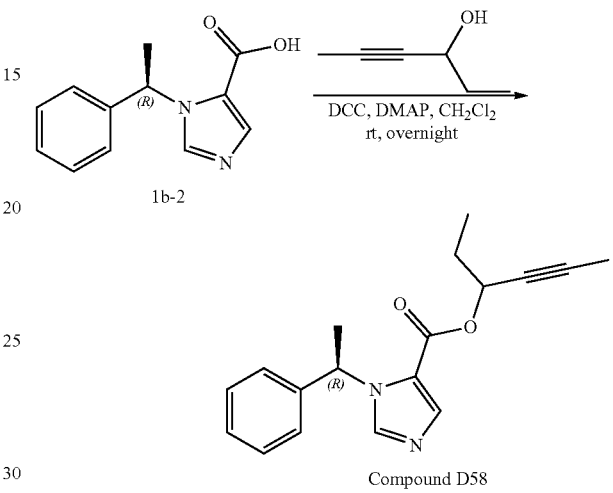

The title compound was prepared according to the general procedure A, using 1b-2 (100 mg, 0.46 mmol) and hex-4-yn-3-ol (68 mg, 0.69 mmol) as raw materials. The crude product was purified by Prep-TLC (ethyl acetate/petroleum ether (v/v)=1/1) and the fraction with Rf=0.4~0.6 was collected and dried to give the product D58 (100 mg, yield 73%) as colorless oil. ESI[M+H]$^+$=297.2

$^1$H NMR (400 MHz, CDCl$_3$) δ 7.80 (d, J=3.2 Hz, 1H), 7.72 (m, 1H), 7.39-7.25 (m, 3H), 7.25-7.10 (m, 2H), 6.49-6.25 (m, 1H), 5.60-5.35 (m, 1H), 1.94-1.74 (m, 5H), 1.55-1.43 (m, 3H), 0.98-0.85 (m, 3H).

Example D58 Preparation of Compound D59

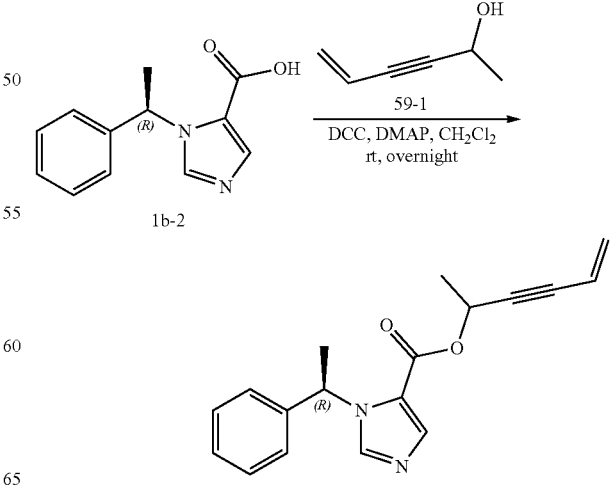

The preparation method of compound 59-1 was the same as compound 37-1 using but-3-yn-2-ol and bromoethene as raw materials.

The target compound D59 was prepared according to the general procedure A, using 1b-2 (100 mg, 0.46 mmol) and 59-1 (66 mg, 0.69 mmol) as raw materials according to the general procedure A. The crude product was purified by Prep-TLC (ethyl acetate/petroleum ether (v/v)=1/1) and the fraction with Rf=0.4~0.6 was collected and dried to give the product D59 (98 mg, yield 72%) as colorless oil. ESI[M+H]$^+$=295.2

$^1$H NMR (400 MHz, CDCl$_3$) δ 7.98 (s, 1H), 7.85 (s, 1H), 7.39-7.27 (m, 3H), 7.25-7.11 (m, 2H), 6.38 (q, J=7.1 Hz, 1H), 5.85-5.72 (m, 1H), 5.63-5.48 (m, 3H), 1.85 (d, J=7.1 Hz, 3H), 1.75 (s, 3H).

Example D59 Preparation of Compound D60

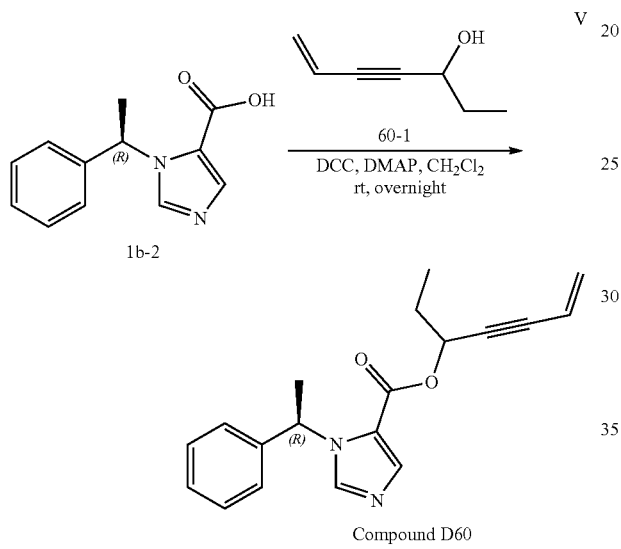

The preparation method of compound 60-1 was the same as compound 37-1 using pent-1-yn-3-ol and bromoethene as raw materials.

The target compound D60 was prepared according to the general procedure A, using 1b-2 (100 mg, 0.46 mmol) and 60-1 (76 mg, 0.69 mmol) as raw materials. The crude product was purified by Prep-TLC (ethyl acetate/petroleum ether (v/v)=1/1) and the fraction with Rf=0.4~0.6 was collected and dried to give the product D60 (76 mg, yield 54%) as colorless oil. ESI[M+H]$^+$=309.2

$^1$H NMR (400 MHz, CDCl$_3$) δ 7.79 (s, 1H), 7.71 (s, 1H), 7.38-7.26 (m, 3H), 7.25-7.12 (m, 2H), 6.38 (q, J=7.1 Hz, 1H), 5.84~5.77 (m, 1H), 5.64-5.59 (m, 2H), 5.50-5.46 (m, 1H), 2.03-1.92 (m, 2H), 1.87 (d, J=7.1 Hz, 3H), 0.95 (t, J=7.3 Hz, 3H).

Example E1 Preparation of Compound E1

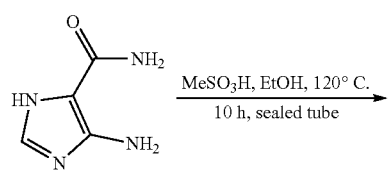

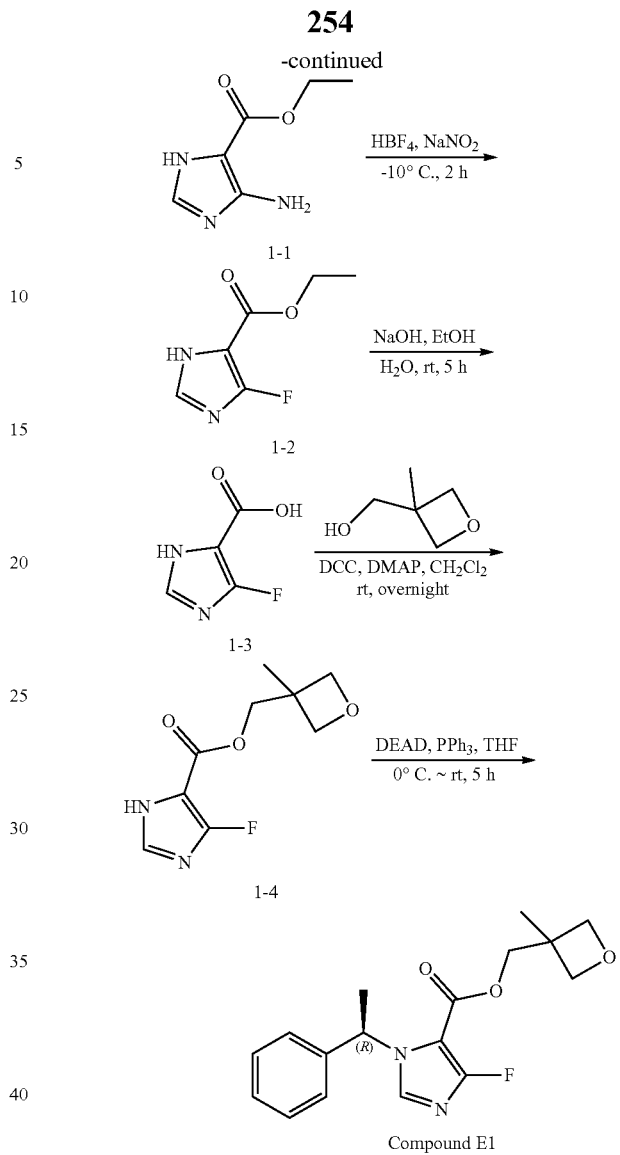

1. Preparation of Ethyl 4-amino-1H-imidazole-5-carboxylate (1-1)

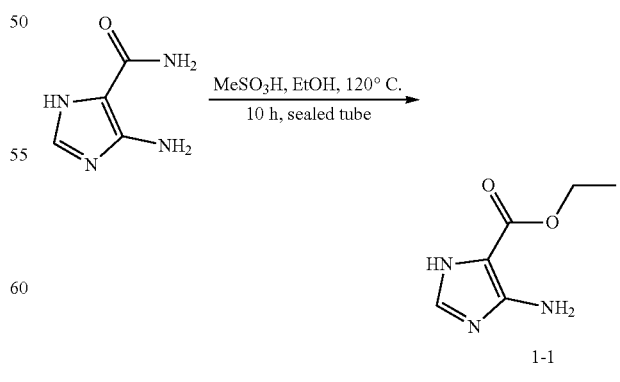

At room temperature, 4-amino-1H-imidazole-5-carbox-amide (3.0 g, 23.8 mmol), ethanol (30 mL) and MeSO$_3$H (6 mL) were added into a sealed tube, then it was allowed to react at 120° C. for 10 hrs. The reaction solution was concentrated under reduced pressure The residue was adjusted pH to 8 with saturated NaHCO₃ solution and extracted with ethyl acetate (3×150 mL). The combined organic layers washed with saturated brine (100 mL), dried over anhydrous sodium sulfate, filtered and concentrated under reduced pressure to give compound 1-1 (3.0 g, yield 81%) as a white solid.

2. Preparation of ethyl 4-amino-1H-imidazole-5-carboxylate (1-2)

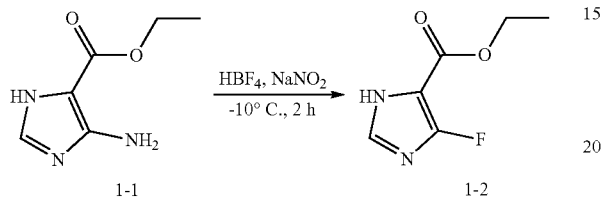

In an ice-salt bath, 1-1 (250 mg, 1.61 mmol) was dissolved in the HBF₄ (40%), and then NaNO₂ (117 mg, 1.69 mmol) in the water (0.15 mL) was added dropwise into solution at −10° C. The mixture was allowed to react under the irradiation of a mercury lamp (254 nm) for 2 hrs. The reaction was monitored by TLC until completion, and then the reaction solution was adjusted pH to 7 with 1N NaOH solution in an ice-water bath. The mixture was extracted with ethyl acetate (3×10 mL). The combined organic layers were washed with saturated brine, dried over anhydrous sodium sulfate, filtered and concentrated under reduced pressure. The crude product was purified by silica gel column chromatography with ethyl acetate/petroleum ether (v/v=1/1) and the eluate was monitored by TLC (ethyl acetate/petroleum ether (v/v)=1/1). The fraction with Rf=0.4~0.5 was collected to give compound 1-2 (100 mg, yield 39%) as colorless oil.

3. Preparation of ethyl 4-fluoro-1H-imidazole-5-carboxylate (1-3)

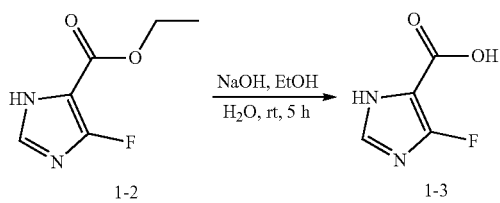

At room temperature, NaOH (50 mg, 1.26 mmol) and 1-2 (100 mg, 0.63 mmol) were dissolved in ethanol/water (5 mL, v/v=1/1), and then it was reacted at room temperature for 5 hrs. After the reaction was completed, the mixture was concentrated under reduced pressure, cooled and adjusted pH to 5 with 1 N HCl solution. The mixture was extracted with ethyl acetate (3×5 mL). The combined organic layers were washed with saturated brine, dried over anhydrous sodium sulfate, filtered and concentrated under reduced pressure to give compound 1-3 (74 mg, total yield 90%) as a gray solid. ESI[M+H]⁺=131.0

4. Preparation of (3-Methyloxetan-3-yl)methyl 4-fluoro-1H-imidazole-5-carboxylate (1-4)

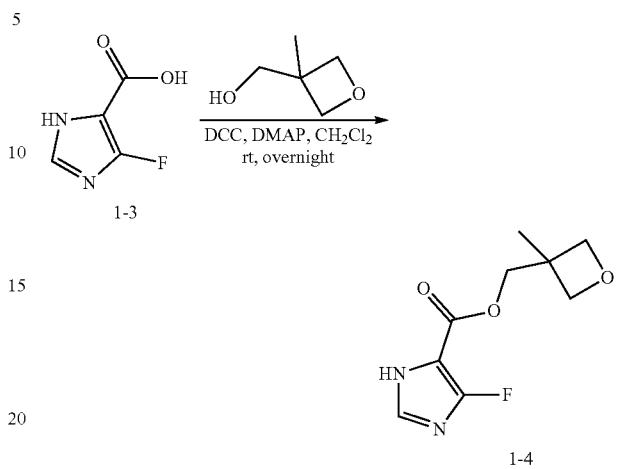

At room temperature, 1-3 (74 mg, 0.57 mmol), DCC (173 mg, 0.84 mmol) and DMAP (103 mg, 0.84 mmol) were dissolved in dichloromethane (5 mL). After stirring 5 min, (3-methyloxetan-3-yl)methanol (86 mg, 0.84 mmol) was added slowly into the mixture using a syringe and the mixture was stirred at room temperature overnight. The mixture was concentrated under reduced pressure and methyl tert-butyl ether was added. The mixture was stirred, filtered and concentrated under reduced pressure to give crude product. The crude product was purified by silica gel column chromatography (ethyl acetate/petroleum ether (v/v)=1/3) and the eluate was monitored by TLC (ethyl acetate/petroleum ether (v/v)=1/1). The fraction Rf=0.5~0.6 was collected and dried to give product 1-4 (109 mg, yield 89%) as colorless oil. ESI[M+H]⁺=215.1

5. Preparation of Compound E1

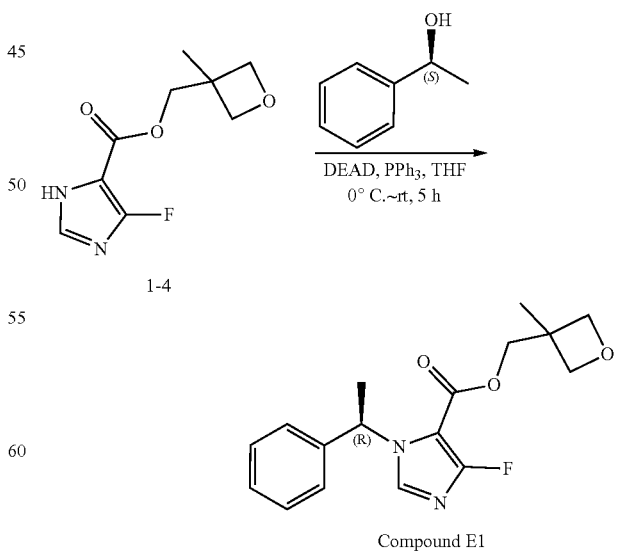

In an ice-water bath, 1-4 (109 mg, 0.51 mmol), S-1-phenylethan-1-ol (94 mg, 0.77 mmol) and PPh₃ (202 mg, 0.77 mmol) were dissolved in THF (10 mL), then DEAD (230 mg, 1.32 mmol) was added slowly into the mixture using a syringe. The reaction was warmed slowly to room temperature and stirred for 5 hrs. The reaction was monitored by TLC until completion, then it was quenched with the saturated brine (10 mL) and extracted with ethyl acetate (3×10 mL). The combined organic layers were washed with saturated brine (50 mL), dried over anhydrous sodium sulfate, filtered and concentrated under reduced pressure to give crude product. The crude product was purified by Prep-TLC (ethyl acetate/petroleum ether (v/v)=1/1) and the fraction with Rf=0.4~0.6 was collected and dried to give the product E1 (102 mg, yield 63%) as colorless oil. ESI[M+H]$^+$=319.2

$^1$H NMR (400 MHz, CDCl$_3$) δ 7.42-7.28 (m, 4H), 7.24-7.17 (m, 2H), 6.26 (q, J=7.0 Hz, 1H), 4.52 (dd, J=6.0, 2.8 Hz, 2H), 4.40 (dd, J=6.1, 1.5 Hz, 2H), 4.33 (q, J=11.0 Hz, 2H), 1.85 (d, J=7.1 Hz, 3H), 1.36 (s, 3H).

The preparation method of the target compounds listed below were similar as the compound E1. 2-fluoro-1H-imidazole-5-carboxylic acid, 4-fluoro-1H-imidazole-5-carboxylic acid or 2,4-difluoro-1H-imidazole-5-carboxylic acid reacted with corresponding alcohols to give corresponding imidazole-5-formate ester derivatives as intermediates, which reacted with (S)-1-phenylethan-1-ol to give the correspondent target compounds.

The compound E2: 50 mg, ESI[M+H]$^+$=347.2

$^1$H NMR (400 MHz, CDCl$_3$) δ 7.41-7.28 (m, 4H), 7.25-7.18 (m, 2H), 6.30 (q, J=7.1 Hz, 1H), 4.25 (dd, J=25.0, 10.8 Hz, 2H), 3.40 (s, 2H), 3.33 (s, 3H), 1.98-1.86 (m, 6H), 1.85 (d, J=7.1 Hz, 3H).

The compound E3: 50 mg, ESI[M+H]$^+$=339.2

$^1$H NMR (400 MHz, CDCl$_3$) δ 7.71 (s, 1H), 7.47-7.21 (m, 5H), 6.26 (q, J=7.0 Hz, 1H), 4.29-4.14 (m, 2H), 2.77-2.60 (m, 2H), 2.59-2.30 (m, 3H), 1.81 (d, J=7.1 Hz, 3H).

The compound E4: 51 mg, ESI[M+H]$^+$=315.4

$^1$H NMR (400 MHz, CDCl$_3$) δ 7.41-7.29 (m, 4H), 7.21 (d, J=6.8 Hz, 2H), 6.20 (d, J=7.1 Hz, 1H), 4.93 (t, J=6.5 Hz, 2H), 4.87 (d, J=7.4 Hz, 1H), 4.75 (d, J=8.0 Hz, 1H), 2.78 (s, 1H), 1.85 (d, J=7.1 Hz, 3H).

The compound E5: 40 mg, ESI[M+H]$^+$=305.2

$^1$H NMR (400 MHz, CDCl$_3$) δ 7.71 (s, 1H), 7.35-7.19 (m, 5H), 6.13 (q, J=7.0 Hz, 1H), 4.51-4.35 (m, 2H), 2.77 (td, J=6.3, 2.2 Hz, 2H), 2.20 (s, 3H), 1.91 (d, J=7.1 Hz, 3H).

The compound E6: 32 mg, ESI[M+H]$^+$=305.2

$^1$H NMR (400 MHz, CDCl$_3$) δ 7.42 (s, 1H), 7.33 (dd, J=13.7, 6.2 Hz, 3H), 7.14 (d, J=6.9 Hz, 2H), 6.17 (q, J=7.0 Hz, 1H), 1.91 (s, 3H), 1.84 (d, J=7.1 Hz, 3H), 1.52 (s, 3H), 1.47 (s, 3H).

The compound E7: 50 mg, ESI[M+H]$^+$=303.2

$^1$H NMR (400 MHz, CDCl$_3$) δ 7.70 (s, 1H), 7.45-7.19 (m, 5H), 6.25 (q, J=7.0 Hz, 1H), 4.24-4.07 (m, 2H), 2.75-2.56 (m, 1H), 2.16-1.98 (m, 2H), 1.97-1.71 (m, 4H), 1.79 (d, J=7.1 Hz, 3H).

The compound E8: 83 mg, ESI[M+H]$^+$=289.0

$^1$H NMR (400 MHz, CDCl$_3$) δ 7.40-7.28 (m, 4H), 7.23-7.16 (m, 2H), 6.28 (q, J=7.0 Hz, 1H), 4.19-3.92 (m, 2H), 1.85 (d, J=7.1 Hz, 3H), 1.24-1.11 (m, 1H), 0.65-0.49 (m, 2H), 0.39-0.20 (m, 2H).

The compound E9: 63 mg, ESI[M+H]$^+$=289.0

$^1$H NMR (400 MHz, CDCl$_3$) δ 7.42-7.28 (m, 4H), 7.23-7.14 (m, 2H), 6.26 (q, J=6.8 Hz, 1H), 5.31-4.92 (m, 1H), 2.49-2.29 (m, 2H), 2.25-2.06 (m, 2H), 1.83 (d, J=7.1 Hz, 3H), 1.90-1.76 (m, 1H), 1.72-1.59 (m, 1H).

The compound E10: 93 mg, ESI[M+H]$^+$=291.0

$^1$H NMR (400 MHz, CDCl$_3$) δ 7.45-7.28 (m, 4H), 7.22-7.13 (m, 2H), 6.18 (q, J=7.0 Hz, 1H), 5.56 (p, J=5.9 Hz, 1H), 5.00-4.78 (m, 2H), 4.76-4.57 (m, 2H), 1.85 (d, J=7.1 Hz, 3H).

The compound E11: 33 mg, ESI[M+H]$^+$=307.0

$^1$H NMR (400 MHz, CDCl$_3$) δ 7.46-7.28 (m, 4H), 7.22-7.08 (m, 2H), 6.19 (q, J=7.1 Hz, 1H), 5.75 (p, J=8.0 Hz, 1H), 3.64-3.43 (m, 2H), 3.42-3.16 (m, 2H), 1.84 (d, J=7.1 Hz, 3H).

The compound E12: 63 mg, ESI[M+H]$^+$=291.1

$^1$H NMR (400 MHz, CDCl$_3$) δ 7.42-7.27 (m, 4H), 7.24-7.17 (m, 2H), 6.27 (q, J=6.6 Hz, 1H), 1.84 (d, J=7.1 Hz, 3H), 1.51 (s, 9H).

The compound E13: 29 mg, ESI[M+H]$^+$=333.0

$^1$H NMR (400 MHz, CDCl$_3$) δ 7.47 (s, 1H), 7.41-7.28 (m, 3H), 7.22-7.03 (m, 2H), 6.21-5.97 (m, 1H), 5.10-4.57 (m, 4H), 2.13 (s, 3H), 1.85 (d, J=7.1 Hz, 3H).

The compound E14: 63 mg, ESI[M+H]$^+$=317.0

$^1$H NMR (400 MHz, CDCl$_3$) δ 7.48 (s, 1H), 7.42-7.25 (m, 3H), 7.24-7.01 (m, 2H), 6.20-5.96 (m, 1H), 2.17 (s, 3H), 1.86 (d, J=7.1 Hz, 3H), 1.21-0.85 (m, 4H).

The compound E15: 104 mg, ESI[M+H]$^+$=329.0

$^1$H NMR (400 MHz, CDCl$_3$) δ 7.46-7.29 (m, 4H), 7.24-7.15 (m, 2H), 6.21 (q, J=7.1 Hz, 1H), 4.95-4.79 (m, 3H), 4.73 (d, J=7.3 Hz, 1H), 1.89 (s, 3H), 1.85 (d, J=7.1 Hz, 3H).

The compound E16: 88 mg, ESI[M+H]$^+$=301.0

$^1$H NMR (400 MHz, CDCl$_3$) δ 7.41-7.28 (m, 4H), 7.24-7.16 (m, 2H), 6.37-6.17 (m, 1H), 5.61-5.37 (m, 1H), 1.91-1.77 (m, 6H), 1.51 (d, J=6.6 Hz, 3H).

The compound E17: 56 mg, ESI[M+H]$^+$=315.1

$^1$H NMR (400 MHz, CDCl$_3$) δ 7.41-7.27 (m, 4H), 7.26-7.18 (m, 2H), 6.30 (q, J=7.0 Hz, 1H), 1.84 (d, J=5.4 Hz, 6H), 1.70 (s, 3H), 1.67 (s, 3H).

The compound E18: 36 mg, ESI[M+H]$^+$=301.0

$^1$H NMR (400 MHz, CDCl$_3$) δ 7.47-7.29 (m, 4H), 7.24-7.15 (m, 2H), 6.34-6.22 (m, 1H), 5.58-5.44 (m, 1H), 5.37-5.23 (m, 1H), 4.95-4.73 (m, 2H), 1.85 (d, J=7.0 Hz, 3H), 1.47-1.31 (m, 3H).

The compound E19: 39 mg, ESI[M+H]$^+$=315.0

$^1$H NMR (400 MHz, CDCl$_3$) δ 7.44-7.27 (m, 4H), 7.24-7.17 (m, 2H), 6.37-6.17 (m, 1H), 6.00-5.59 (m, 1H), 5.46-4.71 (m, 2H), 2.01-1.65 (m, 6H), 1.59 (d, J=5.1 Hz, 3H).

The compound E20: 94 mg, ESI[M+H]$^+$=313.0

$^1$H NMR (400 MHz, CDCl$_3$) δ 7.45-7.28 (m, 4H), 7.25-7.09 (m, 2H), 6.38-6.16 (m, 1H), 5.90-5.73 (m, 1H), 5.73-5.58 (m, 2H), 5.56-5.37 (m, 1H), 1.85 (d, J=7.1 Hz, 3H), 1.56 (d, J=6.7 Hz, 3H).

The compound E21: 88 mg, ESI[M+H]$^+$=327.1

$^1$H NMR (400 MHz, CDCl$_3$) δ 7.39-7.27 (m, 4H), 7.25-7.19 (m, 2H), 6.30 (q, J=7.0 Hz, 1H), 5.88-5.74 (m, 1H), 5.67-5.57 (m, 1H), 5.50-5.41 (m, 1H), 1.84 (d, J=7.1 Hz, 3H), 1.75 (s, 3H), 1.71 (s, 3H).

The compound E22: 87 mg, ESI[M+H]$^+$=305.1

$^1$H NMR (400 MHz, CDCl$_3$) δ 7.40-7.28 (m, 4H), 7.23-7.15 (m, 2H), 6.28 (q, J=5.9 Hz, 1H), 4.90 (p, J=6.3 Hz, 1H), 1.85 (d, J=7.0 Hz, 3H), 1.69-1.54 (m, 4H), 0.90 (t, J=7.4 Hz, 3H), 0.83 (t, J=7.4 Hz, 3H).

The compound E23: 36 mg, ESI[M+H]$^+$=373.1

$^1$H NMR (400 MHz, CDCl$_3$) 7.44-7.15 (m, 6H), 6.27 (q, J=7.1 Hz, 1H), 5.86 (s, 1H), 2.49-2.08 (m, 4H), 1.89 (d, J=7.1 Hz, 3H), 1.68-1.44 (m, 6H).

The compound E24: 62 mg, ESI[M+H]$^+$=277.0

$^1$H NMR (400 MHz, CDCl$_3$) δ 7.49-7.28 (m, 4H), 7.24-7.12 (m, 2H), 6.35-6.19 (m, 1H), 5.28-5.03 (m, 1H), 1.85 (d, J=6.7 Hz, 3H), 1.34-1.26 (m, 6H).

The compound E25: 48 mg, ESI[M+H]$^+$=301.0
$^1$H NMR (400 MHz, CDCl$_3$) δ 7.41-7.18 (m, 6H), 6.30 (q, J=6.3 Hz, 1H), 2.59 (s, 1H), 1.84 (d, J=6.9 Hz, 3H), 1.74 (s, 3H), 1.72 (s, 3H).

The compound E26: 73 mg, ESI[M+H]$^+$=305.1
$^1$H NMR (400 MHz, CDCl$_3$) δ 7.44-7.28 (m, 4H), 7.25-7.17 (m, 2H), 6.30 (q, J=6.6 Hz, 1H), 3.91 (dd, J=31.2, 10.4 Hz, 2H), 1.85 (d, J=7.0 Hz, 3H), 0.98 (s, 9H).

The compound E27: 48 mg, ESI[M+H]$^+$=303.1
$^1$H NMR (400 MHz, CDCl$_3$) δ 7.44-7.28 (m, 4H), 7.24-7.16 (m, 2H), 6.33-6.18 (m, 1H), 2.44-2.29 (m, 2H), 2.25-2.10 (m, 2H), 1.84 (d, J=6.7 Hz, 3H), 1.74-1.66 (m, 2H), 1.56 (s, 3H).

The compound E28: 27 mg ESI[M+H]$^+$=305.1
$^1$H NMR (400 MHz, CDCl$_3$) δ 7.41-7.28 (m, 4H), 7.24-7.17 (m, 2H), 6.27 (q, J=6.9 Hz, 1H), 1.90-1.74 (m, 5H), 1.49 (s, 1H), 1.47 (s, 3H), 0.88 (t, J=7.5 Hz, 3H).

The compound E29: 28 mg, ESI[M+H]$^+$=319.0
$^1$H NMR (400 MHz, CDCl$_3$) δ 7.41-7.27 (m, 4H), 7.24-7.12 (m, 2H), 6.27 (q, J=6.4 Hz, 1H), 1.83 (d, J=6.9 Hz, 3H), 1.80-1.74 (m, 2H), 1.48 (s, 3H), 1.48 (s, 3H), 1.41-1.20 (m, 2H), 0.88 (t, J=7.3 Hz, 3H).

The compound E30: 16 mg, ESI[M+H]$^+$=319.0
$^1$H NMR (400 MHz, CDCl$_3$) δ 7.39-7.27 (m, 4H), 7.23-7.14 (m, 2H), 6.27 (q, J=7.0 Hz, 1H), 1.98-1.86 (m, 2H), 1.83 (d, J=7.1 Hz, 3H), 1.82-1.71 (m, 2H), 1.44 (s, 3H), 0.84 (td, J=7.5, 5.0 Hz, 6H).

The compound E31: 14 mg, ESI[M+H]$^+$=343.0
$^1$H NMR (400 MHz, CDCl$_3$) δ 7.50-7.42 (m, 1H), 7.41-7.27 (m, 5H), 7.22-7.15 (m, 1H), 6.24-6.13 (m, 1H), 2.82-2.52 (m, 3H), 2.40-2.27 (m, 2H), 2.22 (s, 1H), 2.03-1.74 (m, 6H).

The compound E32: 40 mg, ESI[M+H]$^+$=303.1
$^1$H NMR (400 MHz, CDCl$_3$) δ 7.42-7.28 (m, 4H), 7.23-7.16 (m, 2H), 6.27 (q, J=7.0 Hz, 1H), 6.08 (dd, J=17.5, 10.9 Hz, 1H), 5.15 (dd, J=48.6, 14.2 Hz, 2H), 1.82 (d, J=7.0 Hz, 3H), 1.57 (s, 6H).

The compound E33: 36 mg, ESI[M+H]$^+$=303.1
$^1$H NMR (400 MHz, CDCl$_3$) δ 7.40-7.28 (m, 4H), 7.24-7.16 (m, 2H), 6.40-6.04 (m, 1H), 1.84 (d, J=6.4 Hz, 3H), 1.59 (s, 3H), 1.37-1.24 (m, 2H), 0.99-0.82 (m, 1H), 0.74-0.61 (m, 1H).

The compound E34: 70 mg, ESI[M+H]$^+$=275.0
$^1$H NMR (400 MHz, CDCl$_3$) δ 7.41-7.29 (m, 4H), 7.24-7.16 (m, 2H), 6.26 (q, J=7.0 Hz, 1H), 4.28-4.14 (m, 1H), 1.84 (d, J=7.1 Hz, 3H), 0.86-0.60 (m, 4H).

The compound E35: 72 mg, ESI[M+H]$^+$=287.0
$^1$H NMR (400 MHz, CDCl$_3$) δ 7.42-7.28 (m, 4H), 7.24-7.17 (m, 2H), 6.26 (q, J=7.1 Hz, 1H), 4.89-4.68 (m, 2H), 1.94-1.79 (m, 6H).

The compound E36: 48 mg ESI[M+H]$^+$=355.1
$^1$H NMR (400 MHz, CDCl$_3$) 7.40-7.29 (m, 4H), 7.22-7.15 (m, 2H), 6.28 (q, J=7.1 Hz, 1H), 5.61-5.51 (m, 1H), 5.00-4.95 (m, 2H), 2.46-2.08 (m, 4H), 1.90 (d, J=7.0 Hz, 3H), 1.65-1.49 (m, 6H).

The compound E37: 680 mg, ESI[M+H]$^+$=329.0
$^1$H NMR (400 MHz, CDCl$_3$) δ 7.40-7.29 (m, 4H), 7.22-7.15 (m, 2H), 6.18 (q, J=7.1 Hz, 1H), 5.62 (t, J=6.6 Hz, 1H), 5.03-4.86 (m, 3H), 4.84-4.71 (m, 3H), 1.84 (d, J=7.1 Hz, 3H).

The compound E38: 55 mg, ESI[M+H]$^+$=305.0
$^1$H NMR (400 MHz, CDCl$_3$) δ 7.42-7.29 (m, 4H), 7.21-7.16 (m, 2H), 6.17 (q, J=7.0 Hz, 1H), 4.80 (dd, J=28.1, 7.2 Hz, 2H), 4.55-4.48 (m, 2H), 1.84 (d, J=7.1 Hz, H), 1.73 (s, 3H).

The compound E39: 58 mg, ESI[M+H]$^+$=317.2
$^1$H NMR (400 MHz, CDCl$_3$) δ 7.40-7.21 (m, 4H), 7.18-7.09 (m, 2H), 6.16 (q, J=7.0 Hz, 1H), 2.50-2.28 (m, 2H), 2.21-2.07 (m, 2H), 1.79 (d, J=7.1 Hz, 3H), 1.85-1.56 (m, 4H), 0.94 (t, J=7.3 Hz, 3H).

The compound E40: 52 mg, ESI[M+H]$^+$=331.2
$^1$H NMR (400 MHz, CDCl$_3$) δ 7.40-7.20 (m, 4H), 7.15-7.10 (m, 2H), 6.20 (q, J=7.0 Hz, 1H), 2.50-2.28 (m, 2H), 2.21-2.07 (m, 2H), 1.80 (d, J=7.1 Hz, 3H), 1.85-1.56 (m, 4H), 1.41-1.20 (m, 2H), 0.88 (t, J=7.3 Hz, 3H).

The compound E41: 44 mg, ESI[M+H]$^+$=303.1
$^1$H NMR (400 MHz, CDCl$_3$) δ 7.45-7.22 (m, 4H), 7.20-7.16 (m, 2H), 6.25 (q, J=7.0 Hz, 1H), 4.50-4.31 (m, 1H), 1.84 (d, J=7.1 Hz, 3H), 1.56-1.40 (m, 3H), 1.24-1.11 (m, 1H), 0.65-0.49 (m, 2H), 0.39-0.20 (m, 2H).

The compound E43: 56 mg, ESI[M+H]$^+$=319.2
$^1$H NMR (400 MHz, CDCl$_3$) δ 7.45-7.25 (m, 4H), 7.22-7.15 (m, 2H), 6.27 (q, J=7.0 Hz, 1H), 4.87-4.72 (m, 2H), 4.64-4.50 (m, 2H), 2.24-2.05 (m, 2H), 1.85 (d, J=7.1 Hz, 3H), 0.91 (t, J=7.5 Hz, 3H).

The compound E44: 24 mg, ESI[M+H]$^+$=333.2
$^1$H NMR (400 MHz, CDCl$_3$) δ 7.48-7.15 (m, 6H), 6.26 (q, J=7.0 Hz, 1H), 4.85-4.70 (m, 4H), 2.10 (td, J=7.1, 3.0 Hz, 2H), 1.87 (d, J=7.1 Hz, 3H), 1.38-1.21 (m, 2H), 0.94 (t, J=7.3 Hz, 3H).

The compound E45: 32 mg, ESI[M+H]$^+$=321.2
$^1$H NMR (400 MHz, CDCl$_3$) δ 7.49-7.28 (m, 4H), 7.23-7.10 (m, 2H), 6.25 (q, J=7.1 Hz, 1H), 5.00-4.78 (m, 2H), 4.76-4.57 (m, 2H), 1.80 (d, J=7.1 Hz, 3H), 1.73 (s, 3H).

The compound E46: 39 mg, ESI[M+H]$^+$=333.1
$^1$H NMR (400 MHz, CDCl$_3$) δ 7.40-7.28 (m, 4H), 7.26-7.17 (m, 2H), 6.25 (q, J=7.0 Hz, 1H), 2.90-2.75 (m, 2H), 1.88 (d, J=7.1 Hz, 3H), 1.52 (s, 3H), 1.44 (s, 3H), 1.38 (t, J=7.2 Hz, 3H).

The compound E47: 46 mg, ESI[M+H]$^+$=347.0
$^1$H NMR (400 MHz, CDCl$_3$) δ 7.43 (s, 1H), 7.42-7.27 (m, 3H), 7.25-7.03 (m, 2H), 6.21-5.97 (m, 1H), 5.10-4.57 (m, 4H), 2.70-2.55 (m, 2H), 1.86 (d, J=7.1 Hz, 3H), 1.38 (t, J=7.2 Hz, 3H).

The compound E48: 54 mg, ESI[M+H]$^+$=361.1
$^1$H NMR (400 MHz, CDCl$_3$) δ 7.48-7.20 (m, 4H), 7.19-7.15 (m, 2H), 6.23 (q, J=7.0 Hz, 1H), 3.80-3.66 (m, 4H), 2.19-1.90 (m, 7H), 1.84 (d, J=7.1 Hz, 3H).

The compound E49: 39 mg, ESI[M+H]$^+$=331.1
$^1$H NMR (400 MHz, CDCl$_3$) δ 7.47-7.21 (m, 4H), 7.20-7.15 (m, 2H), 6.24 (q, J=7.1 Hz, 1H), 2.61-2.40 (m, 4H), 2.20 (s, 3H), 1.84 (d, J=7.1 Hz, 3H), 1.80-1.74 (m, 2H).

The compound E50: 54 mg, ESI[M+H]$^+$=345.2
$^1$H NMR (400 MHz, CDCl$_3$) δ 7.47-7.21 (m, 4H), 7.20-7.15 (m, 2H), 6.24 (q, J=7.0 Hz, 1H), 2.75-2.49 (m, 4H), 2.25 (s, 3H), 1.89-1.53 (m, 7H).

The compound E51: 50 mg, ESI[M+H]$^+$=359.2
$^1$H NMR (400 MHz, CDCl$_3$) δ 7.45-7.20 (m, 4H), 7.19-7.15 (m, 2H), 6.22 (q, J=7.0 Hz, 1H), 2.75-2.49 (m, 4H), 2.27 (s, 3H), 1.89-1.53 (m, 9H).

The compound E54: 42 mg, ESI[M+H]$^+$=343.2
$^1$H NMR (400 MHz, CDCl$_3$) δ 7.47-7.24 (m, 4H), 7.19-7.13 (m, 2H), 6.23 (q, J=7.1 Hz, 1H), 3.98-3.65 (m, 4H), 2.72 (s, 1H), 2.33-2.19 (m, 2H), 2.16-2.00 (m, 2H), 1.88 (d, J=7.1 Hz, 3H).

The compound E55: 59 mg, ESI[M+H]$^+$=341.2
$^1$H NMR (400 MHz, CDCl$_3$) δ 7.48-7.20 (m, 4H), 7.19-7.15 (m, 2H), 6.23 (q, J=7.1 Hz, 1H), 2.66 (s, 1H), 2.25-1.90 (m, 4H), 1.86 (d, J=7.1 Hz, 3H), 1.72-1.32 (m, 6H).

The compound E56: 38 mg, ESI[M+H]$^+$=327.2
$^1$H NMR (400 MHz, CDCl$_3$) δ 7.47-7.15 (m, 6H), 6.27 (q, J=7.1 Hz, 1H), 2.66 (s, 1H), 2.36-1.90 (m, 4H), 1.89 (d, J=7.1 Hz, 3H), 1.85-1.55 (m, 4H).

The compound E57: 36 mg, ESI[M+H]$^+$=313.1
$^1$H NMR (400 MHz, CDCl$_3$) δ 7.48-7.22 (m, 4H), 7.19-7.14 (m, 2H), 6.24 (q, J=7.1 Hz, 1H), 2.70-2.62 (m, 2H), 2.61 (s, 1H), 2.56-2.36 (m, 2H), 2.08-1.88 (m, 2H), 1.86 (d, J=7.1 Hz, 3H).

The compound E58: 24 mg, ESI[M+H]$^+$=357.2
$^1$H NMR (400 MHz, CDCl$_3$) δ 7.45-7.22 (m, 4H), 7.20-7.14 (m, 2H), 6.20 (q, J=7.1 Hz, 1H), 3.96-3.65 (m, 4H), 2.34-2.19 (m, 2H), 2.17-2.00 (m, 2H), 1.90 (d, J=7.1 Hz, 3H), 1.88 (s, 3H).

The compound E59: 40 mg, ESI[M+H]$^+$=355.3
$^1$H NMR (400 MHz, CDCl$_3$) δ 7.48-7.20 (m, 4H), 7.19-7.15 (m, 2H), 6.26 (q, J=7.0 Hz, 1H), 2.15-1.90 (m, 4H), 1.88 (d, J=7.1 Hz, 3H), 1.86 (s, 3H), 1.69-1.29 (m, 6H).

The compound E60: 47 mg, ESI[M+H]$^+$=341.2
$^1$H NMR (400 MHz, CDCl$_3$) δ 7.49-7.21 (m, 4H), 7.20-7.14 (m, 2H), 6.22 (q, J=7.0 Hz, 1H), 2.50-2.10 (m, 4H), 1.86 (d, J=7.1 Hz, 3H), 1.80-1.63 (m, 4H), 1.61 (s, 3H).

The compound E61: 27 mg, ESI[M+H]$^+$=327.1
$^1$H NMR (400 MHz, CDCl$_3$) δ 7.47-7.22 (m, 4H), 7.20-7.14 (m, 2H), 6.23 (q, J=7.0 Hz, 1H), 2.46-2.10 (m, 4H), 1.87 (d, J=7.1 Hz, 3H), 1.78-1.65 (m, 2H), 1.60 (s, 3H).

The compound E62: 34 mg, ESI[M+H]$^+$=357.2
$^1$H NMR (400 MHz, CDCl$_3$) δ 7.47-7.22 (m, 4H), 7.20-7.14 (m, 2H), 6.23 (q, J=7.0 Hz, 1H), 5.68-5.63 (m, 1H), 5.03-4.87 (m, 2H), 3.75-3.65 (m, 4H), 2.22-2.01 (m, 4H), 1.93 (d, J=7.0 Hz, 3H).

The compound E63: 46 mg, ESI[M+H]$^+$=341.2
$^1$H NMR (400 MHz, CDCl$_3$) δ 7.44-7.20 (m, 4H), 7.19-7.15 (m, 2H), 6.24 (q, J=7.0 Hz, 1H), 5.67-5.64 (m, 1H), 5.04-4.86 (m, 2H), 2.74-2.00 (m, 4H), 1.89-1.55 (m, 7H).

The compound E64: 24 mg, ESI[M+H]$^+$=327.1
$^1$H NMR (400 MHz, CDCl$_3$) δ 7.43-7.28 (m, 4H), 7.24-7.15 (m, 2H), 6.25 (q, J=6.9 Hz, 1H), 5.59 (t, J=6.6 Hz, 1H), 5.01-4.80 (m, 2H), 2.51-2.33 (m, 4H), 1.83 (d, J=7.1 Hz, 3H), 1.79-1.66 (m, 2H).

The compound E65: 41 mg, ESI[M+H]$^+$=343.1
$^1$H NMR (400 MHz, CDCl$_3$) δ 7.48-7.14 (m, 6H), 6.23 (q, J=7.1 Hz, 1H), 4.99-4.74 (m, 4H), 2.45-2.25 (m, 2H), 1.88 (d, J=7.1 Hz, 3H), 1.38 (t, J=7.1 Hz, 3H).

The compound E66: 45 mg, ESI[M+H]$^+$=315.2
$^1$H NMR (400 MHz, CDCl$_3$) δ 7.47-7.22 (m, 4H), 7.20-7.14 (m, 2H), 6.27 (q, J=7.1 Hz, 1H), 5.64-5.32 (m, 1H), 2.45-1.25 (m, 2H), 1.94-1.74 (m, 6H), 1.36-1.14 (m, 3H).

The compound E67: 52 mg, ESI[M+H]$^+$=329.2
$^1$H NMR (400 MHz, CDCl$_3$) δ 7.42-7.15 (m, 6H), 6.30 (q, J=7.1 Hz, 1H), 2.38-2.25 (m, 2H), 1.84 (d, J=7.0 Hz, 3H), 1.71 (s, 3H), 1.68 (s, 3H), 1.36-1.14 (m, 3H).

The compound E68: 43 mg, ESI[M+H]$^+$=329.2
$^1$H NMR (400 MHz, CDCl$_3$) δ 7.41-7.26 (m, 4H), 7.23-7.16 (m, 2H), 6.38-6.17 (m, 1H), 5.61-5.37 (m, 1H), 2.38-2.25 (m, 4H), 1.36-1.14 (m, 6H).

The compound E69: 25 mg, ESI[M+H]$^+$=327.1
$^1$H NMR (400 MHz, CDCl$_3$) δ 7.45-7.28 (m, 4H), 7.25-7.09 (m, 2H), 6.38-6.16 (m, 1H), 5.90-5.73 (m, 1H), 5.73-5.58 (m, 2H), 5.56-5.37 (m, 1H), 2.12-2.03 (m, 2H), 1.85 (d, J=7.1 Hz, 3H), 1.36-1.14 (m, 3H).

The compound E70: 48 mg, ESI[M+H]$^+$=315.2
$^1$H NMR (400 MHz, CDCl$_3$) δ 7.42-7.16 (m, 6H), 6.35-6.17 (m, 1H), 5.61-5.37 (m, 1H), 2.37-2.25 (m, 2H), 1.92-1.80 (m, 6H), 1.37-1.14 (m, 3H).

The compound E71: 33 mg, ESI[M+H]$^+$=363.1
$^1$H NMR (400 MHz, CDCl$_3$) δ 7.42-7.29 (m, 4H), 7.22-7.15 (m, 2H), 6.55 (s, 1H), 6.19 (q, J=7.1 Hz, 1H), 5.08-4.92 (m, 2H), 3.91-3.75 (m, 2H), 3.65-3.39 (m, 2H), 1.84 (d, J=7.1 Hz, 3H).

The compound E72: 41 mg, ESI[M+H]$^+$=345.1
$^1$H NMR (400 MHz, CDCl$_3$) δ 7.46-7.15 (m, 6H), 6.55 (s, 1H), 6.27 (q, J=6.5 Hz, 1H), 2.65-2.43 (m, 4H), 1.83 (d, J=7.1 Hz, 3H), 1.84-1.71 (m, 2H).

The compound E73: 45 mg, ESI[M+H]$^+$=359.1
$^1$H NMR (400 MHz, CDCl$_3$) δ 7.43-7.15 (m, 6H), 6.54 (s, 1H), 6.28 (q, J=7.1 Hz, 1H), 2.84-1.55 (m, 11H).

The compound E74: 18 mg, ESI[M+H]$^+$=375.1
$^1$H NMR (400 MHz, CDCl$_3$) δ 7.45-7.21 (m, 4H), 7.20-7.15 (m, 2H), 6.53 (s, 1H), 6.21 (q, J=7.1 Hz, 1H), 3.79-3.61 (m, 4H), 2.25-2.00 (m, 4H), 1.93 (d, J=6.7 Hz, 3H).

The compound E75: 28 mg, ESI[M+H]$^+$=333.1
$^1$H NMR (400 MHz, CDCl$_3$) δ 7.43-7.26 (m, 4H), 7.23-7.16 (m, 2H), 6.58 (s, 1H), 6.38-6.16 (m, 1H), 2.06-1.65 (m, 6H), 1.60 (d, J=5.2 Hz, 3H).

The compound E76: 20 mg, ESI[M+H]$^+$=319.1
$^1$H NMR (400 MHz, CDCl$_3$) δ 7.46-7.28 (m, 4H), 7.24-7.16 (m, 2H), 6.57 (s, 1H), 6.33-6.19 (m, 1H), 5.37-5.23 (m, 1H), 1.87 (d, J=7.1 Hz, 3H), 1.49-1.29 (m, 3H).

The compound E77: 32 mg, ESI[M+H]$^+$=315.2
$^1$H NMR (400 MHz, CDCl$_3$) δ 7.47-7.29 (m, 4H), 7.24-7.15 (m, 2H), 6.34-6.22 (m, 1H), 5.58-5.44 (m, 1H), 5.37-5.23 (m, 1H), 4.95-4.73 (m, 2H), 1.97-1.81 (m, 5H), 1.17-0.97 (m, 3H).

The compound E78: 24 mg, ESI[M+H]$^+$=348.1
$^1$H NMR (400 MHz, CDCl$_3$) δ 7.45-7.28 (m, 4H), 7.23-7.15 (m, 2H), 6.20 (q, J=7.1 Hz, 1H), 5.33-5.00 (m, 4H), 1.85 (d, J=7.1 Hz, 3H).

The compound E79: 21 mg, ESI[M+H]$^+$=346.1
$^1$H NMR (400 MHz, CDCl$_3$) δ 7.44-7.29 (m, 4H), 7.24-7.15 (m, 2H), 6.20 (q, J=7.1 Hz, 1H), 6.64 (s, 1H), 5.23-4.71 (m, 4H), 1.87 (d, J=7.1 Hz, 3H).

The compound E80: 19 mg, ESI[M+H]$^+$=329.0
$^1$H NMR (400 MHz, CDCl$_3$) δ 7.45-7.15 (m, 6H), 6.20 (q, J=7.1 Hz, 1H), 5.69 (t, J=6.8 Hz, 1H), 5.53-4.70 (m, 6H), 1.85 (d, J=7.1 Hz, 3H).

The compound E81: 33 mg, ESI[M+H]$^+$=371.0
$^1$H NMR (400 MHz, CDCl$_3$) 7.45-7.15 (m, 6H), 6.30 (q, J=7.1 Hz, 1H), 5.90-5.75 (m, 1H), 5.25-5.00 (m, 2H), 2.76-2.28 (m, 4H), 1.91 (d, J=7.0 Hz, 3H), 1.68-1.41 (m, 6H).

The compound E82: 30 mg, ESI[M+H]$^+$=373.2
$^1$H NMR (400 MHz, CDCl$_3$) δ 7.48-7.14 (m, 6H), 6.21 (q, J=7.1 Hz, 1H), 5.70-5.63 (m, 1H), 5.23-4.96 (m, 2H), 3.85-3.65 (m, 4H), 2.42-2.16 (m, 2H), 2.33-2.00 (m, 2H), 1.89 (d, J=7.1 Hz, 3H).

The compound E83: ESI[M+H]$^+$=2357.2
$^1$H NMR (400 MHz, CDCl$_3$) δ 7.45-7.15 (m, 6H), 6.28 (q, J=7.1 Hz, 1H), 5.75-5.68 (m, 1H), 5.24-4.98 (m, 2H), 2.84-1.55 (m, 11H).

The compound E84: 23 mg, ESI[M+H]$^+$=289.0
$^1$H NMR (400 MHz, CDCl$_3$) δ 7.45-7.15 (m, 6H), 6.23 (q, J=7.0 Hz, 1H), 5.78 (t, J=6.6 Hz, 1H), 5.61-4.85 (m, 2H), 2.65-2.32 (m, 4H), 1.80 (d, J=7.1 Hz, 3H), 1.85-1.64 (m, 2H).

The compound E85: 34 mg, ESI[M+H]$^+$=345.1
$^1$H NMR (400 MHz, CDCl$_3$) δ 7.47-7.29 (m, 4H), 7.25-7.14 (m, 2H), 6.24 (q, J=7.1 Hz, 1H), 5.30-4.64 (m, 4H), 1.91 (s, 3H), 1.88 (d, J=7.1 Hz, 3H).

The compound E86: 38 mg, ESI[M+H]$^+$=303.0
$^1$H NMR (400 MHz, CDCl$_3$) δ 7.45-7.29 (m, 4H), 7.25-7.16 (m, 2H), 6.31 (q, J=7.1 Hz, 1H), 4.95-4.70 (m, 2H), 2.05-1.75 (m, 6H).

The compound E87: 47 mg, ESI[M+H]$^+$=331.1
$^1$H NMR (400 MHz, CDCl$_3$) δ 7.45-7.16 (m, 6H), 6.30 (q, J=7.0 Hz, 1H), 6.08 (dd, J=17.5, 10.9 Hz, 1H), 4.47-4.14 (m, 1H), 2.18-2.01 (m, 2H), 1.39 (d, J=7 Hz, 3H), 1.15 (t, J=8 Hz, 3H)

The compound E88: 51 mg, ESI[M+H]$^+$=331.1
$^1$H NMR (400 MHz, CDCl$_3$) δ 7.45-7.28 (m, 4H), 7.26-7.16 (m, 2H), 6.28 (q, J=7.0 Hz, 1H), 1.95 (s, 3H), 1.83 (s, 3H), 1.79 (s, 3H), 1.68 (s, 3H).

The compound E89: 56 mg, ESI[M+H]$^+$=319.2
$^1$H NMR (400 MHz, CDCl$_3$) δ 7.42-7.16 (m, 6H), 6.29 (q, J=7.1 Hz, 1H), 6.08-5.15 (m, 3H), 1.85 (d, J=7.1 Hz, 3H), 1.65 (s, 6H).

The compound E90: 16 mg, ESI[M+H]$^+$=329.0
$^1$H NMR (400 MHz, CDCl$_3$) δ 7.40-7.30 (m, 4H), 7.21-7.15 (m, 2H), 6.18 (q, J=6.9 Hz, 1H), 5.74 (t, J=6.7 Hz, 1H), 5.08-4.92 (m, 2H), 3.78 (dd, J=23.0, 10.3 Hz, 2H), 3.41-3.34 (m, 2H), 1.83 (d, J=7.1 Hz, 3H).

The compound E91: 25 mg, ESI[M+H]$^+$=345.1
$^1$H NMR (400 MHz, CDCl$_3$) δ 7.45-7.25 (m, 4H), 7.25-7.08 (m, 2H), 6.28 (q, J=7.0 Hz, 1H), 5.05-4.74 (m, 4H), 1.88 (s, 3H), 1.88 (d, J=7.1 Hz, 3H).

The compound E92: 19 mg, ESI[M+H]$^+$=346.1
$^1$H NMR (400 MHz, CDCl$_3$) δ 7.47-7.15 (m, 6H), 6.28 (q, J=7.1 Hz, 1H), 3.02-2.62 (m, 4H), 1.85 (d, J=7.1 Hz, 3H), 1.95-1.67 (m, 2H).

The compound E93: 34 mg, ESI[M+H]$^+$=373.1
$^1$H NMR (400 MHz, CDCl$_3$) 7.42-7.15 (m, 6H), 6.24 (q, J=7.1 Hz, 1H), 5.71-5.62 (m, 1H), 5.14-5.00 (m, 2H), 1.89 (d, J=7.1 Hz, 3H), 1.85-1.34 (m, 10H).

The compound E94: 39 mg, ESI[M+H]$^+$=287.1
$^1$H NMR (400 MHz, CDCl$_3$) δ 7.49-7.08 (m, 6H), 6.18 (q, J=7.1 Hz, 1H), 4.95-4.55 (m, 2H), 1.98-1.73 (m, 6H).

The compound E95: 18 mg, ESI[M+H]$^+$=329.2
$^1$H NMR (400 MHz, CDCl$_3$) δ 7.48-7.09 (m, 6H), 6.20 (q, J=7.1 Hz, 1H), 5.69 (t, J=6.7 Hz, 1H), 5.08 (d, J=6.6 Hz, 2H), 4.84-4.70 (m, 4H), 1.89 (d, J=7.1 Hz, 3H).

The compound E96: 21 mg, ESI[M+H]$^+$=348.1
$^1$H NMR (400 MHz, CDCl$_3$) δ 7.48-7.06 (m, 6H), 6.19 (q, J=7.1 Hz, 1H), 5.30-4.96 (m, 4H), 1.87 (d, J=7.1 Hz, 3H).

The compound E97: 56 mg, ESI[M+H]$^+$=316.1
$^1$H NMR (400 MHz, CDCl$_3$) δ 7.45-7.01 (m, 6H), 6.21 (q, J=7.1 Hz, 1H), 5.52-5.01 (m, 4H), 1.87 (d, J=7.1 Hz, 3H).

The compound E98: 56 mg, ESI[M+H]$^+$=305.1
$^1$H NMR (400 MHz, CDCl$_3$) δ 7.42-7.10 (m, 5H), 6.28 (q, J=7.1 Hz, 1H), 4.90-4.65 (m, 2H), 1.95-1.75 (m, 6H).

The compound E99: 31 mg, ESI[M+H]$^+$=347.1
$^1$H NMR (400 MHz, CDCl$_3$) δ 7.45-7.10 (m, 5H), 6.62 (q, J=7.1 Hz, 1H), 5.70 (t, J=6.6 Hz, 1H), 5.10 (d, J=6.6 Hz, 2H), 4.89-4.72 (m, 4H), 1.90 (d, J=7.1 Hz, 3H).

Example E2 Preparation of Compounds E100, E128 and E129

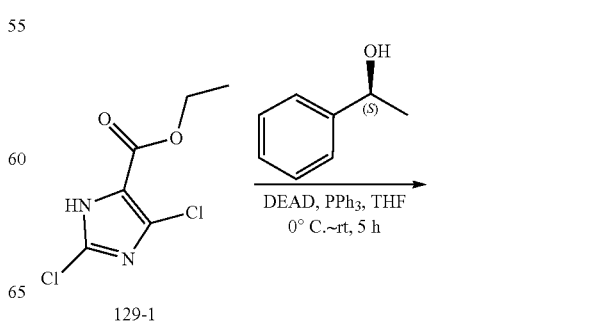

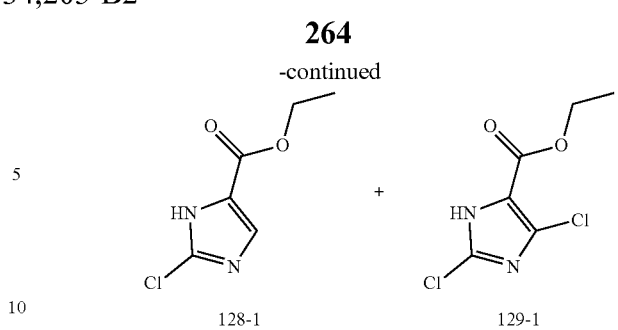

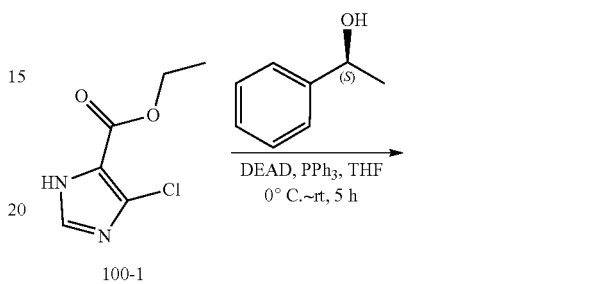

Compound E100

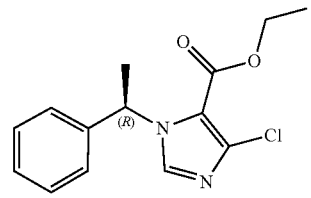

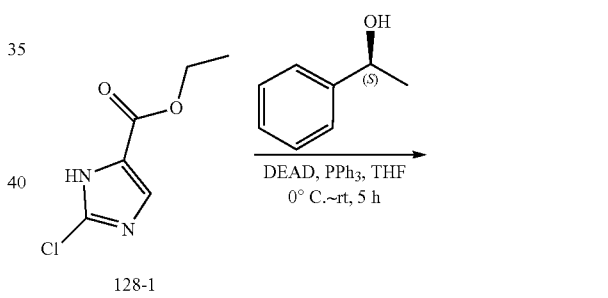

Compound E128

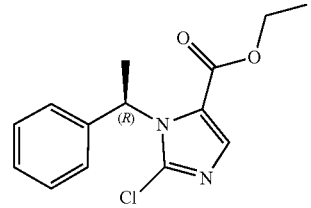

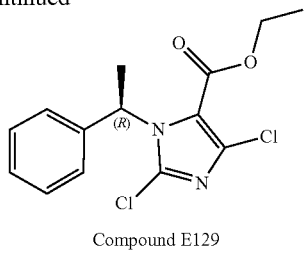

Compound E129

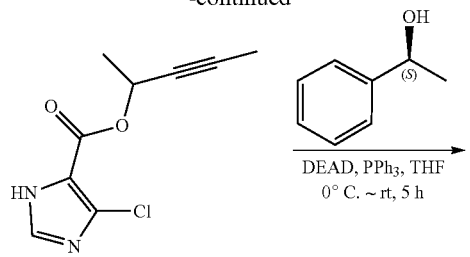

116-1

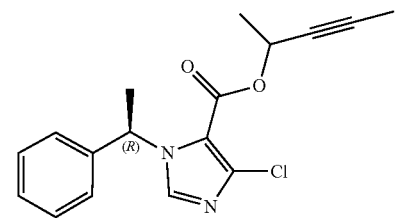

Compound E116

Ethyl 1H-imidazole-5-carboxylate (1 eq) and NCS (2 eq) were dissolved in MeCN (10 mL/mmol). The reaction was stirred at reflux for 3 hrs. The reaction was monitored by TLC until completion. The mixture was cooled to room temperature, quenched with the water (100 mL) and extracted with EtOAc (3×20 mL). The combined organic layers were washed with saturated brine (50 mL), dried over anhydrous sodium sulfate, filtered and concentrated under reduced pressure. The residue was purified by silica gel column chromatography (ethyl acetate/petroleum ether (v/v)=1/100) and monitored by TLC (ethyl acetate/petroleum ether (v/v)=1/30) to give the intermediates 100-1, 128-1 and 129-1, which reacted with S-1-phenylethan-1-ol respectively to give the target compounds E100, E128 and E129 according to the preparation method of the compound E1.

The compound E100, 1.56 g, colorless oil, Yield 39%, ESI[M+H]$^+$=279.0

$^1$H NMR (400 MHz, CDCl$_3$) δ 7.72 (s, 1H), 7.38-7.27 (m, 3H), 7.21-7.14 (m, 2H), 6.73 (q, J=7.1 Hz, 1H), 4.29 (q, J=7.1 Hz, 2H), 1.98 (d, J=7.2 Hz, 3H), 1.34 (t, J=7.1 Hz, 3H).

The compound E128, 1.54 g, colorless oil, Yield 39%, ESI[M+H]$^+$=279.0

$^1$H NMR (400 MHz, CDCl$_3$) δ 7.59 (s, 1H), 7.42-7.28 (m, 3H), 7.22-7.13 (m, 2H), 6.33 (q, J=7.1 Hz, 1H), 4.41~4.22 (m, 2H), 1.85 (d, J=7.1 Hz, 3H), 1.34 (t, J=7.1 Hz, 3H).

The compound E129, 1.10 g, colorless oil, Yield 39%, ESI[M+H−104]$^+$=209.0

$^1$H NMR (400 MHz, CDCl$_3$) δ 7.41-7.28 (m, 3H), 7.22-7.14 (m, 2H), 6.65 (q, J=6.9 Hz, 1H), 4.39-4.24 (m, 2H), 1.97 (d, J=7.2 Hz, 3H), 1.35 (t, J=7.1 Hz, 3H).

Example E3 Preparation of Compounds E116 and E125

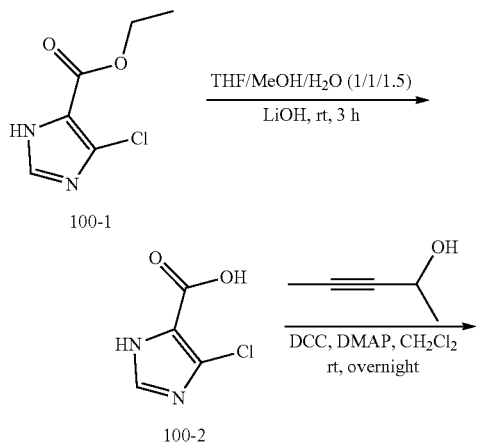

LiOH.H$_2$O (2 eq) was added into the solution of the compound 100-1 (1 eq) in MeOH/THF/H$_2$O (10 mL/mmol, V/V/V=1/1/1.5), then the mixture was stirred at room temperature for 3 hrs. After the reaction was complete, the mixture was concentrated under reduced pressure, and the residue was adjusted to PH=5 with 1 N HCl and extracted with ethyl acetate (3×20 mL). The combined organic layers were washed with saturated brine (50 mL), dried over anhydrous sodium sulfate, filtered and concentrated under reduced pressure to give crude compound 100-2 as a white solid. Compound 100-2 reacted with alchol to give intermediate 116-1 by condensation reaction, which reacted with S-1-phenylethan-1-ol to give the crude compound E116 according to the preparation method of the compound E1. The crude product was purified by Prep-TLC (ethyl acetate/petroleum ether (v/v)=1/1) and the fraction with Rf=0.4~0.5 was collected and dried to give the product E116 (52 mg) as colorless oil. ESI[M+H]$^+$=317.0

$^1$H NMR (400 MHz, CDCl$_3$) δ 7.77 (s, 1H), 7.41-7.27 (m, 3H), 7.24-7.11 (m, 2H), 6.79-6.62 (m, 1H), 5.61-5.45 (m, 1H), 2.04-1.94 (m, 3H), 1.90-1.78 (m, 3H), 1.53 (t, J=6.2 Hz, 3H).

The preparation method of the compound E125 was the similar as the compound E116. 4-Chloro-1H-imidazole-5-carboxylic acid reacted with corresponding alcohol to give corresponding 4-chloro-1H-imidazole-5-formate ester derivative as intermediate, which reacted with (S)-1-phenylethan-1-ol to give the compound E125 (53 mg). ESI[M+H]$^+$=379.1

$^1$H NMR (400 MHz, CDCl$_3$) δ 7.79 (s, 1H), 7.41-7.10 (m, 5H), 6.84 (s, 1H), 6.57 (q, J=7.1 Hz, 1H), 4.89-4.40 (m, 4H), 1.99 (d, J=7.2 Hz, 3H).

The preparation method of the target compounds listed below were similar as the compound E116 of example E3.

The compound E52: 55 mg, ESI[M+H]$^+$=363.0

$^1$H NMR (400 MHz, CDCl$_3$) δ 7.78 (s, 1H), 7.40-7.11 (m, 5H), 6.58 (q, J=7.1 Hz, 1H), 4.99-4.64 (m, 4H), 2.73 (q, J=7.2 Hz, 2H), 1.88 (d, J=7.1 Hz, 3H), 1.41 (t, J=7.2 Hz, 3H).

The compound E101: 28 mg, ESI[M+H]$^+$=335.2

$^1$H NMR (400 MHz, CDCl$_3$) δ 7.60 (s, 1H), 7.42-7.28 (m, 3H), 7.19 (d, J=7.0 Hz, 2H), 6.36-6.34 (m, 1H), 4.55 (dd, J=6.0, 1.3 Hz, 2H), 4.45-4.33 (m, 4H), 1.86 (d, J=7.1 Hz, 3H), 1.40 (s, 3H).

The compound E102: 150 mg, ESI[M+H]⁺=363.3

¹H NMR (400 MHz, CDCl₃) δ 7.57 (s, 1H), 7.34 (dt, J=13.5, 6.9 Hz, 3H), 7.21 (d, J=7.0 Hz, 2H), 6.39 (d, J=7.1 Hz, 1H), 4.28 (q, J=10.9 Hz, 2H), 3.44 (s, 2H), 3.34 (s, 3H), 1.96-1.81 (m, 9H).

The compound E103: 112 mg, ESI[M+H]⁺=355.1

¹H NMR (400 MHz, CDCl₃) δ 7.57 (s, 1H), 7.40-7.25 (m, 3H), 7.18 (d, J=7.0 Hz, 2H), 6.39 (d, J=7.1 Hz, 1H), 4.23-4.19 (m, 2H), 2.66-2.35 (m, 5H), 1.86 (d, J=7.1 Hz, 3H).

The compound E104: 38 mg, ESI[M+H]⁺=331.2.

¹H NMR (400 MHz, CDCl₃) δ 7.61 (s, 1H), 7.34 (dq, J=14.2, 7.0 Hz, 3H), 7.18 (d, J=6.9 Hz, 2H), 6.26 (q, J=7.1 Hz, 1H), 4.94 (t, J=8.0 Hz, 2H), 4.88 (d, J=7.9 Hz, 1H), 4.74 (d, J=7.6 Hz, 1H), 2.78 (s, 1H), 1.86 (d, J=7.1 Hz, 3H).

The compound E105: 64 mg, ESI[M+H]⁺=321.2

¹H NMR (400 MHz, CDCl₃) δ 7.58 (s, 1H), 7.40-7.25 (m, 3H), 7.18 (d, J=7.0 Hz, 2H), 6.31-6.28 (m, 1H), 4.53-4.34 (m, 2H), 2.81-2.77 (m, 2H), 2.18 (s, 3H), 1.86 (d, J=7.1 Hz, 3H).

The compound E106: 28 mg, ESI[M+H]⁺=335.1

¹H NMR (400 MHz, CDCl₃) δ 7.68 (s, 1H), 7.39-7.28 (m, 3H), 7.11 (d, J=7.5 Hz, 2H), 6.23 (d, J=6.4 Hz, 1H), 1.90 (s, 3H), 1.85 (d, J=6.9 Hz, 3H), 1.54 (s, 3H), 1.48 (s, 3H).

The compound E107: 83 mg, ESI[M+H]⁺=319.2

¹H NMR (400 MHz, CDCl₃) δ 7.74 (s, 1H), 7.38-7.13 (m, 5H), 6.65 (q, J=7.1 Hz, 1H), 4.25-4.00 (m, 2H), 2.60-2.50 (m, 1H), 2.48-1.98 (m, 4H), 1.88 (d, J=7.2 Hz, 3H), 1.80-1.69 (m, 2H).

The compound E108: 108 mg, ESI[M+H]⁺=305.0

¹H NMR (400 MHz, CDCl₃) δ 7.76 (s, 1H), 7.39-7.27 (m, 3H), 7.23-7.13 (m, 2H), 6.74 (q, J=7.1 Hz, 1H), 4.10-4.04 (m, 2H), 1.99 (d, J=7.2 Hz, 3H), 1.24-1.11 (m, 1H), 0.69-0.54 (m, 2H), 0.40-0.24 (m, 2H).

The compound E109: 76 mg, ESI[M+H]⁺=305.0

¹H NMR (400 MHz, CDCl₃) δ 7.74 (s, 1H), 7.41-7.27 (m, 3H), 7.21-7.09 (m, 2H), 6.73 (q, J=7.0 Hz, 1H), 5.25-5.04 (m, 1H), 2.52-2.32 (m, 2H), 2.25-2.08 (m, 2H), 1.98 (d, J=7.2 Hz, 3H), 1.91-1.78 (m, 1H), 1.75-1.56 (m, 1H).

The compound E110: 89 mg, ESI[M+H]⁺=307.0

¹H NMR (400 MHz, CDCl₃) δ 7.82 (s, 1H), 7.39-7.27 (m, 3H), 7.19-7.10 (m, 2H), 6.61 (q, J=6.7 Hz, 1H), 5.56 (p, J=6.0 Hz, 1H), 4.92 (q, J=6.8 Hz, 2H), 4.79-4.61 (m, 2H), 1.98 (d, J=7.2 Hz, 3H).

The compound E111: 79 mg, ESI[M+H]⁺=323.0, ESI[M+H−104]⁺=219.0

¹H NMR (400 MHz, CDCl₃) δ 7.78 (s, 1H), 7.47-7.20 (m, 3H), 7.21-7.08 (m, 2H), 6.80-6.51 (m, 1H), 5.95-5.60 (m, 1H), 3.73-3.45 (m, 2H), 3.42-3.16 (m, 2H), 1.99 (d, J=7.1 Hz, 3H).

The compound E112: 91 mg, ESI[M+H]⁺=307.0

¹H NMR (400 MHz, CDCl₃) δ 7.62 (s, 1H), 7.39-7.27 (m, 3H), 7.21-7.12 (m, 2H), 6.74 (q, J=7.0 Hz, 1H), 1.98 (d, J=7.2 Hz, 3H), 1.52 (s, 9H).

The compound E113: 43 mg, ESI[M+Na]⁺=370.9

¹H NMR (400 MHz, CDCl₃) δ 7.89 (s, 1H), 7.39-7.27 (m, 3H), 7.18-7.07 (m, 2H), 6.52-6.42 (m, 1H), 5.02-4.68 (m, 4H), 2.25 (s, 3H), 1.99 (d, J=7.0 Hz, 3H).

The compound E114: 46 mg, ESI[M+H]⁺=333.0

¹H NMR (400 MHz, CDCl₃) δ 7.82 (s, 1H), 7.40-7.25 (m, 3H), 7.17-7.07 (m, 2H), 6.54-6.44 (m, 1H), 2.21 (s, 3H), 1.99 (d, J=7.0 Hz, 3H), 1.19-0.80 (m, 4H).

The compound E115: 101 mg, ESI[M+H]⁺=345.0

¹H NMR (400 MHz, CDCl₃) δ 7.77 (s, 1H), 7.41-7.28 (m, 3H), 7.22-7.09 (m, 2H), 6.70-6.53 (m, 1H), 5.09-4.48 (m, 4H), 2.04-1.97 (m, 3H), 1.90 (d, J=3.3 Hz, 3H).

The compound E117: 48 mg, ESI[M+H]⁺=331.0

¹H NMR (400 MHz, CDCl₃) δ 7.69 (s, 1H), 7.42-7.28 (m, 3H), 7.22-7.12 (m, 2H), 6.84-6.70 (m, 1H), 2.01 (d, J=7.0 Hz, 3H), 1.84 (s, 3H), 1.72 (s, 3H), 1.69 (s, 3H).

The compound E118: 70 mg, ESI[M+H]⁺=317.0

¹H NMR (400 MHz, CDCl₃) δ 7.76 (s, 1H), 7.41-7.28 (m, 3H), 7.21-7.12 (m, 2H), 6.81-6.70 (m, 1H), 5.58-5.45 (m, 1H), 5.42-5.26 (m, 1H), 4.99-4.84 (m, 2H), 2.00 (d, J=7.1 Hz, 3H), 1.43 (t, J=5.9 Hz, 3H).

The compound E119: 71 mg, ESI[M+H]⁺=331.0

¹H NMR (400 MHz, CDCl₃) δ 7.75 (s, 1H), 7.41-7.15 (m, 5H), 6.58 (q, J=7.1 Hz, 1H), 5.85-4.69 (m, 3H), 2.01-1.58 (m, 9H).

The compound E120: 219 mg, ESI[M+H]⁺=317.0

¹H NMR (400 MHz, CDCl₃) δ 7.68 (s, 1H), 7.40-7.27 (m, 3H), 7.21-7.11 (m, 2H), 6.74 (q, J=6.8 Hz, 1H), 2.60 (s, 1H), 2.00 (d, J=7.2 Hz, 3H), 1.76 (s, 3H), 1.73 (s, 3H).

The compound E121: 100 mg, ESI[M+H]⁺=329.0

¹H NMR (400 MHz, CDCl₃) δ 7.80 (s, 1H), 7.40-7.28 (m, 3H), 7.22-7.13 (m, 2H), 6.79-6.65 (m, 1H), 5.87-5.77 (m, 1H), 5.74-5.64 (m, 2H), 5.57-5.51 (m, 1H), 2.00 (d, J=6.8 Hz, 3H), 1.62-1.56 (m, 3H).

The compound E122: 79 mg, ESI[M+H]⁺=343.0

¹H NMR (400 MHz, CDCl₃) δ 7.72 (s, 1H), 7.40-7.28 (m, 3H), 7.22-7.15 (m, 2H), 6.85-6.72 (m, 1H), 5.87-5.76 (m, 1H), 5.68-5.59 (m, 1H), 5.53-5.44 (m, 1H), 2.01 (d, J=7.0 Hz, 3H), 1.77 (s, 3H), 1.75 (s, 3H).

The compound E123: 6 mg, ESI[M+H]⁺=359.0

¹H NMR (400 MHz, CDCl₃) δ 7.95-7.78 (m, 1H), 7.41-7.24 (m, 4H), 7.21-7.13 (m, 1H), 6.70-6.49 (m, 1H), 2.82-2.69 (m, 2H), 2.66-2.58 (m, 1H), 2.39-2.28 (m, 1H), 2.25 (s, 1H), 2.11-1.86 (m, 7H).

The compound E124: 90 mg, ESI[M+H]⁺=321.0

¹H NMR (400 MHz, CDCl₃) δ 7.73 (s, 1H), 7.40-7.28 (m, 3H), 7.21-7.13 (m, 2H), 6.82-6.69 (m, 1H), 4.96-4.85 (m, 1H), 2.00 (d, J=7.0 Hz, 3H), 1.74-1.56 (m, 4H), 0.93 (t, J=7.4 Hz, 3H), 0.88 (t, J=7.3 Hz, 3H).

The compound E126: 110 mg, ESI[M+H]⁺=303.0

¹H NMR (400 MHz, CDCl₃) δ 7.78 (s, 1H), 7.40-7.27 (m, 3H), 7.23-7.12 (m, 2H), 6.78-6.61 (m, 1H), 4.79 (d, J=1.7 Hz, 2H), 1.99 (d, J=6.7 Hz, 3H), 1.88 (s, 3H).

The compound E127: 119 mg, ESI[M+H]⁺=345.0

¹H NMR (400 MHz, CDCl₃) δ 7.75 (s, 1H), 7.39-7.27 (m, 3H), 7.19-7.10 (m, 2H), 6.58 (q, J=6.9 Hz, 1H), 5.63 (t, J=6.6 Hz, 1H), 5.02 (d, J=6.6 Hz, 2H), 4.89 (d, J=7.4 Hz, 1H), 4.84-4.70 (m, 3H), 1.99 (d, J=7.2 Hz, 3H).

Example E4 Preparation of Compound E132

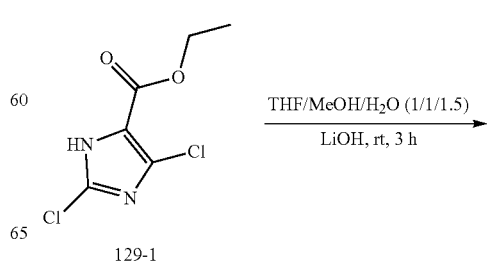

129-1

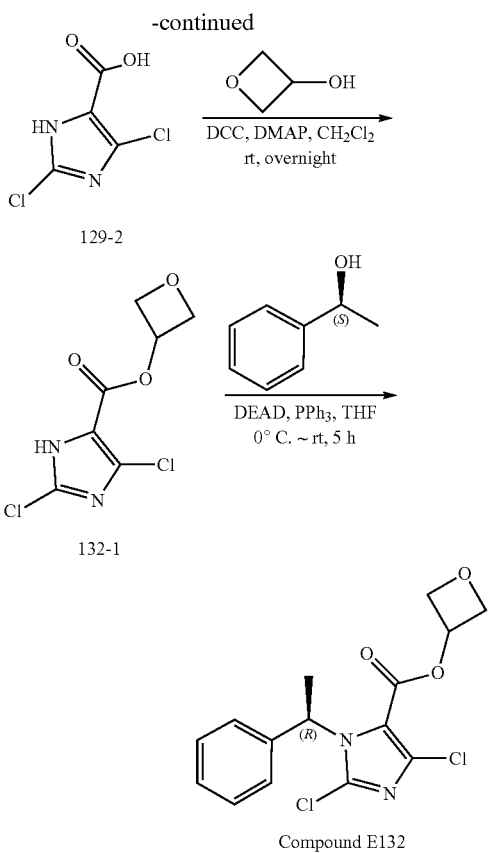

Compound E132

LiOH.H$_2$O (2 eq) was added into the solution of the compound 129-1 (1 eq) in MeOH/THF/H$_2$O (10 mL/mmol, V/V/V=1/1/1.5), then the mixture was stirred at room temperature for 3 hrs. After the reaction was complete, the mixture was concentrated under reduced pressure, and the residue was adjusted to PH=5 with 1 N HCl and extracted with ethyl acetate (3×20 mL). The combined organic layers were washed with saturated brine (50 mL), dried over anhydrous sodium sulfate, filtered and concentrated under reduced pressure to give crude compound 129-2 as a white solid.

Compound 129-2 reacted with oxetan-3-ol to give intermediate 132-1 by condensation reaction, which reacted with S-1-phenylethan-1-ol to give crude compound E132 according to the preparation method of the compound E1. The crude product was purified by Prep-TLC (ethyl acetate/petroleum ether (v/v)=1/1) and the fraction with Rf=0.4~0.5 was collected and dried to give the product E132 (51 mg) as colorless oil. ESI[M+H]$^+$=341.0

$^1$H NMR (400 MHz, CDCl$_3$) δ 7.42-7.28 (m, 3H), 7.20-7.10 (m, 2H), 6.56 (q, J=7.2 Hz, 1H), 5.66-5.45 (m, 1H), 4.98-4.57 (m, 4H), 1.98 (d, J=7.2 Hz, 3H).

The preparation method of the target compounds listed below was similar as the compound E132. 2,4-dichloro-1H-imidazole-5-carboxylic acid reacted with corresponding alcohols to give corresponding imidazole-5-formate ester derivatives as intermediates, which reacted with (S)-1-phenylethan-1-ol to give the correspondent target compounds.

The compound E130: 145 mg, ESI[M+Na]$^+$=360.9

$^1$H NMR (400 MHz, CDCl$_3$) δ 7.41-7.28 (m, 3H), 7.22-7.14 (m, 2H), 6.64 (q, J=7.1 Hz, 1H), 4.19-4.02 (m, 2H), 1.98 (d, J=7.2 Hz, 3H), 1.28-1.12 (m, 1H), 0.66-0.53 (m, 2H), 0.40-0.26 (m, 2H).

The compound E131: 98 mg, ESI[M+H−104]$^+$=235.0

$^1$H NMR (400 MHz, CDCl$_3$) δ 7.39-7.27 (m, 3H), 7.22-7.12 (m, 2H), 6.63 (q, J=7.0 Hz, 1H), 5.42-4.84 (m, 1H), 2.54-2.31 (m, 2H), 2.27-2.07 (m, 2H), 1.97 (d, J=7.2 Hz, 3H), 1.92-1.78 (m, 1H), 1.75-1.63 (m, 1H).

The compound E133: 29 mg, ESI[M+H]$^+$=356.9

$^1$H NMR (400 MHz, CDCl$_3$) δ 7.41-7.28 (m, 3H), 7.22-7.11 (m, 2H), 6.57 (q, J=7.1 Hz, 1H), 5.75 (p, J=8.0 Hz, 1H), 3.64-3.44 (m, 2H), 3.41-3.19 (m, 2H), 1.97 (d, J=7.2 Hz, 3H).

The compound E134: 44 mg, ESI[M+H−104]$^+$=290.9

$^1$H NMR (400 MHz, CDCl$_3$) δ 7.41-7.29 (m, 3H), 7.24-7.11 (m, 2H), 6.55 (q, J=6.9 Hz, 1H), 5.33 (p, J=5.2 Hz, 1H), 3.90-3.70 (m, 4H), 1.99 (d, J=7.2 Hz, 3H).

The compound E135: 44 mg, ESI[M+H−160]$^+$=181.0

$^1$H NMR (400 MHz, CDCl$_3$) δ 7.38-7.27 (m, 3H), 7.21-7.14 (m, 2H), 6.59 (q, J=7.0 Hz, 1H), 1.98 (d, J=7.2 Hz, 3H), 1.53 (s, 9H).

The compound E136: 18 mg, ESI[M+Na]$^+$=404.9

$^1$H NMR (400 MHz, CDCl$_3$) δ 7.41-7.27 (m, 3H), 7.20-7.09 (m, 2H), 6.42 (q, J=6.9 Hz, 1H), 5.08-4.58 (m, 4H), 2.25 (s, 3H), 1.98 (d, J=7.2 Hz, 3H).

The compound E137: 24 mg, ESI[M+H]$^+$=367.0

$^1$H NMR (400 MHz, CDCl$_3$) δ 7.39-7.25 (m, 3H), 7.20-7.12 (m, 2H), 6.60 (q, J=7.1 Hz, 1H), 1.99 (d, J=7.1 Hz, 3H), 1.15-0.79 (m, 4H).

The compound E138: 117 mg, ESI[M+H]$^+$=379.0

$^1$H NMR (400 MHz, CDCl$_3$) δ 7.39-7.28 (m, 3H), 7.21-7.13 (m, 2H), 6.56 (q, J=6.8 Hz, 1H), 4.92-4.82 (m, 3H), 4.69 (d, J=7.3 Hz, 1H), 2.00 (d, J=7.2 Hz, 3H), 1.90 (s, 3H).

The compound E139: 121 mg, ESI[M+Na]$^+$=373.0

$^1$H NMR (400 MHz, CDCl$_3$) δ 7.42-7.27 (m, 3H), 7.23-7.11 (m, 2H), 6.76-6.50 (m, 1H), 5.60-5.46 (m, 1H), 1.98 (dd, J=7.2, 2.3 Hz, 2H), 1.89-1.81 (m, 3H), 1.54 (d, J=6.7 Hz, 3H).

The compound E140: 89 mg, ESI[M+Na]$^+$=386.9

$^1$H NMR (400 MHz, CDCl$_3$) δ 7.42-7.27 (m, 3H), 7.24-7.10 (m, 2H), 6.64 (q, J=6.9 Hz, 1H), 1.99 (d, J=7.2 Hz, 3H), 1.84 (s, 3H), 1.73 (s, 1H), 1.69 (s, 3H).

The compound E141: 45 mg, ESI[M+Na−104]$^+$=247.0

$^1$H NMR (400 MHz, CDCl$_3$) δ 7.38-7.28 (m, 3H), 7.21-7.15 (m, 2H), 6.62 (q, J=6.9 Hz, 1H), 5.60-5.46 (m, 1H), 5.38-5.24 (m, 1H), 4.97-4.78 (m, 2H), 1.98 (d, J=7.2 Hz, 3H), 1.43 (t, J=6.8 Hz, 3H).

The compound E142: 35 mg, ESI[M+H]$^+$=265.0

$^1$H NMR (400 MHz, CDCl$_3$) δ 7.41-7.29 (m, 3H), 7.25-7.15 (m, 2H), 6.59 (q, J=7.1 Hz, 1H), 6.05-5.58 (m, 1H), 5.47-4.69 (m, 2H), 2.01-1.58 (m, 9H).

The compound E143: 130 mg, ESI[M+Na]$^+$=372.9

$^1$H NMR (400 MHz, CDCl$_3$) δ 7.39-7.27 (m, 3H), 7.22-7.13 (m, 2H), 6.63 (q, J=7.1 Hz, 1H), 2.60 (s, 1H), 1.99 (d, J=7.2 Hz, 3H), 1.77 (s, 3H), 1.73 (s, 3H).

The compound E144: 125 mg, ESI[M+Na]$^+$=384.9

$^1$H NMR (400 MHz, CDCl$_3$) δ 7.42-7.27 (m, 3H), 7.25-7.11 (m, 2H), 6.69-6.54 (m, 1H), 5.89-5.74 (m, 1H), 5.72-5.61 (m, 2H), 5.58-5.42 (m, 1H), 2.02-1.94 (m, 3H), 1.62-1.55 (m, 3H).

The compound E145: 83 mg, ESI[M+Na]$^+$=398.9

$^1$H NMR (400 MHz, CDCl$_3$) δ 7.39-7.27 (m, 3H), 7.23-7.10 (m, 2H), 6.64 (q, J=7.0 Hz, 1H), 5.89-5.74 (m, 1H), 5.69-5.56 (m, 1H), 5.54-5.40 (m, 1H), 1.99 (d, J=7.2 Hz, 3H), 1.77 (s, 3H), 1.74 (s, 3H).

The compound E146: 6 mg, ESI[M+Na]$^+$=414.9

$^1$H NMR (400 MHz, CDCl$_3$) δ 7.39-7.27 (m, 4H), 7.22-7.15 (m, 1H), 6.67-6.51 (m, 1H), 2.77-2.71 (m, 1H), 2.69-2.61 (m, 1H), 2.35-2.29 (m, 1H), 2.24 (s, 1H), 2.07-1.88 (m, 8H).

The compound E147: 166 mg, ESI[M+Na]⁺=377.0

¹H NMR (400 MHz, CDCl₃) δ 7.39-7.27 (m, 3H), 7.22-7.15 (m, 2H), 6.64 (q, J=7.0 Hz, 1H), 4.94 (p, J=6.1 Hz, 1H), 1.99 (d, J=7.2 Hz, 3H), 1.73-1.59 (m, 4H), 0.95 (t, J=7.4 Hz, 3H), 0.88 (t, J=7.4 Hz, 3H).

The compound E148: 198 mg, ESI[M+H]⁺=365.0

¹H NMR (400 MHz, CDCl₃) δ 7.42-7.27 (m, 3H), 7.23-7.09 (m, 2H), 6.54 (q, J=7.0 Hz, 1H), 4.99-4.83 (m, 3H), 4.69 (d, J=7.4 Hz, 1H), 2.80 (s, 1H), 2.00 (d, J=7.2 Hz, 3H).

Example E5 Preparation of Compounds E149~E153

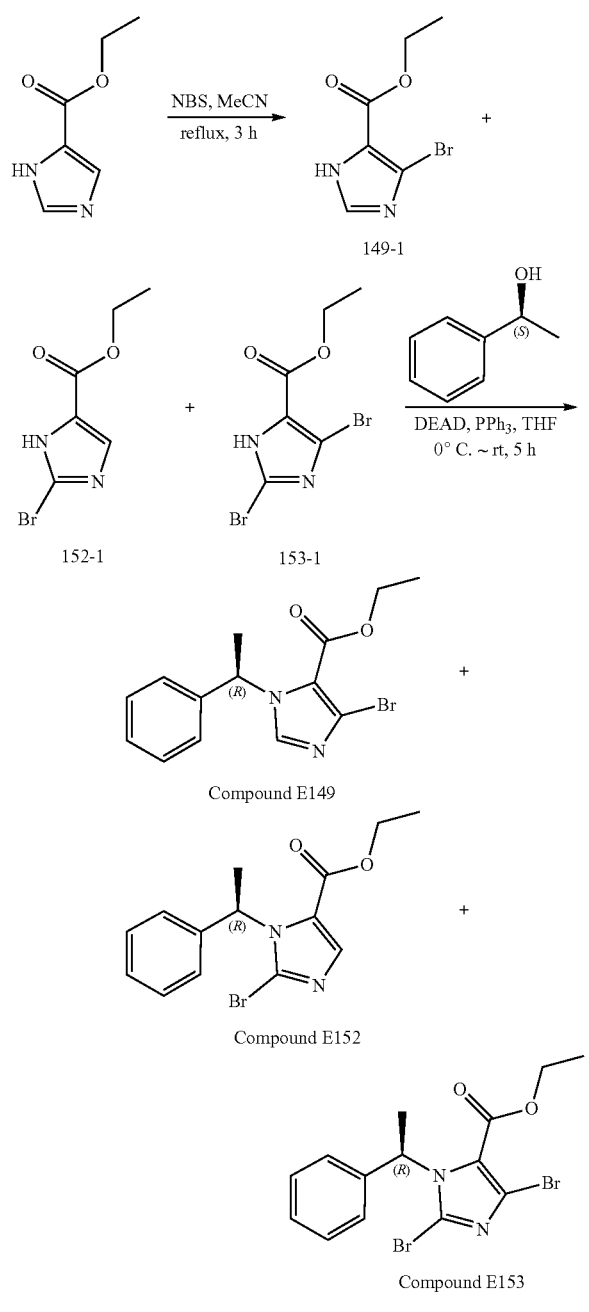

The preparation method of the compounds E149, E152 and E153 was similar as the preparation method of the example E2. Ethyl 1H-imidazole-5-carboxylate reacted with NBS to give corresponding intermediates as colorless oil. The target compounds were purified by silica gel column chromatography (EA/PE (v/v)=1/100), monitored by TLC (ethyl acetate/petroleum ether (v/v)=1/30), collected and dried to give the target compounds.

The compound E149, 3.81 g, colorless oil, yield 53%, ESI[M+H]⁺=323.0

¹H NMR (400 MHz, CDCl₃) δ 7.77 (s, 1H), 7.39-7.28 (m, 3H), 7.20-7.10 (m, 2H), 6.78-6.58 (m, 1H), 4.35-4.16 (m, 2H), 2.01 (d, J=7.2 Hz, 3H), 1.31 (t, J=7.1 Hz, 3H).

The compound E152, 570 mg, ESI[M+H]⁺=323.0

¹H NMR (400 MHz, CDCl₃) δ 7.64 (s, 1H), 7.42-7.28 (m, 3H), 7.22-7.11 (m, 2H), 6.35 (q, J=7.0 Hz, 1H), 4.39-4.20 (m, 2H), 1.85 (d, J=7.1 Hz, 3H), 1.36 (t, J=7.1 Hz, 3H).

The compound E153, 15 mg, ESI[M+H−104]⁺=296.9

¹H NMR (400 MHz, CDCl₃) δ 7.39-7.27 (m, 3H), 7.19-7.09 (m, 2H), 6.54 (q, J=6.8 Hz, 1H), 4.40-4.14 (m, 2H), 2.00 (d, J=7.1 Hz, 3H), 1.32 (t, J=7.1 Hz, 3H).

Compound 4-bromo-1H-imidazole-5-carboxylic acid was obtained by hydrolyzed of compound 149-1, then it reacted with corresponding alchols to give corresponding imidazole-5-formate ester derivatives as intermediates by condensation reaction, which reacted with S-1-phenylethan-1-ol to give corresponding target compounds listed below.

The compound E150: 158 mg, ESI[M+H]⁺=347.0

¹H NMR (400 MHz, CDCl₃) δ 7.82 (s, 1H), 7.38-7.27 (m, 3H), 7.21-7.08 (m, 2H), 6.72-6.52 (m, 1H), 4.78-4.71 (m, 2H), 2.02 (d, J=7.1 Hz, 3H), 1.87 (t, J=2.1 Hz, 3H).

The compound E151: 130 mg, ESI[M+H]⁺=388.9

¹H NMR (400 MHz, CDCl₃) δ 7.80 (s, 1H), 7.38-7.28 (m, 3H), 7.18-7.06 (m, 2H), 6.59-6.45 (m, 1H), 5.59 (t, J=6.6 Hz, 1H), 5.00 (d, J=6.7 Hz, 2H), 4.86 (d, J=7.4 Hz, 1H), 4.77-4.67 (m, 3H), 2.01 (d, J=7.1 Hz, 4H).

Example E6 Preparation of Compound E154

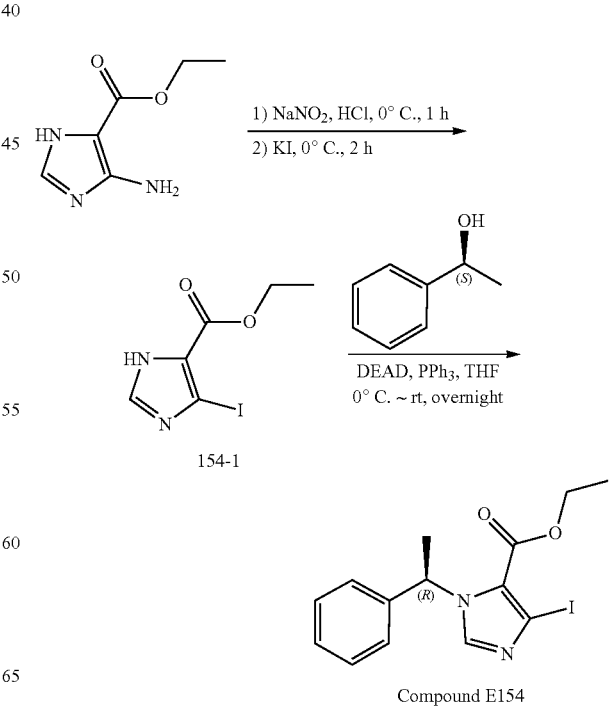

1. Preparation of Ethyl 4-iodo-1H-imidazole-5-carboxylate (154-1)

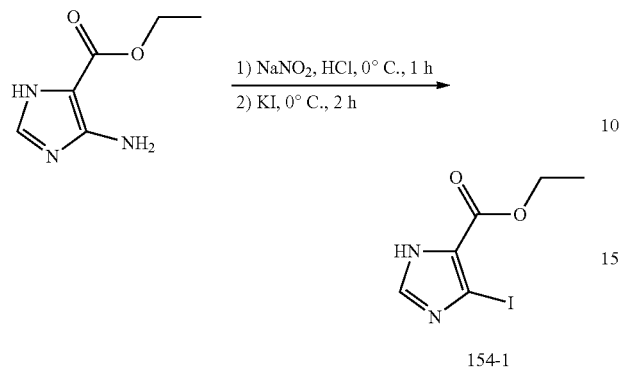

In an ice-water bath, ethyl 4-amino-1H-imidazole-5-carboxylate (5.43 g, 35.0 mmol) was dissolved in HCl (6 M, 65 mL), and then NaNO$_2$ (6.04 g, 87.5 mmol) in water (10 mL) was added into the mixture dropwise over a 10-min period at 0° C. After stirring at 0° C. for 1 hour, KI (46.5 g, 280 mmol) was added in portions into the mixture at 0° C., then it was stirred at 0° C. for 2 hrs. After the reaction was completed, the mixture was extracted with ethyl acetate (3×30 mL). The combined organic layers were washed with saturated brine (50 mL), dried over anhydrous sodium sulfate, filtered and concentrated under reduced pressure. The residue was purified by silica gel column chromatography (ethyl acetate/petroleum ether (v/v)=1/1) and the eluate was monitored by TLC (ethyl acetate/petroleum ether (v/v)=1/1). The fraction with Rf=0.3~0.4 was collected and dried to give compound 154-1 (6.78 g, yield 73%) as colorless oil. ESI[M+H]$^+$=267.0.

2. Preparation of Compound E154

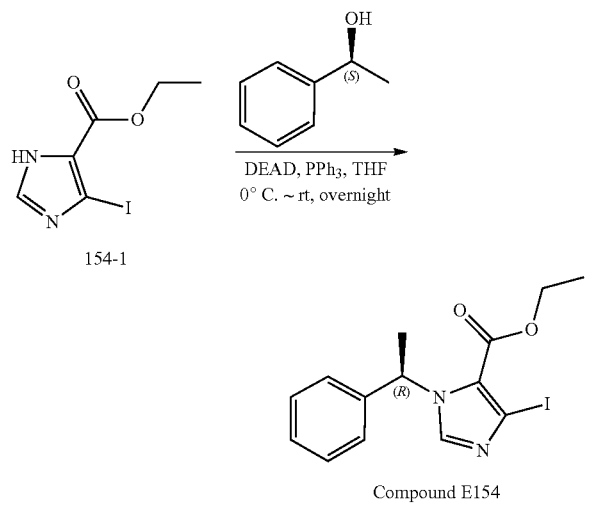

In an ice-water bath, DEAD (6.66 g, 38.2 mmol) in THF (5 mL) was added dropwise into a solution of S-1-phenylethan-1-ol (4.05 g, 33.1 mmol), 154-1 (6.78 g, 25.5 mmol) and PPh$_3$ (10.0 g, 38.1 mmol) in the THF (100 mL) at 0° C. at the rate of 0.5 mmol/min, then the mixture was warmed slowly to room temperature and stirred at this temperature overnight. The mixture was concentrated under reduced pressure. The residue was purified by silica gel column chromatography (ethyl acetate/petroleum ether (v/v)=1/10) and the eluate was monitored by TLC (ethyl acetate/petroleum ether (v/v)=1/3). The fraction with Rf=0.5~0.6 was collected and dried to give product E154 (7.0 g, yield 68%) as colorless oil. ESI[M+H]$^+$=370.9

$^1$H NMR (400 MHz, CDCl$_3$) δ 7.65 (s, 1H), 7.42-7.28 (m, 3H), 7.22-7.11 (m, 2H), 6.37 (q, J=6.0 Hz, 1H), 4.44-4.18 (m, 2H), 1.84 (d, J=6.9 Hz, 3H), 1.38 (t, J=7.1 Hz, 3H).

Example E7 Preparation of Compounds E155 and E156

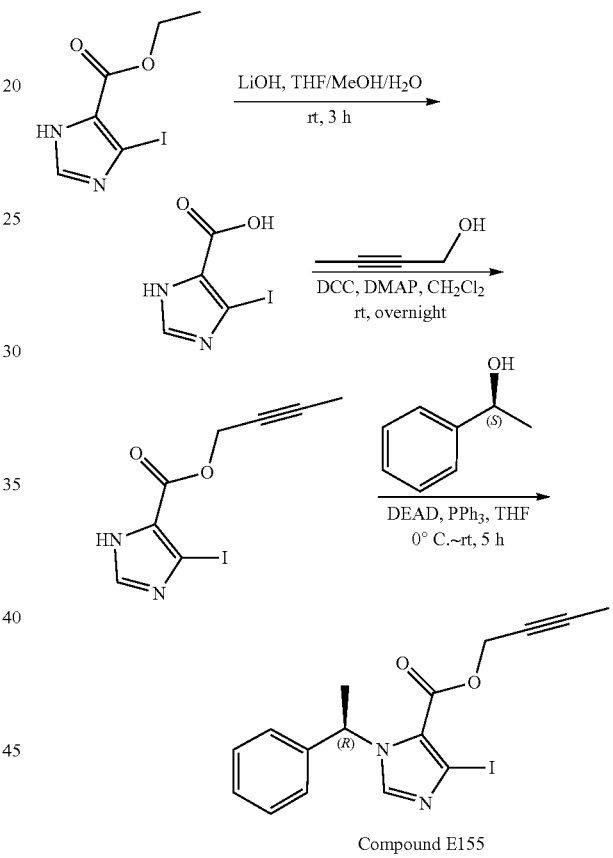

The preparation method of compounds E155 and E156 was similar as Example E3.

4-iodo-1H-imidazole-5-carboxylate was hydrolyzed by lithium hydroxide to give acid, which reacted with corresponding alchols to give intermediates, then it reacted with S-phenylethanol to give target compounds.

The compound E155: 110 mg, ESI[M+H]$^+$=394.9

$^1$H NMR (400 MHz, CDCl$_3$) δ 7.68 (s, 1H), 7.42-7.28 (m, 3H), 7.23-7.12 (m, 2H), 6.34 (q, J=7.0 Hz, 1H), 4.81 (q, J=2.4 Hz, 2H), 1.87 (t, J=2.4 Hz, 3H), 1.85 (d, J=7.1 Hz, 3H).

The compound E156: 73.0 mg, ESI[M+H]$^+$=436.9

$^1$H NMR (400 MHz, CDCl$_3$) δ 7.79 (s, 1H), 7.42-7.28 (m, 3H), 7.20-7.10 (m, 2H), 6.29 (q, J=6.5 Hz, 1H), 5.60 (t, J=6.6 Hz, 1H), 5.07-4.91 (m, 3H), 4.88 (d, J=7.6 Hz, 1H), 4.78 (t, J=7.0 Hz, 2H), 1.85 (d, J=6.9 Hz, 3H).

Example E8 Preparation of Compounds E157 and E164

1. Preparation of Ethyl 4-(trifluoromethyl)-1H-imidazole-5-carboxylate (164-1)

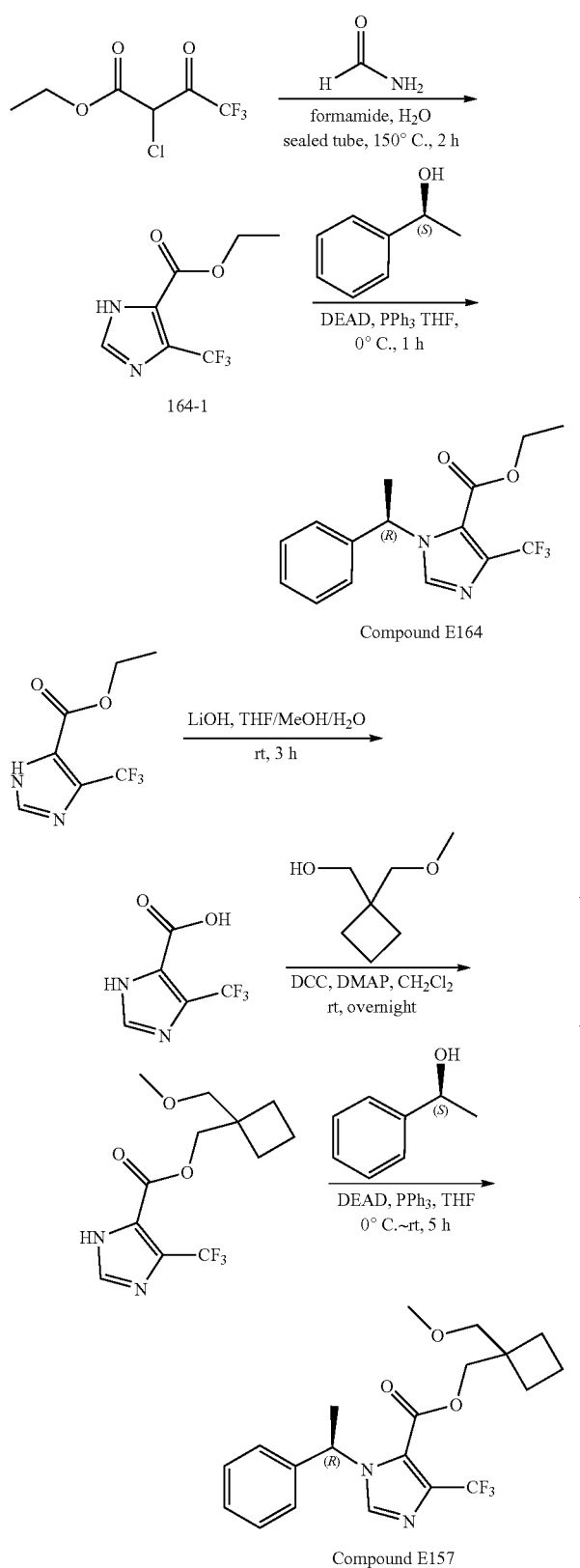

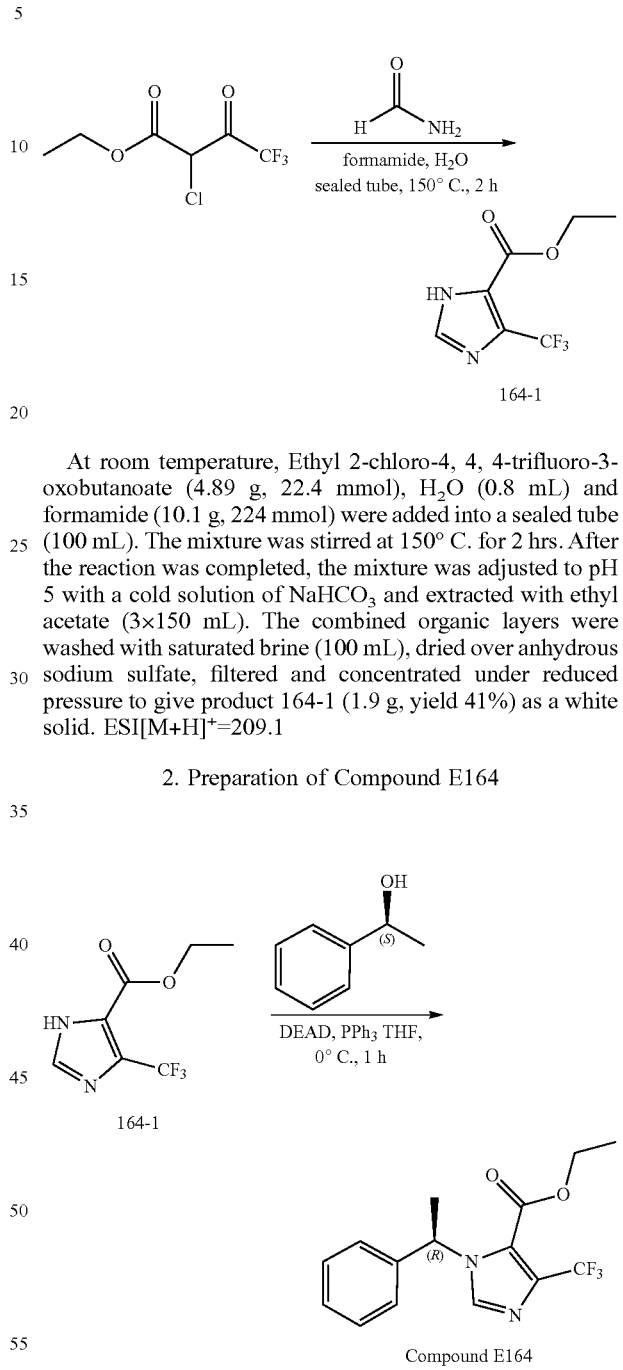

At room temperature, Ethyl 2-chloro-4, 4, 4-trifluoro-3-oxobutanoate (4.89 g, 22.4 mmol), $H_2O$ (0.8 mL) and formamide (10.1 g, 224 mmol) were added into a sealed tube (100 mL). The mixture was stirred at 150° C. for 2 hrs. After the reaction was completed, the mixture was adjusted to pH 5 with a cold solution of $NaHCO_3$ and extracted with ethyl acetate (3×150 mL). The combined organic layers were washed with saturated brine (100 mL), dried over anhydrous sodium sulfate, filtered and concentrated under reduced pressure to give product 164-1 (1.9 g, yield 41%) as a white solid. ESI[M+H]$^+$=209.1

2. Preparation of Compound E164

In an ice-water bath, DEAD (2.37 g, 13.6 mmol) in THF (5 mL) was added dropwise into a solution of S-1-phenylethan-1-ol (1.66 g, 13.6 mmol), 164-1 (1.9 g, 9.1 mmol) and PPh$_3$ (3.57 g, 13.6 mmol) in the THF (50 mL) at 0° C. at the rate of 0.5 mmol/min, then the mixture was warmed slowly to room temperature and stirred at this temperature for 1 hour. The mixture was concentrated under reduced pressure. The residue was purified by silica gel column chromatography (ethyl acetate/petroleum ether (v/v)=1/10) and the eluate was monitored by TLC (ethyl acetate/petroleum ether (v/v)=1/10). The fraction with Rf=0.3~0.4 was collected and dried to give product E164 (2.2 g, yield 77%) as colorless oil. ESI[M+H]⁺=313.1

¹H NMR (400 MHz, CDCl₃) δ 7.68 (s, 1H), 7.41-7.30 (m, 3H), 7.23-7.16 (m, 2H), 6.34 (q, J=7.0 Hz, 1H), 4.40-4.24 (m, 2H), 1.89 (d, J=7.1 Hz, 3H), 1.32 (t, J=7.1 Hz, 3H).

The preparation method of the target compounds listed below was similar as the compound E157 in example E8

Compound E42: 37 mg, ESI[M+H]⁺=383.1

¹H NMR (400 MHz, CDCl₃) δ 7.70 (s, 1H), 7.45-7.30 (m, 3H), 7.24-7.13 (m, 2H), 6.28 (q, J=7.1 Hz, 1H), 4.81 (d, J=7.3 Hz, 1H), 4.75 (d, J=7.3 Hz, 1H), 4.57 (t, J=7.2 Hz, 2H), 2.10 (td, J=7.1, 3.0 Hz, 2H), 1.86 (d, J=7.1 Hz, 3H), 1.34-1.25 (m, 2H), 0.95 (t, J=7.3 Hz, 3H).

Compound E53: 53 mg, ESI[M+H]⁺=383.3

¹H NMR (400 MHz, CDCl₃) δ 7.66 (s, 1H), 7.45-7.29 (m, 3H), 7.24-7.14 (m, 2H), 6.30 (q, J=7.1 Hz, 1H), 2.84 (q, J=7.2 Hz, 2H), 1.89 (d, J=7.1 Hz, 3H), 1.54 (s, 3H), 1.48 (s, 3H), 1.45 (t, J=7.2 Hz, 3H).

Compound E157: 51.4 mg, ESI[M+H]⁺=397.0

¹H NMR (400 MHz, CDCl₃) δ 7.68 (s, 1H), 7.41-7.29 (m, 3H), 7.23-7.15 (m, 2H), 6.38 (q, J=5.8 Hz, 1H), 4.36-4.23 (m, 2H), 3.45-3.34 (m, 2H), 3.32 (s, 3H), 1.97-1.77 (m, 9H).

Compound E158: 35 mg, ESI[M+H]⁺=299.0

¹H NMR (400 MHz, CDCl₃) δ 7.68 (s, 1H), 7.41-7.29 (m, 3H), 7.22-7.15 (m, 2H), 6.32 (q, J=7.0 Hz, 1H), 3.86 (s, 3H), 1.89 (d, J=7.1 Hz, 3H).

Compound E159: 81.4 mg, ESI[M+H]⁺=355.0

¹H NMR (400 MHz, CDCl₃) δ 7.72 (s, 1H), 7.42-7.30 (m, 3H), 7.20-7.11 (m, 2H), 6.22 (q, J=7.0 Hz, 1H), 4.75 (dd, J=38.4, 7.2 Hz, 2H), 4.51 (dd, J=10.6, 7.2 Hz, 2H), 1.90 (d, J=7.1 Hz, 3H), 1.70 (s, 3H).

Compound E160: 35.8 mg, ESI[M+H]⁺=369.0

¹H NMR (400 MHz, CDCl₃) δ 7.76 (s, 1H), 7.39-7.27 (m, 3H), 7.16-7.07 (m, 2H), 6.26 (q, J=6.9 Hz, 1H), 1.89 (s, 3H), 1.88 (d, J=5.6 Hz, 3H), 1.53 (s, 3H), 1.44 (s, 3H).

Compound E161: 70.8 mg, ESI[M+H]⁺=337.0

¹H NMR (400 MHz, CDCl₃) δ 7.68 (s, 1H), 7.42-7.29 (m, 3H), 7.24-7.16 (m, 2H), 6.30 (q, J=7.1 Hz, 1H), 4.91-4.69 (m, 2H), 1.89 (d, J=7.1 Hz, 3H), 1.86 (t, J=2.4 Hz, 3H).

Compound E162: 43 mg, ESI[M+H]⁺=405.1

¹H NMR (400 MHz, CDCl₃) δ 7.73 (s, 0.38H), 7.62 (s, 0.61H), 7.41-7.28 (m, 3H), 7.22-7.12 (m, 2H), 6.38-6.23 (m, 1H), 5.59-5.46 (m, 1H), 4.93-4.79 (m, 2H), 2.40-2.14 (m, 1H), 2.14-1.99 (m, 2H), 1.93-1.85 (m, 3H), 1.85-1.76 (m, 1H), 1.46-1.36 (m, 2H).

Compound E163: 74 mg, ESI[M+H]⁺=379.0

¹H NMR (400 MHz, CDCl₃) δ 7.72 (s, 1H), 7.40-7.29 (m, 3H), 7.22-7.10 (m, 2H), 6.30-6.16 (m, 1H), 5.55 (t, J=6.6 Hz, 1H), 4.99 (qd, J=11.8, 6.7 Hz, 2H), 4.85 (d, J=7.5 Hz, 1H), 4.76 (d, J=7.6 Hz, 1H), 4.74 (s, 2H), 1.90 (d, J=6.9 Hz, 3H).

Compound E165: 61 mg, ESI[M+H]⁺=337.0

¹H NMR (400 MHz, CDCl₃) δ 7.65-7.29 (m, 4H), 7.25-7.13 (m, 2H), 6.34 (q, J=7.1 Hz, 1H), 4.90-4.65 (m, 2H), 1.85 (d, J=7.1 Hz, 3H), 1.84 (t, J=2.4 Hz, 3H).

Compound E166: 31 mg, ESI[M+H]⁺=379.1

¹H NMR (400 MHz, CDCl₃) δ 7.66-7.29 (m, 4H), 7.26-7.13 (m, 2H), 6.35 (q, J=7.1 Hz, 1H), 5.57 (t, J=6.6 Hz, 1H), 4.99-4.76 (m, 6H), 1.89 (d, J=7.0 Hz, 3H).

Example E9 Preparation of Compound E167

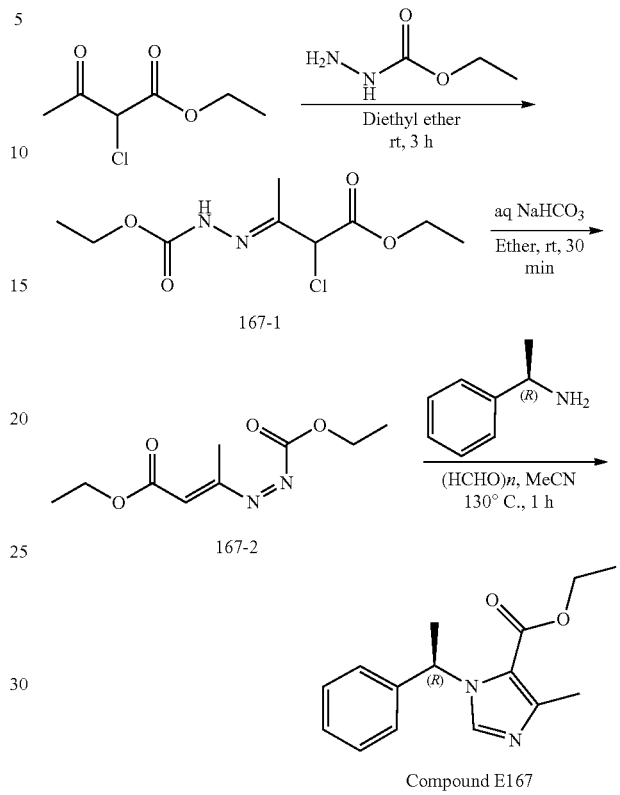

Compound E167

1. Preparation of Ethyl (Z)-2-((E)-4-ethoxy-4-oxobut-2-en-2-yl)diazene-1-carboxylate (167-2)

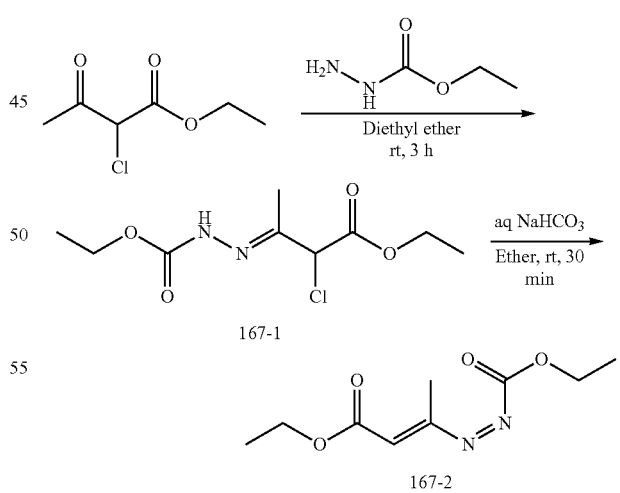

At room temperature, ethyl 2-chloro-3-oxobutanoate (1.5 g, 9.1 mmol) and ethyl hydrazinecarboxylate (947 mg, 9.1 mmol) were dissolved in the diethyl ether (10 mL). The mixture was stirred at room temperature for 3 hrs. After the reaction was completed, saturated sodium bicarbonate solution (10 mL) was added into mixture and stirred at room temperature for 30 min. The mixture was extracted with ethoxyethane (3×10 mL). The combined organic layers were washed with saturated brine (30 mL), dried over anhydrous sodium sulfate, filtered and concentrated under reduced pressure to give crude compound 167-2 (770 mg, yield 39%) as colorless oil, which was used for next step directly without further purification.

2. Preparation of Compound E167

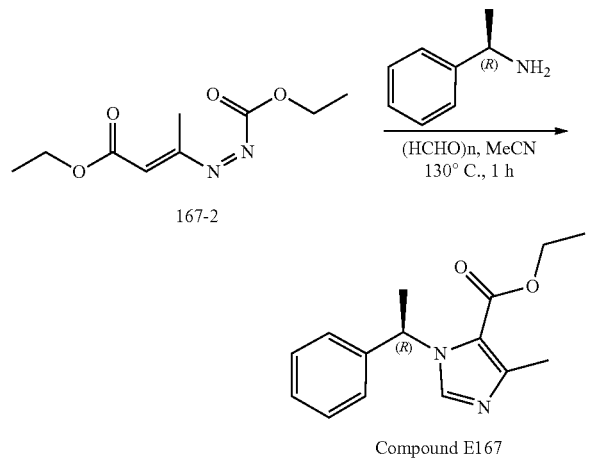

Compound E167

167-2 (100 mg, 0.47 mmol), (R)-1-phenylethan-1-amine (57 mg, 0.47 mmol) and (HCHO)$_n$ (28 mg, 0.94 mmol) were dissolved in the MeCN (10 mL), then the mixture was stirred in the sealed tube at 130° C. for 1 hour. The mixture was cooled and concentrated under reduced pressure. The residue was purified by Prep-TLC (ethyl acetate/petroleum ether (v/v)=1/3) and the fraction with Rf=0.4~0.5 was collected and dried to give the product E167 (51 mg, yield 42%) as colorless oil. ESI[M+H]$^+$=259.3

$^1$H NMR (400 MHz, CDCl$_3$) δ 7.62 (s, 1H), 7.39-7.27 (m, 3H), 7.19-7.11 (m, 2H), 6.32 (q, J=7.1 Hz, 1H), 4.35~4.18 (m, 2H), 2.50 (s, 3H), 1.83 (d, J=7.1 Hz, 3H), 1.32 (t, J=7.1 Hz, 3H).

The following examples illustrate the beneficial effects of the present invention:

Example 1

The Anesthetic Activity of the Compounds was Assessed in Rats Using a Loss of Righting Reflexes (LORR) Assay Adult male Sprague-Dawley rats (250-300 g) were selected for the experiment. The compounds in the above examples and the control drugs, etomidate and CPMM, were dissolved in dimethyl sulfoxide (DMSO), and the same volume of DMSO was given as the blank control group. The anesthesia effects of the compounds were assessed in rats using a LORR assay and a period >30 s was considered as an indicator of general anesthesia. Then the up and down method was used to determine 50% effective dose (ED$_{50}$). The drugs were administered through the tail vein of rats in a volume of 0.6 mL and at a rate of 0.1 mL/s. As shown in Tables A1-E1, the results suggest that the compounds of the present invention, similar to the control etomidate and CPMM, provide a definite and transient effect of general anesthesia. Besides the compounds have the same or better potency as etomidate and CPMM.

TABLE A1

The ED$_{50}$ value with LORR and minimal lethal dose of the compounds in rats

| Compound/drug | ED$_{50}$ (mg/kg) | Minimal lethal dose (mg/kg) | Approximate therapeutic index |
| --- | --- | --- | --- |
| Etomidate | 0.75 (0.72-0.77)* | 12.75 | 17 |
| CPMM | 0.78 (0.74-0.82)* | >7.8 | >10 |
| DMSO | / | / | / |
| Compound A8 | B | >2 | >10 |
| Compound A9 | B | >5 | >13 |
| Compound A11 | A | >1 | >12 |
| Compound A12 | C | >10 | >16 |
| Compound A13 | B | >4 | >10 |
| Compound A16 | B | >10 | >33 |
| Compound A17 | C | >6 | >11 |
| Compound A18 | B | >5 | >22 |
| Compound A19 | B | >5 | >10 |
| Compound A20 | A | >3 | >22 |
| Compound A21 | B | >5 | >16 |

TABLE B1

The ED$_{50}$ value with LORR and minimal lethal dose of the compounds in rats

| Compound/drug | ED$_{50}$ (mg/kg) | Minimal lethal dose (mg/kg) | Approximate therapeutic index |
| --- | --- | --- | --- |
| Etomidate | 0.75 (0.72-0.77)* | 12.75 | 17 |
| CPMM | 0.78 (0.74-0.82)* | >7.8 | >10 |
| DMSO | / | / | / |
| Compound B5 | B | >10 | >11 |
| Compound B8 | C | >10 | >10 |
| Compound B9 | C | >18 | >12 |
| Compound B19 | C | >20 | >11 |
| Compound B20 | C | >17 | >10 |
| Compound B22 | C | >17 | >10 |
| Compound B28 | B | >10 | >13 |

TABLE C1

The ED$_{50}$ value with LORR and minimal lethal dose of the compounds in rats

| Compound/drug | ED$_{50}$ (mg/kg) | Minimal lethal dose (mg/kg) | Approximate therapeutic index |
| --- | --- | --- | --- |
| Etomidate | 0.75 (0.72-0.77)* | 12.75 | 17 |
| CPMM | 0.78 (0.74-0.82)* | >7.8 | >10 |
| DMSO | / | / | / |
| Compound C1 | A | >20 | >90 |
| Compound C3 | C | >10 | >14 |
| Compound C7 | B | >4 | >10 |
| Compound C16 | C | >10 | >14 |
| Compound C18 | B | >5 | >14 |
| Compound C19 | B | >5 | >20 |
| Compound C20 | B | >7 | >16 |
| Compound C24 | A | >1 | >11 |
| Compound C25 | B | >4 | >10 |
| Compound C26 | C | >6 | >11 |
| Compound C27 | C | >9 | >11 |
| Compound C30 | C | >11 | >11 |

TABLE D1

The $ED_{50}$ value with LORR and minimal lethal dose of the compounds in rats

| Compound/drug | $ED_{50}$ (mg/kg) | Minimal lethal dose (mg/kg) | Approximate therapeutic index |
|---|---|---|---|
| Etomidate | 0.75 (0.72-0.77)* | 12.75 | 17 |
| CPMM | 0.78 (0.74-0.82)* | >7.8 | >10 |
| DMSO | / | / | / |
| Compound D1 | B | >6 | >14 |
| Compound D3 | C | >8 | >10 |
| Compound D7 | C | >6 | >10 |
| Compound D10 | C | >6 | >12 |
| Compound D12 | C | >10 | >14 |
| Compound D13 | A | >6 | >12 |
| Compound D14 | B | >3 | >13 |
| Compound D15 | B | >4 | >10 |
| Compound D16 | C | >6 | >12 |
| Compound D18 | B | >3 | >12 |
| Compound D21 | A | >1 | >16 |
| Compound D22 | B | >2 | >11 |
| Compound D24 | C | >7 | >13 |
| Compound D26 | B | >4 | >10 |
| Compound D27 | C | >10 | >10 |
| Compound D28 | A | >10 | >16 |
| Compound D29 | C | >10 | >13 |
| Compound D30 | C | >5 | >11 |
| Compound D31 | C | >9 | >13 |
| Compound D32 | B | >5 | >16 |
| Compound D33 | C | >8 | >10 |
| Compound D34 | C | >8 | >13 |
| Compound D36 | B | >4 | >15 |
| Compound D37 | C | >10 | >13 |
| Compound D39 | C | >9 | >15 |
| Compound D40 | B | >4 | >16 |
| Compound D42 | C | >9 | >12 |
| Compound D43 | A | >1 | >13 |
| Compound D59 | B | >13 | >11 |

TABLE E1

The $ED_{50}$ value with LORR and minimal lethal dose of the compounds in rats

| Compound/drug | $ED_{50}$ (mg/kg) | Minimal lethal dose (mg/kg) | Approximate therapeutic index |
|---|---|---|---|
| Etomidate | 0.75 (0.72-0.77)* | 12.75 | 17 |
| CPMM | 0.78 (0.74-0.82)* | >7.8 | >10 |
| DMSO | / | / | / |
| Compound E2 | B | >5 | >25 |
| Compound E4 | B | >10 | >20 |
| Compound E6 | C | >10 | >24 |
| Compound E8 | B | >4 | >22 |
| Compound E9 | B | >6 | >48 |
| Compound E10 | C | >10 | >14 |
| Compound E11 | A | >4 | >60 |
| Compound E15 | B | >5 | >32 |
| Compound E16 | B | >4 | >20 |
| Compound E17 | B | >9 | >32 |
| Compound E18 | A | >1 | >20 |
| Compound E19 | A | >4 | >40 |
| Compound E20 | A | >5 | >80 |
| Compound E21 | C | >9 | >12 |
| Compound E22 | B | >4 | >30 |
| Compound E24 | A | >4 | >45 |
| Compound E25 | B | >6 | >24 |
| Compound E26 | A | >4 | >50 |
| Compound E27 | B | >6 | >24 |
| Compound E28 | B | >6 | >16 |
| Compound E29 | B | >6 | >15 |
| Compound E30 | B | >6 | >42 |
| Compound E32 | B | >4 | >30 |
| Compound E33 | B | >4 | >30 |
| Compound E34 | B | >2 | >12 |
| Compound E35 | B | >4 | >17 |
| Compound E36 | C | >5 | >26 |
| Compound E37 | A | >0.6 | >30 |
| Compound E38 | B | >7 | >20 |
| Compound E64 | A | >1.5 | >40 |
| Compound E77 | C | >10 | >12 |
| Compound E79 | B | >14 | >10 |
| Compound E90 | A | >1.5 | >30 |
| Compound E91 | C | >20 | >6 |
| Compound E100 | B | >12 | >30 |
| Compound E116 | C | >10 | >16 |
| Compound E125 | C | >24 | >5 |
| Compound E129 | B | >9 | >30 |
| Compound E132 | C | >10 | >14 |
| Compound E133 | C | >10 | >12 |
| Compound E148 | C | >10 | >12 |

Notes:

*The values in brackets indicate 95% confidence limit (mg/kg).

A indicates that the measured $ED_{50}$ is in the range of 0.01-0.10 mg/kg (including 0.01 and 0.10 mg/kg).

B means that the measured $ED_{50}$ is in the range of 0.10-0.50 mg/kg (excluding 0.10 mg/kg, including 0.50 mg/kg).

C indicates that the measured $ED_{50}$ is in the range of 0.50-1.00 mg/kg (excluding 0.50 mg/kg, including 1.00 mg/kg).

Example 2

Comparison of Pharmacological Characteristics of the Compounds at Equivalent Doses ($2 \times ED_{50}$) in Rats Adult male Sprague-Dawley rats (250-300 g) were selected for the experiment (n=8). The compounds and the control drugs, etomidate and CPMM, were dissolved in DMSO, and the same volume of DMSO was given as the blank control group. The drugs were administered at a dose twice their $ED_{50}$ through the tail vein of rats in a volume of 0.6 mL and at a rate of 0.1 mL/s. In addition, the time of LORR was recorded as the onset time of anesthesia. The results show that the compounds of the present invention, Similar to the etomidate and CPMM, exhibit rapid onset and recovery (Tables A2-E2). Furthermore, the duration of the pharmacological effects is sufficient to meet the time requirements for rapid induction of general anesthesia and for diagnostic examinations, some short invasive clinical examinations, or operations. In the experiment, the types and incidence of adverse reactions of the compounds of the present invention are less than those of etomidate and CPMM.

TABLE A2

Comparison of pharmacological characteristics of the compounds at equivalent doses (2 × $ED_{50}$) in rats

| Compound/ drug | 2 $ED_{50}$ (mg/kg) | Onset time (min) | Righting reflex duration (min) | Sedation duration (mg/kg) | Types and incidence of adverse reactions |
|---|---|---|---|---|---|
| Etomidate | 1.49 | 0.11 ± 0.03 | 4.92 ± 1.19 | 11.08 ± 2.16 | Tremor (10/10), Facial muscle twitching (4/10), Tongue stretching (8/10) |
| CPMM | 1.56 | 0.26 ± 0.08 | 1.62 ± 0.63 | 4.99 ± 0.87 | Convulsions (4/10), Tremor (5/10), Myoclonus (5/10) |
| DMSO | — | — | — | — | Red urine (10/10) |
| Compound A8 | 2B | 0.34 ± 0.21 | 2.25 ± 2.64 | 6.75 ± 3.93 | Red urine (8/8) |
| Compound A9 | 2B | 0.40 ± 0.15 | 4.80 ± 1.25 | 11.06 ± 1.80 | Tremor (5/8), Red urine (8/8) |
| Compound A11 | 2A | 0.21 ± 0.10 | 3.81 ± 1.49 | 10.48 ± 2.02 | Red urine (8/8) |
| Compound A12 | 2C | 0.16 ± 0.06 | 4.04 ± 1.65 | 8.65 ± 1.53 | Restlessness (2/8), Red urine (8/8) |
| Compound A13 | 2B | 0.56 ± 0.12 | 2.31 ± 2.14 | 9.30 ± 2.75 | Red urine (8/8) |
| Compound A16 | 2B | 0.16 ± 0.07 | 2.63 ± 1.20 | 6.67 ± 1.60 | Tremor (2/8), Red urine (8/8) |
| Compound A17 | 2C | 0.13 ± 0.03 | 5.78 ± 2.28 | 24.82 ± 11.42 | Tongue stretching (2/8), Red urine (8/8) |
| Compound A18 | 2B | 0.20 ± 0.09 | 4.77 ± 1.73 | 8.44 ± 2.04 | Red urine (8/8) |
| Compound A19 | 2B | 0.36 ± 0.16 | 6.13 ± 2.87 | 13.70 ± 5.14 | Red urine (8/8) |
| Compound A20 | 2A | 0.11 ± 0.03 | 1.90 ± 0.74 | 4.79 ± 0.79 | Red urine (8/8) |
| Compound A21 | 2B | 0.27 ± 0.19 | 1.75 ± 0.26 | 3.66 ± 1.12 | Red urine (8/8) |

TABLE B2

Comparison of pharmacological characteristics of the compounds at equivalent doses (2 × $ED_{50}$) in rats

| Compound/ drug | 2 $ED_{50}$ (mg/kg) | onset time (min) | Righting reflex duration (min) | Sedation duration (mg/kg) | Types and incidence of adverse reactions |
|---|---|---|---|---|---|
| Etomidate | 1.49 | 0.11 ± 0.03 | 4.92 ± 1.19 | 11.08 ± 2.16 | Tremor (10/10), Facial muscle twitching (4/10), Tongue stretching (8/10) |
| CPMM | 1.56 | 0.26 ± 0.08 | 1.62 ± 0.63 | 4.99 ± 0.87 | Convulsions (4/10), Tremor (5/10), Myoclonus (5/10) |
| DMSO | / | / | / | / | Red urine (10/10) |
| Compound B5 | 2B | 0.11 ± 0.02 | 3.98 ± 1.34 | 7.18 ± 1.31 | Red urine (8/8) |
| Compound B8 | 2C | 0.13 ± 0.05 | 5.00 ± 1.25 | 8.31 ± 2.09 | Red urine (8/8) |
| Compound B9 | 2C | 0.39 ± 0.1 | 1.98 ± 1.21 | 6.83 ± 1.39 | Restlessness (1/8), Red urine (8/8) |
| Compound B19 | 2C | 0.31 ± 0.13 | 1.99 ± 1.39 | 8.41 ± 2.52 | Tremor (2/8), Red urine (8/8) |
| Compound B20 | 2C | 0.28 ± 0.14 | 2.59 ± 0.99 | 7.30 ± 1.85 | Red urine (8/8) |
| Compound B22 | 2C | 0.92 ± 0.14 | 1.24 ± 0.12 | 7.88 ± 1.94 | Tremor (4/8), Red urine (8/8) |
| Compound B28 | 2B | 0.29 ± 0.15 | 3.32 ± 0.72 | 7.91 ± 1.20 | Red urine (8/8) |

TABLE C2

Comparison of pharmacological characteristics of the compounds at equivalent doses ($2 \times ED_{50}$) in rats

| Compound/drug | 2 $ED_{50}$ (mg/kg) | onset time (min) | Righting reflex duration (min) | Sedation duration (mg/kg) | Types and incidence of adverse reactions |
|---|---|---|---|---|---|
| Etomidate | 1.49 | 0.11 ± 0.03 | 4.92 ± 1.19 | 11.08 ± 2.16 | Tremor (10/10), Facial muscle twitching (4/10), Tongue stretching (8/10) |
| CPMM | 1.56 | 0.26 ± 0.08 | 1.62 ± 0.63 | 4.99 ± 0.87 | Convulsions (4/10), Tremor (5/10), Myoclonus (5/10) |
| DMSO | — | — | — | — | Red urine (10/10) |
| Compound C1 | 2A | 0.15 ± 0.09 | 1.9 ± 0.64 | 3.8 ± 0.75 | Tremor (8/8), Red urine (8/8) |
| Compound C3 | 2C | 0.36 ± 0.12 | 1.31 ± 0.95 | 6.89 ± 1.75 | Restlessness (3/8), Red urine (8/8) |
| Compound C7 | 2B | 0.15 ± 0.06 | 1.68 ± 0.88 | 4.98 ± 3.48 | Muscle twitching (4/8), Red urine (8/8) |
| Compound C16 | 2C | 0.73 ± 0.23 | 1.31 ± 0.95 | 6.89 ± 1.75 | Red urine (8/8) |
| Compound C18 | 2B | 0.25 ± 0.13 | 1.96 ± 1.39 | 4.96 ± 1.66 | Tremor (5/8), Red urine (8/8) |
| Compound C19 | 2B | 0.45 ± 0.23 | 1.26 ± 0.99 | 9.49 ± 2.37 | Red urine (8/8) |
| Compound C20 | 2B | 0.43 ± 0.07 | 3.59 ± 2.63 | 6.93 ± 3.34 | Tremor (2/8), Red urine (8/8) |
| Compound C24 | 2A | 0.49 ± 0.15 | 2.21 ± 1.28 | 5.49 ± 2.05 | Convulsions (1/8), Red urine (8/8) |
| Compound C25 | 2B | 0.72 ± 0.20 | 2.03 ± 1.32 | 6.22 ± 1.12 | Tremor (6/8), Red urine (8/8) |
| Compound C26 | 2C | 0.30 ± 0.09 | 2.11 ± 1.02 | 5.42 ± 1.24 | Muscle twitching (1/8), Red urine (8/8) |
| Compound C27 | 2C | 0.12 ± 0.07 | 3.06 ± 1.50 | 5.43 ± 1.14 | Red urine (8/8) |
| Compound C30 | 2C | 0.23 ± 0.03 | 3.67 ± 1.48 | 10.33 ± 1.98 | Red urine (8/8) |

TABLE D2

Comparison of pharmacological characteristics of the compounds at equivalent doses ($2 \times ED_{50}$) in rats

| Compound/drug | 2 $ED_{50}$ (mg/kg) | Onset time (min) | Righting reflex duration (min) | Sedation duration (mg/kg) | Types and incidence of adverse reactions |
|---|---|---|---|---|---|
| Etomidate | 1.49 | 0.11 ± 0.03 | 4.92 ± 1.19 | 11.08 ± 2.16 | Tremor (10/10), Facial muscle twitching (4/10), Tongue stretching (8/10) |
| CPMM | 1.56 | 0.26 ± 0.08 | 1.62 ± 0.63 | 4.99 ± 0.87 | Convulsions (4/10), Tremor (5/10), Myoclonus (5/10) |
| DMSO | — | — | — | — | Red urine (10/10) |
| Compound D1 | 2B | 0.26 ± 0.10 | 4.28 ± 1.78 | 7.37 ± 1.19 | Red urine (8/8) |
| Compound D3 | 2C | 0.19 ± 0.05 | 1.05 ± 0.29 | 3.58 ± 0.47 | Restlessness (4/8), Red urine (8/8) |
| Compound D7 | 2C | 0.10 ± 0.01 | 3.20 ± 0.81 | 5.47 ± 1.12 | Red urine (8/8) |
| Compound D10 | 2C | 0.14 ± 0.03 | 6.04 ± 2.27 | 9.96 ± 2.41 | Tremor (2/8), Red urine (8/8) |
| Compound D12 | 2C | 0.32 ± 0.09 | 2.15 ± 1.03 | 9.73 ± 1.26 | Red urine (8/8) |
| Compound D13 | 2A | 0.25 ± 0.06 | 5.09 ± 1.89 | 18.73 ± 10.19 | Red urine (8/8) |
| Compound D14 | 2B | 0.24 ± 0.09 | 2.09 ± 1.08 | 4.71 ± 1.67 | Red urine (8/8) |
| Compound D15 | 2B | 0.21 ± 0.10 | 2.25 ± 0.79 | 5.70 ± 0.98 | Tremor (2/8), Red urine (7/8) |
| Compound D16 | 2C | 0.36 ± 0.19 | 1.17 ± 0.98 | 7.63 ± 2.38 | Red urine (8/8) |
| Compound D18 | 2B | 0.22 ± 0.11 | 1.88 ± 0.95 | 4.36 ± 0.81 | Convulsions (1/8), Red urine (8/8) |

TABLE D2-continued

Comparison of pharmacological characteristics of the compounds at equivalent doses ($2 \times ED_{50}$) in rats

| Compound/drug | $2\,ED_{50}$ (mg/kg) | Onset time (min) | Righting reflex duration (min) | Sedation duration (mg/kg) | Types and incidence of adverse reactions |
|---|---|---|---|---|---|
| Compound D21 | 2A | 0.15 ± 0.05 | 1.93 ± 0.95 | 5.42 ± 0.88 | Hindlimb rigidity (2/8), Red urine (8/8) |
| Compound D22 | 2B | 0.24 ± 0.07 | 4.51 ± 1.63 | 7.99 ± 1.91 | Euphoria (1/8), Red urine (8/8) |
| Compound D24 | 2C | 0.56 ± 0.31 | 0.80 ± 0.20 | 8.88 ± 4.62 | Red urine (8/8) |
| Compound D26 | 2B | 0.56 ± 0.19 | 1.36 ± 0.52 | 6.95 ± 0.94 | Myoclonus (3/8), Red urine (8/8) |
| Compound D27 | 2C | 0.32 ± 0.09 | 2.15 ± 1.03 | 9.73 ± 1.26 | Red urine (8/8) |
| Compound D28 | 2A | 0.25 ± 0.06 | 5.09 ± 1.89 | 18.73 ± 10.19 | Red urine (8/8) |
| Compound D29 | 2C | 0.73 ± 0.10 | 1.19 ± 0.64 | 10.44 ± 1.49 | Tremor (3/8), Red urine (8/8) |
| Compound D30 | 2C | 0.43 ± 0.22 | 1.32 ± 0.61 | 8.31 ± 2.76 | Myoclonus (2/8), Red urine (8/8) |
| Compound D31 | 2C | 0.41 ± 0.15 | 2.65 ± 1.10 | 10.46 ± 2.46 | Red urine (8/8) |
| Compound D32 | 2B | 0.49 ± 0.23 | 2.14 ± 1.23 | 8.20 ± 2.19 | Tongue stretching (2/8), Red urine (8/8) |
| Compound D33 | 2C | 0.71 ± 0.22 | 0.92 ± 0.33 | 4.19 ± 2.72 | Red urine (8/8) |
| Compound D34 | 2C | 0.11 ± 0.04 | 4.50 ± 0.86 | 8.58 ± 1.91 | Red urine (8/8) |
| Compound D36 | 2B | 0.31 ± 0.14 | 2.63 ± 1.78 | 8.88 ± 2.53 | Tongue stretching (4/8), Hindlimb rigidity (2/8), Red urine (8/8) |
| Compound D37 | 2C | 0.24 ± 0.11 | 3.09 ± 2.03 | 7.92 ± 1.85 | Red urine (8/8) |
| Compound D39 | 2C | 0.20 ± 0.05 | 1.11 ± 0.34 | 5.80 ± 1.48 | Hindlimb rigidity (1/8), Myoclonus (1/8), Red urine (8/8) |
| Compound D40 | 2B | 0.73 ± 0.43 | 1.78 ± 1.94 | 6.59 ± 2.21 | Hindlimb rigidity (1/8), Red urine (8/8) |
| Compound D42 | 2C | 0.13 ± 0.02 | 2.50 ± 1.18 | 7.48 ± 2.63 | Red urine (8/8) |
| Compound D43 | 2A | 0.22 ± 0.07 | 1.45 ± 0.78 | 5.54 ± 3.92 | Hindlimb rigidity (2/8), Red urine (8/8) |
| Compound D59 | 2B | 0.15 ± 0.02 | 5.83 ± 1.06 | 10.80 ± 1.58 | Red urine (8/8) |

TABLE E2

Comparison of pharmacological characteristics of the compounds at equivalent doses ($2 \times ED_{50}$) in rats

| Compound/drug | $2\,ED_{50}$ (mg/kg) | Onset time (min) | Righting reflex duration (min) | Sedation duration (mg/kg) | Types and incidence of adverse reactions |
|---|---|---|---|---|---|
| Etomidate | 1.49 | 0.11 ± 0.03 | 4.92 ± 1.19 | 11.08 ± 2.16 | Tremor (10/10), Facial muscle twitching (4/10), Tongue stretching (8/10) |
| CPMM | 1.56 | 0.26 ± 0.08 | 1.62 ± 0.63 | 4.99 ± 0.87 | Convulsions (4/10), Tremor (5/10), Myoclonus (5/10) |
| DMSO | / | / | / | / | Red urine (10/10) |
| Compound E2 | 2B | 0.23 ± 0.07 | 2.20 ± 1.11 | 6.15 ± 0.91 | Red urine (8/8) |
| Compound E4 | 2B | 0.45 ± 0.05 | 4.38 ± 1.29 | 10.65 ± 1.31 | Red urine (8/8) |
| Compound E6 | 2C | 0.13 ± 0.04 | 2.73 ± 1.08 | 5.76 ± 0.80 | Tremor (1/8), Red urine (8/8) |
| Compound E8 | 2B | 0.38 ± 0.06 | 1.90 ± 0.82 | 7.12 ± 0.81 | Red urine (8/8) |
| Compound E9 | 2B | 0.42 ± 0.20 | 1.24 ± 0.79 | 9.29 ± 2.07 | Red urine (8/8) |
| Compound E10 | 2C | 0.21 ± 0.05 | 2.59 ± 0.85 | 7.55 ± 4.94 | Red urine (8/8) |
| Compound E11 | 2A | 0.57 ± 0.25 | 1.52 ± 0.53 | 9.31 ± 3.16 | Red urine (8/8) |
| Compound E15 | 2B | 0.42 ± 0.13 | 1.10 ± 0.89 | 6.52 ± 3.53 | Tremor (2/8), Red urine (8/8) |

TABLE E2-continued

Comparison of pharmacological characteristics of the compounds at equivalent doses (2 × $ED_{50}$) in rats

| Compound/drug | 2 $ED_{50}$ (mg/kg) | Onset time (min) | Righting reflex duration (min) | Sedation duration (mg/kg) | Types and incidence of adverse reactions |
|---|---|---|---|---|---|
| Compound E16 | 2B | 0.30 ± 0.09 | 3.59 ± 1.22 | 9.80 ± 3.02 | Red urine (8/8) |
| Compound E17 | 2B | 0.26 ± 0.07 | 3.12 ± 1.61 | 7.64 ± 1.10 | Muscle twitching (1/8), Red urine (8/8) |
| Compound E18 | 2A | 0.40 ± 0.20 | 2.51 ± 1.69 | 8.10 ± 2.17 | Red urine (8/8) |
| Compound E19 | 2A | 0.34 ± 0.13 | 0.80 ± 0.30 | 3.89 ± 1.24 | Tremor (3/8), Red urine (8/8) |
| Compound E20 | 2A | 0.51 ± 0.16 | 0.75 ± 0.21 | 4.01 ± 1.33 | Tongue stretching (2/8), Red urine (8/8) |
| Compound E21 | 2C | 0.49 ± 0.20 | 2.76 ± 2.17 | 7.71 ± 3.03 | Red urine (8/8) |
| Compound E22 | 2B | 0.73 ± 0.13 | 0.99 ± 0.70 | 5.51 ± 1.13 | Tremor (4/8), Red urine (8/8) |
| Compound E24 | 2A | 0.38 ± 0.14 | 1.00 ± 0.29 | 5.24 ± 0.78 | Red urine (8/8) |
| Compound E25 | 2B | 0.25 ± 0.09 | 2.10 ± 0.86 | 5.92 ± 1.18 | Restlessness (2/8), Red urine (8/8) |
| Compound E26 | 2A | 0.48 ± 0.09 | 1.45 ± 0.41 | 6.37 ± 1.31 | Red urine (8/8) |
| Compound E27 | 2B | 0.31 ± 0.10 | 4.13 ± 1.12 | 10.23 ± 1.60 | Red urine (8/8) |
| Compound E28 | 2B | 0.43 ± 0.19 | 2.69 ± 1.07 | 8.30 ± 1.97 | Red urine (8/8) |
| Compound E29 | 2B | 0.48 ± 0.21 | 2.74 ± 2.63 | 7.84 ± 3.05 | Red urine (8/8) |
| Compound E30 | 2B | 0.60 ± 0.18 | 1.23 ± 0.58 | 6.10 ± 1.28 | Red urine (8/8) |
| Compound E32 | 2B | 0.30 ± 0.14 | 3.86 ± 1.13 | 8.70 ± 2.07 | Tremor (3/8), Red urine (8/8) |
| Compound E33 | 2B | 0.20 ± 0.09 | 3.97 ± 1.77 | 7.99 ± 2.01 | Red urine (8/8) |
| Compound E34 | 2B | 0.29 ± 0.20 | 1.78 ± 1.09 | 4.81 ± 1.58 | Tongue stretching (1/8), Red urine (8/8) |
| Compound E35 | 2B | 0.32 ± 0.11 | 2.30 ± 0.80 | 6.77 ± 1.36 | Tremor (4/8), Red urine (8/8) |
| Compound E36 | 2C | 0.49 ± 0.17 | 2.21 ± 1.86 | 6.44 ± 1.61 | Red urine (8/8) |
| Compound E37 | 2A | 0.25 ± 0.15 | 1.75 ± 0.26 | 3.66 ± 1.12 | Red urine (8/8) |
| Compound E38 | 2B | 0.25 ± 0.13 | 1.96 ± 1.39 | 4.96 ± 1.66 | Red urine (8/8) |
| Compound E64 | 2A | 0.31 ± 0.06 | 2.28 ± 1.28 | 6.24 ± 1.58 | Tremor (2/8), Red urine (8/8) |
| Compound E77 | 2C | 0.11 ± 0.03 | 1.90 ± 0.74 | 4.79 ± 0.79 | Tremor (2/8), Red urine (8/8) |
| Compound E79 | 2B | 0.25 ± 0.13 | 1.96 ± 1.39 | 4.96 ± 1.66 | Red urine (8/8) |
| Compound E90 | 2A | 0.50 ± 0.20 | 1.29 ± 0.64 | 5.70 ± 1.51 | Tremor (1/8), Red urine (8/8) |
| Compound E91 | 2C | 0.48 ± 0.21 | 1.24 ± 0.63 | 6.76 ± 1.49 | Red urine (8/8) |
| Compound E100 | 2B | 0.60 ± 0.24 | 1.98 ± 1.85 | 5.82 ± 2.11 | Tremor (5/8), Red urine (8/8) |
| Compound E116 | 2C | 0.61 ± 0.23 | 1.18 ± 0.56 | 7.10 ± 2.80 | Red urine (8/8) |
| Compound E125 | 2C | 0.85 ± 0.13 | 1.52 ± 0.93 | 5.67 ± 2.12 | Red urine (8/8) |
| Compound E129 | 2B | 0.87 ± 0.26 | 0.68 ± 0.34 | 5.41 ± 2.43 | Tremor (3/8), Red urine (8/8) |
| Compound E132 | 2C | 0.18 ± 0.06 | 2.70 ± 1.15 | 6.60 ± 1.11 | Restlessness (2/8), Red urine (8/8) |
| Compound E133 | 2C | 0.25 ± 0.10 | 2.10 ± 0.86 | 5.92 ± 1.18 | Tremor (4/8), Red urine (8/8) |
| Compound E148 | 2C | 0.75 ± 0.24 | 0.49 ± 0.38 | 7.35 ± 2.34 | Tremor (5/8), Red urine (8/8) |

Notes:

A indicates that the measured $ED_{50}$ is in the range of 0.01-0.10 mg/kg (including 0.01 and 0.10 mg/kg).

B means that the measured $ED_{50}$ is in the range of 0.10-0.50 mg/kg (excluding 0.10 mg/kg, including 0.50 mg/kg).

C indicates that the measured $ED_{50}$ is in the range of 0.50-1.00 mg/kg (excluding 0.50 mg/kg, including 1.00 mg/kg).

Example 3

The Effects of the Compounds on Adrenocortical Function In Vitro Test

The H295R cell line was selected and treated with vehicle (i.e., DMSO) and different concentrations of etomidate, CPMM, etomidate metabolite (i.e., etomidate acid), and the compounds of the present invention. Then secretion of the cortisol and corticosterone in the supernatant, was measured using HPLC-MS/MS method to determine whether the compounds of the present invention had adrenotoxic potential.

The results show that the compounds of the present invention meet the design requirements (see Tables A3-E3), and none of the compounds inhibit adrenocortical function in the experiment.

TABLE A3

The effects of the compounds on adrenocortical function in vitro test

| Compound/drug | $EC_{50}$ (Cortisol) | Cortisol as an indicator to determine the presence of inhibition | $EC_{50}$ (Corticosterone) | Corticosterone as an indicator to determine the presence of inhibition |
|---|---|---|---|---|
| Etomidate | >1 nM | 2 | >10 nM | 2 |
| CPMM | >10 nM | 1 | >100 nM | 1 |
| Etomidate acid | >10000 nM | 0 | >10000 nM | 0 |
| DMSO | >10000 nM | 0 | >10000 nM | 0 |
| Blank medium | >10000 nM | 0 | >10000 nM | 0 |

TABLE A3-continued

The effects of the compounds on adrenocortical function in vitro test

| Compound/drug | EC$_{50}$ (Cortisol) | Cortisol as an indicator to determine the presence of inhibition | EC$_{50}$ (Corticosterone) | Corticosterone as an indicator to determine the presence of inhibition |
|---|---|---|---|---|
| Compound A8 | >1000 nM | 0 | >1000 nM | 0 |
| Compound A9 | >10000 nM | 0 | >10000 nM | 0 |
| Compound A11 | >10000 nM | 0 | >10000 nM | 0 |
| Compound A12 | >1000 nM | 0 | >0000 nM | 0 |
| Compound A13 | >10000 nM | 0 | >10000 nM | 0 |
| Compound A16 | >1000 nM | 0 | >1000 nM | 0 |
| Compound A17 | >10000 nM | 0 | >10000 nM | 0 |
| Compound A18 | >1000 nM | 0 | >1000 nM | 0 |
| Compound A19 | >10000 nM | 0 | >10000 nM | 0 |
| Compound A20 | >10000 nM | 0 | >10000 nM | 0 |
| Compound A21 | >1000 nM | 0 | >1000 nM | 0 |
| Compound A28 | >1000 nM | 0 | >1000 nM | 0 |
| Compound A46 | >100 nM | 0 | >100 nM | 0 |

Cell line: H295R
Incubation concentration and concentration range: 0.1 nM, 1 nM, 10 nM, 50 nM, 100 nM, 500 nM, 1000 nM, 10000 nM
Cortisol and corticosterone determination: HPLC-MS/MS method
The effect determination of compounds or drugs on adrenal function:
1. No inhibition (using blank culture medium, or DMSO, or etomidate metabolite, i.e., etomidate acid, as a control), marked as "0" in the table.
2. Mild inhibition (using CPMM as a control), marked as "1" in the table.
3. Obvious inhibition (with etomidate as a control), marked as "2" in the table.

TABLE B3

The effects of the compounds on adrenocortical function in vitro test

| Compound/drug | EC$_{50}$ (Cortisol) | Cortisol as an indicator to determine the presence of inhibition | EC$_{50}$ (Corticosterone) | Corticosterone as an indicator to determine the presence of inhibition |
|---|---|---|---|---|
| Etomidate | >1 nM | 2 | >10 nM | 2 |
| CPMM | >10 nM | 1 | >100 nM | 1 |
| Etomidate acid | >10000 nM | 0 | >10000 nM | 0 |
| DMSO | >10000 nM | 0 | >10000 nM | 0 |
| Blank medium | >10000 nM | 0 | >10000 nM | 0 |
| Compound B5 | >1000 nM | 0 | >10000 nM | 0 |
| Compound B9 | >10000 nM | 0 | >10000 nM | 0 |
| Compound B10 | >1000 nM | 0 | >1000 nM | 0 |
| Compound B18 | >1000 nM | 0 | >1000 nM | 0 |
| Compound B19 | >10000 nM | 0 | >10000 nM | 0 |
| Compound B20 | >1000 nM | 0 | >1000 nM | 0 |
| Compound B25 | >1000 nM | 0 | >0000 nM | 0 |
| Compound B29 | >10000 nM | 0 | >10000 nM | 0 |

Cell line: H295R
Incubation concentration and concentration range: 0.1 nM, 1 nM, 10 nM, 50 nM, 100 nM, 500 nM, 1000 nM, 10000 nM
Cortisol and corticosterone determination: HPLC-MS/MS method
The effect determination of compounds or drugs on adrenal function:
1. No inhibition (using blank culture medium, or DMSO, or etomidate metabolite, i.e., etomidate acid, as a control), marked as "0" in the table.
2. Mild inhibition (using CPMNI as a control), marked as "1" in the table.
3. Obvious inhibition (with etomidate as a control), marked as "2" in the table.

TABLE C3

The effects of the compounds on adrenocortical function in vitro test

| Compound/drug | EC$_{50}$ (Cortisol) | Cortisol as an indicator to determine the presence of inhibition | EC$_{50}$ (Corticosterone) | Corticosterone as an indicator to determine the presence of inhibition |
|---|---|---|---|---|
| Etomidate | >1 nM | 2 | >10 nM | 2 |
| CPMM | >10 nM | 1 | >100 nM | 1 |
| Etomidate acid | >10000 nM | 0 | >10000 nM | 0 |
| DMSO | >10000 nM | 0 | >10000 nM | 0 |
| Blank medium | >10000 nM | 0 | >10000 nM | 0 |
| Compound C3 | >1000 nM | 0 | >1000 nM | 0 |
| Compound C4 | >1000 nM | 0 | >1000 nM | 0 |
| Compound C5 | >1000 nM | 0 | >1000 nM | 0 |
| Compound C7 | >1000 nM | 0 | >1000 nM | 0 |
| Compound C9 | >10000 nM | 0 | >10000 nM | 0 |
| Compound C10 | >10000 nM | 0 | >10000 nM | 0 |
| Compound C11 | >1000 nM | 0 | >1000 nM | 0 |
| Compound C12 | >1000 nM | 0 | >1000 nM | 0 |
| Compound C13 | >10000 nM | 0 | >10000 nM | 0 |
| Compound C16 | >1000 nM | 0 | >1000 nM | 0 |
| Compound C18 | >1000 nM | 0 | >1000 nM | 0 |
| Compound C19 | >1000 nM | 0 | >1000 nM | 0 |
| Compound C20 | >10000 nM | 0 | >10000 nM | 0 |
| Compound C24 | >1000 nM | 0 | >1000 nM | 0 |
| Compound C25 | >1000 nM | 0 | >1000 nM | 0 |

TABLE C3-continued

The effects of the compounds on adrenocortical function in vitro test

| Compound/drug | EC$_{50}$ (Cortisol) | Cortisol as an indicator to determine the presence of inhibition | EC$_{50}$ (Corticosterone) | Corticosterone as an indicator to determine the presence of inhibition |
|---|---|---|---|---|
| Compound C26 | >10000 nM | 0 | >10000 nM | 0 |
| Compound C27 | >1000 nM | 0 | >1000 nM | 0 |
| Compound C30 | >1000 nM | 0 | >0000 nM | 0 |

Cell line: H295R
Incubation concentration and concentration range: 0.1 nM, 1 nM, 10 nM, 50 nM, 100 nM, 500 nM, 1000 nM, 10000 nM
Cortisol and corticosterone determination: HPLC-MS/MS method
The effect determination of compounds or drugs on adrenal function:
1. No inhibition (using blank culture medium, or DMSO, or etomidate metabolite, i.e., etomidate acid, as a control), marked as "0" in the table.
2. Mild inhibition (using CPMM as a control), marked as "1" in the table.
3. Obvious inhibition (with etomidate as a control), marked as "2" in the table.

TABLE D3

The effects of the compounds on adrenocortical function in vitro test

| Compound/drug | EC$_{50}$ (Cortisol) | Cortisol as an indicator to determine the presence of inhibition | EC$_{50}$ (Corticosterone) | Corticosterone as an indicator to determine the presence of inhibition |
|---|---|---|---|---|
| Etomidate | >1 nM | 2 | >10 nM | 2 |
| CPMM | >10 nM | 1 | >100 nM | 1 |
| Etomidate acid | >10000 nM | 0 | >10000 nM | 0 |
| DMSO | >10000 nM | 0 | >10000 nM | 0 |
| Blank medium | >10000 nM | 0 | >10000 nM | 0 |
| Compound D2 | >1000 nM | 0 | >1000 nM | 0 |
| Compound D13 | >10000 nM | 0 | >10000 nM | 0 |
| Compound D14 | >10000 nM | 0 | >10000 nM | 0 |
| Compound D15 | >10000 nM | 0 | >10000 nM | 0 |
| Compound D18 | >10000 nM | 0 | >10000 nM | 0 |
| Compound D20 | >10000 nM | 0 | >10000 nM | 0 |
| Compound D21 | >1000 nM | 0 | >1000 nM | 0 |
| Compound D28 | >10000 nM | 0 | >10000 nM | 0 |
| Compound D35 | >1000 nM | 0 | >1000 nM | 0 |
| Compound D36 | >1000 nM | 0 | >1000 nM | 0 |
| Compound D37 | >1000 nM | 0 | >1000 nM | 0 |
| Compound D38 | >10000 nM | 0 | >10000 nM | 0 |
| Compound D39 | >1000 nM | 0 | >1000 nM | 0 |
| Compound D40 | >1000 nM | 0 | >1000 nM | 0 |
| Compound D41 | >10000 nM | 0 | >10000 nM | 0 |
| Compound D42 | >1000 nM | 0 | >1000 nM | 0 |
| Compound D43 | >10000 nM | 0 | >10000 nM | 0 |

Cell line: H295R
Incubation concentration and concentration range: 0.1 nM, 1 nM, 10 nM, 50 nM, 100 nM, 500 nM, 1000 nM, 10000 nM
Cortisol and corticosterone determination: HPLC-MS/MS method
The effect determination of compounds or drugs on adrenal function:
1. No inhibition (using blank culture medium, or DMSO, or etomidate metabolite, i.e., etomidate acid, as a control), marked as "0" in the table.
2. Mild inhibition (using CPMM as a control), marked as "1" in the table.
3. Obvious inhibition (with etomidate as a control), marked as "2" in the table.

TABLE E3

The effects of the compounds on adrenocortical function in vitro test

| Compound/drug | EC$_{50}$ (Cortisol) | Cortisol as an indicator to determine the presence of inhibition | EC$_{50}$ (Corticosterone) | Corticosterone as an indicator to determine the presence of inhibition |
|---|---|---|---|---|
| Etomidate | >1 nM | 2 | >10 nM | 2 |
| CPMM | >10 nM | 1 | >100 nM | 1 |
| Etomidate acid | >10000 nM | 0 | >10000 nM | 0 |
| DMSO | >10000 nM | 0 | >10000 nM | 0 |
| Blank medium | >10000 nM | 0 | >10000 nM | 0 |
| Compound E2 | >10000 nM | 0 | >10000 nM | 0 |
| Compound E6 | >10000 nM | 0 | >10000 nM | 0 |
| Compound E8 | >100 nM | 0 | >100 nM | 0 |
| Compound E12 | >10000 nM | 0 | >10000 nM | 0 |
| Compound E31 | >10000 nM | 0 | >10000 nM | 0 |
| Compound E35 | >10000 nM | 0 | >10000 nM | 0 |
| Compound E37 | >10000 nM | 0 | >10000 nM | 0 |
| Compound E38 | >10000 nM | 0 | >10000 nM | 0 |
| Compound E102 | >10000 nM | 0 | >10000 nM | 0 |
| Compound E146 | >10000 nM | 0 | >10000 nM | 0 |
| Compound E157 | >10000 nM | 0 | >10000 nM | 0 |
| Compound E160 | >10000 nM | 0 | >10000 nM | 0 |
| Compound E161 | >10000 nM | 0 | >10000 nM | 0 |
| Compound E163 | >10000 nM | 0 | >10000 nM | 0 |
| Compound E164 | >10000 nM | 0 | >10000 nM | 0 |

Cell line: H295R
Incubation concentration and concentration range: 0.1 nM, 1 nM, 10 nM, 50 nM, 100 nM, 500 nM, 1000 nM, 10000 nM
Cortisol and corticosterone determination: HPLC-MS/MS method
The effect determination of compounds or drugs on adrenal function:
1. No inhibition (using blank culture medium, or DMSO, or etomidate metabolite, i.e., etomidate acid, as a control), marked as "0" in the table.
2. Mild inhibition (using CPMNI as a control), marked as "1" in the table.
3. Obvious inhibition (with etomidate as a control), marked as "2" in the table.

Example 4

The Effects of the Compounds on the Circulatory Function were Measured in Rats Using a Small Animal Implanted Physiological Signal Telemetry System The anesthetic activity of the compounds was assessed in rats using a LORR assay and the up and down method was used to determine $ED_{50}$. The drugs were administered at a dose twice their $ED_{50}$ through the tail vein of rats (n=6). A small animal implantable physiological signal telemetry system from DSI (Data Science International, Inc.) was used to measure the changes in heart rate (HR) and blood pressure in rats during 30 min after administration. Then mean arterial pressure (MAP) and HR were used as representative indicators to determine hemodynamic stability of the compounds of the present invention in rats.

The main test equipments are as follows:

A small animal implantable physiological signal telemetry system from DSI (Data Science International, Inc.) including implants (RATHD-521, DSI, United States), receiver boards (RPC-1, DSI, United States), signal conversion devices (DEM, DSI, USA), perfusion glue (DSI, USA), fibrin membrane (DSI, USA), etc.

A small animal ventilator (HX-101E, Chengdu Taimeng Technology Co., Ltd.); An electronic balance (ME215S, Sartorius, Germany).

First, animal models were established. A left ventricular catheter, an abdominal aortic catheter and ECG wires were placed into rats. At least one week after surgery, data were recorded.

Administration procedure: rats were put into a restraint device with a 20 G indwelling catheter placed into a lateral tail vein. After administration of 0.2 mL heparin, a pre-filled extension tube was attached and taped to the tail vein to secure the extension tube. Then the rats were removed from the restraint device to a cage before placing them together on the signal receiver. After the rats acclimatized for 30 min, the compounds were injected with a dose at 2-fold the $ED_{50}$ via the catheter. Finally, the pharmacological effects, adverse reactions, and behavioural manifestations of the rats were observed and recorded Data collection: After setting the data collection parameters on the software, the power of the implant was turned on to start data collection. In this experiment, data recording frequency was set to 15 s. Data collection was continuously recorded for 30 min before and after administration of the drugs in rats. After data acquisition, the test was stopped.

Figure 5:
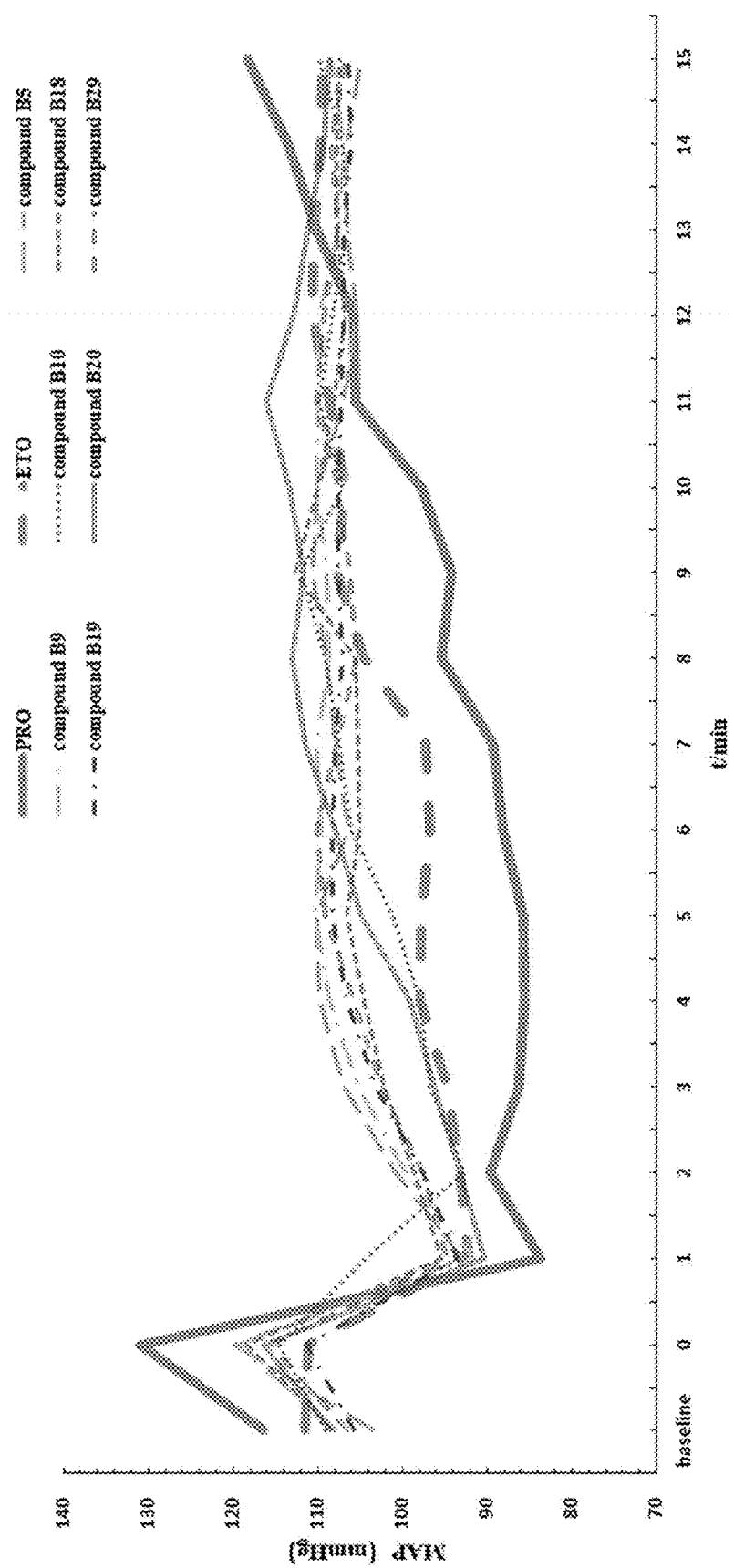
Figure 9:
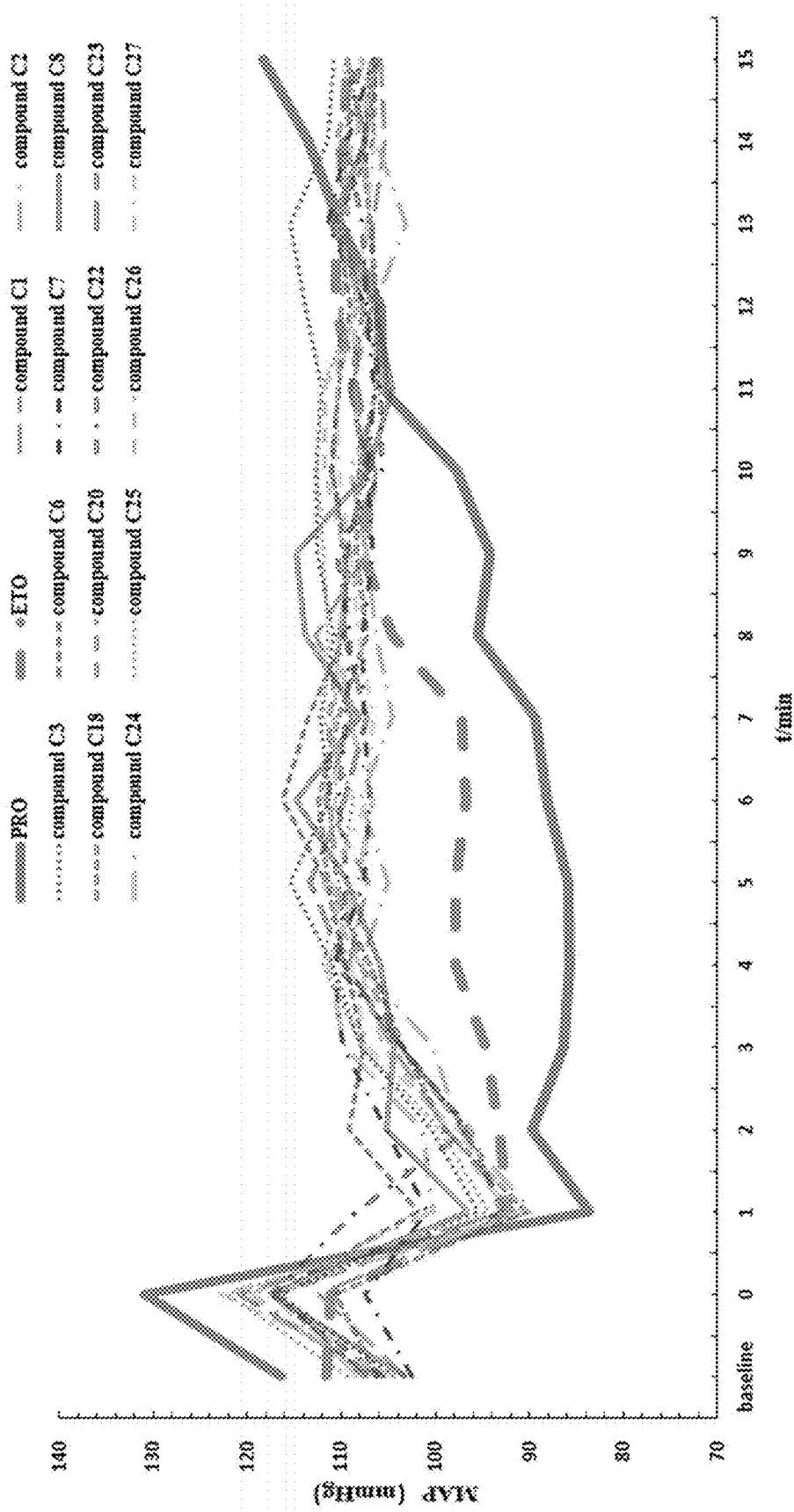
Figure 13:
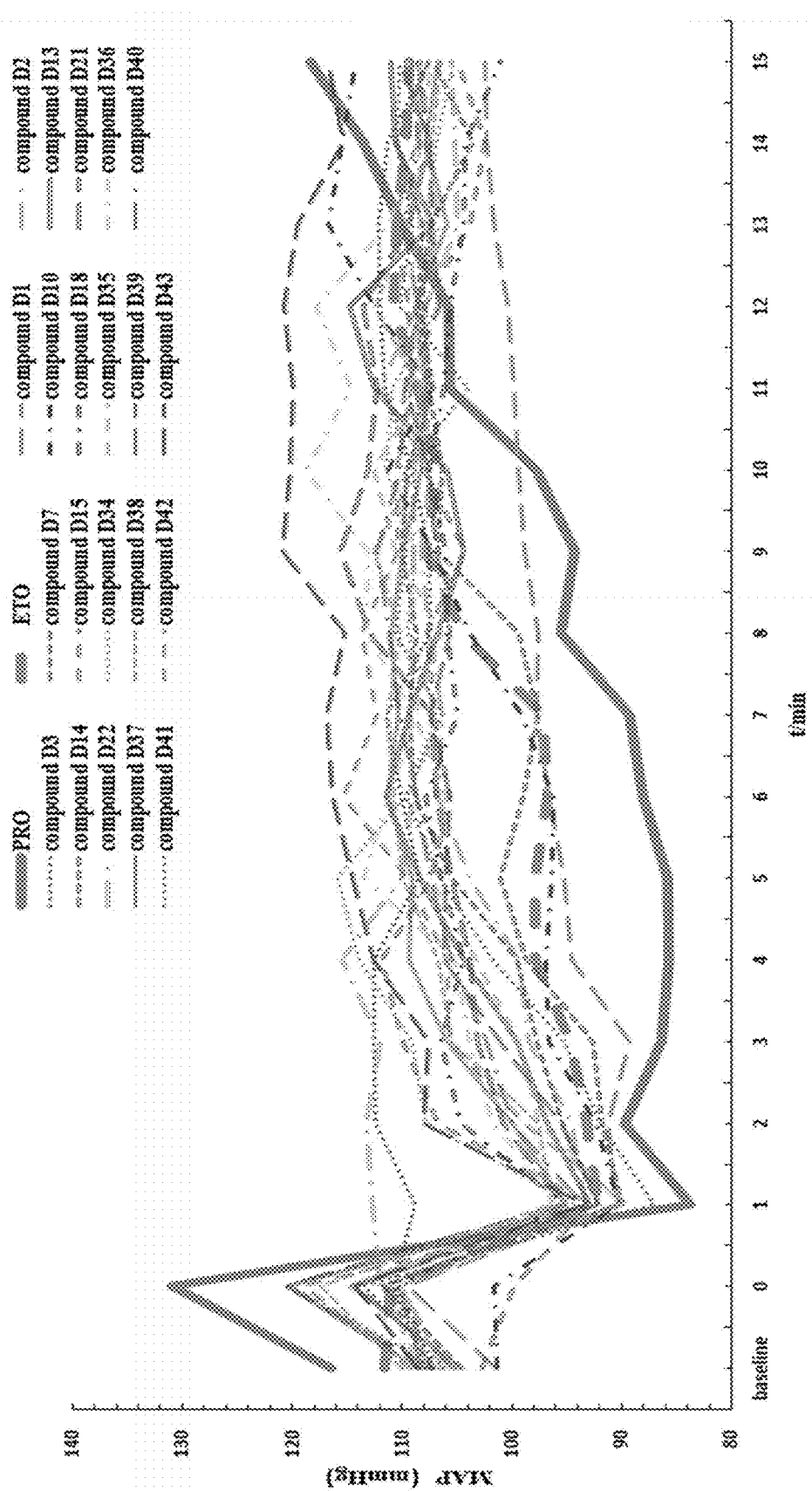
Figure 17:
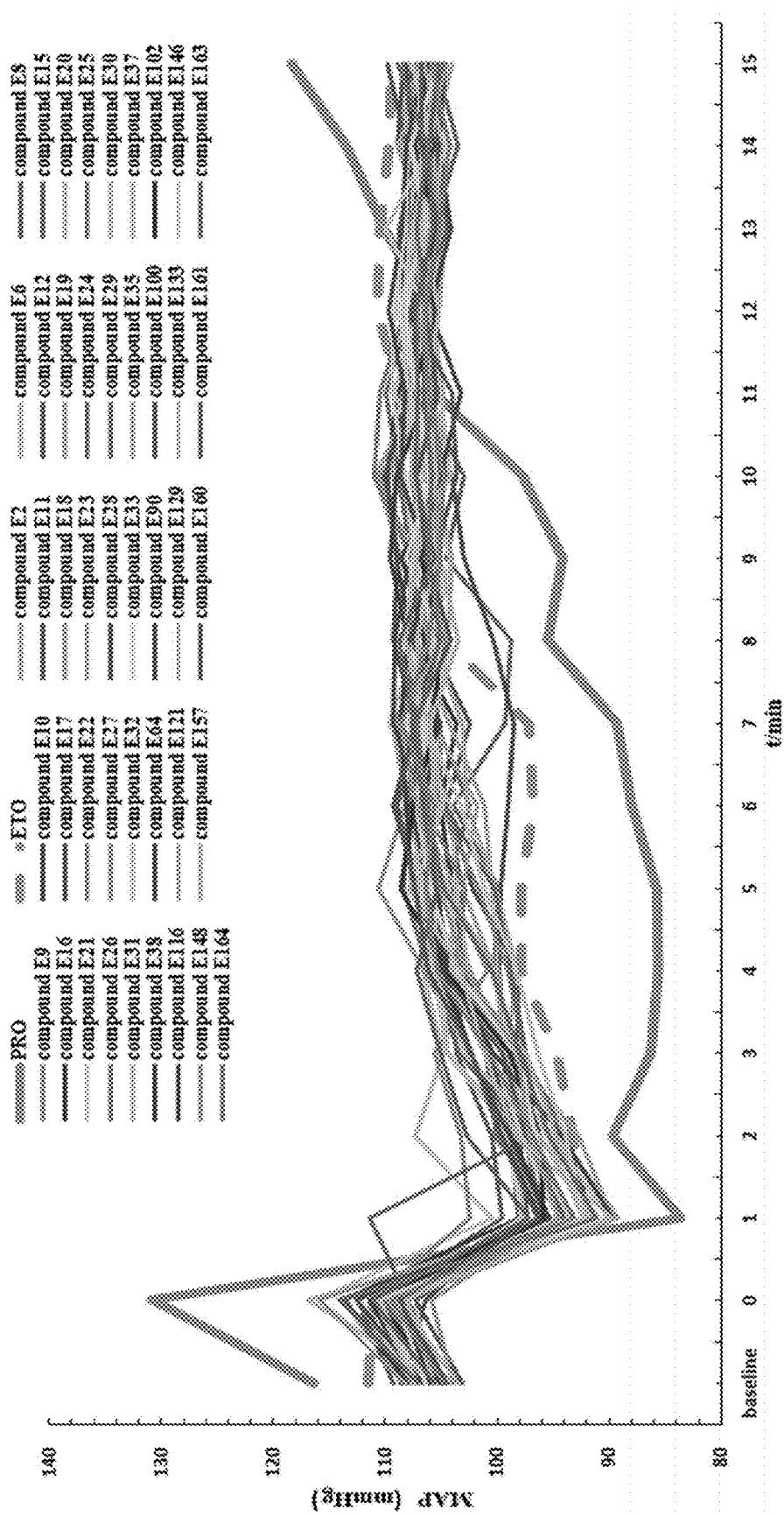

The results suggest that the compounds of the present invention had almost no inhibitory effect on the circulatory function as does the control etomidate and CPMM, while the control propofol exhibit significant inhibition of the circulatory function (see FIG. 1-20).

Example 5

Pharmacological Effects of the Compounds on Continuous Infusion in Rats

Adult male Sprague-Dawley rats with body weight ranging from 250 to 300 gm were selected for continuous infusion test. The compounds of the present invention and the control drugs, etomidate and CPMM, were prepared as emulsion before the test, which was continuously infused through the tail vein of the rats at 2 times the MIR (minimum infusion rate) and the LORR was maintained for 1 hour. Time to recovery of righting reflex from stopping infusion, and time to fully awake from stopping infusion were recorded. The results are shown in Table A4-E4 which illustrate that the recovery time after 1 hour of continuous infusion under 2×MIR conditions is not significantly longer than that of the compounds of the present invention after a single intravenous injection of 2×$ED_{50}$, and the recovery time is considerably shorter than that of etomidate. Furthermore, the types and incidence of adverse reactions are also significantly less than etomidate and CPMM.

TABLE A4

Pharmacological effects of the compounds on continuous infusion in rats

| Compound/drug | Onset time (min) | Recovery time after stopping infusion (min) | Types and incidence of adverse reactions |
|---|---|---|---|
| Etomidate | 4-5 | 25-30 | Tremor (6/6), Facial muscle twitching (4/6), Tongue stretching (5/6) |
| CPMM | 3-4 | 7-8 | Convulsions (3/6), Tremor (5/6), Myoclonus (5/6) |
| DMSO | / | / | Red urine (8/8) |
| Compound A7 | 2-3 | 7-9 | Tremor (4/6) |
| Compound A8 | 3-4 | 9-14 | Tremor (1/6) |
| Compound A11 | 3-4 | 14-18 | Tremor (5/6) |
| Compound A12 | 3-4 | 13-16 | Tremor (4/6) |
| Compound A15 | 2-3 | 12-15 | Tremor (5/6) |
| Compound A16 | 2-3 | 12-14 | Tremor (3/6) |
| Compound A17 | 2-3 | 19-25 | Tremor (2/6) |
| Compound A18 | 3-4 | 11-15 | Tremor (5/6) |
| Compound A21 | 3-4 | 15-25 | No |

TABLE B4

Pharmacological effects of the compounds on continuous infusion in rats

| Compound/drug | Onset time (min) | Recovery time after stopping infusion (min) | Types and incidence of adverse reactions |
|---|---|---|---|
| Etomidate | 4-5 | 25-30 | Tremor (6/6), Facial muscle twitching (4/6), Tongue stretching (5/6) |
| CPMM | 3-4 | 7-8 | Convulsions (3/6), Tremor (5/6), Myoclonus (5/6) |
| DMSO | / | / | Red urine (8/8) |
| Compound B5 | 3-4 | 12-14 | Tremor (2/6) |
| Compound B9 | 2-3 | 10-13 | Restlessness (2/6), Tremor (1/6) |
| Compound B10 | 3-4 | 9-12 | Tremor (3/6) |
| Compound B18 | 3-4 | 15-18 | Tremor (4/6) |
| Compound B19 | 3-4 | 12-17 | Tremor (5/6) |
| Compound B29 | 2-3 | 8-10 | No |

TABLE C4

Pharmacological effects of the compounds on continuous infusion in rats

| Compound/drug | Onset time (min) | Recovery time after stopping infusion (min) | Types and incidence of adverse reactions |
|---|---|---|---|
| Etomidate | 4-5 | 25-30 | Tremor (6/6), Facial muscle twitching (4/6), Tongue stretching (5/6) |
| CPMM | 3-4 | 7-8 | Convulsions (3/6), Tremor (5/6), Myoclonus (5/6) |
| DMSO | / | / | Red urine (8/8) |
| Compound C1 | 3-4 | 10-11 | Tremor (6/6) |
| Compound C3 | 3-4 | 10-14 | Restlessness (2/6), Tremor (3/6) |
| Compound C7 | 3-4 | 8-14 | Tremor (6/6) |
| Compound C18 | 3-4 | 10-14 | Tremor (1/6) |
| Compound C20 | 3-4 | 8-15 | Tremor (3/6), Myoclonus (1/6) |
| Compound C24 | 3-4 | 9-13 | Tremor (1/6) |
| Compound C25 | 3-4 | 12-15 | Tongue stretching (2/6), Tremor (2/6) |
| Compound C26 | 2-3 | 9-13 | Tremor (2/6) |
| Compound C27 | 3-4 | 10-11 | Tremor (2/6) |

TABLE D4

Pharmacological effects of the compounds on continuous infusion in rats

| Compound/drug | Onset time (min) | Recovery time after stopping infusion (min) | Types and incidence of adverse reactions |
|---|---|---|---|
| Etomidate | 4-5 | 25-30 | Tremor (6/6), Facial muscle twitching (4/6), Tongue stretching (5/6) |
| CPMM | 3-4 | 7-8 | Convulsions (3/6), Tremor (5/6), Myoclonus (5/6) |
| DMSO | / | / | Red urine (8/8) |
| Compound D1 | 3-4 | 11-14 | Tremor (2/6) |
| Compound D3 | 2-3 | 7-9 | Restlessness (2/6), Tremor (3/6) |
| Compound D10 | 3-4 | 13-17 | Tremor (6/6) |
| Compound D13 | 2-3 | 13-22 | Tremor (4/6) |
| Compound D14 | 2-3 | 11-14 | Tremor (5/6) |
| Compound D15 | 2-3 | 10-11 | Tremor (3/6) |
| Compound D18 | 3-4 | 11-13 | Convulsions (1/6), Tremor (4/6) |
| Compound D21 | 2-3 | 8-9 | Tremor (4/6), Myoclonus (1/6) |
| Compound D22 | 3-4 | 14-18 | Euphoria (2/6), Tremor (4/6) |
| Compound D28 | 3-4 | 13-16 | Tremor (2/6) |
| Compound D36 | 3-4 | 12-17 | Tongue stretching (2/6), Tremor (5/6) |
| Compound D37 | 2-3 | 12-18 | Tremor (4/6) |
| Compound D38 | 3-4 | 12-14 | Tremor (5/6) |
| Compound D40 | 2-3 | 10-15 | Tremor (5/6) |
| Compound D42 | 3-4 | 12-16 | Tremor (6/6) |
| Compound D43 | 2-3 | 11-14 | Tremor (4/6) |

TABLE E4

Pharmacological effects of the compounds on continuous infusion in rats

| Compound/drug | Onset time (min) | Recovery time after stopping infusion (min) | Types and incidence of adverse reactions |
|---|---|---|---|
| Etomidate | 4-5 | 25-30 | Tremor (6/6), Facial muscle twitching (4/6), Tongue stretching (5/6) |
| CPMM | 3-4 | 7-8 | Convulsions (3/6), Tremor (5/6), Myoclonus (5/6) |
| DMSO | / | / | Red urine (8/8) |
| Compound E2 | 3-4 | 11-13 | Tremor (2/6) |
| Compound E6 | 2-3 | 9-11 | Tremor (4/6) |
| Compound E8 | 3-4 | 12-14 | Tremor (1/6), Tongue stretching (4/6) |
| Compound E12 | 2-3 | 11-23 | Tremor (2/6) |
| Compound E31 | 3-4 | 8-11 | Tremor (3/6) |
| Compound E32 | 2-3 | 12-16 | Tremor (2/6), Tongue stretching (3/6) |
| Compound E33 | 2-3 | 11-14 | Tremor (1/6) |
| Compound E35 | 2-3 | 10-13 | Tongue stretching (2/6), Tremor (3/6) |
| Compound E37 | 2-3 | 7-10 | Tremor (2/6) |
| Compound E38 | 2-3 | 8-13 | Tremor (3/6) |
| Compound E64 | 2-3 | 11-14 | No |
| Compound E90 | 2-3 | 9-12 | Tremor (2/6) |
| Compound E100 | 2-3 | 9-14 | Tremor (3/6) |
| Compound E116 | 3-4 | 11-15 | Tremor (1/6), Tongue stretching (3/6) |
| Compound E129 | 3-4 | 8-13 | No |
| Compound E133 | 3-4 | 9-12 | Tremor (4/6) |
| Compound E148 | 3-4 | 11-16 | Myoclonus (2/6), Tremor (3/6) |

In summary, the present invention discloses a class of structurally novel etomidate derivatives which have better depressant effects on the central nervous system and produce sedative, hypnotic and/or anesthetic action as well as control of epilepsy persistence. Besides they provide a new choice for clinical screening and/or preparation of drugs with sedative, hypnotic and/or anesthetic effects and drugs for the control of epilepsy persistence.

The invention claimed is:

1. A compound of formula I, or stereoisomer thereof, or pharmaceutically acceptable salt thereof, or solvate thereof:

Formula I

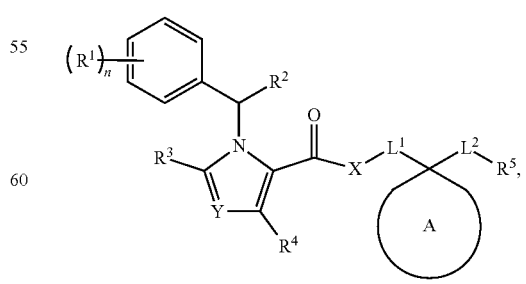

wherein, in Formula I:
X is O, S, or $NR^{30}$, in which $R^{30}$ is hydrogen, deuterium, or $C_{1-8}$ alkyl;

Y is N;

R$^1$ is independently selected from the group consisting of deuterium, halogen, —CN, —NO$_2$, —OR$^{32}$, —C(O)R$^{32}$, —CO$_2$R$^{32}$, —CON(R$^{32}$)$_2$, —N(R$^{32}$)$_2$, —OC(O)R$^{32}$, —SO$_2$R$^{32}$, substituted or unsubstituted 3-8-membered heterocyclic groups, substituted or unsubstituted C$_{1-8}$ alkyls, substituted or unsubstituted C$_{2-8}$ alkenyls, and substituted or unsubstituted C$_{2-8}$ alkynyls;

R$^{32}$ is independently of each other selected from the group consisting of hydrogen, deuterium, substituted or unsubstituted C$_{1-8}$ alkyls, substituted or unsubstituted C$_{2-8}$ alkenyls, substituted or unsubstituted C$_{2-8}$ alkynyls, substituted or unsubstituted C$_{3-8}$ cycloalkyls, substituted or unsubstituted 3-8-membered heterocyclic groups, substituted or unsubstituted aryls, and substituted or unsubstituted heteroaryls; said substituents are independently selected from deuterium, cyano, hydroxyl, carboxyl, halogen, C$_{3-8}$ cycloalkyls or their halogenated derivatives, 3-8-membered heterocyclic groups or their halogenated derivatives, aryls or their halogenated derivatives, and heteroaryls or their halogenated derivatives;

n is an integer of 0-5;

R$^2$ is selected from the group consisting of hydrogen, deuterium, halogen, C$_{1-8}$ alkyls or their halogenated derivatives, C$_{1-8}$ alkoxyl or their halogenated derivatives, C$_{2-8}$ alkenyls or their halogenated derivatives, C$_{2-8}$ alkynyls or their halogenated derivatives, and 3-8-membered heterocyclic groups or their halogenated derivatives;

R$^3$ and R$^4$ are independently of each other selected from the group consisting of hydrogen, deuterium, halogen, substituted or unsubstituted C$_{1-8}$ alkyls; said substituents are deuterium, halogen, C1-s alkyls or their halogenated derivatives, C$_{1-8}$ alkoxyls or their halogenated derivatives, C$_{3-8}$ cycloalkyls or their halogenated derivatives, 3-8-membered heterocyclic groups or their halogenated derivatives, aryls or their halogenated derivatives, and heteroaryls or their halogenated derivatives;

L$^1$ and L$^2$ are independently selected from the group consisting of none, substituted or unsubstituted C$_{1-8}$ alkylenyls; said substituents are independently selected from deuterium, cyano, hydroxyl, carboxyl, halogen, C$_{1-8}$ alkyls or their halogenated derivatives, C$_{1-8}$ alkoxyl or their halogenated derivatives, C$_{3-8}$ cycloalkyls or their halogenated derivatives, 3-8-membered heterocyclic groups or their halogenated derivatives, aryls or their halogenated derivatives, and heteroaryls or their halogenated derivatives;

R$^5$ is selected from the group consisting of hydrogen, deuterium, halogen, cyano, propadienyl, isocyano, isothiocyano,

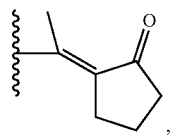

substituted or unsubstituted C$_{1-8}$ alkyls, substituted or unsubstituted C$_{2-8}$ alkenyls substituted or unsubstituted C$_{2-8}$ alkynyls, —OR$^{33}$, —SR$^{33}$, —OC(O)R$^{33}$, —C(O)R$^{33}$, —C(S)R$^{33}$, —S(O)R$^{33}$, —CON(R$^{33}$)$_2$, —SO$_2$R$^{33}$, C$_{3-8}$ membered cycloalkyls, 3-8-membered heterocyclic groups, aryls, heteroaryls, —N(R$^{33}$)$_2$; R$^{33}$ are independently selected from the group consisting of hydrogen, deuterium, methylsulfonyl, substituted or unsubstituted C$_{1-8}$ alkyls, substituted or unsubstituted C$_{2-8}$ alkenyls, substituted or unsubstituted C$_{2-8}$ alkynyls, -L$^{31}$-COO-L$^{32}$, substituted or unsubstituted C$_{3-8}$ membered cycloalkyls, substituted or unsubstituted 3-8-membered heterocyclic groups, substituted or unsubstituted aryls, substituted or unsubstituted heteroaryls, —S—C$_{1-8}$ alkyls; L$^{31}$ is selected from substituted or unsubstituted C$_{1-8}$ alkylenyls; L$^{32}$ is selected from substituted or unsubstituted C$_{1-8}$ alkyls;

For above R$^5$ and R$^{33}$, said substituents are deuterium, cyano, hydroxyl, carboxyl, halogen, C$_{1-4}$ alkyls or their halogenated derivatives, C$_{1-4}$ alkoxyl or their halogenated derivatives, C$_{3-8}$ membered cycloalkyls or their halogenated derivatives, 3-8-membered heterocyclic groups or their halogenated derivatives, aryls or their halogenated derivatives, heteroaryls or their halogenated derivatives, —S—C$_{1-4}$ alkyls, =R$^{39}$, and substituted or unsubstituted C$_{2-8}$ alkenyls or C$_{2-8}$ alkynyls; in which R$^{39}$ is O, S, NR$^{40}$, or C(R$^{40}$)$_2$, R$^{40}$ is selected from hydrogen, deuterium, halogen, and C$_{1-4}$ alkyls or their halogenated derivatives, substituents in said C$_{2-8}$ alkenyls or C$_{2-8}$ alkynyls are selected from deuterium, cyano, hydroxyl, carboxyl, halogen, and C$_{1-4}$ alkyls;

Ring A is selected from 4-6-membered saturated carbocycles, 4-6-membered unsaturated carbocycles, 4-6-membered saturated heterocycles or 4-6-membered unsaturated heterocycles, all of which are substituted by 0-4 R$^{34}$;

R$^{34}$ is independently selected from the group consisting of deuterium, halogen, cyano, isocyano, isothiocyano, nitro, C$_{1-8}$ alkyls or their halogenated derivatives, C$_{2-8}$ alkenyls or their halogenated derivatives, C$_{2-8}$ alkynyls or their halogenated derivatives, —OC(O) R$^{35}$, —C(O)R$^{35}$, —S(O)R$^{35}$, —C(O)N(R$^{35}$)$_2$, -L$^{33}$-R$^{36}$, and =R$^{37}$;

L$^{33}$ is selected from C$_{1-4}$ alkylenyls;

R$^{36}$ is selected from cyano, nitro, —OC(O) R$^{35}$, —C(O)R$^{35}$, —S(O)R$^{35}$, and —C(O)N(R$^{35}$)$_2$;

R$^{35}$ is independently selected from C$_{1-4}$ alkyls or their halogenated derivatives;

R$^{37}$ is selected from O, S, N(R$^{38}$), and C(R$^{38}$)$_2$; R$^{38}$ is H or C$_{1-4}$ alkyl;

Wherein, when R$^5$ is H and L$^2$ is none, then ring A is not 4-6-membered saturated heterocycles;

When ring A is a 4-6-membered saturated heterocycle not substituted by R$^{34}$, if L$^2$ is none, then R$^5$ is not H; if R$^5$ is H, then L$^2$ is not none.

2. The compound according to claim 1, or stereoisomer thereof, or pharmaceutically acceptable salt thereof, or solvate thereof, wherein:

Y is N;

R$^3$ and R$^4$ are independently selected from the group consisting of hydrogen, deuterium, halogen, and substituted or unsubstituted C$_{1-8}$ alkyls; said substituents are selected from deuterium, halogen, C$_{1-8}$ alkyls or their halogenated derivatives, C$_{1-8}$ alkoxyls or their halogenated derivatives, C$_{3-8}$ cycloalkyls or their halogenated derivatives, 3-8-membered heterocyclic groups or their halogenated derivatives, aryls or their halogenated derivatives, and heteroaryls or their halogenated derivatives;

Or, X is or S;

Or, R$^1$ is independently selected from the group consisting of deuterium, halogen, —CN, —NO$_2$, —OR$^{32}$, —C(O)R$^{32}$, —CO$_2$R$^{32}$, —CON(R$^{32}$)$_2$, —N(R$^{32}$)$_2$, —OC(O)R$^{32}$, C$_{1-3}$ alkyls, C$_{2-3}$ alkenyls, and C$_{2-3}$ alkynyls;

Wherein, $R^{32}$ is independently selected from the group consisting of hydrogen, deuterium, $C_{1-3}$ alkyls, $C_{2-3}$ alkenyls, and $C_{2-3}$ alkynyls;

Or, n is an integer of 0-2;

Or, $R^2$ is selected from hydrogen, deuterium, halogen, and $C_{1-3}$ alkyls or their halogenated derivatives.

3. The compound according to claim 1, or stereoisomer thereof, or pharmaceutically acceptable salt thereof, or solvate thereof, wherein: said compound has a structural formula of formula I:

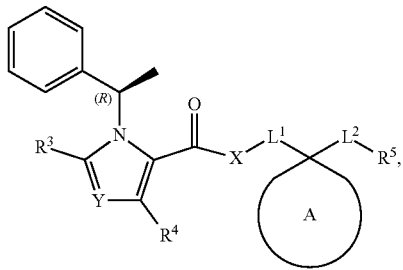

Formula II wherein, in Formula I:
Y is N;
X is O or S;
$R^5$ is selected from hydrogen, deuterium, halogen, cyano, propadienyl, isocyano, isothiocyano,

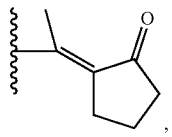

, substituted or unsubstituted $C_{1-8}$ alkyls, substituted or unsubstituted $C_{2-8}$ alkenyls, substituted or unsubstituted $C_{2-8}$ alkynyls, —OR$^{33}$, —SR$^{33}$, —OC(O)R$^{33}$, —C(O)R$^{33}$, —C(S)R$^{33}$, —S(O)R$^{33}$, —CON(R$^{33}$)$_2$, —SO$_2$R$^{33}$, $C_{3-8}$-membered cycloalkyls, 3-8-membered heterocyclic groups, aryls, heteroaryls, —N(R$^{33}$)$_2$; in which, $R^{33}$ are independently of each other selected from the group consisting of hydrogen, deuterium, methylsulfonyl, substituted or unsubstituted $C_{1-8}$ alkyls, substituted or unsubstituted $C_{2-8}$ alkenyls substituted or unsubstituted $C_{2-8}$ alkynyls, substituted or unsubstituted $C_{3-8}$-membered cycloalkyls, substituted or unsubstituted 3-8-membered heterocyclic groups, substituted or unsubstituted aryls, and substituted or unsubstituted heteroaryls;

in $R^5$ and $R^{33}$, said substituents are selected from deuterium, cyano, hydroxyl, carboxyl, halogen, $C_{1-4}$ alkyls or their halogenated derivatives, $C_{1-4}$ alkoxyl or their halogenated derivatives, C3-s-membered cycloalkyls or their halogenated derivatives, 3-8-membered heterocyclic groups or their halogenated derivatives, aryls or their halogenated derivatives, heteroaryls or their halogenated derivatives, —S—$C_{1-4}$ alkyls, =R$^{39}$, and substituted or unsubstituted $C_{2-6}$ alkenyls or $C_{2-6}$ alkynyls; in which, $R^{39}$ is O, S, NR$^{40}$, or C(R$^{40}$)$_2$, $R^{40}$ is selected from hydrogen, deuterium, halogen, and $C_{1-4}$ alkyls or their halogenated derivatives; in $C_{2-6}$ alkenyls or $C_{2-6}$ alkynyls, said substituents are selected from deuterium, cyano, hydroxyl, carboxyl, halogen, and $C_{1-4}$ alkyls;

Ring A is selected from 4-6-membered saturated carbocycles, 4-6-membered unsaturated carbocycles, 4-6-membered saturated heterocycles, and 4-6-membered unsaturated heterocycles, all of which are substituted by 0-4 $R^{34}$;

Wherein, $R^{34}$ is independently selected from the group consisting of deuterium, halogen, cyano, isocyano, isothiocyano, nitro, $C_{1-8}$ alkyls or their halogenated derivatives, $C_{2-8}$ alkenyls or their halogenated derivatives, $C_{2-8}$ alkynyls or their halogenated derivatives, —OC(O) R$^{35}$, —C(O)R$^{35}$, —S(O)R$^{35}$, —C(O)N (R$^{35}$)$_2$, -L$^{33}$-R$^{36}$, and =R$^{37}$;

$L^{33}$ is selected from $C_{1-4}$ alkylenyls;

$R^{36}$ is selected from cyano, nitro, —OC(O) R$^{35}$, —C(O) R$^{35}$, —S(O)R$^{35}$, and —C(O)N(R$^{35}$)$_2$;

$R^{35}$ is independently selected from $C_{1-4}$ alkyls or their halogenated derivatives;

$R^{37}$ is O, S, or N(R$^{38}$); $R^{38}$ is H or a $C_{1-4}$ alkyl.

4. The compound according to claim 1, or stereoisomer thereof, or pharmaceutically acceptable salt thereof, or solvate thereof wherein:
Y is N;
X is O or S;
$R^3$ and $R^4$ are independently selected from the group consisting of hydrogen, deuterium, halogen, and substituted or unsubstituted $C_{1-4}$ alkyls; said substituents are selected from deuterium, halogen, $C_{1-4}$ alkyls or their halogenated derivatives, $C_{1-4}$ alkoxyls or their halogenated derivatives, $C_{3-6}$ cycloalkyls or their halogenated derivatives, and 3-6-membered heterocyclic groups or their halogenated derivatives;

Or, $R^5$ is selected from hydrogen, deuterium, halogen, propadienyl, cyano, isocyano, isothiocyano,

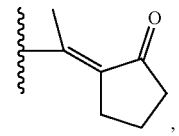 [SMILES: */C(C)=C1\CCCC1=O]

, substituted or unsubstituted $C_{1-8}$ alkyls, substituted or unsubstituted $C_{2-8}$ alkenyls, substituted or unsubstituted $C_{2-8}$ alkynyls, —OR$^{33}$, —SR$^{33}$, —OC(O)R$^{33}$, —C(O)R$^{33}$, —C(S)R$^{33}$, —S(O)R$^{33}$, —CON(R$^{33}$)$_2$, —SO$_2$R$^{33}$, $C_{3-8}$-membered cycloalkyls, 3-8-membered heterocyclic groups, aryls, heteroaryls, —N(R$^{33}$)$_2$; $R^{33}$ are independently selected from the group consisting of hydrogen, deuterium, methylsulfonyl, substituted or unsubstituted $C_{1-4}$ alkyls, substituted or unsubstituted $C_{2-4}$ alkenyls, substituted or unsubstituted $C_{2-4}$ alkynyls, $C_{3-8}$-membered cycloalkyls, 3-8-membered heterocyclic groups, aryls, and heteroaryls;

in $R^5$ and $R^{33}$, substituents are selected from deuterium, cyano, hydroxyl, carboxyl, halogen, $C_{1-4}$ alkyls or their halogenated derivatives, $C_{1-4}$ alkoxyls or their halogenated derivatives, $C_{3-8}$-membered cycloalkyls, 3-8-membered heterocyclic groups, aryls, heteroaryls, —S—$C_{1-4}$ alkyls, =R$^{39}$, substituted or unsubstituted $C_{2-4}$ alkenyls, and substituted or unsubstituted $C_{2-4}$ alkynyls; in which, $R^{39}$ is selected from O, S, NR$^{40}$, or C(R$^{40}$)$_2$, $R^{40}$ is selected from hydrogen, deuterium, halogen, and $C_{1-4}$ alkyls or their halogenated derivatives; substituents in said $C_{2-4}$ alkenyls or $C_{2-4}$ alkynyls are selected from deuterium, cyano, hydroxyl, carboxyl, halogen, and $C_{1-4}$ alkyls;

Or, L¹ and L² are independently of selected from none, substituted or unsubstituted $C_{1-4}$ alkylenyls; said substituents are selected from deuterium, cyano, hydroxyl, carboxyl, halogen, $C_{1-4}$ alkyls or their halogenated derivatives, $C_{1-4}$ alkoxyl or their halogenated derivatives, $C_{3-5}$ cycloalkyls or their halogenated derivatives, 3-5-membered heterocyclic groups or their halogenated derivatives, aryls or their halogenated derivatives, and heteroaryls or their halogenated derivatives;

Or ring A is selected from 4-6-membered saturated carbocycles, 4-6-membered unsaturated carbocycles, 4-6-membered saturated heterocycles, and 4-6-membered unsaturated heterocycles, all of which are substituted by 0-4 $R^{34}$; $R^{34}$ is independently selected from deuterium, halogen, cyano, isocyano, isothiocyano, $C_{1-4}$ alkyls or their halogenated derivatives, $C_{2-4}$ alkenyls or their halogenated derivatives, $C_{2-4}$ alkynyls or their halogenated derivatives, and $=R^{37}$; and $R^{37}$ is O or S.

5. The compound according to claim 1, or stereoisomer thereof, or pharmaceutically acceptable salt thereof, or solvate thereof, wherein:

Y is N;

X is O or S;

$R^3$ and $R^4$ are independently from the group consisting of hydrogen, deuterium, halogen, and substituted or unsubstituted $C_{1-2}$ alkyls; said substituents are selected from deuterium, halogen, $C_{1-2}$ alkyls or their halogenated derivatives, and $C_{1-2}$ alkoxyl or their halogenated derivatives;

Or, $R^5$ is selected from hydrogen, deuterium, halogen, propadienyl, cyano, isocyano, isothiocyano,

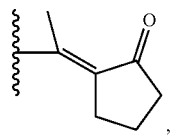

, substituted or unsubstituted $C_{1-8}$ alkyls, substituted or unsubstituted $C_{2-8}$ alkenyls, substituted or unsubstituted $C_{2-8}$ alkynyls, —$OR^{33}$, —$SR^{33}$, —$OC(O)R^{33}$, —$C(O)R^{33}$, —$C(S)R^{33}$, —$S(O)R^{33}$, —$CON(R^{33})_2$, —$SO_2R^{33}$, $C_{3-8}$-membered cycloalkyls, 3-8-membered heterocyclic groups, aryls, heteroaryls, —$N(R^{33})_2$; $R^{33}$ are independently selected from the group consisting of hydrogen, deuterium, methylsulfonyl, substituted or unsubstituted $C_{1-2}$ alkyls, $C_{3-6}$-membered cycloalkyls, 3-6-membered heterocyclic groups, aryls, and heteroaryls;

substituents in $R^5$ and $R^{33}$ are selected from deuterium, halogen, cyano, hydroxyl, $C_{1-3}$ alkyls or their halogenated derivatives, $C_{1-3}$ alkoxyl or their halogenated derivatives, $C_{3-6}$-membered cycloalkyls, 3-6-membered heterocyclic groups, aryls, heteroaryls, —S—$C_{1-2}$ alkyls, $=R^{39}$, substituted or unsubstituted $C_{2-4}$ alkenyls, and substituted or unsubstituted $C_{2-4}$ alkenyls $C_{2-4}$ alkynyls; in which, $R^{39}$ is selected from O, S, $NR^{40}$, and $C(R^{40})_2$, $R^{40}$ is selected from hydrogen, deuterium, halogen, and $C_{1-3}$ alkyls or their halogenated derivatives; substituents in said $C_{2-4}$ alkenyls or $C_{2-4}$ alkynyls are selected from deuterium, cyano, hydroxyl, carboxyl, halogen, and $C_{1-3}$ alkyls;

Or, L¹ and L² are independently selected from none, and substituted or unsubstituted $C_{1-3}$ alkylenyls; said substituents are selected from deuterium, halogen, $C_{1-3}$ alkyls or their halogenated derivatives, and $C_{1-3}$ alkoxyl or their halogenated derivatives;

Or ring A is selected from 4-6-membered saturated carbocycles, 4-6-membered unsaturated heterocycles, and 4-6-membered saturated heterocycles, all of which are substituted by 0-3 $R^{34}$;

Wherein, $R^{34}$ is independently selected from deuterium, halogen, cyano, isocyano, isothiocyano, $C_{1-3}$ alkyls, $C_{2-3}$ alkenyls, $C_{2-3}$ alkynyls, and $=R^{37}$;

$R^{37}$ is O or S.

6. The compound according to claim 1, or stereoisomer thereof, or pharmaceutically acceptable salt thereof, or solvate thereof, wherein:

Y is N;

X is O or S;

$R^3$ and $R^4$ are independently selected from the group consisting of hydrogen, deuterium, halogen, and halogenated or un-halogenated methyl;

Or, $R^5$ is selected from hydrogen, deuterium, halogen, propadienyl, cyano, isocyano, isothiocyano,

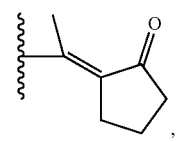 [SMILES: */C(C)=C1\CCCC1=O]

, substituted or unsubstituted $C_{1-8}$ alkyls, substituted or unsubstituted $C_{2-6}$ alkenyls, substituted or unsubstituted $C_{2-6}$ alkynyls, —$OR^{33}$, —$SR^{33}$, —$OC(O)R^{33}$, —$C(O)R^{33}$, —$C(S)R^{33}$, —$S(O)R^{33}$, —$CON(R^{33})_2$, —$SO_2R^{33}$, $C_{3-8}$-membered cycloalkyls, 3-8-membered heterocyclic groups, aryls, heteroaryls, —$N(R^{33})_2$;

Wherein, $R^{33}$ is selected from hydrogen, deuterium, methylsulfonyl, acetyl, and $C_{1-2}$ alkyls;

Said substituents in above-mentioned $R^5$ and $R^{33}$ are deuterium, halogen, hydroxyl, cyano, $C_{1-2}$ alkyls, 3-5-membered heterocyclic groups, —S—$CH_3$, $=R^{39}$, substituted or unsubstituted $C_{2-4}$ alkenyls, and substituted or unsubstituted $C_{2-4}$ alkynyls; wherein, $R^{39}$ is selected from O, S, $NR^{40}$ or $C(R^{40})$, $R^{40}$ is selected from hydrogen, deuterium, halogen, $C_{1-3}$ alkyls;

substituents in said $C_{2-4}$ alkenyls or $C_{2-4}$ alkynyls are selected from deuterium, cyano, hydroxyl, carboxyl, halogen, and $C_{1-2}$ alkyls;

Or, L¹ and L² are independently of each other selected from none, substituted or unsubstituted $C_{1-2}$ alkylenyls; said substituents are selected from deuterium, halogen, and $C_{1-2}$ alkyls;

Or ring A is selected from 4-6-membered saturated carbocycles, 4-6-membered unsaturated heterocycles, and 4-6-membered saturated heterocycles, all of which are substituted by 0-2 $R^{34}$;

Wherein, $R^{34}$ is independently of each other selected from deuterium, halogen, cyano, isocyano, isothiocyano, $C_{2-3}$ alkenyls, $C_{2-3}$ alkynyls, $C_{1-2}$ alkyls, and $=R^{37}$; and $R^{37}$ is O or S.

7. The compound according to claim 1, or stereoisomer thereof, or pharmaceutically acceptable salt thereof, or solvate thereof, wherein: said compound has a structural formula of formula IIAA:

Formula IIAA

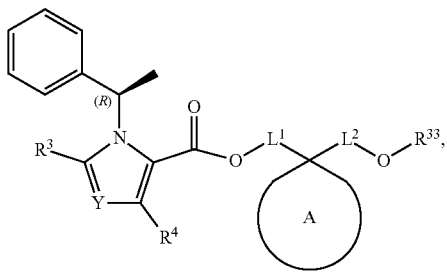

wherein, in Formula IIAA:
Y is N;
$R^3$ and $R^4$ are independently hydrogen or deuterium;
$L^1$ and $L^2$ are independently none or methylene;
$R^{33}$ is selected from hydrogen, deuterium, $C_{1-2}$ alkyls, $-L^{33}$-COO-$L^{32}$, and 6-membered heterocyclic groups;
$L^{31}$ is methylene; $L^{32}$ is methyl;
Ring A is a 4-membered saturated carbocycle;
Or,
Said compound has a structural formula of formula IIAB:

Formula IIAB

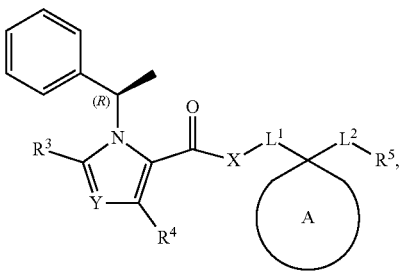

wherein, wherein, in Formula IIAB:
Y is N;
X is O or S;
$R^3$ and $R^4$ are independently hydrogen or deuterium;
$L^1$ and $L^2$ are independently selected from none, substituted or unsubstituted $C_{1-2}$ alkylenyls; said substituents are independently selected from deuterium, F, and methyl;
$R^5$ is selected from hydrogen, deuterium, halogen, substituted or unsubstituted methyl, —OC(O)$R^{33}$, and 3-membered heterocyclic groups;
Wherein, $R^{33}$ is methyl; said substituents are selected from deuterium, F, $C_{1-2}$ alkyls, and 3-membered heterocyclic groups;
Ring A is selected from 4-6-membered saturated carbocycles substituted by 0-2 $R^{34}$; wherein,
$R^{34}$ is independently selected from deuterium F, and =$R^{37}$; and $R^{37}$ is O;
Or,
Said compound has a structural formula of formula IIAC:

Formula IIAC

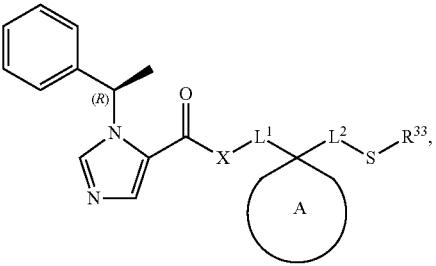

Wherein, in Formula IIAC:
X is O or S;
$L^1$ and $L^2$ are independently none or methylene;
$R^{33}$ is selected from $C_{1-2}$ alkyls and —S—$CH_3$;
Ring A is selected from 4-membered saturated carbocycles;
Or,
Said compound has a structural formula of formula IIAD:

Formula IIAD

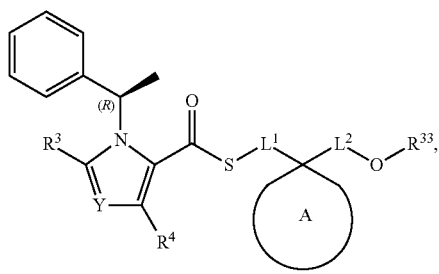

Wherein, in Formula IIAD:
Y is N;
$R^3$ and $R^4$ are independently of hydrogen or deuterium;
$L^1$ and $L^2$ are independently none or methylene;
$R^{33}$ is selected from hydrogen, deuterium, $C_{1-2}$ alkyls, -$L^{31}$-COO-$L^{32}$, and 6-membered heterocyclic groups;
$L^{31}$ is methylene; $L^{32}$ is methyl;
Ring A is selected from 4-membered saturated carbocycles;
Or,
Said compound has a structural formula of formula IIBA:

Formula IIBA

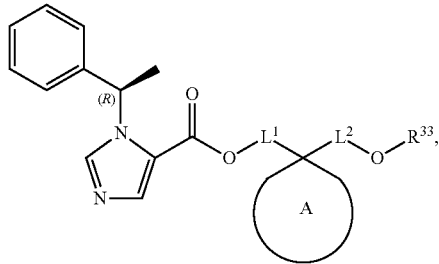

wherein, in Formula IIBA:
$L^1$ and 1: are independently none, substituted or unsubstituted methylene; said substituents are deuterium or methyl;
$R^{33}$ is selected from hydrogen, deuterium, methylsulfonyl, acetyl, and methyl;
Ring A is selected from 4-membered saturated heterocycles;

Or,
Said compound has a structural formula of formula IIBB:

Formula IIBB

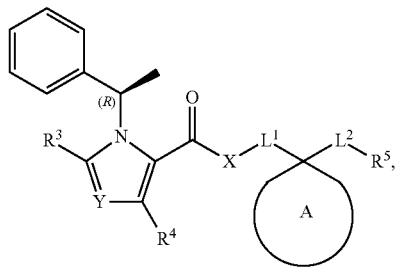

wherein, in Formula IIBB:
Y is N;
X is O or S;
R³ and R⁴ are independently hydrogen or deuterium;
L¹ and L² are independently selected from none, substituted or unsubstituted $C_{1-2}$ alkylenyls; said substituents are selected from deuterium, F, Cl, $C_{1-2}$ alkyls;
R⁵ is selected from hydrogen, deuterium, F, Cl, substituted or unsubstituted $C_{1-2}$ alkyls, and 3-membered heterocyclic groups;
said substituents are selected from deuterium, F, Cl, $C_{1-2}$ alkyls, 3-membered heterocyclic groups, and —S—CH₃;
Ring A is selected from 4-membered saturated heterocycles substituted by 0-2 $R^{34}$; Wherein, $R^{34}$ is independently deuterium or methyl;
Or,
Said compound has a structural formula of formula IIBC:

Formula IIBC

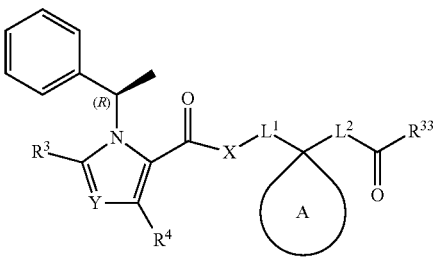

wherein, in Formula IIBC:
L¹ is none or methylene;
Ring A is selected from 4-5-membered saturated heterocycles and 5-membered unsaturated heterocycles, all of which are substituted by one $R^{34}$; wherein, $R^{34}$ is O;
Or,
Said compound has a structural formula of formula IICA:

Formula IICA

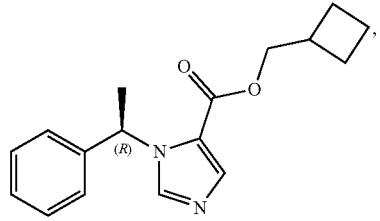

wherein, in Formula IICA: X is O or S;
Y is N;
R³ and R⁴ are independently hydrogen, deuterium,
L¹ and L² are independently selected from none, substituted or unsubstituted $C_{1-2}$ alkylenyls; said substituent is deuterium or methyl;

$R^{33}$ is selected from hydrogen, deuterium, and $C_{1-2}$ alkyls; and
Ring A is selected from 4-6-membered saturated carbocycles and 4-membered saturated heterocycles.

8. The compound according to claim 1, or stereoisomer thereof, or pharmaceutically acceptable salt thereof, or solvate thereof, wherein said compound is one of the following compounds:

Compound A8

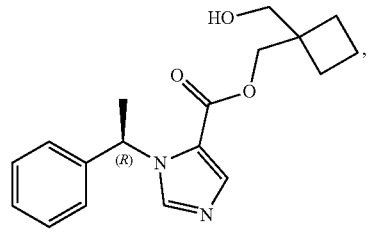

Compound A10

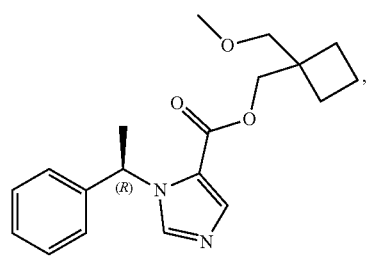

Compound A11

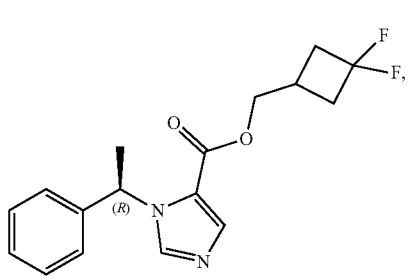

Compound A12

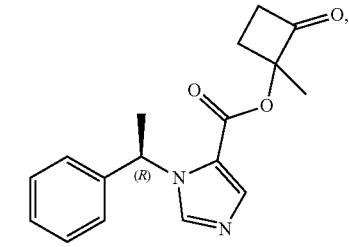

Compound A13

Compound A14
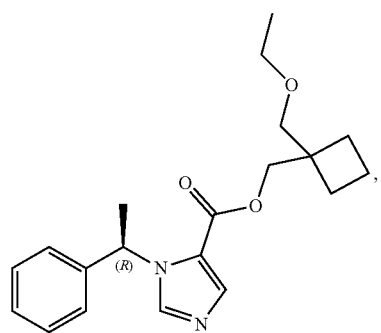
Compound A17
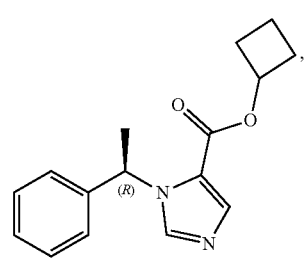
Compound A18
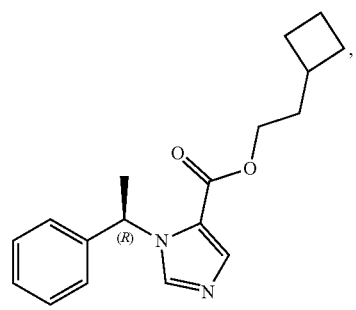
Compound A19
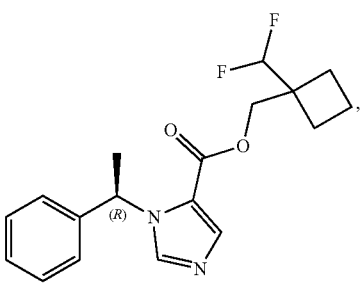
Compound A20
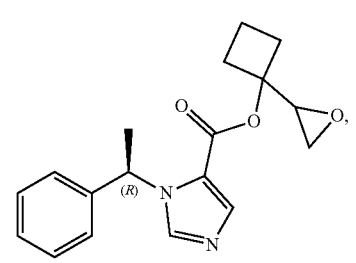
Compound A21
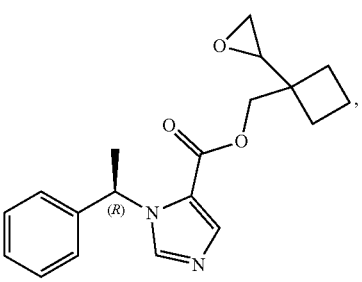
Compound A22
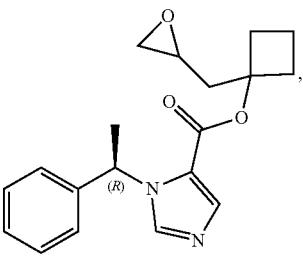
Compound A23
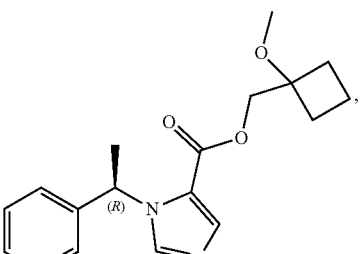
Compound A24
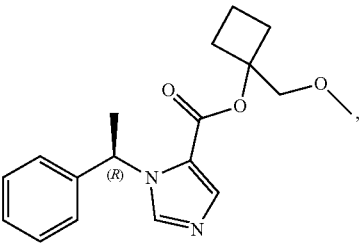
Compound A25
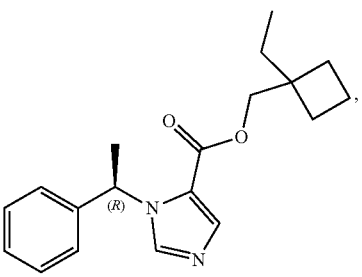
Compound A26
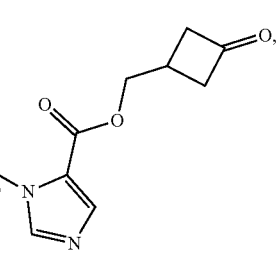

-continued
Compound A27
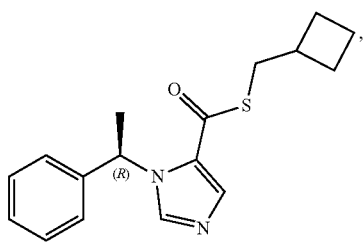
Compound A28
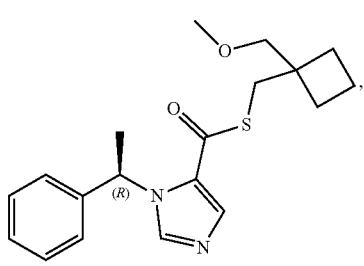
Compound A29
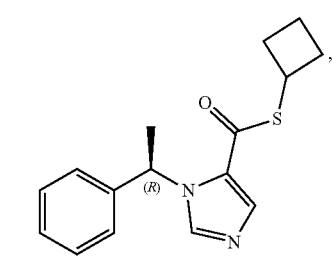
Compound A31
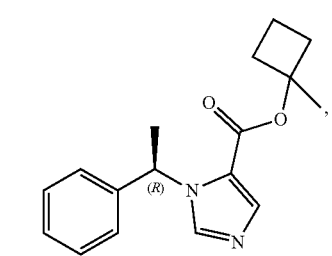
Compound A32
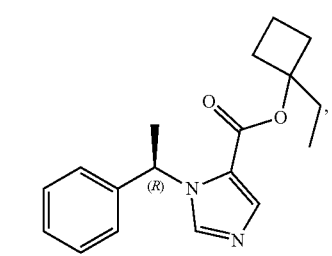
Compound A33
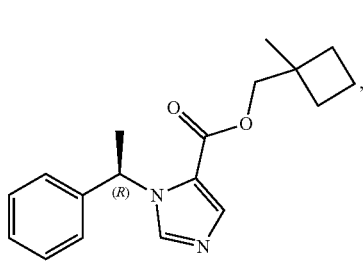
-continued
Compound A34
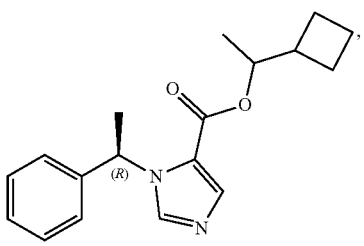
Compound A35
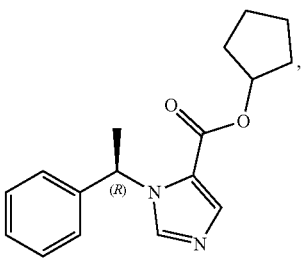
Compound A36
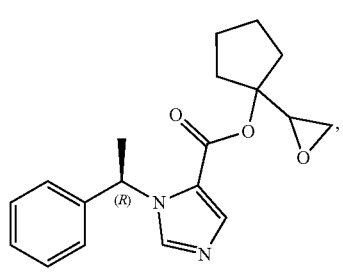
Compound A37
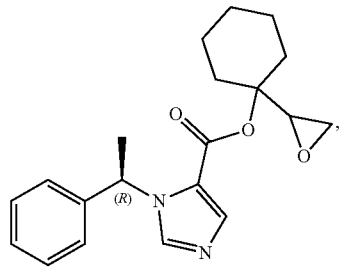
Compound A38
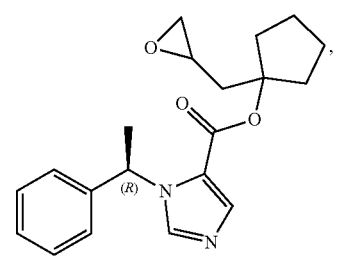
Compound A39
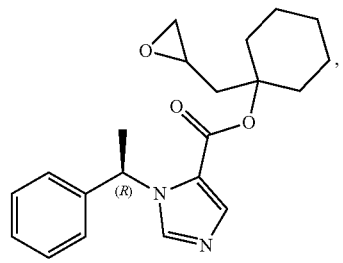

Compound A40
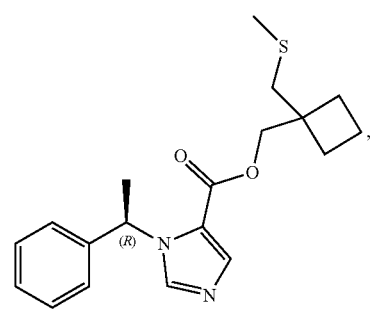
Compound A41
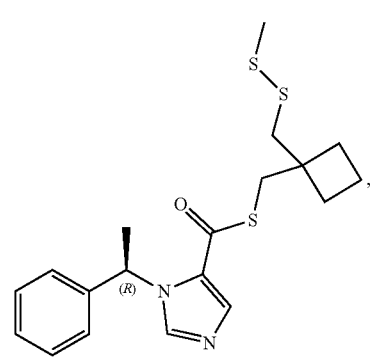
Compound A42
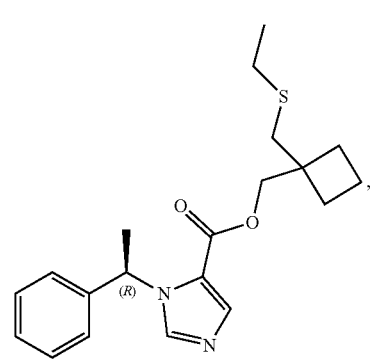
Compound A45
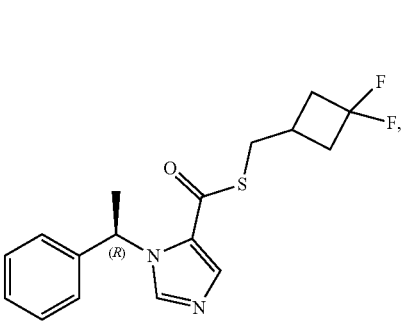
Compound A46
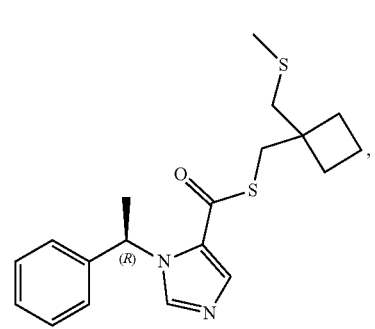
Compound B1
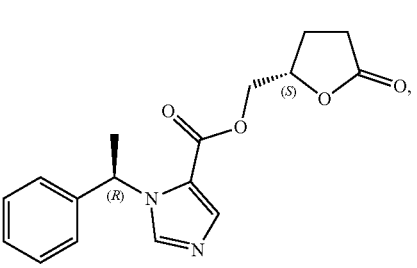
Compound B2
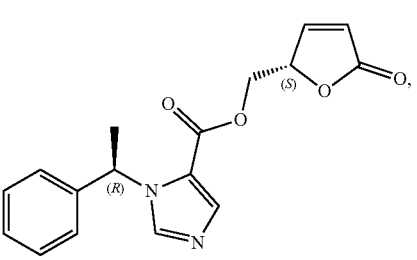
Compound B3
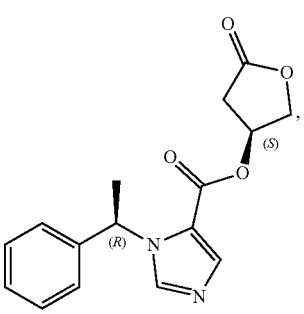
Compound B4
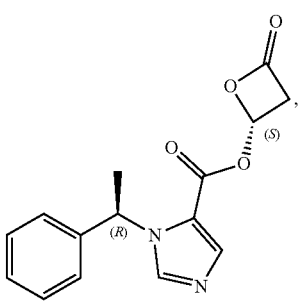
Compound B8
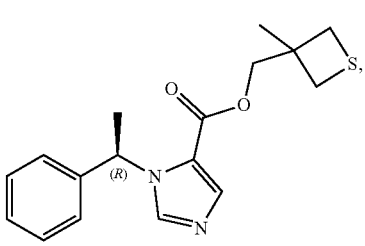
Compound B21
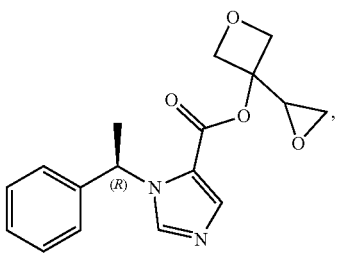

315
-continued
Compound B22
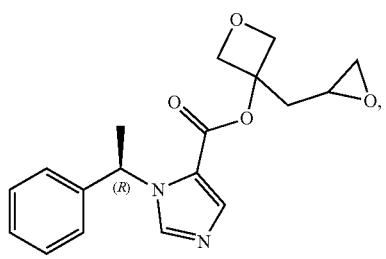
Compound B23
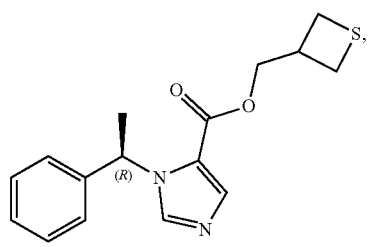
Compound B24
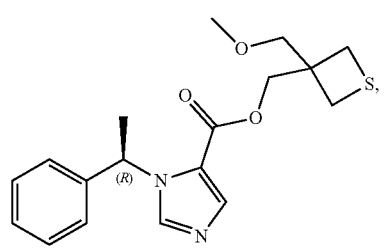
Compound B29
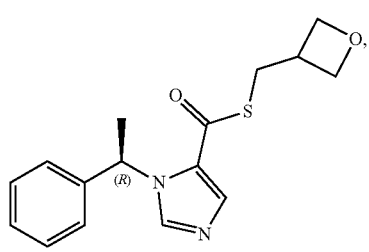
Compound B30
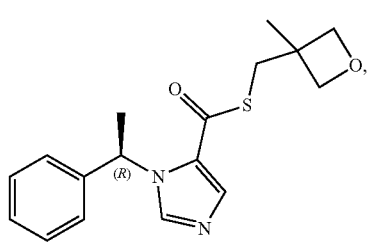
Compound B31
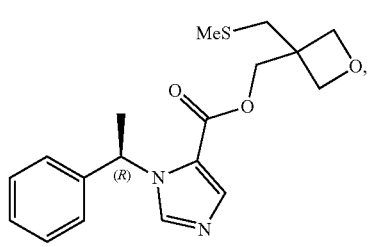
316
-continued
Compound C2
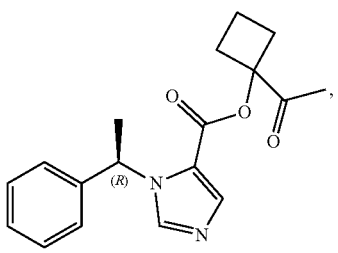
Compound C3
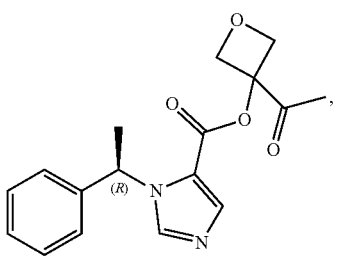
Compound C5
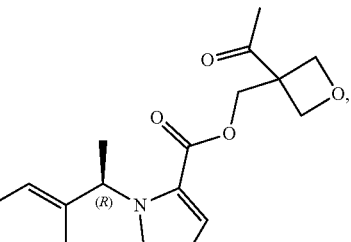
Compound C11
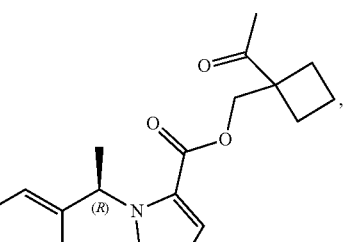
Compound C12
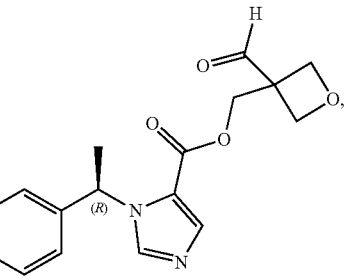

-continued

Compound C17

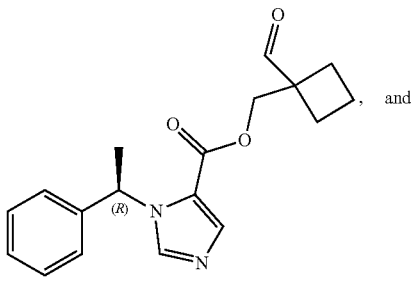

, and

Compound C28

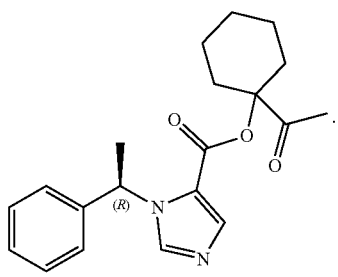

.

9. A pharmaceutical composition comprising the compound according to claim 1, or stereoisomer thereof, or pharmaceutically acceptable salt thereof, or solvate thereof, or their combinations as active ingredients and pharmaceutically acceptable excipients.

10. A compound, or stereoisomer thereof, or pharmaceutically acceptable salt thereof, or solvate thereof, wherein said compound has a structural formula of Formula IICB:

Formula IICB

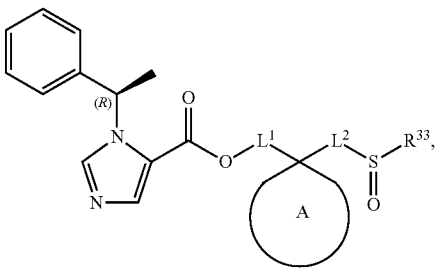

wherein, in Formula IICB:
$L^1$ and $L^2$ are independently selected from none and $C_{1-2}$ alkylenyls;
$R^{33}$ is methyl;
Ring A is none;
Or,
Said compound has a structural formula of Formula IICC:

Formulla IICC

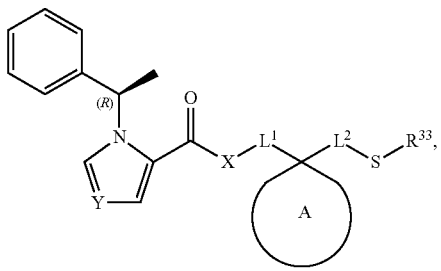

wherein, in Formula IICC:
X is O or S;
Y is N;
$L^1$ and $L^2$ are independently selected from none and $C_{1-2}$ alkylenyls;
$R^{33}$ is methyl; and
Ring A is none;
Or,
Said compound has a structure of Formula IIDA:

Formula IIDA

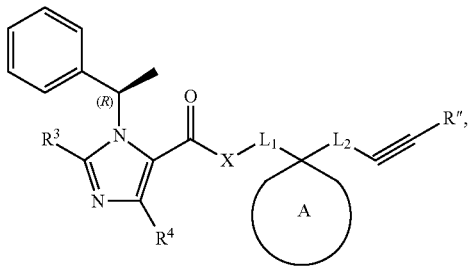

wherein, in Formula IIDA:
Y is selected from N;
$L^1$ and $L^2$ are independently selected from none, substituted $C_{1-2}$ alkylenyls, and unsubstituted $C_{1-2}$ alkylenyls; said substituted substituents are deuterium $C_{1-2}$ alkyls;
R, R' are independently of each other selected from the group consisting of hydrogen, deuterium, $C_{1-2}$ alkyls, $C_{1-2}$ alkoxyl, substituted or unsubstituted $C_{2-4}$ alkenyls or $C_{2-4}$ alkynyls, and said substituents are selected from hydroxyl, $C_{1-2}$ alkyls;
Ring A is none, or ring A is selected from 3-6-membered saturated carbocycles or 4-membered saturated heterocycles;
Or,
Said compound has a structural formula of Formula IIDB:

Formula IIDB wherein, in Formula IIDB:
X is O or S;
$R^3$ and $R^4$ are independently hydrogen or deuterium;
$L^1$ and $L^2$ are independently selected from none, substituted methylene, and unsubstituted methylene; said substituent is deuterium or a $C_{1-2}$ alkyl;
R" is selected from hydrogen, deuterium, $C_{1-2}$ alkyls, $C_{1-2}$ alkoxyl, substituted or unsubstituted $C_{2-4}$ alkenyls, and substituted or unsubstituted $C_{2-4}$ alkynyls, and said substituent is selected from hydroxyl and $C_{1-2}$ alkyls;
Ring A is none, or ring A is selected from 3-6-membered saturated carbocycles and 4-6-membered saturated heterocycles;

Or,
Said compound has a structural formula of of Formula IIDC:

Formula IIDC

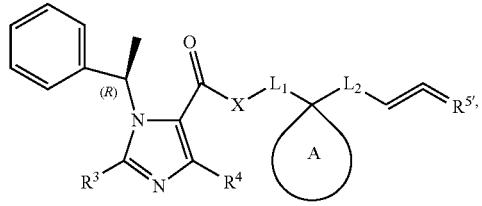

wherein, in Formula IIDC:
X is O or S;
$R^3$ and $R^4$ are independently hydrogen or deuterium;
$L^1$ and $L^2$ are independently selected from none, substituted or unsubstituted methylene;
said substituent is deuterium or a $C_{1-2}$ alkyl;
$R^{5'}$ is S or $CH_2$;
Ring A is none, or ring A is selected from 3-6-membered saturated carbocycles and 4-6-membered saturated heterocycles;
Or,
Said compound has a structural formula of Formula IIEA:

Formula IIEA

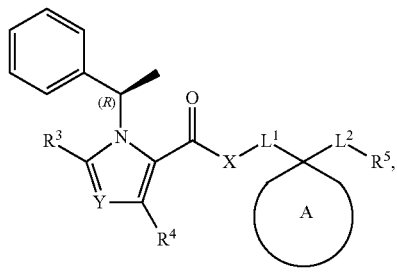

wherein, in Formula IIEA:
Y is N;
X is O or S;
Ring A is selected from 3-6-membered saturated carbocycles substituted by 0-2 $R^{34}$, wherein $R^{34}$ is independently selected from deuterium, halogen, cyano, and isothiocyano;
$R^3$ and $R^4$ are independently selected from the group consisting of hydrogen, deuterium, halogen, halogenated or un-halogenated methyl, with the proviso that both of $R^3$ and $R^4$ are not simultaneously hydrogen or deuterium;
$L^1$ and $L^2$ are independently selected from none, substituted methylene, and unsubstituted methylene, and substituents are selected from deuterium and $C_{1-4}$ alkyls;
$R^5$ is selected from hydrogen, deuterium, cyano, isocyano, isothiocyano,

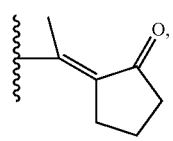

$C_{1-2}$ alkyls, substituted or unsubstituted $C_{2-4}$ alkenyls, substituted or unsubstituted $C_{2-4}$ alkynyls, $-OR^{33}$, and $-C(O)R^{33}$;
Wherein, $R^{33}$ is independently selected from $C_{1-2}$ alkyls; said substituent in $R^5$ is selected from $=R^{39}$, $C_{2-4}$ alkenyls, and $C_{2-4}$ alkynyls, and $R^{39}$ is S or $CH_2$;
Or,
in Formula IIEA:
Y is N;
X is O or S;
Ring A is selected from 3-6-membered saturated heterocycles substituted by 0-2 $R^{34}$, and $R^{34}$ is independently selected from deuterium, halogen, cyano, and isothiocyano;
$R^3$ and $R^4$ are independently selected from the group consisting of hydrogen, deuterium, halogen, halogenated or un-halogenated methyl, with the proviso that both of $R^3$ and $R^4$ are not simultaneously hydrogen or deuterium;
$L^1$ and $L^2$ are independently of each other selected from none, substituted or unsubstituted methylene, and said substituents are selected from deuterium and $C_{1-4}$ alkyls;
$R^5$ is selected from hydrogen, deuterium, cyano, isocyano, isothiocyano,

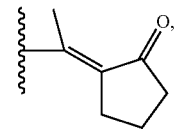 [SMILES: */C(C)=C1\CCCC1=O]

$C_{1-2}$ alkyls, substituted or unsubstituted $C_{2-4}$ alkenyls, substituted or unsubstituted $C_{2-4}$ alkynyls, $-OR^{33}$, and $-C(O)R^{33}$;
Wherein, $R^{33}$ is selected from $C_{1-2}$ alkyls; the substituent in $R^5$ is selected from $=R^{39}$, $C_{2-4}$ alkenyls, or $C_{2-4}$ alkynyls, and $R^{39}$ is S or $CH_2$;
Or,
in the Formula IIEA:
Y is N;
X is O or S;
Ring A is none;
$R^3$ and $R^4$ are independently selected from the group consisting of hydrogen, deuterium, halogen, and halogenated or un-halogenated methyl, with the proviso that both of $R^3$ and $R^4$ are not simultaneously hydrogen or deuterium;
$L^1$ and $L^2$ are independently selected from none and substituted or unsubstituted methylene;
said substituents are selected from deuterium and $C_{1-4}$ alkyls;
$R^5$ is selected from hydrogen, deuterium, cyano, isocyano, isothiocyano,

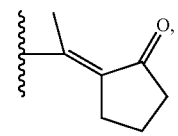 [SMILES: */C(C)=C1\CCCC1=O]

$C_{1-2}$ alkyls, substituted or unsubstituted $C_{2-4}$ alkenyls, substituted or unsubstituted $C_{2-4}$ alkynyls, $-OR^{33}$, and $-C(O)R^{33}$;
wherein R is independently selected from $C_{1-2}$ alkyls and said substituent in $R^5$ is selected from $=R^{33}$, $C_{2-4}$ alkenyls, and $C_{2-4}$ alkynyls, and $R^{39}$ is S or $CH_2$.

11. The compound according to claim 10, or stereoisomer thereof, or pharmaceutically acceptable salt thereof, or solvate thereof wherein said compound is one of the following compounds:
Compound C9
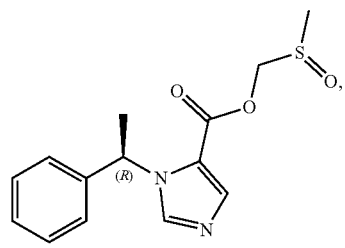
Compound C26
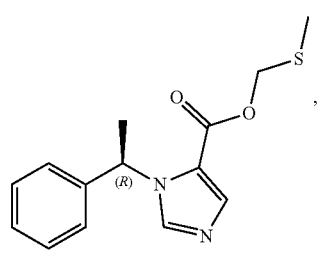
Compound C27
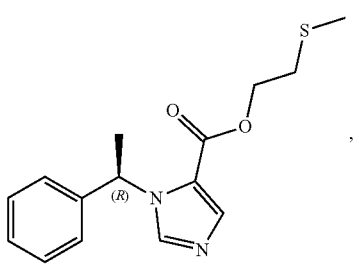
Compound C10
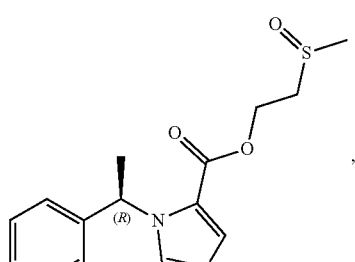
Compound C29
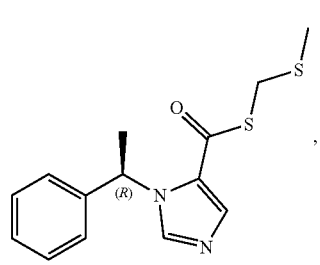
-continued
Compound C30
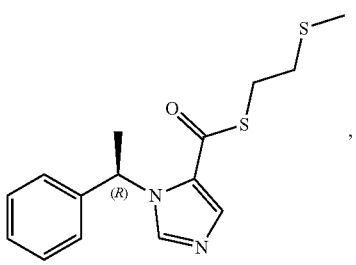
Compound D1
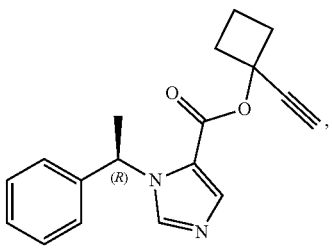
Compound D2
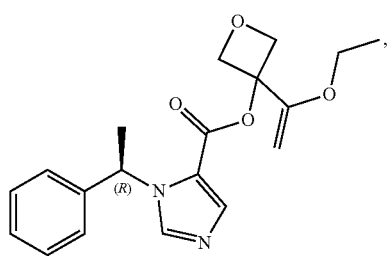
Compound D3
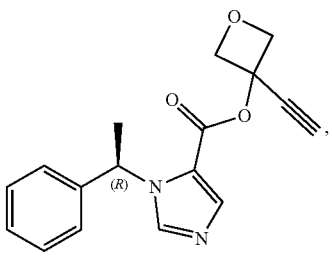
Compound D4
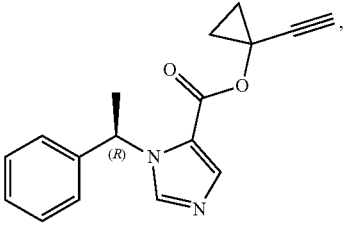
Compound D5
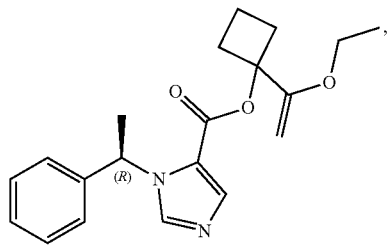

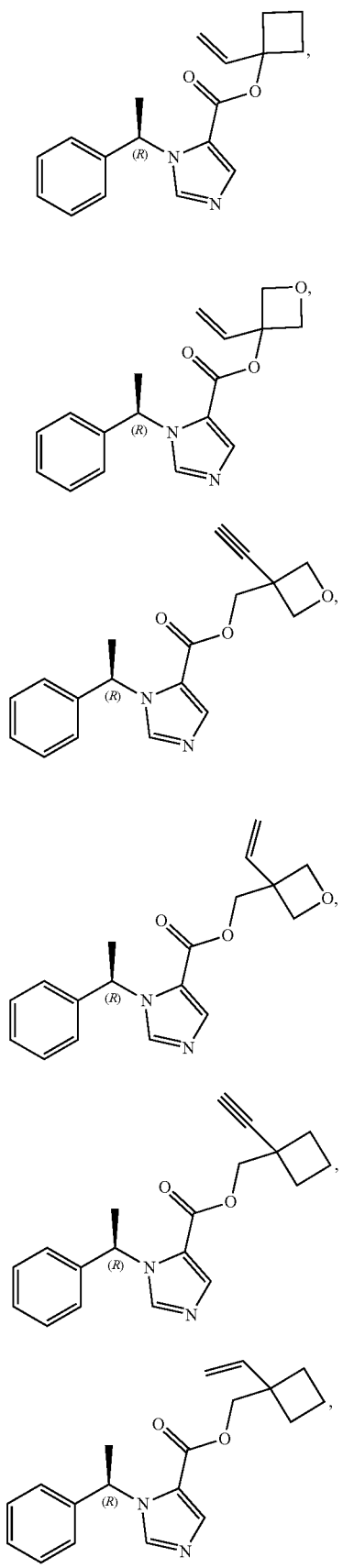

Compound D18
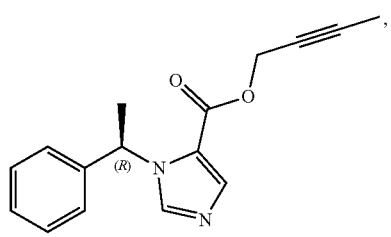
Compound D19
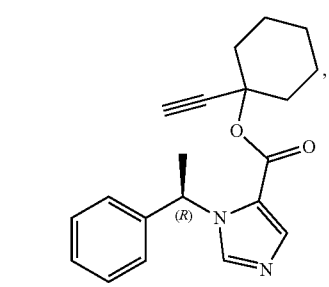
Compound D20
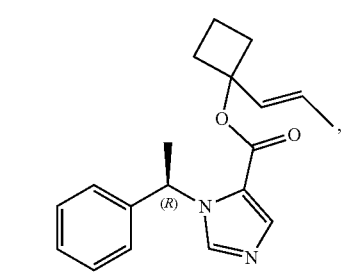
Compound D21
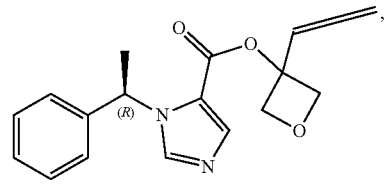
Compound D22
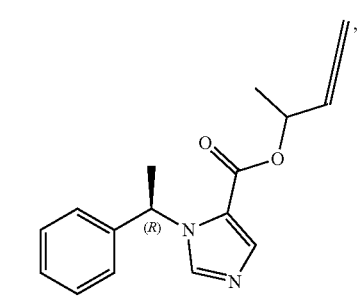
Compound D23
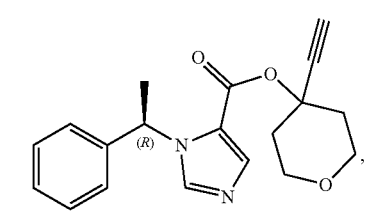
Compound D24
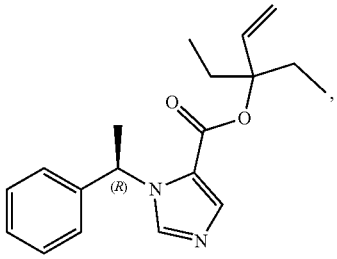
Compound D25
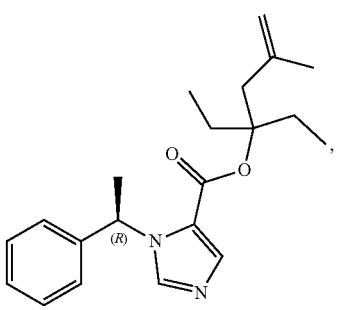
Compound D26
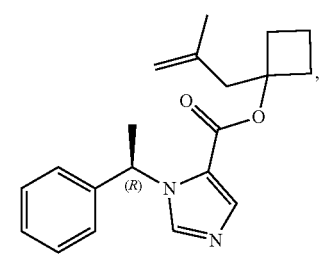
Compound D27
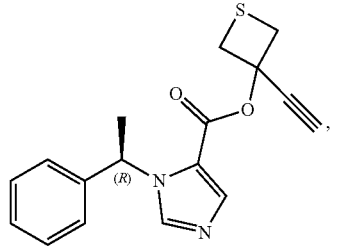
Compound D28
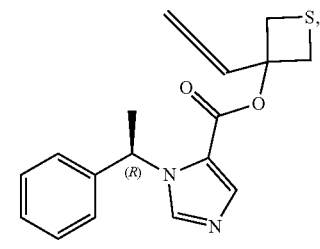
Compound D29
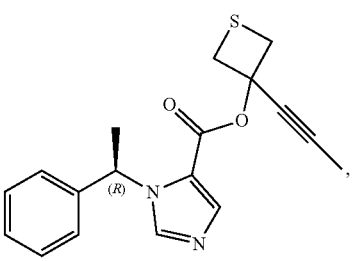

Compound D30
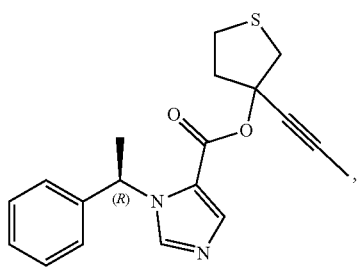
Compound D31
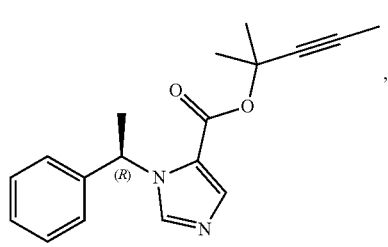
Compound D32
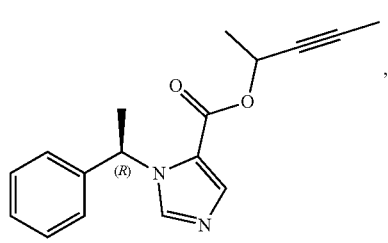
Compound D33
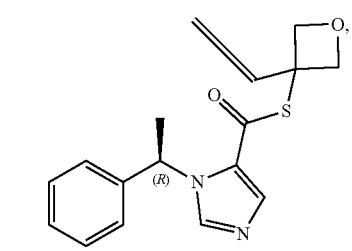
Compound D34
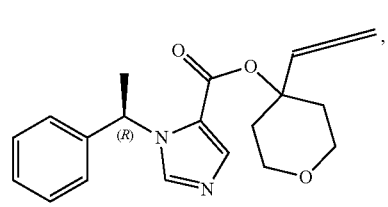
Compound D35
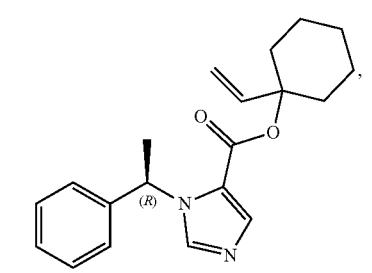
Compound D36
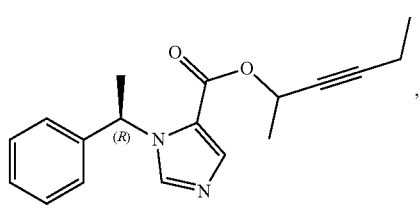
Compound D37
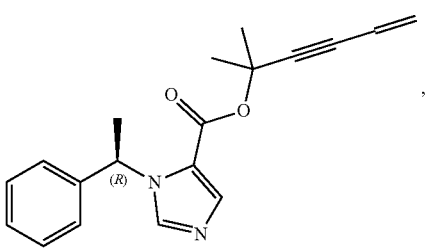
Compound D38
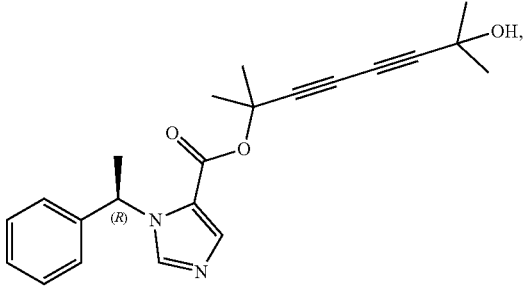
Compound D39
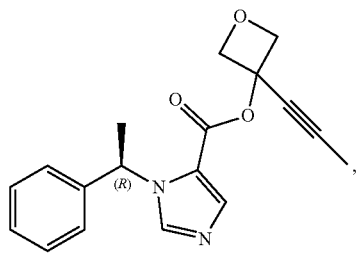
Compound D40
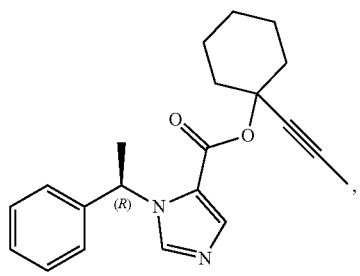
Compound D41
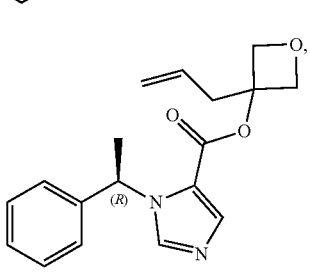

329
-continued
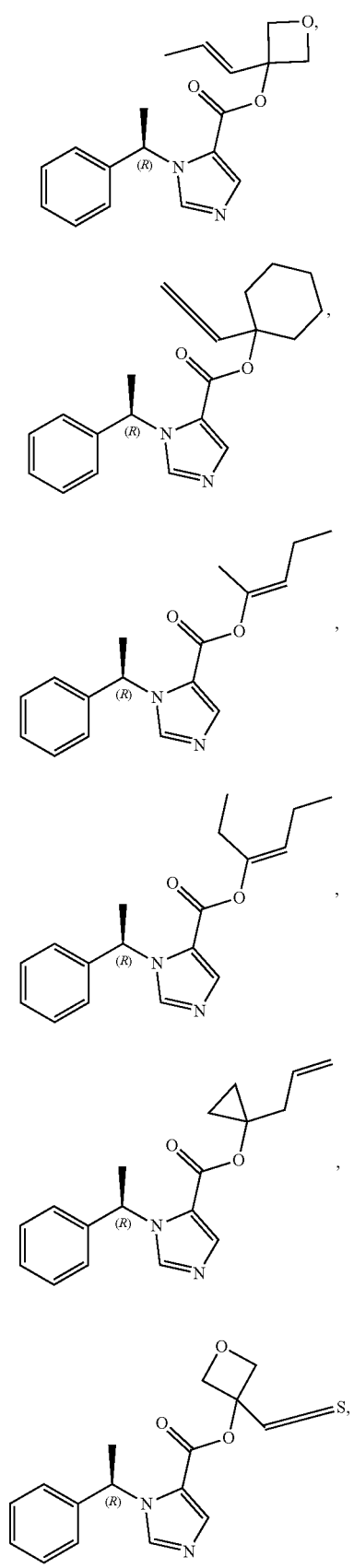
Compound D42
Compound D43
Compound D44
Compound D45
Compound D46
Compound D47
330
-continued
Compound D48
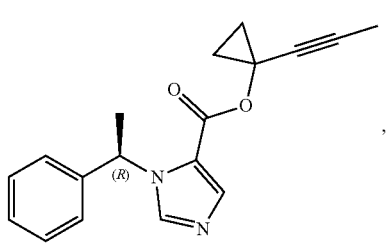
Compound D49
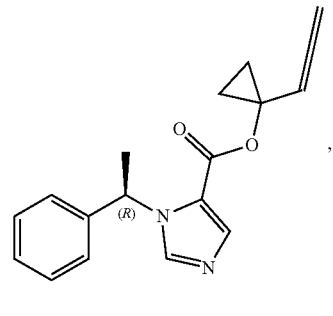
Compound D50
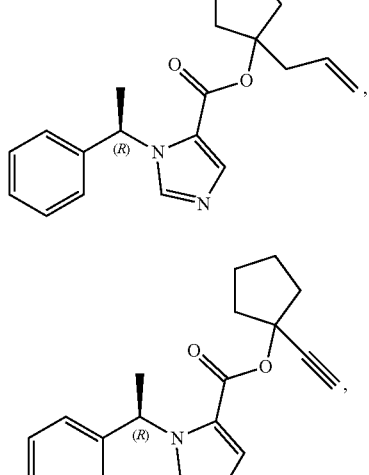
Compound D51
Compound D52
Compound D53
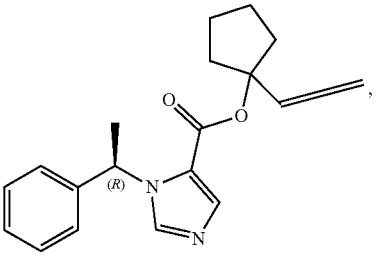

Compound D54
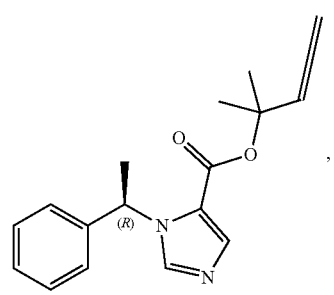
Compound D55
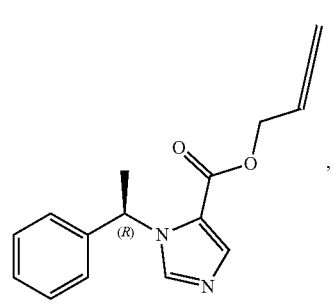
Compound D56
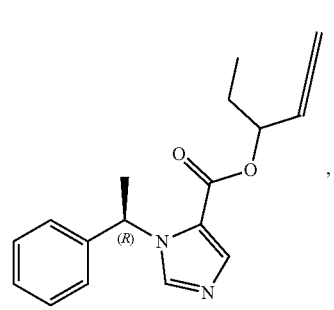
Compound D57
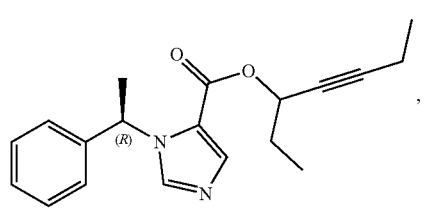
Compound D58
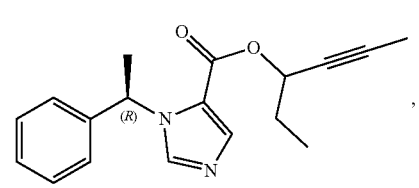
Compound D59
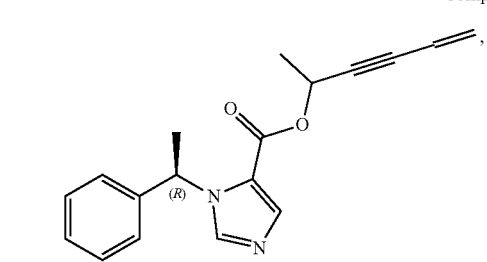
Compound D60
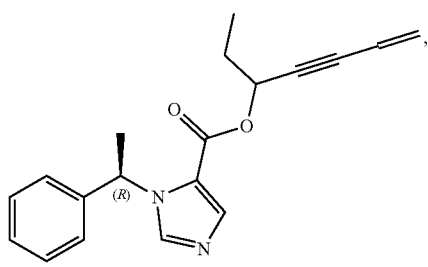
Compound E1
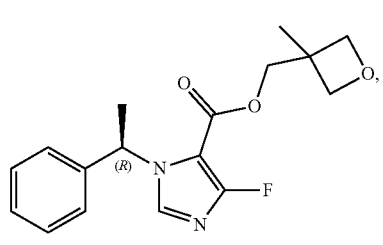
Compound E2
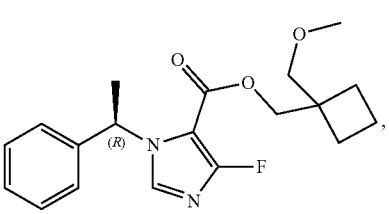
Compound E3
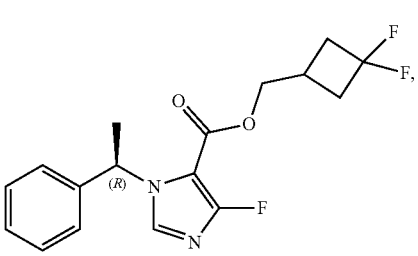
Compound E4
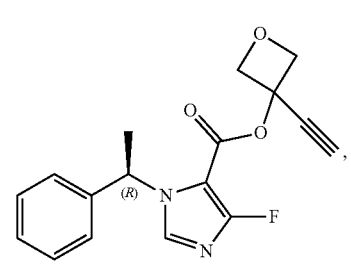
Compound E5
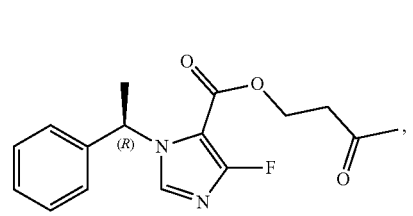

Compound E6
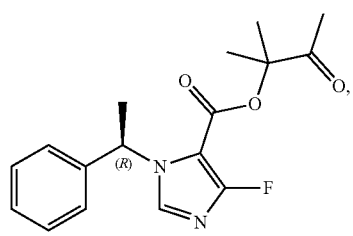
Compound E7
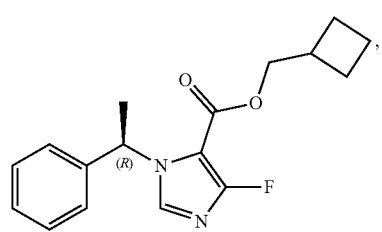
Compound E8
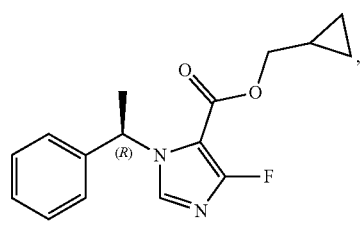
Compound E9
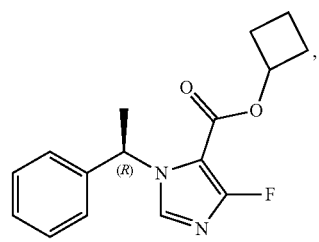
Compound E10
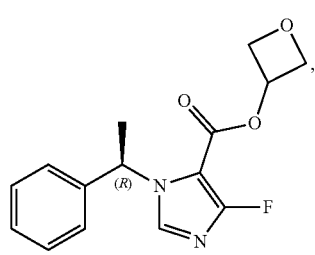
Compound E11
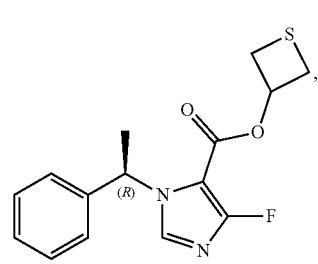
Compound E12
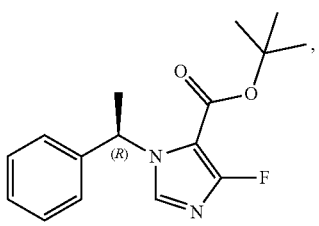
Compound E13
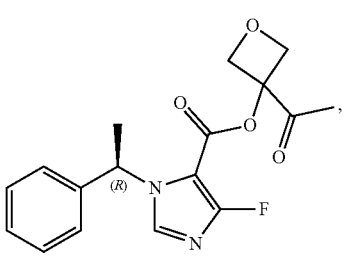
Compound E14
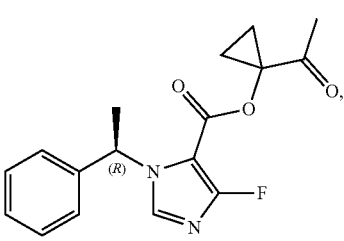
Compound E15
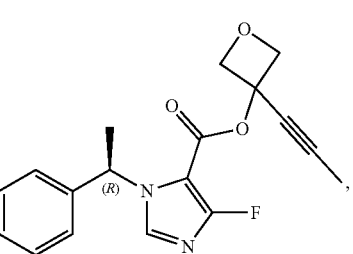
Compound E16
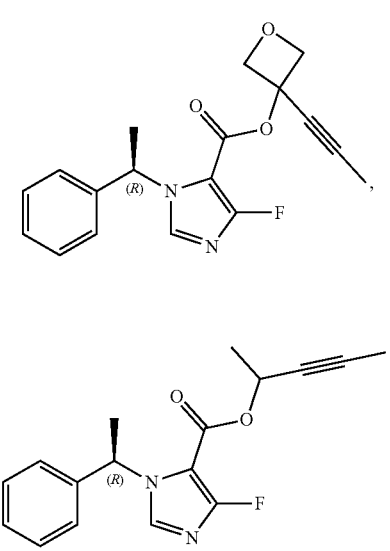
Compound E17
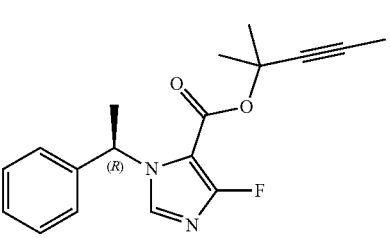

Compound E18
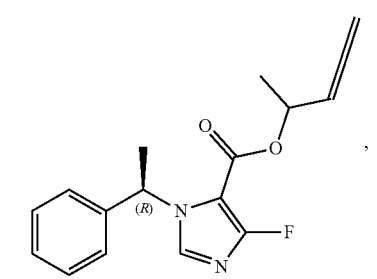
Compound E19
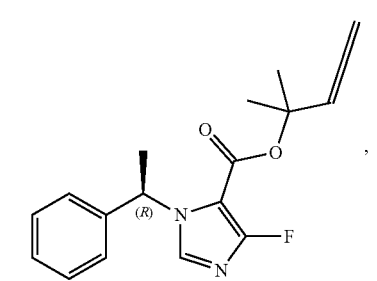
Compound E20
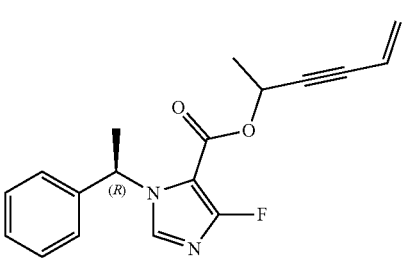
Compound E21
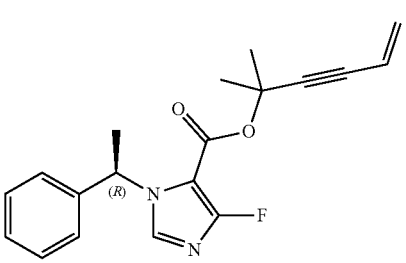
Compound E22
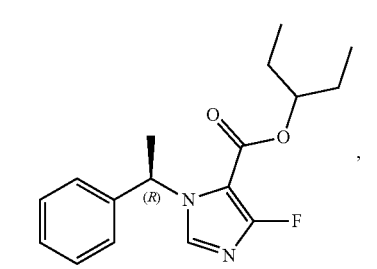
Compound E23
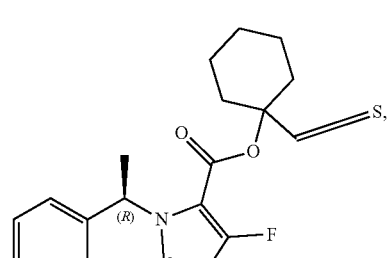
Compound E24
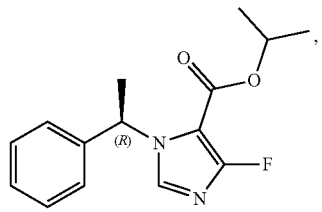
Compound E25
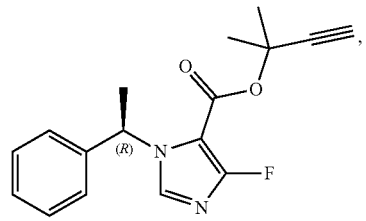
Compound E26
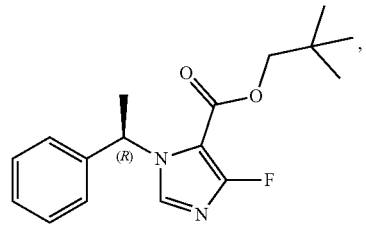
Compound E27
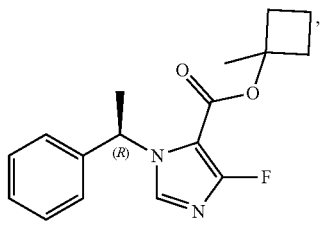
Compound E28
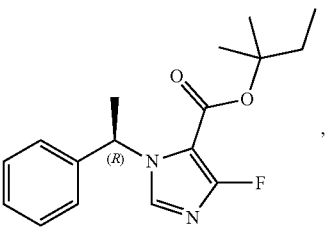
Compound E29
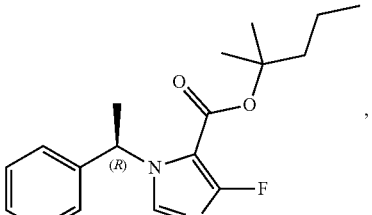

Compound E30
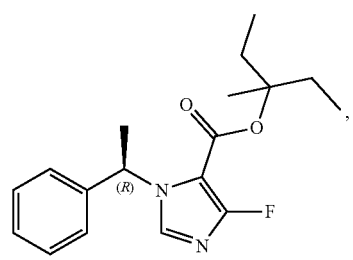
Compound E31
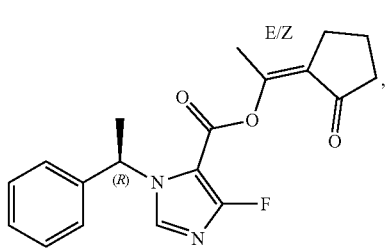
Compound E32
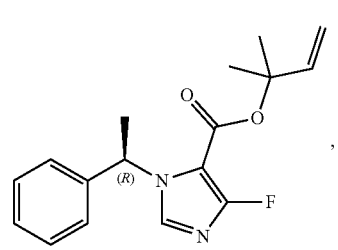
Compound E33
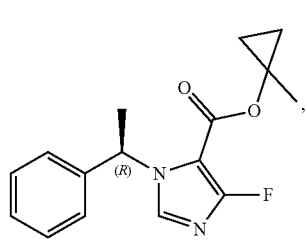
Compound E34
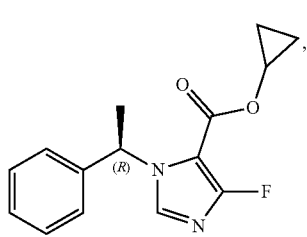
Compound E35
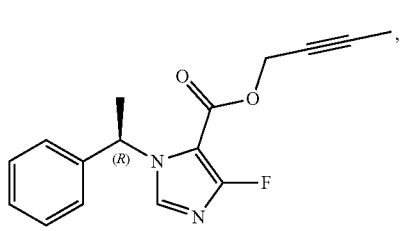
Compound E36
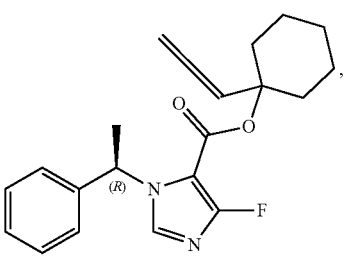
Compound E37
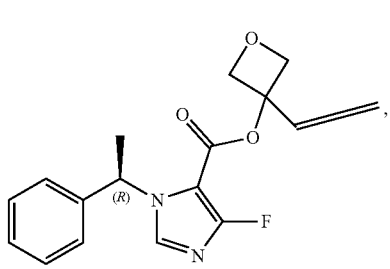
Compound E38
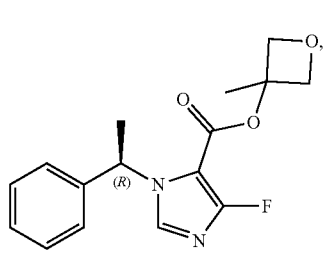
Compound E39
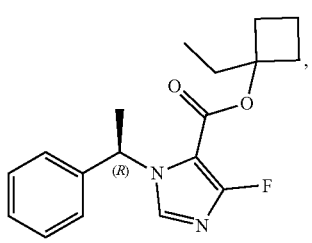
Compound E40
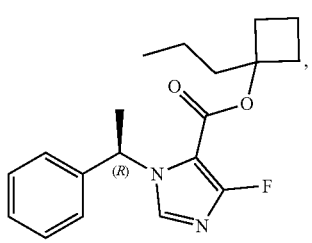
Compound E41
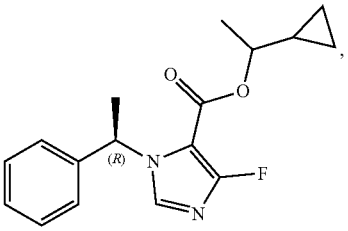

Compound E42
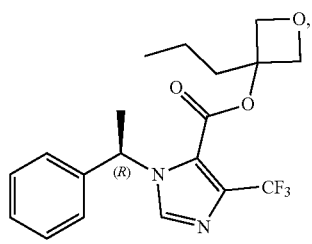
Compound E43
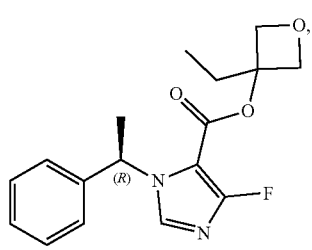
Compound E44
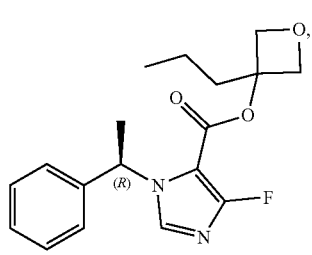
Compound E45
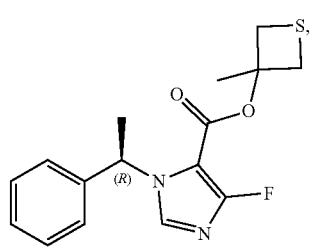
Compound E46
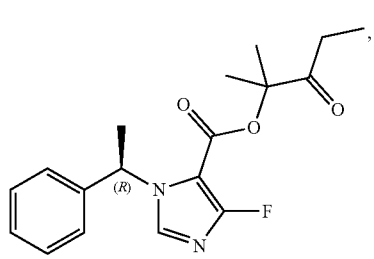
Compound E47
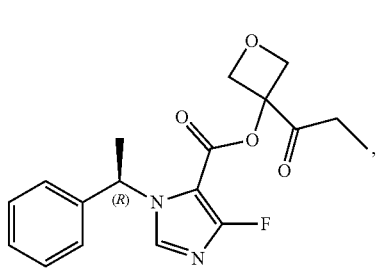
Compound E48
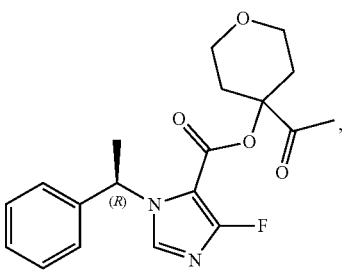
Compound E49
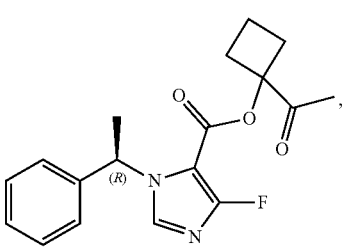
Compound E50
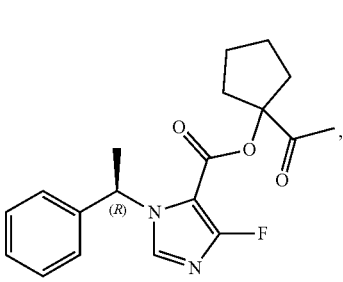
Compound E51
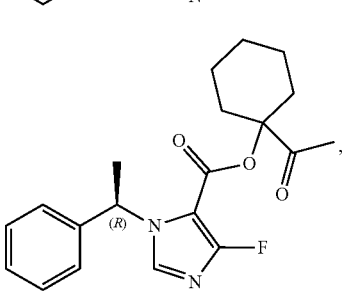
Compound E52
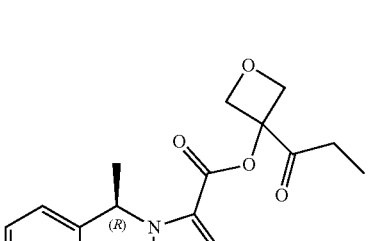
Compound E53
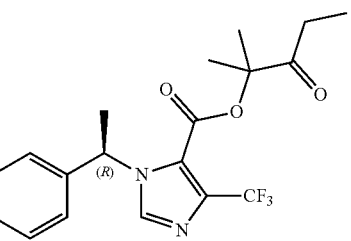

Compound E54
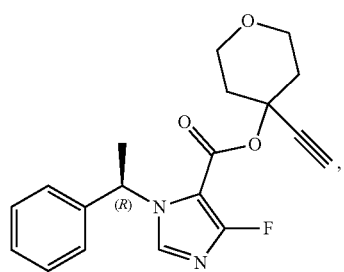
Compound E55
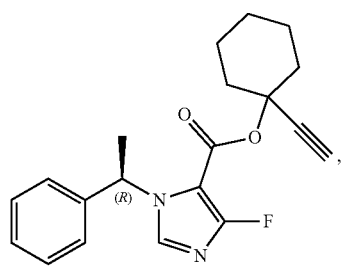
Compound E56
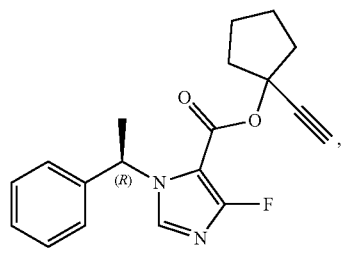
Compound E57
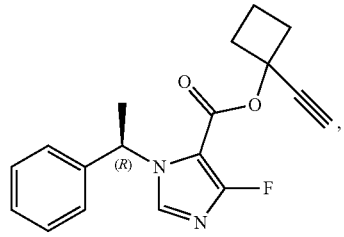
Compound E58
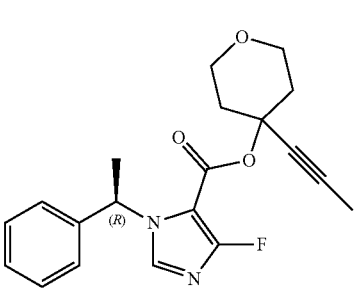
Compound E59
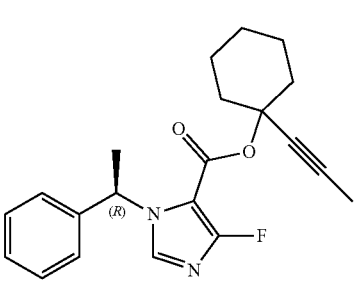
Compound E60
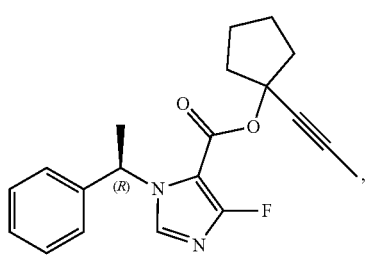
Compound E61
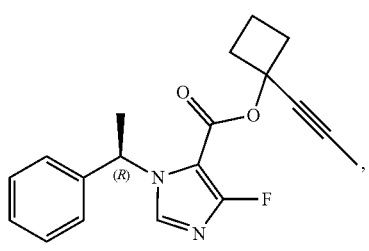
Compound E62
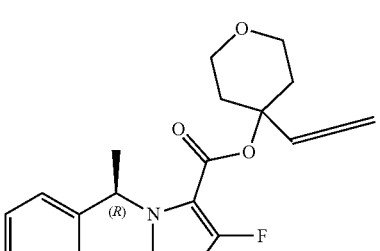
Compound E63
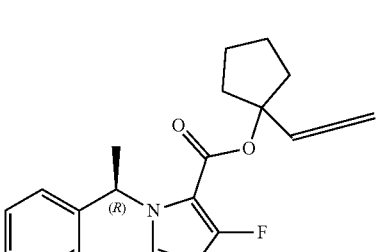
Compound E64
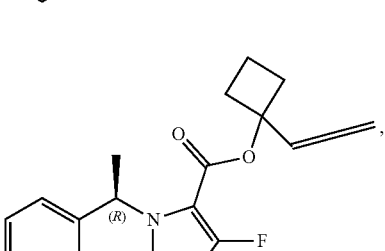
Compound E65
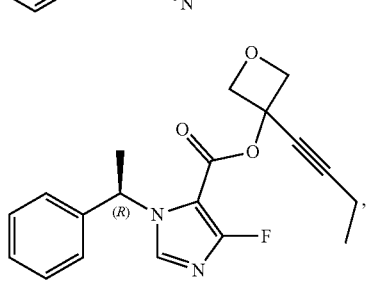

Compound E66
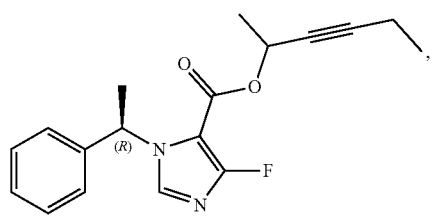
Compound E67
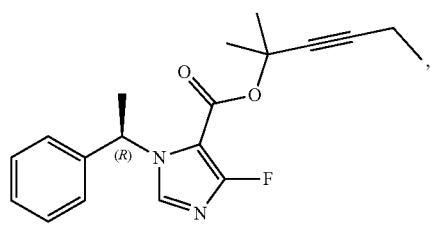
Compound E68
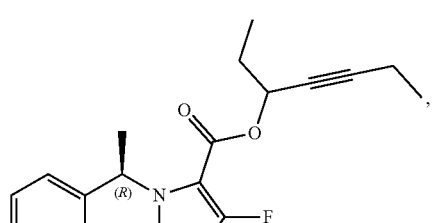
Compound E69
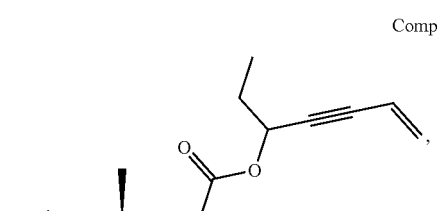
Compound E70
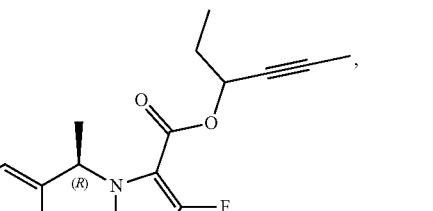
Compound E71
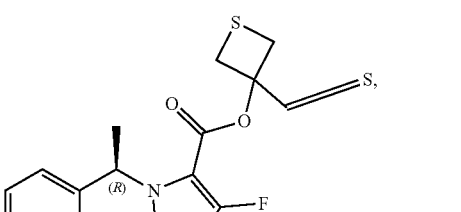
Compound E72
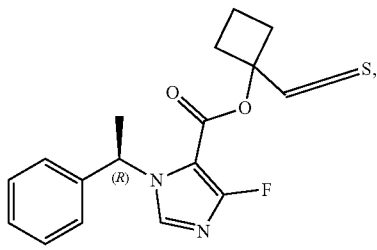
Compound E73
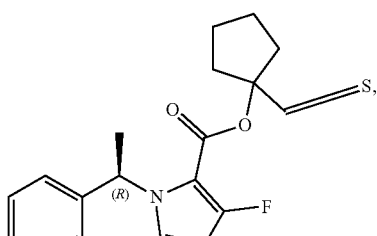
Compound E74
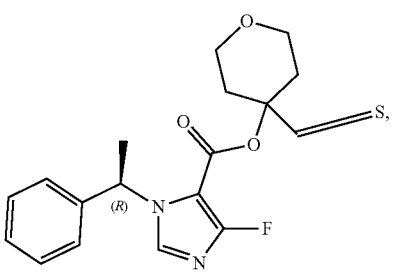
Compound E75
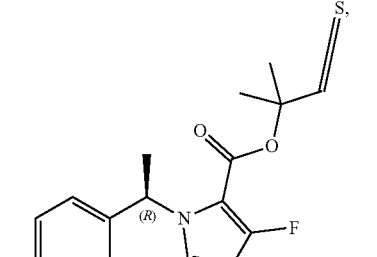
Compound E76
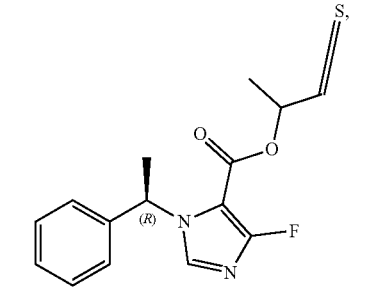

-continued
Compound E77
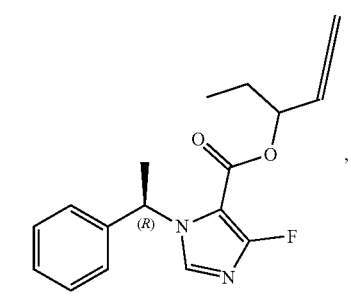
Compound E78
Compound E79
Compound E80
Compound E81
Compound E82
-continued
Compound E83
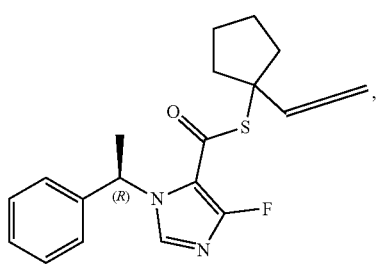
Compound E84
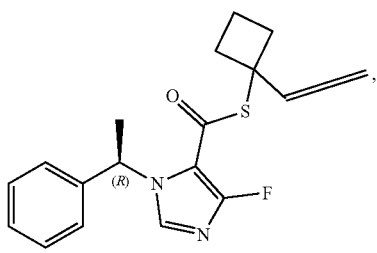
Compound E85
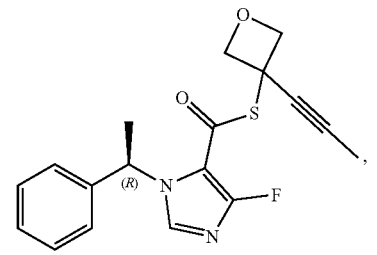
Compound E86
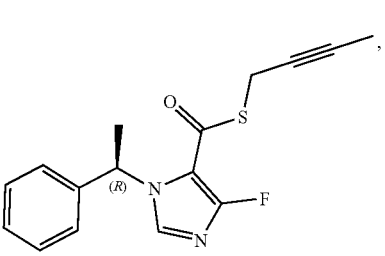
Compound E87
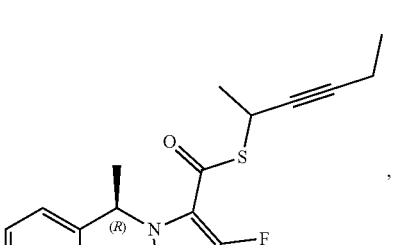
Compound E88
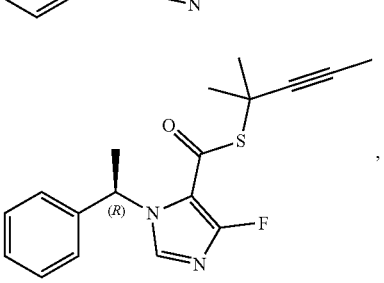

-continued
Compound E89
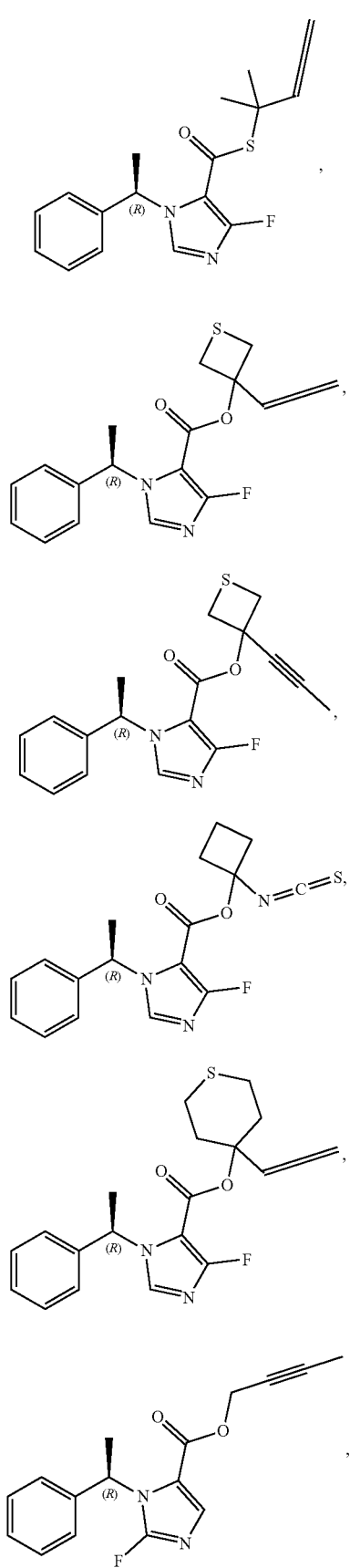
Compound E90
Compound E91
Compound E92
Compound E93
Compound E94
-continued
Compound E95
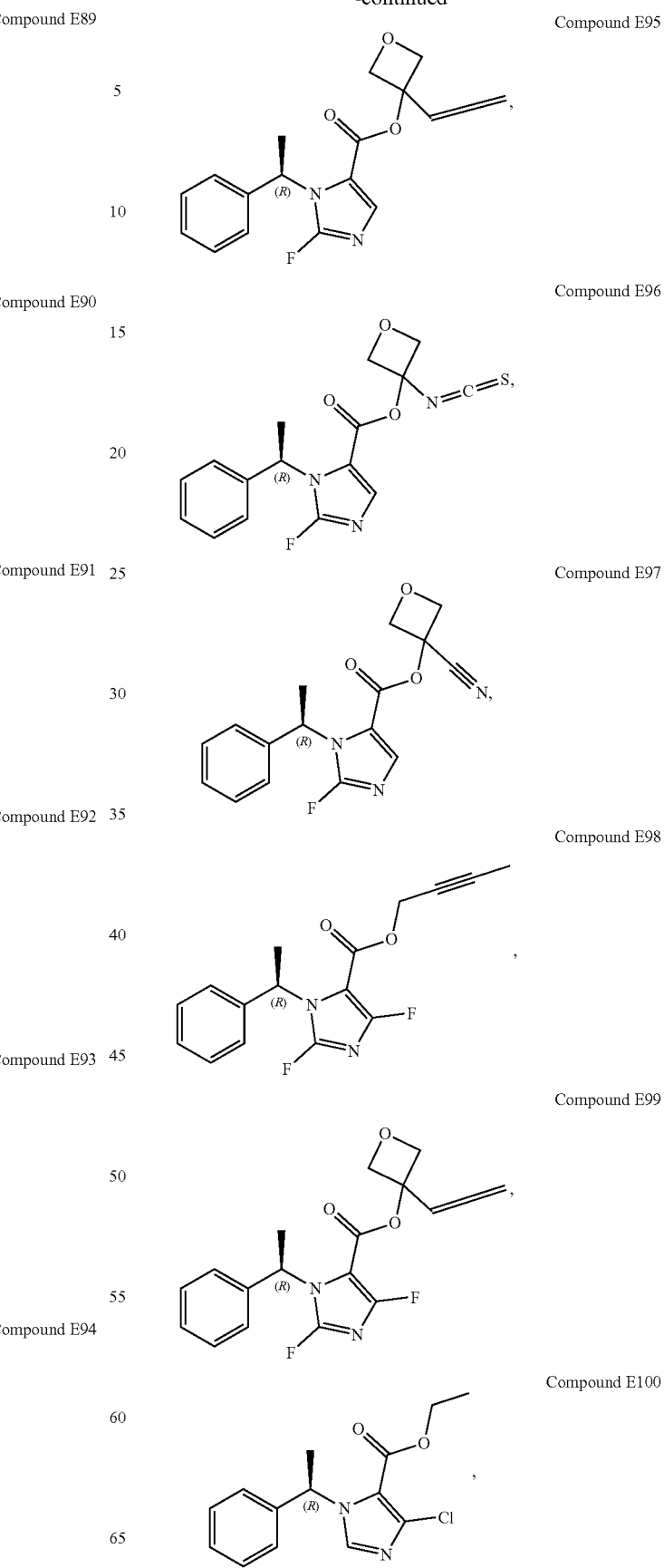
Compound E96
Compound E97
Compound E98
Compound E99
Compound E100

Compound E101
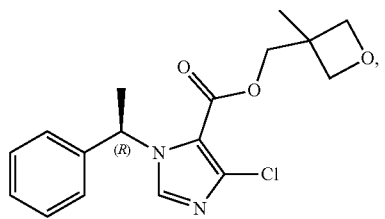
Compound E102
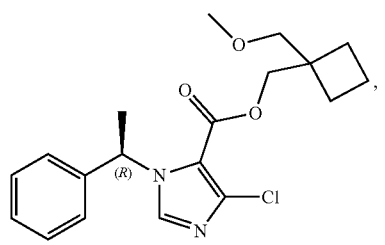
Compound E103
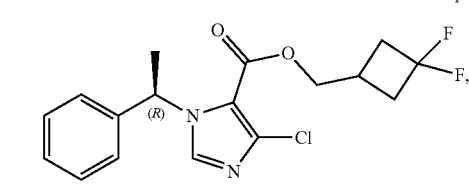
Compound E104
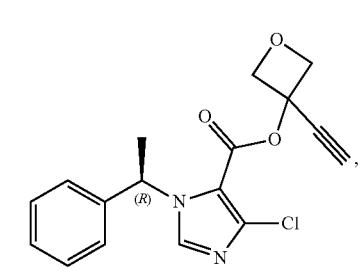
Compound E105
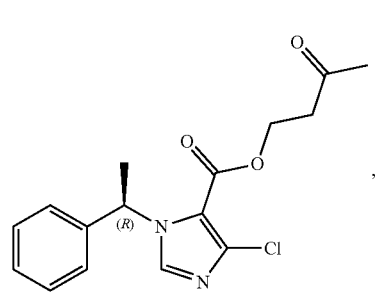
Compound E106
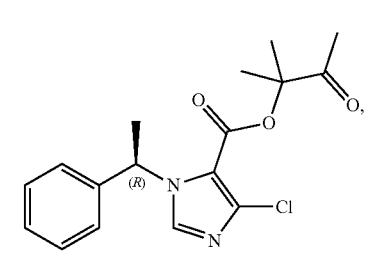
Compound E107
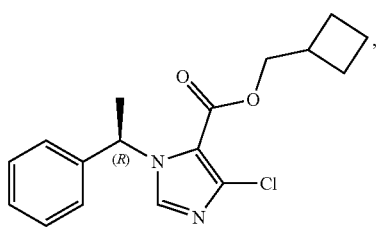
Compound E108
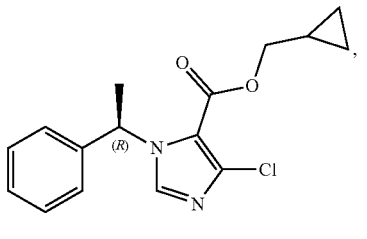
Compound E109
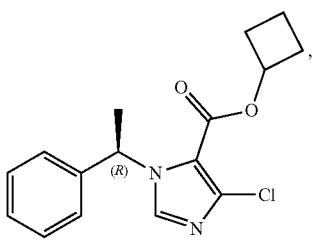
Compound E110
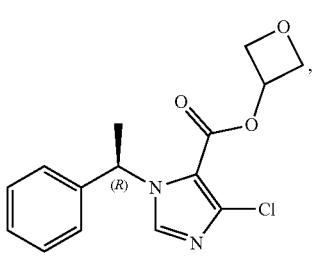
Compound E111
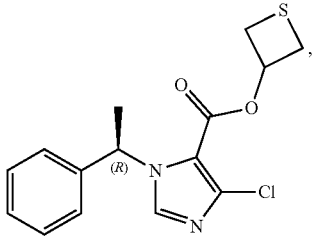
Compound E112
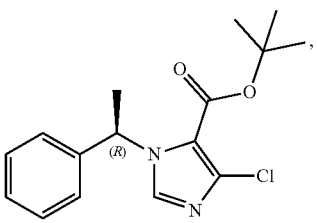

Compound E113
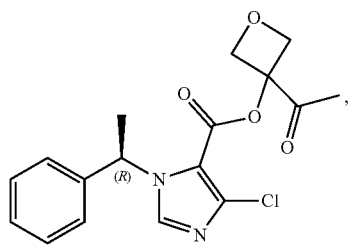
Compound E114
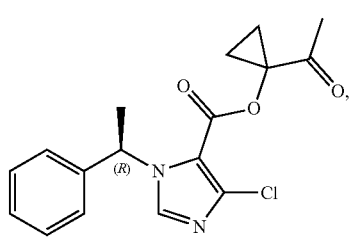
Compound E115
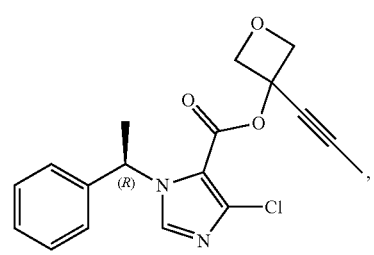
Compound E116
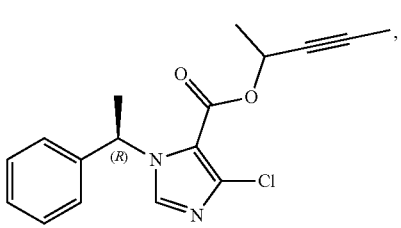
Compound E117
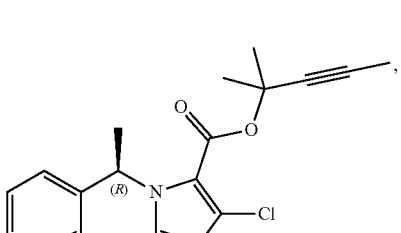
Compound E118
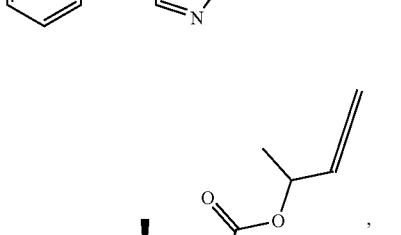
Compound E119
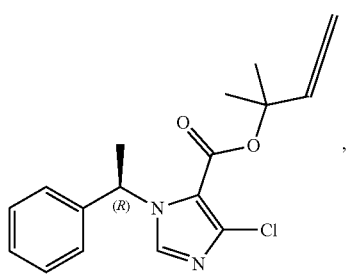
Compound E120
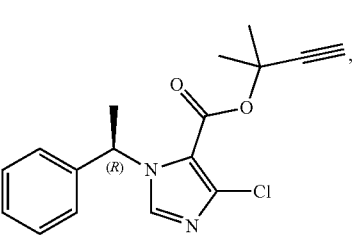
Compound E121
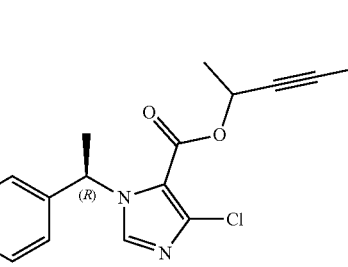
Compound E122
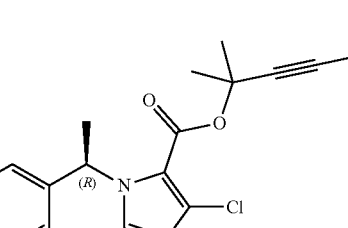
Compound E123
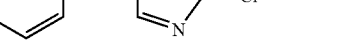
Compound E124
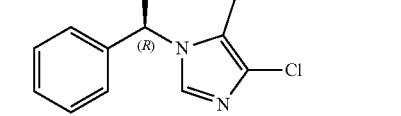

Compound E125
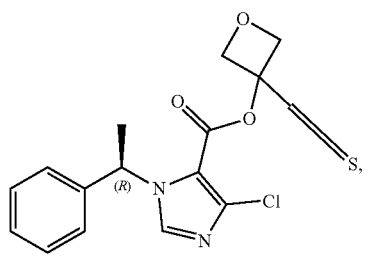
Compound E126
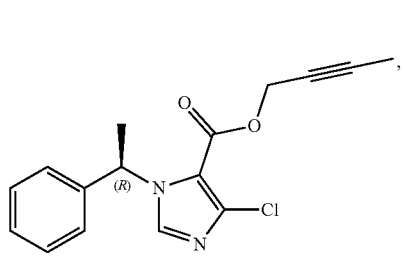
Compound E127
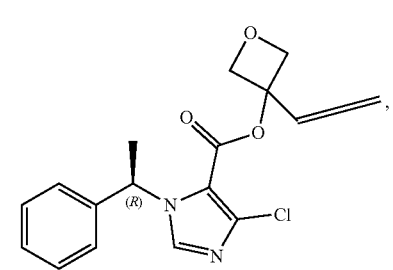
Compound E128
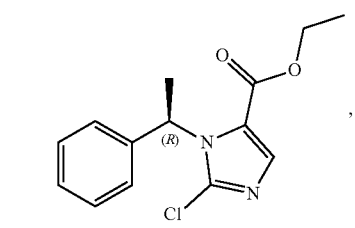
Compound E129
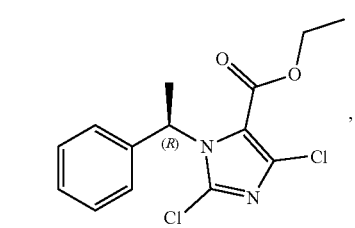
Compound E130
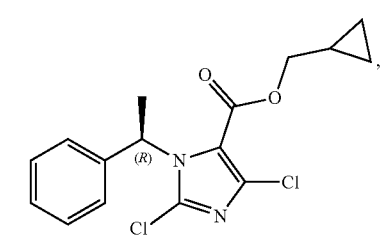
Compound E131
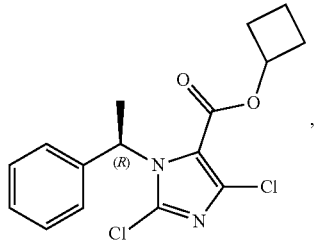
Compound E132
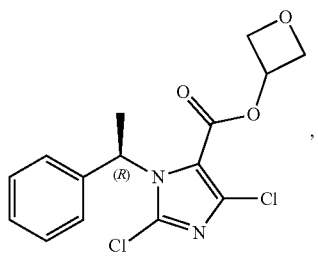
Compound E133
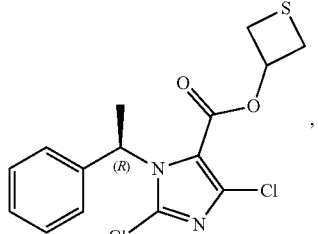
Compound E134
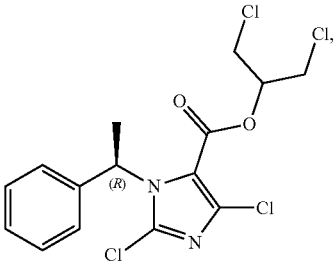
Compound E135
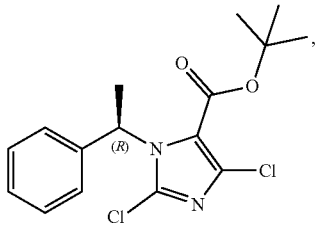
Compound E136

Compound E137
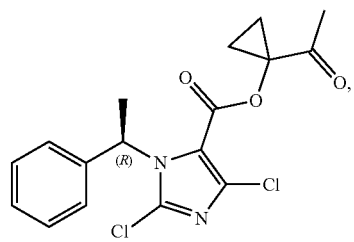
Compound E138
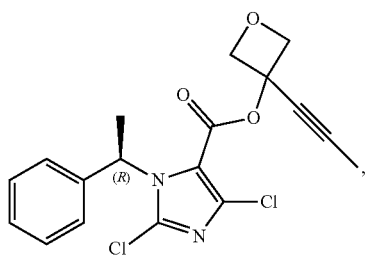
Compound E139
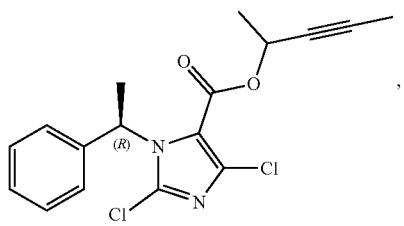
Compound E140
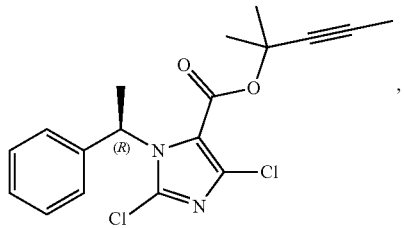
Compound E141
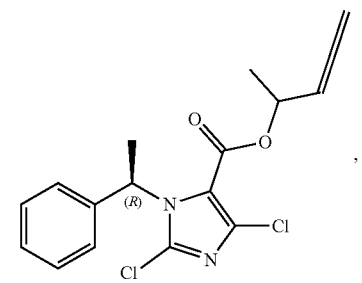
Compound E142
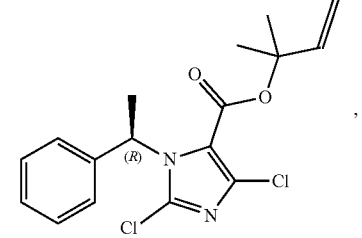
Compound E143
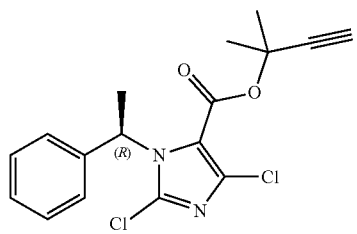
Compound E144
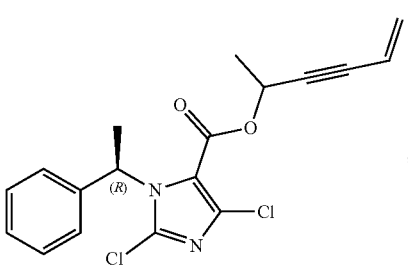
Compound E145
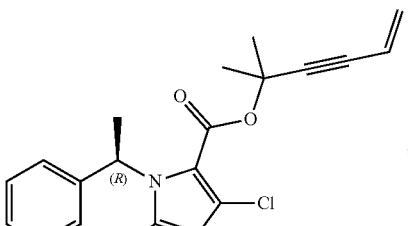
Compound E146
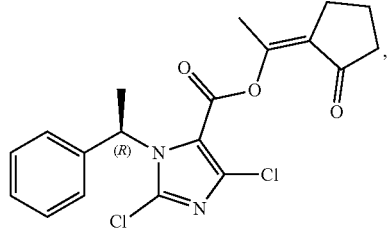
Compound E147
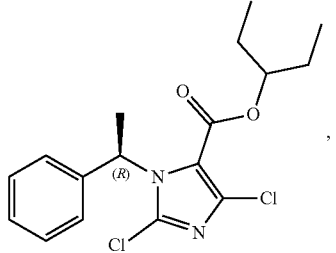
Compound E148
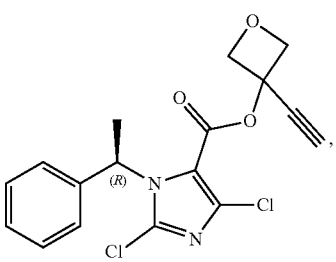

Compound E149
Compound E150
Compound E151
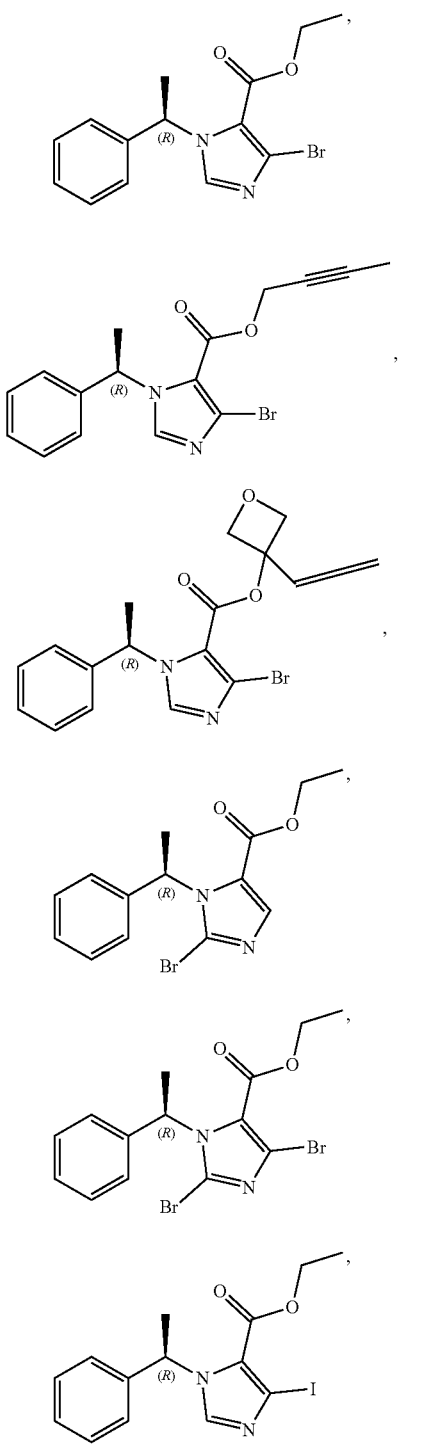
Compound E152
Compound E153
Compound E154
Compound E155
Compound E156
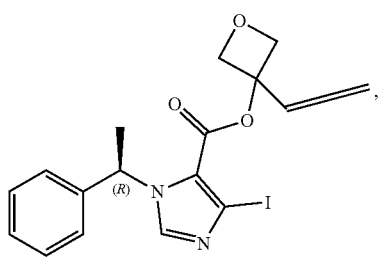
Compound E157
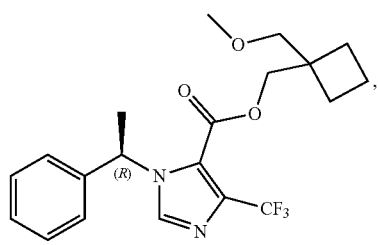
Compound E158
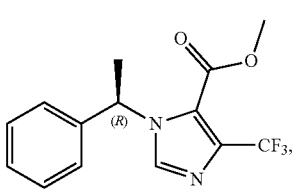
Compound E159
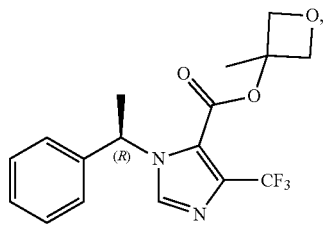
Compound E160
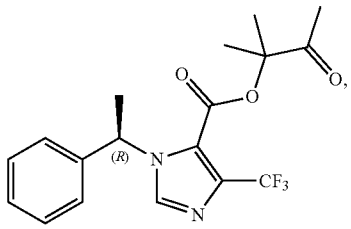
Compound E161
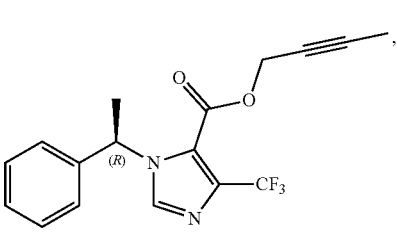

Compound E162

Compound E163

Compound E164

Compound E165

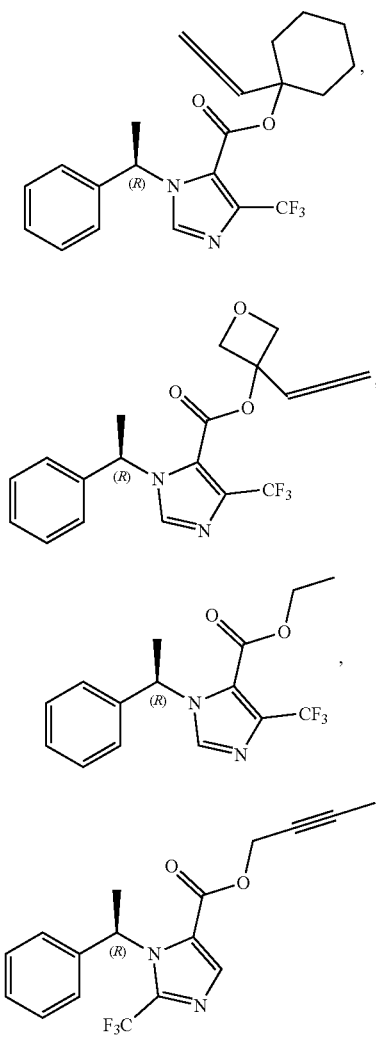

Compound E166

Compound E167

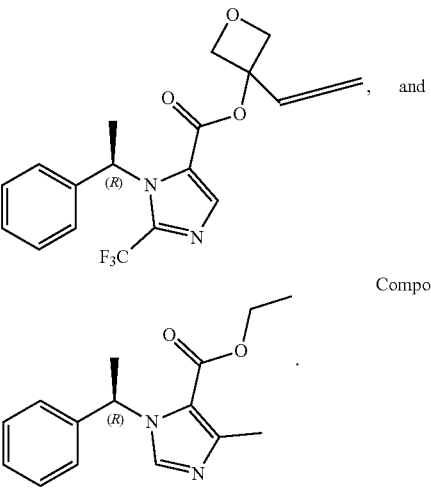

12. A pharmaceutical composition comprising the compound according to claim 10, or stereoisomer thereof, or pharmaceutically acceptable salt thereof, or solvate thereof, or their combinations as active ingredients and pharmaceutically acceptable excipients.

13. A method of sedating, hypnotizing, or anesthetize a subject in need thereof, comprising administering a therapeutically effective amount of a composition to the subject, wherein the composition comprises the compound according to claim 1, or stereoisomer thereof, or pharmaceutically acceptable salt thereof, or solvate thereof, or their combinations.

14. A method of sedating, hypnotizing, or anesthetize a subject in need thereof comprising administering a therapeutically effective amount of a composition to the subject, wherein the composition comprises the compound according to claim 10, or stereoisomer thereof, or pharmaceutically acceptable salt thereof, or solvate thereof, or their combinations.

\* \* \* \* \*